(12) United States Patent
Ferrie et al.

(10) Patent No.: US 12,329,201 B2
(45) Date of Patent: Jun. 17, 2025

(54) SMOKING SUBSTITUTE SYSTEM

(71) Applicant: Imperial Tobacco Limited, Bristol (GB)

(72) Inventors: Kate Ferrie, Liverpool (GB); Ross Shenton, Liverpool (GB); Pete Lomas, Liverpool (GB); Nikhil Aggarwal, Liverpool (GB); Chris Lord, Liverpool (GB); Samantha Murray, Liverpool (GB); Tom Sudlow, Liverpool (GB)

(73) Assignee: Imperial Tobacco Limited, Bristol (GB)

( * ) Notice: Subject to any disclaimer, the term of this patent is extended or adjusted under 35 U.S.C. 154(b) by 505 days.

(21) Appl. No.: 17/481,889

(22) Filed: Sep. 22, 2021

(65) Prior Publication Data

US 2022/0095684 A1     Mar. 31, 2022

Related U.S. Application Data

(63) Continuation of application No. PCT/EP2020/056776, filed on Mar. 13, 2020, and a
(Continued)

(30) Foreign Application Priority Data

Mar. 22, 2019  (EP) .................................... 19020137
Mar. 22, 2019  (EP) .................................... 19020138
(Continued)

(51) Int. Cl.
A24F 40/46     (2020.01)
A24F 40/20     (2020.01)
(Continued)

(52) U.S. Cl.
CPC .............. *A24F 40/46* (2020.01); *A24F 40/20* (2020.01); *A24F 40/70* (2020.01);
(Continued)

(58) Field of Classification Search
CPC ........... A24F 40/46; A24F 40/20; A24F 40/70
See application file for complete search history.

(56) References Cited

U.S. PATENT DOCUMENTS

| 1,459,625 A | 6/1923 | Gulliver |
| 3,853,132 A | 12/1974 | Patton |

(Continued)

FOREIGN PATENT DOCUMENTS

| CA | 300272 A1 | 4/2017 |
| CN | 105142433 A | 12/2015 |

(Continued)

OTHER PUBLICATIONS

International Search Report and Written Opinion (PCT/EP2020/056769); Aug. 4, 2020; 17 pgs.
(Continued)

*Primary Examiner* — Christopher M Rodd
*Assistant Examiner* — Jennifer A Kessie
(74) *Attorney, Agent, or Firm* — DUNLAP CODDING, P.C.

(57) ABSTRACT

A smoking substitute device comprising a heater connected to a main body of the device. The device includes a cap covering at least a portion of the heater. The cap is releasably engaged with a main body of the device. The cap is configured to be released from engagement with the main body of the device using a removal key.

27 Claims, 129 Drawing Sheets

Related U.S. Application Data continuation of application No. PCT/EP2020/056861, filed on Mar. 13, 2020, and a continuation of application No. PCT/EP2020/056863, filed on Mar. 13, 2020, and a continuation of application No. PCT/EP2020/056825, filed on Mar. 13, 2020, and a continuation of application No. PCT/EP2020/056868, filed on Mar. 13, 2020, and a continuation of application No. PCT/EP2020/056784, filed on Mar. 13, 2020, and a continuation of application No. PCT/EP2020/056786, filed on Mar. 13, 2020, and a continuation of application No. PCT/EP2020/056788, filed on Mar. 13, 2020, and a continuation of application No. PCT/EP2020/056870, filed on Mar. 13, 2020, and a continuation of application No. PCT/EP2020/056854, filed on Mar. 13, 2020, and a continuation of application No. PCT/EP2020/056822, filed on Mar. 13, 2020, and a continuation of application No. PCT/EP2020/056838, filed on Mar. 13, 2020, and a continuation of application No. PCT/EP2020/056823, filed on Mar. 13, 2020, and a continuation of application No. PCT/EP2020/056836, filed on Mar. 13, 2020, and a continuation of application No. PCT/EP2020/056818, filed on Mar. 13, 2020, and a continuation of application No. PCT/EP2020/056769, filed on Mar. 13, 2020, and a continuation of application No. PCT/EP2020/056792, filed on Mar. 13, 2020, and a continuation of application No. PCT/EP2020/056777, filed on Mar. 13, 2020, and a continuation of application No. PCT/EP2020/056782, filed on Mar. 13, 2020, and a continuation of application No. PCT/EP2020/056837, filed on Mar. 13, 2020, and a continuation of application No. PCT/EP2020/056772, filed on Mar. 13, 2020.

(30) Foreign Application Priority Data

| | | | |
|---|---|---|---|
| Mar. 22, 2019 | (EP) | ................................ | 19020142 |
| Mar. 22, 2019 | (EP) | ................................ | 19020147 |
| Mar. 22, 2019 | (EP) | ................................ | 19020150 |
| Mar. 22, 2019 | (EP) | ................................ | 19020153 |
| Mar. 22, 2019 | (EP) | ................................ | 19020155 |
| Mar. 22, 2019 | (EP) | ................................ | 19020156 |
| Mar. 22, 2019 | (EP) | ................................ | 19020158 |
| Mar. 22, 2019 | (EP) | ................................ | 19020159 |
| Mar. 22, 2019 | (EP) | ................................ | 19020164 |
| Mar. 22, 2019 | (EP) | ................................ | 19020168 |
| Mar. 22, 2019 | (EP) | ................................ | 19020169 |
| Mar. 22, 2019 | (EP) | ................................ | 19020173 |
| Mar. 22, 2019 | (EP) | ................................ | 19020176 |
| Mar. 22, 2019 | (EP) | ................................ | 19020179 |
| Mar. 22, 2019 | (EP) | ................................ | 19020183 |
| Mar. 22, 2019 | (EP) | ................................ | 19020185 |
| Mar. 22, 2019 | (EP) | ................................ | 19020189 |
| Mar. 22, 2019 | (EP) | ................................ | 19020197 |
| Mar. 22, 2019 | (EP) | ................................ | 19020201 |
| Mar. 22, 2019 | (EP) | ................................ | 19020203 |
| Mar. 22, 2019 | (EP) | ................................ | 19020206 |
| Mar. 22, 2019 | (EP) | ................................ | 19020209 |
| Mar. 22, 2019 | (EP) | ................................ | 19020210 |
| Mar. 22, 2019 | (EP) | ................................ | 19020212 |
| Mar. 22, 2019 | (EP) | ................................ | 19020213 |
| Mar. 22, 2019 | (EP) | ................................ | 19020216 |
| Mar. 22, 2019 | (EP) | ................................ | 19020223 |
| Feb. 14, 2020 | (EP) | ................................ | 20157500 |

(51) Int. Cl.

| | |
|---|---|
| *A24F 40/70* | (2020.01) |
| *A46B 15/00* | (2006.01) |
| *B25B 27/14* | (2006.01) |
| *H05B 3/06* | (2006.01) |
| *A61M 11/04* | (2006.01) |

(52) U.S. Cl.
CPC .......... *A46B 15/0055* (2013.01); *B25B 27/14* (2013.01); *H05B 3/06* (2013.01); *A46B 2200/3073* (2013.01); *A61M 11/042* (2014.02); *A61M 2209/10* (2013.01)

(56) References Cited

U.S. PATENT DOCUMENTS

| | | | |
|---|---|---|---|
| 4,553,455 A | 11/1985 | Wilcox et al. | |
| 5,875,534 A | 3/1999 | Jackson | |
| 6,089,857 A | 7/2000 | Matsuura et al. | |
| 6,119,700 A | 9/2000 | Fleischhauer et al. | |
| 6,164,287 A | 12/2000 | White | |
| 9,375,034 B2 | 6/2016 | Alima | |
| 9,826,780 B2 | 11/2017 | Krietzman | |
| 10,039,323 B2 | 8/2018 | Schuler et al. | |
| 2007/0074734 A1 | 4/2007 | Braunshteyn et al. | |
| 2007/0151426 A1 | 7/2007 | Kuo | |
| 2008/0092912 A1 | 4/2008 | Robinson et al. | |
| 2009/0223515 A1 | 9/2009 | Watanabe | |
| 2010/0163063 A1 | 7/2010 | Fernando et al. | |
| 2011/0271971 A1 | 11/2011 | Conner et al. | |
| 2013/0160764 A1 | 6/2013 | Liu | |
| 2013/0192615 A1 | 8/2013 | Tucker et al. | |
| 2013/0228190 A1 | 9/2013 | Weiss et al. | |
| 2013/0298905 A1 | 11/2013 | Levin et al. | |
| 2013/0327327 A1 | 12/2013 | Edwards et al. | |
| 2013/0333709 A1 | 12/2013 | Shimizu | |
| 2014/0216485 A1 | 8/2014 | Egoyants et al. | |
| 2014/0254055 A1 | 9/2014 | Xiang | |
| 2014/0261495 A1 | 9/2014 | Novak, III et al. | |
| 2014/0311506 A1 | 10/2014 | Liu | |
| 2014/0338686 A1 | 11/2014 | Plojoux et al. | |
| 2014/0345634 A1 | 11/2014 | Zuber et al. | |
| 2014/0353856 A1 | 12/2014 | Dubief | |
| 2014/0360515 A1 | 12/2014 | Vasiliev et al. | |
| 2015/0013696 A1 | 1/2015 | Plojoux et al. | |
| 2015/0020832 A1 | 1/2015 | Greim et al. | |
| 2015/0164135 A1 | 6/2015 | Boring | |
| 2015/0173422 A1* | 6/2015 | Liu | A24F 40/485 131/329 |
| 2015/0181936 A1 | 7/2015 | Lyubomirskiy et al. | |
| 2015/0257441 A1 | 9/2015 | Gerkin | |
| 2015/0296882 A1 | 10/2015 | Mironov et al. | |
| 2015/0342254 A1 | 12/2015 | Mironov et al. | |
| 2016/0044961 A1 | 2/2016 | Liu | |
| 2016/0050975 A1 | 2/2016 | Worm et al. | |
| 2016/0057811 A1 | 2/2016 | Alarcon et al. | |
| 2016/0213062 A1 | 7/2016 | Doyle | |
| 2016/0302486 A1 | 10/2016 | Eroch | |
| 2016/0310624 A1 | 10/2016 | Wynalda, Jr. | |
| 2017/0035108 A1 | 2/2017 | Zinovik et al. | |
| 2017/0042243 A1 | 2/2017 | Plojoux et al. | |
| 2017/0055580 A1 | 3/2017 | Blandino et al. | |
| 2017/0055583 A1 | 3/2017 | Blandino et al. | |
| 2017/0095002 A1 | 4/2017 | Silvestrini | |
| 2017/0099873 A1 | 4/2017 | Benjamignan et al. | |
| 2017/0119052 A1 | 5/2017 | Williams et al. | |
| 2017/0208866 A1 | 7/2017 | Liu | |
| 2017/0215478 A1 | 8/2017 | Harrison et al. | |
| 2017/0215479 A1 | 8/2017 | Kies | |
| 2017/0224014 A1 | 8/2017 | Fraser | |
| 2017/0258133 A1 | 9/2017 | Ampolini et al. | |
| 2017/0295844 A1 | 10/2017 | Thevenaz et al. | |

(56) References Cited

U.S. PATENT DOCUMENTS

| | | |
|---|---|---|
| 2017/0295846 A1 | 10/2017 | Liu |
| 2017/0347708 A1 | 12/2017 | Shin |
| 2017/0347712 A1 | 12/2017 | Singh |
| 2018/0027878 A1 | 2/2018 | Dendy et al. |
| 2018/0027884 A1 | 2/2018 | Zuber et al. |
| 2018/0043115 A1 | 2/2018 | Gould et al. |
| 2018/0049472 A1 | 2/2018 | Mahler et al. |
| 2018/0093054 A1 | 4/2018 | Bowen et al. |
| 2018/0098570 A1 | 4/2018 | Hon |
| 2018/0110263 A1 | 4/2018 | Borkovec et al. |
| 2018/0132533 A1 | 5/2018 | Chen |
| 2018/0140015 A1 | 5/2018 | Carroll et al. |
| 2018/0153216 A1 | 6/2018 | Wong et al. |
| 2018/0177231 A1 | 6/2018 | Woodbine et al. |
| 2018/0199627 A1 | 7/2018 | Bowen et al. |
| 2019/0183177 A1 | 6/2019 | Hubbard et al. |
| 2019/0307167 A1 | 10/2019 | Steiner |
| 2020/0093183 A1 | 3/2020 | Zheng et al. |

FOREIGN PATENT DOCUMENTS

| | | |
|---|---|---|
| CN | 105310112 A | 2/2016 |
| CN | 205648930 U | 10/2016 |
| CN | 106388008 A | 2/2017 |
| CN | 107156917 A | 9/2017 |
| CN | 206507314 U | 9/2017 |
| CN | 107242606 A | 10/2017 |
| CN | 206542921 U | 10/2017 |
| CN | 206687163 U | 12/2017 |
| CN | 107713019 A | 2/2018 |
| CN | 107752130 A | 3/2018 |
| CN | 108185528 A | 6/2018 |
| CN | 207479044 U | 6/2018 |
| CN | 207544339 U | 6/2018 |
| CN | 108402526 A | 8/2018 |
| CN | 108497559 A | 9/2018 |
| CN | 108497560 A | 9/2018 |
| CN | 108552598 A | 9/2018 |
| CN | 108618205 A | 10/2018 |
| CN | 108669658 A | 10/2018 |
| CN | 108713796 A | 10/2018 |
| CN | 108783601 A | 11/2018 |
| CN | 108851248 A | 11/2018 |
| CN | 208096008 U | 11/2018 |
| CN | 109007991 A | 12/2018 |
| CN | 109077366 A | 12/2018 |
| CN | 109744586 A | 5/2019 |
| DE | 4308627 A1 | 9/1944 |
| DE | 202004003804 U | 6/2004 |
| DE | 102007011120 A1 | 9/2008 |
| EP | 0951219 A1 | 10/1999 |
| EP | 3078283 A1 | 10/2016 |
| EP | 3145345 A1 | 3/2017 |
| EP | 3155907 A1 | 4/2017 |
| EP | 3192382 A1 | 7/2017 |
| EP | 3308658 A1 | 4/2018 |
| EP | 3349603 A1 | 7/2018 |
| EP | 3381305 A1 | 10/2018 |
| GB | 168587 A | 2/1922 |
| GB | 2513627 A1 | 11/2014 |
| GB | 2534211 A | 7/2016 |
| JP | 2018191550 A | 12/2018 |
| KR | 20180070458 A | 6/2018 |
| WO | WO9632854 A2 | 10/1996 |
| WO | WO2008034455 A1 | 3/2008 |
| WO | WO 2012/164033 A1 | 12/2012 |
| WO | WO2013012157 A1 | 1/2013 |
| WO | WO 2013/076098 A2 | 5/2013 |
| WO | WO 2013/083635 A1 | 6/2013 |
| WO | WO 2013/098409 A1 | 7/2013 |
| WO | WO2013131763 A1 | 9/2013 |
| WO | WO2014132045 A2 | 9/2014 |
| WO | WO2014195687 A1 | 12/2014 |
| WO | WO 2015/006929 A1 | 1/2015 |
| WO | WO 2015/100361 A1 | 7/2015 |
| WO | WO2015165709 A1 | 11/2015 |
| WO | WO 2016/008217 A1 | 1/2016 |
| WO | WO 2016/124550 A1 | 8/2016 |
| WO | WO 2016/207407 A1 | 12/2016 |
| WO | WO 2017/051150 A1 | 3/2017 |
| WO | WO2017072648 A1 | 5/2017 |
| WO | WO 2017/108721 A1 | 6/2017 |
| WO | WO2017153443 A1 | 9/2017 |
| WO | WO2017178932 A1 | 10/2017 |
| WO | WO 2017/194762 A1 | 11/2017 |
| WO | WO 2017/194763 A1 | 11/2017 |
| WO | WO2017194763 A2 | 11/2017 |
| WO | WO2017197584 A1 | 11/2017 |
| WO | WO 2017/207419 A1 | 12/2017 |
| WO | WO 2017/207584 A1 | 12/2017 |
| WO | WO 2018/019786 A1 | 2/2018 |
| WO | WO 2018/050613 A1 | 3/2018 |
| WO | WO2018050612 A1 | 3/2018 |
| WO | WO2018059493 A1 | 4/2018 |
| WO | WO2018069676 A1 | 4/2018 |
| WO | WO 2018/099999 A1 | 6/2018 |
| WO | WO 2018/122389 A1 | 7/2018 |
| WO | WO2018127484 A1 | 7/2018 |
| WO | WO 2018/150039 A1 | 8/2018 |
| WO | WO 2018/216961 A1 | 11/2018 |
| WO | WO 2018/220558 A1 | 12/2018 |
| WO | WO 2019/012151 A1 | 1/2019 |
| WO | WO 2019/016740 A1 | 1/2019 |
| WO | WO2019020151 A1 | 1/2019 |
| WO | WO 2019/030166 A1 | 2/2019 |
| WO | WO 2019/030167 A1 | 2/2019 |
| WO | WO 2019/030168 A1 | 2/2019 |
| WO | WO2019/030170 A1 | 2/2019 |
| WO | WO2019030360 A1 | 2/2019 |
| WO | WO 2019/170886 A1 | 9/2019 |
| WO | WO2019/170897 A1 | 9/2019 |
| WO | WO2019170893 A1 | 9/2019 |
| WO | WO2019185745 A1 | 10/2019 |
| WO | WO2019224310 A1 | 11/2019 |
| WO | WO2020017821 A1 | 1/2020 |

OTHER PUBLICATIONS

International Search Report and Written Opinion (PCT/EP2020/056772); Jun. 2, 2020; 9 pgs.
International Search Report and Written Opinion (PCT/EP2020/056776); Aug. 17, 2020; 16 pgs.
International Search Report and Written Opinion (PCT/EP2020/056777); Jun. 25, 2020; 8 pgs.
International Search Report and Written Opinion (PCT/EP2020/056782); Jul. 9, 2020; 8 pgs.
International Search Report and Written Opinion (PCT/EP2020/056784); Jun. 15, 2020; 9 pgs.
International Search Report and Written Opinion (PCT/EP2020/056786); Jun. 15, 2020; 10 pgs.
International Search Report and Written Opinion (PCT/EP2020/056788); Jun. 15, 2020; 10 pgs.
International Search Report and Written Opinion (PCT/EP2020/056792); Jun. 8, 2020; 14 pgs.
International Search Report and Written Opinion (PCT/EP2020/056818); Sep. 8, 2020; 11 pgs.
International Search Report and Written Opinion (PCT/EP2020/056822); Jul. 2, 2020; 9 pgs.
International Search Report and Written Opinion (PCT/EP2020/056823); Jul. 15, 2020; 10 pgs.
International Search Report and Written Opinion (PCT/EP2020/056825); Jul. 2, 2020; 9 pgs.
International Search Report and Written Opinion (PCT/EP2020/056836); Jul. 24, 2020; 10 pgs.
International Search Report and Written Opinion (PCT/EP2020/056837); Jun. 26, 2020; 9 pgs.
International Search Report and Written Opinion (PCT/EP2020/056838); Jul. 16, 2020; 9 pgs.
International Search Report and Written Opinion (PCT/EP2020/056854); Jun. 25, 2020; 8 pgs.

(56) References Cited

OTHER PUBLICATIONS

International Search Report and Written Opinion (PCT/EP2020/056861); Jul. 15, 2020; 10 pgs.
International Search Report and Written Opinion (PCT/EP2020/056863); Jun. 25, 2020; 8 pgs.
International Search Report and Written Opinion (PCT/EP2020/056868); Jul. 21, 2020; 10 pgs.
International Search Report and Written Opinion (PCT/EP2020/056870); Jun. 8, 2020; 9 pgs.
European Patent Office; Extended European Search Report regarding European Patent Application No. 19020137.6, filed Mar. 22, 2019, dated Oct. 17, 2019.
European Patent Office; Extended European Search Report regarding European Patent Application No. 19020138.4, filed Mar. 22, 2019, dated Sep. 11, 2019.
European Patent Office; Extended European Search Report regarding European Patent Application No. 19020142.6, filed Mar. 22, 2019, dated Oct. 30, 2019.
European Patent Office; Extended European Search Report regarding European Patent Application No. 19020147.5, filed Mar. 22, 2019, dated Oct. 30, 2019.
European Patent Office; Extended European Search Report regarding European Patent Application No. 19020150.9, filed Mar. 22, 2019, dated Jun. 19, 2021.
European Patent Office; Extended European Search Report regarding European Patent Application No. 19020153.3, filed Mar. 22, 2019, dated Oct. 24, 2019.
European Patent Office; Extended European Search Report regarding European Patent Application No. 19020155.8, filed Mar. 22, 2019, dated Sep. 16, 2019.
European Patent Office; Extended European Search Report regarding European Patent Application No. 19020156.6, filed Mar. 22, 2019, dated Sep. 16, 2019.
European Patent Office; Extended European Search Report regarding European Patent Application No. 19020158.2, filed Mar. 22, 2019, dated Sep. 9, 2019.
European Patent Office; Extended European Search Report regarding European Patent Application No. 19020159.0, filed Mar. 22, 2019, dated Nov. 4, 2019.
European Patent Office; Extended European Search Report regarding European Patent Application No. 19020164.0, filed Mar. 22, 2019, dated Oct. 17, 2019.
European Patent Office; Extended European Search Report regarding European Patent Application No. 19020168.1, filed Mar. 22, 2019, dated Sep. 19, 2019.
European Patent Office; Extended European Search Report regarding European Patent Application No. 19020169.9, filed Mar. 22, 2019, dated Sep. 11, 2019.
European Patent Office; Extended European Search Report regarding European Patent Application No. 19020173.1, filed Mar. 22, 2019, dated Sep. 12, 2019.
European Patent Office; Extended European Search Report regarding European Patent Application No. 19020176.4, filed Mar. 22, 2019, dated Jan. 3, 2020.
European Patent Office; Extended European Search Report regarding European Patent Application No. 19020179.8, filed Mar. 22, 2019, dated Oct. 8, 2019.
European Patent Office; Extended European Search Report regarding European Patent Application No. 19020183.0, filed Mar. 22, 2019, dated Oct. 30, 2019.
European Patent Office; Extended European Search Report regarding European Patent Application No. 19020185.5, filed Mar. 22, 2019, dated Sep. 12, 2019.
European Patent Office; Extended European Search Report regarding European Patent Application No. 19020189.7, filed Mar. 22, 2019, dated Sep. 12, 2019.
European Patent Office; Extended European Search Report regarding European Patent Application No. 19020197.0, filed Mar. 22, 2019, dated Sep. 23, 2019.
European Patent Office; Extended European Search Report regarding European Patent Application No. 19020201.0, filed Mar. 22, 2019, dated Oct. 17, 2019.
European Patent Office; Extended European Search Report regarding European Patent Application No. 19020203.6, filed Mar. 22, 2019, dated Apr. 17, 2020.
European Patent Office; Extended European Search Report regarding European Patent Application No. 19020206.9, filed Mar. 22, 2019, dated Aug. 6, 2019.
European Patent Office; Extended European Search Report regarding European Patent Application No. 19020209.3, filed Mar. 22, 2019, dated Oct. 8, 2019.
European Patent Office; Extended European Search Report regarding European Patent Application No. 19020210.1, filed Mar. 22, 2019, dated Sep. 12, 2019.
European Patent Office; Extended European Search Report regarding European Patent Application No. 19020212.7, filed Mar. 22, 2019, dated Oct. 8, 2019.
European Patent Office; Extended European Search Report regarding European Patent Application No. 19020213.5, filed Mar. 22, 2019, dated Sep. 12, 2019.
European Patent Office; Extended European Search Report regarding European Patent Application No. 19020216.8, filed Mar. 22, 2019, dated Oct. 8, 2019.
European Patent Office; Extended European Search Report regarding European Patent Application No. 19020223.4, filed Mar. 22, 2019, dated Nov. 18, 2019.
European Patent Office; Extended European Search Report regarding European Patent Application No. 20157500.8, filed Mar. 13, 2020, dated Sep. 9, 2020.
European Patent Office; Extended European Search Report regarding European Patent Application No. 20157501.6, filed Mar. 13, 2020, dated Sep. 9, 2020.
Taiwan Intellectual Property Office, Office Action regarding Taiwan patent application No. 109109122, dated Aug. 5, 2024, with English translation.
European Patent Office, Extended European Search Report regarding European patent application No. 24165311.2, dated Jun. 14, 2024, 10 pages.

\* cited by examiner

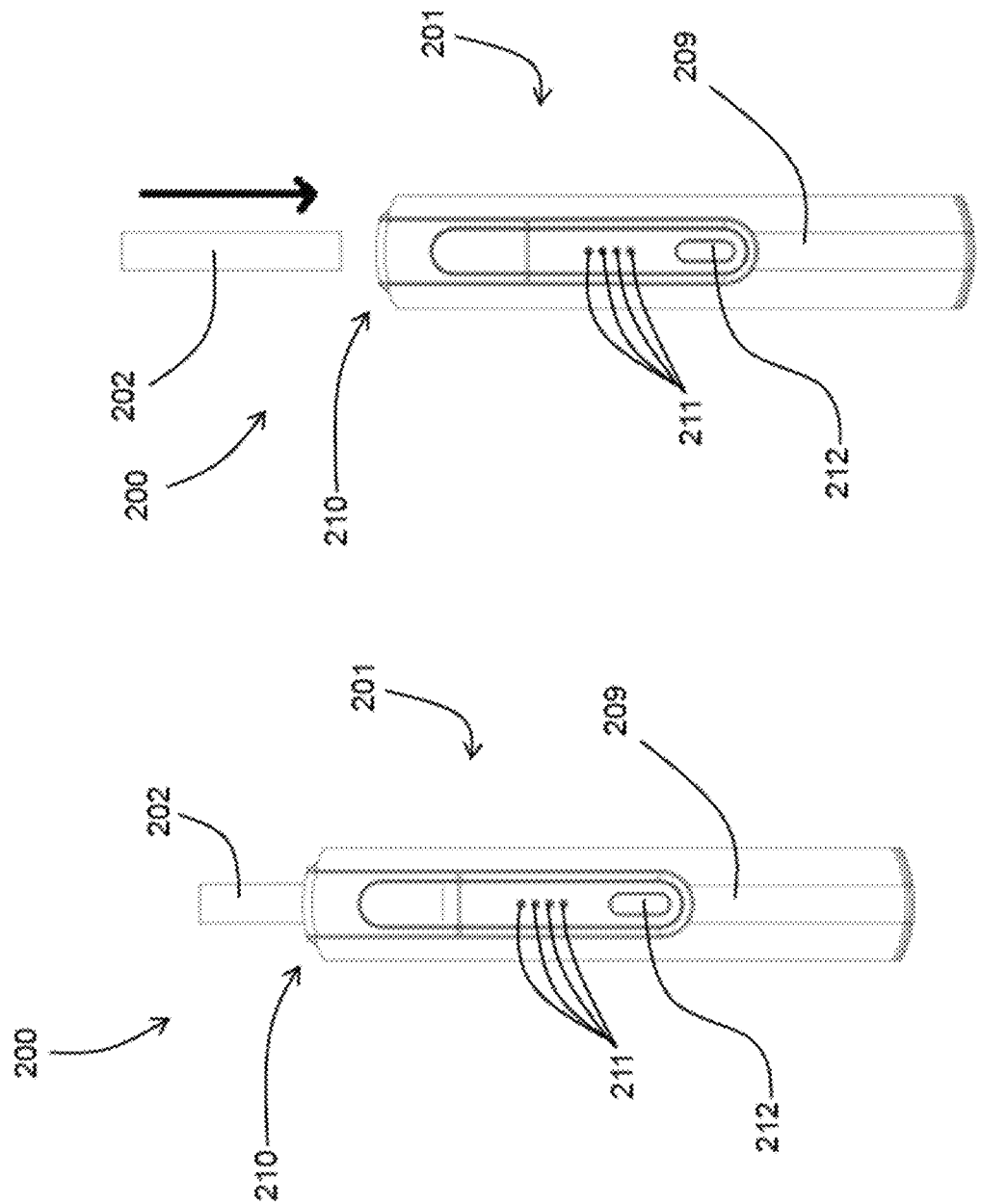

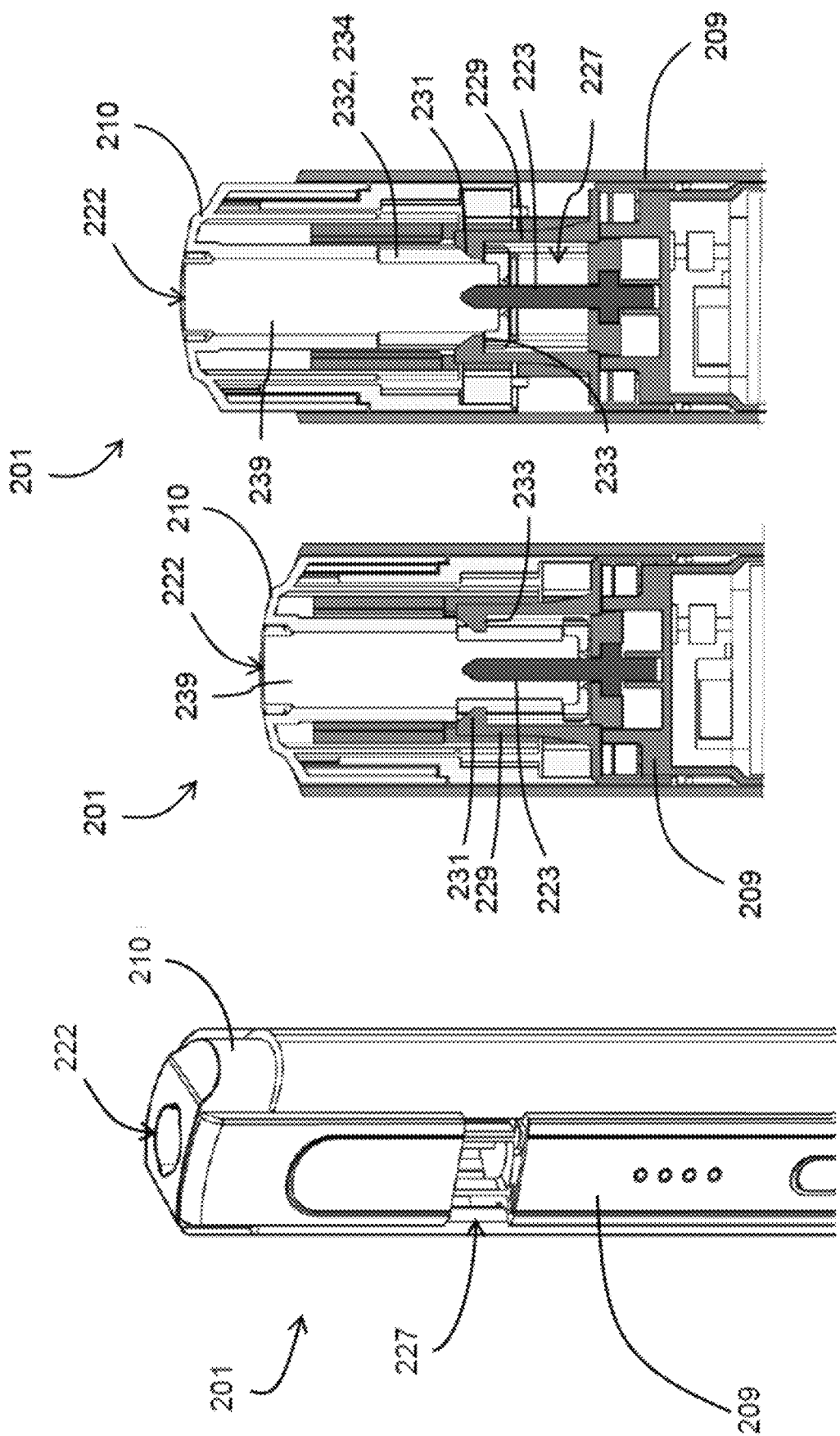

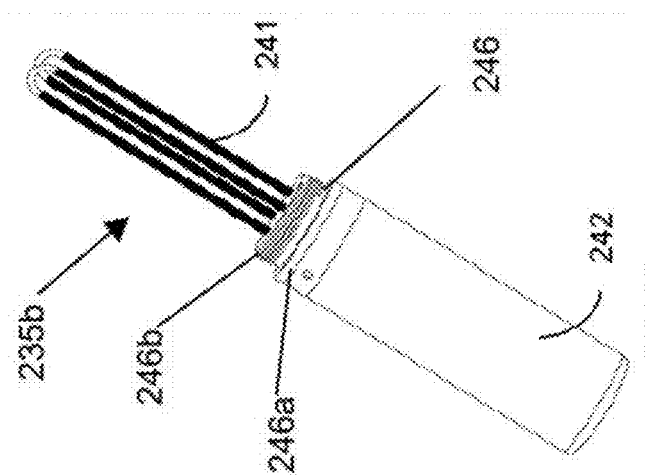
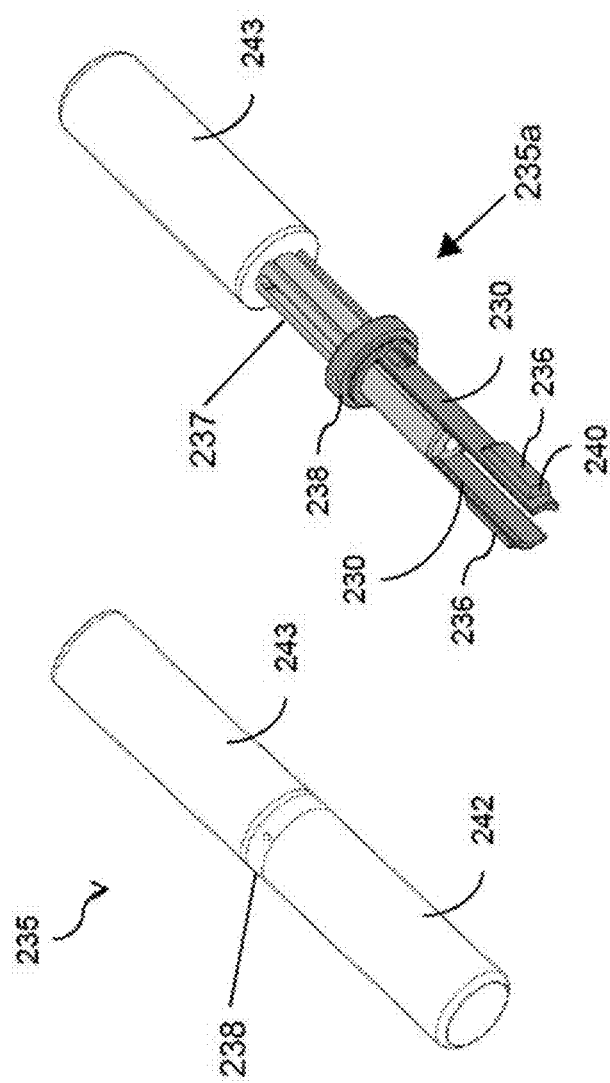
FIG. 5C
FIG. 5B
FIG. 5A

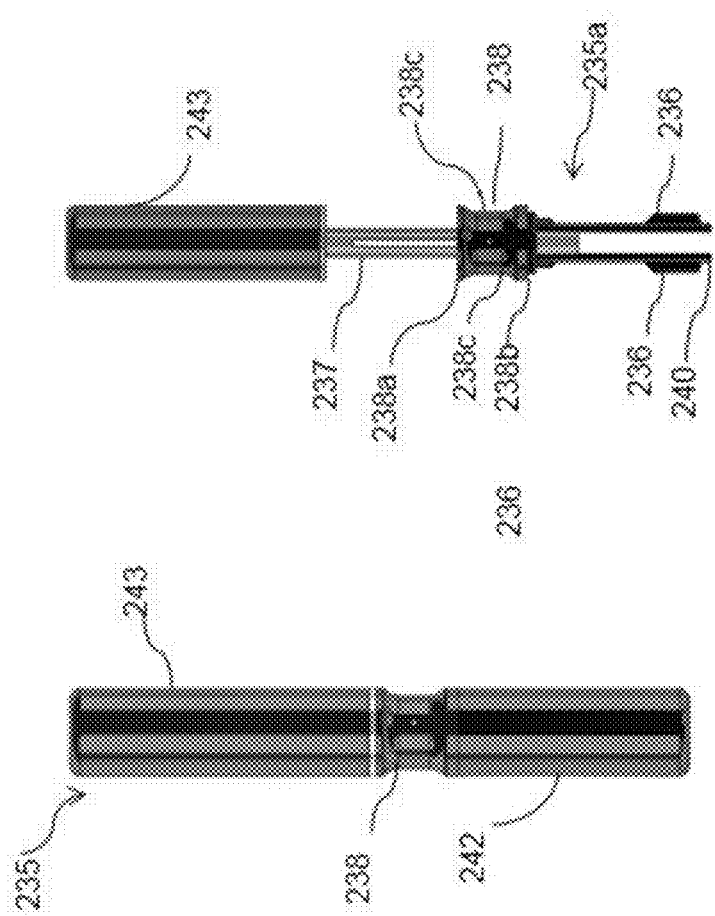

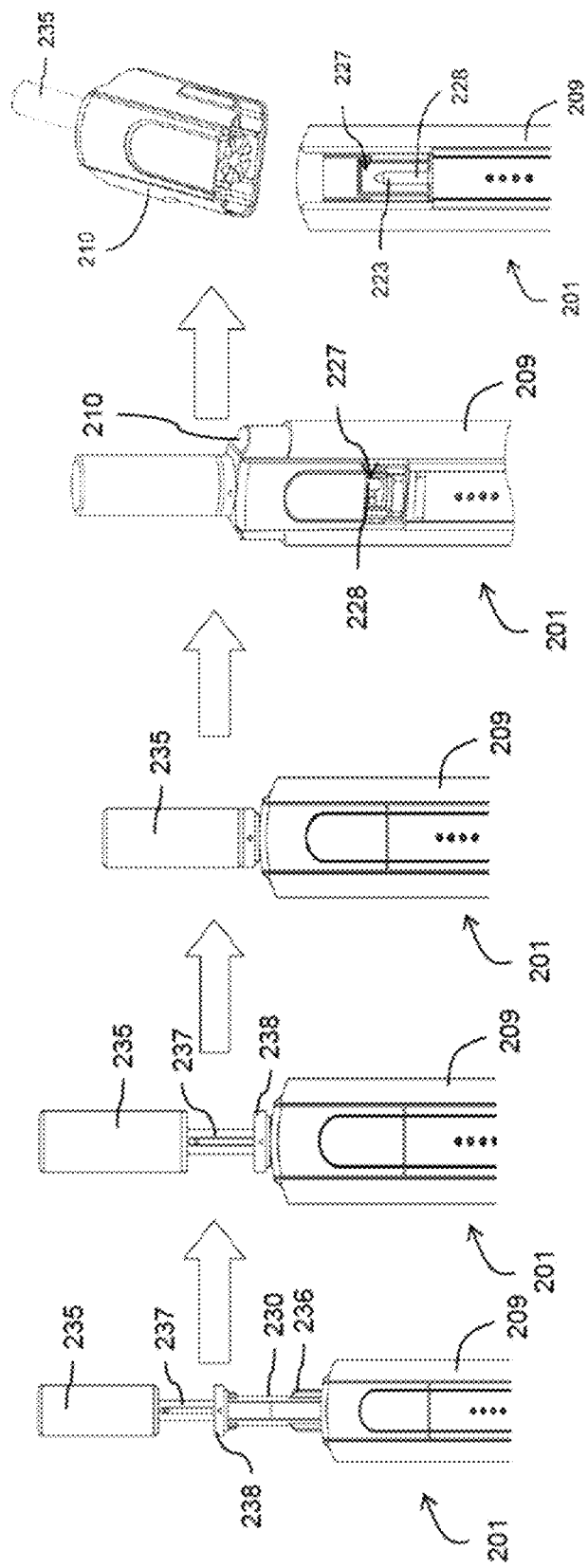

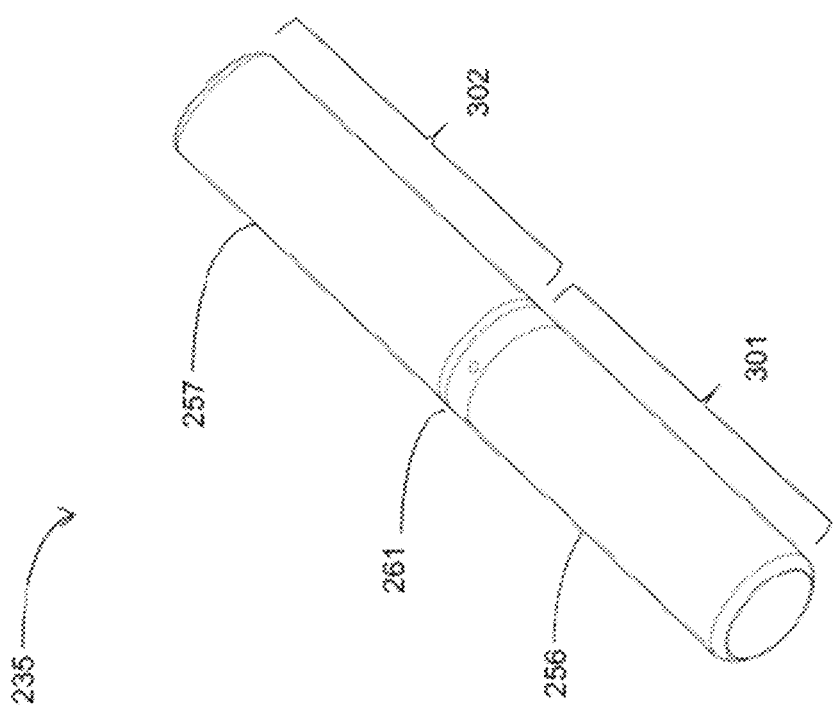

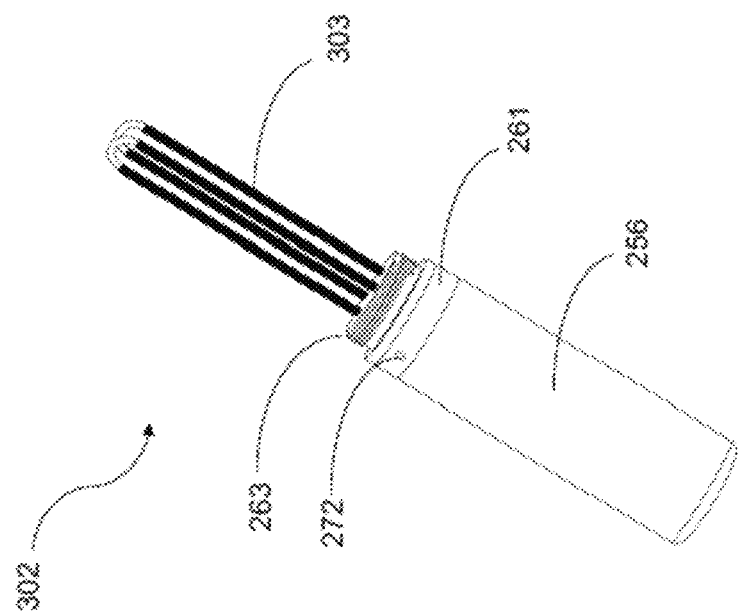
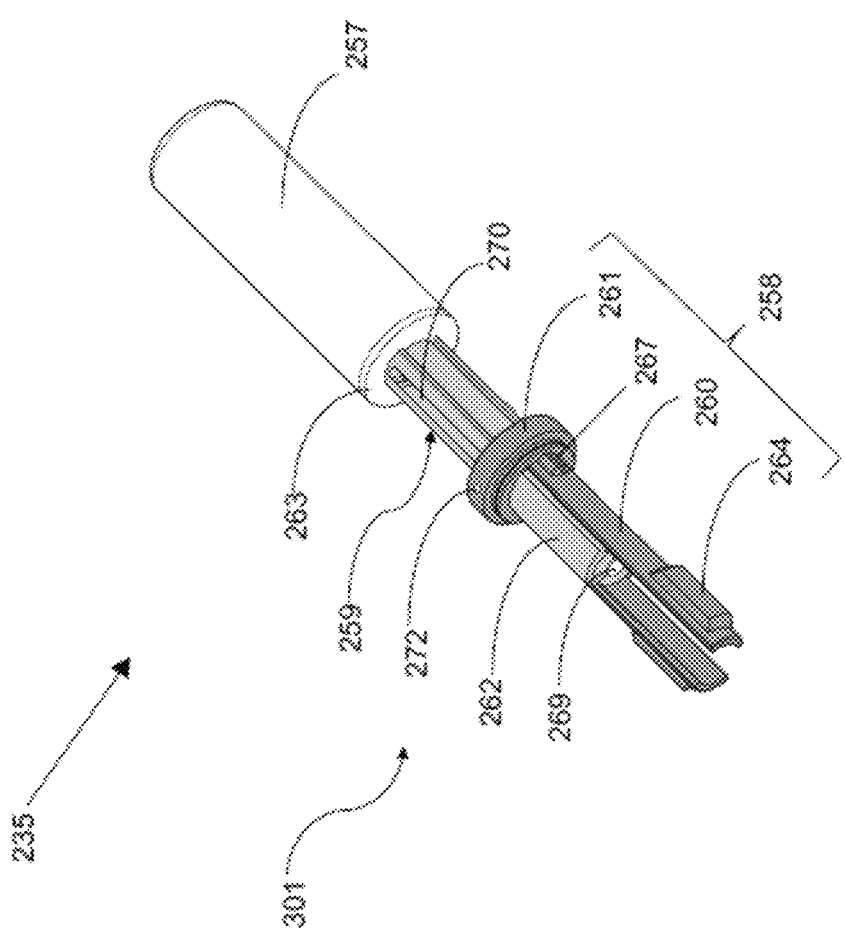
Fig. 10D
Fig. 10C

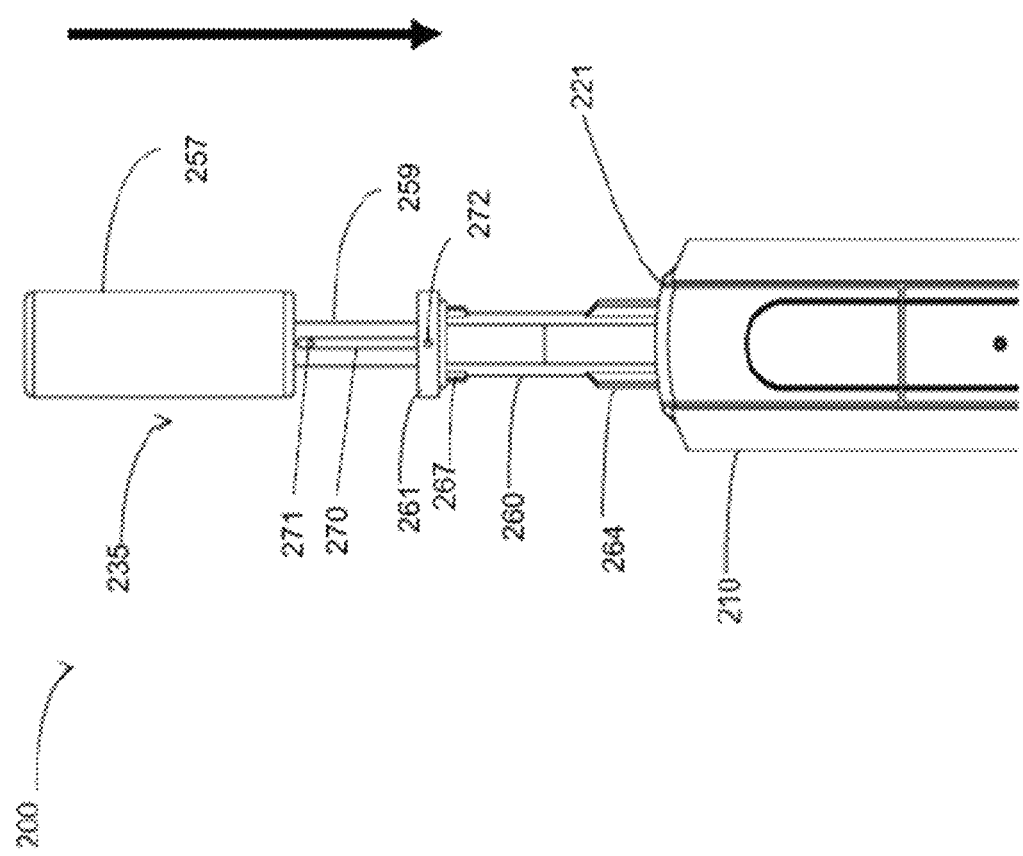

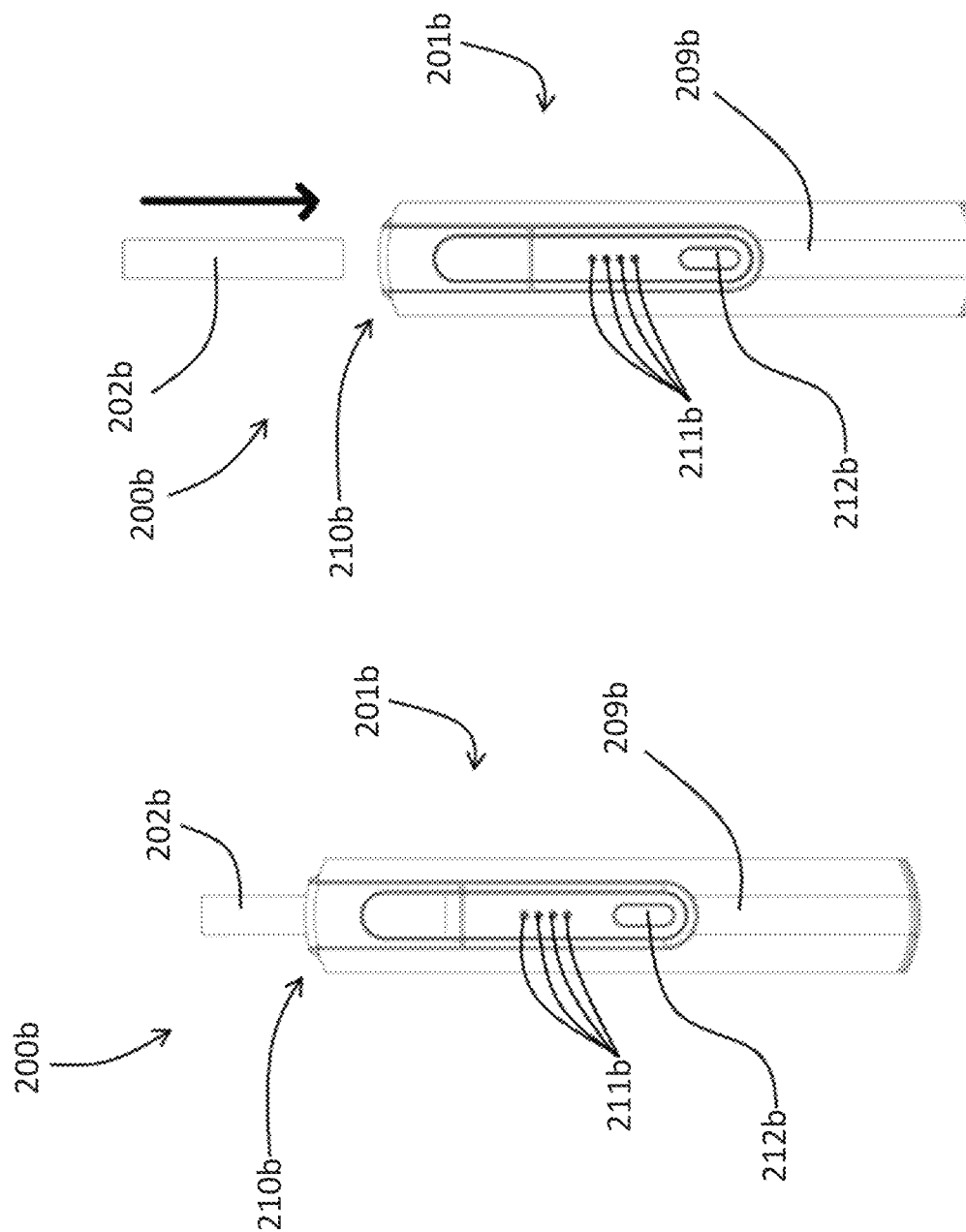

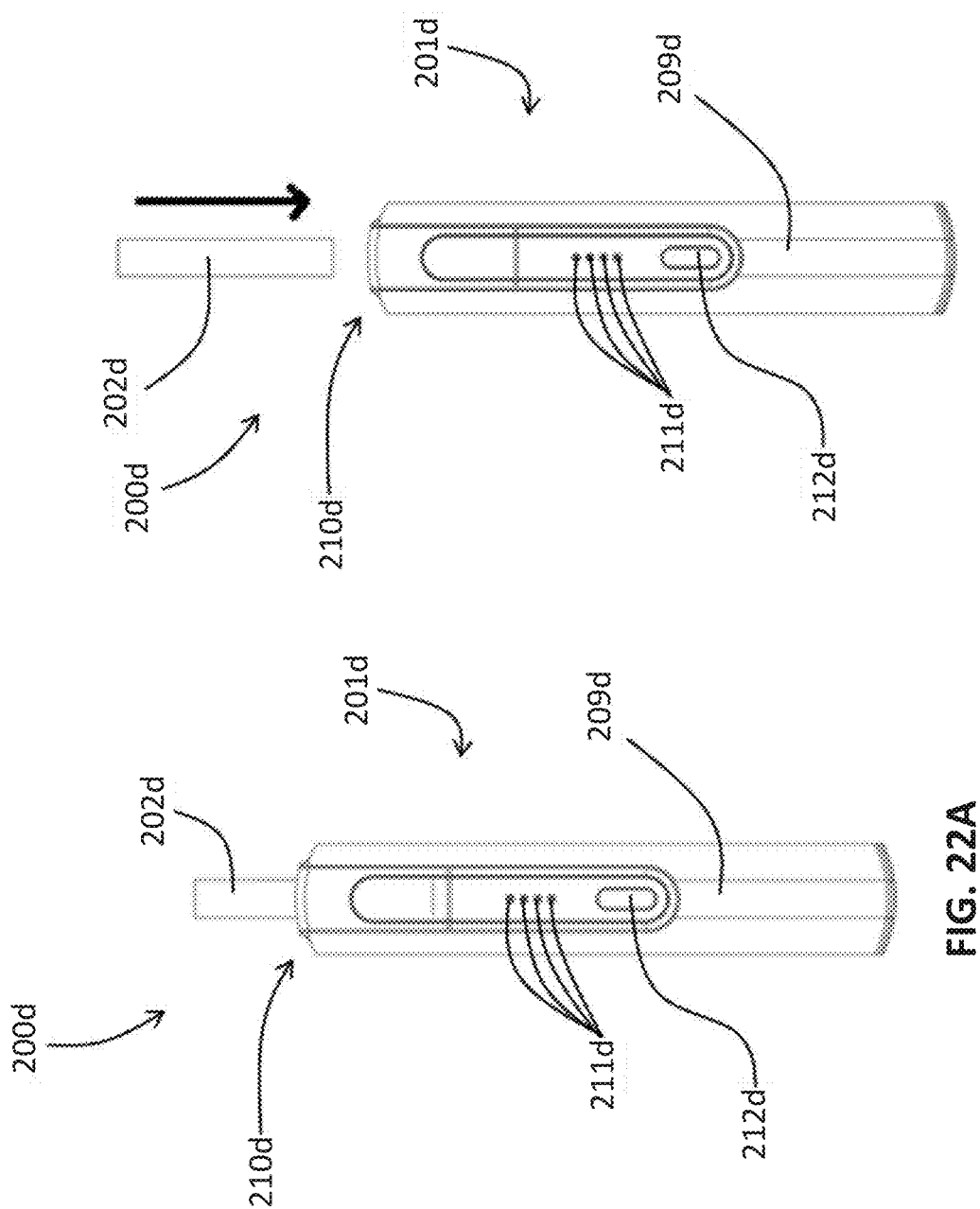

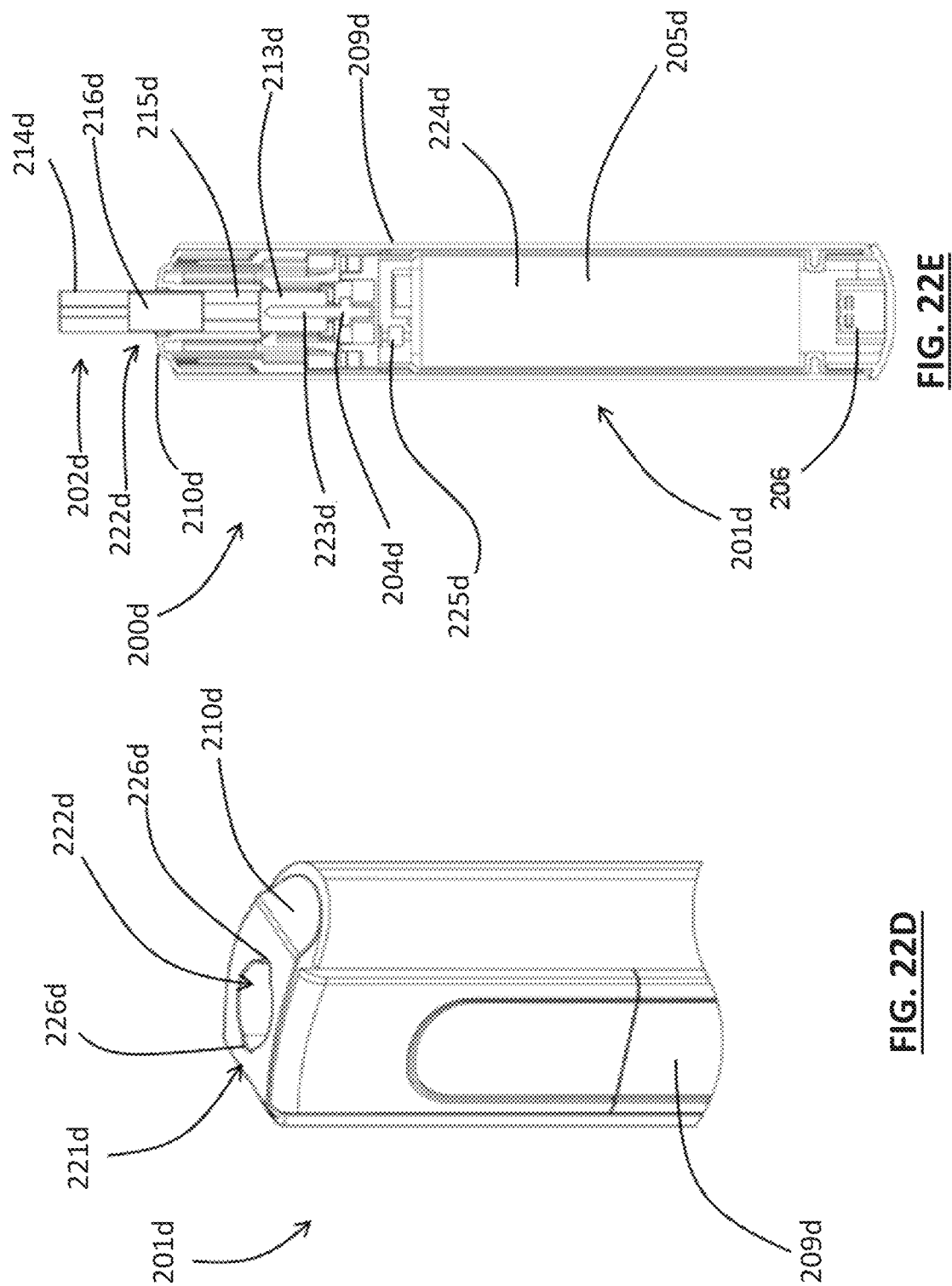

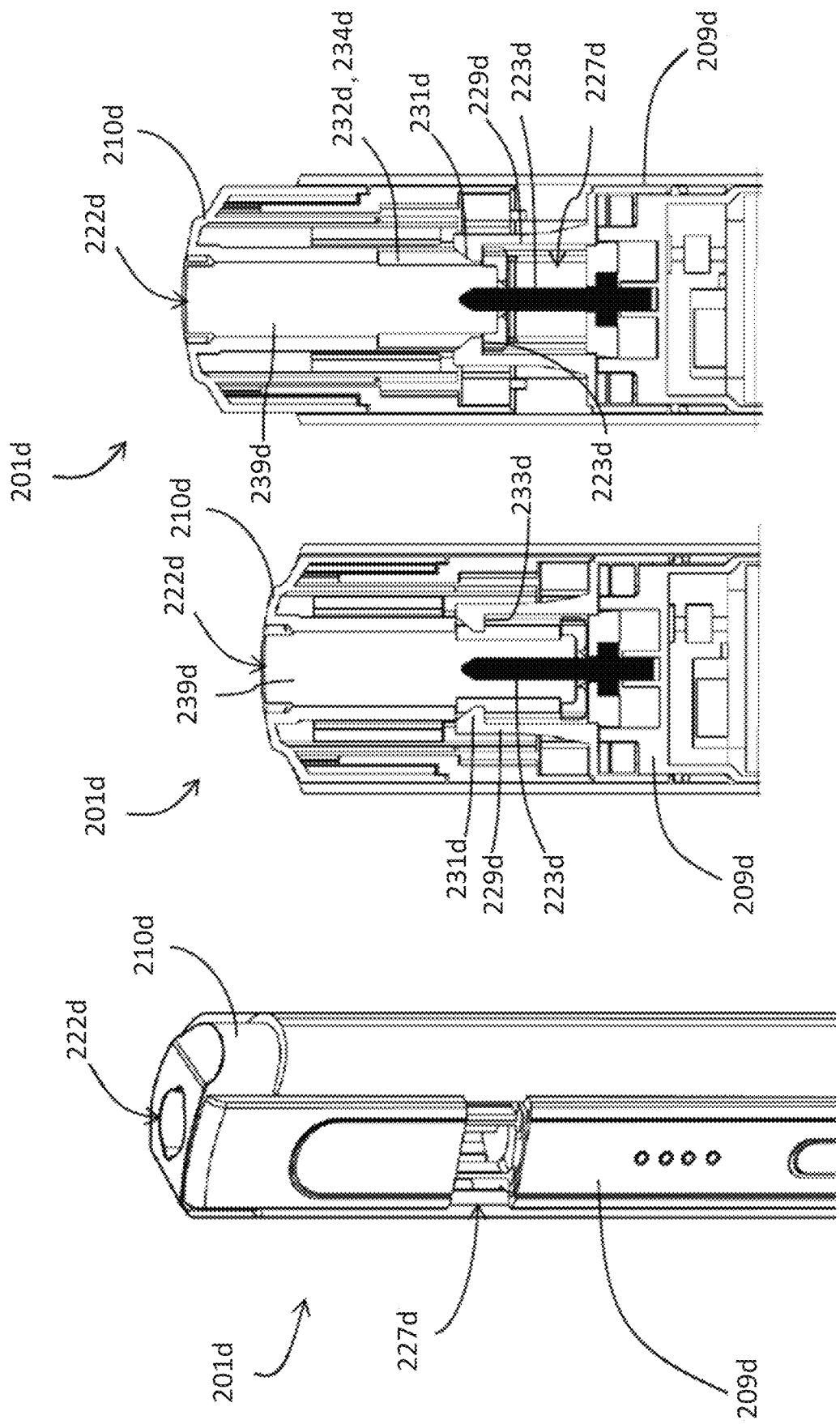

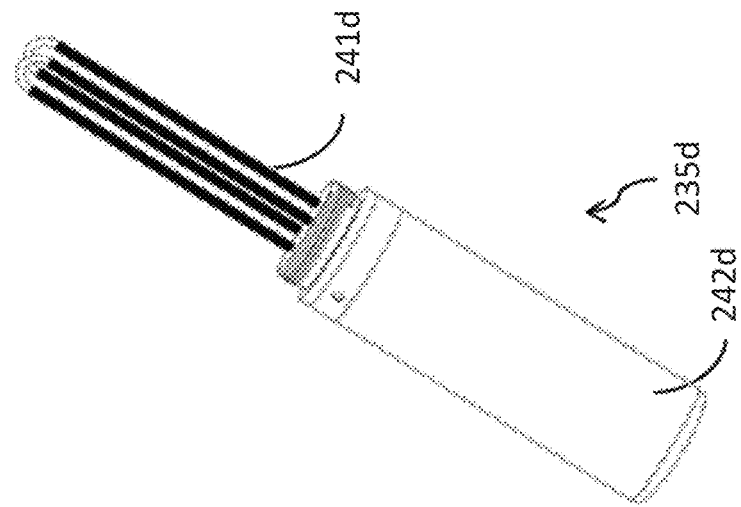
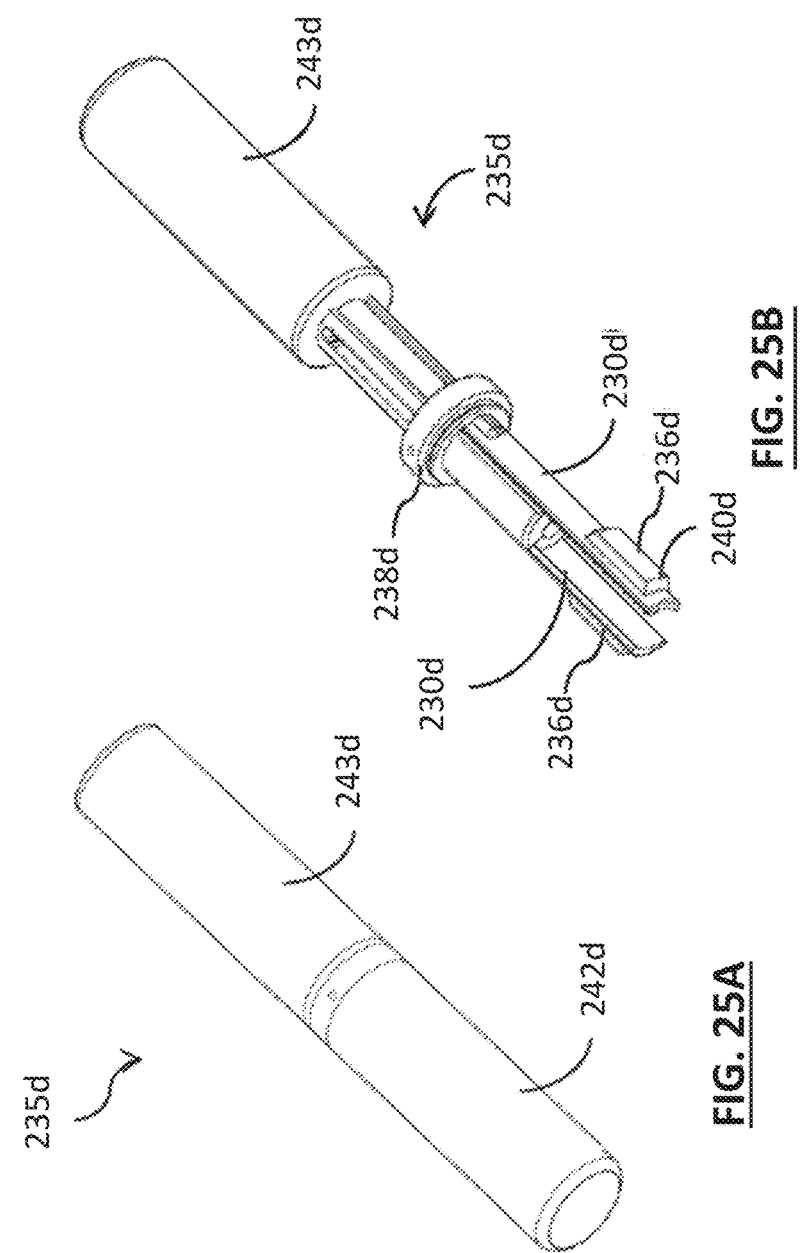

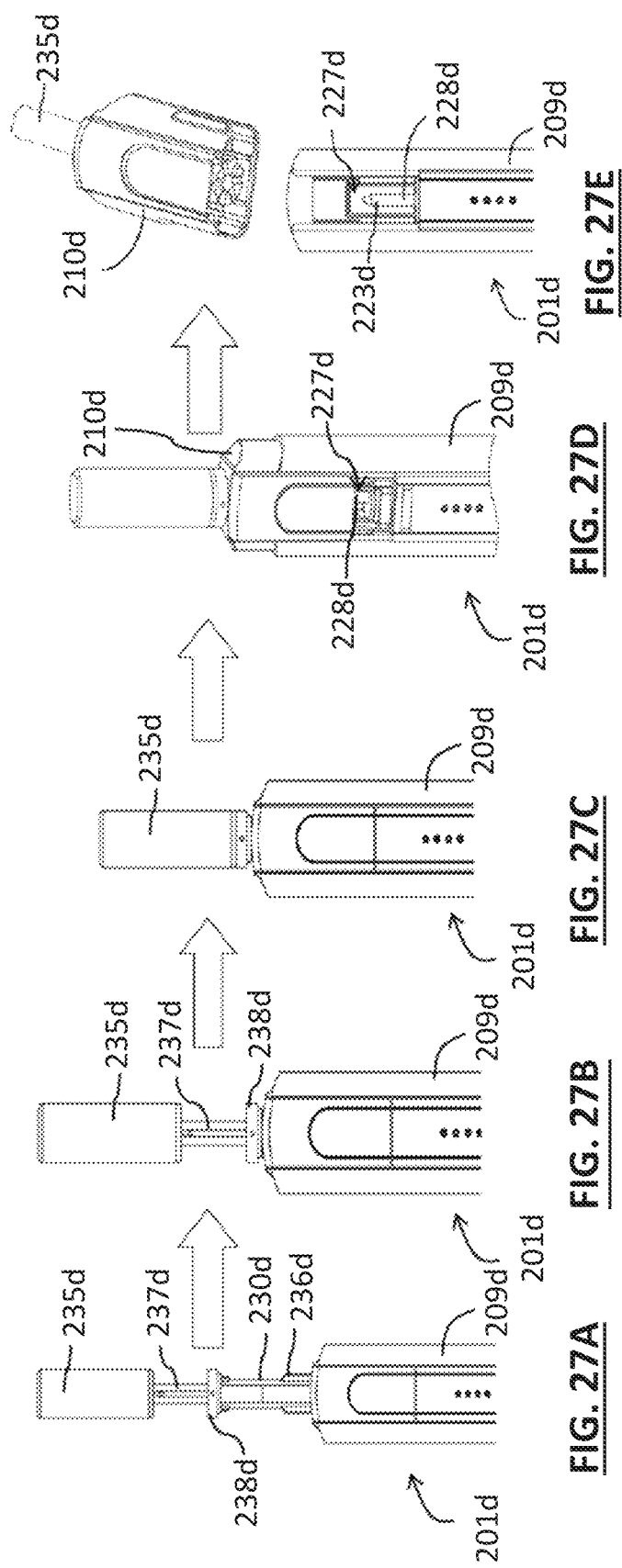

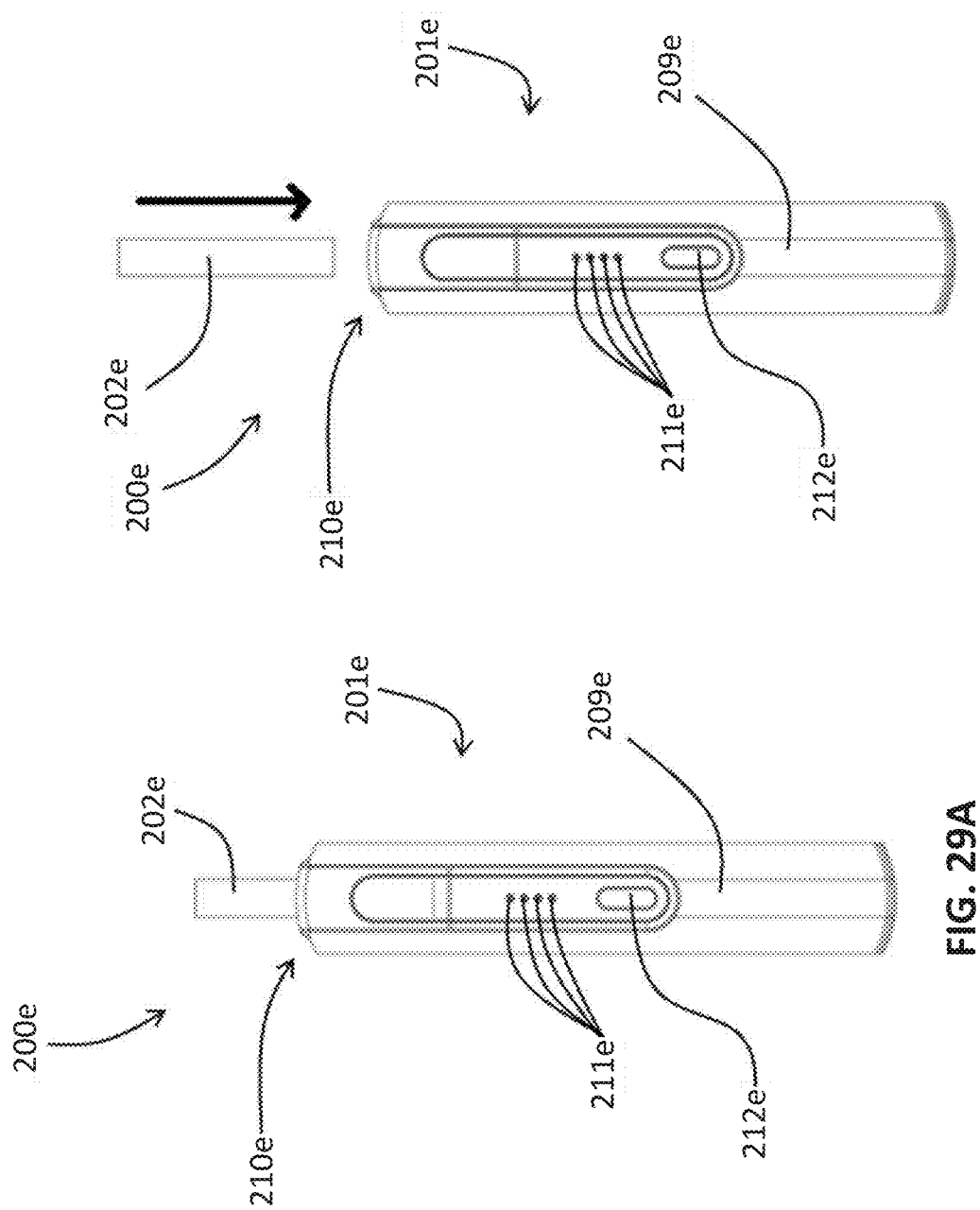

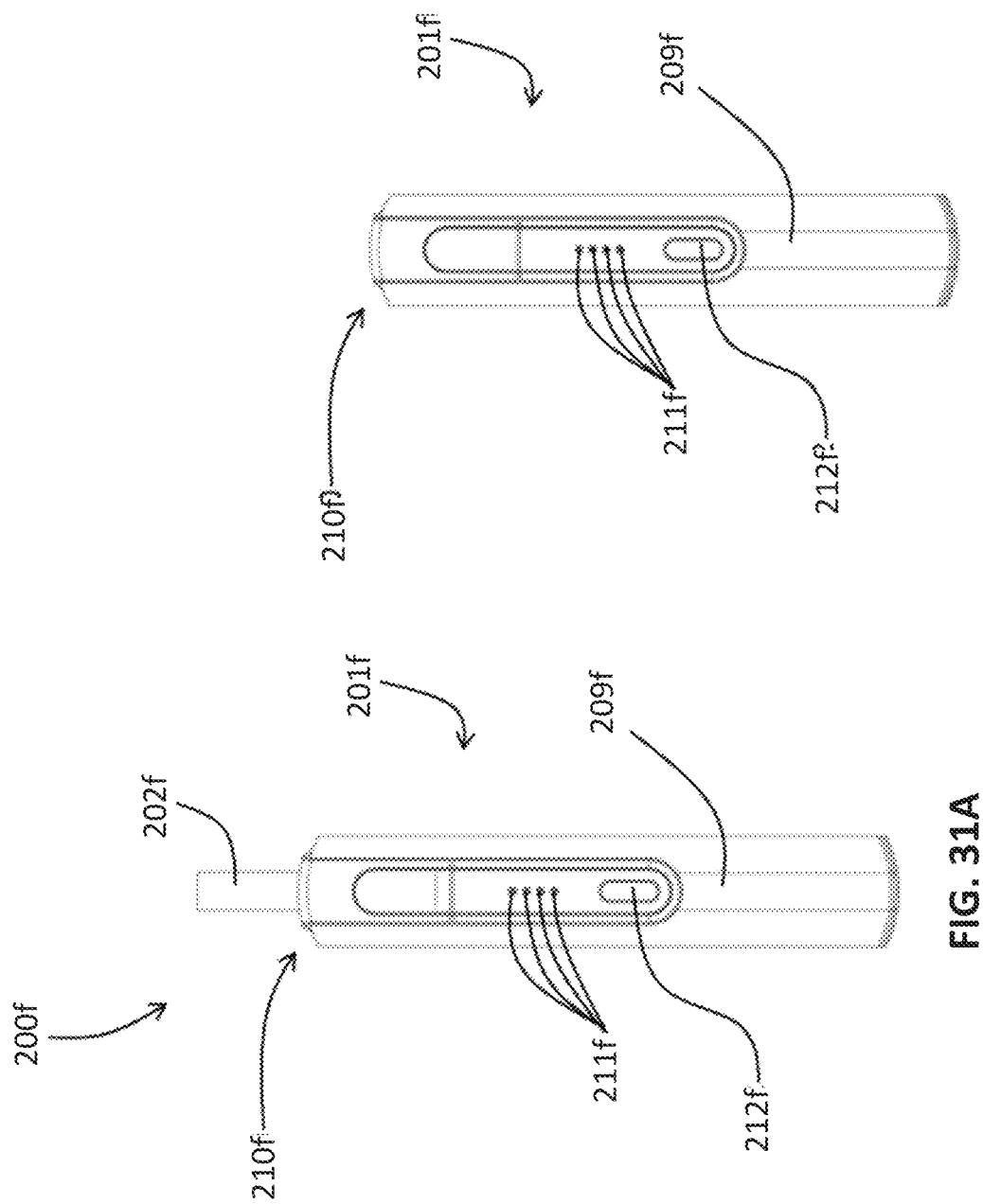

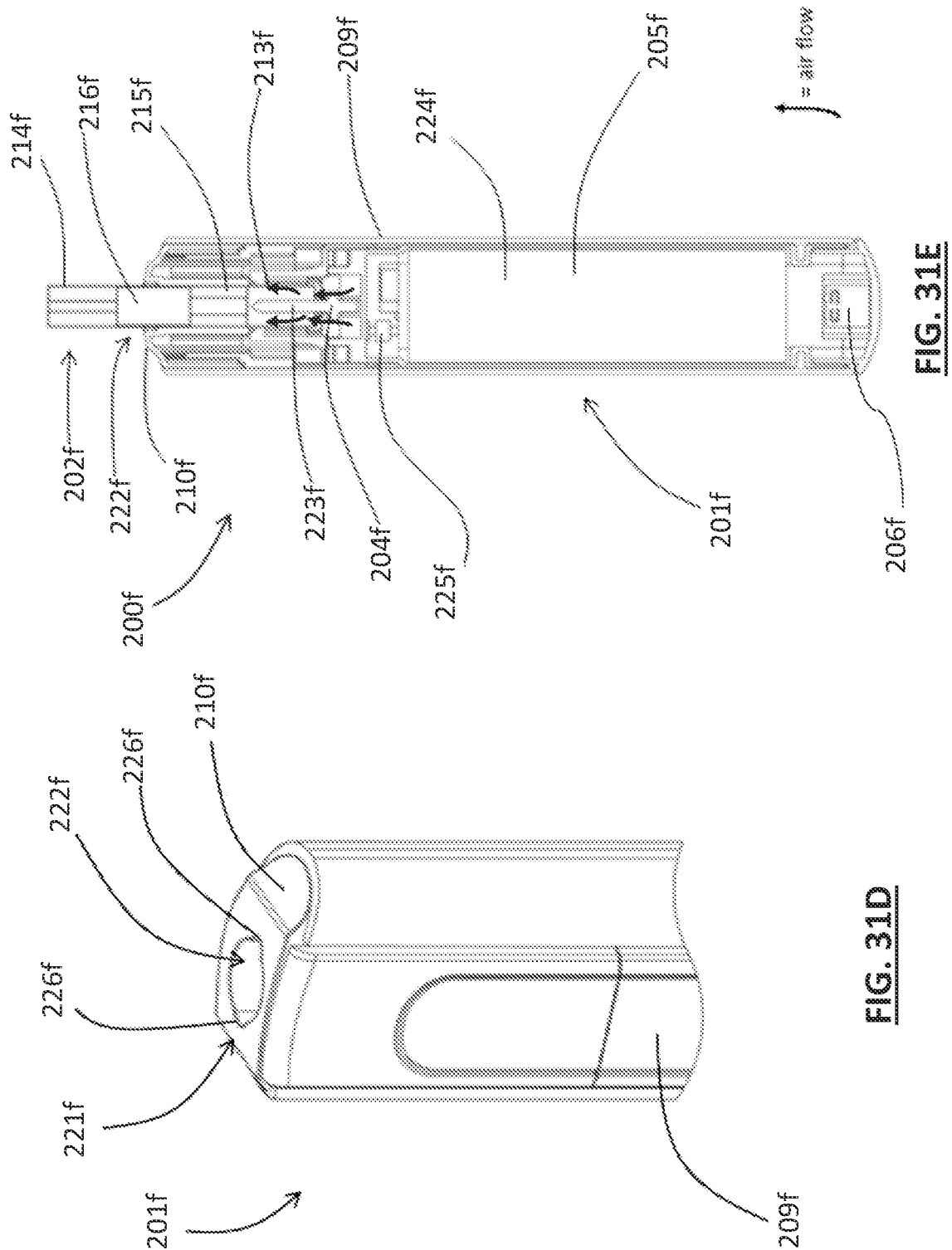

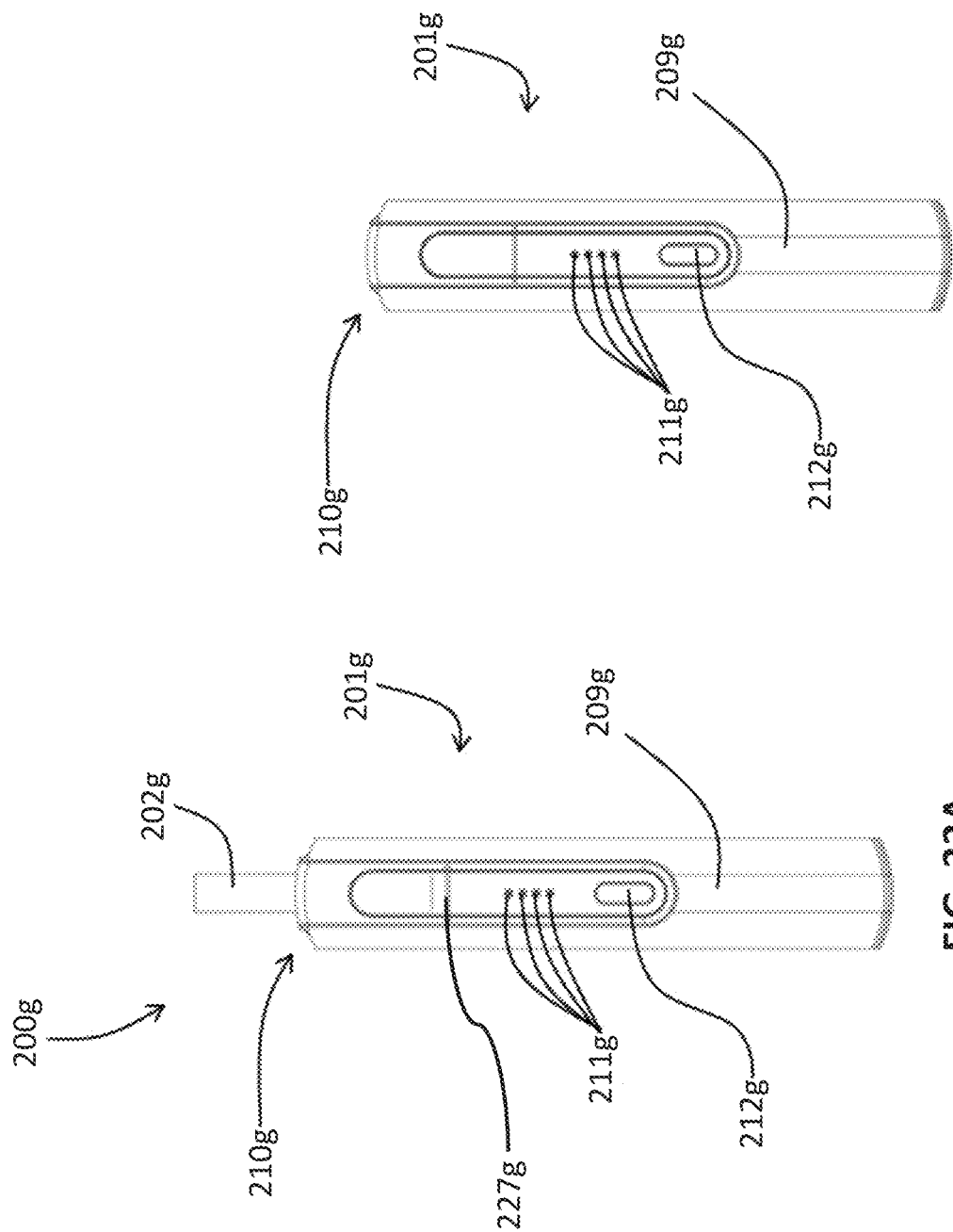

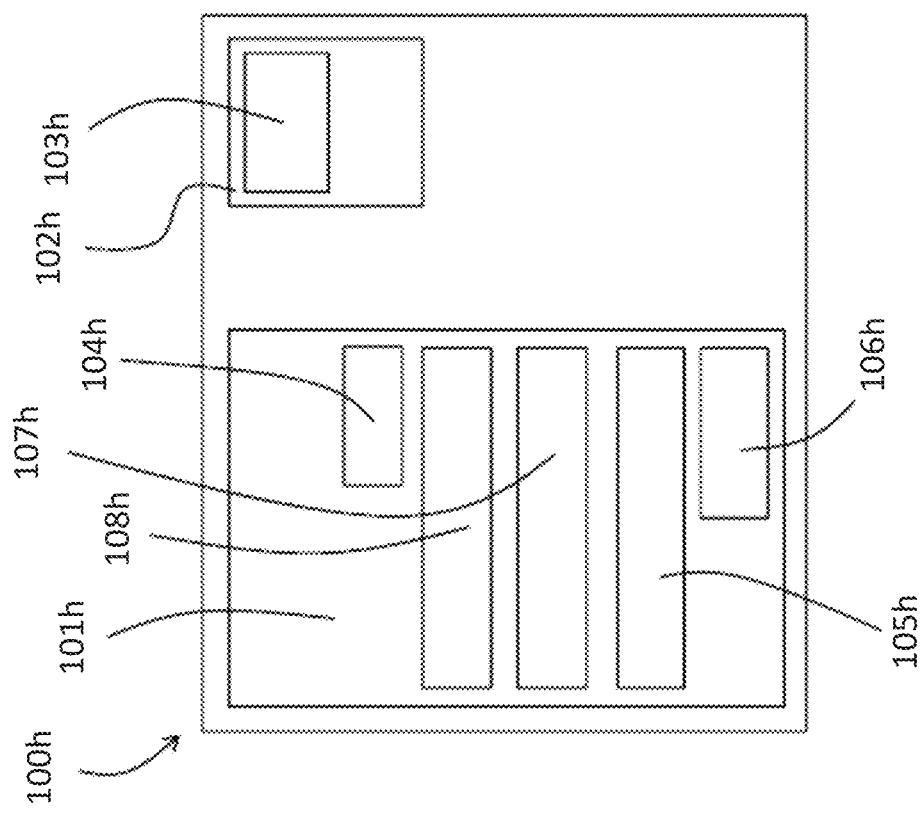
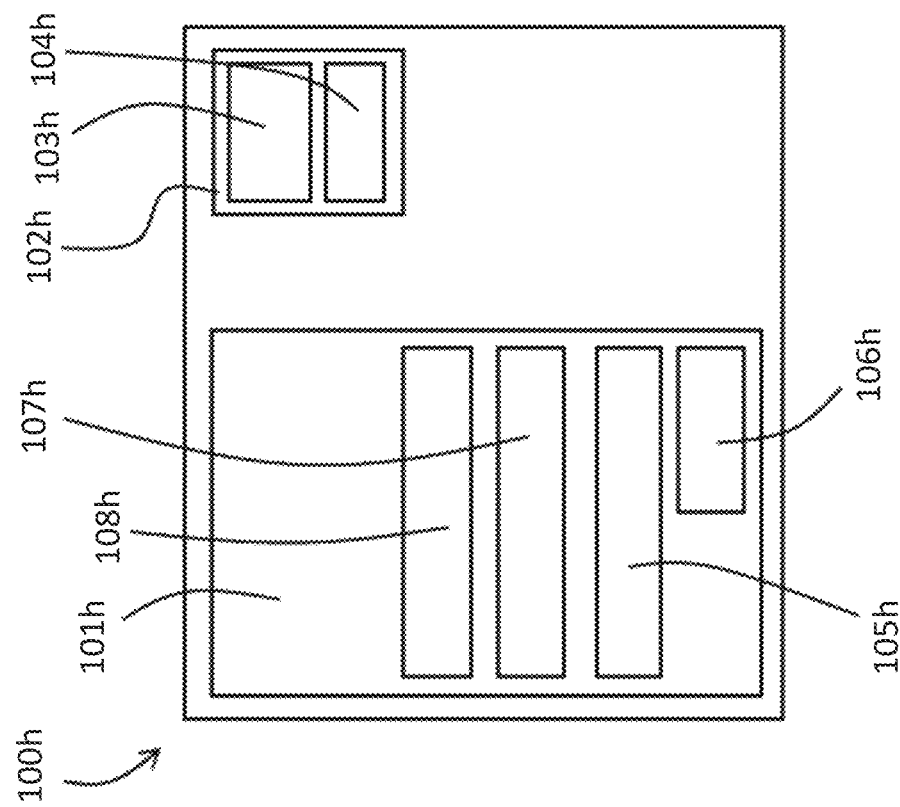

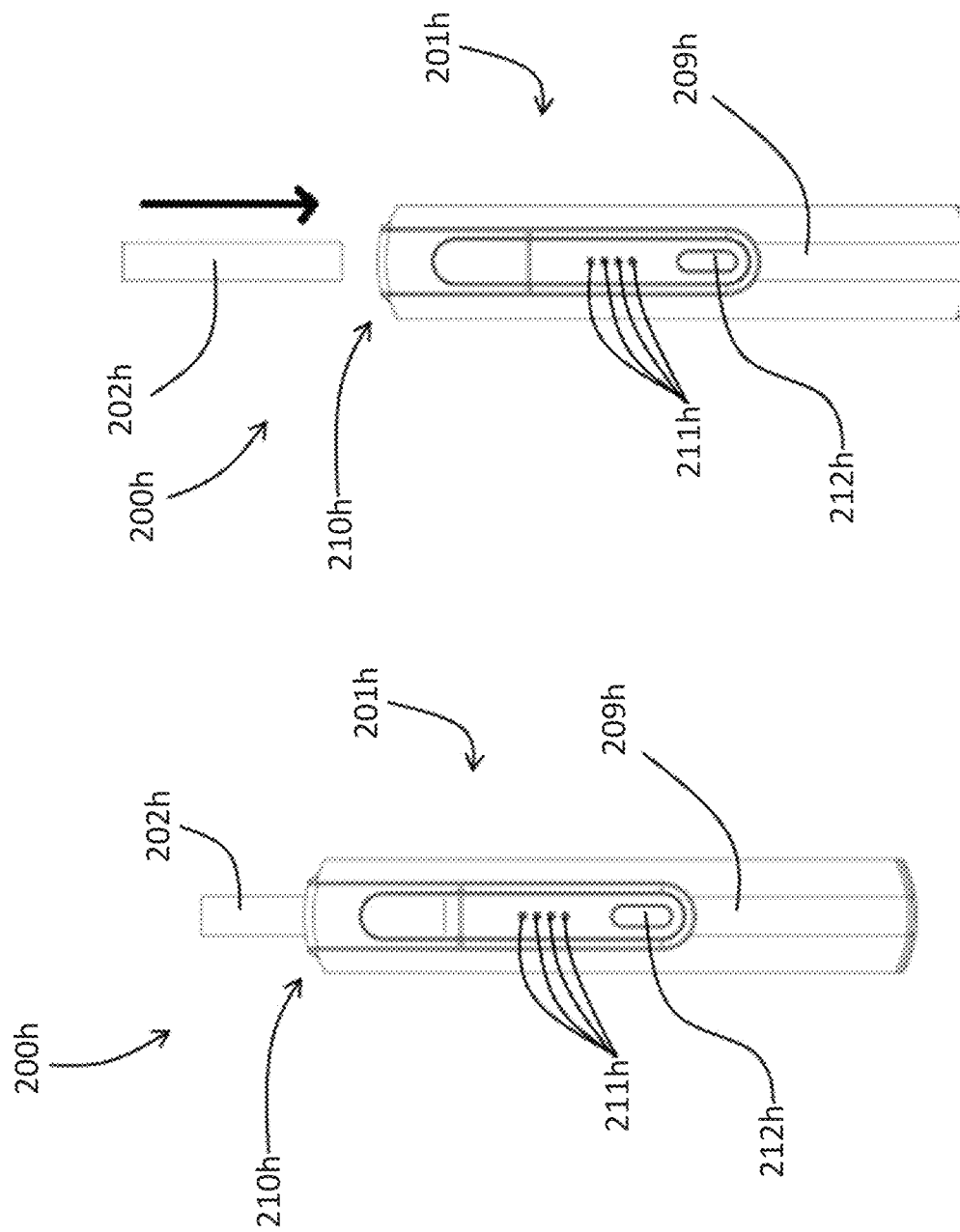

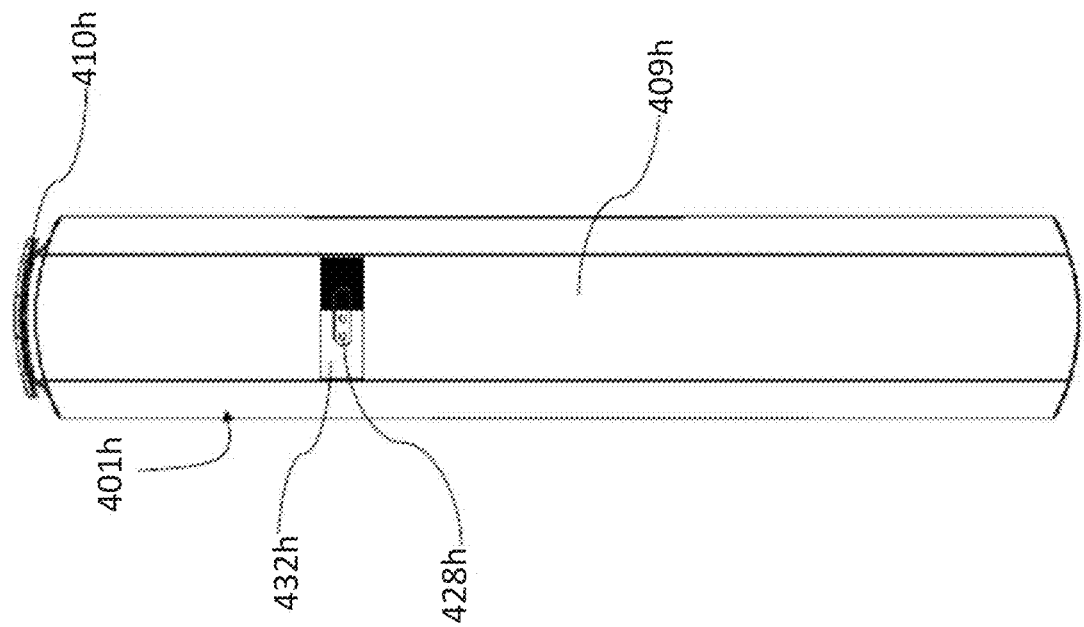
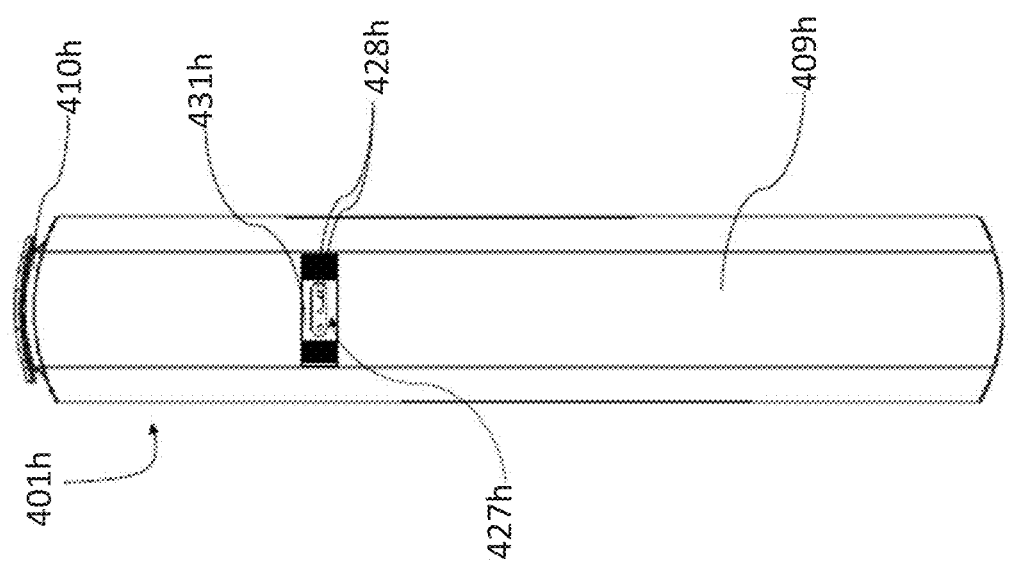

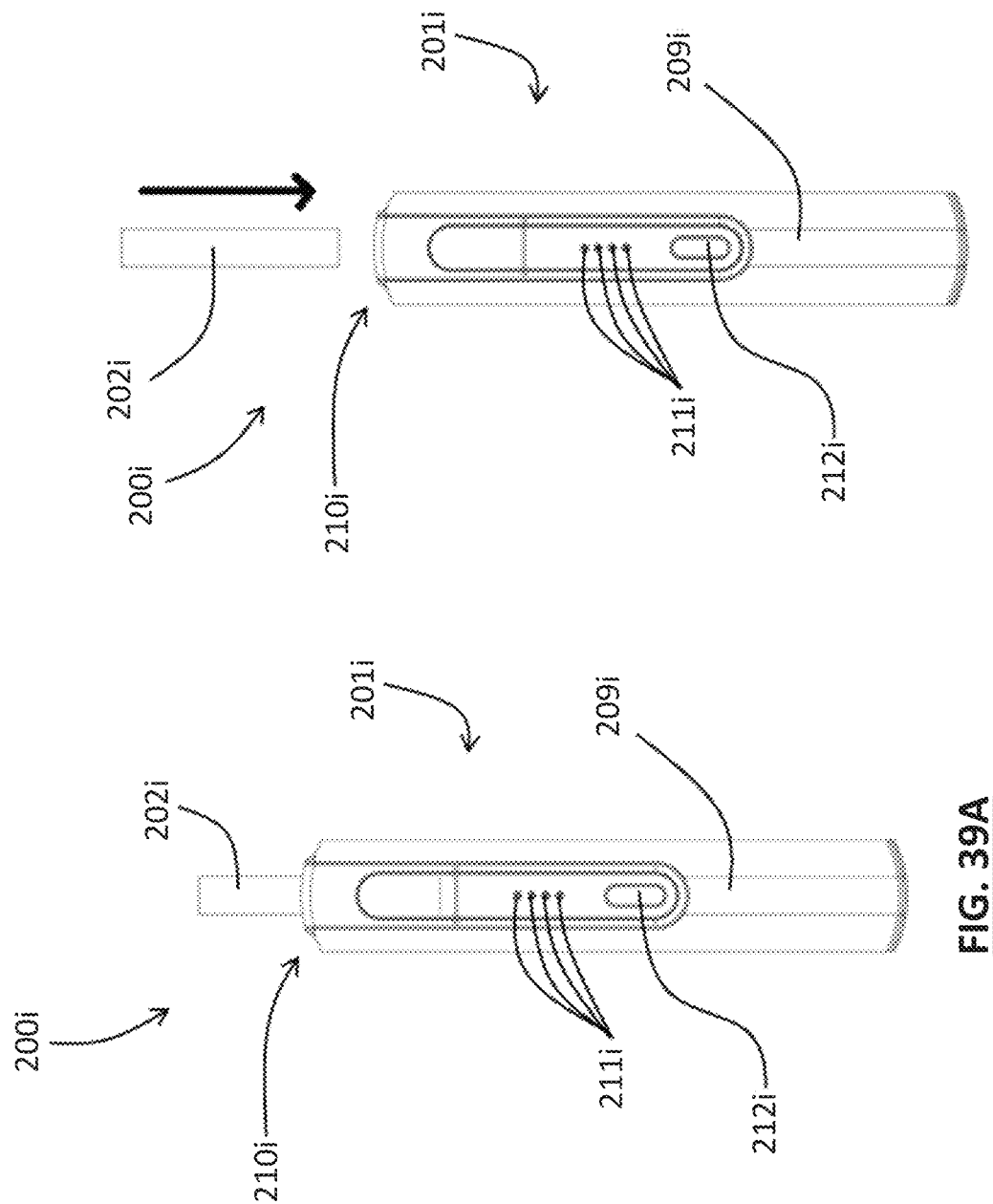

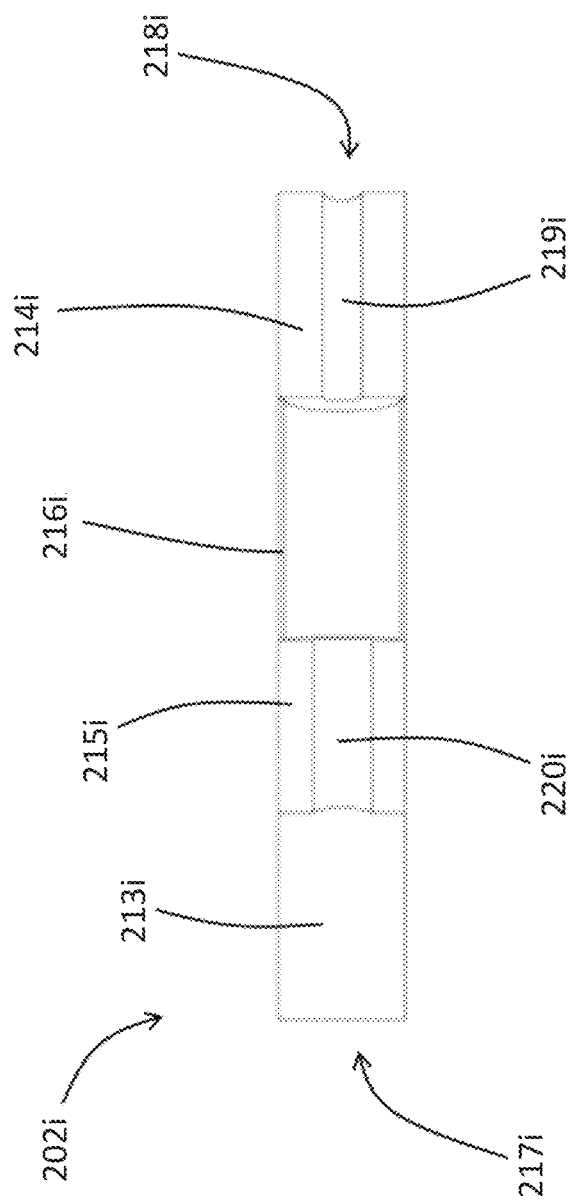

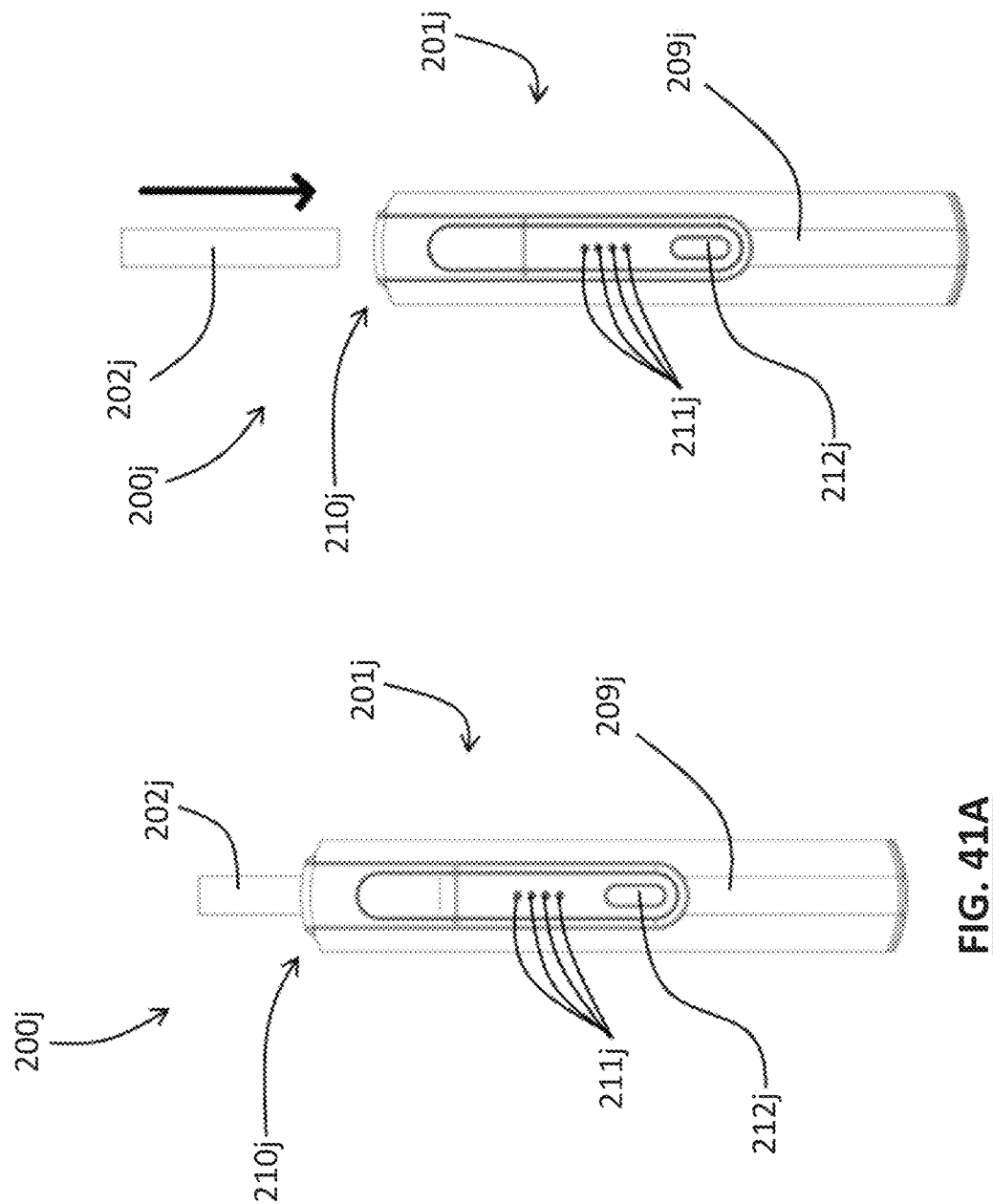

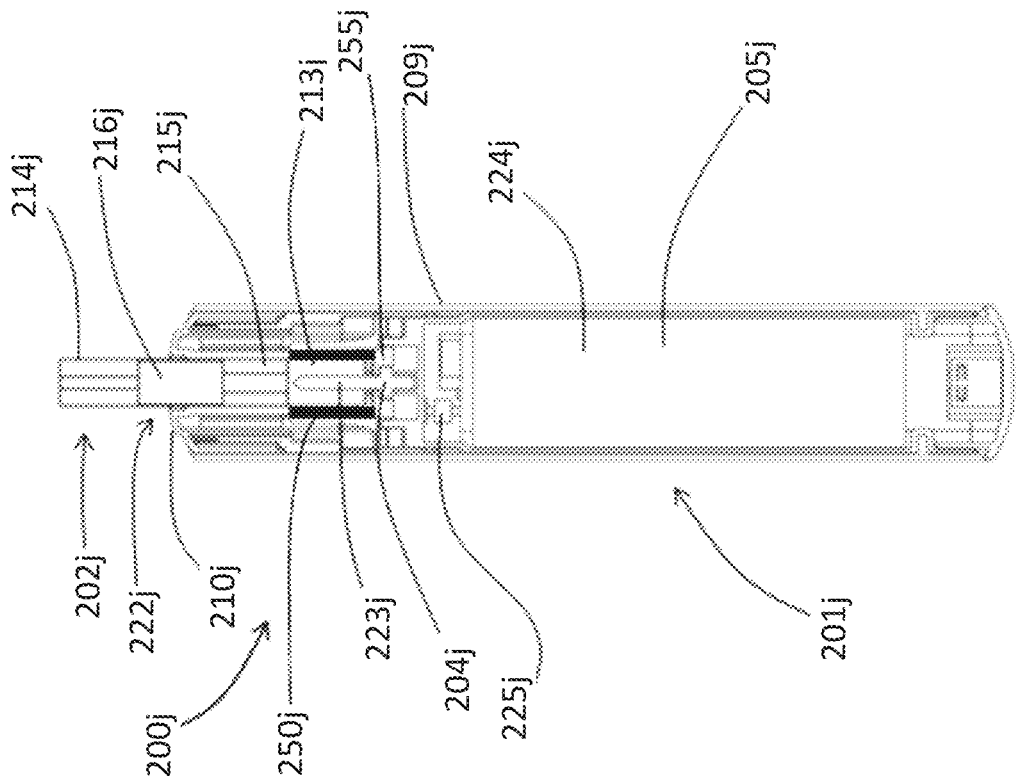
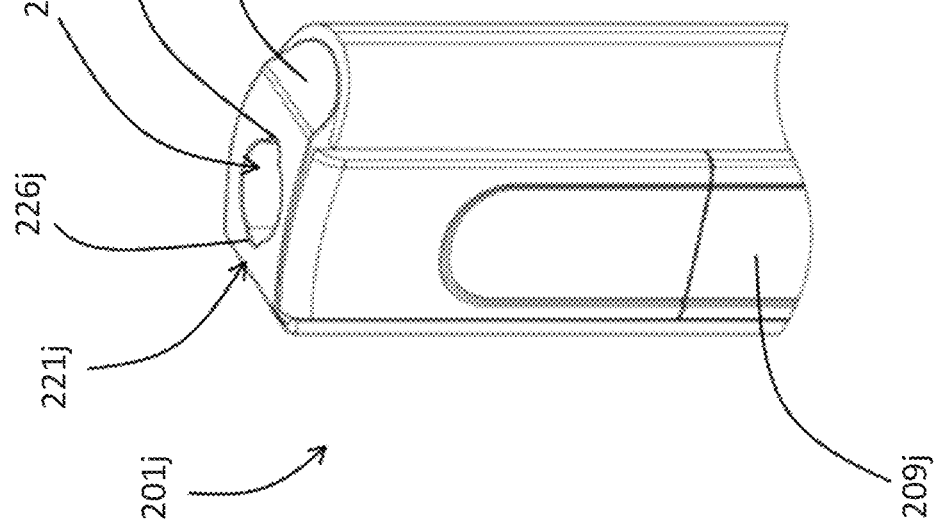

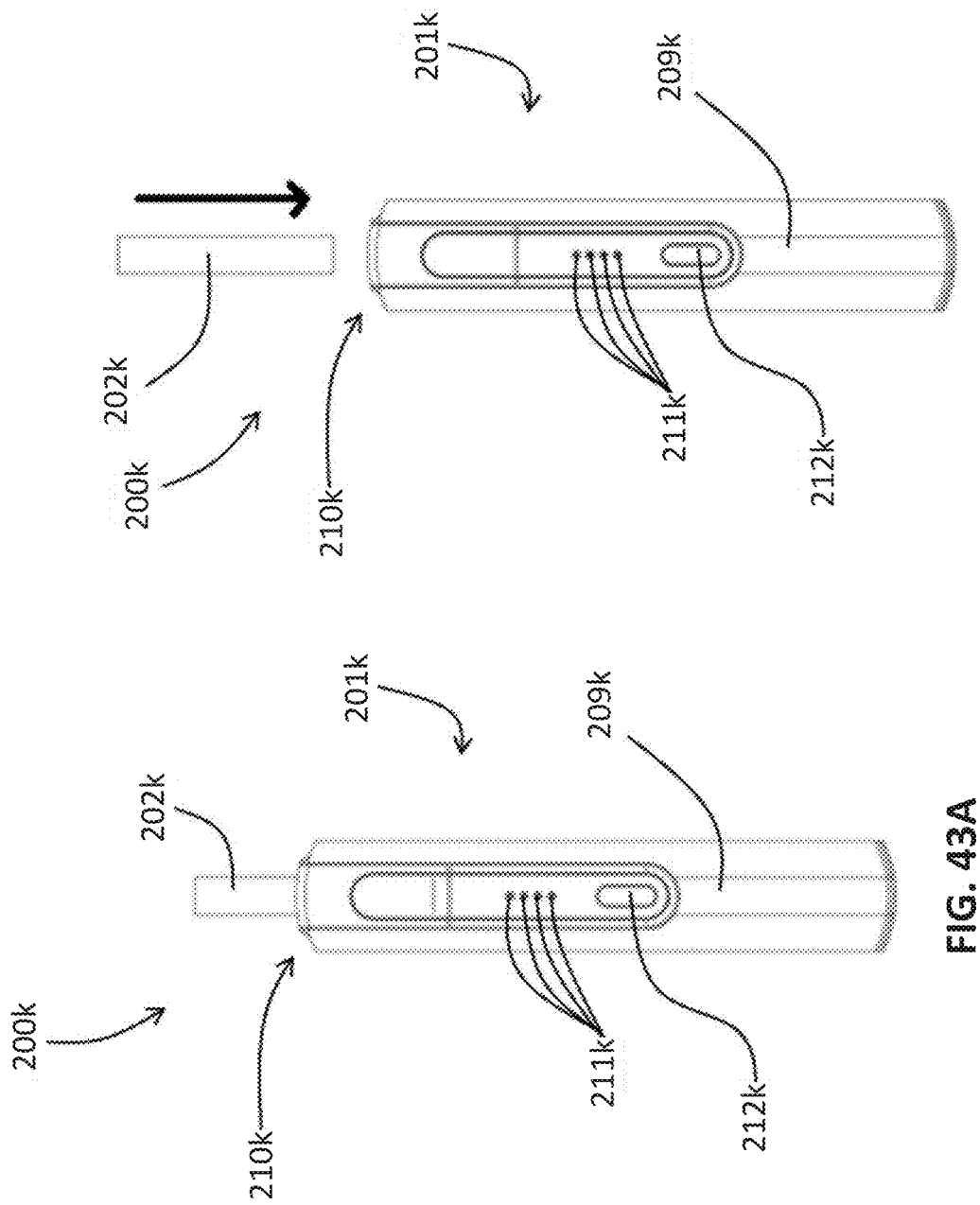

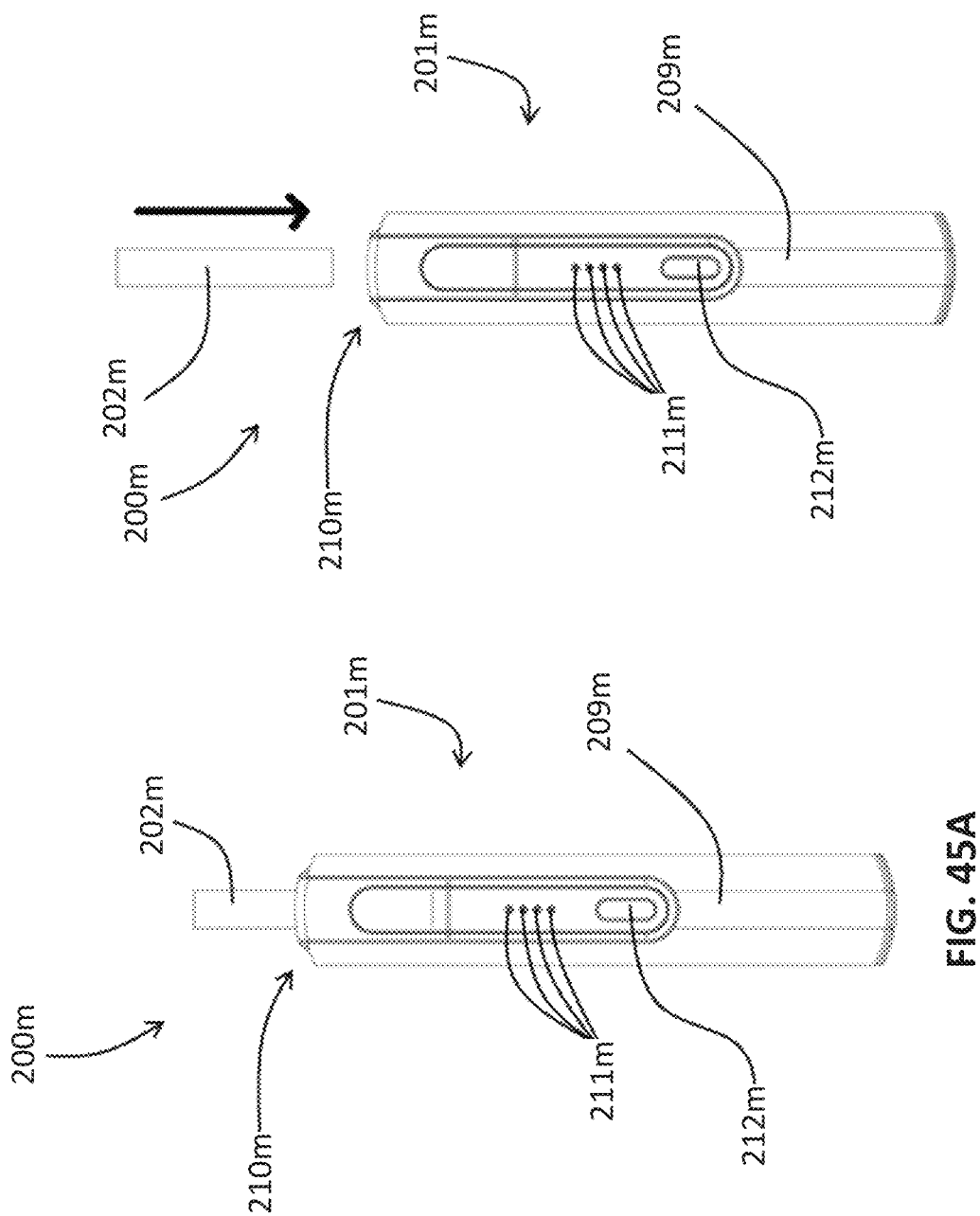

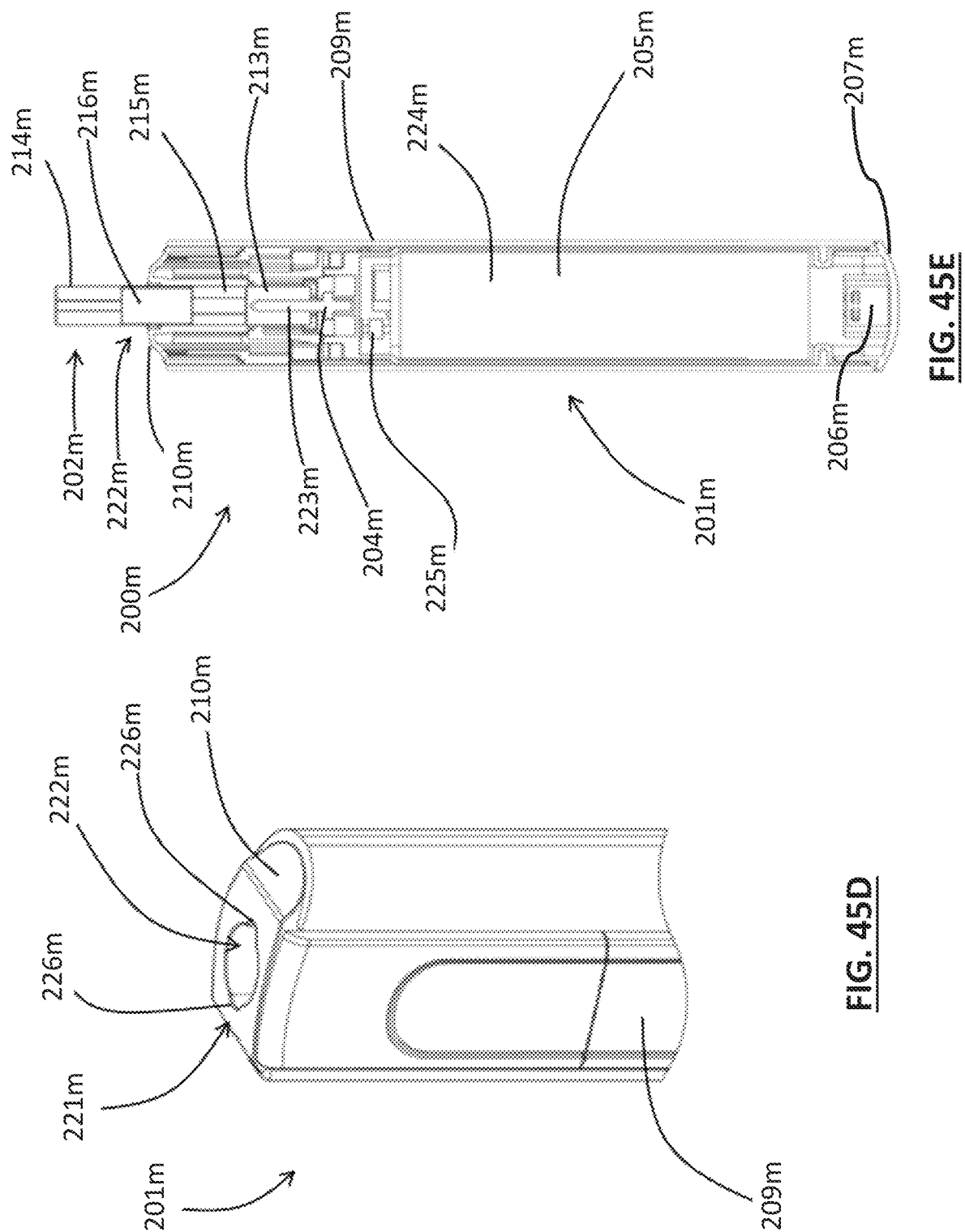

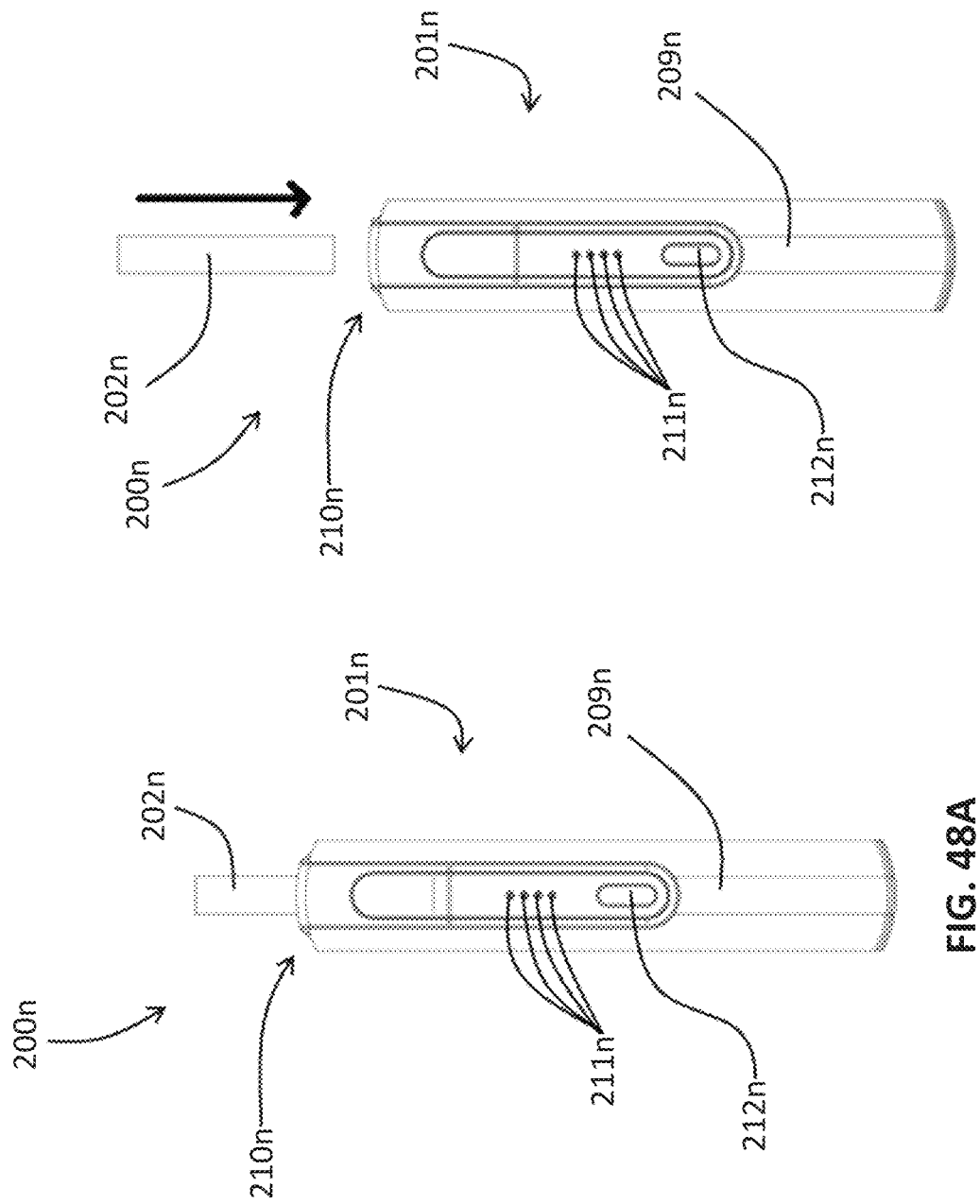

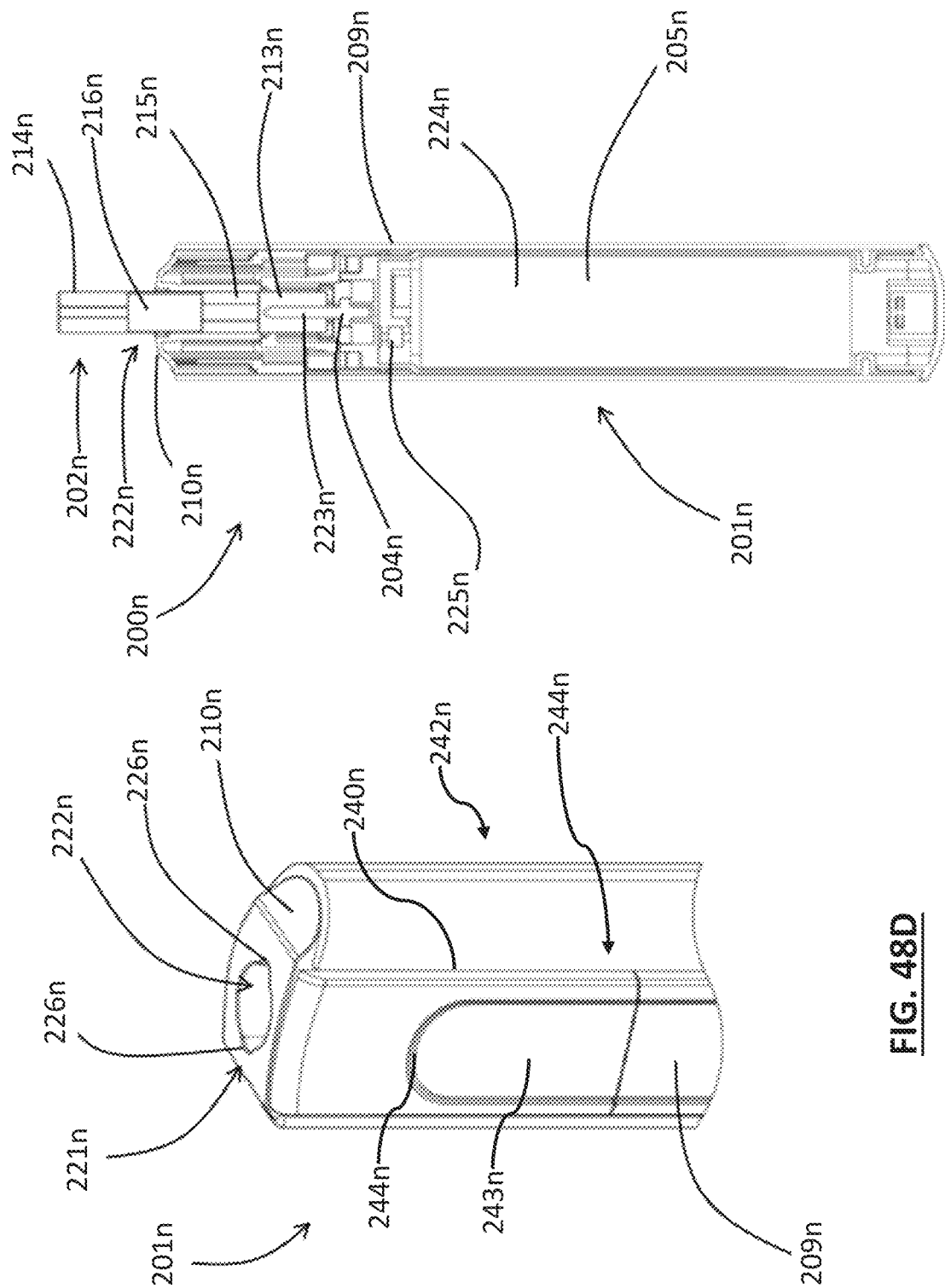

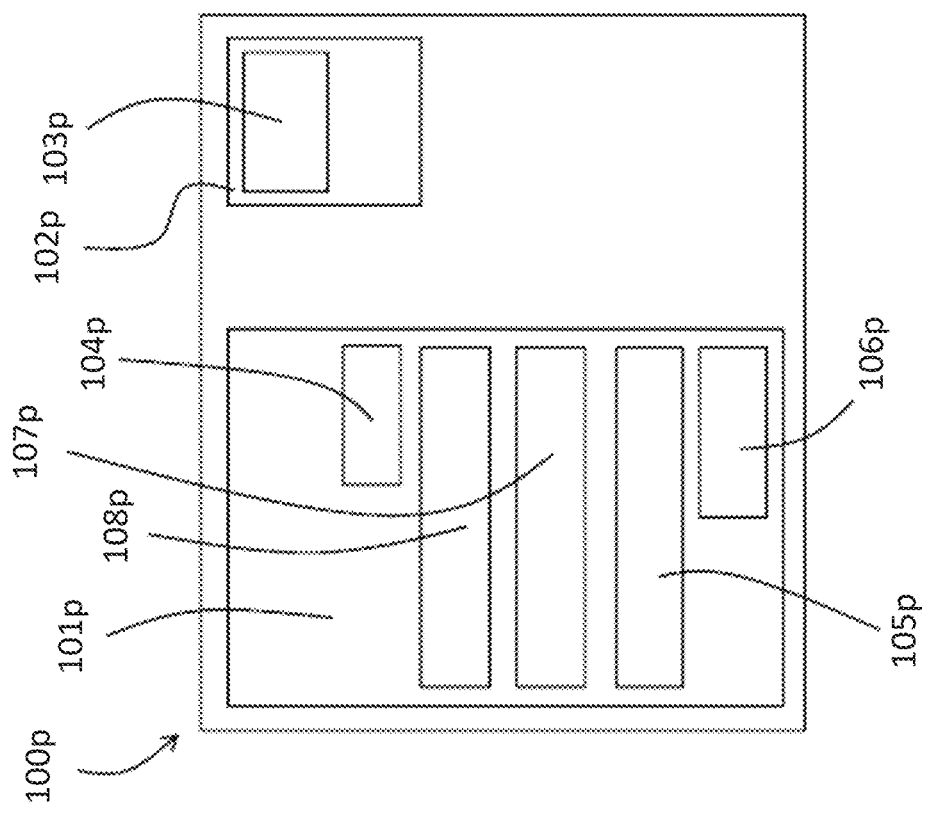
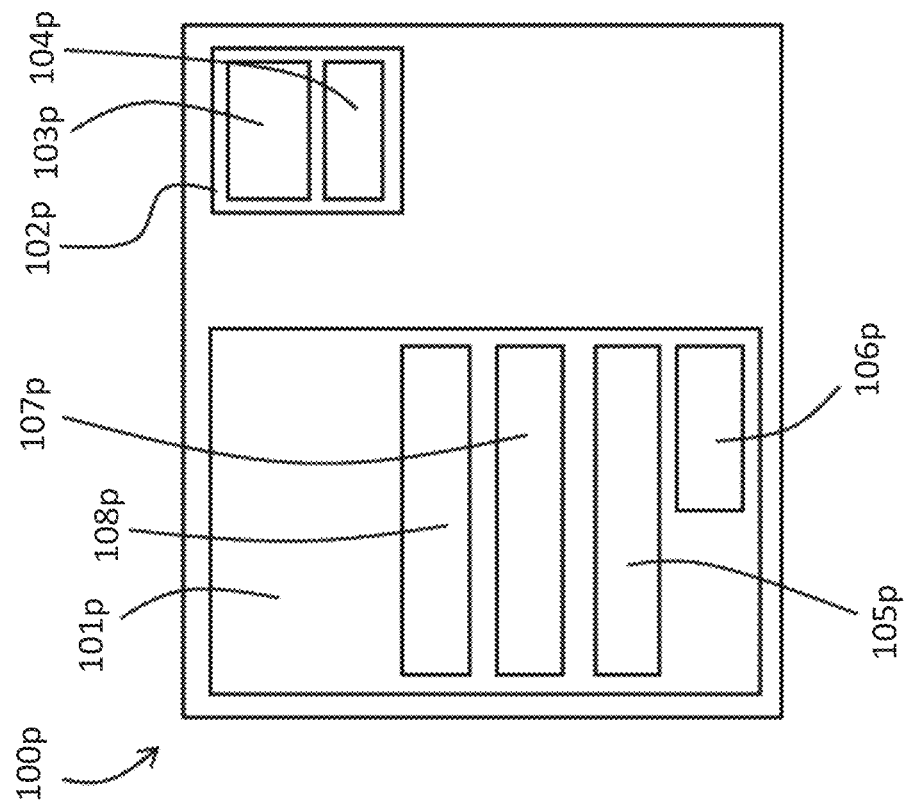

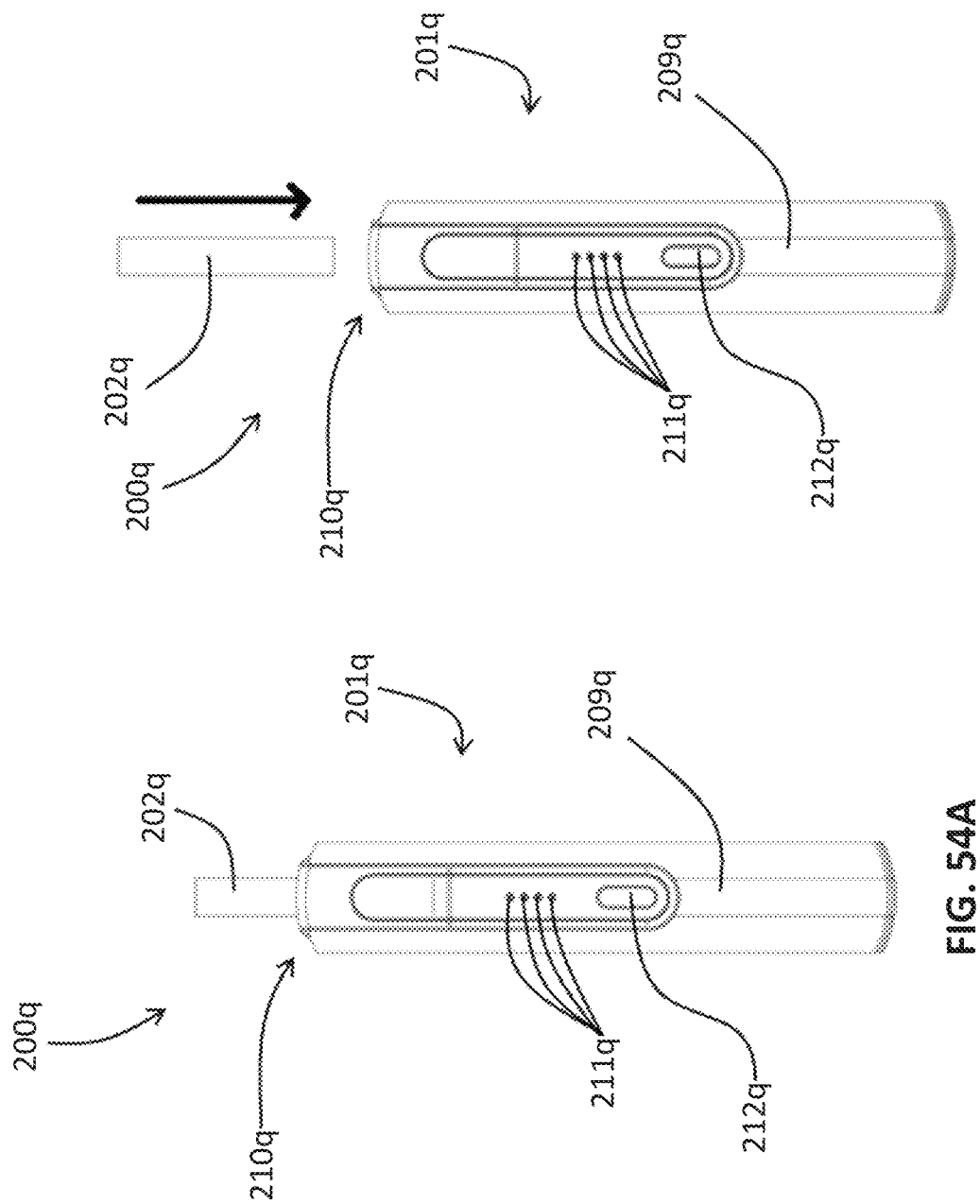

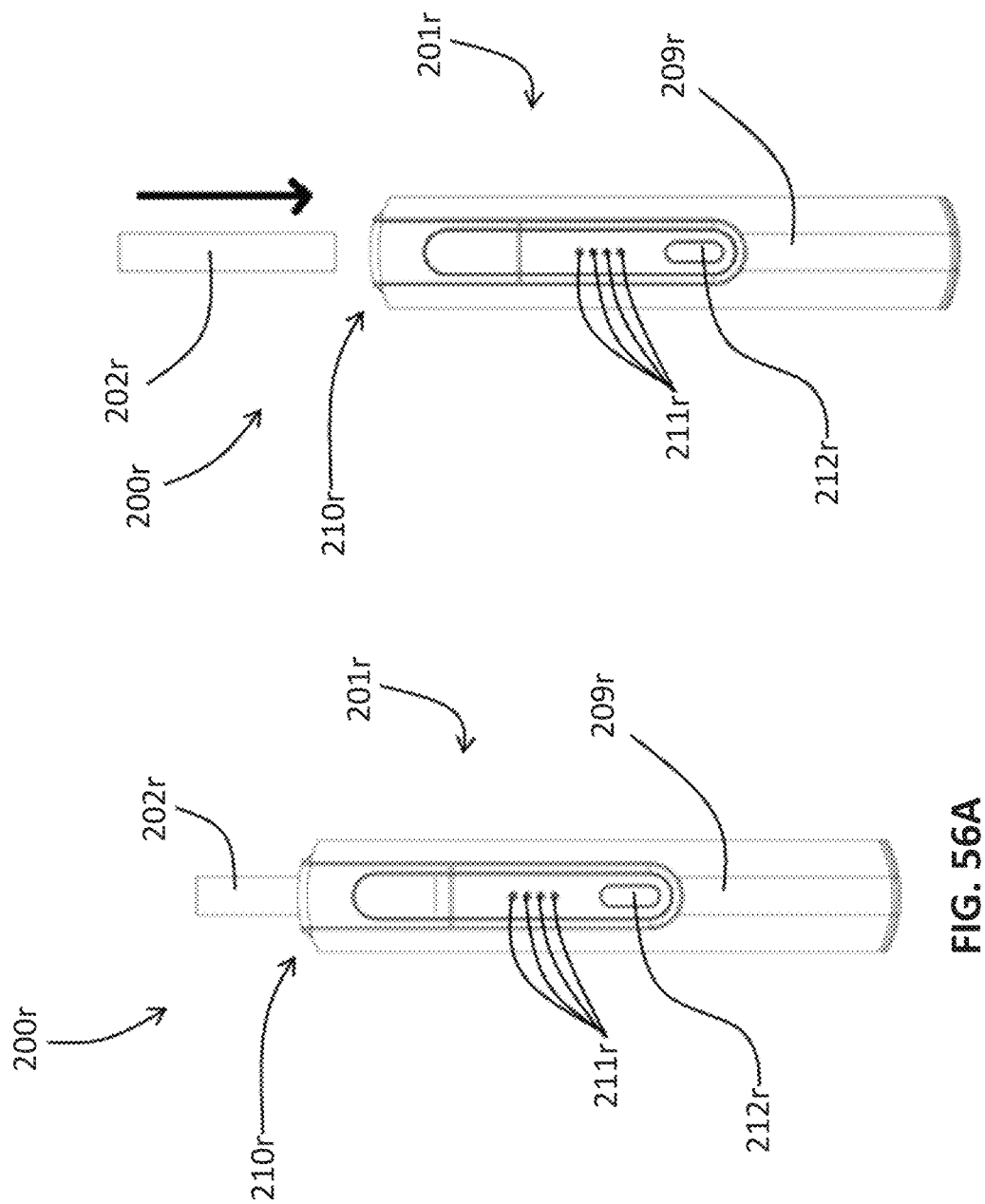

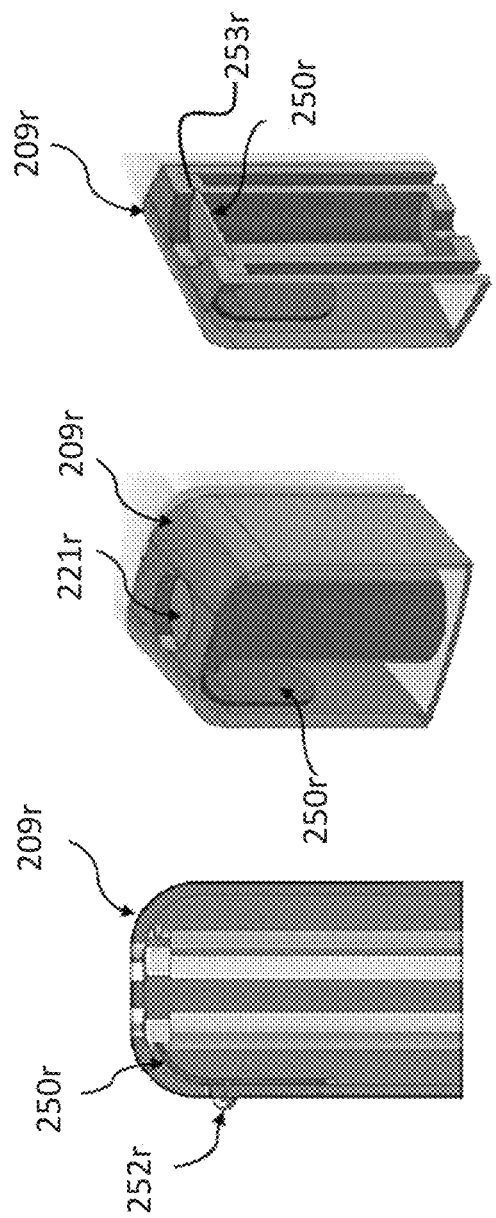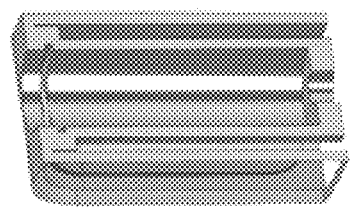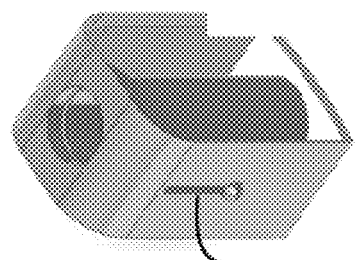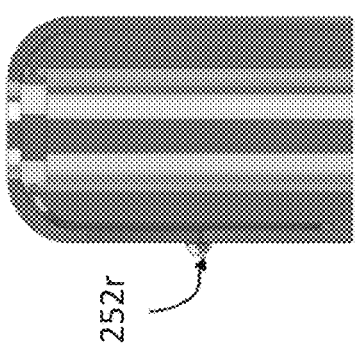

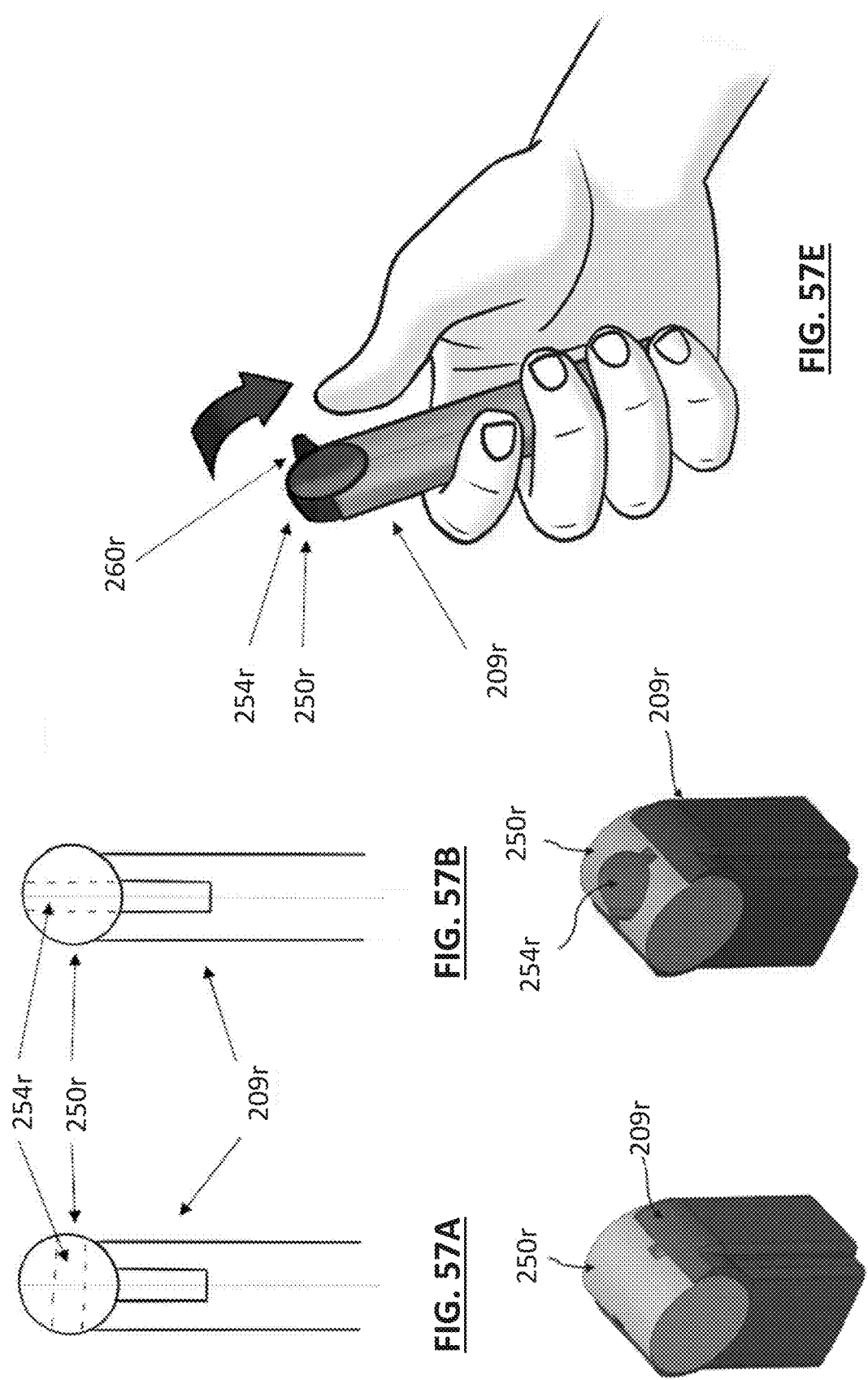

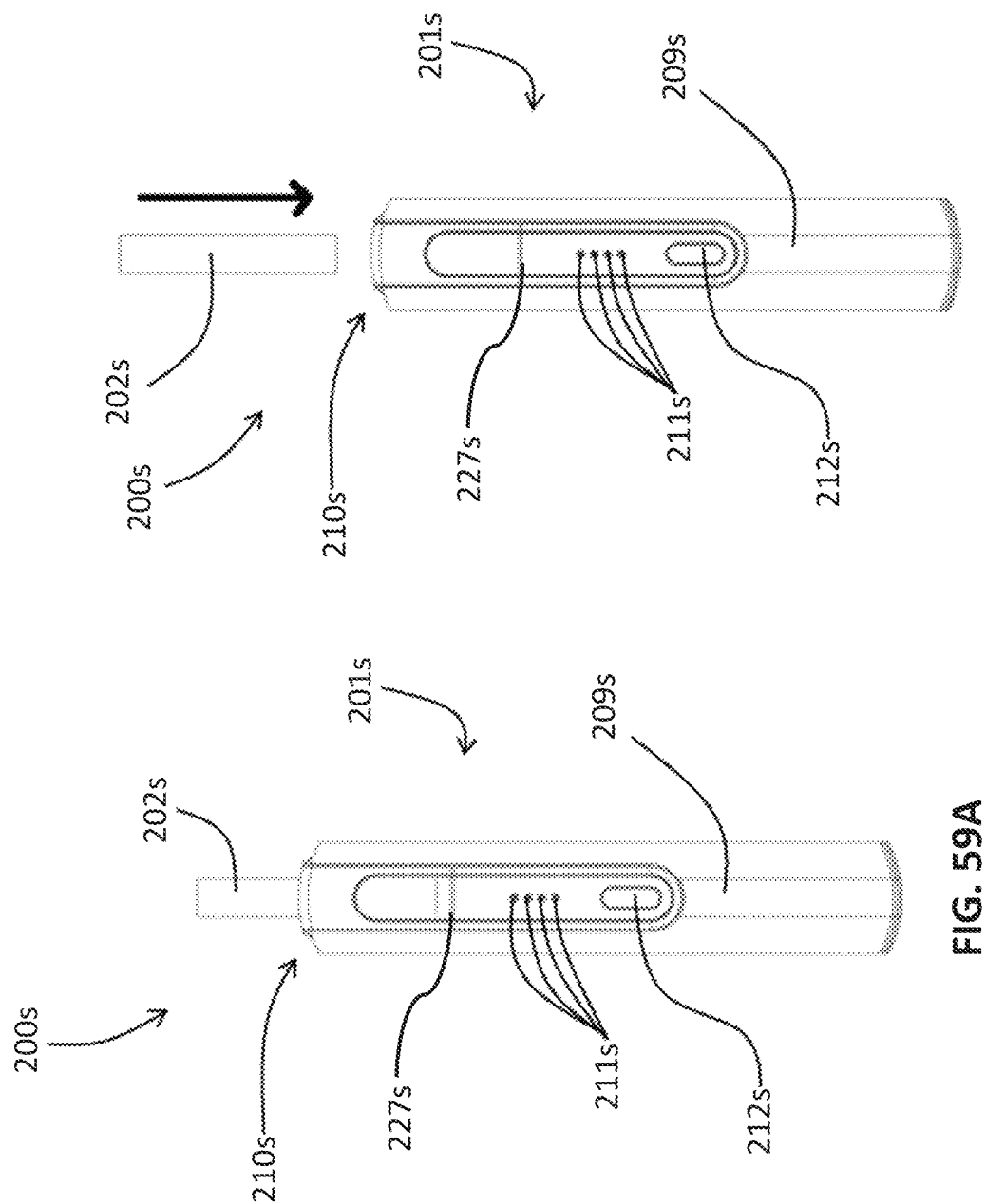

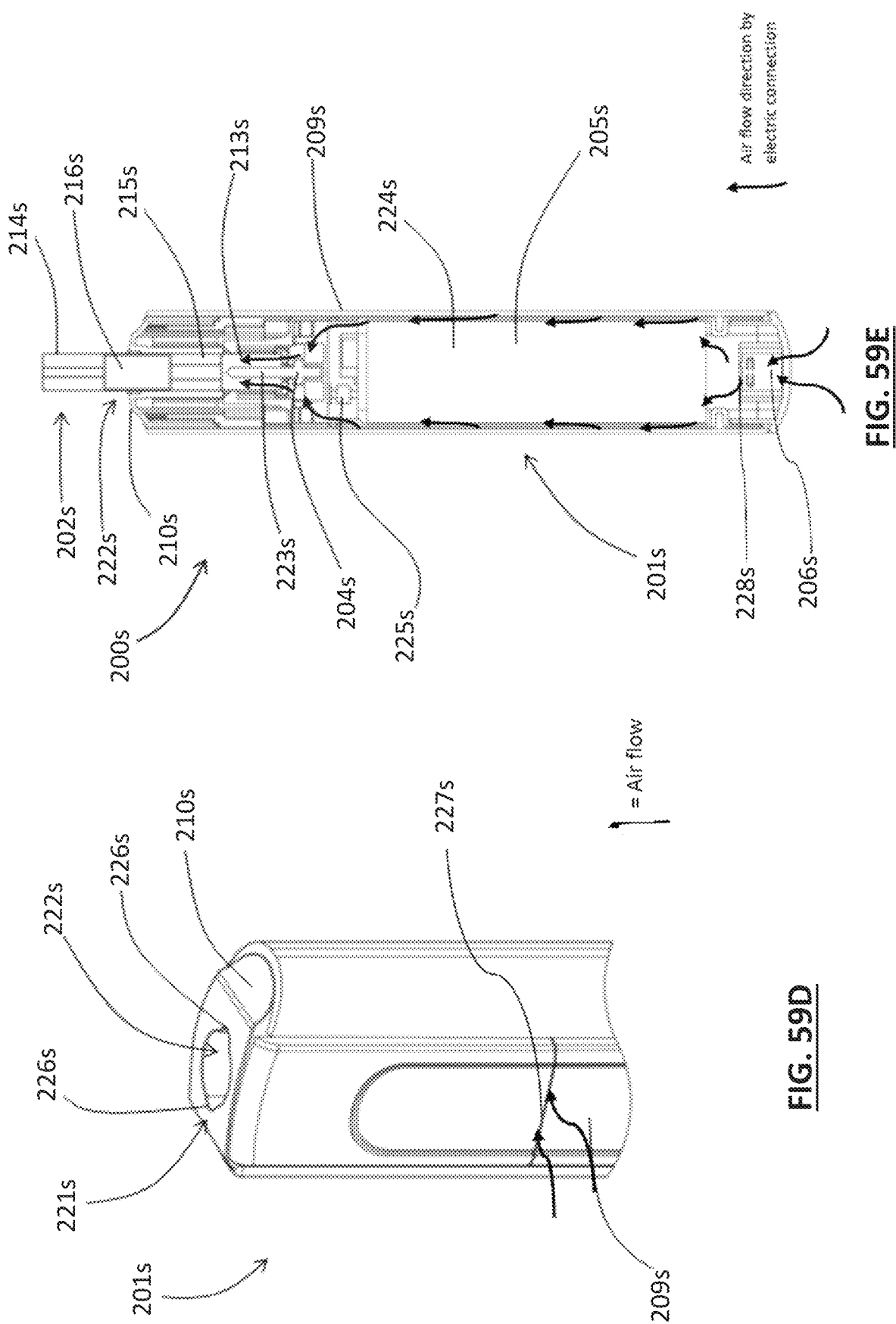

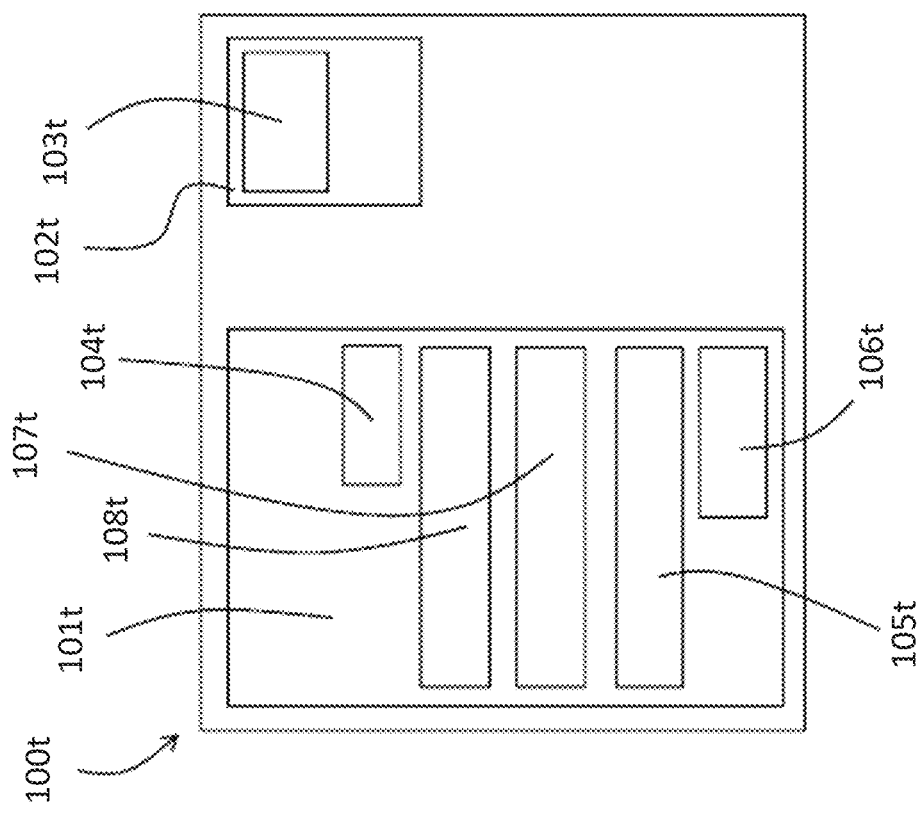
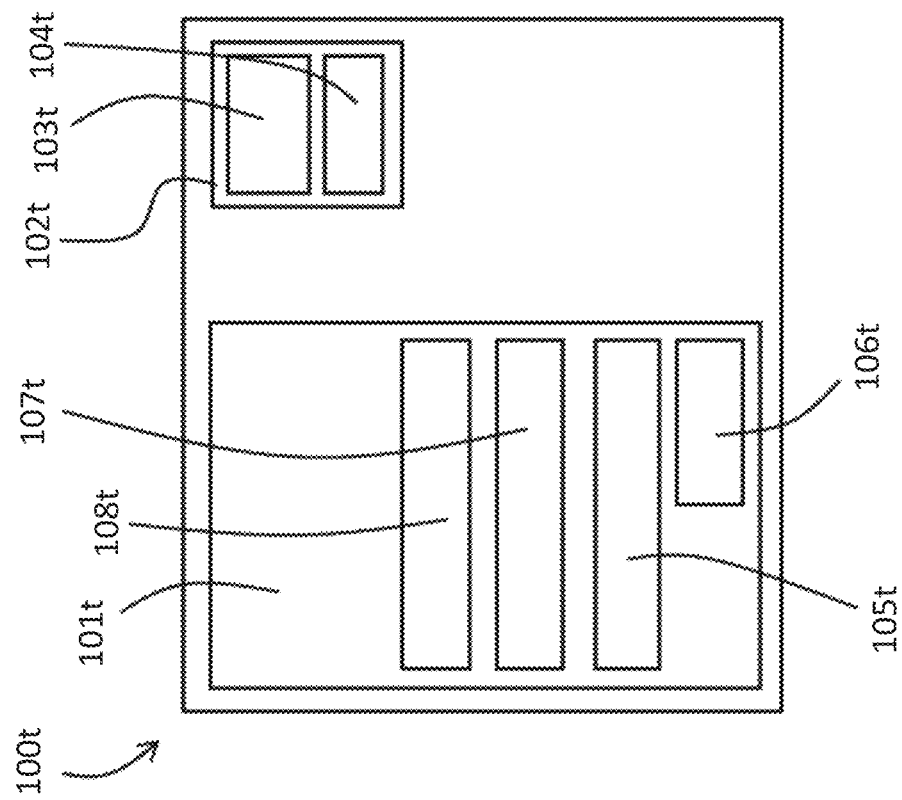

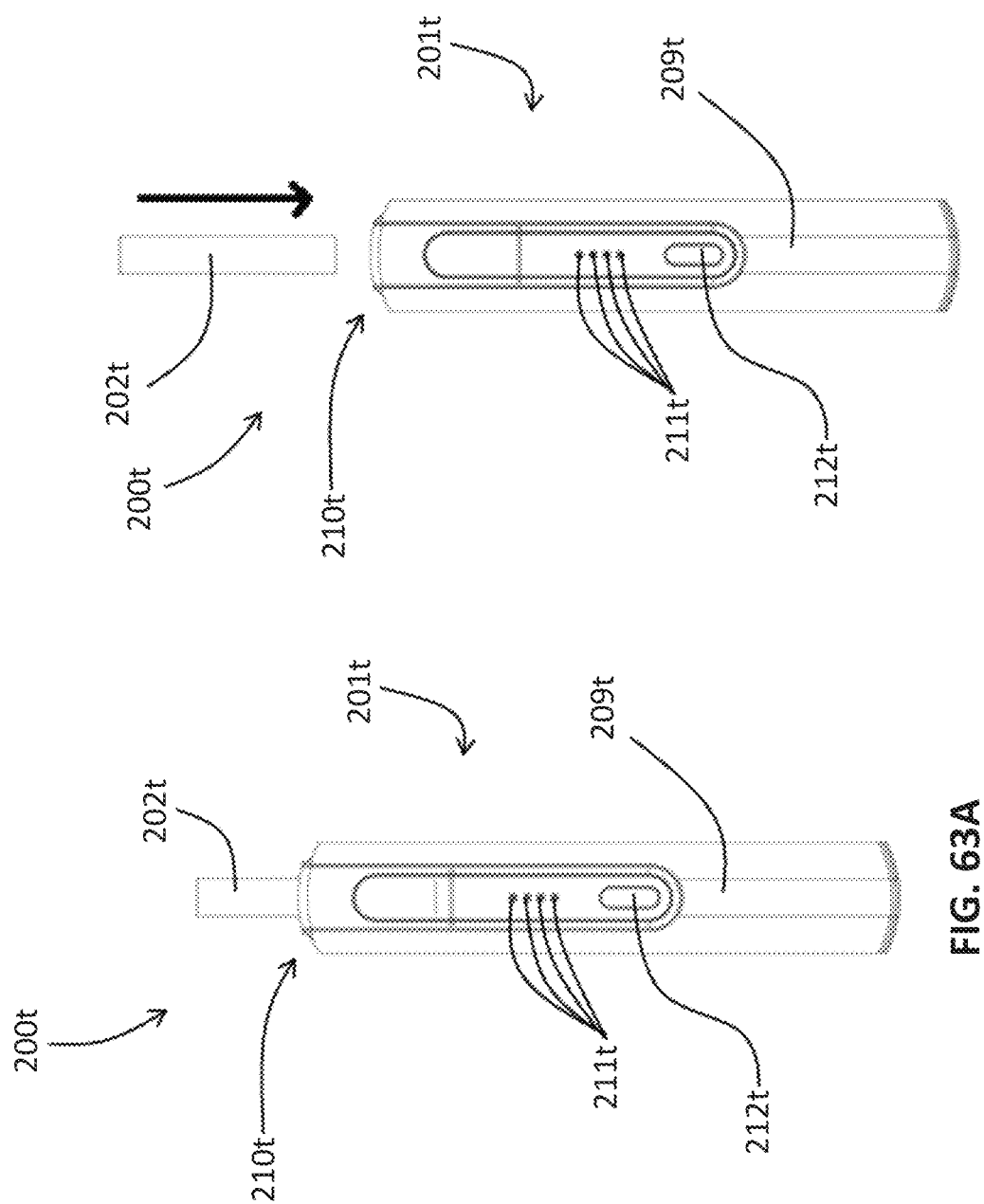

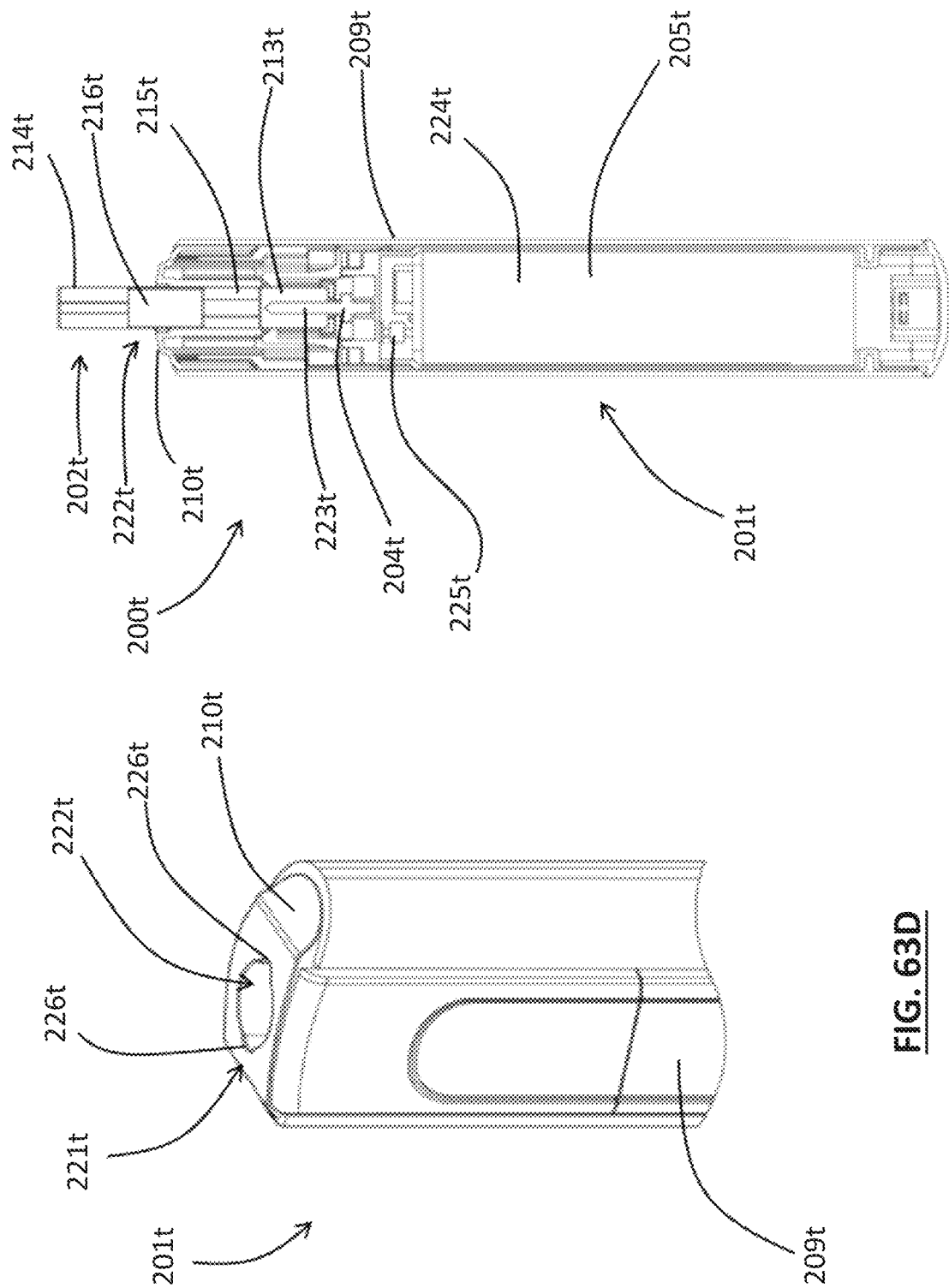

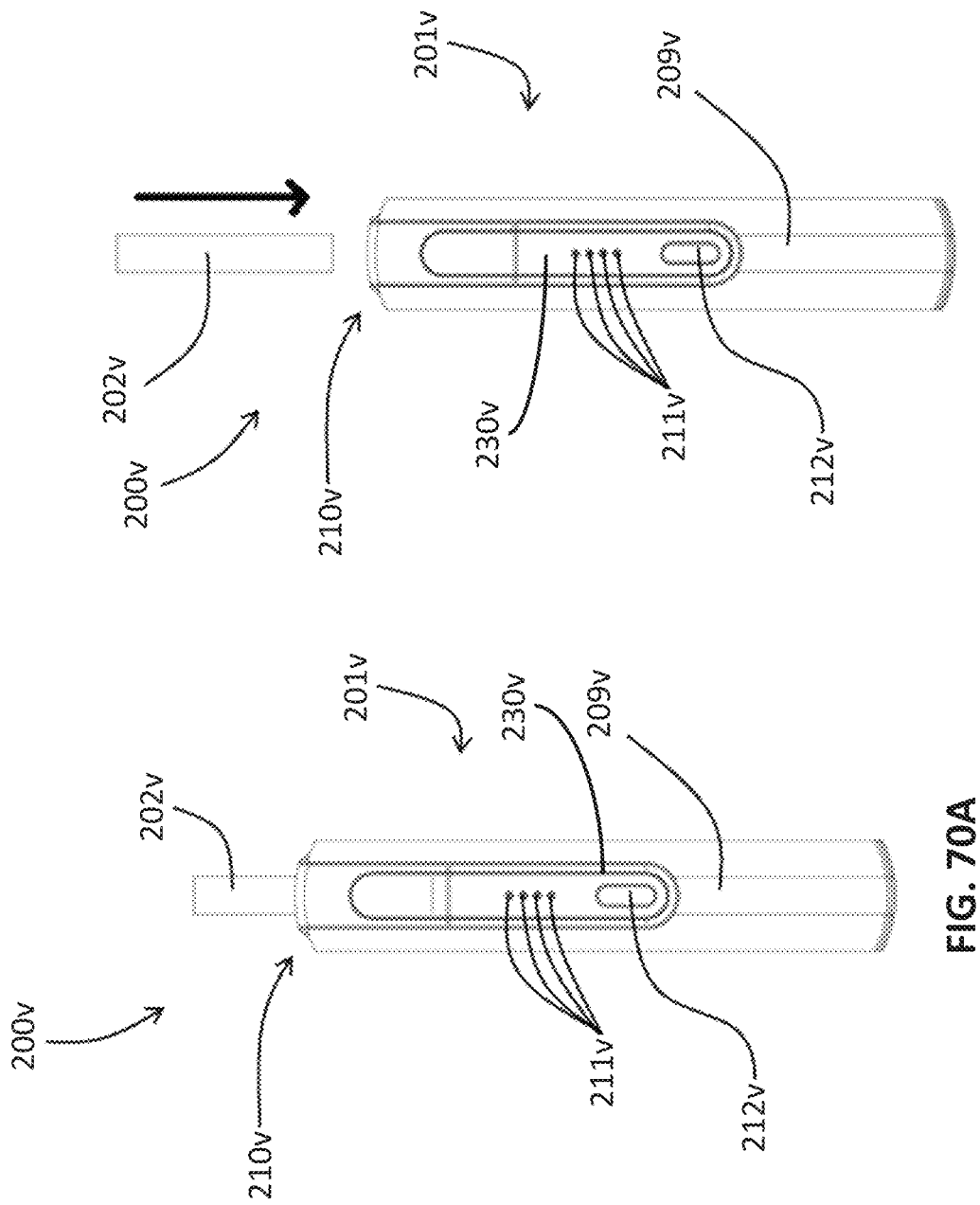

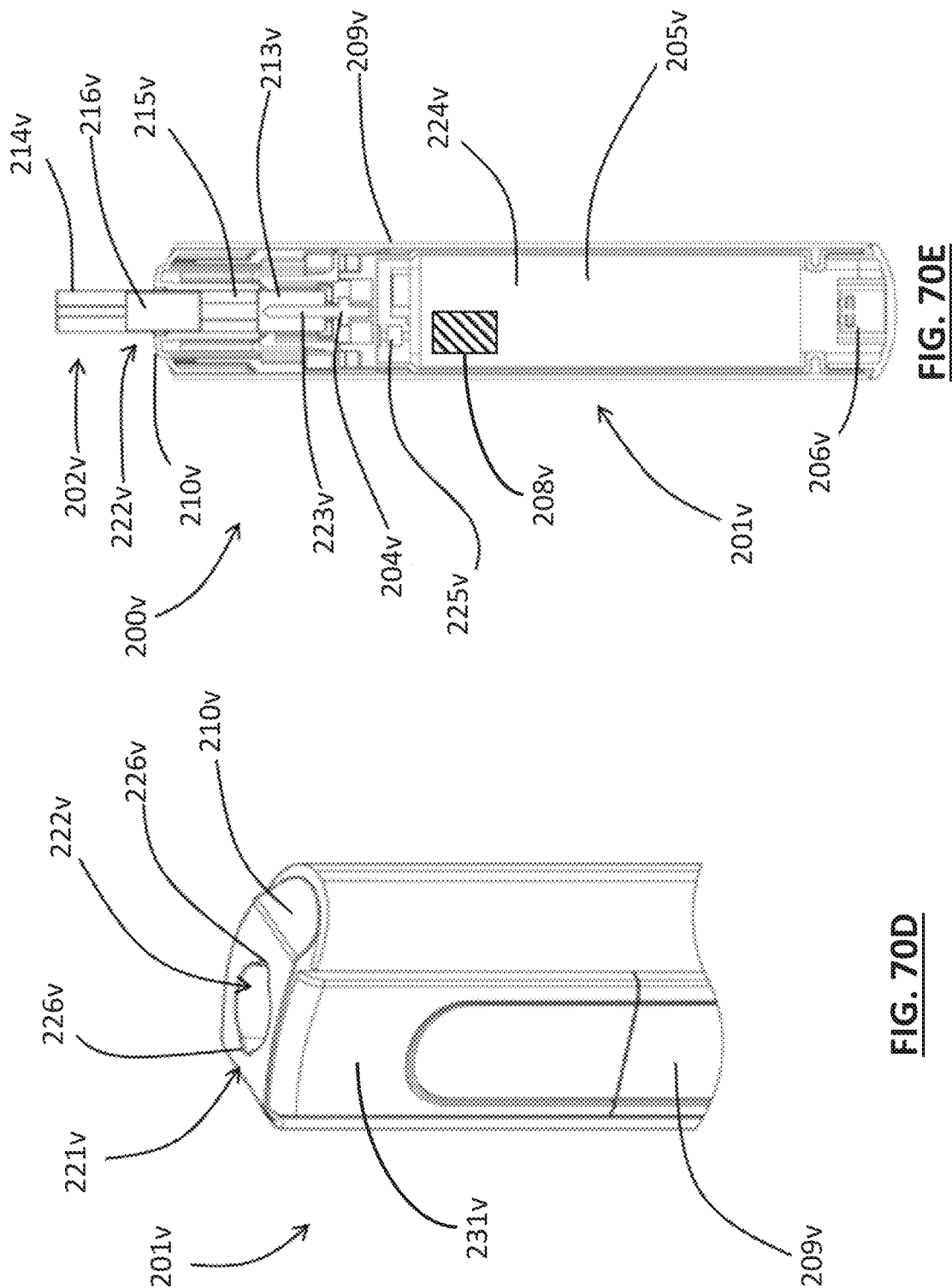

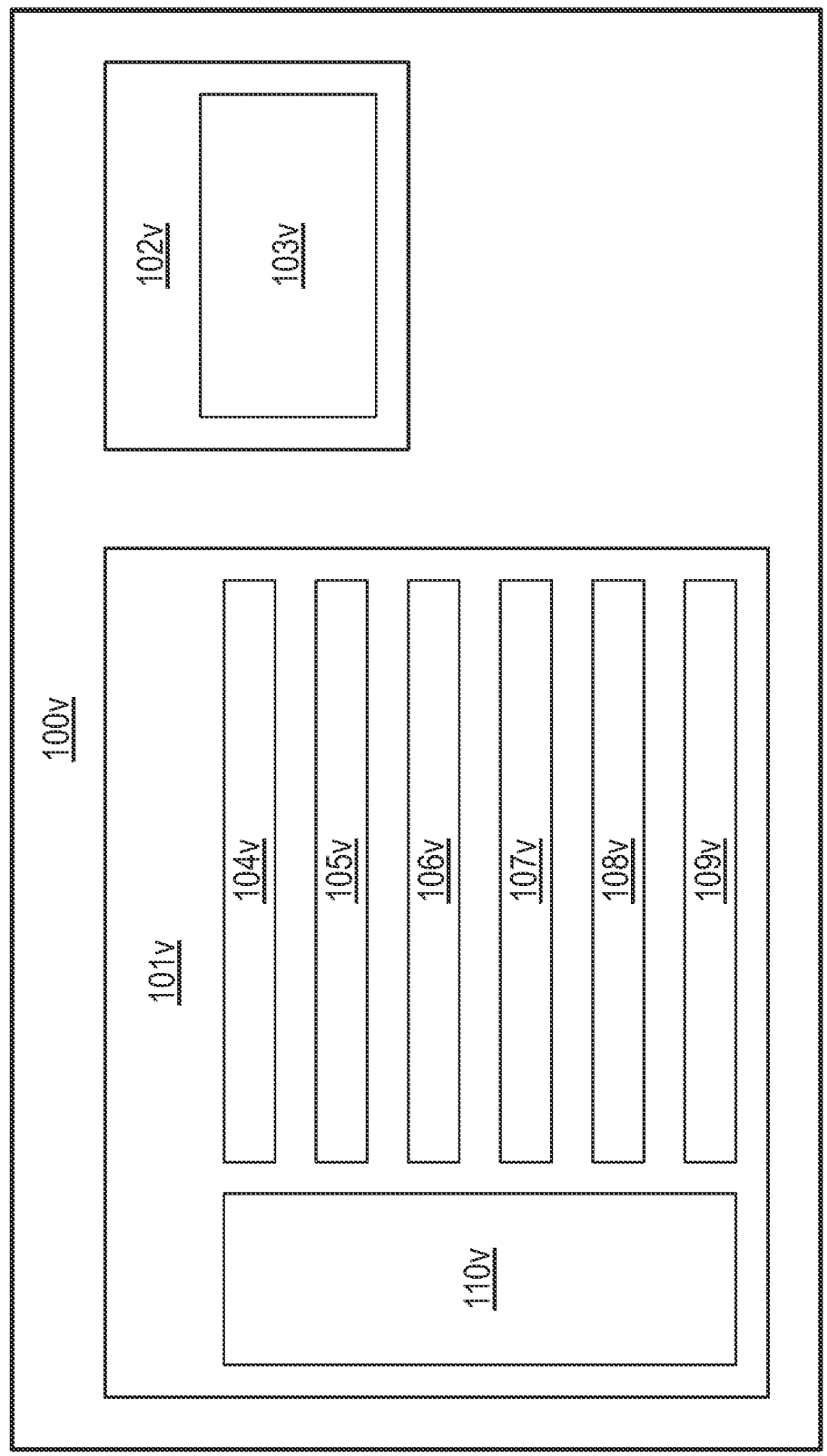

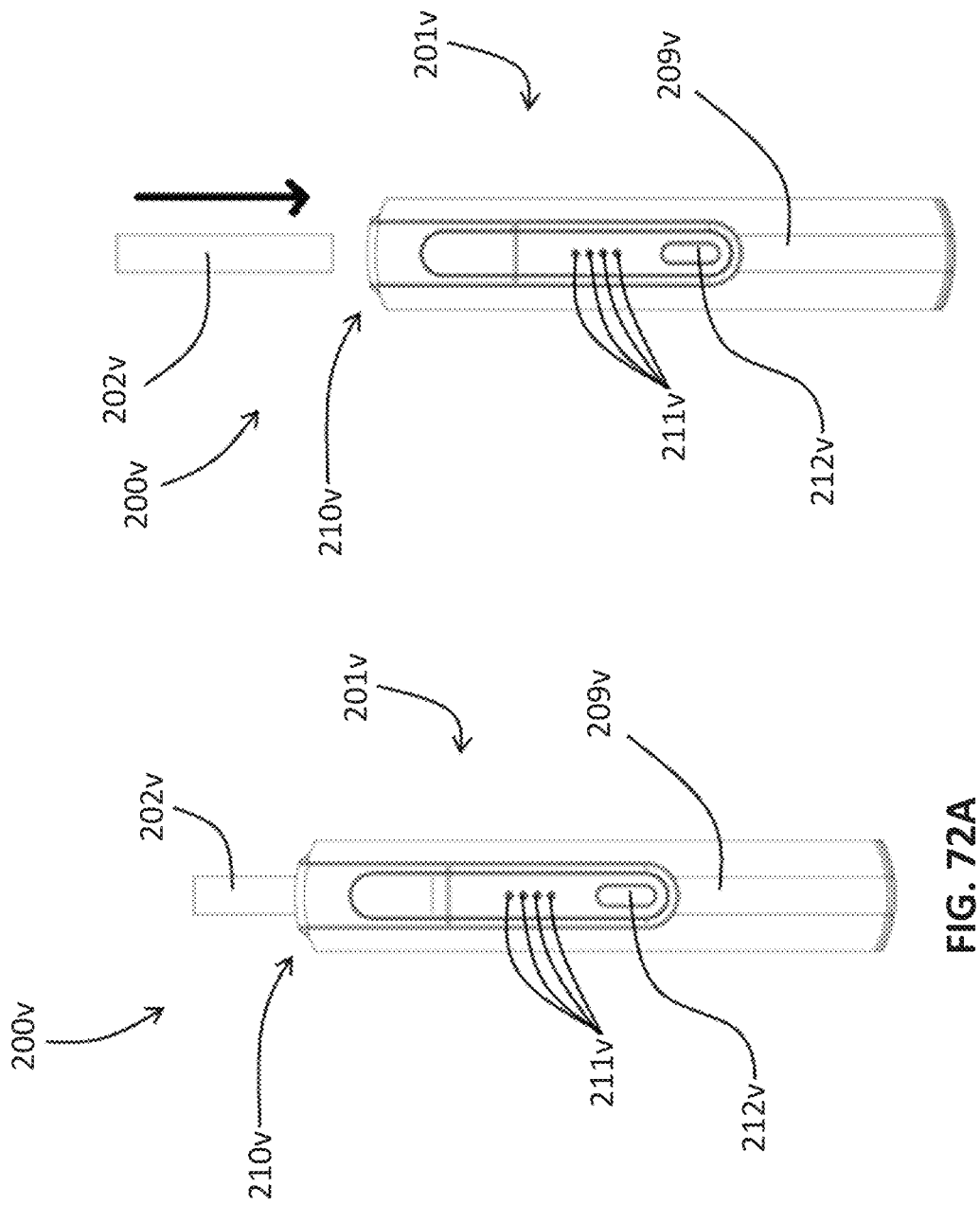

SMOKING SUBSTITUTE SYSTEM

CROSS REFERENCE TO RELATED APPLICATIONS/INCORPORATION BY REFERENCE STATEMENT

This application is a non-provisional application claiming benefit to the international application no. PCT/EP2020/56769 filed on Mar. 13, 2020, which claims priority to EP 19020153.3 filed on Mar. 22, 2019 and to EP 20157500.8 filed on Feb. 14, 2020. This application also claims benefit to the international application no. PCT/EP2020/56772 filed on Mar. 13, 2020, which claims priority to EP 19020150.9 filed on Mar. 22, 2019. This application also claims benefit to the international application no. PCT/EP2020/56776 filed on Mar. 13, 2020, which claims priority to EP 19020137.6 filed on Mar. 22, 2019, EP 19020138.4 filed on Mar. 22, 2019, EP 19020159.0 filed on Mar. 22, 2019, EP 19020173.1 filed on Mar. 22, 2019, EP 19020176.4 filed on Mar. 22, 2019, EP 19020185.5 filed on Mar. 22, 2019, EP 19020189.7 filed on Mar. 22, 2019, EP 19020210.1 filed on Mar. 22, 2019, EP 19020213.5 filed on Mar. 22, 2019, and EP 19020169.9 filed on Mar. 22, 2019. This application also claims benefit to the international application no. PCT/EP2020/56777 filed on Mar. 13, 2020, which claims priority to EP 19020183.0 filed on Mar. 22, 2019. This application also claims benefit to the international application no. PCT/EP2020/56782 filed on Mar. 13, 2020, which claims priority to EP 19020179.8 filed on Mar. 22, 2019. This application also claims benefit to the international application no. PCT/EP2020/56784 filed on Mar. 13, 2020, which claims priority to EP 19020216.8 filed on Mar. 22, 2019. This application also claims benefit to the international application no. PCT/EP2020/56786 filed on Mar. 13, 2020, which claims priority to EP 19020212.7 filed on Mar. 22, 2019. This application also claims benefit to the international application no. PCT/EP2020/56788 filed on Mar. 13, 2020, which claims priority to EP 19020209.3 filed on Mar. 22, 2019. This application also claims benefit to the international application no. PCT/EP2020/56792 filed on Mar. 13, 2020, which claims priority to EP 19020203.6 filed on Mar. 22, 2019. This application also claims benefit to the international application no. PCT/EP2020/56818 filed on Mar. 13, 2020, which claims priority to EP 19020168.1 filed on Mar. 22, 2019. This application also claims benefit to the international application no. PCT/EP2020/56822 filed on Mar. 13, 2020, which claims priority to EP 19020155.8 filed on Mar. 22, 2019. This application also claims benefit to the international application no. PCT/EP2020/56823 filed on Mar. 13, 2020, which claims priority to EP 19020156.6 filed on Mar. 22, 2019. This application also claims benefit to the international application no. PCT/EP2020/56825 filed on Mar. 13, 2020, which claims priority to EP 19020159.0 filed on Mar. 22, 2019. This application also claims benefit to the international application no. PCT/EP2020/56836 filed on Mar. 13, 2020, which claims priority to EP 19020164.0 filed on Mar. 22, 2019. This application also claims benefit to the international application no. PCT/EP2020/56837 filed on Mar. 13, 2020, which claims priority to EP 19020223.4 filed on Mar. 22, 2019. This application also claims benefit to the international application no. PCT/EP2020/56838 filed on Mar. 13, 2020, which claims priority to EP 19020158.2 filed on Mar. 22, 2019. This application also claims benefit to the international application no. PCT/EP2020/56854 filed on Mar. 13, 2020, which claims priority to EP 19020147.5 filed on Mar. 22, 2019. This application also claims benefit to the international application no. PCT/EP2020/56861 filed on Mar. 13, 2020, which claims priority to EP 19020197.0 filed on Mar. 22, 2019. This application also claims benefit to the international application no. PCT/EP2020/56863 filed on Mar. 13, 2020, which claims priority to EP 19020142.6 filed on Mar. 22, 2019. This application also claims benefit to the international application no. PCT/EP2020/56868 filed on Mar. 13, 2020, which claims priority to EP 19020201.0 filed on Mar. 22, 2019. This application also claims benefit to the international application no. PCT/EP2020/56870 filed on Mar. 13, 2020, which claims priority to EP 19020206.9 filed on Mar. 22, 2019. The entire contents of each of the above referenced applications are hereby incorporated herein by reference in their entirety.

FIELD OF THE DISCLOSURE

The present disclosure relates to a smoking substitute system and particularly, although not exclusively, to a smoking substitute device, of a smoking substitute system, with a safety feature. The disclosure also relates to a smoking substitute system comprising a smoking substitute device and a tool for the device. The present disclosure also relates to a smoking substitute system and particularly, although not exclusively, to a smoking substitute system comprising a device, an aerosol-forming article and a tool.

The present disclosure also relates to a smoking substitute system and particularly, although not exclusively, to a smoking substitute system comprising an aerosol-forming article and a device for heating the aerosol-forming article.

The present disclosure also relates to the field of smoking tobacco. In particular, the present disclosure relates to smoking substitute systems and particularly, although not exclusively, to a heat-not-burn (HNB) smoking substitute system. Further in particular, the present disclosure relates to a smoking substitute system having a shroud.

The present disclosure also relates to a smoking substitute system and particularly, although not exclusively, to a smoking substitute system comprising a smoking substitute device and a tool for the device.

The present disclosure also relates to a smoking substitute system and particularly, although not exclusively, to a smoking substitute system comprising a smoking substitute device and an aerosol-forming article for use with the device.

The present disclosure also relates to a smoking substitute system and particularly, although not exclusively, to a smoking substitute system comprising a heat not burn (HNB) device and an aerosol-forming article.

The present disclosure also relates to a smoking substitute system and particularly, although not exclusively, to a smoking substitute system comprising a device and an aerosol-forming article. More particularly, a device comprising a mechanical means for activating a crush ball within the aerosol forming article.

The present disclosure also relates to a smoking substitute system and particularly, although not exclusively, to a smoking substitute system comprising a device for heating a consumable.

The present disclosure also relates to a smoking substitute system and particularly, although not exclusively, to a smoking substitute system comprising a device comprising a cap and/or a housing and a cap engaged with the housing.

The present disclosure also relates to a smoking substitute system and particularly, although not exclusively, to a smoking substitute system comprising a device having a closure to close a cavity configured for receipt of at least a portion of a consumable.

The present disclosure also relates to a stopper of a smoking substitute device and particularly, although not exclusively, to a stopper for closing a cavity of the smoking substitute device.

The present disclosure further relates to a smoking substitute system and particularly, although not exclusively, to a smoking substitute system comprising a heat dissipation element.

The present disclosure also relates to a smoking substitute system and particularly, although not exclusively, to a smoking substitute system comprising a heated tobacco device.

BACKGROUND

The smoking of tobacco is generally considered to expose a smoker to potentially harmful substances. It is generally thought that a significant amount of the potentially harmful substances is generated through the heat caused by the burning and/or combustion of the tobacco and the constituents of the burnt tobacco in the tobacco smoke itself.

Conventional combustible smoking articles, such as cigarettes, typically comprise a cylindrical rod of tobacco comprising shreds of tobacco which is surrounded by a wrapper, and usually also a cylindrical filter axially aligned in an abutting relationship with the wrapped tobacco rod. The filter typically comprises a filtration material which is circumscribed by a plug wrap. The wrapped tobacco rod and the filter are joined together by a wrapped band of tipping paper that circumscribes the entire length of the filter and an adjacent portion of the wrapped tobacco rod. A conventional cigarette of this type is used by lighting the end opposite to the filter, and burning the tobacco rod. The smoker receives mainstream smoke into their mouth by drawing on the mouth end or filter end of the cigarette.

Combustion of organic material such as tobacco is known to produce tar and other potentially harmful by-products. There have been proposed various smoking substitute systems (or "substitute smoking systems") in order to avoid the smoking of tobacco.

Such smoking substitute systems can form part of nicotine replacement therapies aimed at people who wish to stop smoking and overcome a dependence on nicotine.

Smoking substitute systems include electronic systems that permit a user to simulate the act of smoking by producing an aerosol (also referred to as a "vapor") that is drawn into the lungs through the mouth (inhaled) and then exhaled. The inhaled aerosol typically bears nicotine and/or flavorings without, or with fewer of, the odor and health risks associated with traditional smoking.

In general, smoking substitute systems are intended to provide a substitute for the rituals of smoking, whilst providing the user with a similar experience and satisfaction to those experienced with traditional smoking and with combustible tobacco products. Some smoking substitute systems use smoking substitute articles (also referred to as a "consumable") that are designed to resemble a traditional cigarette and are cylindrical in form with a mouthpiece at one end.

The popularity and use of smoking substitute systems has grown rapidly in the past few years. Although originally marketed as an aid to assist habitual smokers wishing to quit tobacco smoking, consumers are increasingly viewing smoking substitute systems as desirable lifestyle accessories.

There are a number of different categories of smoking substitute systems, each utilizing a different smoking substitute approach.

One approach for a smoking substitute system is the so-called Heated Tobacco ("HT") approach in which tobacco (rather than an "e-liquid") is heated or warmed to release vapor. HT is also known as "heat not burn" ("HNB"). The tobacco may be leaf tobacco or reconstituted tobacco. The vapor may contain nicotine and/or flavorings. In the HT approach the intention is that the tobacco is heated but not burned, i.e., the tobacco does not undergo combustion.

A typical HT smoking substitute system may include a device and a consumable. The consumable may include the tobacco material. The device and consumable may be configured to be physically coupled together. For example, the consumable may be inserted into a cavity or heating chamber and thereby establishing physical contact with a heating element located in the cavity. In use, heat may be imparted to the tobacco material by a heating element of the device, wherein airflow through the tobacco material causes components in the tobacco material to be released as vapor. A vapor may also be formed from a carrier in the tobacco material (this carrier may for example include propylene glycol and/or vegetable glycerin) and additionally volatile compounds released from the tobacco. The released vapor may be entrained in the airflow drawn through the tobacco.

As the vapor passes through the consumable (entrained in the airflow) from the location of vaporization to an outlet of the consumable (e.g., a mouthpiece), the vapor cools and condenses to form an aerosol for inhalation by the user. The aerosol will normally contain the volatile compounds.

A consumable may be provided with additional flavor capsules or crush balls. These crush balls have an outer shell which encapsulates a liquid flavorant or an aerosol forming substance. Before use, the user must manually crush the crush ball in order to release the flavorant into the mainstream vapor when the consumable is later inserted into the device and heated. Generally, the consumables are provided with a pressable region having an indicative mark to help the user locate the crush ball for crushing.

However, a major limitation associated with existing HT smoking substitute systems is that users are required to crush/activate the crush ball within the consumable by hand, thereby causing inconvenience. Moreover, users are left with the option of either activating the crush ball in a fresh consumable before placing the consumable in the device, or removing a partially consumed consumable from the device in order to activate the crush ball on demand and replacing in the consumable in the device (should they decide they wish to activate the crush ball mid-way through a smoking cycle). Both situations deteriorate the user experience.

In HT smoking substitute systems, heating as opposed to burning the tobacco material is believed to cause fewer, or smaller quantities, of the more harmful compounds ordinarily produced during smoking. Consequently, the HT approach may reduce the odor and/or health risks that can arise through the burning, combustion and pyrolytic degradation of tobacco.

For some HT smoking substitute systems, in use, the aerosol-forming article is received in a cavity of the device where the tobacco material is heated by the heating element. Unlike smoking substitute device that heat a e-liquid where the said heating element are well enclosed, currently available HT smoking substitute devices do not provide any form of protection for the heating element. That is, the cavity is often exposed when the aerosol-forming article is not received therein. As such, there is a risk of damaging the heating element when foreign objects enter into the cavity. Further, dust and dirt may ingress into the cavity and thereby adhere onto the heating element, and as such they may release unwanted volatiles into the aerosol or creates a burnt smell during heating.

A limitation associated with existing HT smoking substitute systems is that, due to the physical contact between the heating element and tobacco material, residue from the heating of tobacco may form on the heating element with every use of the device, e.g., loose tobacco material accumulates or sticks to the surface of the heating element of the device. Such residue formation and build-up may result in undesired burnt smell when using the device, and therefore affecting the user experience. Therefore, currently available HT smoking systems often require the user to remove a cap from the device to expose the heating element before carrying out a cleaning procedure with a dedicated cleaning tool or an alcohol swab. For example, the user may require to clean the heating element with the use of a brush or a disposable solvent swap. However, currently available HT systems may only provide access to the heating element through an opening towards at the end of the cavity. Further, the user may require removing a cap covering said opening to gain access to the heating element prior to cleaning. Such arrangement may be inconvenient. In some currently available HT devices, the cap may be easily removed from the device and thus present a risk by exposing the heating element inadvertently.

Additionally, currently available HT smoking systems often require the user to carry out a cleaning procedure once a given number of consumables has been consumed. For example, a user may use a dedicated cleaning tool or an alcohol swab to physically remove residue build-up from the heating element once the device has consumed consumables. However, not only this is inconvenient, such cleaning tool or alcohol swab may not always available for the user to carry out cleaning, e.g., the user may not always carry such accessories or they may get misplaced. Further, as residue forms on the heating element with every use, such prior art devices may nevertheless allow some residue to build up in between cleaning cycles, and therefore they may not provide an optimal experience in every use.

Therefore, some users may only clean the heating element once the device has consumed a given number of consumables, e.g., twenty (20) consumables, when the residue built up becomes detrimental to the experience, e.g., when a burnt taste is perceivable.

In some HT smoking substitute systems, the heating element (for heating the tobacco material) may be directly in contact with the tobacco material. In such systems some of the heated material may stick to the heater when heated and may remain on the heater when the consumable is removed from the heater. This can reduce the performance of the heater during subsequent heating cycles.

Whilst the heating element is not heated to a temperature that burns the tobacco, when heated, its temperature does present a safety hazard to users. That is, if a user were to come into direct contact with the heater it could cause significant injury to the user.

In some smoking substitute systems, when the consumable is removed from the heater, parts of the consumable can remain on or around the heater (e.g., in a cavity containing the heater). This can be caused by those parts of the consumable adhering to the heater (e.g., due to the heat imparted by the heater) and/or can be due to portions of the consumable crumbling or breaking down.

Currently available HT smoking substitute devices typically require airflow to enter the device at a location distanced from the consumable. In such devices, air inlets are often provided at a location away from a major surface of the device, in order to reduce the likelihood of blocking said air inlets when the user grips onto the device. Therefore, in some other prior art devices, air inlets are provided at a location away from the major surface of the device, in order to reduce the likelihood of such inadvertent blockage. For example, air inlets in some devices are provided on a cap of the device and thus an airflow is required to flow through a length of air channel or annulus before it reaches the consumable. Such arrangements may increase draw resistance during a puff and in some cases may even limit the amount of airflow that is available for entraining the vapor released from the tobacco. Furthermore, such arrangement may result in a diffused air supply to the heating element, thus impacting heater transfer within the aerosol-forming article.

Other currently available HT smoking substitute devices comprise one or more air inlets for allowing an airflow to enter the device and pass through the tobacco material, thereby forming an aerosol. The airflow entering the device, e.g., the rate of airflow and the associated draw resistance, may solely depend on the manner a user puffs on the mouthpiece, and therefore the user experience may not be consistent amongst different users. Further, the users may each have different preferences and expectations where such devices cannot satisfy. For example, some users may prefer higher draw resistance than others.

Further, it is often the case that residual debris left by a consumable remains within the body of a HNB device after use. For example, pieces of tobacco may become dislodged from the consumable during use, falling into the cavity of the device in which the consumable resides. In some cases, the debris may remain in contact with the heater inside the device, which is a safety risk since the debris could eventually burn or ignite. This could also impair the flavor of a subsequent consumable. It is often difficult for a user to properly clean the heating element between smoking cycles to ensure that such debris is removed.

In some cases, heating of the consumable can result in a housing of the device becoming hot. This can make the housing uncomfortable to hold by a user and, in some cases, can present a safety risk.

Therefore, there is a need for improved design of smoking substitute systems, in particular HT smoking substitute systems, to enhance the user experience and improve the function of the HT smoking substitute system. Specifically, an HT smoking substitute system that overcomes the one or more disadvantages associated with the prior art.

The present disclosure has been devised in the light of the above considerations.

SUMMARY OF THE DISCLOSURE

First Mode: A Smoking Substitute Kit which Provides a Secondary Safety Feature

At its most general, a first mode of the present disclosure relates to a smoking substitute kit which provides a secondary safety feature.

Also in a general sense, the present disclosure relates to smoking substitute system with a smoking substitute device having a cap movable between two positions to selectively conceal or expose a heating element of the smoking substitute device. This may allow the user to physically access and clean the heating element in a more convenient manner, and thereby facilitate a more frequent cleaning routine. The present disclosure also relates to a tool for removing the cap form the device, and thereby preventing inadvertent removal of the cap. The tool may further comprise a cleaning means to conveniently allow the user to clean the heating element once the cap is removed by the tool.

At its most general, another aspect of the first mode of the present disclosure relates to a tool for a smoking substitute system. Another aspect of the first mode of the present disclosure relates to a tool for removing a cap of a smoking substitute device. Therefore, the smoking substitute device may be configured in that the cap cannot be removed by hand but by the tool, and thereby advantageously it may reduce the risk of inadvertently exposing the heating element. Furthermore, the tool may comprise a cover that is configured to cover a cap removal portion extending from a main body of the tool. In use, the cover may be arranged such that it does not rotate relatively with the main body. The tool may further comprise a cleaning portion extending from the main body opposite the cap removal portion. Therefore advantageously, a user may be able to clean a heating element of the device, via a rotating motion, by rotating the cover when it is engaged with the device.

In another general sense, the present disclosure relates to a tool for removing a cap of a smoking substitute device. Therefore, the smoking substitute device may be configured in that the cap cannot be removed by hand but by the tool, and thereby advantageously it may reduce the risk of inadvertently exposing the heating element. Furthermore, the tool may comprise a cover that is configured to cover a cap removal portion extending from a main body of the tool. In use, the cover may be arranged such that it does not rotate relatively with the main body. The tool may further comprise a cleaning portion extending from the main body opposite the cap removal portion. Therefore advantageously, a user may be able to clean a heating element of the device, via a rotating motion, by rotating the cover when it is engaged with the device.

According to a first aspect of the first mode there is provided a smoking substitute device comprising: a heater connected to a main body of the device; the device further including a cap covering at least a portion of the heater, wherein the cap is releasably engaged with a main body of the device, and wherein the cap is configured to be released from engagement with the main body of the device using a removal key.

By providing a device comprising a safety feature i.e., a removal key the device may be able to provide less access to the heating element by a child thereby saving him as well as the hearing element from damage.

The present smoking substitute device provides a safety feature because the cap cannot be separated from the body of the device without using a separate element i.e., a removal key. It ensures that if heating element is on or cooling down, it is not exposed to outside environment and does not come in contact with a human being.

According to a second aspect of the first mode of the present disclosure, there is provided a smoking substitute device having a body, a heating element extending from the body and a cap removably attached to the body. The cap is movable between a first position and a second position along a longitudinal axis of the body. In the first position the heating element is concealed in the cap and in the second position the heating element is at least partially exposed.

For example, in the first position, the cap may cover a window or an opening at the sidewall of the body that extends into a transverse cavity containing the heating element, and thereby conceals the heating element. In the second position, the cap is moved or slide to a location where it may no longer cover the opening, and thereby the heating element may be at least partially exposed through the opening. More specifically, the opening may be located adjacent to exposed portion of the heating element and therefore it may provide physical access to said exposed portion of the heating element.

By providing a device comprising a cap movable between two positions, the heating element may be cleaned in a more convenient manner. For example, when the cap is moved to the second position, the heating element may be exposed through a window or opening from the side of the device, as such said heating element may be visually inspected or cleaned through said opening. Advantageously, the user may thereby carry out a brief cleaning at the heating element without requiring a dedicated cleaning tool. For example, the user may simply blow through the opening or physically shaking, tilting and/or tapping the device to dislodge loose debris that are formed on the heating element. The user may also physically clean the exposed portion of the heating element, e.g., a base of the heating element, with the use of a tool, e.g., a brush. Further, the smoking substitute as disclosed herein may prolong the usability of the device before it requires deep cleaning or other such maintenance.

According to a third aspect of the first mode of the present disclosure, there is provided a tool for a HNB device. The HNB device comprises a main body and a cap, where the cap is defined with an opening and is removably attached to the main body. Further, the tool is adapted to disengage the cap and the main body. The tool may be insertable into the opening in the cap, in at least one defined orientation.

According to a fourth aspect of the first mode of the present disclosure, there is provided a tool for a HNB device. The HNB device comprises a main body and a cap, where the cap is removably attached to the main body. Further, the tool is adapted to disengage the cap and the main body.

By providing the tool, the cap of the device may be operable to open (e.g., expose) interior of the main body of the HNB device.

According to a fifth aspect of the first mode of the present disclosure, there is provided a tool for a heat-not-burn device, the heat-not-burn device including a cap that is releasably connected to a main body of the device, wherein the tool is configured to disengage the cap from the main body.

By providing the tool according to the fourth or fifth aspects of the first mode, a safer device is provided because the cap may not be removed without the key.

According to a sixth aspect of the first mode of the present disclosure, there is provided a tool for an HNB device. The HNB device comprises a main body and a cap, where the cap is removably attached to the main body. The tool is adapted to disengage the cap and the main body. Furthermore, the tool is adapted for indicating an orientation of the tool relative to the HNB device.

By providing the tool for the HNB device, comprising a means for visually indicating an orientation of the tool, relative to the HNB device, may facilitate in precise positioning and engagement of the tool with the HNB device, and thereby facilitating easy disengaging of the cap and the main body of the HNB device.

According to a seventh aspect of the first mode of the present disclosure, there is provided a tool for an HNB device. The HNB device comprises a main body and a cap, where the cap is removably attached to the main body. Further, the tool is adapted to disengage the cap and the main body. Furthermore, the tool is adapted for performing a cleaning operation of the HNB device.

By providing a tool according to the seventh aspect of the first mode, removal of debris in a cavity and debris deposited on the heating element is facilitated. By providing a tool, cap and the body of the device may be disengaged, and the device may be cleaned. This feature of the tool facilitates in using a same (i.e., a single tool) for both disengaging and cleaning operations.

According to an eighth aspect of the first mode of the present disclosure, there is provided a tool for removing a cap of a smoking substitute device, the tool comprising a cover, a main body; wherein the main body and the cover are configured to engage with each other to prevent relative rotation there between.

The cover may engage with the main body using any suitable engagement means that prevents relative rotation between the two.

The phrase "main body" may refer a portion of the tool which is configured to engage with the cover. For example, it may comprise a collar and a connector of the tool.

By providing a tool that comprises a cover configured to engage with a main body in a manner where relative rotation is prevented, the main body may advantageously be rotated about its longitudinal axis by rotating the cover. For example, this may allow accessories such as a cleaning portion, e.g., a brush, or a cap removal portion that is attached onto the main body to be used in a rotational manner by gripping onto the cover without having to grip onto a part of the main body. That is, the cover forms an extension to the main body.

The term "tool" is intended to refer to an implement, which may be used to disengage the cap and the main body of the HNB device, and optionally for performing a cleaning operation of the HNB device.

Optional features will now be set out. These are applicable singly or in any combination with any aspect of the first mode.

Optionally, the main body comprises a cap removal portion extending from a first end and a cleaning portion extending from a second end opposite to the first end, wherein the cover is configured to engage with the first end of the main body. For example, said cleaning portion may be used to clean the surface of a heating element of the device so as to scrape or brush the debris off said heating element. Advantageously, the cover may provide a surface for a user to grip onto during the cleaning process, without having to grip onto the cap removal portion. During use, it is critical that all of the rotational movements are transmitted from the cover to the cleaning tool, and therefore such arrangement may provide efficient cleaning at the surface of the heating element.

Optionally, the cover comprises a cavity configured to receive the cap removal portion; the said cavity comprises an opening. For example, the main body may comprise a connector and a collar movable relative to the connector, wherein the cleaning portion may extend from a second end of connector and the cap removal portion may extend from a first end of the connector. The cover may be configured to engage with the collar at the first end of the connector, so as to receive the cap removal extending therefrom.

Optionally, the first end of the main body comprises a flange portion, said flange portion is configured to engage with the opening of the cover. That is, the flange portion may form on the collar.

Optionally, one of the flange portions and the opening comprises one or more notches configured to engage with one or more protrusions formed on the other one of flange portion and the opening, so as to prevent relation rotation between the cover and the main body when they are engaged with each other.

Optionally, the flange portion comprises one or more notches configured to engage with one or more protrusions formed at an opening of cover, so as to prevent relation rotation between the cover and the main body when they are engaged with each other.

For example, the one or more protrusions and notches may form along the longitudinal axis of respective opening and flange, and therefore the cover may engage with the main body by pushing the flange into the opening along the longitudinal axis of the main body. The notch may also be referred to as a groove or depression. When the cover is engaged with the main body, each of the one or more protrusions is received in respective notch and abut a sidewall of the said notch, thereby prevents relative rotation.

Optionally, there is more than one pair notch and corresponding protrusion between the flange and opening of the cover for engaging the main body and the cover. Advantageously, this may allow a more robust engagement between the cover and the main body. Preferably, two notches are formed on the flange each configured to engage with a corresponding protrusion at the opening of the cover.

Optionally, the one or more protrusions formed at the opening of the cover extends longitudinally along a wall of the cavity. For example, the one or more protrusions extend along the internal surface of aside wall of the cavity.

Optionally, the cover and the main body in configured to engage with each other via a push fit mechanism or a bump fit mechanism. Optionally, the bump fit mechanism or the push fit mechanism comprises a non-circular cross-sectional profile. Said bump fit mechanism or the push fit mechanism may be provided as an alternative, or additional, means to the notch/protrusion arrangement between the cover and the main body. Advantageously, such arrangement provides a secure engagement between the cover and the main body, as well as preventing relative rotation between the two.

Optionally, the tool further comprises a second cover configured to engage with the second end of the main body, wherein the second cover comprises a second cavity for receiving the cleaning portion.

For example, the second cover may engage with the second end of the main body with any suitable mechanism, for example a screw tread connection that engages by relative rotation between the two, or by push fit/bump fit mechanism or protrusion/notch arrangement as described to prevent relative rotation between the two.

Optionally, the cleaning portion comprises one or more elongate elements extending from the main body, whereby rotating the cover about the longitudinal axis of the tool causes the one or more elongate elements to rotate about a heating element of the smoking substitute device when the tool is engaged with said smoking substitute device. For example, each of the one or more elongate elements may comprise a brush. The brush may comprise cleaning bristles that is configured to clean the heating element of the device by rotating around said heating element. There, the present disclosure may ensure that the cleaning bristles can be rotated about the heating element by twisting the cover that is engaged with the main body.

Optionally, the cap removal portion comprises a central rod and at least one unlocking arm extending along a longitudinal axis of the central rod, said at least one unlocking arm having an unlocking protrusion disposed thereon for engaging with a corresponding locking protrusion formed on the cap of device.

Optionally, the main body comprises a collar around the central rod, the collar being movable between an insertion position and an unlocking position, wherein in the insertion position the at least one unlocking arm is allowed to flex and in the unlocking position the central rod prevents the flexing of the unlocking arm.

Optionally, the flange comprises one or more grooves around its periphery which are configured to receive and engage with the protrusion of the cover thereby preventing the relation rotation there between.

Optionally, a push fit or a bump fit is provided between the grooves and the protrusions when the protrusions are fully inserted into the grooves.

Optionally, the brush may have an elongate surface having substantially circular cross section with circular tip.

Optionally, cleaning bristles formed the cleaning portion may be rubbed on the outer surface of a heating element to clean or scrap off any debris or residuals from the heating element.

Optionally, the cleaning portion and the cap removal portion is covered by respective second cover and cover.

Optionally, the tool may comprise a rigid member and a movable member. The rigid member may include a plurality of flexible engaging arms, which may be operable between a first condition and a second condition. Also, the movable member may be configured to slide coaxially within the rigid member between a first position and a second position.

Advantageously, operation of the movable member between the first position and the second position may translate the plurality of flexible engaging arms between the first condition and the second condition, whereby at the second condition of the flexible engaging arms, the cap may be disengaged from the body. This operational movement of the movable member and the rigid member may allow disengagement of the cap and the body, to allow cleaning of the foreign particles like debris from the main body and the cap.

Optionally, each of the plurality of flexible engaging arms may include a protruding tab. The protruding tab may be configured to extend outwardly from an external surface of each of the plurality of flexible engaging arms, to engage with the main body of the device. By configuring the protruding tabs it may be possible to operate a hook of the at least one flexure bearing of the main body with ease.

Conveniently, the movable member may be operated from the first position to the second position.

Optionally, the tool may comprise a locating tab, which may laterally extend from an external surface to align the tool in the at least one defined orientation. The opening in the cap may be defined with at least one notch, where the locating tab may be aligned with the at least one notch in the at least one defined orientation. Due to this, the tool and the cap and/or the device may be oriented in one common orientation. This way, forceful insertion the tool into the cap may be avoided, thereby avoiding causing of damage to the tool and/or the cap.

Optionally, the tool may comprise a cap removal portion and a cleaning portion.

Advantageously, the cap removal portion may comprise a rigid member and a movable member.

Optionally, the rigid member comprises a plurality of flexible engaging arms, wherein the plurality of flexible engaging arms are operable between a first condition and a second condition. By operating the flexible engaging arms, the cap and the body may be disengaged.

Advantageously, the cap removal portion and the cleaning portion may be separated by a base element.

Conveniently, the cap removal portion and the cleaning portion extend from either sides of the base element.

Optionally, the cap removal portion and the cleaning portion extend from a base element in a substantially opposite direction to each other. This configuration of the tool facilitates multipurpose use for the tool. In other words, same tool may be used for cap removal and the cleaning of the device.

Conveniently, the movable member is configured to slide coaxially within the rigid member, between a first position and a second position. This movement of the movable member between the first position and the second position, facilitates in disengaging the cap and the body.

Conveniently, the cleaning portion, comprises one or more cleaning elements, adapted to clean the HNB device.

Optionally, the one or more cleaning elements may be at least one of brushes or bristles. The cleaning elements facilitate removing debris deposited on the heating element and the body.

Advantageously, the cap removal portion and the cleaning portion may be enclosed by at least one enclosure. The enclosure provides provision for handling the tool during operation of the tool.

Conveniently, the enclosure is engaged with the tool by one of a threaded connection, a snap fit connection and an interference fit connection. This configuration of the enclosure facilitates in easy disengagement of the enclosure to expose either of the cap removal portion and the cleaning portion of the tool.

Conveniently, the tool includes a rigid member and a movable member. The rigid member may include a plurality of flexible engaging arms. The plurality of flexible engaging arms may be operable between a first condition and a second condition.

Advantageously, the movable member may be configured to slide coaxially within the rigid member, between a first position and the second position. This operational movement of the movable member within the rigid member may allow disengagement of the cap and the body, for removing foreign particles, like debris, from the main body and the cap.

Conveniently, the movable member comprises a plunger and a recess extending from one end of the plunger.

Advantageously, the tool may be received by a cavity defined in the device, the plunger may contact a portion of the inner wall of the cavity and trace the same for removing debris deposited on the inner wall of the cavity.

Advantageously, the recess may be adapted to receive a heating element of the HNB device, and remove debris deposited on the heating element. Removing the debris deposited on the heating element may facilitate in effective heat dissipation of the heating element.

According to a ninth aspect of the first mode of the present disclosure, there is provided an HNB device, capable of being operable by a tool. The HNB device comprises a cap and a main body, where the cap is removably attached to the main body.

Conveniently, the cap and the main body of the device may be disengaged by the tool.

Optionally, the HNB device may be cleaned by the tool.

The locating tab of the tool may be configured to extend on at least one flexible engaging arm of the plurality of flexible engaging arms.

Conveniently, the complete alignment of the locating tab with the at least one notch may define a dead stop for the tool with respect to the device.

In some embodiments, the cap is releaseably secured to the main body of the device by a retaining means.

In some embodiments, the retaining means comprises: at least one flexible locking arm extending from the main body; and a locking protrusion disposed on each of the at least one locking arm, the locking protrusion configured to extend into a corresponding slot located in the cap.

In some embodiments, each locking protrusion includes a hooked end of the corresponding locking arm.

In some embodiments, the locking protrusion abuts a first end of the corresponding slot to limit an extent of movement of the cap relative to the main body, and to thereby prevent removal of the cap from the main body.

In some embodiments, the cap includes a cavity for receiving at least a portion of a smoking substitute consumable.

In some embodiments, the removal key is sized so that at least a portion of the removal key is received in the cavity to release the cap from the main body.

In some embodiments, the slot is formed through a wall of the cavity.

Optionally, the tool comprises a static member and a movable member.

Optionally, the static member comprises a collar and a plurality of flexible engaging arms extending from the collar, and wherein the plurality of flexible engaging arms are moveable between a contracted arm position and a separated arm position.

Optionally, the plurality of flexible engaging arms are insertable into a cavity formed in the cap, through an opening of the cavity.

Optionally, the movable member comprises a plunger, configured to slide co-axially within the collar, between a first plunger positon and a second plunger position.

Optionally, the plunger in the second plunger position maintains the flexible arms in the separated arm position.

Optionally, at least a portion of the plunger is configured to contact the cavity, to thereby scrape debris deposited on a wall of cavity, during movement from the first plunger position to the second plunger position.

Optionally, wherein the plurality of flexible engaging arms engages with at least one moveable hinge in the main body of the device, on insertion into the cavity of the cap, to thereby disengage the cap.

According to a tenth aspect of the first mode there is provided, a smoking substitute system, comprising a heat not burn device; and a tool according to the third, fourth, fifth, sixth, seventh and eighth aspects of the first mode.

Optionally, the smoking substitute system further comprises a heat not burn consumable, wherein at least a portion of the consumable is insertable into the cap of the device.

According to an eleventh aspect of the first mode, there is provided a heat not burn device comprising: a main body; and a cap releasably connected to the main body, wherein the cap and the main body are configured to be mutually disengaged by a tool.

According to a twelfth aspect of the first mode, there is provided a smoking substitute kit including a substitute smoking device according to the first aspect of the first mode, further including the removal key.

In some embodiments, the removal key is shaped to disengage the retaining means to thereby permit the disengagement of the cap from the main body.

In some embodiments, the removal key includes at least one projection, wherein each of the at least one projection intrudes into the corresponding slot to disengage the locking protrusion from the corresponding slot.

In some embodiments, the projection is located on an unlocking arm of the removal key.

In some embodiments, the removal key includes two or more locking arms.

In some embodiments, the removal key includes a separator to hold the locking arms in a mutually separated position to thereby disengage each corresponding locking protrusion from the corresponding slot.

In some embodiments, the separator is moveable relative to the locking arms.

According to a thirteenth aspect of the first mode, there is provided a removal key for a smoking substitute device according to the first aspect of the first mode.

According to a fourteenth aspect of the first mode, there is provided a removal key for a smoking substitute kit according to the twelfth aspect of the first mode.

In some embodiments of any aspect of the first mode, the smoking substitute device is a heat not burn device.

In some embodiments of the first mode, the body includes a transverse cavity extending transverse to the longitudinal axis of the body. The transverse cavity may extend laterally and may be located in the body such that at least the base of the heating element is parallel to the transverse cavity.

In some embodiments, at least one locking arm extends from the body. The locking arms lock or retain the cap with the body. The locking arms are provided with a locking protrusion at a distal end. The locking protrusion extends transversely to the longitudinal axis of the body. The locking arms are positioned such that when the cap is mounted on the body, the locking arms engage the cap to retain the cap on the body.

In some embodiments, the removal key may be configured to displace the locking arms to enable separation of the cap from the body. In some embodiments, the removal key has at least one unlocking arm. The unlocking arms are adapted to engage the locking arms to displace the locking arms for separating the cap from the body. Each unlocking arm may be provided with an unlocking projection. The unlocking projection may extend in a direction transverse to the longitudinal axis of the unlocking arm. The unlocking projections are adapted to engage the locking protrusions to displace the locking protrusions for releasing the cap from the body.

In some embodiments, the removal key includes separator. In some embodiments, the separator is a central rod. A collar may be positioned concentrically on the central rod. The collar may be placed movably on the central rod such that the collar moves relative to the central rod along a longitudinal axis of the central rod. The unlocking arms may extend from the collar along the longitudinal axis of the central rod. The collar may be movable on the central rod between an insertion portion and an unlocking position. In the insertion position, the central rod may be kept away from the unlocking protrusions and the unlocking arms may flex radially inwards relative to the longitudinal axis of the central rod. In the unlocking position, the central rod moves adjacent to the unlocking protrusions to prevent flexing of the unlocking arms in a direction radially inwards relative to the longitudinal axis of the central rod. The collar may be biased to move towards the insertion position using any suitable means such as a coil spring.

The removal key may be configured for insertion into the cavity. The unlocking protrusions are configured such that when the unlocking arms are inserted into the cavity, the unlocking arm displaces the locking arms to release engagement of the locking arms from the slots. The unlocking protrusions may have dimensions that interfere with the width of the cavity. In order to allow insertion of the unlocking arms in the cavity, in the insertion position, the central rod is away from the distal ends of the unlocking arms to allow the distal ends of the unlocking arms to flex radially inwards to enable insertion of the unlocking arms with the unlocking protrusions into the cavity. The flexing may be achieved when the unlocking protrusions abut and slide against an inner surface of cap defining the internal cavity. The unlocking protrusions, as shown in the embodiment illustrated, may be provided with tapered surfaces to guide the flexing movement of the unlocking arms in and out from the cavity and the slots.

In some embodiments, the removal key includes a first cover to cover the unlocking arms when not in use.

Optionally, the cap may be retainable on the body in the second position by a retaining means.

Optionally, the retaining means may be any suitable retaining means, for example interference fit or latch mechanism. Advantageously, said retaining means may allow the cap to be positioned and retained in the second position during visual inspection and/or cleaning, and may stop it from moving further along the longitudinal axis once it reaches the second position, thereby it may prevent the cap from being inadvertently removed from the body.

Optionally, the retaining means comprises at least one flexible locking arm extending from the body, and a locking protrusion disposed on the at least one locking arm. The locking protrusion may be configured to engage a slot defined in the cap to retain the cap on the body. Optionally, the locking protrusion may be retained in the slot when the cap moves between the first position and the second position. Advantageously, the locking protrusion may slide along the slot when the cap moves from the first position to the second position, and thereby prevents relative rotation between the cap and the body.

Optionally, the body defines a transverse cavity that opens through a first side wall of the body, the opening may be juxtaposed with a base of the heating element to at least partially expose the base of the heating element when the cap is in the second position. For example, the opening at the side wall of body leads to said transverse cavity. The transverse cavity may be juxtaposed lateral to the base of the heating element, or in other words, the transverse cavity may open in a direction orthogonal to the longitudinal axis of the body.

Optionally, the transverse cavity may extend from the first side wall of the body to a second side wall opposite to the first side wall. In other words, the transverse cavity may be a through hole extending through both the first side wall and the second side wall of the body. Advantageously, this may allow loose debris to be effectively discharged from the opening or through hole.

Optionally, the locking protrusion is configured to prevent separation of the cap from the device by abutting an end of the slot once the cap has moved to the second position, as such blocking further movement of the cap. In other words, the locking protrusion may prevent detachment of the cap by blocking movement of the cap by abutting a peripheral surface of the cap defining the slot when the cap is in the second position.

Optionally, the cap may define a cavity for receiving at least a portion of an aerosol-forming article. Optionally, the slot may be connected with or open to the cavity.

In a fifteenth aspect of the first mode according to the present disclosure, there is provided a tool for separating the cap from the body of the smoking substitute device is disclosed. The tool may be used to separate or dislodge the cap from the device for a deep cleaning of the heating element. The tool has unlocking means at one end and a cleaning means at another end. The tool may provide for a compact and easy maintenance of the smoking substitute device of the smoking substitute system of the present disclosure.

The tool may have at least one unlocking arm and an unlocking protrusion disposed on the unlocking arm. The unlocking protrusion may be configured to displace a corresponding locking protrusion disposed on a locking arm extending from the body of the device to disengage the locking protrusion from a slot in the cap. Advantageously, the tool prevents the inadvertent removal of the cap from the body of the device.

Optionally, the tool further comprises a cleaning means for cleaning the heating element. Advantageously, the cleaning means to conveniently allow the user to physically clean the heating element once the cap is removed by the tool, and thereby allowing the heating element to be better clean, e.g., to "deep clean" the heating element. Optionally, the cleaning means comprises at least one cleaning bristle. Advantageously, in use the bristle may scrape on the surface of the heating element, and thereby it may allow the heating element to be cleaned in a more efficient manner.

Optionally, the tool further comprises a central rod, the at least one unlocking arm extending along a longitudinal axis of the central rod in a first direction and the cleaning means extending in a second direction opposite to the first direction.

Optionally, the tool comprises a collar around the central rod having the unlocking arm extended in the first direction, the collar being movable between an insertion position and an unlocking position, wherein in the insertion position the at least one unlocking arm is allowed to flex and in the unlocking position the central rod prevents the flexing of the unlocking arm. The collar may comprise a ring-shaped collar. The collar may be positioned concentrically on the central rod.

Optionally, the tool further comprises a first cover configured to cover the at least one unlocking arm and a second cover configured to cover the cleaning means.

Optionally, the tool has an external profile similar to that of an aerosol-forming article for a smoking substitute system.

Optionally, the tool may comprise a rigid member and a movable member.

Conveniently, the tool further comprises an element disposed in the rigid member. The element may extend from the rigid member, into a sliding path defined on the movable member.

Optionally, the element may facilitate in locking the movable member in a first position and a second position, relative to the rigid member.

Advantageously, the element is adapted for visually indicating the orientation of the tool relative to the HNB device.

Conveniently, the visual indication of the orientation of the tool assists a user in locating the tool in a correct position relative to the HNB device.

Conveniently, the rigid member may comprise a plurality of flexible engaging arms, wherein the plurality of flexible engaging arms are operable between a first condition and a second condition. The operation of the flexible engaging arms to a second condition may facilitate in disengaging the cap and the body.

Advantageously, the movable member may be configured to slide coaxially within the rigid member, between a first position and a second position. This sliding movement of the movable member may facilitate in disengaging the cap and the main body.

Advantageously, the first position of the movable member, corresponds to a fully disengaged position of the tool and the second position corresponds to fully engaged position of the tool. The fully engaged position of the tool facilitates in disengaging the cap and the main body.

Conveniently, the movable member may be defined with a slot for receiving the element. The slot may facilitate in locking the movable member at the first position and the second position.

According to a sixteenth aspect of the first mode of the present disclosure, there is provided a cap removal tool for removing the cap of a smoking substitute device, the tool comprising: a cap removal portion for engagement with the cap, the cap removal portion being movable between a first position and a second position relative to a handle portion of the tool.

Optionally, the handle portion comprises a cleaning portion.

Optionally, the handle portion includes a collar.

Optionally, the collar includes a grip portion allowing the user to grip the tool when moving the cap removal portion between the first position and the second position.

Optionally, the cleaning portion includes a cleaning cover.

Optionally, the cap removal portion includes a cap removal cover.

Optionally, the cap removal portion and the cleaning portion are located at opposing ends of the tool, wherein the tool is elongate.

Optionally, the collar is located between the cleaning portion and the cap removal portion.

Optionally, a width of the collar is different from a width of the cleaning portion.

Optionally, a width of the collar is different from a width of the cap removal portion.

Optionally, the collar includes the visual indicator for alignment of the cap removal portion with the cap.

Optionally, movement of the collar relative to the cap removal portion activates the cap removal mechanism.

Optionally, longitudinal movement of the collar relative to a cap removal end of the tool activates the cap removal mechanism.

Optionally, the collar moves longitudinally on a central rod along a longitudinal axis of the central rod.

Optionally, locking arms extends from one end of the collar along the longitudinal axis of the central rod.

In some embodiments, the device has an elongate body which may also referred as "main body" or "body". An end of the elongate body may be configured for engagement with an aerosol-forming article. For example, the body may be configured for engagement with a heated tobacco (HT) consumable (or heat-not-burn (HNB) consumable) The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The body may define a transverse cavity extending orthogonal to the longitudinal axis of the body. The transverse cavity may extend laterally and may be located on the body such that at least the base of the heating element is juxtaposed with the transverse cavity.

Further, at least one locking arm may extend from the body. The locking arms may lock or retain the cap with the body. The locking arms may be provided with a locking protrusion at a distal end. The locking protrusion may extend transversely to the longitudinal axis of the body. The locking arms may be positioned such that when the cap is mounted on the body, the locking arms may engage the cap to retain the cap on the body.

The cap may be provided with a slot extending along the longitudinal axis of the body (when the cap is retained on the body), and the locking protrusions may be configured to engage the slot. The slot may be elongated such that the cap may be moved or slide relative to the body along the longitudinal axis of the body. The locking protrusion may have an abutment surface to engage a peripheral surface of the cap that defines the slot to retain or lock the cap with the body.

The cap may be movable between a first position and a second position. When the cap is in the first position, the cap may conceal the heating element. When the cap is in the second position, the heating element may be at least partially exposed, e.g., through a window or opening at the side wall of the body. When the heating element is partially exposed, the heating element may be examined visually to ascertain if cleaning of the heating element is required. If required, when the cap is in the second position, the heating element may be at least partly cleaned by blowing air through the opening or simply shaking, tilting and or tapping the device gently to dislodge and remove the debris.

The smoking substitute system of the present disclosure may further include a tool for separation of the cap from the body. The tool may be configured to displace the locking arms to enable separation of the cap from the body. The tool may comprise at least one unlocking arm. The unlocking arms may be adapted to engage the locking arms to displace the locking arms for separating the cap from the body.

Each unlocking arm may be provided with an unlocking protrusion. The unlocking protrusion may extend in a direction orthogonal to the longitudinal axis of the unlocking arm. The unlocking protrusions may be adapted to engage the locking protrusions to displace the locking protrusions for releasing the cap from the body.

The tool may further include a central rod. A collar may be positioned concentrically on the central rod. The collar may be placed movably on the rod such that the collar moves relative to the central rod along a longitudinal axis of the central rod. The unlocking arms may extend from the collar along the longitudinal axis of the central rod. The collar may be movable on the central rod between an insertion portion and an unlocking position. In the insertion position, the central rod may be kept away from the unlocking protrusions and the unlocking arms may flex radially inwards relative to the longitudinal axis of the central rod. In the unlocking position, the central rod may move adjacent to the unlocking protrusions to prevent flexing of the unlocking arms in a direction radially inwards relative to the longitudinal axis of the central rod. The collar may be biased to move towards the insertion position using any suitable means such as a coil spring.

The tool may be configured for insertion into the cavity. The unlocking protrusions may be configured such that when the unlocking arms are inserted into the cavity, the unlocking arm displaces the locking arms to release engagement of the locking arms from the slots. The unlocking protrusions may have dimensions that interfere with the width of the cavity. In order to allow insertion of the unlocking arms in the cavity, in the insertion position, the central rod may be spaced from the distal ends of the unlocking arms to allow the distal ends of the unlocking arms to flex radially inwards to enable insertion of the unlocking arms with the unlocking protrusions into the cavity. The flexing may be achieved when the unlocking protrusions abut and slide against an inner surface of cap defining the internal cavity. The unlocking protrusions, as shown in the embodiment illustrated, may be provided with tapered surfaces to guide the flexing movement of the unlocking arms in and out from the cavity and the slots.

The tool may further comprise a cleaning means for cleaning the heating element. The cleaning means may be in form of cleaning bristles. The cleaning bristles may be rubbed on the outer surface of the heating element to clean or scrap off any debris or residuals from the heating element.

The tool may include a first cover to cover the unlocking arms when not in use. Further, a second cover may be provided to cover the cleaning bristles when not in use.

The device may include a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slideably engaged with the body of the device, and may be slideable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

In some embodiments, the smoking substitute system may be provided with the tool for disengaging the cap and the body of the device. The tool may comprise a cap removable portion for disengaging the cap and the main body of the device. Further, a cleaning portion may also be provided for cleaning the device. The tool may be insertable into the cavity defined by the cap or the cap and the body of the device. The tool may be capable of operating between a first position and a second position, for disengaging the cap and the body, and cleaning the device.

The tool may be configured such that, when the tool is engaged with the device (e.g., received in the cavity), only a portion of the tool is received in the cavity. Further, a portion of the tool (not received by the cavity), may protrude from (i.e., extend beyond) the opening. The protruding portion of the tool may be defined with a handle, which may be used for the purpose of gripping and operating the tool, to disengage the cap and the body, and cleaning the device.

In one instance, when the cap removal portion is inserted into the cavity, the enclosure enclosing the cleaning portion may define a handle for operating the cap removal portion and when the cleaning portion is being engaged in the cavity, the enclosure enclosing the cap removal portion may define a handle for operating the cleaning portion of the tool.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or WiFi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a seventeenth aspect of the first mode, there is provided a system (e.g., a smoking substitute system) comprising a device or kit according to the first, second, eighth or twelfth aspects of the first mode and an aerosol-forming article. In an eighteenth aspect of the first mode, there is provided a system (e.g., a smoking substitute system) comprising a tool according to the third, fourth, fifth, sixth, seventh, eighth or fifteenth aspects of the first mode along with a device and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

The system may include a device which may include the main body and the cap, where the cap may be removably attached to the body. Further, the system may include the tool, as provided in the first aspect of the first mode, which may be adapted for disengaging the cap and the main body. The tool may be adapted for insertion into the opening of the cap, in at least one defined orientation. Further, the plurality of flexible engaging arms of the tool may be insertable into a cavity defined in the cap in at least one defined orientation, to engage with at least one flexure bearing defined in the main body of the HNB device. The movable member, of the tool, on operation from the first position to the second position, may be configured to translate the plurality of flexible engaging arms to the second condition, for displacing the at least one flexure bearing of the HNB device to disengage the cap and the main body. The hook of the at least one flexure bearing may generally be referred to as a locking element that engages and disengages with the cap, when using the tool for the HNB device described herein.

Optionally, the at least one flexure bearing may be moved from a lock position, where it is engaged with the cap to an un-lock position where a hook of the at least one flexure bearing is moved out of a slit defined in the cavity of the cap to disengage the cap and the main body. This ensures safe disengagement of the cap and the main body.

The tool or at least the portion of the tool may be insertable into the cavity, only upon removal (e.g., dislodging or disengaging) of the aerosol-forming substrate or the portion of the aerosol-forming substrate accommodated within the cavity, to render the cavity empty. The empty cavity may provide sufficient volume for the tool or at least portion of the tool to be accommodated, whereby operation of the tool may then be uninterrupted for disengaging the cap and the body.

The device may include the main body and the cap, where the cap may be releasably attached to the body. Further, the tool, as provided in the first aspect of the first mode, included in the system, may be configured to disengage the cap from the main body. The tool may include a rigid member, which may be configured with a collar and a plurality of flexible engaging arms extending from the collar. The plurality of flexible engaging arms may be operable between a first condition and a second condition. Further, the tool may also include a movable member, which may be coaxial with the rigid member. The movable member may be operable between a first position and a second position that may deform the plurality of flexible engaging arms between the first contracted position and the second separated position.

Optionally, an end of each of the plurality of flexible engaging arms may define a clearance of 0.5 mm to 1.5 mm with the rigid base region of a cavity defined by the cap, when the tool may be fully inserted into the device.

The tool or at least the portion of the tool may be insertable into the cavity, only upon dislodging of the aerosol-forming substrate or the portion of the aerosol-forming substrate accommodated within the cavity. The dislodging of the aerosol-forming substrate or the portion of the aerosol-forming substrate from the cavity may provide sufficient volume for the tool or at least portion of the tool to be accommodated, whereby operation of the tool may then be uninterrupted for disengaging the cap and the body.

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming article may be capable of engaging with the device (i.e., received by the cavity of the cap). The aerosol-forming substrate is capable of being heated to release at least one volatile compound that can form an aerosol. The aerosol-forming substrate may be located at the upstream end of the article/consumable.

The tool of the system may be capable of engaging with the device (i.e., received by the cavity of the cap), upon dislodging the aerosol-forming article, to disengage the cap and the main body of the device. The tool may comprise the cap removal portion and the cleaning portion. The cap removal portion may comprise a rigid member a movable member.

Optionally, the movable member may be configured to slide co-axially within the rigid member in a first position and a second position, to facilitate disengaging of the cap and the main body.

Conveniently, the cleaning portion of the tool may comprise one or more cleaning elements, which extending from the base element in a direction opposite to the direction of the plurality of flexible arms outwardly. The one or more cleaning elements may be at least one of brushes and bristles. The brushes or the bristles may be adapted for cleaning the heating element (thus, the heater), which will be exposed once the cap and the body are disengaged.

Advantageously, the cap removal portion of the tool may comprises a plurality of flexible engaging arms, which may be insertable into a cavity defined in the cap, to engage with at least one flexure bearing defined in the main body of the HNB device, and displacement of the movable member from the first position to the second position, is configured to translate the plurality of flexible engaging arms to the second condition, for displacing the at least one flexure bearing of the HNB device to disengage the cap and the main body.

The system mainly includes a device which may include the main body and the cap, where the cap may be removably attached to the body. Further, the system may include a tool, as provided in the first aspect of the first mode, which may be adapted for disengaging the cap and the main body. The tool may include a rigid member, which may comprise a plurality of flexible engaging. The plurality of flexible engaging arms may be operable between a first condition and a second condition. Further, the tool may also include a movable member, which may be coaxial with the rigid member. The movable member may be operable between a first position and a second position that may translate the plurality of flexible engaging arms between the first condition and the second condition.

Optionally, each of the at least one flexure bearing may include a hook, adaptable to engage in a slit defined in the cap, to retain the cap in the main body. Further, the at least one flexure bearing may be moved from a locked position where the at least one flexure bearing may be engaged with the cap to a un-locked position where the hook of the at least one flexure bearing may be moved out of a slit defined in the cavity of the cap to disengage the cap and the main body. The hook of the at least one flexure bearing may be displaced outwardly from the slit by the movable member to disengage the cap and the main body. This way, the cap may be disengaged from the body by engaging the tool. The hook of the at least one flexure bearing may generally be referred to as a locking element that engages and disengages with the cap, when using the tool for the HNB device describes herein.

The tool or at least the portion of the tool may be insertable into the cavity, only upon removal (e.g., dislodging or disengaging) of the aerosol-forming substrate or the portion of the aerosol-forming substrate accommodated within the cavity, to render the cavity empty. The empty cavity may provide sufficient volume for at least a portion of the tool to be accommodated, whereby the tool may be operated to disengage the cap and the body.

In some embodiments, the plurality of flexible engaging arms may be insertable into a cavity defined in the cap. The plurality of flexible engaging arms may engage with at least one flexure bearing defined in the main body of the HNB device, on complete insertion into the cap. Further, the movable member, on operation from the first position to the second position, may be configured to translate the plurality of flexible engaging arms to the second condition. At the second condition, the plurality of flexible engaging arms may displace the at least one flexure bearing of the HNB device, to disengage the cap and the main body.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris,* Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco). *Lobelia siphilitica, Nepeta cataria* (Catnip). *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (Damniana), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a nineteenth aspect of the first mode of the present disclosure, there is provided a HNB device. The HNB device may comprise a main body and a cap, where the cap may be releasably attached to the main body. The cap and the main body may be configured to be disengaged by a tool.

According to a twentieth aspect of the first mode of the present disclosure, there is provided an HNB device, which may be capable of being operated by a tool. The device comprises a cap and a body, where the cap may be removably attached to the main body.

Conveniently, the cap and the main body are disengaged by the tool. The main body and the cap are disengaged by the cap removal portion of the tool.

Conveniently, the device is cleaned by the tool. The device is cleaned by the cleaning portion of the tool.

According to a twenty-first aspect of the first mode of the present disclosure, there is provided a method of cleaning the HNB device. The method comprising inserting the tool into the device, to clean the cavity and the heating element of the device.

In some embodiments the method may comprise operating the tool to displace the movable member coaxially within the rigid member from a first position to a second position, to scrape debris on the inner wall, and enclose the heating element and to scrape debris deposited on the heating element of the device.

Conveniently, the tool may be received by a cavity defined in the cap of the device. Upon insertion of the tool, the plurality of engaging arms engages with at least one flexure bearing defined in the main body of the device, Further, operation of the movable member from the first position to the second position may translate the plurality of flexible engaging arms to the second condition, for displacing the hook of the at least one flexure bearing of the device to disengage the cap and the main body.

According to a twenty-second aspect of the first mode of the present disclosure, there is provided a HNB device, which may comprise a main body and a cap.

Conveniently, the cap may be removably attached to the main body, and may be disengaged by a tool.

In some embodiments, the cap may be defined with the cavity to receive the tool. Further, the plurality of flexible engaging arms of the tool may be insertable in the cavity of the cap. The plurality of flexible engaging arms may engage with at least one flexure bearing defined in the main body of the HNB device. Also, the movable member of the tool, on operation from the first position to the second position, may be configured to translate the plurality of flexible engaging arms to the second condition. In the second condition, the plurality of flexible engaging arms may displace the at least one flexure bearing of the HNB device to disengage the cap and the main body.

According to a twenty-third aspect of the first mode of the present disclosure, there is provided a method of disengaging a cap and a main body of a HNB device. The method comprises acts of inserting a tool into the cap and the HNB device. Further, the tool may be operated to disengage the cap and the main body.

Conveniently, a cavity defined in the cap, may be configured to receive the tool. The plurality of flexible engaging arms of the tool may be inserted in the cavity of the cap, so as to engage with at least one flexure bearing defined in the main body of the HNB device. Further, the movable member of the tool may be operated from the first position to the second position, to translate the plurality of flexible engaging arms to the second condition. The plurality of flexible engaging arms, at the second condition, may displace the at least one flexure bearing of the HNB device to disengage the cap and the main body.

The disclosure includes the combination of the aspects and preferred features of the first mode described except where such a combination is clearly impermissible or expressly avoided.

The skilled person will appreciate that except where mutually exclusive, a feature or parameter described in relation to any one of the above aspects of the first mode may be applied to any other aspect of the first mode. Furthermore, except where mutually exclusive, any feature or parameter of the first mode described herein may be applied to any aspect and/or combined with any other feature or parameter of the first mode described herein.

Second Mode: A Heated Tobacco Device Comprising a Mechanism for Easy Removal of a Consumable from the Device At its most general, a second mode of the present disclosure relates to a heated tobacco device comprising a mechanism for easy removal of a consumable from the device.

According to a first aspect of the second mode of the present disclosure, there is provided a smoking substitute device comprising a housing, a cavity for receipt of an aerosol-forming article, a heater projecting into the cavity along a longitudinal axis so as to be inserted into the aerosol-forming article when received in the cavity, and an article interaction component rotatably engaged with the housing for rotating the aerosol-forming article about the longitudinal axis of the heater.

A device having an article interaction component that is able to rotate the consumable, may allow easier and/or cleaner removal of a consumable from the heater of the device. That is, rotation of the consumable relative to the heater (as opposed to e.g., lifting of the consumable along the heater) may break the connection between the consumable and the heater in a manner that minimizes the quantity of material (of the consumable) that remains on the heater.

Optional features will now be set out. These are applicable singly or in any combination with any aspect of the second mode.

The article interaction component may be configured to move the aerosol-forming article along the longitudinal axis of the heater. The article interaction component may be slidably engaged with the housing. The article interaction component may be configured to rotate the aerosol forming article about the longitudinal axis as the aerosol-forming article is moved along the longitudinal axis of the heater. In other words, the article interaction component may be configured to twist the aerosol-forming article to release it from the heater. The article interaction component may be engaged with the housing via a threaded connection or helical track.

The article interaction component may comprise a user interaction portion configured such that a user can move (i.e., rotate and/or translate) the article interaction component relative to the housing. The user interaction portion may comprise an outer surface arranged for gripping by a user. The outer surface may comprise a surface finish (e.g., a textured surface) or surface features (e.g., ridges) to facilitate gripping by a user. The outer surface may define an outer (i.e., exposed) surface of the device.

The article interaction component may comprise an engagement portion for engaging the aerosol forming article. The engagement portion may be in the form of one or more inwardly directed projections. The one or more projections may be movable in a radial direction between a position in which they engage the consumable and a position in which they are spaced from the consumable. The engagement portion may otherwise be in the form of an iris mechanism that closes around the article so as to grip the article. The engagement portion may alternatively be in the form of a deformable region that can be squeezed by a user so as to grip the article. In this respect, the engagement portion may be an element or region that can be moved inwardly (i.e., with respect to the housing) so as to grip the article.

The article interaction component may partly or fully define the cavity (into which the article is received). The article interaction component may comprise one or more walls at least partly defining the cavity for receipt of the aerosol-forming article. The one or more walls may be arranged so as to form a friction fit with the aerosol-forming article when received in the cavity. The one or more walls may comprise ribs (e.g., longitudinally extending ribs) for engaging the article. The ribs may define the engagement portion. Thus, the engagement portion may simply be a portion that grips the article (and may not necessarily be movable).

The one or more walls may be inclined relative to the longitudinal axis. In this way, the one or more walls may define a cavity that is tapered (i.e., tapers outwardly from a base (proximate a base of the heater) to an opening (distal from a base of the heater)). In this respect, the one or more walls may define a cavity having a generally frustoconical shape. The article may be gripped by the one or more walls at the narrower end of the cavity. The frustoconical shape may also guide the article into the cavity as it is inserted so as to center the article in the cavity.

The one or more walls may comprise a base portion. The base portion may define a base of the cavity opposing an opening of the cavity (into which the article is received). The base portion may support an end of the aerosol-forming article when received in the cavity. The heater may project through an aperture formed in the base portion and into the cavity.

The article interaction component may be a cap of the device. The article interaction component may form part of a cap of the device. The cap may be a removable cap of the device. As is set forth above, the cap may at least partly define the cavity. The cap may be slidably mounted with respect to the housing of the device. In this respect, the cap may be slidable along the longitudinal axis towards and away from the housing. The cap may be slidable between an open position (e.g., away from the housing) and a closed position (towards the housing). In the closed position the heater may project through the aperture in the base portion. In the open position the heater may not project through the aperture, or only a portion of the heater (e.g., a distal end of the heater) may project through the aperture.

When the cap is removed or partially removed from the housing, the base portion may move the article (i.e., by contact with the end of the article) longitudinally along the heater so as to remove or at least partially remove the article from the heater. That is, the base portion may lift or pull the article away from the heater as the cap is removed from the housing.

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise an elongate body, which may constitute (or may comprise) the housing. An end of the elongate body may be configured for engagement with the aerosol-forming article. The aerosol-forming article may be of the type that comprises an aerosol former (e.g., carried by an aerosol-forming substrate). The aerosol-forming article may be a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The housing may define the cavity (i.e., that is configured for receipt of at least a portion of the consumable).

The heater may comprise a heating element, which may be in the form of a rod that extends from the body of the device (i.e., so as to project into the cavity). The heating element may extend from the end of the body that is configured for engagement with the aerosol-forming article.

The heater (and thus the heating element) may be rigidly mounted to the body. The heating element may be elongate and may, for example, have a transverse profile (i.e., transverse to the longitudinal axis of the heating element) that is substantially circular (i.e., the heating element may be generally cylindrical). The heating element may alternatively be in the shape of a tube. The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The length of the heating element (i.e., along the longitudinal axis of the heater) may be less than the depth of the cavity. Hence, the heating element may extend for only a portion of the length of the cavity.

As is set forth above, the heater is configured for insertion into an aerosol-forming article (e.g., a HT consumable) when the aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate the aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of the aerosol-forming article (e.g., a HT consumable).

Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

The article interaction component may interact with the article at an axial location or region that is adjacent to or proximate to the heater. That is, rotation of the article (by the article interaction component) may occur at the part of the article that is penetrated by the heater.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The article interaction component may comprise an actuator (e.g., comprising a motor), which may be configured to rotate the article. The actuator may be controllable by the controller.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the second mode, there is provided a system (e.g., a smoking substitute system) comprising a device as described above with respect to the first aspect of the second mode, and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

As is discussed above, a cavity defined by the article interaction component of the device may be configured for a friction fit with the article such that the article is able to be rotated by rotation of the article interaction component.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris,* Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a third aspect of the second mode of the present disclosure, there is provided a method of using the system according to the second aspect of the second mode, the method comprising inserting the article into the device and heating the article using the heater of the device.

In some embodiments the method may comprise inserting the article into a cavity within the housing of the device and penetrating the article with the heating element of the device upon insertion of the article.

The method may comprise rotating the article interaction component of the device so as to rotate the article to release the article from the heater. The method may comprise rotating the article interaction component, so as to rotate the article, after an operating cycle of the device in which the article is consumed. In other words, the article may be rotated for removal (by rotation of the article interaction component) once it is consumed by way of a heating cycle (and corresponding consumption by the user).

The disclosure includes the combination of the aspects and preferred features of the second mode described except where such a combination is clearly impermissible or expressly avoided.

The skilled person will appreciate that except where mutually exclusive, a feature or parameter described in relation to any one of the above aspects of the second mode may be applied to any other aspect. Furthermore, except where mutually exclusive, any feature or parameter of the second mode described herein may be applied to any aspect and/or combined with any other feature or parameter of the second mode described herein.

Third Mode: An Aerosol-Forming Delivery System Such as an HNB System

At its most general, a third mode of the present disclosure relates to an aerosol-forming delivery system, e.g., a smoking substitute system such as an HNB system. More specifically, the present disclosure relates to a smoking substitute device having a shroud for thermally insulating or thermally separating a heating element, in particular an isolative, or insulated, shroud, in particular at least partially covering or surrounding a smoking substitute consumable.

According to a first aspect of the third mode of the present disclosure, there is provided a smoking substitute device comprising a main body, a cavity and a heating element, wherein the cavity is arranged in the main body, wherein the heating element is arranged in the interior of the cavity, wherein the smoking substitute device is adapted for receiving a smoking substitute consumable, wherein the heating element is adapted for heating the smoking substitute consumable and wherein the smoking substitute device comprises a shroud at least partially surrounding the cavity, in particularly thermally insulating the heating element (14).

According to a further aspect of the third mode of the present disclosure, there is provided a smoking substitute system comprising a smoking substitute device in accordance with the present disclosure and a smoking substitute consumable.

According to a third aspect of the third mode of the present disclosure, there is provided a method of using a smoking substitute system according to the present disclosure, the method comprising inserting a smoking substitute consumable into a smoking substitute device and heating the smoking substitute consumable using a heating element.

Ideas and concepts of this disclosure may be considered to be based on the following observations and findings.

As mentioned before, the present disclosure is concerned with smoking substitute systems. A smoking substitute system may comprise a smoking substitute device or an aerosol-forming device, which may be a heat-not-burn (HNB) smoking substitute device. An HNB device is a device that is adapted for heating but not combusting the aerosol-forming substrate. This substrate may be made of tobacco material and may comprise additives assisting in the forming of the aerosol by the smoking substitute device. The smoking substitute device may comprise a main body for housing a heating element. The heating element may comprise an elongated, e.g., rod-shaped, tube-shaped or blade-shaped heating element. The heating element may project into or surround a cavity within the main body of the smoking substitute device, which cavity is for receiving a smoking substitute consumable.

The smoking substitute device may comprise an electrical power supply, e.g., a (rechargeable) battery for powering the heating element. It may further comprise a control unit to control the supply of power to the heating element.

In some embodiments, when a consumable is inserted into the cavity within the main body, a portion of the smoking substitute consumable is penetrated by the heating element upon insertion of the smoking substitute consumable. In particular, the heating element may penetrate the smoking substitute consumable in an area of the consumable where the aerosol-forming substrate, e.g., tobacco material, is arranged.

The heating element is thus arranged inside of the smoking substitute consumable and in particular inside of the tobacco material. When energy is provided to the heating element, the heating element is heated to a target temperature, preferably in the range above the vaporization temperature of nicotine contained in the tobacco material, but below the temperature where the tobacco material would start to burn or combust, e.g., the heating element may be heated to a temperature of above 170° C., the vaporization temperature of nicotine, but below 400° C. to avoid burning of the tobacco material in the consumable. Preferably, the target temperature may not exceed approx. 350° C.

Optional features will now be set out. These are applicable singly or in any combination with any aspect of the third mode of the present disclosure. In the context of the specification, the terms isolating shroud, insulating shroud, isolative shroud and shroud shall be understood as exchangeable.

In accordance with the present disclosure, the smoking substitute device comprises a shroud. The in particular isolative shroud may be arranged in the vicinity of the heating element and may be arranged for maintaining or keeping heat energy within the smoking substitute device and shielding the heat generated within the smoking substitute device from the outside, e.g., from a user holding the smoking substitute device.

In other words, the isolative shroud may be arranged to keep heat energy contained within its interior, which in particular may receive the smoking substitute consumable while maintaining a substantially lower outside temperature, e.g., a cooler temperature suitable for contact with skin of a user so as to avoid injury due to heat. The isolative shroud may be embodied as an elongated, substantially cylindrical tube of suitable dimensions for receiving a smoking substitute consumable. During operation of the smoking substitute device, a consumable may be inserted into the cavity of the smoking substitute device and in particular into the isolative shroud surrounding the cavity. A heating element may be arranged in a central part of the cavity and the isolative shroud respectively so as to provide a source of heat within the interior volume of the isolative shroud, e.g., the heating element may penetrate the smoking substitute consumable in an appropriate area or region to come into contact with tobacco material or another aerosol-forming substrate situated within at least a part of the smoking substitute consumable. The smoking substitute consumable in turn may be surrounded by the isolative shroud. In other words, an inserted smoking substitute consumable may be sandwiched between the heating element and the isolative shroud.

Heat generated by the heating element and released to the tobacco material thus heats the tobacco material to a desired temperature of operation. As mentioned before, the heating element is arranged within the tobacco material. During the process of heating or during operation of the smoking substitute device, tobacco material is substantially uniformly heated resulting in an outer surface area or peripheral region of the smoking substitute consumable to be heated to the temperature of operation as well. Accordingly, the isolative shroud surrounding at least a part of the smoking substitute consumable prevents heat from exiting the volume contained within the isolative shroud at least partially. In other words, the isolative shroud forms a protective barrier, in particular a heat barrier, between the interior of the isolative shroud containing the smoking substitute consumable and the heating element and the outside of the isolative shroud which may relate to an outside of the smoking substitute device with which a user may come into bodily contact with.

Optional features will be set out now. These are applicable singly or in any combination with any aspect of the third mode of the present disclosure.

The shroud may be coated in a thermally reflective substance to reflect heat towards the consumable to encourage internal heating and insulate the outer surface. The shroud may a tubular part into which the cavity for the consumable sits, in use. The shroud may extend at least the full length of the heater rod, may be part of the device, and may include engagement means to releasably engage the cap. The shroud may engage with the cavity, and may include a component (e.g., a hinged arm) that penetrates through the cavity wall for access from the cavity. The shroud may have an aperture for cleaning of the rod heater base. The aperture may be small enough to prevent a finger touching the rod heater. Increased isolation and heat retention may increase battery efficiency and may prevent reaching an outside of the device from going above a desired, in particular safe operating or handling temperature.

According to an embodiment of the present disclosure, the heating element may be arranged as a heater rod disposed with the main body and wherein the shroud (38) may enclose at least a portion of the heater rod so as to thermally isolate or insulate the heater rod.

According to an embodiment of the present disclosure, the cavity may be adapted for receiving the smoking substitute consumable and the isolative shroud may be at least partially surrounding at least a part of the received smoking substitute consumable.

By arranging the smoking substitute consumable in the interior of the isolative shroud, heat contained within aerosol generating material, e.g., tobacco material within the smoking substitute consumable, may be maintained inside of the isolative shroud while maintaining cooler surroundings.

According to a further embodiment of the present disclosure, the heating element may be adapted for penetrating the outer surface of the smoking substitute consumable to get into contact with tobacco material located inside the smoking substitute consumable upon insertion of the smoking substitute consumable into the smoking substitute device, for heating the tobacco material.

The tobacco material is thus sandwiched between the heating element and the isolative shroud to provide a volume of preferred heat transmission into the tobacco material while maintaining a cooler surrounding area.

According to a further embodiment of the present disclosure, the isolative shroud may be thermally insulating the interior of the isolative shroud from the exterior of the isolative shroud.

The isolative shroud is thus constituting a thermal barrier within the smoking substitute device, separating a volume of higher temperature in the interior of the isolative shroud from an outside with a reduced temperature.

According to a further embodiment of the present disclosure, the isolative shroud may be made of a polymer material, in particular may be made of polyether ether ketone (PEEK).

A polymer material may be a preferred material for forming an insulating element. PEEK is a linear, semicrystalline, thermoplastic high-performance plastic (high performance material) with a very high melting temperature of over 330° C. PEEK has a very high temperature resistance and good chemical resistance. PEEK is resistant to almost all organic and inorganic chemicals, even to hydrolysis up to about 280° C. It has a very high continuous service temperature of up to 260° C. and very high strength, very high rigidity and high toughness. Furthermore, PEEK has excellent abrasion resistance and excellent sliding properties as well as a low coefficient of linear thermal expansion. The plastic is flame retardant and self-extinguishing and produces very little smoke in the event of fire.

According to a further embodiment of the present disclosure, the interior of the isolative shroud may be coated with a thermally reflective coating for reflection of thermal energy towards the smoking substitute consumable.

An according heat reflecting coating may further enhance the barrier functionality of the isolative shroud insulating an interior of the shroud from an outside of the shroud.

According to a further embodiment of the present disclosure, the smoking substitute device may further comprise a second heating element, wherein the second heating element may be arranged between the smoking substitute consumable and the isolative shroud for heating at least a part of the outer surface of the smoking substitute consumable.

With an according arrangement, it may be possible to heat a smoking substitute consumable from both sides, i.e., from within by the first heating element as well as from the outside by the second heating element. Such may contribute to a more uniform heating of the tobacco material within the smoking substitute consumable. The second heating element may form integral part of the isolative shroud, or may be arranged as two separate devices which may be removable separate from each other from the smoking substitute device.

According to a further embodiment of the present disclosure, the heating element may be a rod-shaped heating element and the length of the isolative shroud may be at least the length of the rod-shaped heating element.

Accordingly, the isolative shroud may substantially completely encompass the heating element arranged within its interior, within the cavity respectively. The length of the isolative shroud may thus correspond to the length of the heating element.

According to a further embodiment of the present disclosure, the isolative shroud may comprise an aperture for allowing access to the interior of the cavity.

In particular, the aperture may allow access to the inside of the cavity for allowing access to the heating element. By said access, and in particular using an appropriate tool, the heating element may be cleaned. E.g., by an elongated cleaning element, the heating element may be cleaned by removing access or old tobacco material stuck to the heating element upon removal of the smoking substitute consumable.

According to a further embodiment of the present disclosure, the aperture may be located distal from an outward facing opening of the cavity.

In other words, the outward facing opening allows insertion of the smoking substitute consumable into the cavity while the aperture is arranged distal from said opening, e.g., at the base of the cavity close to the emerging heating element. In particular, in a case where the length of the isolative shroud is longer, in particular substantially longer, than the length of the heating element, arranging an aperture at the bottom of the cavity allows readily access to the heating element for cleaning purposes.

According to a further embodiment of the present disclosure, the aperture may be arranged in size such that a user of the smoking substitute device may not come into bodily contact with the heating element, in particular wherein the aperture on the shroud is sized to prevent finger access.

In other words, the aperture may be sized to accommodate a cleaning element while being too small to allow a user the touching of the heating elements, e.g., with their hands, in particular with a finger. By providing an accordingly sized aperture, injury of a user by a potentially still hot heating element may be prevented.

According to a further embodiment of the present disclosure, the smoking substitute device may be a heat-not-burn smoking substitute device. The skilled person will appreciate that except where mutually exclusive, a feature or parameter of the third mode described in relation to any one of the above aspects may be applied to any other aspect of the third mode. Furthermore, except where mutually exclusive, any feature or parameter of the third mode described herein may be applied to any aspect and/or combined with any other feature or parameter of the third mode described herein.

Fourth Mode: A Smoking Substitute System with a Smoking Substitute Device Having a Cap Movable Between Two Positions At its most general, a fourth mode of the present disclosure relates to a smoking substitute system with a smoking substitute device having a cap movable between two positions to selectively conceal or expose a heating element of the smoking substitute device. This may allow the user to physically access and clean the heating element in a more convenient manner, and thereby facilitate a more frequent cleaning routine. The present disclosure also relates to a tool for removing the cap form the device, and thereby preventing inadvertent removal of the cap. The tool may further comprise a cleaning means to conveniently allow the user to clean the heating element once the cap is removed by the tool.

According to a first aspect of the fourth mode of the present disclosure, there is provided a smoking substitute device having a body, a heating element extending from the body and a cap removably attached to the body. The cap is movable between a first position and a second position along a longitudinal axis of the body. In the first position the heating element is concealed in the cap and in the second position the heating element is at least partially exposed.

For example, in the first position, the cap may cover a window or an opening at the sidewall of the body that extends into a transverse cavity containing the heating element, and thereby conceals the heating element. In the second position, the cap is moved or slide to a location where it may no longer cover the opening, and thereby the heating element may be at least partially exposed through the opening. More specifically, the opening may be located adjacent to exposed portion of the heating element and therefore it may provide physical access to said exposed portion of the heating element.

By providing a device comprising a cap movable between two positions, the heating element may be cleaned in a more convenient manner. For example, when the cap is moved to the second position, the heating element may be exposed through a window or opening from the side of the device, as such said heating element may be visually inspected or cleaned through said opening. Advantageously, the user may thereby carry out a brief cleaning at the heating element without requiring a dedicated cleaning tool. For example, the user may simply blow through the opening or physically shaking, tilting and/or tapping the device to dislodge loose debris that are formed on the heating element. The user may also physically clean the exposed portion of the heating element, e.g., a base of the heating element, with the use of a tool, e.g., a brush. Further, the smoking substitute as disclosed herein may prolong the usability of the device before it requires deep cleaning or other such maintenance.

Optional features will now be set out. These are applicable singly or in any combination with any aspect of the fourth mode.

Optionally, the cap may be retainable on the body in the second position by a retaining means. Optionally, the retaining means may be any suitable retaining means, for example interference fit or latch mechanism. Advantageously, said retaining means may allow the cap to be positioned and retained in the second position during visual inspection and/or cleaning, and may stop it from moving further along the longitudinal axis once it reaches the second position, thereby it may prevent the cap from being inadvertently removed from the body.

Optionally, the retaining means comprises at least one flexible locking arm extending from the body, and a locking protrusion disposed on the at least one locking arm. The locking protrusion may be configured to engage a slot defined in the cap to retain the cap on the body. Optionally, the locking protrusion may be retained in the slot when the cap moves between the first position and the second position. Advantageously, the locking protrusion may slide along the slot when the cap moves from the first position to the second position, and thereby prevents relative rotation between the cap and the body.

Optionally, the body defines a transverse cavity that opens through a first side wall of the body, the opening may be juxtaposed with a base of the heating element to at least partially expose the base of the heating element when the cap is in the second position. For example, the opening at the side wall of body leads to said transverse cavity. The transverse cavity may be juxtaposed lateral to the base of the heating element, or in other words, the transverse cavity may open in a direction orthogonal to the longitudinal axis of the body.

Optionally, the transverse cavity may extend from the first side wall of the body to a second side wall opposite to the first side wall. In other words, the transverse cavity may be a through hole extending through both the first side wall and the second side wall of the body. Advantageously, this may allow loose debris to be effectively discharged from the opening or through hole.

Optionally, the locking protrusion is configured to prevent separation of the cap from the device by abutting an end of the slot once the cap has moved to the second position, as such blocking further movement of the cap. In other words, the locking protrusion may prevent detachment of the cap by blocking movement of the cap by abutting a peripheral surface of the cap defining the slot when the cap is in the second position.

Optionally, the cap may define a cavity for receiving at least a portion of an aerosol-forming article. Optionally, the slot may be connected with or open to the cavity.

In a second aspect of the fourth mode according to the present disclosure, there is provided a tool for separating the cap from the body of the smoking substitute device is disclosed. The tool may be used to separate or dislodge the cap from the device for a deep cleaning of the heating element. The tool has unlocking means at one end and a cleaning means at another end. The tool may provide for a compact and easy maintenance of the smoking substitute device of the smoking substitute system of the present disclosure.

The tool may have at least one unlocking arm and an unlocking protrusion disposed on the unlocking arm. The unlocking protrusion may be configured to displace a corresponding locking protrusion disposed on a locking arm extending from the body of the device to disengage the locking protrusion from a slot in the cap. Advantageously, the tool prevents the inadvertent removal of the cap from the body of the device.

Optionally, the tool further comprises a cleaning means for cleaning the heating element. Advantageously, the cleaning means to conveniently allow the user to physically clean the heating element once the cap is removed by the tool, and thereby allowing the heating element to be better clean, e.g., to "deep clean" the heating element. Optionally, the cleaning means comprises at least one cleaning bristle. Advantageously, in use the bristle may scrape on the surface of the heating element, and thereby it may allow the heating element to be cleaned in a more efficient manner.

Optionally, the tool further comprises a central rod, the at least one unlocking arm extending along a longitudinal axis of the central rod in a first direction and the cleaning means extending in a second direction opposite to the first direction.

Optionally, the tool comprises a collar around the central rod having the unlocking arm extended in the first direction, the collar being movable between an insertion position and an unlocking position, wherein in the insertion position the at least one unlocking arm is allowed to flex and in the unlocking position the central rod prevents the flexing of the unlocking arm. The collar may comprise a ring-shaped collar. The collar may be positioned concentrically on the central rod.

Optionally, the tool further comprises a first cover configured to cover the at least one unlocking arm and a second cover configured to cover the cleaning means.

Optionally, the tool having an external profile similar to that of an aerosol-forming article for a smoking substitute system.

The device may comprise an elongate body. An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The body may define a transverse cavity extending orthogonal to the longitudinal axis of the body. The transverse cavity may extend laterally and may be located on the body such that at least the base of the heating element is juxtaposed with the transverse cavity.

Further, at least one locking arm may extend from the body. The locking arms may lock or retain the cap with the body. The locking arms may be provided with a locking protrusion at a distal end. The locking protrusion may extend transversely to the longitudinal axis of the body. The locking arms may be positioned such that when the cap is mounted on the body, the locking arms may engage the cap to retain the cap on the body.

The cap may be provided with a slot extending along the longitudinal axis of the body (when the cap is retained on the body), and the locking protrusions may be configured to engage the slot. The slot may be elongated such that the cap may be moved or slide relative to the body along the longitudinal axis of the body. The locking protrusion may have an abutment surface to engage a peripheral surface of the cap that defines the slot to retain or lock the cap with the body.

The cap may be movable between a first position and a second position. When the cap is in the first position, the cap may conceal the heating element. When the cap is in the second position, the heating element may be at least partially exposed, e.g., through a window or opening at the side wall of the body. When the heating element is partially exposed, the heating element may be examined visually to ascertain if cleaning of the heating element is required. If required, when the cap is in the second position, the heating element may be at least partly cleaned by blowing air through the opening or simply shaking, tilting and or tapping the device gently to dislodge and remove the debris.

The smoking substitute system of the present disclosure may further include a tool for separation of the cap from the body. The tool may be configured to displace the locking arms to enable separation of the cap from the body. The tool may comprise at least one unlocking arm. The unlocking arms may be adapted to engage the locking arms to displace the locking arms for separating the cap from the body. Each unlocking arm may be provided with an unlocking protrusion. The unlocking protrusion may extend in a direction orthogonal to the longitudinal axis of the unlocking arm. The unlocking protrusions may be adapted to engage the locking protrusions to displace the locking protrusions for releasing the cap from the body.

The tool may further include a central rod. A collar may be positioned concentrically on the central rod. The collar may be placed movably on the rod such that the collar moves relative to the central rod along a longitudinal axis of the central rod. The unlocking arms may extend from the collar along the longitudinal axis of the central rod. The collar may be movable on the central rod between an insertion portion and an unlocking position. In the insertion position, the central rod may be kept away from the unlocking protrusions and the unlocking arms may flex radially inwards relative to the longitudinal axis of the central rod. In the unlocking position, the central rod may move adjacent to the unlocking protrusions to prevent flexing of the unlocking arms in a direction radially inwards relative to the longitudinal axis of the central rod. The collar may be biased to move towards the insertion position using any suitable means such as a coil spring.

The tool may be configured for insertion into the cavity. The unlocking protrusions may be configured such that when the unlocking arms are inserted into the cavity, the unlocking arm displaces the locking arms to release engagement of the locking arms from the slots. The unlocking protrusions may have dimensions that interfere with the width of the cavity. In order to allow insertion of the unlocking arms in the cavity, in the insertion position, the central rod may be spaced from the distal ends of the unlocking arms to allow the distal ends of the unlocking arms to flex radially inwards to enable insertion of the unlocking arms with the unlocking protrusions into the cavity. The flexing may be achieved when the unlocking protrusions abut and slide against an inner surface of cap defining the internal cavity. The unlocking protrusions, as shown in the embodiment illustrated, may be provided with tapered surfaces to guide the flexing movement of the unlocking arms in and out from the cavity and the slots.

The tool may further comprise a cleaning means for cleaning the heating element. The cleaning means may be in form of cleaning bristles. The cleaning bristles may be rubbed on the outer surface of the heating element to clean or scrap off any debris or residuals from the heating element.

The tool may include a first cover to cover the unlocking arms when not in use. Further, a second cover may be provided to cover the cleaning bristles when not in use.

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 μm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the body that is configured for engagement with an aerosol-forming article. Where the device comprises a heater having a heating element, the cap may at least partially enclose the heating element. The cap may be moveable between an open position, or a second position, in which access is provided to the heating element, and a closed position in which the cap at least partially encloses the heating element. The cap may be slidably engaged with the body of the device, and may be sliceable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a third aspect of the fourth mode, there is provided a system (e.g., a smoking substitute system) comprising the device according to the first aspect of the fourth mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum*, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Turnera diffusa* (Damiana), *Verbascum* (Mullein),

*Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

In a fourth aspect of the fourth mode, there is provided kit comprising the device according to the first aspect of the fourth mode and the tool according to the second aspect of the fourth mode.

The disclosure includes the combination of the aspects and preferred features of the fourth mode described except where such a combination is clearly impermissible or expressly avoided.

The skilled person will appreciate that except where mutually exclusive, a feature or parameter described in relation to any one of the above aspects of the fourth mode may be applied to any other aspect of the fourth mode. Furthermore, except where mutually exclusive, any feature or parameter of the fourth mode described herein may be applied to any aspect and/or combined with any other feature or parameter of the fourth mode described herein.

Fifth Mode: A Smoking Substitute Device Provided with Increased Stability of the Consumable During Removal At its most general, a fifth mode of the present disclosure relates to a smoking substitute device provided with increased stability of the consumable during removal.

According to a first aspect of the fifth mode of the present disclosure, there is provided a smoking substitute device comprising: a body; an elongate heating element projecting from the body along a longitudinal axis; a cap engageable with the body for at least partly enclosing the heating element, the cap movable along the longitudinal axis between a first position and a second position that is further from the body than the first position; wherein the cap is configured for engagement with an aerosol-forming article such that, when engaged, the article is moved along the longitudinal axis with the cap, and wherein a portion of the article remains in contact with the heating element when the cap is in each of the first and second positions.

By maintaining contact of the consumable with the heating element in the first and second positions, the consumable may be supported by the heating element as it is removed from the device. This may, in some cases, help to improve the stability of the consumable as it is removed from the device.

Optional features will now be set out. These are applicable singly or in any combination with any aspect of the fifth mode.

The portion of the article may remain in contact with the heating element while the cap is moved from the first position to the second position. That is, the portion of the article may remain in contact with the heating element throughout the movement.

In the second position, the heating element may remain in contact with article for a longitudinal length of between 1 mm and 5 mm, or e.g., between 2 mm and 4 mm, or about 3 mm. In the second position, the heating element may remain in contact with article for a longitudinal length that is between 5% and 30% of the longitudinal length of the heating element or e.g., between 10% and 20%, or about 15%. In the second position, the heating element may remain in contact with article for a longitudinal length that is between 2% and 10% of the longitudinal length of an aerosol-forming substrate of the article or e.g., between 4% and 8%, or about 6%.

When in the first position, the article (i.e., when engaged with the cap) may be in a position in which it is suitable for consumption (e.g., by operation of the device). That is, the first position may represent an operating position of the device. The second position may conversely represent a non-operating position. In the second position the article may be in a semi-released position.

The device may comprise a stop feature for restricting movement of the cap along the longitudinal axis beyond the second position. This may, for example, allow a user to remove the consumable from the device in a subsequent movement (e.g., without the aid from movement of the cap). For example, once the cap is stopped in the second position a user may twist the article to fully remove it from contact with the heating element. Thus, movement of the cap from the first position to the second position may partially disengage the article and the subsequent movement by a user may fully disengage the consumable. Twisting the article when in the second position may avoid breakage of the article when being removed.

The stop feature may be in the form of a hook portion disposed on the cap or the body. The hook portion may engage with a corresponding aperture (or recess) of the other of the cap or the body. The hook portion may operate in the manner of a snap engagement mechanism. In that respect, the hook portion may snap engage in the aperture when the cap is engaged with the body. The aperture may extend longitudinally so as to allow (limited) longitudinal movement of the cap relative to the body (when the hook portion is engaged with the aperture). In this respect, the aperture may be in the form of a slot. The hook portion may engage an edge of the aperture or slot so as to prevent further movement of the cap relative to the body when in the second position. The hook portion may be connected to the cap or body via a flexible arm, which may flex to allow the hook portion to snap engage.

As may be appreciated, the stop feature may take other forms and may, for example, be a protrusion or projection, or a lip (for engagement with the aperture). Similarly, the stop feature may engage with a feature other than an edge of an aperture. For example, the stop feature may engage with a lip or a rib, etc. The device may comprise multiple stop features.

The stop feature may be releasable to permit movement of the cap along the longitudinal axis beyond the second position. Release of the stop feature may permit (i.e., full) disengagement of the cap from the body. Thus, a user may only be able to disengage the cap from the body by release of the stop feature. Full disengagement of the cap from the body may expose the heating element of the device and could thus present safety risk. Thus, preventing such disengagement without a further release step may improve the safety of the device. In this respect, the stop feature may (e.g., only) be releasable by interaction with a user handheld tool.

The device and/or cap may comprise a guide portion for guiding the cap along the longitudinal axis. The guide portion may be a protrusion received in a slot (extending parallel to the longitudinal axis). The guide portion and stop feature may be the same part of the device and/or cap. That is, the guide portion may act as a stop feature.

Where the stop feature is in the form of a snap engagement portion, a tool may be inserted into a cavity defined by the cap and may e.g., move a hook of the snap engagement portion out of engagement with a corresponding aperture. This may subsequently allow full release of the cap from the body.

The device may comprise a retainer for retaining the cap in the first and/or second positions. For example, the device may comprise a retainer for retaining the cap in the second position. That is, the retainer may maintain the position of the cap, without further force from a user, in the first and/or second position. The retainer may comprise a magnetic arrangement configured to provide magnetic interaction between the cap and the body so as to retain the cap in the first and/or second positions. For example, a magnet may be disposed on the cap or body and a ferromagnetic element may be disposed on the other of the cap or the body. The magnet and ferromagnetic element may align when the cap is in the first or second position and, when aligned, the magnetic interaction between the magnet and the ferromagnetic element may retain the cap in that position. The magnetic interaction may be such that it increases the force to move the cap away from the first or second position, but may still allow a user to move the cap from those positions by hand (i.e., without the use of a further tool). The retainer may otherwise be in the form of a detent feature formed on the cap or body. Similarly, the retainer may be in the form of a snap engagement mechanism.

The cap may comprise a cavity into which the article is received for engagement. The heating element may project into the cavity. The cavity may be generally elongate along the longitudinal axis. Thus, one or more sidewalls defining the cavity may be parallel to one or more outer surfaces of the heating element. The cavity may be configured so as to form a friction fit with the article when received therein. The cap may be rotatably relative to the body such that the article, when received in the cavity, may be rotated by rotation of the cap.

The heating element may be configured for insertion into the article. A portion of the heating element may be received in the article in each of the first and second positions. A distal end of the heating element (i.e., distal from a base of the heating element where it is mounted to the device) may comprise a tapered portion, which may facilitate insertion of the heating element into the aerosol-forming article. The heating element may fully penetrate the aerosol-forming article when the aerosol-forming article is received in the cavity and the cap is in the first position. That is, the entire length, or substantially the entire length, of the heating element may be received in the aerosol-forming article when the cap is in the first position. A distal portion of the heating element may be received in the aerosol-forming article when the cap is in the second position.

The cap may comprise a base portion defining a base of the cavity. The base portion may comprise an aperture through which the heating element projects. When an article is received in the cavity and the cap is moved along the longitudinal axis the base portion may engage and move the article (i.e., along the longitudinal axis). In this respect, the cap may pull the article along the heating element. The aperture may be sized and shaped so as to correspond to a transverse cross section of the heating element. In that respect there may be a close fit of the heating element in the aperture. Thus, there may be minimal gap (e.g., for debris from the article) between the heating element and the base portion.

The cap may be slidably engageable with the body for movement along the longitudinal axis. Alternatively, or additionally, the cap may be rotatably engageable with the body. The cap may be engageable with the body via a threaded engagement. In this respect, the cap may be moved from the first position to the second position by rotation of the cap relative to the body.

The longitudinal distance between first and second positions may be shorter than the longitudinal length of the heating element projecting within the body.

A gap (e.g., a circumferential gap) may be formed between cap and the body when the cap is moved from the first position to the second position. A portion of the heating element (e.g., the portion of the heating element that is not in contact with the article) may be exposed in this gap. This may facilitate cleaning of the heating element.

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The body of the device may be elongate. An end of the elongate body may be configured for engagement with the aerosol-forming article. The body may be configured for engagement with a heated tobacco (HT) consumable (or heat-not-burn (HNB) consumable). That is, the aerosol-forming article may be a HNB consumable. The terms "heated tobacco" and "heat-not-burn" are used interchangeably herein to describe a consumable that is of the type that is heated rather than combusted (or are used interchangeably to describe a device for use with such a consumable). The aerosol-forming article may be of the type that comprises an aerosol former (e.g., carried by an aerosol-forming substrate).

The heating element may be in the form of a rod that extends from the body of the device. The heating element may form part of a heater. The heater (and thus the heating element) may be rigidly mounted to the body. The heating element may have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. Thus, the longitudinal distance between the first and second positions may be less than 15 mm to 25 mm, e.g., less than 18 mm to 20 mm, e.g., less than 19 mm. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in a cavity (defined by the device), and may extend (e.g., along the longitudinal axis) from an internal base of the cavity towards an opening of the cavity. A portion of the cap may be received in this cavity (and the heating element may be received through an aperture in the base of the portion of the cap. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may have a length that is less than, or substantially the same as, an axial length of an aerosol-forming substrate forming part of an aerosol-forming article (e.g., a HT consumable). Thus, when such an aerosol-forming article is engaged with the device (and the cap is in the first position), the heating element may only penetrate the aerosol-forming substrate, rather than other components of the aerosol-forming article. When the cap is in the first position, the heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity and the cap is in the first position, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a cap position sensor for detecting a position of the cap. For example, the cap position sensor may be configured to detect if the device is in the first position. The cap position sensor may, for example, be in the form of a Hall effect sensor and the cap may comprise a magnet that is arranged to be detected by the Hall effect sensor when the cap is in the first position.

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection. The controller may be configured to prevent activation of the heater when the cap position sensor detects that the cap is not in the first position.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

According to a second aspect of the fifth mode of the present disclosure, there is provided a smoking substitute device comprising a body; an elongate heating element projecting from the body along a longitudinal axis from a base end at the body to an opposing distal end; and a cap engageable with the body so as to be movable along the longitudinal axis between a first position and a second position that is further away from the body than the first position, the cap comprising an engagement portion for engaging a consumable and moving the consumable with the cap and wherein the longitudinal distance between the first and second positions is less than the longitudinal distance between the base and distal ends of the heating element.

The device of the second aspect of the fifth mode may otherwise be as described with respect to the first aspect of the fifth mode above.

In a third aspect of the fifth mode, there is provided a system (e.g., a smoking substitute system) comprising a device as described above with respect to the first or second aspect of the fifth mode and an aerosol-forming article for engagement with the cap of the device. The aerosol-forming article may comprise an aerosol-forming substrate at an upstream end of the aerosol-forming article. When the article is engaged with the cap of the device, the aerosol-forming substrate may remain in contact with the heating element of the device in both the first and second positions. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (Damiana), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a fourth aspect of the fifth mode of the present disclosure, there is provided a method of using the system according to the third aspect of the fifth mode, the method comprising inserting the aerosol-forming article into the device; and heating the article using the heater of the device.

In some embodiments the method may comprise inserting the article into a cavity within a body of the device and penetrating the article with the heating element of the device upon insertion of the article. The method may comprise moving the cap of the device from the first position to the second position so as to move the article along the heating element of the device, whereby the article remains in contact with the heating element in the first and second positions (and therebetween).

The disclosure includes the combination of the aspects and preferred features of the fifth mode described except where such a combination is clearly impermissible or expressly avoided.

The skilled person will appreciate that except where mutually exclusive, a feature or parameter of the fifth mode described in relation to any one of the above aspects may be applied to any other aspect of the fifth mode. Furthermore, except where mutually exclusive, any feature or parameter of the fifth mode described herein may be applied to any aspect and/or combined with any other feature or parameter of the fifth mode described herein.

Sixth Mode: A HNB Device Having Air Inlets for Facilitating Airflow to Enter the Housing of the HNB Device Adjacent to an End of Aerosol-Forming Article At its most general, a sixth mode of the present disclosure relates to an HNB device having air inlets for facilitating airflow to enter the housing of the HNB device adjacent to an end of aerosol-forming article. Such arrangement may reduce draw resistance and thereby increases airflow through the aerosol-forming article.

According to a first aspect of the sixth mode of the present disclosure, there is provided a heat not burn device. The device comprises a housing, which may be configured to receive an aerosol-forming article. Further, the device comprises a plurality of air inlets defined at the housing. The plurality of air inlets is configured to allow an airflow to enter the housing adjacent to an end of the aerosol-forming article when said aerosol-forming article is received in the housing.

By providing a device with a plurality of air inlets defined at the housing for providing air flow adjacent to the end of the aerosol-forming article, it may allow an air flow to enter the housing or a body of the device and directly flow towards the end of aerosol-forming article. That is, in absence of an extended air flow channel, the draw resistance during a puff may be significantly reduced. Therefore advantageously, such arrangement may enhance the process of aerosol generation, increase the amount of total particulate matter (TPM) of aerosol, as well as improved user experience associated with reduced draw resistance. Said end of the aerosol-forming article may be defined an end of the aerosol-forming article comprising tobacco, and is heated by the heater of the device. Through said end the airflow enters the aerosol-forming article and flows through the length of said substrate, entraining vapor from the tobacco and forms an aerosol.

Optional features will now be set out. These are applicable singly or in any combination with any aspect of the sixth mode.

Optionally, the plurality of air inlets are located adjacent to the end of aerosol-forming article when it is received in the housing. Optionally, the plurality of air inlets are configured to allow the airflow entering the housing to directly flow towards the end of aerosol-forming article. Optionally, each of the plurality of air inlets comprises a through hole. For example, the air inlets may be openings provided at the housing at a location immediately adjacent to the end of the aerosol-forming article. As such, there exists no constriction in the path of airflow, thereby advantageously it may result in minimal draw resistance during a puff.

Optionally, the plurality of air inlets are configured to allow the airflow to enter the house through one or more air inlets of the plurality of air inlets when the other one or more air inlets of the plurality of air inlets are blocked. In other words, the plurality of air inlets may provide redundancy in case of blockage in one or more of the air inlets. Advantageously, the provision of redundancy may allow an uninterrupted aerosol generation even if one or more of the air inlets are inadvertently blocked by a user. Moreover, since the air inlets are located adjacent to the end of aerosol-forming article, where residue built up could present a significant problem, the provision of redundancy may advantageously ensure the device continues to function even if one or more of the air inlets are blocked by residue.

Optionally, one or more of the plurality of air inlets are configured to be blocked to control the amount of airflow from entering the housing. Advantageously, the user may opt to cover one or more of the air inlets with a finger in order to adjust the amount of airflow entering the device according to his/her needs. For example, the user may limit the air flow by covering one or more of the air inlets to reduce the amount of TPM in the aerosol. Further, the user may vary the draw resistance of a puff to a level that mimics a conventional cigarette.

Optionally, the housing comprises a raised surface, and wherein the plurality of air inlets are defined adjacent to the raised surface. The raised surfaces may provide a surface for the user to grip onto during the use of the device. Therefore advantageously, the provision of air inlets adjacent to the raised surface may prevent the user from inadvertently blocking the air inlets, because the user's finger may no longer be able to form an air tight seal around the air inlets where there is a difference in level between the raised surface and the housing of the device.

Optionally, the plurality of air inlets are defined at a major surface of the housing. Said major surface may be a surface where the user grips onto when using the device. For example, the major surface may be a front panel or a rear panel of the device, or it may be a side wall of the housing of a device cylindrical in shape. Optionally, the major surface comprises a front panel of the housing.

Optionally, the major surface comprises a front panel of the housing. Optionally, the raised surface are formed on a front panel of the housing. Advantageously, by providing the air inlets at the front panel of the device, the user may be able to visualize the locations of the air inlet during the use of the device and thereby the user may be able to i) avoid blocking the air inlets or ii) selectively blocking one or more air inlets as desired.

Optionally, the air inlets are air channels extending through the housing, wherein said air flow channels are provided at an angle to the longitudinal axis of the device. More specifically, the air flow channels may resemble through holes that opens at an angle to the longitudinal axis of the devices. Said angle may range from 5° to 85° to the longitudinal axis of the device, and preferably at 45° to longitudinal axis of the device. Advantageously, such arrangement may reduce the amount of flow turning in the air flow as it enters the housing, and thereby further reducing draw resistance during a puff.

Optionally, the device comprises a cap defining a cavity for receiving the aerosol-forming article, wherein the cap is slidable between a first position where the cap is positioned adjacent to the housing and a second position where the cap is retracted from the housing. Optionally, the plurality of air inlets are provided adjacent to the cap when said cap is in the first position. For example, there may be a gap existed in between the cap and housing when the cap is put into the first position. The gap may form a valley or a recess where air inlets may be provided. In use, the airflow may enter the housing through the gap and the air inlets. Advantageously, this may allow the air inlets to be hidden in the recess, and thereby it may prevent the air inlets from being blocked accidentally.

Optionally, the device comprises a puff sensor, and wherein the air inlets are provided adjacent to the puff sensor. Optionally, the size of the air inlets is configured to relate to draw resistance and associated pressure drop. Advantageously, such arrangement may increase pressure drop detectable by the puff sensor, and thereby it may result in a more effective and accurate puff detection.

The device may comprise an elongate housing. An end of the elongate housing may be configured for engagement with an aerosol-forming article. For example, the housing may be configured for engagement with a heated tobacco (HT) consumable (or heat-not-burn (HNB) consumable) The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The housing may be defined with a raised surface on a first major surface, wherein the raised surface may facilitate in gripping the HNB device, by the user. Further, a plurality of air inlets may be defined at a first major surface of the housing, adjacent to the raised surface. The plurality of air inlets may allow air flow to enter the housing adjacent to an end of the aerosol-forming article when said aerosol-forming article is received in the housing.

The device may comprise a heater for heating the aerosol-forming article. The heater may comprise a heating element, which may be in the form of a rod that extends from the housing of the device. The heating element may extend from the end of the housing that is configured for engagement with the aerosol-forming article.

The heater (and thus the heating element) may be rigidly mounted to the housing. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 μm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol-forming article of the aerosol-forming article. That is, when an aerosol-forming article is engaged with the device, the aerosol-forming article of the aerosol-forming article may be located adjacent an inner surface of the (tubular) heating element. When the heating element is activated, heat may be transferred radially inwardly from the inner surface of the heating element to heat the aerosol-forming article.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the housing that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the housing of the device, and may be slidable between the open and closed positions.

The cap may define at least a portion of the cavity of the device. That is, the cavity may be fully defined by the cap, or each of the cap and housing may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the housing of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may, e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the sixth mode, there is provided a system (e.g., a smoking substitute system) comprising a heat not burn device according to the e.g., first aspect of the sixth mode and an aerosol-forming substrate. The aerosol-forming article may comprise an aerosol-forming substrate at an upstream end of the aerosol-forming article. Conveniently, the article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum nocturnum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum*, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Turnera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor.

The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the sixth mode described except where such a combination is clearly impermissible or expressly avoided.

The skilled person will appreciate that except where mutually exclusive, a feature or parameter of the sixth mode described in relation to any one of the above aspects of the sixth mode may be applied to any other aspect. Furthermore, except where mutually exclusive, any feature or parameter of the sixth mode described herein may be applied to any aspect and/or combined with any other feature or parameter of the sixth mode described herein.

Seventh Mode: A Heat not Burn (HNB) Device Having Air Inlets for Facilitating Airflow to Enter the Housing of the HNB Device Adjacent to a Base of Heating Element At its most general, a seventh mode of the present disclosure relates to a heat not burn (HNB) device having air inlets for facilitating airflow to enter the housing of the HNB device adjacent to a base of heating element. Such arrangement may advantageously reduce draw resistance and thereby increases airflow through the aerosol-forming article, as well as improving the heat transfer within the aerosol-forming article.

According to a first aspect of the seventh mode of the present disclosure, there is provided a heat not burn device. The heat not burn device comprises a housing, which may be configured for engagement with a heated tobacco (HT) consumable, and a heating element having a base in connection with the housing. The heat not burn device comprises a plurality of air inlets defined at the housing. The plurality of air inlets are configured to allow air flow to enter the housing adjacent to the base of the heating element.

In use, the heating element may be configured to be inserted into an aerosol-forming article. Once it is fully inserted, an end of the aerosol-forming article may abut the base of heating element. Therefore, during a user puff, the airflow entering the housing adjacent to the base of the heating element may directly flow towards and through the aerosol-forming article, thereby entraining vapor from the tobacco and forms an aerosol.

By providing a heat not burn device having a plurality of air inlets defined at the housing for providing air flow adjacent to the base of the heating element, it may allow an air flow to enter the housing and to flow through an aerosol-forming article through the length of the heater, and thereby it may improve the heat transfer from the heater onto a HNB consumable. This may improve aerosol generation in the HNB device. Furthermore, in absence of an extended air flow conduit, the draw resistance during a puff may be significantly reduced. Therefore advantageously, such arrangement may enhance the process of aerosol generation, increase the amount of total particulate matter (TPM) of aerosol, as well as improving user experience associated with reduced draw resistance.

Optional features will now be set out. These are applicable singly or in any combination with any aspect of the seventh mode.

Optionally, the plurality of air inlets are defined at the housing at a position adjacent to the base of the heating element. Optionally, each of the plurality of air inlets are defined as a through hole. For example, the air inlets may be openings provided at the housing at a location immediately adjacent to the base of the heating element. As such, there exists no constriction in the path of airflow, thereby advantageously it may result in minimal draw resistance during a puff.

Optionally, the device further comprises a cap having a cavity for receiving an aerosol-forming article and a cap engaging portion extending from an end of the housing, wherein the cap is configured to engage with the cap engaging portion, and wherein the plurality of air inlets are defined at the cap engaging portion of the housing. The cap engaging portion may form together with the housing, or it may be formed separate to the housing and attachable to the end of housing. Optionally, the cap engaging portion is configured to surround at least the base of the heating element. Advantageously, such arrangement enables the airflow entering the housing to flow directly towards the base of heating element.

Optionally, the cap is slidable between an engaged position where the cap is spaced from first end of housing by a gap and a disengaged position where the cap is retracted from the housing, and wherein the plurality of air inlets are defined at the cap engaging portion adjacent to said gap. For example, the gap may form a valley or a recess where air inlets may be provided. In use, the airflow may enter the housing through the gap and the air inlets. Advantageously, this may allow the air inlets to be hidden in the recess, and thereby it may prevent the air inlets from being inadvertently blocked by a user's finger.

Optionally, the air inlets are air channels extending through the housing, wherein said air flow channels are provided at an angle to the longitudinal axis of the device. More specifically, the air flow channels may resemble through holes that opens at an angle to the longitudinal axis of the devices. Said angle may range from 5° to 85° to the longitudinal axis of the device, and preferably at 45° to longitudinal axis of the device. Advantageously, such arrangement may reduce the amount of flow turning in the air flow as it enters the housing, and thereby further reducing draw resistance during a puff.

Optionally, the plurality of air inlets are circumferentially arranged at the same position along the longitudinal axis of the housing. Advantageously, such arrangement may allow the separation between each of the air inlet and the base of heating element to be kept to a minimum.

Optionally, the cap engaging portion may extend from the housing through a step portion.

Optionally, the plurality of air inlets may be defined at a major surface of the cap engaging portion.

Optionally the plurality of air inlets may allow air to enter into the housing transverse to the longitudinal axis of the housing. The flow air into the housing transverse to the longitudinal axis of the housing may generate a swirl of air in the housing, and thereby improves the performance of the HNB device.

The heat not burn device (hereinafter referred to as device), may comprise a housing. An end of the housing may be configured for engagement with an aerosol-forming article. For example, the housing may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the housing of the device. The heating element may extend from the end of the housing that is configured for engagement with the aerosol-forming article.

The heater (and thus the heating element) may be rigidly mounted to the housing. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the housing of the device may be defined with a cap engaging portion at a first end. The cap engaging portion may adjoin to the first end of the housing through a step portion. The cap engaging portion may be configured to receive at least a portion of the cap, and thus facilitates in engagement of the cap and the housing. The cap may be configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the housing of the device, and may be slidable between the open and closed positions.

The cap may define at least a portion of the cavity of the device. That is, the cavity may be fully defined by the cap, or each of the cap and housing may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

In some embodiments, the cap engaging portion may be defined with a plurality of air inlets, configured to allow air flow to enter the housing onto the bottom portion or base of the heating element, and adjacent to the base of the heating element.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the housing of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the seventh mode, there is provided a system (e.g., a smoking substitute system) comprising a heat not burn device according to the first aspect of the seventh mode and an aerosol-forming article. The aerosol-forming article may comprise an aerosol-forming substrate at an upstream end of the aerosol-forming article. Optionally, the article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa (Damiana), Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the seventh mode described except where such a combination is clearly impermissible or expressly avoided.

The skilled person will appreciate that except where mutually exclusive, a feature or parameter described in relation to any one of the above aspects of the seventh mode may be applied to any other aspect of the seventh mode. Furthermore, except where mutually exclusive, any feature or parameter described herein may be applied to any aspect of the seventh mode and/or combined with any other feature or parameter of the seventh mode described herein.

Eighth Mode: A Configuration of Selectively Blocking One or More of the Plurality of Openings of an Air Inlet in a Smoking Substitute Device At its most general, an eighth mode of the present disclosure relates to a configuration of selectively blocking one or more of the plurality of openings of an air inlet in a smoking substitute device, to vary quantity of airflow entering into the device. Advantageously, this may allow the draw resistance of a puff to be controlled or varied according to a user's preference. Such arrangement may also allow the vapor or aerosol temperature to be changed by changing the quantity of airflow entering the housing, for example when a user puffs at a given suction pressure.

According to a first aspect of the eighth mode of the present disclosure, there is provided a smoking substitute device. The device comprises a housing and an air inlet comprising a plurality of openings, defined at the housing for allowing an airflow to enter into the housing. The one or more of the plurality of openings are configured to be blocked so as to vary the quantity of airflow entering into the housing.

For example, each of plurality of openings may be apertures formed on the housing for providing fluid communication between the heater or the heating element in the housing and an external environment. Under a give suction pressure, each of the openings may allow passage for a given quantity, or rate, of airflow during a puff.

Therefore, by providing a device where one or more of the plurality of openings of an air inlet are selectively blockable, the present disclosure allows the quantity of airflow or air flow entering into the device to be varied or regulated. Advantageously, this may allow the user to control one or more of the aerosol delivery, aerosol temperature, and aerosol draw resistance according to the user's preferences.

The term "blocking" may refer to complete closing of the one or more of the plurality of openings to vary quantity of airflow entering into the device. It may mean "filling" the opening and/or "covering" the opening.

Optional features will now be set out. These are applicable singly or in any combination with any aspect of the eighth mode.

Optionally, the device further comprises a closure member movable relative to the housing, and wherein the closure member is configured to move between an open position where it does not block any of the plurality of openings and a partially closed position where it blocks the one or more of the plurality of openings. The partially closed position may comprise a plurality of partially closed positions each configured to block a particular number of openings out of the plurality of openings. For example, the closure member may be put into a first partially closed position to block one of the openings. The closure member may be put into a second partially closed position to block two of the openings, etc. Advantageously, such arrangement may allow the quantity of airflow entering the housing to range between a maximum quantity of airflow where no opening is blocked to a minimum quantity of airflow where all but a single opening are blocked.

Optionally, the closure member comprises least one of a door and a ring each movable relative to the housing. Optionally, the door is configured to slide relative to the housing for blocking the one or more of the plurality of openings, e.g., when the door is moved to the partially opened position. For example, the door may be any suitable slidable member such as a slidable gate that is arranged to toggle and be retainable at one or more partially opened positions to block one or more or the openings.

Advantageously, such mechanism may allow the closure member to move and be retained in a predetermined position such that a consistent airflow may be consistently achieved with every puff.

Optionally, the ring is configured to rotate about a longitudinal axis of the housing for blocking the one or more of the plurality of openings. The ring may be an inner sleeve or an outer sleeve that co-axially and circumferentially retained in the housing or surrounding the housing. For example, the ring may comprise openings or a slit corresponding to the plurality of the openings that are circumferentially distributed around the housing. Therefore, by rotating the ring about the longitudinal axis of the housing, the ring may selectively block one or more of the openings. Optionally, the ring is threadedly engaged with the housing. For example, the ring may be retained in or over the housing by a threaded slot.

Alternatively, the treaded connection is effected by a screw thread. For example, by rotating the ring about the longitudinal axis of the housing, the ring may traverse along the axial direction of the housing and thereby selectively blocking one or more openings that are axially defined in the housing. Advantageously, such mechanism may allow the closure member to move and be retained in a predetermined position such that a consistent airflow may be consistently achieved with every puff.

Optionally, the device further comprises a cap configured to engage with the housing, wherein the cap is movable relative to the housing so as to block the one or more of the plurality of openings. For example, the cap may move along and be retainable at different locations along the axial direction of the housing and thereby a portion of the cap may be configured to block the one or more of the openings at said different locations within the range of movement. The cap may be slidable, relative to the housing, between an open position and closed position, wherein said different locations may be locations between the closed position and the open position. Advantageously, such mechanism does not require additional movable parts to be included in the device.

Optionally, the one or more of the plurality of openings are configured to be blocked by user's finger to vary the quantity of airflow entering into the housing. This may be provided as alternative, or in addition to the other mechanism described, e.g., the closure member or the cap. For example, the plurality of openings may be provided on a major surface of the device such that the user may conveniently position a finger over the one or openings during use. Advantageously, such arrangement may allow the user to promptly regulate the amount of airflow for each of the puffs without the need to adjust the position of the closure member or the cap.

The device may comprise a housing in the form of an elongate body. An end of the housing may be configured for engagement with an aerosol-forming article. For example, the housing may be configured for engagement with a heated tobacco (HT) consumable (or heat-not-burn (HNB) consumable). The housing may be defined with an air inlet comprising a plurality of openings to facilitate airflow entering into the housing. Further, the housing may comprise a closure member to block or close one or more of the plurality of openings, to vary quantity of airflow entering into the housing. The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the housing of the device. The heating element may extend from the end of the housing that is configured for engagement with the aerosol-forming article.

The heater (and thus the heating element) may be rigidly mounted to the housing. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 μm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the housing that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the housing of the device, and may be slidable between the open and closed positions relative to the housing. This sliding movement of the cap may facilitate in blocking the one or more of the plurality of openings of the air inlet to vary quantity of airflow entering into the housing of the device.

The cap may define at least a portion of the cavity of the device. That is, the cavity may be fully defined by the cap, or each of the cap and housing may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the housing of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the eighth mode, there is provided a system (e.g., a smoking substitute system) comprising a smoking substitute device according to the first aspect of the eighth mode and an aerosol-forming article. The aerosol-forming article may comprise an aerosol-forming substrate at an upstream end of the aerosol-forming article. Conveniently, the article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a third aspect of the eighth mode of the present disclosure, there is provided a method of varying a quantity of airflow entering into the housing of the smoking substitute device according to the first aspect of the eighth mode, comprising blocking one or more of the plurality of openings of the air inlet.

Optionally, said blocking comprises blocking the one or more of the plurality of openings by at least one of a door, a ring and a cap of the device, and/or a user's finger.

The eighth mode of the disclosure includes the combination of the aspects and preferred features described except where such a combination is clearly impermissible or expressly avoided.

The skilled person will appreciate that except where mutually exclusive, a feature or parameter described in relation to any one of the above aspects of the eighth mode may be applied to any other aspect of the eighth mode. Furthermore, except where mutually exclusive, any feature or parameter described herein may be applied to any aspect of the eighth mode and/or combined with any other feature or parameter of the eighth mode described herein.

Ninth Mode: A Heated Tobacco Device Comprising a Provision for Activating a Crush Ball At its most general, a ninth mode of the present disclosure relates to a heated tobacco device comprising a provision for activating a crush ball with a consumable configured with the device.

According to a first aspect of the ninth mode of the present disclosure, there is provided a heat not burn (HNB) device. The HNB device comprises a cavity formed in a body for receiving a consumable and an activator being adapted to selectively intrude into the cavity to activate a crush ball within the consumable when the consumable is present in the cavity.

By providing a device comprising an activator, the device may be able to activate a crush ball within the consumable located within the device. In other words, the crush ball is only activated (i.e., broken, crushed, fractured etc. to release all or part of its contents) once the consumable is engaged with the device. In this way, the user is not required to activate the crush ball manually before placing the consumable in the device, as is necessary with current devices on the market. Accordingly, the present device reduces chances of the residue from the crush ball leaking onto the user's hands. Manual activation of the crush ball by hand is difficult, fiddly and can be messy if the liquid from the crush ball leaks onto the user's hands.

The term "activator" is intended to refer to a mechanical means that may be capable of activating the crush ball, i.e., releasing its contents by e.g., crushing, breaking, piercing, fracturing, etc.

Optional features will now be set out. These are applicable singly or in any combination with any aspect of the ninth mode.

Optionally, the intrusion by the activator includes narrowing of the cavity to activate the crush ball. Narrowing of the cavity in this way will put the consumable and crush ball under pressure, thereby crushing and fracturing the crush ball to release its contents.

In some embodiments, the activator comprises a squeezing member to at least partially squeeze a portion of the engaged consumable. In some embodiments, the activator comprises an iris aperture within the cavity which is movable between positions of increased and reduced aperture diameter.

In some embodiments, the activator includes a member adapted to penetrate into the consumable for selectively activating the crush ball. In some embodiments at least one such member is provided. In some embodiments, the member is a pin adapted and located so as to pierce the crush ball. The pin may have a generally cylindrical configuration with a conical tip extending towards the crush ball. The conical tip, upon activation of the activator, pierces the crush ball within the consumable engaged with the device.

In some embodiments, the device comprises an actuator movable by the user and configured to trigger the activator to activate the crush ball. In this way the user may decide at what time to activate the crush ball, improving the user experience.

In some embodiments, the actuator comprises a movable component outside the body of the device. In some embodiments, the actuator comprises a button, switch, lever or knob operably connected to the activator within the device, thereby permitting the user to trigger the activator and activate the crush ball by actuation of the button, switch, lever or knob.

In some embodiments, a cap of the device comprises the actuator, and twisting of the cap triggers the activator.

In some embodiments, the crush ball contains a flavorant and/or an aerosol forming substance.

In some embodiments, the crush ball within the consumable is adapted to be resistant to activation by hand. For example, a crush ball may be provided with a thicker shell, or a shell made from less frangible material. In this way, the crush ball is less likely to be activated inadvertently before use of the consumable in the device. The user may therefore be more certain that the crush ball will only become activated when the activator of the device is triggered once the consumable is engaged.

Optionally, the device comprises a heating element.

In some embodiments, the device comprises a controller configured to regulate the power supplied to the heating element based on the activation state of the activator. In some embodiments, the controller is configured to reduce the power supplied to the heater when the crush ball is activated.

In some embodiments, the device comprises a controller configured to regulate the duration of a heating cycle based on the activation state of the activator. In some embodiments, the controller is configured to extend the duration of a heating cycle when the crush ball is activated.

The device may comprise an elongate body. An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable).

Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

The device may further comprise a provision, preferably a mechanical means to intrude into the cavity. In an aspect, the mechanical means may be an activator. The activator may be capable of undergoing elastic deformation when an external force such as a pressing/squeezing force is applied. The activator regains its original shape upon removal of the external force. In an embodiment, activator may be formed on a portion of the wall. The portion of the wall may be flexible to permit squeezing of the activator towards the cavity.

In one embodiment, the activator may be in the form of two prongs formed on either side of the cavity to squeeze the consumable and pierce or fracture a crush ball disposed in the consumable. In another embodiment, the activator may be a penetrating component such as, but not limited to, a pin. The pin may be configured to penetrate/pierce through the consumable to activate a flavor delivery shell within the consumable.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slideably engaged with the body of the device, and may be slideable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

In some embodiments, the activator may be operationally configured with the cap by means of a rotary mechanism. During use, a pre-defined rotation of the cap causes, through the rotary mechanism, the activator to activate the crush ball within the consumable.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may, e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

In an embodiment, the controller is configured to control the heater based on the activation of the activator. For example, if the activation means is activated, the heater may be controlled to operate at a different (e.g., lower) power than it otherwise would. Optionally, the controller may be configured to change (e.g., extend) the duration of the heating cycle based on the activation of the activator.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the ninth mode, there is provided a system (e.g., a smoking substitute system) comprising a device according to the first aspect of the ninth mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum*, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

In an aspect of the ninth mode, the article may be a heat-not-burn consumable. The consumable may comprise a crush ball containing a flavorant and/or an aerosol forming substance. The crush ball comprises an external shell that may be broken, pierced, fractured etc., to release its contents. The crush ball is configured to release the flavorant and/or aerosol forming substance into the mainstream vapor from the heated tobacco upon being crushed/activated.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to another aspect of the ninth mode of the present disclosure, there is provided a method of using the system according to the second aspect of the ninth mode. The method comprises inserting the aerosol-forming article into the device; and heating the article using the heater of the device.

In some embodiments the method may comprise inserting the article into a cavity within a body of the device and penetrating the article with the heating element of the device upon insertion of the article.

According to an aspect of the ninth mode of the present disclosure, there is provided a smoking substitute system comprising an HNB device and an aerosol forming article.

Optionally, the article is a heat-not-burn consumable comprising a crush ball.

In some embodiments, the crush ball contains flavorant and/or an aerosol forming substance.

In some embodiments, the device comprises a heating element and the aerosol forming article is heatable by the heating element.

The disclosure includes the combination of the aspects and preferred features of the ninth mode described except where such a combination is clearly impermissible or expressly avoided.

The skilled person will appreciate that except where mutually exclusive, a feature or parameter described in relation to any one of the above aspects of the ninth mode may be applied to any other aspect of the ninth mode. Furthermore, except where mutually exclusive, any feature or parameter described herein may be applied to any aspect of the ninth mode and/or combined with any other feature or parameter of the ninth mode described herein.

Tenth Mode: A Heat not Burn (HNB) Device Having a Thermally Conductive Shroud Thermally Connected to a Heating Element for Heating a HNB Consumable At its most general, a tenth mode of the present disclosure relates to a heat not burn (HNB) device having a thermally conductive shroud thermally connected to a heating element for heating a HNB consumable.

According to a first aspect of the tenth mode of the present disclosure, there is provided a heat not burn (HNB) device comprising a thermally conductive shroud at least partially defining a cavity for receipt of a heat not burn consumable, a heater projecting into the cavity, and a thermally conductive path connecting the heater to the shroud.

The provision of an HNB device having a thermally conductive shroud may provide external heating of the HNB consumable and may avoid the need for an additional external heater for external heating of the HNB consumable. The thermally conductive shroud may transfer heat to an outer surface of the HNB consumable, which may facilitate even heating across the HNB consumable. This may result in consistent delivery of vapor from a HNB consumable engaged with the device. Furthermore, the thermally conductive shroud may increase vapor yield from a HNB consumable by reducing condensation of vapor that may otherwise occur at e.g., an internal surface of an outer wrapping layer of the consumable.

Optional features will now be set out. These are applicable singly or in any combination with any aspect of the tenth mode.

The heater may be elongate so as to define a longitudinal axis. The heater may be arranged to penetrate a portion of the consumable when received in the cavity. Thus, the heater may heat the consumable internally whilst the shroud heats the consumable externally.

The thermally conducting shroud may be configured to extend longitudinally to an extent that is greater than or equal to a longitudinal extent of the heater. That is, the heating element may not extend beyond an end of the shroud (i.e., it may be fully contained in the cavity defined by the shroud).

The shroud may be generally tubular. The shroud may have a generally circular cross-section, or may alternatively have a triangular, rectangular, etc. cross section. The shroud may be in the form of a section (or an arc) of a tubular shape (i.e., it may not be a complete tubular shape). In this respect, the shroud may only extend partially about a consumable when received in the cavity.

The shroud may be elongate. The cavity defined by the shroud may be generally cylindrical. In this respect, the shroud may be configured such that, when a consumable is received in the cavity, an inner surface of the shroud is substantially in contact with an outer surface of the consumable. Thus, the internal diameter of the shroud (when tubular) may be substantially the same as an external diameter of a consumable. In this way, a portion of the consumable may closely fit within the cavity defined by the shroud. That is, the shroud may be configured so as to be in contact with an outer surface of the consumable when received in the cavity.

The thermally conductive shroud may comprise an inner surface facing the cavity (i.e., or a consumable received within the cavity). The shroud may comprise an opposing outer surface facing away from the cavity (or away from a consumable when received in the cavity). The thermal emissivity of the inner surface may be greater than the thermal emissivity of the outer surface. That is, the inner surface may be configured so as to be more effective than the outer surface at emitting energy as thermal radiation. For example, the inner and outer surfaces may comprise different materials or coatings (so as to have different emissivity properties).

The thermally conductive shroud may be formed partly or wholly of a thermally conductive material. The shroud may comprise e.g., a ceramic material, aluminum and/or stainless steel.

The thermally conductive path may be formed partly or wholly of a thermally conductive material. The thermally conductive path may comprise a thermally conductive plastic or ceramic for transferring heat from the heater to the shroud. The thermally conductive path and shroud may be formed of the same material. The thermally conductive path and shroud may be integrally formed. Alternatively, the thermally conductive path and the shroud may be separate components that are in contact (or can be brought into contact).

The device may comprise a mount for mounting the heater to the device. The mount may form at least part of the thermally conductive path. The mount may define the entire thermally conductive path. That is, the mount may thermally connect the heater to the shroud (i.e., so as to transfer heat from the heater to the shroud). A portion of the mount may comprise a thermally insulative material. For example, the mount may comprise zirconia. This thermally insulative portion of the mount may restrict heat transfer from the heater to the device. Where the mount defines part of the thermally conductive path, that portion of the mount may comprise a thermally conductive material (i.e., such as those discussed above with respect to the thermally conductive path). The mount may be integrally formed with the heater and/or the shroud.

The thermally conductive shroud may be at least partially surrounded by a thermally insulative housing. The thermally insulative housing may extend circumferentially about the shroud. The thermally insulative housing may extend fully about a circumference of the shroud. The thermally insulative housing may form part of a housing of the device. In this respect, the thermally insulative housing may define an outer surface of the device. Alternatively, the thermally insulative housing may be in the form of a component separate to the housing of the device and e.g., may be disposed between a housing of the device and the shroud. The thermally insulative housing may be arranged to restrict heat transfer between the shroud and an external surface of a housing of the device.

The thermally conductive shroud may form part of a removable cap of the device. In this respect, the thermally conductive shroud may be movable relative to the heater. The thermally conductive path may form part of the removable cap and/or the device. The thermally conductive path may (only) connect the shroud and the heater when the cap is engaged with the device.

The device may comprise an elongate body. An end of the elongate body may be configured for engagement with an HNB consumable. The device may comprise a cavity that is configured for receipt of at least a portion of the consumable (i.e., for engagement with the consumable). The heater and shroud may be disposed in (e.g., project into) this cavity. In this respect, the cavity defined by the shroud may define a portion of the cavity of the device.

The heater may comprise a heating element, which may be in the form of a rod that extends from the body of the device. The heating element may be rigidly mounted to the body (e.g., by the mount). The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. Similarly, the shroud may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 μm. The thermally conductive path may connect the heating track to the shroud. The heating track may form part of the thermally conductive path.

As is set forth above, the heating element projects into a cavity defined by the shroud (e.g., along a longitudinal axis). The shroud and the heating element may be located within a cavity of the device (e.g., defined by a body of the device). In this respect, the heater and shroud may extend from an internal base of the cavity towards an opening of the cavity. The length of the heating element and/or the shroud (i.e., along the longitudinal axis of the heating element) may be less than the depth of the cavity. Hence, the heating element may extend for only a portion of the length of the cavity. That is, the heating element may not extend through (or beyond) the opening of the cavity.

The heating element may be configured for insertion into a HNB consumable when received in the cavity defined by the shroud. In that respect, a distal end (i.e., distal from a base of the heating element where it is mounted to the device) of the heating element may comprise a tapered portion, which may facilitate insertion of the heating element into the consumable. The heating element may fully penetrate the consumable when received in the cavity. That is, the entire length, or substantially the entire length, of the heating element may be received in the consumable.

The heating element may have a length that is less than, or substantially the same as, an axial length of an aerosol-forming substrate forming part of a consumable. Thus, when such a consumable is engaged with the device, the heating element may only penetrate the aerosol-forming substrate, rather than other components of the consumable. The heating element may penetrate the aerosol-forming substrate for substantially the entire axial length of the aerosol forming-substrate. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element).

Similarly, the shroud may have a length that is less than or substantially the same as, an axial length of an aerosol-forming substrate forming part of a consumable. Thus, when such a consumable is engaged with the device, the shroud may surround the aerosol-forming substrate, rather than other components of the consumable. Thus, heat may be transferred from (e.g., the inner surface of) the shroud to the surrounding aerosol-forming substrate. That is, heat may be transferred radially inwardly from the shroud to the aerosol-forming substrate.

As is set forth above, the device may comprise a removable cap. The cap may be disposed at the end of the body that is configured for engagement with a consumable. The cap may at least partially enclose the heating element. The cap may be moveable between an open position in which access is provided to the heating element, and a closed position in which the cap at least partially encloses the heating element. The cap may be slidably engaged with the body of the device, and may be slidable between the open and closed positions. When the shroud forms part of the cap, the thermally conductive path may only connect the shroud and the heating element when the cap is in the closed position.

The cap may define at least a portion of the cavity of the device (i.e., in which the heating element and shroud are located). That is, the cavity may be fully defined by the cap, or each of the cap and body may define a portion of the cavity. The cap may comprise an opening to the cavity. The opening may be configured for receipt of at least a portion of an HNB consumable. That is, an HNB consumable may be inserted through the opening and into the cavity (so as to be engaged with the device).

The cap may be configured such that when an HNB consumable is engaged with the device (e.g., received in the cavity), only a portion of the HNB consumable is received in the cavity. That is, a portion of the HNB consumable (not received in the cavity) may protrude from (i.e., extend beyond) the opening. This (protruding) portion of the HNB consumable may be a terminal (e.g., mouth) end of the HNB consumable, which may be received in a user's mouth for the purpose of inhaling aerosol formed by the device.

The device may comprise a power source or may be connectable to a power source (e.g., a power source separate to the device). The power source may be electrically connectable to the heating element. In that respect, altering (e.g., toggling) the electrical connection of the power source to the heating element may affect a state of the heating element. For example, toggling the electrical connection of the power source to the heating element may toggle the heating element between an on state and an off state. The power source may be a power store. For example, the power source may be a battery or rechargeable battery (e.g., a lithium-ion battery).

The device may comprise an input connection (e.g., a USB port, Micro USB port, USB-C port, etc.).

The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or HNB consumable) indicated to the user may comprise a condition indicative of the operation of the heater. For example, the condition may comprise whether the heating element is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the tenth mode, there is provided a system (e.g., a smoking substitute system) comprising a device according to the first aspect of the tenth mode and a HNB consumable. The consumable may comprise an aerosol-forming substrate at an upstream end of the consumable.

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris,* Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (Damiana), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a third aspect of the tenth mode of the present disclosure, there is provided a method of using the system according to the second aspect of the tenth mode, the method comprising inserting the consumable into the device; and heating the consumable using the heater and the shroud of the device.

In some embodiments the method may comprise inserting the article into a cavity within a body of the device and penetrating the article with the heating element of the device upon insertion of the article.

The disclosure includes the combination of the aspects and preferred features of the tenth mode described except where such a combination is clearly impermissible or expressly avoided.

The skilled person will appreciate that except where mutually exclusive, a feature or parameter described in relation to any one of the above aspects of the tenth mode may be applied to any other aspect of the tenth mode. Furthermore, except where mutually exclusive, any feature or parameter described herein may be applied to any aspect of the tenth mode and/or combined with any other feature or parameter of the tenth mode described herein.

Eleventh Mode: A Smoking Substitute Device Having a Cap Configured to be in Physical Contact with the Heating Element At its most general, an eleventh mode of the present disclosure relates to a smoking substitute device having a cap configured to be in physical contact with the heating element, and thereby moving the cap relative to the heating element removes debris formed on the surface of the heating element. This may allow the heating element to be cleaned more frequently, e.g., after each session when the cap is moved or retracted to remove an exhausted consumable. Advantageously, such cleaning may only involve sliding of the cap along the heating element, without requiring the user to fully remove the cap that is otherwise required to provide access for performing a more detailed cleaning at the heating element.

According to a first aspect of the eleventh mode of the present disclosure, there is provided smoking substitute device comprising a body, a heating element extending from the body and a cap. The cap comprises an aperture through which the heating element extends. The cap is configured to engage with the body and is movable with respect to the heating element. The heating element abuts the aperture, such that moving the cap with respect to the heating element removes residue formed on the heating element.

For example, the aperture may abut and maintains a physical contact with a surface of the heating element as it moves relatively to the heating element. The heating element may otherwise be referred to as a heater. The heating element may be in the form of a rod or a blade having a substantially consistent cross-sectional profile along its longitudinal axis. The shape of the aperture may correspond with the cross-section profile of the heating element.

By providing a device comprising a heating element abutting an aperture of the cap, the device may facilitate the removal of residue formed on the heating element. For example, an edge of the aperture may form a scraper that scrapes along the surface of the heating element as the cap moves, and thereby carries out physical cleaning thereat. Advantageously, such arrangement may allow a cleaning tool to form a part of the device, and thereby warrants their availability. Further, it may also allow the user to carry out physical cleaning in a more convenient manner and thereby it may encourage the user to clean the heating element at more frequent intervals, e.g., after every use.

Optional features will now be set out. These are applicable singly or in any combination with any aspect of the eleventh mode.

Optionally, the cap is slidable along a longitudinal axis of the heating element to remove said residue. Further, the cap may be slidable along a longitudinal axis of the heating element to discharge or remove an aerosol-forming article from the heating element. Advantageously, this may allow the user to additionally carry out cleaning at the heating element as the user removes an exhausted aerosol-forming article after every use. That is, the action of discharging or disengaging the exhausted aerosol-forming article may simultaneously effect the removal of residue from the heating element, and therefore such arrangement may ensure the heating element can perform optimally with every use of the device.

Optionally, the cap is rotatable about the longitudinal axis of the heating element to remove said residue. For example, the heating element may be in the shape of a cylindrical rod and the aperture may be a circular opening. Advantageously, such arrangement allows the heating element to be cleaned by rotating the cap relative to the heating element such that residue formed on the surface of the heating element may be scraped off by such lateral movement. Additionally, the cap may be rotated as it slides along the longitudinal axis when removing said residue, and thereby it may result in a more effective cleaning process.

Optionally, the aperture abuts one or more peripheral surfaces of the heating element. Optionally, the aperture abuts all of the peripheral surfaces of the heating element. The aperture may form around the heating element and in physical contact with all of the surfaces at the side of the heating element. For example, the aperture may be a circular opening that forms an interference fit around a rod-shaped heating element. For example, the aperture may be a rectangular opening that forms an interference fit around a blade shaped heating element.

Optionally, the cap further comprises a cavity for receiving an aerosol-forming article. Optionally, the heating element extends from the body into the cavity through the aperture. As the cap moves relative to the heating element, it may remove the residue and an expired aerosol-forming article from the heating element, and both may be retained in the cavity. Advantageously, this allows the residue to be collected and be disposed with the expired aerosol-forming article and thereby reduces the amount of residue left or trapped in the device, e.g., in a heating chamber or a cavity where the heater is located.

Optionally, the aperture comprises a cleaning means for removing said residue. For example, the aperture may comprise bristles or brushes that abuts the heating element. Optionally, the cleaning means may form from elastic materials. Optionally, the cleaning means may be flexible. Optionally, the cleaning means may bias against the surface of the heating element. Advantageously, such arrangement reduces wear on the heating element. And because of the biasing force imparted by the elastic cleaning means, such arrangement may allow the surface of the heating element to be cleaned in a more efficient manner.

The device may comprise an elongate body. An end of the elongate body may be configured for engagement with an aerosol-forming article (e.g., a heated tobacco (HT) consumable. The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity through an aperture. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably and/or rotatably engaged with the body of the device, and may be slidable and/or rotatable between the open and closed positions.

The cap may comprise an aperture configured to allow the heating element to extend therethrough such that the aperture at least abuts and physically contract with at least a surface of the heating element. The cap may be movable with respect to the heating element. The movement of the cap may either be slidable along a longitudinal axis of the heating element or rotatable about the longitudinal axis of the heating element. In a non-limiting embodiment, the heating element may be cylindrical and the cap may be both slidable and rotatable with respect to the said heating element. During movement of the cap with respect to the heating element, the physical contact between the aperture and the heating element may remove at least some residue that is formed on the heating element by a scraping action.

The cap may define at least a portion of the cavity of the device. That is, the cavity may be fully defined by the cap, or each of the cap and body may define a portion of the cavity. The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the eleventh mode, there is provided a system (e.g., a smoking substitute system) comprising the smoking substitute device according to the first aspect of the eleventh mode and an aerosol-forming article for use with the device. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

Optionally, at least a portion of the aerosol forming article is receivable in the cavity of the cap through an opening of the cap.

Optionally, the aerosol-forming article is penetrated by the heating element upon insertion in the cavity of the cap.

Optionally, the cap is slidable along a longitudinal axis of the heating element to remove said aerosol-forming articles from the heating element.

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum*, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Tumera diffusa* (Damiana), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a third aspect of the eleventh mode of the present disclosure, there is provided a method of using the smoking substitute system according to the second aspect of the eleventh mode, the method comprising inserting the aerosol-forming article into the device; and heating the article using the heater of the device.

Optionally, the method comprises inserting the article into a cavity within a body of the device and penetrating the article with the heating element of the device upon insertion of the article.

According to a fourth aspect of the eleventh mode of the present disclosure, there is provided a method of using the smoking substitute device according to the first aspect of the eleventh mode, the method comprising: moving the cap with respect to the heating element so as to remove residue formed on the heating element.

Optionally, said moving comprises sliding the cap along the longitudinal axis of the heating element.

The disclosure includes the combination of the aspects and preferred features of the eleventh mode described except where such a combination is clearly impermissible or expressly avoided.

The skilled person will appreciate that except where mutually exclusive, a feature or parameter described in relation to any one of the above aspects of the eleventh mode may be applied to any other aspect of the eleventh mode. Furthermore, except where mutually exclusive, any feature or parameter described herein may be applied to any aspect of the eleventh mode and/or combined with any other feature or parameter of the eleventh mode described herein.

Twelfth Mode: A HNB Device Comprising a Housing and a Cartridge Receivable by the Housing, Such that the Housing Substantially Encloses the Cartridge At its most general, a twelfth mode of the present disclosure relates to a HNB device comprising a housing and a cartridge receivable by the housing, such that the housing substantially encloses the cartridge.

According to a first aspect of the twelfth mode of the present disclosure, there is provided a heat not burn (HNB) device. The device comprises a hollow elongate housing having an opening at one end and a cartridge. The cartridge comprises a heater and a power source for supplying power to the heater and is receivable in the housing through the opening, such that the heater and power source are substantially enclosed by the housing when the cartridge is received therein.

This configuration provides easy assembling of the HNB device and convenient access to the internal components of the device, by disengaging the cartridge from the housing.

The term "cartridge" is intended to refer to a structure comprising an assembly of the internal components of the device.

The term "housing" in the context of the hollow elongate housing refers to an external, outermost, protective structure adapted to accommodate the cartridge. During use, the housing is the outermost structure of the device, and the outermost surface of the housing is substantially or fully visible during normal use. Therefore, the term "housing" does not encompass intermediate structures intended themselves to be held within a further outermost structure. The housing thus comprises an external surface adapted to be handled by the user during use of the device.

Optional features will now be set out. These are applicable singly or in any combination with any aspect of the twelfth mode.

Optionally, the housing may define a continuous profile, to facilitate sliding of the cartridge within the housing. The term "continuous profile" refers to the cross section of the internal cavity of the housing being substantially continuous along its length. In this way, the cartridge may slide freely within the housing. In some embodiments, the inner surface of the housing comprises an adaptation to facilitate the sliding of the cartridge, for example a runner or guideway comprising a ridge or channel running longitudinally along the internal surface.

In some embodiments, the cartridge includes a stopping feature for limiting the extent of insertion of the cartridge into the housing. In some embodiments, the housing includes a stopping feature for limiting the extent of insertion of the cartridge into the housing. In some embodiments, the housing and cartridge include corresponding stopping features for limiting the extent of insertion of the cartridge into the housing. In some embodiments, the stopping feature includes an abutment surface which prevents further travel of the cartridge into the housing when the abutment surface contacts another surface.

In some embodiments, the housing comprises a metallic material, such as aluminum or stainless steel. This provides a robust housing which is more resilient, provides improved protection for the fragile internal components and provides an improved aesthetic for the device, signifying a higher quality product. In some embodiments, the housing is substantially made from the metallic material. In some embodiments, the outer surface of the housing comprises the metallic material.

Optionally, the housing comprises a substantially circular cross-section. The term "substantially circular" encompasses housing geometries with a circular cross-section (i.e., a cylindrical housing) but also cross sections which are "flattened" circles, such as an oval, ellipse, superellipse, squircle, egg-shape, etc. Such cross-sections provide a housing with a smooth outer surface which improves handling by the user, and also facilitate sliding of the cartridge within the housing. In some embodiments the housing has a cross-section which comprises at least two lines of symmetry. In this way, the cartridge may be inserted into the housing in multiple orientations, improving the user experience. In some embodiments, the housing has a cross-section which is a superellipse (i.e., a square or rectangle with rounded corners).

In some embodiments, the housing comprises a retaining mechanism for retaining the cartridge within the housing. The retaining mechanism may be configured to selectively disengage the cartridge from the housing for any maintenance operations. Also, the retaining mechanism may be configured to prevent accidental dislodgment of the cartridge from the housing. In some embodiments, the retaining mechanism comprises a catch which engages when the cartridge reaches a certain extent of insertion, the catch preventing subsequent removal of the cartridge from the housing until it is released. The catch may be released by user action, e.g., by a button or switch on the housing.

Optionally, the retaining mechanism may comprise at least one of a magnetic mechanism and a snap fit mechanism. In some embodiments, the snap fit mechanism comprises one or more protrusions on the outer surface of the cartridge which engage in a snap fit with one or more corresponding recesses on the internal surface of the housing.

Optionally, the cartridge may comprise a casing configured to enclose at least a portion of the heater. In some embodiments, the cartridge comprises a casing configured to enclose at least a portion of the power source. In some embodiments, the cartridge comprises a casing configured to enclose at least a portion of each of the heater and the power source. In this way the heater and power source are protected from damage or tampering even when the cartridge is removed from the housing.

Optionally, an outer surface of the housing comprises a brushed or polished surface finish. In some embodiments, the outer surface of the housing comprises a smooth surface finish.

Optionally, the smooth surface finish to the outer surface of the housing may be obtained by a manufacturing process comprising polishing. The smoother surface finish on the housing may improve the aesthetic appearance of the device.

Conveniently, the hollow elongated housing may be configured to extend substantially for length of the cartridge. In this way the cartridge may be fully accommodated within the housing.

In some embodiments, the opening in the housing for receiving the cartridge is in an end of the housing distal the end which is adapted to receive a consumable.

The device may comprise an elongate body. The elongate body comprises the hollow elongate housing and the cartridge contained therein. An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the body that is configured for engagement with an aerosol-forming article. The cap may form a terminal part of the hollow elongate housing. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the body of the device, and may be slidable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the housing of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may, e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g. indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the twelfth mode, there is provided a system (e.g., a smoking substitute system) comprising a heat not but burn device according to the first aspect of the twelfth mode and an aerosol-forming article. The aerosol-forming article may comprise an aerosol-forming substrate at an upstream end of the aerosol-forming article. Conveniently, the aerosol forming article, may be in the form of a smoking substitute article, e.g., heated tobacco (HT) consumable (also known as a heat-not-burn (HNB) consumable).

A third aspect of the twelfth mode of the disclosure is a cartridge for a heat not burn device comprising a heater and a power source for supplying power to the heater, the cartridge adapted to be receivable in a hollow elongate housing through an opening in the housing such that the heater and power source are substantially enclosed by the housing when the cartridge is received therein.

Optional features of the third aspect of the twelfth mode are as set out above in respect of the first aspect of the twelfth mode, mutatis mutandis.

A fourth aspect of the twelfth mode of the disclosure is a hollow elongate housing for a heat not burn device having an opening at one end adapted for receiving a cartridge comprising a heater and a power source for supplying power to the heater, such that the heater and power source are substantially enclosed by the housing when the cartridge is received therein.

Optional features of the fourth aspect of the twelfth mode are as set out above in respect of the first aspect of the twelfth mode, mutatis mutandis.

A fifth aspect of the twelfth mode of the disclosure is a kit comprising a cartridge according to the third aspect of the twelfth mode and a hollow elongate body according to the fifth aspect of the twelfth mode, the cartridge being receivable in the housing through the opening such that the heater and power source are substantially enclosed by the housing when the cartridge is received therein.

Optional features of the fifth aspect of the twelfth mode are as set out above in respect of the first aspect of the twelfth mode, mutatis mutandis.

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris,* Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the twelfth mode described except where such a combination is clearly impermissible or expressly avoided.

The skilled person will appreciate that except where mutually exclusive, a feature or parameter described in relation to any one of the above aspects of the twelfth mode may be applied to any other aspect of the twelfth mode. Furthermore, except where mutually exclusive, any feature or parameter of the twelfth mode described herein may be applied to any aspect of the twelfth mode and/or combined with any other feature or parameter described herein.

Thirteenth Mode: The Configuration of a Cap of a Smoking Substitute Device

At its most general, a thirteenth mode of the present disclosure relates to the configuration of a cap of a smoking substitute device.

According to a first aspect of the thirteenth mode of the present disclosure, there is provided a smoking substitute device, comprising: a cap, wherein at least a portion of the cap is slidably received within a housing of the smoking substitute device, the cap slidably engaged to move in a longitudinal direction of the device between a seated position and a raised position; wherein the housing includes an opening through a first transverse side, wherein a portion of the cap is exposed for user interaction through the opening, wherein the housing includes a grip surface located on an opposite side of the housing to the side including the opening, wherein the cap movement is relative to the grip surface.

By providing a smoking substitute device according to the first aspect of the thirteenth mode, single handed movement of the movement of the cap may be facilitated.

Optional features will now be set out. These are applicable singly or in any combination with any aspect of the thirteenth mode.

Optionally, the grip surface is disposed on the housing.

Optionally, the grip surface is located directly opposite the opening.

Optionally, the cap includes a grip portion to move the cap between the seated and the raised position.

Optionally, the grip portion is provided with a recess complementary to a shape of a finger for a user interaction to move the cap between the seated and the raised position.

Optionally, the grip portion is provided at and end of the cap distal from an opening provided in the cap for receiving a consumable.

Optionally, a user output means is provided on the housing at least 2 centimeters ("cm") from the grip portion when the cap is in the seated position.

Optionally the grip portion has a non-slip surface.

Optionally, wherein, when the cap is in the raised position, at least a portion of a heating element of the device is exposed.

Optionally, the at least a portion of the heating element of the device is exposed from a transverse direction.

Optionally, the at least a portion of the heating element of the device is exposed from a transverse direction through the opening.

Optionally, the cap is substantially stopped from being moved beyond the raised position.

Optionally, the cap includes a cavity extending in a longitudinal direction of the device. Further, the cavity includes raised walls and a base to define a structure of the cavity.

Optionally, the engaged position corresponds to a fully engaged position of cap with the housing, and the raised position corresponds to a partially lifted position of the cap along the longitudinal direction of the device.

Optionally, the raised position of the cap facilitates cleaning of the cap and a heating element of the device.

The device may comprise an elongate body having a major longitudinal and minor transverse axis. An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 μm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity.

Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the heater may form part of an aerosol-forming article for use with the device. In such cases the device may not comprise a heater. Rather, the aerosol-forming article may comprise a heater. Such arrangements may, for example, be suited to e-cigarette systems in which the aerosol-forming article comprises a tank containing an aerosol former (e.g., in liquid form). In such embodiments, the device may comprise means for connecting the device the heater of an aerosol-forming article engaged with the device. For example, the device may comprise one or more device connectors for (e.g., electrically) connecting the device to a corresponding heater connector of the aerosol-forming article.

The connectors (i.e., of both the device and the aerosol-forming article) may be in the form of electrically conductive elements (e.g., plates) that contact when the aerosol-forming article is engaged with the device.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the body of the device, and may be slidable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the thirteenth mode, there is provided a system (e.g., a smoking substitute system) comprising a device according to the first aspect of the thirteenth mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (Damiana), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

In some embodiments the system may be in the form of an e-cigarette system (i.e., rather than a heated tobacco system as described above). In such a system, the consumable may be in the form of an e-cigarette consumable. The e-cigarette system may be configured such that the consumable can be received and retained in the cavity of the device (i.e., so as to be engaged with the device). The consumable may be retained by way of e.g., an interference fit, screwing one onto (or onto) the other, a bayonet fitting, or by way of a snap engagement mechanism.

The consumable may comprise a tank, which may define a reservoir for the storage of an aerosol former. The aerosol former may be in the form of an e-liquid (stored in the reservoir).

The consumable may be a "single-use" consumable. That is, upon exhausting the e-liquid in the tank, the intention may be that the user disposes of the entire consumable. Alternatively, the e-liquid may be the only part of the system that is truly "single-use". For example, the tank may be refillable with e-liquid or another component of the system (internal to the device or external to the device e.g., a refillable cartomizer) may define a reservoir for the e-liquid.

As set forth above, the consumable may comprise a heater (i.e., instead of the heater forming part of the device) configured to heat and vaporize the e-liquid. The consumable may comprise a porous wick that conveys e-liquid from the tank to a heating element of the heater. The heating element may be a heating filament that is wound (e.g., helically) around at least a portion of the porous wick, such that when the heating element is heated (e.g., by the action of electrical current passing through the heating element), heat may be transferred from the heating element to the e-liquid conveyed by the wick. This transfer of heat may vaporize the e-liquid and the resultant vapor may be entrained in an airflow passing through the consumable.

The consumable may further comprise one or more heater connectors for connecting the heater (of the consumable) to the device. The heater connectors may be in the form of electrically conductive element or contacts (e.g., metal plates) and may be disposed on an in-use device-facing surface of the consumable. The heater connectors may be electrically connected to the heater of the consumable, such that electricity supplied via the heater connectors may pass to the heater. In other words, a voltage applied across the heater connectors may generally correspond to a voltage applied across the heating element of the heater.

The heater connectors may be arranged such that they contact corresponding device connectors of the device when the consumable is engaged with the device. The device connectors may be connected (e.g., electrically) to a power source (e.g., battery) of the device. Thus, electricity may be supplied from the power source to the heating element, via in-contact heater and device connectors. In this way, the heater forming part of the consumable may operate (and interact with e.g., a controller) as otherwise described above with respect to a heater forming part of the device.

The disclosure includes the combination of the aspects and preferred features of the thirteenth mode described except where such a combination is clearly impermissible or expressly avoided.

The skilled person will appreciate that except where mutually exclusive, a feature or parameter described in relation to any one of the above aspects of the thirteenth mode may be applied to any other aspect of the thirteenth mode. Furthermore, except where mutually exclusive, any feature or parameter described herein may be applied to any aspect of the thirteenth mode and/or combined with any other feature or parameter of the thirteenth mode described herein.

Fourteenth Mode: A Smoking Substitute Device Provided with a Cap Displacement Feature At its most general, a fourteenth mode of the present disclosure relates to smoking substitute device provided with a cap displacement feature.

According to a first aspect of the fourteenth mode of the present disclosure, there is provided a smoking substitute device.

The device comprises a body and a heating element projecting from the body along a longitudinal axis. Further, the device comprises a cap, engageable with the body for at least partly enclosing the heating element. The cap is moveable away from the body along the longitudinal axis, whilst remaining engaged with the body, so as to define an aperture for accessing the heating element.

By providing a device comprising the cap, which is configured to move relative to the body along the longitudinal axis, and an aperture for accessing the heating element, cleaning of the heating element is facilitated, which may improve aerosol generation of the device. The user is provided with easy access to the heating element when the cap is moved away from the body. Furthermore, the cap remains engaged with the device, reducing the risk of losing the cap during cleaning and the cap is more easily replaced after cleaning the heating element.

The term "aperture" is intended to refer to a gap or an opening defined between the cap and the body, providing access to the heating element by the user.

Optional features will now be set out. These are applicable singly or in any combination with any aspect.

In some embodiments, the cap is defined with a cavity to receive a consumable. In this way, the cap may also function as a convenient means to eject the consumable after use.

In some embodiments, the heating element is configured to penetrate into at least a portion of the consumable.

Optionally, the cap is movable between a first position and a second position relative to the body, along the longitudinal axis, wherein the first position corresponds to a fully engaged condition of the cap with the body, and the second position corresponds to a lifted condition of the cap with respect to the body, defining the aperture.

In some embodiments, movement of the cap from the first position to the second position facilitates lifting of at least a portion of the consumable away from the heating element along the longitudinal axis.

Optionally, the displacement of the cap between the first position and the second position ranges from about 2 mm to about 15 mm, preferably from about 5 mm to about 8 mm. This provides a convenient range of movement which may be accomplished by a user with a single movement of e.g., the thumb, to move the cap between first and second positions.

Optionally, the cap may be engageable with the body by a sliding mechanism or a threading mechanism. This provides convenient and secure means to move the cap.

In some embodiments, the device comprises a retainer mechanism to retain the cap in one or more of the first position and the second position. In this way the cap is held more securely in a given position for ease of use, for example to facilitate cleaning of the heating element through the aperture when the cap is in the second position. In some embodiments, the device comprises a retainer mechanism to retain the cap in the second position.

In some embodiments, the retainer mechanism is configured to restrict movement of the cap beyond the second position. In other words, the second position may be a terminal position along the longitudinal motion of the cap away from the body. This provides a means to prevent inadvertent removal of the cap from the device, thereby reducing the risk of loss of the cap.

Optionally, the retainer mechanism is at least one of a detent mechanism and a magnetic lock mechanism. For example, the retainer mechanism may comprise a catch which holds the cap in one or more of the first and second position when the cap is in that position. The catch may be released when desired by action of the user. In some embodiments, the retainer mechanism comprises a magnetic catch, for example comprising magnets in the body and cap respectively between which a magnetic force of attraction exists which holds the cap in position. To move the cap out of the position the user must overcome this force.

In some embodiments, the retainer mechanism comprises one or more resilient members within the body of the device. In some embodiments, the one or more resilient members comprise a catch or detent which engages with a feature of the cap to prevent travel of the cap further from the body than the second position. In some embodiments the resilient members are deformable to disengage the catch or detent, allowing movement of the cap away from the body beyond the second position. In some embodiments, deformation of the resilient members is achieved by action of the user.

Optionally, the cap is removable from the body when in the second position by means of a tool. In this way the cap is not easily removed from the body so the risk of loss of the cap is low, but the user is able to remove the cap when needed through use of the removal tool. In some embodiments, the device comprises the tool, which is temporarily housed within the device and removable from the device as needed in order to be used to remove the cap. In some embodiments, the tool is adapted to deform the one or more resilient members described above when the tool is engaged, to disengage the catch or detent and permit removal of the cap by movement of the cap away from the body beyond the second position.

In some embodiments, movement of the cap towards the body beyond the first position is prevented by the abutment of a surface of the cap with a surface of the body. For example, an external rim of the cap may abut an external rim of the body. In some embodiments, the cap comprises an internal abutment surface which abuts a corresponding internal abutment surface of the body of the device in the first position.

Optionally, at least a portion of the cap is configured with a tactile finish to facilitate gripping of the cap for movement of the cap between the first position and the second position. In some embodiments, the tactile finish comprises a high-friction surface covering at least a portion of the cap. In some embodiments, the tactile finish comprises one or more raised protrusions, facilitating the engagement of a user's finger or thumb with the cap and the movement of the cap. In this way the user may more easily grip the cap to move it to inspect and/or clean the heating element through the aperture.

In some embodiments, the cap is biased into the second position. This facilitates movement of the cap into the second position for inspection/cleaning of the heating element. The cap and/or body of the device may comprise biasing means to bias the cap into the second position. For example, when the cap is biased into the second position the user need only disengage a retainer mechanism when the cap is in the first position and the cap will then naturally travel into the second position due to the biasing means. In some embodiments, the biasing means comprises a spring.

In some embodiments, the cap defines plurality of apertures when it is moved away from the body along the longitudinal axis. In some embodiments, two apertures are defined, wherein the apertures are defined on opposing sides of the device. This permits the user to access the heating element from either side of the device and further facilitates cleaning by allowing the user to access the heating element through a first aperture, and during cleaning push debris from the heating element out of the second aperture.

The device may comprise a body. An end of the body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, 5 e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments, the device may comprise a cap disposed at the end of the body. The cap may be defined with a cavity for receiving an aerosol-forming article (i.e., consumable). The device comprises a heater having a heating element, the cap may at least partially enclose the heating element. The cap may be moveable between a first position and a second position relative to the body, along the longitudinal axis. The cap in the second position may define an aperture to facilitate access to the heating element, and in the first position the cap at least partially encloses the heating element. The cap may be slidably engaged with the body of the device, and may be slidable between the first and the second positions. The cap may be moved beyond the second position by a tool, which facilitates in disengaging the cap and the body.

In some embodiments, the cap may be movable between the first position and the second position by threading the cap with the housing or vice versa.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may, e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the fourteenth mode, there is provided a system (e.g., a smoking substitute system) comprising a device according to the first aspect of the fourteenth mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum*, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the fourteenth mode described except where such a combination is clearly impermissible or expressly avoided.

The skilled person will appreciate that except where mutually exclusive, a feature or parameter described in relation to any one of the above aspects of the fourteenth mode may be applied to any other aspect of the fourteenth mode. Furthermore, except where mutually exclusive, any feature or parameter described herein may be applied to any aspect and/or combined with any other feature or parameter described herein.

Fifteenth Mode: A Smoking Substitute Device Having a Heating Element that is Deactivated when a Cap of the Device is Moved to Expose the Heater At its most general, a fifteenth mode of the present disclosure relates to a smoking substitute device having a heating element that is deactivated when a cap of the device is moved to expose the heater.

According to a first aspect of the fifteenth mode of the present disclosure, there is provided a smoking substitute device a main body; a heater; a cap engageable with the main body and movable between a closed position in which it substantially encloses the heater and an open position wherein at least a portion of the heater is exposed; a sensor for detecting a position of the cap; and a controller configured to control the device in response to the detection of the position of the cap.

Providing a device having a sensor for detecting the position of a cap and a controller able to control the device in response that detection allows the device to function differently when, for example, the cap is removed. This may allow the implementation of safety controls when the cap is removed (which exposes the heater).

The term "substantially encloses" does not require that the cap fully encloses the heater. An opening may remain for inserting e.g., a smoking substitute article into the device (for engagement) with the heater. However, such an opening (due to its size) would generally not allow a user to touch the heater (so as to present a safety hazard). In this respect, one would not consider the heater to be exposed.

Optional features will now be set out. These are applicable singly or in any combination with any aspect of the fifteenth mode.

The controller may be configured to prevent activation of the heater when the sensor detects that the cap is in the open position. The control of the device may alternatively comprise reducing the temperature of the heater (but not fully deactivating the heater). The control of the device may alternatively comprise locking a user input of the device to prevent user interaction with the device. The controller may be configured not to respond to user input (e.g., by activating the heater) when the cap is detected as being in the open position. The detection of the cap being in the open position may be in the form of the sensor not detecting the cap in the closed position. That is, the sensor may only be configured to detect whether the cap is in the closed position, such that an absence of that detection is a detection of the cap being in the open position.

In the open position, the cap may be (e.g., fully) disengaged from the main body. Alternatively, the cap may be engaged with the main body of the device in the open and closed positions (and may remain engaged with the body between those positions). The cap may be slidably or rotatably engaged with the device so as to be movable between the closed and open positions. In the open position, an opening (exposing the heater) may be formed between the cap and the main body.

The device may comprise a power source for supplying power to the heater. The controller may prevent activation of the heater by preventing a supply of power from the power source to the heater. For example, the controller may prevent the supply of power in circumstances where supply of power would normally be provided (e.g., such as an activation input from a user via a button, switch, touchscreen, etc.).

The device may comprise a magnet disposed on the cap or main body. The device may comprise a sensor disposed on the other of the cap or the main body (i.e., the magnet and sensor may be disposed on different components). The sensor may be configured to detect the presence of the magnet when the cap is engaged with the main body.

The magnet may be disposed on the cap and the sensor may be disposed on the main body. The body may comprise a cavity for receipt of at least a portion of the cap. The sensor may be mounted to or at a wall defining the cavity. The magnet may be mounted to the at least a portion of the cap received in the cavity. Thus, the magnet and sensor may be adjacent or in proximity when the at least a portion of the cap is received in the cavity.

The sensor may be a Hall effect sensor. In other embodiments the sensor may be e.g., a light sensor. For example, the light sensor may receive light through an opening in the device, and that light may be blocked when the cap is in the closed position. Alternatively, the sensor may comprise a switch that is activated when the cap is moved into or out of the closed position.

The device may comprise a magnet disposed on the cap or main body and a ferromagnetic element (e.g., a metal element such as a plate or block) disposed on the other of the cap or the main body. The ferromagnetic element and magnet may be arranged so as to magnetically interact when the cap is in the closed position. That is, the ferromagnetic element and the magnet may align when the cap is in the closed position so as to be adjacent to or proximate one another. The magnet may be configured such that the magnetic interaction retains the cap on the body. The ferromagnetic element may form part of the housing of the cap. The ferromagnetic element and the magnet may interact so as to align the cap with respect to the body. The magnet may be the same magnet (as discussed above) that is detected by the sensor when the cap is in the closed position. One of the ferromagnetic element and magnet may be disposed on a wall defining a cavity of the body, and the other may be disposed on a portion of the cap received in the cavity.

The magnets and/or sensor may be received in respective mounting recesses of their respective components. The magnets and/or sensor may be attached to their respective components (or walls of their respective components) by way of an adhesive.

An end of the main body may be configured for engagement with an aerosol-forming article (i.e., the end of the main body comprising the heater). The main body may be configured for engagement with a heated tobacco (HT) consumable (or heat-not-burn (HNB) consumable) The terms "heated tobacco" and "heat-not-burn" are used interchangeably herein to describe a consumable that is of the type that is heated rather than combusted (or are used interchangeably to describe a device for use with such a consumable). The cavity (which received the at least a portion of the cap) may also be configured for receipt of at least a portion of the consumable (i.e., for engagement with the consumable). The aerosol-forming article may be of the type that comprises an aerosol former (e.g., carried by an aerosol-forming substrate).

The heater may be for heating the aerosol-forming article. The heater may comprise a heating element, which may be in the form of a rod that extends from the main body of the device. The heating element may extend from the end of the main body that is configured for engagement with the aerosol-forming article.

The heater (and thus the heating element) may be rigidly mounted to the main body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element. When the cap is in the open position (but remains engaged with the main body) the heating element may be exposed laterally (e.g., intermediate the ends of the heating element).

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

As mentioned above, the heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

The cap may define at least a portion of the cavity of the device. That is, the cavity may be fully defined by the cap, or each of the cap and main body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

As above, the device may comprise a power source. The device may alternatively be connectable to a power source (e.g., a power source separate to the device). As set forth above, the power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state. As above, the controller may render an input ineffective when the cap is detected as being in the open position.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. The condition may also be the position of the cap (e.g., the closed and/or open position). For example, the UI may indicate to a user that the cap is in an open position. This may only be indicated to a user when the user attempts to activate the heater. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the main body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

As set forth above, the controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state. As above, when the cap is in the open position, the controller may not respond to such "on" and "off" command signals in the usual manner.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor in addition to the cap sensor (e.g., a puff/airflow sensor), the controller may be operatively connected to this further sensor. The controller may be configured to receive a signal from the sensor (e.g., indicative of a condition of the device and/or engaged aerosol-forming article). The controller may be configured to control the heater, or an aspect of the output means, based on the signal from the further sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the fifteenth mode there is provided a method of controlling a smoking substitute device, the method comprising detecting a state of a cap of the device and controlling a heater of the device in response to the detected state of the cap.

The state of the cap may comprise whether the cap is in an open or closed position. In the open position, the heater may be exposed. In the closed position the heater may be substantially enclosed by the cap. In the open position the cap may be (e.g., fully) disengaged from the device (e.g., a main body of the device).

Controlling the heater may comprise preventing activation of the heater when the cap is in the open position (or is disengaged from the device).

In a third aspect of the fifteenth mode, there is provided a system (e.g., a smoking substitute system) comprising a device according to the first and an aerosol-forming article. The aerosol-forming article may comprise an aerosol-forming substrate at an upstream end of the aerosol-forming article.

Conveniently, the article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia* divinorum, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a fourth aspect of the fifteenth mode of the present disclosure, there is provided a method of using the system according to the third aspect of the fifteenth mode, the method comprising inserting the aerosol-forming article into the device; and heating the article using the heater of the device.

In some embodiments the method may comprise inserting the article into a cavity within a body of the device and penetrating the article with the heating element of the device upon insertion of the article.

The disclosure includes the combination of the aspects and preferred features of the fifteenth mode described except where such a combination is clearly impermissible or expressly avoided.

The skilled person will appreciate that except where mutually exclusive, a feature or parameter described in relation to any one of the above aspects of the fifteenth mode may be applied to any other aspect of the fifteenth mode. Furthermore, except where mutually exclusive, any feature or parameter of the fifteenth mode described herein may be applied to any aspect and/or combined with any other feature or parameter of the fifteenth mode described herein.

Sixteenth Mode: A Heat-not-Burn Device Having a Closure for Covering an Opening of a Cavity Configured for Receipt of at Least a Portion of a Consumable At its most general, a sixteenth mode of the present disclosure relates to a heat-not-burn device having a closure for covering an opening of a cavity configured for receipt of at least a portion of a consumable.

According to a first aspect of the sixteenth mode of the present disclosure, there is provided a heat-not-burn (HNB) device comprising a body defining a cavity and an opening to the cavity for receipt of a heat-not-burn consumable therein. The device further includes a closure moveable between a first position and a second position respectively. In the first position the closure covers the opening and in the second position the closure is retracted so as to be substantially concealed within the body.

According to a second aspect of the sixteenth mode of the present disclosure, there is provided a smoking substitute device comprising a body having a cavity and for receiving of an aerosol-generating consumable, a closure moveable between a first position in which it covers the cavity and a second position in which the cavity is substantially uncovered, and a handle for moving the closure between the first and the second position.

In other words, the system provides for covering or hiding from external influence the consumable opening or cavity of a smoking substitute device like a heated tobacco device. In particular, the present disclosure is designed to provide a means of covering the opening when no consumable is inserted into the device. The closure may comprise a channel and may be free to rotate about an axis and may rotate to align with a cavity, which may be channel-shaped as well, allowing the device to be used by allowing a consumable to be inserted. The opening in the closure, an upper channel, may be a complete thru hole, while the lower channel may contain the heating element, e.g., being a cavity in the body of the smoking substitute device.

Thereby, the present disclosure may provide a simple way of covering the consumable receiving opening/cavity, to reduce the chance that dirt or debris enters, ingress or egress from the device, in particular the cavity. The closure may be intuitive in use and easy for the user of a smoking substitute device to perform and may also be user to switch on and/or off the smoking substitute device.

The closure may be provided with a handle external to the body of the device for allowing a user to move the closure between the first position and the second position. In some embodiments, the handle forms part of the closure or is connected to the closure. In some embodiments, the handle comprises a rotatable handle (for example, connected to a rotatable closure, such as the described ball valve). In some embodiments, the handle comprises a movable part outside the body of the device and a connector passing through an outer wall of the device and attached to the closure within the body of the device. Movement of the movable part by the user allows the user to control the position of the closure. In some embodiments the connector is housed within a slot in the outer wall of the device and slidable along the slot by movement of the movable part.

Providing a heat-not-burn device comprising a closure which covers the opening of the cavity helps prevent the entry of dust/dirt particles into the cavity. Further, the presence of the closure may prevent particles of aerosol-forming-substrate (e.g., tobacco) which have accumulated within the device from falling out of the cavity of the device. Additionally, a closure which is substantially concealed when in the second position provides a more ergonomic design to improve the user experience and prevent the closure interfering with the use of the device.

By "substantially concealed within the body", it is meant that a substantial part of the closure lies within the body of the device such that it does not protrude beyond the outer wall of the body of the device, although at least part of the closure may still be visible when looking into the cavity of the device. In some embodiments, "substantially concealed within the body" means that the portion of the closure which, when in the first position, covers the opening, does not protrude beyond the outer wall of the body of the device when in the second position. In some embodiments, "substantially concealed within the body" also means that the closure in not visible, or not substantially visible, when looking into the cavity, for example some or all of the closure may be concealed behind the wall of the device and so is not visible.

Optional features will now be set out. These are applicable singly or in any combination with any aspect of the sixteenth mode.

In some embodiments, the closure is movable between the first and the second position by a rotary movement.

Optionally, the closure may comprise a cylindrical member having a bore therethrough, the cylindrical member being rotatable about an axis of rotation.

Optionally, said bore is perpendicular to said axis of rotation, the closure being configured such that when it is in said second position, the bore is aligned with a longitudinal axis of said body such that the bore and the cavity provide a passage for insertion of said consumable.

Optionally, the closure is configured such that when it is in said first position, the bore is aligned in a direction which is not parallel with said cavity, thereby closing the opening of the cavity.

In some embodiments, in the second position of the closure, an aperture is provided at the opening of sufficient size to permit a consumable to be inserted into the device. In other words, in the second position the closure does not cover the opening, or only covers the opening only to the extent that a consumable may still be inserted into the opening and into the cavity of the device.

Optionally, the closure is at least one of a swiveling closure, a swinging closure, a sliding closure, and a lifting closure.

In some embodiments, the closure comprises a swiveling or rotating closure, such as a ball valve. Such a ball valve may comprise a body of circular or substantially circular cross section which is rotatable, defining a bore passing through the body, such that rotation of the body brings the bore of the body and the cavity of the device into alignment (second position) for insertion of a consumable. When the body is rotated away from this alignment (into a first position) the opening of the cavity in the device is effectively covered. The ball valve may comprise a cylindrical body defining a bore passing through the body in a direction perpendicular to the primary rotational axis of the cylinder. In this way, the user rotates the cylinder until the bore and cavity are in alignment (in a second position) to facilitate insertion of a consumable into the device, and rotates the cylinder so that the bore and cavity are out of alignment (in a first position) to effectively cover or restrict entry to the opening to the cavity. In some embodiments the ball valve structure is contained within the body of the device such that it is substantially concealed within the body.

In some embodiments, the closure comprises a swinging closure, such as a concealed trap door within the device body. For example, the closure may comprise a hinged sheet of material which is biased into the first position (closed) in which the sheet covers the opening, wherein when force is applied to the sheet in a direction into the device to overcome the bias, the sheet swings via the hinge into the second position (open), allowing insertion of a consumable into the cavity. In this way, the user is able to open the closure simply by pressing the end of a consumable against the sheet, into the device, which pushes the closure away from the opening to allow the consumable to pass into the device. In some embodiments, the trap door is biased into the first position (closed). For example, the trap door may be spring-loaded.

In some embodiments, the closure comprises a sliding closure, such as a planar sheet of material which in the first position extends across the opening and in the second position in retracted within the body of the device. In some embodiments, the sheet resides within a slot adjacent to the cavity when in the second position, and slides out of the slot and across the opening when moved into the first position. In some embodiments the planar sheet of material is flexible. In this way, when the sheet is retracted into the second position it may bend or flex to conform to the internal structure of the body of the device to be more easily accommodated.

In some embodiments, the closure comprises a duck-bill valve, i.e., an annular passage which tapers to a closed (e.g., planar) end. Upon insertion of a consumable into the valve, applying pressure will open the tapered end of the valve allowing the consumable to pass through. When the consumable is removed, the resilience of the material of the valve will return the valve to its closed condition, covering the opening of the device. The duck-bill valve may be made from any suitable resilient flexible material, such as rubber or synthetic elastomer.

In some embodiments, the first position is a terminal position along the path of travel of the closure, and the second position is a terminal position along the path of travel of the closure. Thus, the closure may move along a path of travel which terminates at each end in the first and second positions respectively.

Optionally, the closure comprises biasing means which urge the closure into one or both of the first position and the second position. In this way, the risk of accidental movement of the closure away from the first position or away from the second position is reduced. In some embodiments, the biasing means comprises a magnet or spring. For example, the closure and the body of the device may each comprise a magnet, between which a force of attraction exists to hold the closure in position until the user overcomes the force. Alternatively, the closure may be spring-loaded, wherein one or more springs bias the closure into one or more of the first and second positions. In some embodiments, the biasing means urge the closure into the first position when the closure is positioned at a position intermediate the first and second positions.

According to a preferred embodiment of the present disclosure, the closure may be movable between the first and the second position by a rotatory movement.

According to a further preferred embodiment of the present disclosure the device may comprise means to hold the closure in one or more of the first position and the second position.

According to a further preferred embodiment of the present disclosure, the means to hold the closure may be at least one means out of the group consisting of a detent comprising a raised feature on a surface of the device body, a magnet or a spring.

In some embodiments, the device comprises means to hold the closure in one or more of the first position and the second position. In some embodiments, the means to hold the closure comprises an interaction between the closure and a part of the body of the device which occurs at or close to the first and/or second position. In some embodiments, the means to hold the closure comprises a detent comprising a raised feature on a surface of the device body and/or the closure. In some embodiments, the means to hold the closure comprises an interference fit provided between the closure and the body of the device when in the first and/or second positions, wherein the interference fit is removed as the closure moves away from the first and/or second position to facilitate movement between the positions.

In some embodiments, the closure is provided with a handle external to the body of the device for allowing a user to move the closure between the first position and the second position. In some embodiments, the handle forms part of the closure or is connected to the closure. In some embodiments, the handle comprises a rotatable handle (for example, connected to a rotatable closure, such as the ball valve described above). In some embodiments, the handle comprises a slidable handle (for example, connected to a slidable closure, such as the slidable planar sheet of material described above). In some embodiments, the handle comprises a movable part outside the body of the device and a connector passing through an outer wall of the device and attached to the closure within the body of the device. Movement of the movable part by the user allows the user to control the position of the closure. In some embodiments the connector is housed within a slot in the outer wall of the device and slidable along the slot by movement of the movable part.

Optionally, the closure may be interposed between the opening to the cavity and a rod heater disposed within the body of the device. Conveniently, the rod heater is disposed along a longitudinal axis of the body. In some embodiments, the closure when in the first position is set back from the opening in the body of the device, such that a recess is provided at the opening of the cavity when the closure is in the first position (closed).

Optionally, the closure may be made of a flexible material. In some embodiments, the closure is made of flexible plastics material. In this way, the closure is able to bend and flex when moved, to facilitate its accommodation within the body of the device.

In some embodiments, the device further comprises a sensor for detecting a position of the closure, a heater for heating the consumable when received in the cavity, and a controller configured to receive a signal from the sensor, indicative of a position of the closure, and to control the heater in response to the received signal.

According to a further preferred embodiment of the present disclosure, the sensor may be configured to generate a signal upon detecting that the closure is in the first position, and wherein the controller may deactivate the heater based on the received signal.

In some embodiments, the controller prevents activation of the heater when the closure is in the first position. In some embodiments, the controller permits activation of the heater when the closure is in the second position. In some embodiments, the controller activates the heater when the closure is moved into the second position, e.g., by a user operating the handle. In this way, the heater cannot be activated when the closure is "closed" and/or can be activated/is automatically activated when the closure is "open". This provides a safer and more efficient device since accidental activation of the heater e.g., in a pocket or bag is prevented, which saves battery life and is safer. When the user opens the closure, the controller then permits the activation of the heater (e.g., by an appropriate input on a user interface) or automatically activates the heater.

Thus, the sensor may be configured to generate a signal upon detecting that the closure is in the first position. In some embodiments, the controller then deactivates the heater, based on the received signal. In this way, unnecessary power supply to the heater is avoided when the device is not in use.

According to a further preferred embodiment of the present disclosure claims, the closure may comprise biasing means which urge the closure into one or both of the first position and the second position.

According to a further preferred embodiment of the present disclosure, the biasing means may comprise a magnet or spring.

In this way, the risk of accidental movement of the closure away from the first position or away from the second position is reduced. In some embodiments, the biasing means comprises a magnet or spring. For example, the closure and the body of the device may each comprise a magnet, between which a force of attraction exists to hold the closure in position until the user overcomes the force. Alternatively, the closure may be spring-loaded, wherein one or more springs bias the closure into one or more of the first and second positions. In some embodiments, the biasing means urge the closure into the first position when the closure is positioned at a position intermediate the first and second positions.

According to a further preferred embodiment of the present disclosure, the closure may be interposed between an opening to the cavity and a rod heater, wherein the rod heater may be disposed within the cavity along a longitudinal axis of the body.

Conveniently, the rod heater is disposed along a longitudinal axis of the body. In some embodiments, the closure when in the first position is set back from the opening in the body of the device, such that a recess is provided at the opening of the cavity when the closure is in the first position (closed).

According to a further preferred embodiment of the present disclosure, the closure may be at least one of a swiveling closure, a swinging closure, a sliding closure and a rotating closure.

In some embodiments, the closure comprises a swiveling or rotating closure, such as a ball valve. Such a ball valve may comprise a body of circular or substantially circular cross section which is rotatable, defining a bore passing through the body, such that rotation of the body brings the bore of the body and the cavity of the device into alignment (second position) for insertion of a consumable. When the body is rotated away from this alignment (into a first position) the opening of the cavity in the device is effectively covered. The ball valve may comprise a cylindrical body defining a bore passing through the body in a direction perpendicular to the primary rotational axis of the cylinder. In this way, the user rotates the cylinder until the bore and cavity are in alignment (in a second position) to facilitate insertion of a consumable into the device, and rotates the cylinder so that the bore and cavity are out of alignment (in a first position) to effectively cover or restrict entry to the opening to the cavity. In some embodiments the ball valve structure is contained within the body of the device such that it is substantially concealed within the body.

In some embodiments, the closure comprises a swinging closure, such as a concealed trap door within the device body. For example, the closure may comprise a hinged sheet of material which is biased into the first position (closed) in which the sheet covers the opening, wherein when force is applied to the sheet in a direction into the device to overcome the bias, the sheet swings via the hinge into the second position (open), allowing insertion of a consumable into the cavity. In this way, the user is able to open the closure simply by pressing the end of a consumable against the sheet, into the device, which pushes the closure away from the opening to allow the consumable to pass into the device. In some embodiments, the trap door is biased into the first position (closed). For example, the trap door may be spring-loaded.

In some embodiments, the closure comprises a sliding closure, such as a planar sheet of material which in the first position extends across the opening and in the second position in retracted within the body of the device. In some embodiments, the sheet resides within a slot adjacent to the cavity when in the second position, and slides out of the slot and across the opening when moved into the first position. In some embodiments the planar sheet of material is flexible. In this way, when the sheet is retracted into the second position it may bend or flex to conform to the internal structure of the body of the device to be more easily accommodated.

The device may comprise an elongate body. An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate). The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the body of the device, and may be slidable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

A third aspect of the sixteenth mode of the present disclosure is a heat-not-burn device comprising a body defining a cavity and an opening to the cavity for receipt of a heat-not-burn consumable therein and a closure for covering the opening. The device further comprises a sensor for detecting a position of the closure, a heater for heating the consumable when received in a cavity and a controller configured to receive a signal from the sensor, indicative of a position of the closure, and to control the heater in response to the received signal.

This third aspect of the sixteenth mode provides a device in which control of the heater depends upon the position of the closure. A more intelligent device is therefore provided, which can dictate certain functions of the heater depending on the position of the closure.

Optionally, the closure may move between a first position and the second position. The closure covers the opening of the cavity in the first position and in the second position the closure is retracted to be substantiality concealed within the body.

Optionally, the sensor is configured to generate a signal upon detecting that the closure is in the first position. In some embodiments, the controller then deactivates the heater, based on the received signal.

In this way, unnecessary power supply to the heater is avoided when the device is not in use.

All the optional features of the closure described above in the context of the first and second aspects of the sixteenth mode apply equally to the third aspect of the sixteenth mode.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a fourth aspect of the sixteenth mode, there is provided a system (e.g., a smoking substitute system) comprising a device according to the first aspect of the sixteenth mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia* divinorum, *Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa (Damiana), Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a fifth aspect of the sixteenth mode of the present disclosure, there is provided a method of operating a heat not burn device, the method comprises steps of determining a position of a closure for covering an opening of the device into which an aerosol generating consumable or a heat-not-burn consumable is received in use, and controlling a heater of the device based on the determined position of the closure.

Optionally, the method may comprise determining by a sensor associated with the controller, the position of the closure, wherein the controller deactivates the heater based on a signal received from the sensor when the closure is in a first position where the closure covers a cavity in the device.

The disclosure includes the combination of the aspects and preferred features of the sixteenth mode described except where such a combination is clearly impermissible or expressly avoided.

The skilled person will appreciate that except where mutually exclusive, a feature or parameter of the sixteenth mode described in relation to any one of the above aspects may be applied to any other aspect of the sixteenth mode. Furthermore, except where mutually exclusive, any feature or parameter of the sixteenth mode described herein may be applied to any aspect and/or combined with any other feature or parameter of the sixteenth mode described herein.

Seventeenth Mode: A Smoking Substitute Device with an Improved Air Inlet

At its most general, a seventeenth mode of the present disclosure relates to a smoking substitute device with an improved air inlet that may reduce the likelihood of inadvertent blockage by a user. Furthermore, the air inlet may allow airflow to be directed at a base of the heating element, and thereby it may improve aerosol generation and Total Particulate Matter (TPM) output of the aerosol of the HT smoking substitute system.

According to a first aspect of the seventeenth mode of the present disclosure, there is provided a smoking substitute device. The smoking substitute device comprises a housing; and a cap configured to engage with the housing and thereby defines an air inlet between the cap and the housing; wherein the air inlet is configured to facilitate an airflow to enter into the housing.

The cap may be slidable along a longitudinal axis of the device, between a first position where at least a peripheral portion of the cap is positioned adjacent to a corresponding peripheral portion of the housing and a second position where the cap is positioned away, but not necessarily detached, from the housing.

By providing the smoking substitute device comprising an air inlet defined between the cap and the housing, it may advantageously prevent the user from inadvertently blocking said air inlet. This is because the interface between the cap and housing is positioned at an edge or a peripheral portion of the housing and therefore the user may be less likely to hold onto the device by said interface.

Optional features will now be set out. These are applicable singly or in any combination with any aspect of the seventeenth mode.

Optionally, the air inlet extends in a direction transverse to longitudinal axis of the housing. Advantageously, such arrangement may allow the air inlet to position along an edge or a peripheral portion of the housing or the cap.

Optionally, the device further comprises a heating element, and the air inlet provides airflow into the housing underneath the heating element.

Optionally, the air inlet is located adjacent to a heating element of the housing. Optionally, the air inlet facilitates the airflow to flow towards a base of the heating element. For example, the cap may be configured to receive an aerosol-forming article and whereby during use, the heating element may be configured to fully penetrate into said article. Conveniently, the base of the heater may correspond to an end of the cap when the cap is engaged with the housing. Therefore, the air inlet formed between the cap and the housing may be positioned immediately adjacent to the heating element. Advantageously, such arrangement may reduce draw resistant offered by a shorter air flow path, as well as increasing the amount of heat convection by directing the air flow towards the base of the heating element, and thereby it may improve the quality of aerosol generation and Total Particulate Matter (TPM) output of the aerosol.

Optionally, the air inlet is defined by a gap formed between the cap and the housing when the cap is engaged with the housing. More specifically, when the cap is engaged with the housing, at least a portion of the cap is spaced from the housing to form such gap. For example, the device may comprise a stop to prevent the cap from abutting the housing so as to define such gap.

Optionally, the cap and/or housing comprises a notch or indentation formed on a respective edge of the cap and/or housing, wherein the notch or indentation on the cap and/or housing forms the air inlet. As such when the cap is engaged with the housing, a portion of the cap may abut the housing and airflow may enter the device through the notch.

Optionally, the air inlet comprises a slit or a through hole.

Optionally, the smoking substitute device comprises a Heat Not Burn (HNB) device.

According to a second aspect of the seventeenth mode of the present disclosure, there is provided a smoking substitute device comprising a housing and an electrical connection disposed in the housing. The electrical connection comprises an air inlet, to facilitate flow of air into the housing.

For example, the electrical connection may be a socket for receiving an electrical terminal. The electrical connection may comprise an opening that forms the air inlet, which in turn may be arranged to be in fluid communication with the heating element. Therefore, an airflow may enter the housing via said air inlet at the electrical connection. The air inlet may remain open even if the electrical connection is engaged with or receiving a corresponding electrical terminal. Advantageously, the provision of an air inlet at said electrical connection may reduce the likelihood of a user blocking said air inlet because the user is not likely to hold onto the device by the electrical connection.

Optionally, the housing comprises a first end engageable with a cap and a second end opposite to the first end, wherein the electrical connection forms on the second end of the device. Advantageously, by locating the electrical connection towards an end of the device, it may reduce the likelihood of user blocking said air inlet because the user is not likely to hold onto the device by its end.

Optionally, the electrical connection is provided at the housing at a position adjacent to the cap. Advantageously, such arrangement may significantly reduce the length of the air flow path and therefore it may reduce draw resistant and thereby it may improve the quality of aerosol generation and Total Particulate Matter (TPM) output of the aerosol.

Optionally, the air inlet at the electrical connection facilitates the airflow to flow towards a base of a heating element of the housing. Advantageously, such arrangement may increase the amount of heat convection by directing the air flow towards the base of the heating element, and thereby it may promote the aerosol generation and increases TPM output.

Optionally, the electrical connection comprises a Universal Serial Bus (USB) connection. Optionally, the electrical connection comprises a USB socket having the air inlet defined therein.

Optionally, the smoking substitute device comprises a Heat Not Burn (HNB) device.

The smoking substitute device (hereinafter referred as device), may comprise a housing. A first end of the housing may be configured for engagement with a cap, wherein the cap may be configured to receive an aerosol-forming article. For example, the housing may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the housing of the device. The heating element may extend from the end of the housing that is configured for engagement with the aerosol-forming article.

The heater (and thus the heating element) may be rigidly mounted to the housing. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity.

Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or, e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments housing of the device may include a first end for engaging a cap, that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the housing of the device, and may be slidable between the open and closed positions. When the cap is engaged with the housing (i.e., the cap in the closed position), a gap may form between the cap and the housing, which may be configured as an air inlet, to facilitate flow of air into the housing. The air entering the housing may be hence, directed underneath the heating element accommodated in the housing.

The cap may define at least a portion of the cavity of the device. That is, the cavity may be fully defined by the cap, or each of the cap and housing may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an electrical connection or an input connection (e.g., a USB port, Micro USB port, USB-C port, etc.) disposed at a second end of the housing. The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device. Further, the electrical connection may be configured to provide with the air inlet, to facilitate flow of air into the housing (i.e., underneath the heating element accommodated in the housing).

The power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the housing of the device.

The device may further comprise a puff sensor (e.g., airflow sensor), which form part of the input means of the UI. The puff sensor may be configured to detect a user drawing on an end (i.e., terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may, e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a third aspect of the seventeenth mode, there is provided a system (e.g., a smoking substitute system) comprising a device according to the first aspect of the seventeenth mode or the second aspect of the seventeenth mode and an aerosol-forming article. The aerosol-forming article may comprise an aerosol-forming substrate at an upstream end of the aerosol-forming article. Conveniently, the article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Turnera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the seventeenth mode described except where such a combination is clearly impermissible or expressly avoided.

The skilled person will appreciate that except where mutually exclusive, a feature or parameter described in relation to any one of the above aspects of the seventeenth mode may be applied to any other aspect of the seventeenth mode. Furthermore, except where mutually exclusive, any feature or parameter described herein may be applied to any aspect and/or combined with any other feature or parameter of the seventeenth mode described herein.

Eighteenth Mode: A Stopper for a Smoking Substitute Device

At its most general, an eighteenth mode of the present disclosure relates to a stopper for a smoking substitute device. The stopper is configured to cover a cavity of the device and thereby prevent ingress of foreign objects. Advantageously, this may form a shield for protecting the heating element.

According to a first aspect of the eighteenth mode of the present disclosure, there is provided a stopper for a Heat Not Burn (HNB) device, the HNB device having a cavity for receiving an aerosol-forming article, the stopper is configured to close said cavity.

By providing the stopper, the cavity of the HNB device may be closed or covered, when the aerosol-forming article is not engaged with the HNB device. The stopper may be a plug that plugs into and thereby blocks the cavity. The stopper may alternatively be an external cover that covers the cavity, e.g., the stopper may engage with a part of HNB device so as to form a shield for the cavity. Advantageously, the provision of the stopper may prevent ingress of foreign objects, dust, dirt and/or moisture. Not only will this prolong the life of the heating element, by preventing ingress of foreign objects and dust it may also eliminate the possibility of unwarranted release of volatile from said foreign objects and dust.

Optional features will now be set out. These are applicable singly or in any combination with any aspect of the eighteenth mode.

Optionally, the stopper comprises a projection receivable by the cavity. For example, the projection may extend from a main portion of the stopper. Said projection may have the same cross section profile to that of the cavity so as to form a seal with the cavity. For example, when received in the cavity, the projection may abut a side wall of the cavity.

Optionally, the projection is configured to close an opening of a cap that is received in the cavity of the HNB device, and thereby closes the cavity. For example, the HNB device may further comprise a cap received in the cavity, the cap comprises an opening configured to receive an aerosol-generating article; wherein the projection of the stopper is configured to close the opening to close the cavity. The external surface of the cap abuts the internal surface of the cavity. The cap may be slidably received in the cavity. Therefore, by closing the opening of the cap, the stopper may close the cavity. Said projection may have the same cross section profile to that of the opening or internal surface of the cap so as to form a seal with the opening.

Optionally, the projection engages with the opening of the cap to form a hermetic seal. Advantageously, this prevents water ingress into the cavity and therefore it may reduce the risk of short circuits, as well as rust or damage to the heating element. Further, the hermetic seal may prevent any residual smell and aerosol in the cavity from reeking out of the cavity. Such hermetic seal may be formed by a gasket position in between the stopper and the cap. Optionally such hermetic seal may be effected by an interference fit.

Optionally, the projection comprises a threaded portion for engaging with the opening of the cap. Alternatively, the stopper comprises at least one ridge defined on an outer periphery of the projection, said at least one ridge is configured to engage with at least one notch defined along an internal surface the cap. Advantageously, such arrangement allows the stopper to securely fit onto the cap, and thereby reduces the chance of it being removed inadvertently.

Optionally, the projection is receivable by the opening or cavity in at least one defined orientation. Advantageously, this may allow the stopper to be fitted into the cavity more easily.

Optionally, the projection is configured to engage with an additional cavity formed on the device. For example, the projection may be configured to engage with at least one of a storage cavity, an airflow inlet and a power input port of the HNB device, when the stopper is not closing the opening of the cap or the cavity. Advantageously, the additional cavity may provide additional storage space for temporary storing the stopper, as such reduces the risk of it being misplaced.

Optionally, the stopper further comprises a grip, wherein the grip comprises a tactile surface. For example, the tactile surface may comprise an elastic coating and/or one or more protrusions. Adventurously, the grip may allow the user to insert or remove the stopper more easily.

Optionally, the stopper further comprises a visual indication portion for providing information corresponding to the HNB device. The visual indication portion may be configured to indicate at least one of a brand, a category, a flavor, a numeral, and a symbol, that may correspond to the HNB device. Advantageously, such visual indication may allow the user to identify the HNB device, and thereby it may reduce the likelihood of inserting a wrong type of aerosol-forming article into the HNB device.

Optionally, the stopper is formed from an elastic or deformable material, for example it may form from at least one of silicone, leather and elastomer. Advantageously, the use of such material improves the grip of the stopper, as well as effecting an interference fit of the stopper with the cavity or the opening of the cap.

The device may comprise an elongate body. An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The device may comprise a heater for heating the aerosol-forming article. The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the body of the device, and may be slidable between the open and closed positions.

The cap may define at least a portion of the cavity of the device. That is, the cavity may be fully defined by the cap, or each of the cap and body may define a portion of the cavity. Where the cap fully defines the cavity, the cap may comprise an opening for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the eighteenth mode, there is provided a system (e.g., a smoking substitute system) comprising a stopper according to the first aspect of the eighteenth mode and a HNB device having a cavity for receiving an aerosol-generating article. The stopper is configured to close the cavity of the HNB device.

Optionally, the HNB device further comprises a cap received in the cavity; the cap comprises an opening configured to receive an aerosol-generating article therethrough; wherein the projection of the stopper is configured to close the opening to close the cavity.

Optionally, the system further comprises an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

Further, the aerosol-forming article of the system may be receivable by a cavity defined in the HNB device. The system may also comprise the stopper, which may be configured to close said cavity of the HNB device, when the aerosol-forming article is engaged with the HNB device.

Optionally, the stopper may include a projection, which may be receivable by the cavity. Also, the projection may be engageable in an opening defining the cavity, where the opening may be defined in a cap of the HNB device that may receive the aerosol-forming article.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia* divinorum, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the eighteenth mode described except where such a combination is clearly impermissible or expressly avoided.

The skilled person will appreciate that except where mutually exclusive, a feature or parameter described in relation to any one of the above aspects of the eighteenth mode may be applied to any other aspect of the eighteenth mode. Furthermore, except where mutually exclusive, any feature or parameter described herein may be applied to any aspect and/or combined with any other feature or parameter of the eighteenth mode described herein.

Nineteenth Mode: A Smoking Substitute System Comprising a Wire Harness Member

At its most general, a nineteenth mode of the present disclosure relates to a smoking substitute system comprising a wire harness member.

According to a first aspect of the nineteenth mode of the present disclosure, there is provided a wire harness member for a smoking substitute device comprising: a body, one or more apertures extending through the body, and a slit extending from each aperture of the one or more apertures to an edge of the body, for receipt of a wire of the heat not burn device in the one or more apertures.

By providing a wire harness member having an aperture and a slit, a wire (of a smoking substitute device) can easily be inserted into the aperture via the slit (e.g., during assembly) so as to be supported in the aperture.

Optional features will now be set out. These are applicable singly or in any combination with any aspect of the nineteenth mode.

The wire harness member may comprise a plurality of apertures. The wire harness may comprise e.g., two or three apertures (each with a corresponding slit). The wire harness may comprise four apertures. Each of the four apertures may comprise a corresponding slit. The wire harness may comprise more than four apertures (e.g., five, six, etc.).

The plurality of apertures may be arranged in a line. The plurality of aperture may be arranged along a substantially straight line. The plurality of apertures may be arranged along a curved line. The apertures may all be spaced from the edge of the body by the same distance. In this respect, the plurality of apertures may be arranged along a line that follows (but is offset from) the edge.

Thus, the apertures may be aligned so as to be substantially parallel to, but spaced from, the edge of the body. In this way, wires that are supported in the apertures may be spaced from an internal wall of the substitute smoking device (i.e., when the wire harness member is mounted in a device). This can avoid short circuits occurring due to contact between the wires and the housing (especially where the housing is electrically conductive).

The apertures are spaced from one another. The apertures may be the same or similar size (e.g., diameter). The apertures may be circular, or may be another shape (e.g., rectangular, hexagonal, etc.). The apertures may be spaced from one another by a distance that is equal to or greater than a radius of one of the apertures.

The one or more apertures may be proximate the edge of the body. For example, where the one or more apertures are circular, the or each aperture may be spaced from the edge by a distance that is less than or equal to twice (or three times) the diameter of the or each aperture.

The or each slit may comprise a frangible membrane extending between opposing lateral surfaces defining the slit. The or each aperture may comprise a frangible membrane extending thereacross. A single frangible membrane may extend across the or each aperture/slit pair. The or each frangible membrane may be configured to break upon receipt of a wire into a corresponding aperture via the slit. Thus, during assembly a wire may be inserted into an aperture via the corresponding slit, which may cause the frangible portion to be broken (e.g., torn, split, etc.). In this respect, the or each slit and the or each aperture may not be fully formed until the frangible membrane is broken. The frangible membrane(s) may be elastic. In this respect, the frangible membrane(s) may generally return to their original shape after being broken (i.e., other than the split, break, etc. in the membrane), which may help to seal around and retain a wire in a corresponding aperture. The or each frangible membrane may be integrally formed with the body. The or each frangible membrane may be a thinner and/or weaker portion of material of the body.

The opposing lateral surfaces of each slit may each extend between opposing upper and lower surfaces of the body, and between the edge and the corresponding aperture. Each slit may have a width (the distances between the opposing lateral surfaces) that is substantially less than a depth (the distance between the opposing upper and lower surfaces). The width of the or each slit may be substantially the same as, or less than, the diameter of a wire intended for receipt through the slit for support in the corresponding aperture.

The or each slit may extend in a direction that is substantially perpendicular to the edge of the body. The or each slit may extend in a direction (from the edge) that is at an angle to the perpendicular. An entrance to the or each slit (i.e., where the slit meets the edge) may taper outwardly so as to define a wider mouth portion of the slit. This may facilitate insertion of a wire into the slit. The or each slit may extend through the body (i.e., between the upper and lower surfaces) at a non-perpendicular angle (i.e., the slits may be angled with respect to a line perpendicular to the upper and lower surfaces).

The width of each slit (defined by the distance between opposing lateral surfaces defining the slit) may be less than the diameter of the aperture from which it extends. This may help to retain the wire in the aperture (i.e., a narrower slit may help to prevent a wire from being dislodged from the aperture).

The wire harness may be unitary structure. That is the wire harness member may be formed from a single piece of material. This may simplify manufacture of the wire harness member.

The wire harness member may be formed of a thermally insulative material. Thus, the wire harness member may reduce heat transfer between two parts of the device (when installed therein). For example, the wire harness member may restrict heat transfer from a heater of the device to other parts of the device.

The wire harness member may be formed of an electrically insulative material. Thus, the wire harness member may not conduct electricity from the wires it supports.

The wire harness member may be formed of an elastomeric material. Thus, the wire harness member may have some elasticity. This may facilitate assembly of the wire harness member into a housing of device and may also allow the wire harness member to provide a sealing function. The wire harness member may be located in a cavity in (slightly) compressed condition, such that it naturally seals against internal walls defining the cavity. The elastomeric material may be a silicone material.

The wire harness member may comprise a lip that extends about at least a portion of a periphery of the body. The lip may be a downwardly extending lip, or may be an upwardly extending lip. The lip may define a thicker portion of the body at the perimeter. The body may further comprise a planar central portion that is thinner than the lip.

The edge may be a first edge, and the body may further comprise a second edge spaced from and opposing the first edge. The body may further comprise first and second spaced opposing ends extending between the first and second edges. The edges may be longer than the ends. A periphery of the body may be shaped for close-fit receipt in a housing of a corresponding smoking substitute device. The lip may extend along the second edge, and first and second ends.

The wire harness member may comprise an outwardly projecting sealing rib extending along at least a portion of a periphery of the body. The sealing rib may project from the lip of the body. The sealing rib may be configured to seal against an internal wall of a device when the wire harness member is installed therein. The sealing rib may be configured to locate in a corresponding recess or groove of a wall of the housing.

The body may comprise a recess configured to accommodate a component of a device (into which the wire harness member may be installed). The body may comprise a recess configured to accommodate a puff sensor, such as a pressure sensor. The recess may be open at both upper and lower sides of the wire harness member, such that the pressure sensor is exposed to air on both sides of the wire harness member. In this way the pressure sensor may be arranged to measure a difference in pressure between the sides of the wire harness member.

In a second aspect of the nineteenth mode there is provided a smoking substitute system comprising: a heater for heating a smoking substitute article, a power source connectable to the heater by one or more wires; and a wire harness member as described above with respect to the first aspect of the nineteenth mode, the wire harness member located between the heater and the power source such that the one or more wires pass through the one or more apertures of the wire harness member.

The system may comprise a smoking substitute device. The wire harness member and power source may be accommodated in a housing of the device. The heater may be accommodated in the housing of the device. The power source may be located in an internal cavity of the housing. The wire harness member may extend across the internal cavity so as to substantially seal the power source from the heater.

The internal cavity of the housing (accommodating the power source) may be defined by one or more walls of the housing. The one or more walls may comprise a recess or groove for locating the wire harness member. The recess or groove may receive a portion of the wire harness member. For example, the recess or groove may receive the outwardly projecting rib of the wire harness member. The internal cavity of the housing may be sized and shaped so as to closely or snugly accommodate the wire harness member thereacross.

The housing may be elongate. An end of the elongate body may be configured for engagement with an aerosol-forming article. In this respect, the system may comprise an aerosol-forming article. The housing may be configured for engagement with a heated tobacco (HT) consumable (or heat-not-burn (HNB) consumable) or an e-cigarette consumable. The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The wire harness member may be disposed between the article-receiving cavity and the cavity in which the power source is accommodated. The aerosol-forming article may be of the type that comprises an aerosol former (e.g., carried by an aerosol-forming substrate).

The heater may comprise a heating element, which may be in the form of a rod that extends from the housing of the device. The heating element may extend from the end of the housing that is configured for engagement with the aerosol-forming article.

The heater (and thus the heating element) may be rigidly mounted to the housing. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 µm and 220 µm, e.g., between 170 µm and 190 µm, e.g., around 180 µm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 µm.

The heating element may be located in the article-receiving cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

In some embodiments the heater may form part of the aerosol-forming article (rather than the device). In such cases the device itself may not comprise a heater. Such arrangements may, for example, be suited to e-cigarette systems in which the aerosol-forming article comprises a tank containing an aerosol former (e.g., in liquid form). In such embodiments, the device may comprise means for connecting the device the heater of an aerosol-forming article engaged with the device. For example, the device may comprise one or more device connectors for (e.g., electrically) connecting the device to a corresponding heater connector of the aerosol-forming article. The connectors (i.e., of both the device and the aerosol-forming article) may be in the form of electrically conductive elements (e.g., plates) that contact when the aerosol-forming article is engaged with the device. In such arrangement the wire harness member may seal the power source from the heater when the article is engaged with the device.

In some embodiments the device may comprise a cap disposed at the end of the housing that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the housing of the device, and may be slidable between the open and closed positions.

The cap may define at least a portion of the cavity of the device. That is, the cavity may be fully defined by the cap, or each of the cap and housing may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

As set forth above, the power source may be electrically connected to the heater via wire. Thus, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). As an example, the input connection (thus the power source), may be connected to the heating element of the heater via one or more wires. The one or more wires extending between the power source and the heating element (thus the heater), may be accommodated (i.e., supported) by the wire harness member disposed between the heater and the power source in the housing of the device. Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the housing of the device.

The device may further comprise a puff sensor (e.g., airflow sensor). The puff sensor may be accommodated in a recess of the wire harness member. The puff sensor may form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.). As is set forth above, the puff sensor may be mounted in a recess or aperture of the wire harness member. The puff sensor may be mounted so as to be exposed to air on both sides of the wire harness member. In this way, the puff sensor may be arranged to measure a pressure difference between the two sides of the wire harness member.

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

As is provided above, the system of the second aspect of the nineteenth mode may comprise an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris,* Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incarnata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

As is briefly discussed above, the system may be in the form of an e-cigarette system (i.e., rather than a heated tobacco system as described above). In such a system, the consumable may be in the form of an e-cigarette consumable. The e-cigarette system may be configured such that the consumable can be received and retained in the cavity of the device (i.e., so as to be engaged with the device). The consumable may be retained by way of e.g., an interference fit, screwing one onto (or onto) the other, a bayonet fitting, or by way of a snap engagement mechanism.

The consumable may comprise a tank, which may define a reservoir for the storage of an aerosol former. The aerosol former may be in the form of an e-liquid (stored in the reservoir).

The consumable may be a "single-use" consumable. That is, upon exhausting the e-liquid in the tank, the intention may be that the user disposes of the entire consumable. Alternatively, the e-liquid may be the only part of the system that is truly "single-use". For example, the tank may be refillable with e-liquid or another component of the system (internal to the device or external to the device e.g., a refillable cartomizer) may define a reservoir for the e-liquid.

As set forth above, the consumable may comprise a heater (i.e., instead of the heater forming part of the device) configured to heat and vaporize the e-liquid. The consumable may comprise a porous wick that conveys e-liquid from the tank to a heating element of the heater. The heating element may be a heating filament that is wound (e.g., helically) around at least a portion of the porous wick, such that when the heating element is heated (e.g., by the action of electrical current passing through the heating element), heat may be transferred from the heating element to the e-liquid conveyed by the wick. This transfer of heat may vaporize the e-liquid and the resultant vapor may be entrained in an airflow passing through the consumable.

The consumable may further comprise one or more heater connectors for connecting the heater (of the consumable) to the device. The heater connectors may be in the form of electrically conductive element or contacts (e.g., metal plates) and may be disposed on an in-use device-facing surface of the consumable. The heater connectors may be electrically connected to the heater of the consumable, such that electricity supplied via the heater connectors may pass to the heater. In other words, a voltage applied across the heater connectors may generally correspond to a voltage applied across the heating element of the heater.

The heater connectors may be arranged such that they contact corresponding device connectors of the device when the consumable is engaged with the device. The device connectors may be connected (e.g., electrically) to a power source (e.g., battery) of the device. Thus, electricity may be supplied from the power source to the heating element (through wires supported by the wire harness member), via in-contact heater and device connectors. In this way, the heater forming part of the consumable may operate (and interact with e.g., a controller) as otherwise described above with respect to a heater forming part of the device.

According to a third aspect of the nineteenth mode of the present disclosure, there is provided a method of using the system according to the second aspect of the nineteenth mode, the method comprising inserting the aerosol-forming article into the device; and heating the article using the heater of the device.

In some embodiments the method may comprise inserting the article into a cavity within a body of the device and penetrating the article with the heating element of the device upon insertion of the article.

According to a fourth aspect of the nineteenth mode of the present disclosure, there is provided a method of assembling a smoking substitute device (e.g., such as the device/system described above with respect to the second aspect of the nineteenth mode). The method comprises installing a wire harness member (such as that described above with respect to the first aspect of the nineteenth mode) into the device and inserting one or more wires into the apertures of the wire harness member (via the one or more slits). The method may comprise, subsequently, connecting the wires to a heater of the device. The wires may be connected to a power source. In that respect, the power source may be installed in the device prior to the wire harness member.

The disclosure includes the combination of the aspects and preferred features of the nineteenth mode described except where such a combination is clearly impermissible or expressly avoided.

The skilled person will appreciate that except where mutually exclusive, a feature or parameter described in relation to any one of the above aspects of the nineteenth mode may be applied to any other aspect of the nineteenth mode. Furthermore, except where mutually exclusive, any feature or parameter of the nineteenth mode described herein may be applied to any aspect and/or combined with any other feature or parameter of the nineteenth mode described herein.

Twentieth Mode: A Smoking Substitute Device Having a Heat Dissipation Element in the Housing At its most general, a twentieth mode of the present disclosure relates to a smoking substitute device having a heat dissipation element in the housing.

According to the twentieth mode of the present disclosure, there is provided a smoking substitute device having a housing defining an outer surface of the smoking substitute device, a heating element disposed in the housing, and at least one heat dissipation element disposed between the heating element and the outer surface of the housing, the at least one heat dissipation element configured to dissipate heat across the outer surface.

By providing a smoking substitute device comprising a heat dissipation element, the heat from the heating element is dissipated by the heating dissipation element by distributing the heat across a greater surface area. In other words, the heat dissipation element provides a thermal mass adjacent to or in proximity of the heating element. This may help to avoid localized heating and may provide faster heat dissipation by increasing the overall surface area available for heat loss. This may improve the user experience and may also avoid injury or other safety hazards that could otherwise result from localized heating. Further, having improved heat dissipation in the smoking substitute device may also protect components of the smoking substitute device from heat related damage and may result in improved life and low maintenance costs of the smoking substitute device.

The term "heat dissipation element" is intended to refer to a part or portion of the device that is provided for absorbing heat and distributing heat over an area so as to avoid the issue of localized "hot spots". In this respect, the heat dissipation is a thermal conductor rather than a thermal insulator.

Optional features will now be set out. These are applicable singly or in any combination with any aspect of the twentieth mode.

The heat dissipation element may have a thermal conductivity of above 10 W/mK at room temperature, or above 50 W/mK at room temperature, or above e.g., 100 W/mK at room temperature.

The at least one heat dissipation element may be metallic. For example, the at least one heat dissipation element may be formed of copper or aluminum. The at least one heat dissipation element may comprise a coating or surface treatment. The coating or surface treatment may facilitate heat dissipation of the heat dissipation element.

The at least one heat dissipation element may be ceramic. The at least one heat dissipation element may be formed of a combination of materials. Alternatively, the at least one heat dissipation element may be formed of a single material.

The at least one heat dissipation element may be a plate. That is, one dimension of the at least one heat dissipation element may be significantly smaller than the other two dimensions. The at least one heat dissipation element may be substantially planar or may have a curved profile. As should be appreciated, the at least one heat dissipation element may vary in size or shape depending on the heat dissipation requirements of the device.

A surface of the at least one heat dissipation element facing the heating element may have a surface area of at least 2 cm2, or at least 3 cm2, or e.g., at least 4 cm2.

The at least one heat dissipation element may be mounted at an internal surface of the housing. The housing may comprise an outer wall, an outer surface of which may define an outer surface of the device. The at least one heat dissipation element may be mounted at or to an inner surface of the outer wall of the housing. In this respect, the at least one heat dissipation element may be separated from the outer surface of the device by a wall of the housing.

The smoking substitute device may comprise first and second heat dissipation elements mounted to the housing. The first and second heat dissipation elements may be formed of different materials. One of the first and second heat dissipation elements may be formed of aluminium and another of the first and second heat dissipation elements may be formed of copper. The heat dissipation element formed of copper may be located in a cooler part of the housing (during operation) than the heat dissipation element formed of aluminium.

The housing may comprise first and second housing portions detachable from one another. One of the first and second heat dissipation elements (e.g., the first heat dissipation element) may be mounted to the first housing portion. The other of the first and second heat dissipation elements (e.g., the second heat dissipation element) may be mounted to the second housing portion. Alternatively, both of the first and second heat dissipation elements may be mounted to the first or second housing portion. Where one heat dissipation element is mounted to the first housing portion and the other is mounted to the second housing portion, the heat dissipation elements may come into contact (i.e., thermal or physical contact) when the housing portions are engaged with one another (i.e., not detached).

The first housing portion may be a body (which may be elongate) comprising the heating element (e.g., the heating element may be mounted to the body). The second housing portion may be a cap engageable with the body for at least partially enclosing the heating element. A heat dissipation element mounted to the cap may be formed of aluminum (e.g., anodized aluminum) whilst a heat dissipation element mounted to the body may be formed of copper.

The at least one heat dissipation element may be laterally spaced from the heating element. In this respect, there may be an air gap between the at least one heat dissipation element and the heating element. The housing may comprise an internal wall between the at least one heat dissipation element and the heating element and there may be an air gap between the internal wall and the at least one heat dissipation element.

The housing may comprise first and second spaced opposing lateral sides. The first heat dissipation element may be mounted at the first side of the housing and the second heat dissipation element may be mounted at the second side of the housing. The heating element may be located between the sides. In this respect, the first heat dissipation element may be mounted between the first side of the housing and the heating element, and the second heat dissipation element may be mounted between the second side of the housing and the heating element.

The heating element may be generally elongate so as to define a longitudinal axis. The at least one heat dissipation element may be located laterally adjacent to the heating element. Alternatively, the at least one heat dissipation element may be spaced along the longitudinal axis so as not to be laterally in line with the heating element. That is, the at least one heat dissipation element may be above or below the heating element in the housing.

The housing may be made of polymeric material. The housing may comprise a slot or recess for receipt of the at least one heat dissipation element. In this way, the at least one heat dissipation element may be mounted to the housing without adhesive. Alternatively, or additionally the at least one heat dissipation element may be mounted to the housing by way of an adhesive.

The outer surface of the housing may comprise a metallic portion. The metallic portion may be thermally (or physically) connected to the at least one heat dissipation element. In this way, heat from the heat dissipation element may be dissipated via the metallic portion.

An end of the elongate body may be configured for engagement with an aerosol-forming article. For example, the body may be configured for engagement with a heated tobacco (HT) consumable (or heat-not-burn (HNB) consumable). The terms "heated tobacco" and "heat-not-burn" are used interchangeably herein to describe a consumable that is of the type that is heated rather than combusted (or are used interchangeably to describe a device for use with such a consumable). The device may comprise a cavity that is configured for receipt of at least a portion of the consumable (i.e., for engagement with the consumable). The at least one heat dissipation element may at least partially define the cavity (e.g., the at least one heat dissipation element may be a wall of the cavity). The aerosol-forming article may be of the type that comprises an aerosol former (e.g., carried by an aerosol-forming substrate).

The heating element may form part of a heater for heating the aerosol-forming article. The heating element may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track may comprise tungsten and/or rhenium. The heating track may have a thickness of around 20 μm.

As set forth above, the heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

The cap may be disposed at the end of the body that is configured for engagement with an aerosol-forming article. The cap may be moveable between an open position in which access is provided to the heating element, and a closed position in which the cap at least partially encloses the heating element. The cap may be slidably engaged with the body of the device, and may be slidable between the open and closed positions.

The cap may define at least a portion of the cavity of the device. That is, the cavity may be fully defined by the cap, or each of the cap and body may define a portion of the cavity. Where the cap fully defines the cavity, the cap may comprise an aperture for receipt of the heating element into the cavity (when the cap is in the closed position). The cap may comprise an opening to the cavity. The opening may be configured for receipt of at least a portion of an aerosol-forming article. That is, an aerosol-forming article may be inserted through the opening and into the cavity (so as to be engaged with the device). The cap may comprise an internal wall defining the cavity for receipt of the article. The at least one heat dissipation element mounted in the cap may be located between the internal wall of the cap and an external wall of the cap (i.e., defining an outer wall of the housing). There may be an air gap between the at least one heat dissipation element and the internal wall defining the cavity.

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The outer surface of the device may be defined by the body or the cap or partly by the body and partly by the cap. The outer surface may include a first outer surface defined at one lateral side of the device, a second outer surface defined at a second lateral side laterally opposite to the first lateral side. Further, the outer surface may also include a third outer surface disposed laterally adjacent to the first outer surface. The device may include more than one heat dissipation elements. For example, at least one heat dissipation element may be disposed between the heating element and any one or more of the first outer surface, second outer surface and third outer surface. In an embodiment, a heat dissipation element may be disposed internally of the outer surface on all four sides of the device surrounding the heating element. The outer surface may be of the cap and/or the body. The heat dissipation element may be disposed in proximity to the heating element so as to be able to absorb heat from the heating element.

The device may comprise a power source or may be connectable to a power source (e.g., a power source separate to the device). The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device.

Where the power source comprises a rechargeable power source (such as a rechargeable battery), the input connection may be used to charge and recharge the power source.

The device may comprise a user interface (UI). In some embodiments the UI may include input means to receive operative commands from the user. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on a printed circuit board (PCB). The controller may also comprise a memory, e.g., non-volatile memory. The memory may include instructions, which, when implemented, may cause the controller to perform certain tasks or steps of a method. Where the device comprises an input connection, the controller may be connected to the input connection.

The controller may be configured to control the operation of the heater (and e.g., the heating element). Thus, the controller may be configured to control vaporization of an aerosol forming part of an aerosol-forming article engaged with the device. The controller may be configured to control the voltage applied by power source to the heater. For example, the controller may be configured to toggle between applying a full output voltage (of the power source) to the heater and applying no voltage to the heater. Alternatively, or additionally, the control unit may implement a more complex heater control protocol.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the twentieth mode, there is provided a system (e.g., a smoking substitute system) comprising a device according to the first aspect of the twentieth mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius*, *Arctostaphylos uva-ursi* (Bearberry), *Argemone mexicana*, *Arnica*, *Artemisia vulgaris*, Yellow Tees, *Galea zacatechichi*, *Canavalia maritima* (Baybean), *Cecropia mexicana* (Guamura), *Cestrum noctumum*, *Cynoglossum virginianum* (wild comfrey), *Cytisus scoparius*, *Damiana*, *Entada rheedii*, *Eschscholzia californica* (California Poppy), *Fittonia albivenis*, *Hippobroma longiflora*, *Humulus japonica* (Japanese Hops), *Humulus lupulus* (Hops), *Lactuca virosa* (Lettuce Opium), *Laggera alata*, *Leonotis leonurus*, *Leonurus cardiaca* (Motherwort), *Leonurus sibiricus* (Honeyweed), *Lobelia cardinalis*, *Lobelia inflata* (Indian-tobacco), *Lobelia siphilitica*, *Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum*, *Salvia dorrii* (Tobacco Sage), *Salvia* species (Sage), *Scutellaria galericulata*, *Scutellaria lateriflora*, *Scutellaria nana*, *Scutellaria* species (Skullcap), *Sida acuta* (Wireweed), *Sida rhombifolia*, *Silene capensis*, *Syzygium aromaticum* (Clove), *Tagetes lucida* (Mexican Tarragon), *Tarchonanthus camphoratus*, *Turnera diffusa* (Damiana), *Verbascum* (Mullein),

*Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

The disclosure includes the combination of the aspects and preferred features of the twentieth mode described except where such a combination is clearly impermissible or expressly avoided.

The skilled person will appreciate that except where mutually exclusive, a feature or parameter described in relation to any one of the above aspects of the twentieth mode may be applied to any other aspect of the twentieth mode. Furthermore, except where mutually exclusive, any feature or parameter of the twentieth mode described herein may be applied to any aspect and/or combined with any other feature or parameter of the twentieth mode described herein.

Twenty-First Mode: A Heated Tobacco Device, Including a Multilayer Printed Circuit Board (PCB)

At its most general, a twenty-first mode of the present disclosure relates to a heated tobacco device, including a multilayer printed circuit board (PCB).

According to a first aspect of the twenty-first mode, there is provided a heated tobacco device comprising: a power source; a heater; and a printed circuit board (PCB) comprising a power layer connected to the power source, a ground layer, a top layer and a bottom layer. In this respect, the PCB may be considered a multilayer PCB.

The provision of separate power and ground layers may provide noise insulation, signal integrity and an efficient distribution of power.

Optional features will now be set out. These are applicable singly or in any combination with any aspect of the twenty-first mode.

The power and ground layers may be sandwiched between the top and bottom layers. Each of the layers (which may be formed of e.g., copper sheet) may be separated by an insulative layer to provide electrical insulation between the layers. One or more of the layers may be separated by a dielectric layer. One or more of the layers may be separated by a prepreg layer. A plurality of components (e.g., resistors, transistors, microprocessors, etc.) may be mounted to the top and/or bottom layers. The top and bottom layers may each comprise a plurality of traces (or paths) electrically connecting the components mounted thereto. One or both of the top and bottom layers may be electrically connected to the power and ground layers.

The device may comprise a voltage regulator to regulate the voltage supplied by the power source to a regulated voltage value at an output of the voltage regulator. The power layer may be connected to the output of the voltage regulator. This may ensure a consistent voltage is supplied to the power layer.

The device may comprise a first heater control transistor configured to control (e.g., by switching between an "on" and an "off" state) the supply of power to the heater from the power source. The device may further comprise a second heater control transistor connected in series with the first transistor. The first and/or second transistor may be a metal-oxide-semiconductor field-effect transistor (MOSFET). The second transistor may be configured to control the supply of power to the heater from the power source. The heater may be controlled using pulse width modulation. Thus, the transistors may be turned on an off according to a duty cycle. The duty cycle may be altered to alter the temperature of the heater.

The first and second transistors may both be on the return path from the heater to the power source. Alternatively, the first transistor may be on the forward path from the power source to the heater and the second transistor may be on the return path. Alternatively, both transistors may be on the forward path. The use of two transistors may increase the reliability of the device. For example, if one transistor becomes "stuck" in an on position, the other transistor may ensure that an instruction to stop the supply of power (e.g., from a controller) is still acted upon.

The device may comprise a controller connected to a first drive input of the first transistor. The controller may be connected to a second drive input of the second transistor. Thus, the controller may be configured to control (e.g., control switching of) the first and second transistors.

The first drive input and the second drive input may be connected to the same output of the controller. Thus, the first and second transistors may be controlled in a simultaneous manner.

The first drive input and the second drive input may be connected to different outputs of the controller. In this respect, the first and second transistors may be controlled in a different manner to one another. In some cases, the two outputs of the controller may provide the same signal or instruction. In such cases, the use of the two separate outputs may provide redundancy in the system.

The heater may comprise a heating track. The PCB may comprise a heater analog-to-digital converter (HADC) connected to the heater. The controller may be configured to identify a short circuit in the heating track of the heater using the input to the HADC. The controller may be configured to detect changes in the resistance (or impedance) of the heating track. The controller may be configured to determine whether the impedance or resistance of heater falls below a threshold value. The controller may be configured to control the heater in response to the identification of a short circuit in the heating track.

The heater may comprise a temperature sensing track for sensing a temperature of the heater, the PCB comprising a temperature sensing analog-to-digital converter (TSADC) connected to the temperature sensing track. The controller may be configured to determine the temperature of the temperature sensing track using the input to the TSADC. The controller may be configured to determine the temperature of the sensing track using the output from the TSADC.

The controller may be configured to compare the determined temperature with a threshold temperature and control the heater in response to the comparison. The controller may be configured to determine if the impedance of the temperature sensing track is outside a predetermined operating range, and to prevent power supply to the heater if the impedance is outside the predetermined operating range.

The device may comprise an elongate body. An end of the elongate body may be configured for engagement with an aerosol-forming article (e.g., a heated tobacco (HT) consumable). The device may comprise a cavity that is configured for receipt of at least a portion of the consumable (i.e., for engagement with the consumable). The aerosol-forming article may be of the type that comprises an aerosol former (e.g., carried by an aerosol-forming substrate).

The heater may comprise a heating element, which may be in the form of a rod that extends from the body of the device. The heating element may extend from the end of the body that is configured for engagement with the aerosol-forming article.

The heater (and thus the heating element) may be rigidly mounted to the body. The heating element may be elongate so as to define a longitudinal axis and may, for example, have a transverse profile (i.e., transverse to a longitudinal axis of the heating element) that is substantially circular (i.e., the heating element may be generally cylindrical). Alternatively, the heating element may have a transverse profile that is rectangular (i.e., the heater may be a "blade heater"). The heating element may alternatively be in the shape of a tube (i.e., the heater may be a "tube heater"). The heating element may take other forms (e.g., the heating element may have an elliptical transverse profile). The shape and/or size (e.g., diameter) of the transverse profile of the heating element may be generally consistent for the entire length (or substantially the entire length) of the heating element.

The heating element may be between 15 mm and 25 mm long, e.g., between 18 mm and 20 mm long, e.g., around 19 mm long. The heating element may have a diameter of between 1.5 mm and 2.5 mm, e.g., a diameter between 2 mm and 2.3 mm, e.g., a diameter of around 2.15 mm.

The heating element may be formed of ceramic. The heating element may comprise a core (e.g., a ceramic core) comprising Al2O3. The core of the heating element may have a diameter of 1.8 mm to 2.1 mm, e.g., between 1.9 mm and 2 mm. The heating element may comprise an outer layer (e.g., an outer ceramic layer) comprising Al2O3. The thickness of the outer layer may be between 160 μm and 220 μm, e.g., between 170 μm and 190 μm, e.g., around 180 μm. The heating element may comprise a heating track, which may extend longitudinally along the heating element. The heating track may be sandwiched between the outer layer and the core of the heating element. The heating track is an electrically conductive resistive heating track comprising a pair of heater electrodes (not shown) connected to the power supply of the heater. The heating track may comprise tungsten and/or rhenium. The heating track may have a thickness of around 20 μm.

The heating element may be located in the cavity (of the device), and may extend (e.g., along a longitudinal axis) from an internal base of the cavity towards an opening of the cavity. The length of the heating element (i.e., along the longitudinal axis of the heater) may be less than the depth of the cavity. Hence, the heating element may extend for only a portion of the length of the cavity. That is, the heating element may not extend through (or beyond) the opening of the cavity.

The heating element may be configured for insertion into an aerosol-forming article (e.g., a HT consumable) when an aerosol-forming article is received in the cavity. In that respect, a distal end (i.e., distal from a base of the heating element where it is mounted to the device) of the heating element may comprise a tapered portion, which may facilitate insertion of the heating element into the aerosol-forming article. The heating element may fully penetrate an aerosol-forming article when the aerosol-forming article is received in the cavity. That is, the entire length, or substantially the entire length, of the heating element may be received in the aerosol-forming article.

The heating element may have a length that is less than, or substantially the same as, an axial length of an aerosol-forming substrate forming part of an aerosol-forming article (e.g., a HT consumable). Thus, when such an aerosol-forming article is engaged with the device, the heating element may only penetrate the aerosol-forming substrate, rather than other components of the aerosol-forming article. The heating element may penetrate the aerosol-forming substrate for substantially the entire axial length of the aerosol forming-substrate of the aerosol-forming article. Thus, heat may be transferred from (e.g., an outer circumferential surface of) the heating element to the surrounding aerosol-forming substrate, when penetrated by the heating element. That is, heat may be transferred radially outwardly (in the case of a cylindrical heating element) or e.g., radially inwardly (in the case of a tube heater).

Where the heater is a tube heater, the heating element of the tube heater may surround at least a portion of the cavity. When the portion of the aerosol-forming article is received in the cavity, the heating element may surround a portion of the aerosol-forming article (i.e., so as to heat that portion of the aerosol-forming article). In particular, the heating element may surround an aerosol forming substrate of the aerosol-forming article. That is, when an aerosol-forming article is engaged with the device, the aerosol forming substrate of the aerosol-forming article may be located adjacent an inner surface of the (tubular) heating element. When the heating element is activated, heat may be transferred radially inwardly from the inner surface of the heating element to heat the aerosol forming substrate.

The cavity may comprise a (e.g., circumferential) wall (or walls) and the (tubular) heating element may extend around at least a portion of the wall(s). In this way, the wall may be located between the inner surface of the heating element and an outer surface of the aerosol-forming article. The wall (or walls) of the cavity may be formed from a thermally conductive material (e.g., a metal) to allow heat conduction from the heating element to the aerosol-forming article. Thus, heat may be conducted from the heating element, through the cavity wall (or walls), to the aerosol-forming substrate of an aerosol-forming article received in the cavity.

The heater also comprises an electrically conductive temperature measurement track and corresponding pair of temperature measurement electrodes connected to a controller of the device. In one aspect, the temperature measurement track is formed with tungsten.

In some embodiments the device may comprise a cap disposed at the end of the body that is configured for engagement with an aerosol-forming article. Where the device comprises a heater having a heating element, the cap may at least partially enclose the heating element. The cap may be moveable between an open position in which access is provided to the heating element, and a closed position in which the cap at least partially encloses the heating element. The cap may be slidably engaged with the body of the device, and may be slidable between the open and closed positions.

The cap may define at least a portion of the cavity of the device. That is, the cavity may be fully defined by the cap, or each of the cap and body may define a portion of the cavity. The cap may comprise an opening to the cavity. The opening may be configured for receipt of at least a portion of an aerosol-forming article. That is, an aerosol-forming article may be inserted through the opening and into the cavity (so as to be engaged with the device).

The cap may be configured such that when an aerosol-forming article is engaged with the device (e.g., received in the cavity), only a portion of the aerosol-forming article is received in the cavity. That is, a portion of the aerosol-forming article (not received in the cavity) may protrude from (i.e., extend beyond) the opening. This (protruding) portion of the aerosol-forming article may be a terminal (e.g., mouth) end of the aerosol-forming article, which may be received in a user's mouth for the purpose of inhaling aerosol formed by the device.

The device comprises a power source. The power source may be electrically connectable to the heater. In that respect, altering (e.g., toggling) the electrical connection of the power source to the heater may affect a state of the heater. For example, toggling the electrical connection of the power source to the heater may toggle the heater between an on state and an off state. The power source may be a power store. For example, the power source may be a battery or rechargeable battery (e.g., a lithium-ion battery).

The device may comprise an input connection (e.g., a USB port, Micro USB port, USB-C port, etc.). The input connection may be configured for connection to an external source of electrical power, such as a mains electrical supply outlet. The input connection may, in some cases, be used as a substitute for an internal power source (e.g., battery or rechargeable battery). That is, the input connection may be electrically connectable to the heater (for providing power to the heater). Hence, in some forms, the input connection may form at least part of the power source of the device. The input connection may be connected to the PCB.

Where the power source comprises a rechargeable power source (such as a rechargeable battery), the input connection may be used to charge and recharge the power source.

The device may comprise a user interface (UI). In some embodiments the UI may include input means to receive operative commands from the user. The UI may be connected to the PCB. The input means of the UI may allow the user to control at least one aspect of the operation of the device. In some embodiments the input means may comprise a power button to switch the device between an on state and an off state.

In some embodiments the UI may additionally or alternatively comprise output means to convey information to the user. In some embodiments the output means may comprise a light to indicate a condition of the device (and/or the aerosol-forming article) to the user. The condition of the device (and/or aerosol-forming article) indicated to the user may comprise a condition indicative of the operation of the heater. For example, the condition may comprise whether the heater is in an off state or an on state. In some embodiments, the UI unit may comprise at least one of a button, a display, a touchscreen, a switch, a light, and the like. For example, the output means may comprise one or more (e.g., two, three, four, etc.) light-emitting diodes ("LEDs") that may be located on the body of the device.

The device may further comprise a puff sensor (e.g., airflow sensor), which form part of the input means of the UI. The puff sensor may be operatively connected to the PCB. The puff sensor may be configured to detect a user drawing on an end (i.e., a terminal (mouth) end) of the aerosol-forming article. The puff sensor may, for example, be a pressure sensor or a microphone. The puff sensor may be configured to produce a signal indicative of a puff state. The signal may be indicative of the user drawing (an aerosol from the aerosol-forming article) such that it is e.g., in the form of a binary signal. Alternatively, or additionally, the signal may be indicative of a characteristic of the draw (e.g., a flow rate of the draw, length of time of the draw, etc.).

The device may comprise a controller, or may be connectable to a controller that may be configured to control at least one function of the device. The controller may comprise a microcontroller that may e.g., be mounted on the PCB. The controller may comprise a plurality of microcontrollers. The controller may also comprise a memory, e.g., non-volatile memory. The memory may include instructions, which, when implemented, may cause the controller to perform certain tasks or steps of a method. Where the device comprises an input connection, the controller may be connected to the input connection.

The device may further comprise a voltage regulator to regulate the output voltage supplied by the power source to form a regulated voltage. The regulated voltage may subsequently be applied to the heater.

In some embodiments, where the device comprises a UI, the controller may be operatively connected to one or more components of the UI. The controller may be configured to receive command signals from an input means of the UI. The controller may be configured to control the heater in response to the command signals. For example, the controller may be configured to receive "on" and "off" command signals from the UI and, in response, may control the heater so as to be in a corresponding on or off state.

The controller may be configured to send output signals to a component of the UI. The UI may be configured to convey information to a user, via an output means, in response to such output signals (received from the controller). For example, where the device comprises one or more LEDs, the LEDs may be operatively connected to the controller. Hence, the controller may be configured to control the illumination of the LEDs (e.g., in response to an output signal). For example, the controller may be configured to control the illumination of the LEDs according to (e.g., an on or off) state of the heater.

Where the device comprises a sensor (e.g., a puff/airflow sensor), the controller may be operatively connected to the sensor. The controller may be configured to receive a signal from the sensor (e.g., indicative of a condition of the device and/or engaged aerosol-forming article). The controller may be configured to control the heater, or an aspect of the output means, based on the signal from the sensor.

The device may comprise a wireless interface configured to communicate wirelessly (e.g., via Bluetooth (e.g., a Bluetooth low-energy connection) or Wi-Fi) with an external device. Similarly, the input connection may be configured for wired connection to an external device so as to provide communication between the device and the external device.

The external device may be a mobile device. For example, the external device may be a smart phone, tablet, smart watch, or smart car. An application (e.g., app) may be installed on the external device (e.g., mobile device). The application may facilitate communication between the device and the external device via the wired or wireless connection.

The wireless or wired interface may be configured to transfer signals between the external device and the controller of the device. In this respect, the controller may control an aspect of the device in response to a signal received from an external device. Alternatively, or additionally, an external device may respond to a signal received from the device (e.g., from the controller of the device).

In a second aspect of the twenty-first mode, there is provided a system (e.g., a smoking substitute system) comprising a device according to the first aspect of the twenty-first mode and an aerosol-forming article. The aerosol-forming article may comprise an aerosol-forming substrate at an upstream end of the aerosol-forming article. The article may be in the form of a smoking substitute article, e.g., heated tobacco (HT) consumable (also known as a heat-not-burn (HNB) consumable).

As used herein, the terms "upstream" and "downstream" are intended to refer to the flow direction of the vapor/aerosol i.e., with the downstream end of the article/consumable being the mouth end or outlet where the aerosol exits the consumable for inhalation by the user. The upstream end of the article/consumable is the opposing end to the downstream end.

The aerosol-forming substrate is capable of being heated to release at least one volatile compound that can form an aerosol. The aerosol-forming substrate may be located at the upstream end of the article/consumable.

In order to generate an aerosol, the aerosol-forming substrate comprises at least one volatile compound that is intended to be vaporized/aerosolized and that may provide the user with a recreational and/or medicinal effect when inhaled. Suitable chemical and/or physiologically active volatile compounds include the group consisting of: nicotine, cocaine, caffeine, opiates and opioids, cathine and cathinone, kavalactones, mysticin, beta-carboline alkaloids, salvinorin A together with any combinations, functional equivalents to, and/or synthetic alternatives of the foregoing.

The aerosol-forming substrate may comprise plant material. The plant material may comprise least one plant material selected from the list including *Amaranthus dubius, Arctostaphylos uva-ursi* (Bearberry), *Argemone mexicana, Arnica, Artemisia vulgaris*, Yellow Tees, *Galea zacatechichi, Canavalia maritima* (Baybean), *Cecropia mexicana* (Guamura), *Cestrum noctumum, Cynoglossum virginianum* (wild comfrey), *Cytisus scoparius, Damiana, Entada rheedii, Eschscholzia californica* (California Poppy), *Fittonia albivenis, Hippobroma longiflora, Humulus japonica* (Japanese Hops), *Humulus lupulus* (Hops), *Lactuca virosa* (Lettuce Opium), *Laggera alata, Leonotis leonurus, Leonurus cardiaca* (Motherwort), *Leonurus sibiricus* (Honeyweed), *Lobelia cardinalis, Lobelia inflata* (Indian-tobacco), *Lobelia siphilitica, Nepeta cataria* (Catnip), *Nicotiana* species (Tobacco), *Nymphaea alba* (White Lily), *Nymphaea caerulea* (Blue Lily), Opium poppy, *Passiflora incamata* (Passionflower), *Pedicularis densiflora* (Indian Warrior), *Pedicularis groenlandica* (Elephant's Head), *Salvia divinorum, Salvia dorrii* (Tobacco Sage), *Salvia* species (Sage), *Scutellaria galericulata, Scutellaria lateriflora, Scutellaria nana, Scutellaria* species (Skullcap), *Sida acuta* (Wireweed), *Sida rhombifolia, Silene capensis, Syzygium aromaticum* (Clove), *Tagetes lucida* (Mexican Tarragon), *Tarchonanthus camphoratus, Tumera diffusa* (*Damiana*), *Verbascum* (Mullein), *Zamia latifolia* (Maconha Brava) together with any combinations, functional equivalents to, and/or synthetic alternatives of the foregoing.

The plant material may be tobacco. Any type of tobacco may be used. This includes, but is not limited to, flue-cured tobacco, burley tobacco, Maryland Tobacco, dark-air cured tobacco, oriental tobacco, dark-fired tobacco, perique tobacco and *rustica* tobacco. This also includes blends of the above-mentioned tobaccos.

The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon).

The aerosol-forming substrate may comprise a gathered sheet of homogenized (e.g., paper/slurry recon) tobacco or gathered shreds/strips formed from such a sheet.

The aerosol-forming substrate may comprise one or more additives selected from humectants, flavorants, fillers, aqueous/non-aqueous solvents and binders.

The flavorant may be provided in solid or liquid form. It may include menthol, licorice, chocolate, fruit flavor (including e.g., citrus, cherry etc.), vanilla, spice (e.g., ginger, cinnamon) and tobacco flavor. The flavorant may be evenly dispersed throughout the aerosol-forming substrate or may be provided in isolated locations and/or varying concentrations throughout the aerosol-forming substrate.

The aerosol-forming substrate may be formed in a substantially cylindrical shape such that the article/consumable resembles a conventional cigarette. It may have a diameter of between 5 and 10 mm e.g., between 6 and 9 mm or 6 and 8 mm e.g., around 7 mm. It may have an axial length of between 10 and 15 mm e.g., between 11 and 14 mm such as around 12 or 13 mm.

The article/consumable may comprise at least one filter element. There may be a terminal filter element at the downstream/mouth end of the article/consumable.

The or at least one of the filter element(s) (e.g., the terminal filter element) may be comprised of cellulose acetate or polypropylene tow. The at least one filter element (e.g., the terminal filter element) may be comprised of activated charcoal. The at least one filter element (e.g., the terminal element) may be comprised of paper. The or each filter element may be at least partly (e.g., entirely) circumscribed with a plug wrap e.g., a paper plug wrap.

The terminal filter element (at the downstream end of the article/consumable) may be joined to the upstream elements forming the article/consumable by a circumscribing tipping layer e.g., a tipping paper layer. The tipping paper may have an axial length longer than the axial length of the terminal filter element such that the tipping paper completely circumscribes the terminal filter element plus the wrapping layer surrounding any adjacent upstream element.

In some embodiments, the article/consumable may comprise an aerosol-cooling element which is adapted to cool the aerosol generated from the aerosol-forming substrate (by heat exchange) before being inhaled by the user.

The article/consumable may comprise a spacer element that defines a space or cavity between the aerosol-forming substrate and the downstream end of the consumable. The spacer element may comprise a cardboard tube. The spacer element may be circumscribed by the (paper) wrapping layer.

According to a third aspect of the twenty-first mode of the present disclosure, there is provided a method of using the system according to the second aspect of the twenty-first mode, the method comprising inserting the aerosol-forming article into the device; and heating the article using the heater of the device.

In some embodiments the method may comprise inserting the article into a cavity within a body of the device and penetrating the article with the heating element of the device upon insertion of the article.

The disclosure includes the combination of the aspects and preferred features of the twenty-first mode described except where such a combination is clearly impermissible or expressly avoided.

The skilled person will appreciate that except where mutually exclusive, a feature or parameter described in relation to any one of the above aspects of the twenty-first mode may be applied to any other aspect of the twenty-first mode. Furthermore, except where mutually exclusive, any feature or parameter of the twenty-first mode described herein may be applied to any aspect and/or combined with any other feature or parameter of the twenty-first mode described herein.

SUMMARY OF THE FIGURES

So that the disclosure may be understood, and so that further aspects and features thereof may be appreciated, embodiments illustrating the principles of the disclosure will now be discussed in further detail with reference to the accompanying figures, in which:

FIG. 2A is a front view of an embodiment of the first mode of a smoking substitute system with the consumable engaged with the device.

FIG. 2B is a front view of the embodiment of the first mode of the smoking substitute system with the consumable disengaged from the device.

FIG. 3 is perspective view of the embodiment of the first mode of the substitute smoking system with the cap in a partially open position.

FIG. 4A is section view of the embodiment of the first mode of the substitute smoking system with the cap in the closed position.

FIG. 4B is section view of the embodiment of the first mode of the substitute smoking system with the cap in the open position.

FIG. 5A is a perspective view of a removal key or tool in accordance with an embodiment of the first mode.

FIG. 5B is a perspective view of the removal key or tool of FIG. 5A with a first cover removed.

FIG. 5C is a perspective view of the removal key or tool of FIG. 5A with a second cover removed.

FIG. 5D is a perspective view of another tool in accordance with an embodiment of the first mode.

FIG. 5E is a perspective view of the tool of FIG. 5D with a first cover removed.

FIG. 7A to FIG. 7E illustrates stages of using the removal key to separate the cap from the body of the smoking substitute device of the embodiment of the first mode.

FIG. 10A is a perspective view of a tool of the smoking substitute system of the first mode with enclosures.

FIG. 10C is a detailed view of the tool of the substitute smoking system of the first mode without one of the enclosure.

FIG. 10D is a detailed view of the tool of the smoking substitute system of the first mode with the cleaning portion exposed.

FIG. 11 is a front view of the cap and the main body of the device of the first mode, with a portion of the tool inserted into the cap.

FIG. 16A is a front view of a first embodiment of the second mode of a smoking substitute system with the consumable engaged with the device.

FIG. 16B is a front view of the first embodiment of the second mode of the smoking substitute system with the consumable disengaged from the device.

FIG. 22A is a front view of a first embodiment of the fourth mode of a smoking substitute system with the consumable engaged with the device.

FIG. 22B is a front view of the first embodiment of the fourth mode of the smoking substitute system with the consumable disengaged from the device.

FIG. 22D is a detailed view of an end of the device of the first embodiment of the fourth mode of the smoking substitute system.

FIG. 22E is a section view of the first embodiment of the fourth mode of the smoking substitute system.

FIG. 23 is perspective view of the first embodiment of the fourth mode of the substitute smoking system with a cap in a second position.

FIG. 24A is section view of the first embodiment of the fourth mode of the smoking substitute system with the cap in a first position.

FIG. 24B is section view of the first embodiment of the fourth mode of the smoking substitute system with the cap in the second position.

FIG. 25A is a perspective view of the tool in accordance with an embodiment of the fourth mode.

FIG. 25B is a perspective view of the tool of FIG. 25A with a first cover removed.

FIG. 25C is a perspective view of the tool of FIG. 25A with a second cover removed.

FIG. 27A-E illustrates stages of using the tool to separate the cap from the body of the smoking substitute device of the first embodiment of the fourth mode.

FIG. 29A is a front view of a first embodiment of the fifth mode of a smoking substitute system with the consumable engaged with the device.

FIG. 29B is a front view of the first embodiment of the fifth mode of the smoking substitute system with the consumable disengaged from the device.

FIG. 31A is a front view of a first embodiment of the sixth mode of a smoking substitute system with the consumable engaged with the device.

FIG. 31B is a front view of the first embodiment of the sixth mode of the heat not burn device.

FIG. 31D is a detailed view of an end of the device of the first embodiment of the sixth mode of the smoking substitute system.

FIG. 31E is a section view of the first embodiment of the sixth mode of the smoking substitute system.

FIG. 33A is a front view of a first embodiment of the seventh mode of a smoking substitute system with the consumable engaged with the device.

FIG. 33B is a front view of the first embodiment of the seventh mode of the heat not burn device.

FIG. 34A is a schematic of a smoking substitute system of the eighth mode.

FIG. 34B is a schematic of a variation of the smoking substitute system of FIG. 34A.

FIG. 35A is a front view of a first embodiment of the eighth mode of a smoking substitute system with the consumable engaged with the device.

FIG. 35B is a front view of the first embodiment of the eighth mode of the smoking substitute system with the consumable disengaged from the device.

FIG. 37A is a front view of the second embodiment of the eighth mode of the device, comprising an air inlet and a ring.

FIG. 37B is a front view of the second embodiment of the eighth mode of the device, with the ring blocking one of the plurality of openings of the air inlet.

FIG. 39A is a front view of a first embodiment of the ninth mode of a smoking substitute system with the consumable engaged with the device.

FIG. 39B is a front view of the first embodiment of the ninth mode of the smoking substitute system with the consumable disengaged from the device.

FIG. 39C is a section view of the consumable of the first embodiment of the ninth mode of the smoking substitute system.

FIG. 41A is a front view of a first embodiment of the tenth mode of a smoking substitute system with the consumable engaged with the device.

FIG. 41B is a front view of the first embodiment of the tenth mode of the smoking substitute system with the consumable disengaged from the device.

FIG. 41D is a detailed view of an end of the device of the first embodiment of the tenth mode of the smoking substitute system.

FIG. 41E is a section view of the first embodiment of the tenth mode of the smoking substitute system.

FIG. 43A is a front view of a first embodiment of the eleventh mode of a smoking substitute system with the consumable engaged with the device.

FIG. 43B is a front view of the first embodiment of the eleventh mode of the smoking substitute system with the consumable disengaged from the device.

FIG. 44A is a schematic of a smoking substitute system of the twelfth mode.

FIG. 44B is a schematic of a variation of the smoking substitute system of FIG. 44A.

FIG. 45A is a front view of a first embodiment of the twelfth mode of a smoking substitute system with the consumable engaged with the device.

FIG. 45B is a front view of the first embodiment of the twelfth mode of the smoking substitute system with the consumable disengaged from the device.

FIG. 45C is a section view of the consumable of the first embodiment of the twelfth mode of the smoking substitute system.

FIG. 45D is a detailed view of an end of the device of the first embodiment of the twelfth mode of the smoking substitute system.

FIG. 45E is a section view of the first embodiment of the twelfth mode of the substitute smoking system.

FIG. 46A is a perspective view of the heat not burn device of the twelfth mode illustrating cartridge disengaged from the hollow housing.

FIG. 46B is a perspective view of the heat not burn device of the twelfth mode, illustrating the cartridge engaged in the hollow housing.

FIG. 47A is a schematic of a smoking substitute system of the thirteenth mode.

FIG. 47B is a schematic of a variation of the smoking substitute system of FIG. 47A.

FIG. 48A is a front view of a first embodiment of the thirteenth mode of a smoking substitute system with the consumable engaged with the device.

FIG. 48B is a front view of the first embodiment of the thirteenth mode of the smoking substitute system with the consumable disengaged from the device.

Figure 48C:
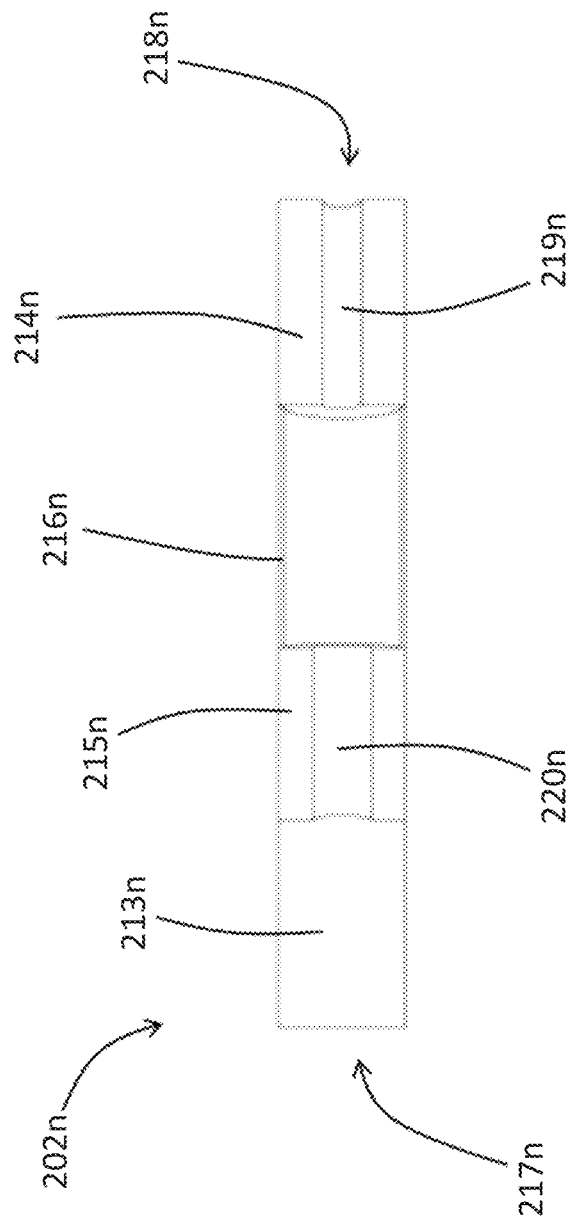

FIG. 48C is a section view of the consumable of the first embodiment of the thirteenth mode of the smoking substitute system.

FIG. 48D is a detailed view of an end of the device of the first embodiment of the thirteenth mode of the smoking substitute system.

FIG. 48E is a section view of the first embodiment of the thirteenth mode of the substitute smoking system.

FIG. 49A is a schematic of a smoking substitute system of the fourteenth mode.

FIG. 49B is a schematic of a variation of the smoking substitute system of FIG. 49A.

Figure 50B:
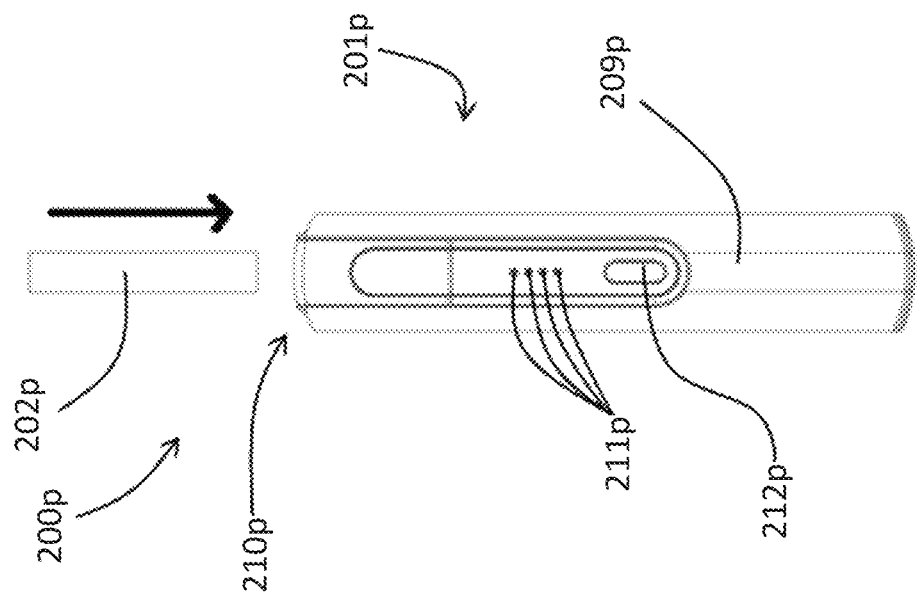
Figure 50A:
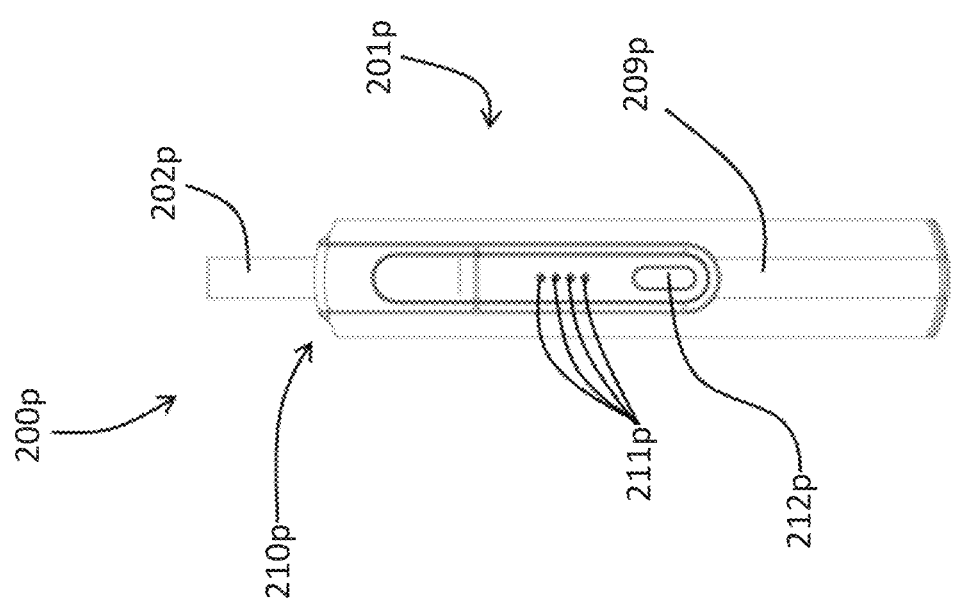

FIG. 50A is a front view of a first embodiment of the fourteenth mode of a smoking substitute system with the consumable engaged with the device.

FIG. 50B is a front view of the first embodiment of the fourteenth mode of the smoking substitute system with the consumable disengaged from the device.

Figure 50C:
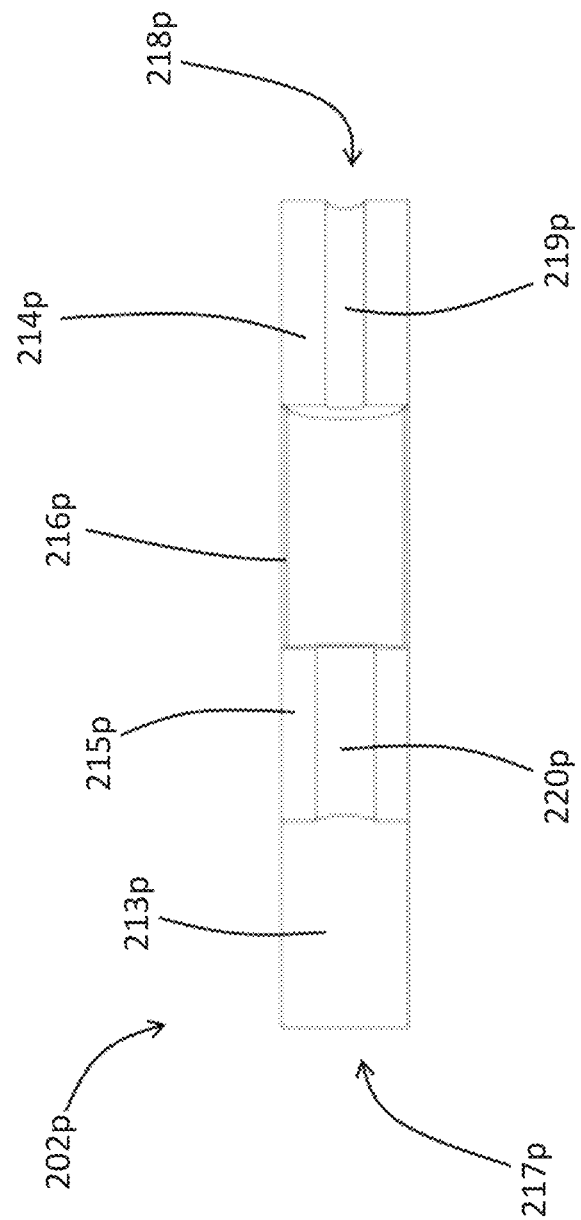

FIG. 50C is a section view of the consumable of the first embodiment of the fourteenth mode of the smoking substitute system.

Figures 50D, 50E:
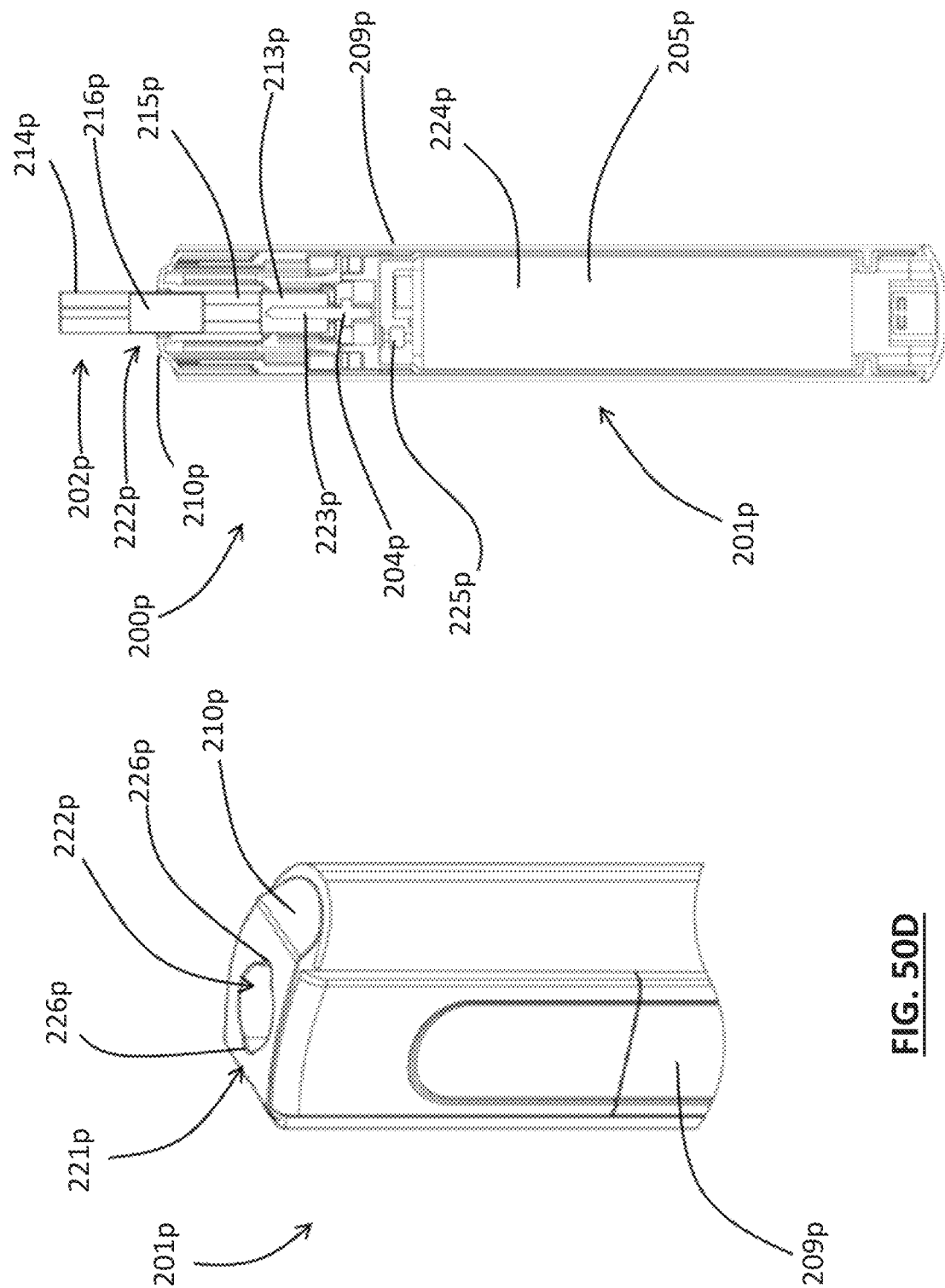

FIG. 50D is a detailed view of an end of the device of the first embodiment of the fourteenth mode of the smoking substitute system.

FIG. 50E is a section view of the first embodiment of the fourteenth mode of the substitute smoking system.

Figure 50G:
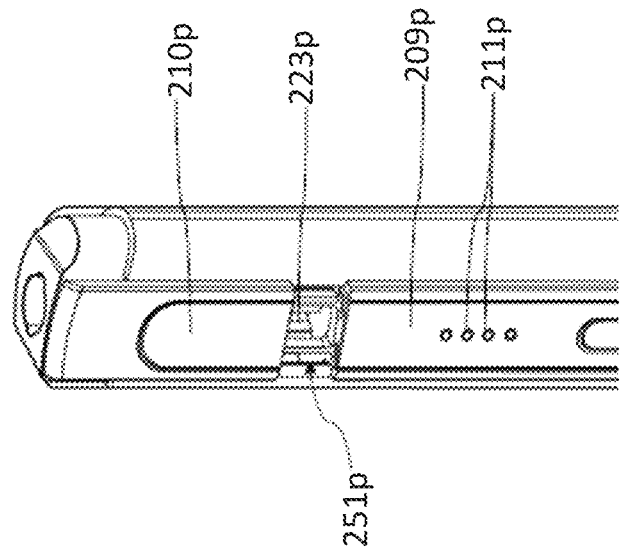
Figure 50F:
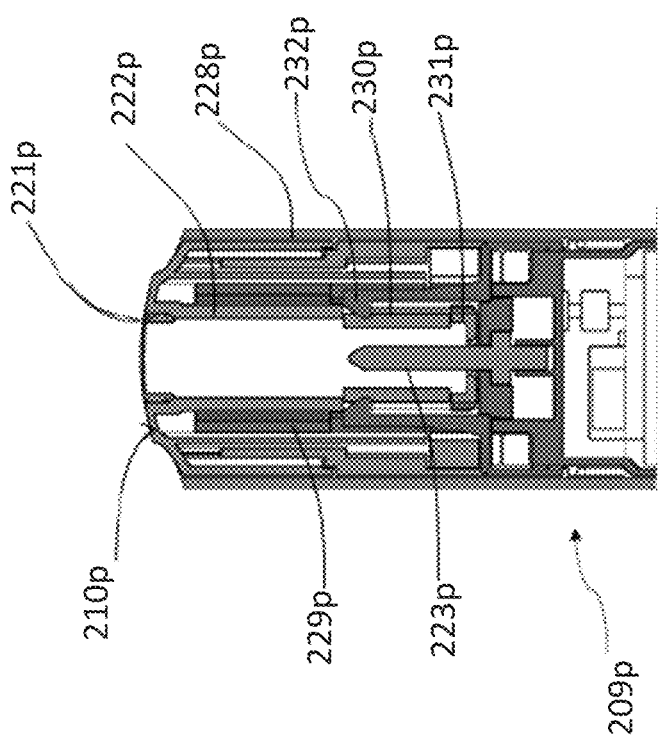

FIG. 50F is a sectional view of the first embodiment of the fourteenth mode of the device, showing the cap engaged with the body.

FIG. 50G is a perspective view of the first embodiment of the fourteenth mode of the device showing the cap in the second position.

Figure 50H:
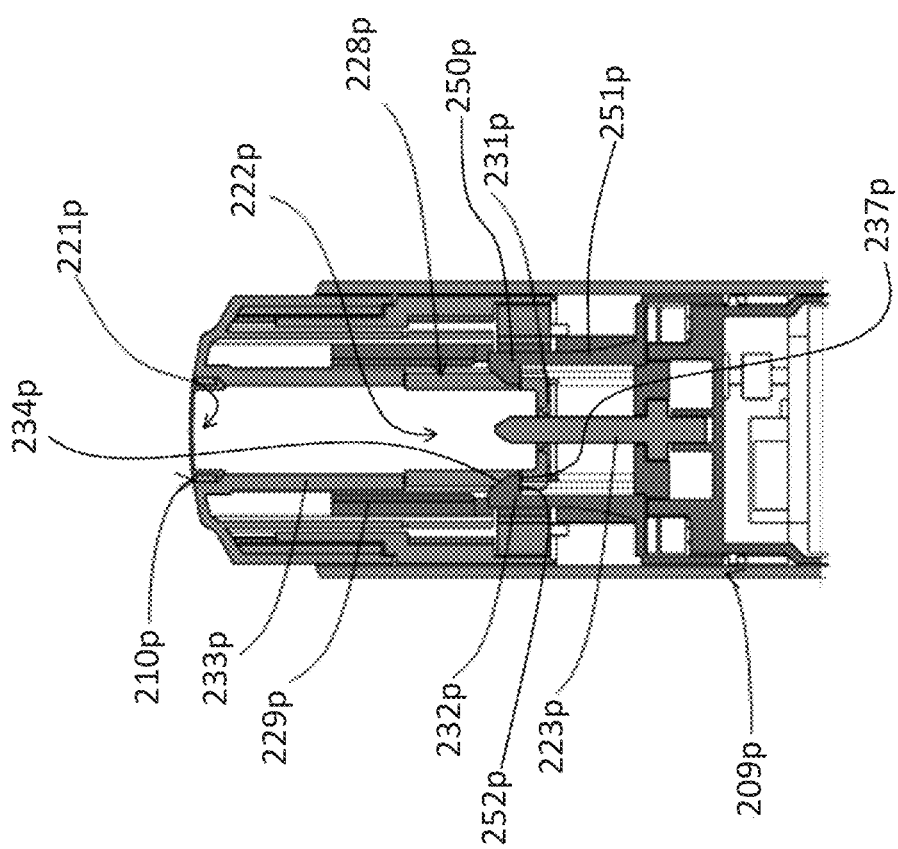

FIG. 50H is a sectional view of the first embodiment of the fourteenth mode of the device, showing the cap in the second position.

Figure 51:
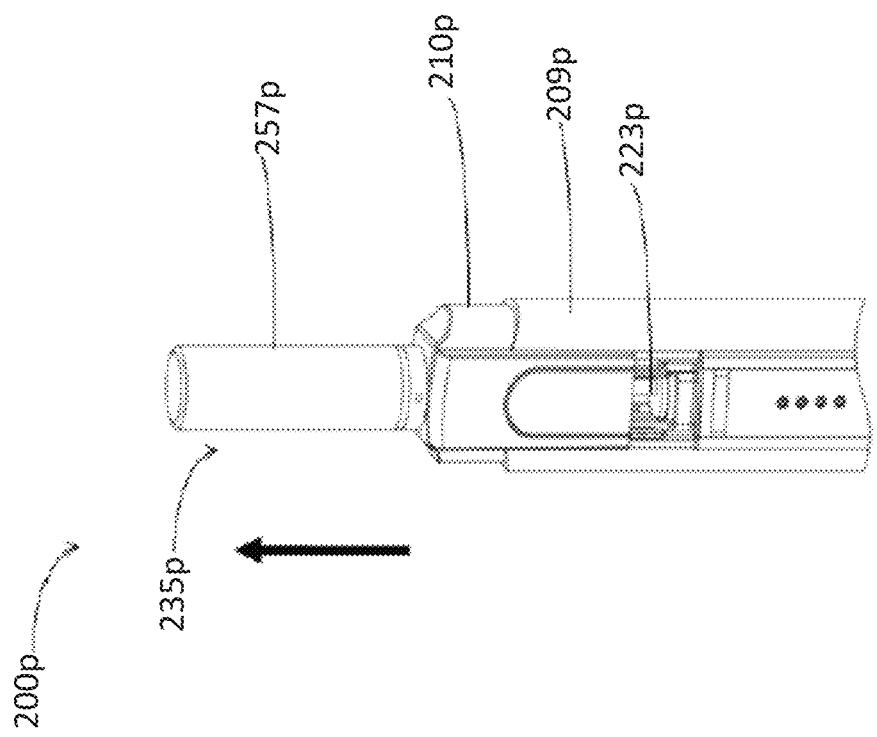

FIG. 51 is a detailed view of the first embodiment of the fourteenth mode of the device, with a tool inserted into the cap.

Figure 52:
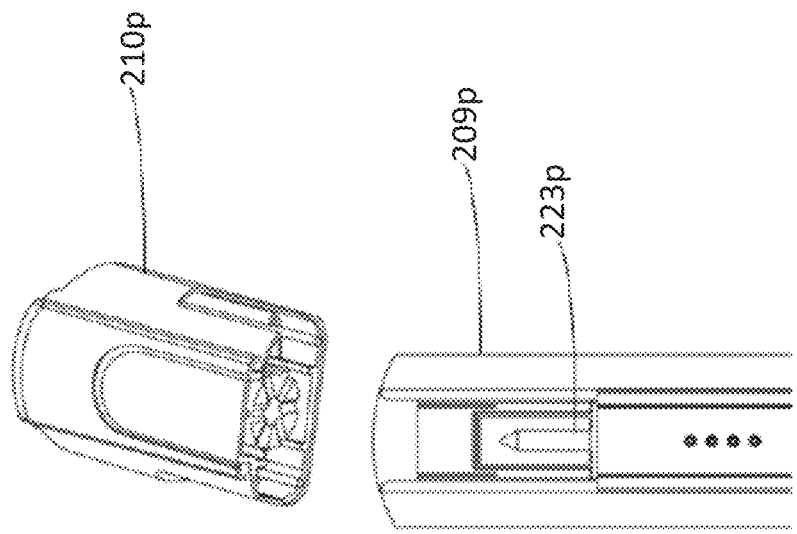

FIG. 52 is a detailed view of the first embodiment of the fourteenth mode of the device, with the cap disengaged from the body.

Figure 53B:
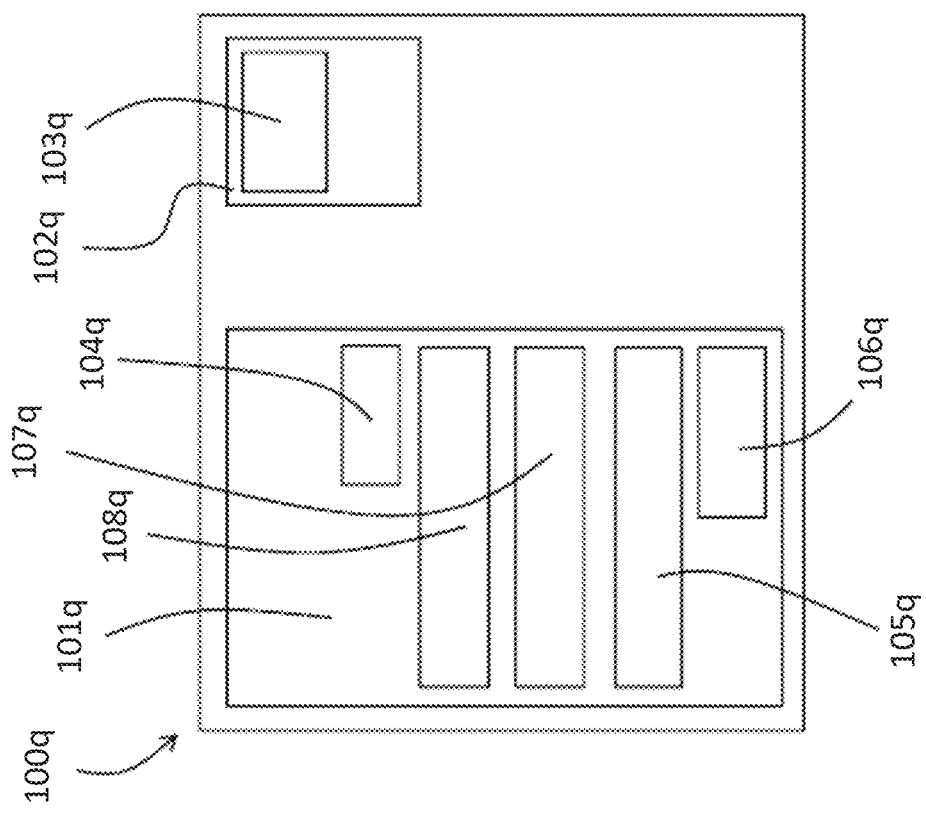
Figure 53A:
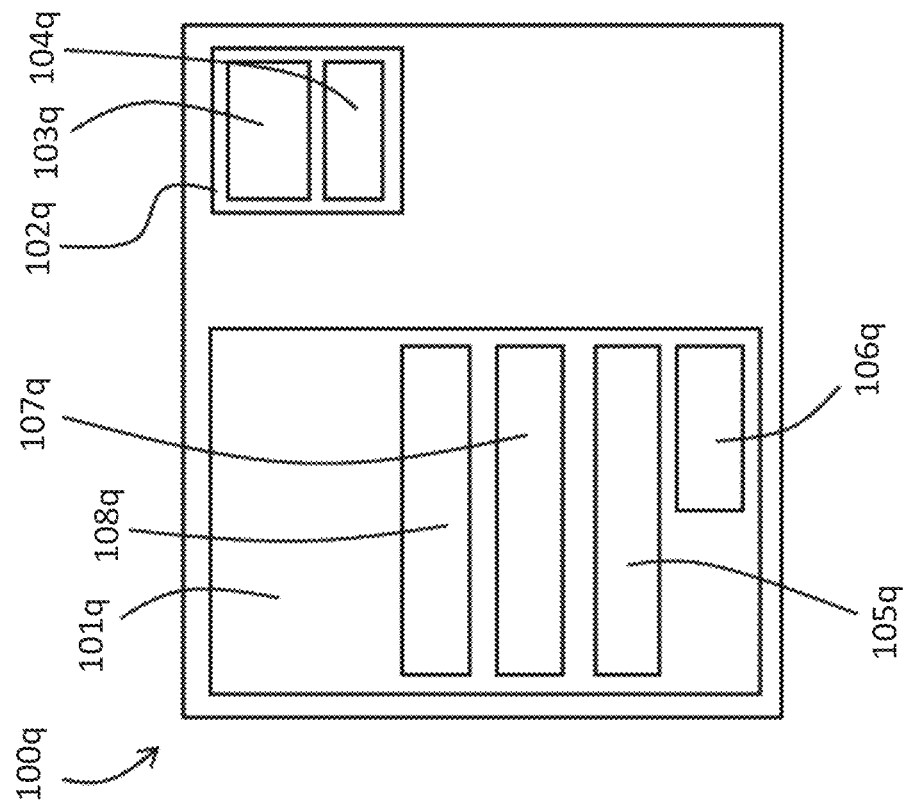

FIG. 53A is a schematic of a smoking substitute system of the fifteenth mode.

FIG. 53B is a schematic of a variation of the smoking substitute system of FIG. 53A.

FIG. 54A is a front view of a first embodiment of the fifteenth mode of a smoking substitute system with the consumable engaged with the device.

FIG. 54B is a front view of the first embodiment of the fifteenth mode of the smoking substitute system with the consumable disengaged from the device.

Figure 54C:
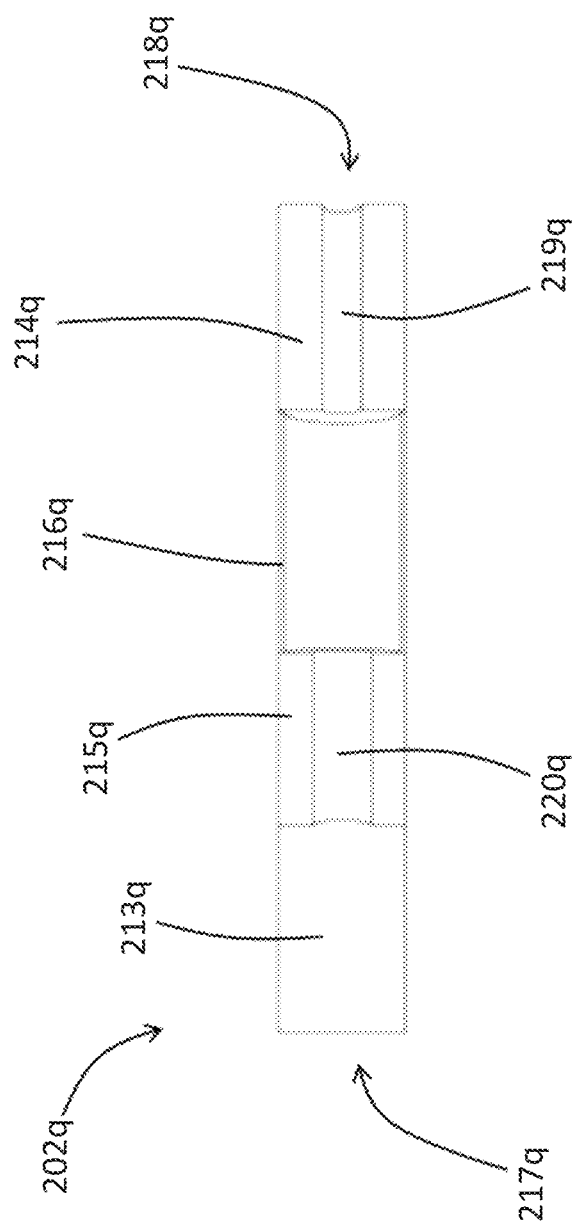

FIG. 54C is a section view of the consumable of the first embodiment of the fifteenth mode of the smoking substitute system.

Figure 54E:
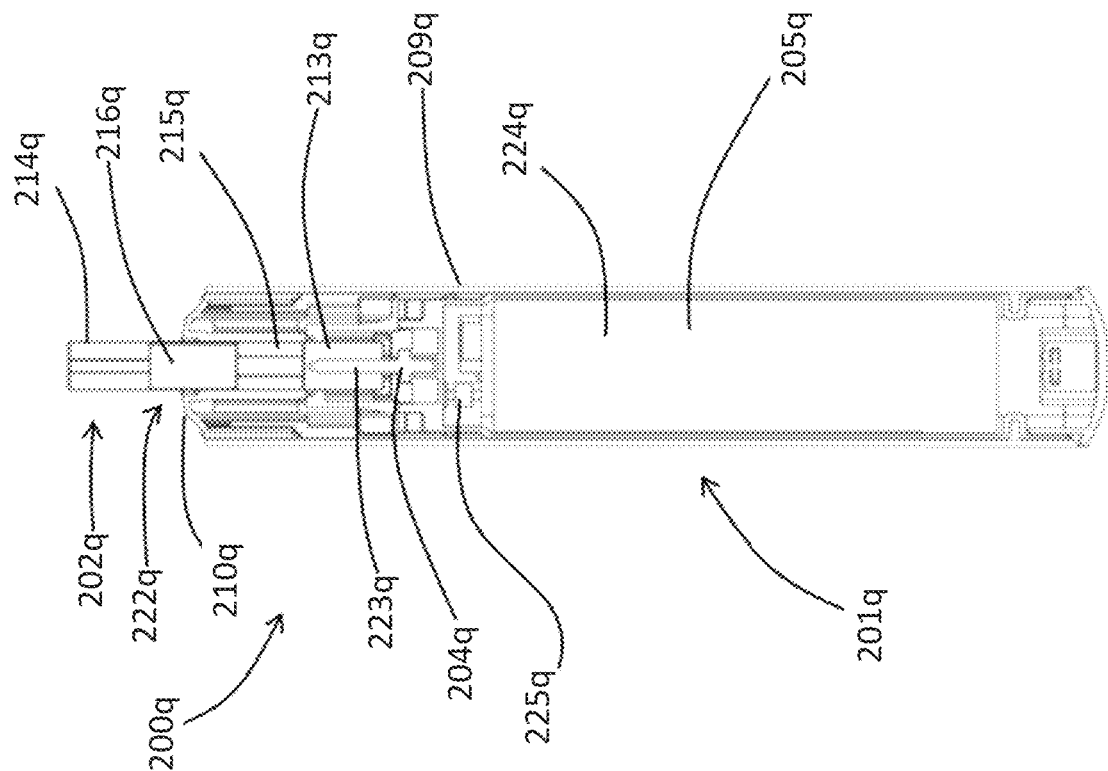
Figure 54D:
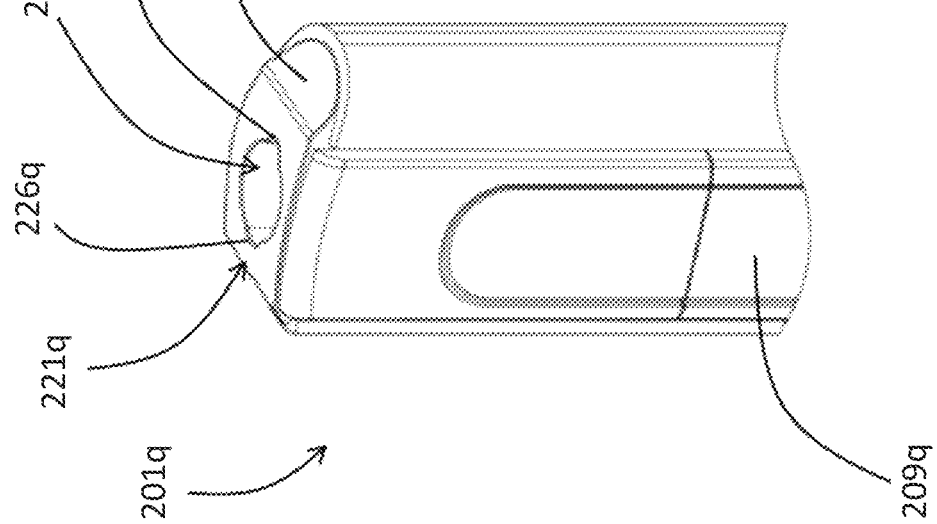

FIG. 54D is a detailed view of an end of the device of the first embodiment of the fifteenth mode of the smoking substitute system.

FIG. 54E is a section view of the first embodiment of the fifteenth mode of the substitute smoking system.

Figure 54G:
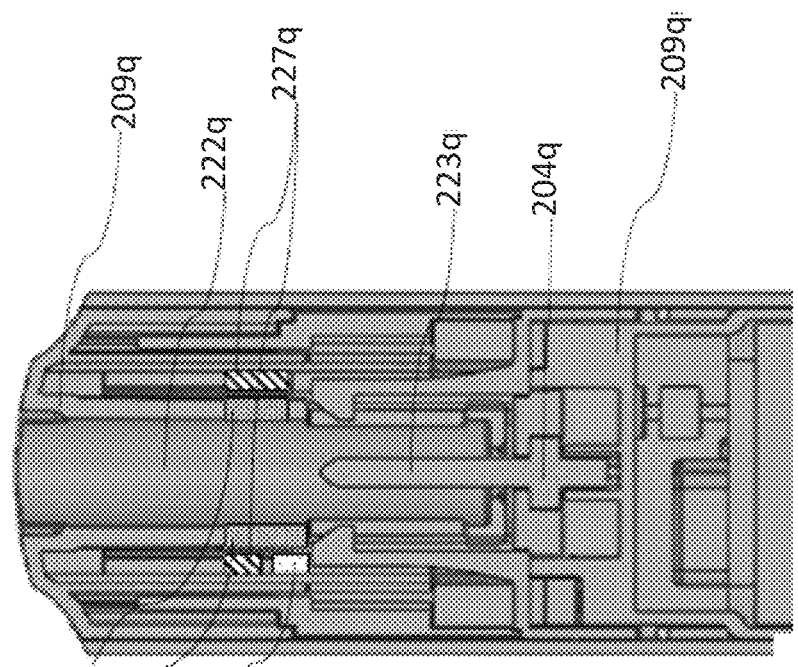
Figure 54F:
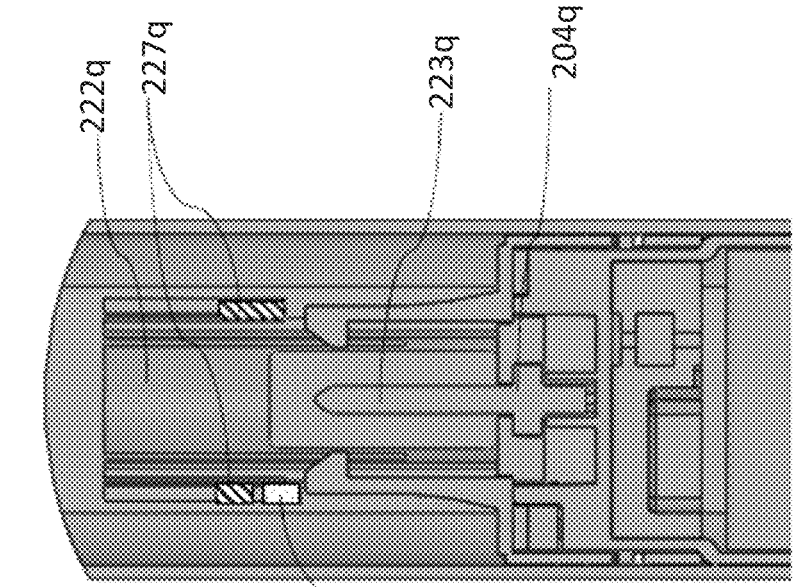

FIG. 54F is a section view of a portion of the main body of the first embodiment of the fifteenth mode with the cap in an open position.

FIG. 54G is section view of a portion of the first embodiment of the fifteenth mode with the cap in a closed position.

Figure 55B:
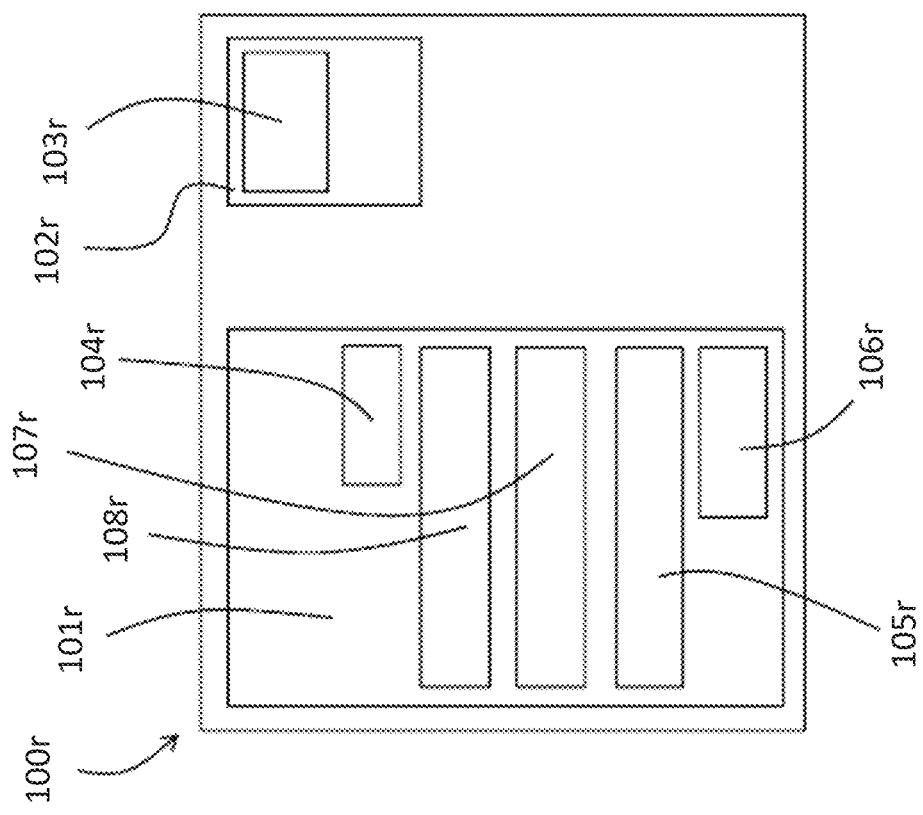
Figure 55A:
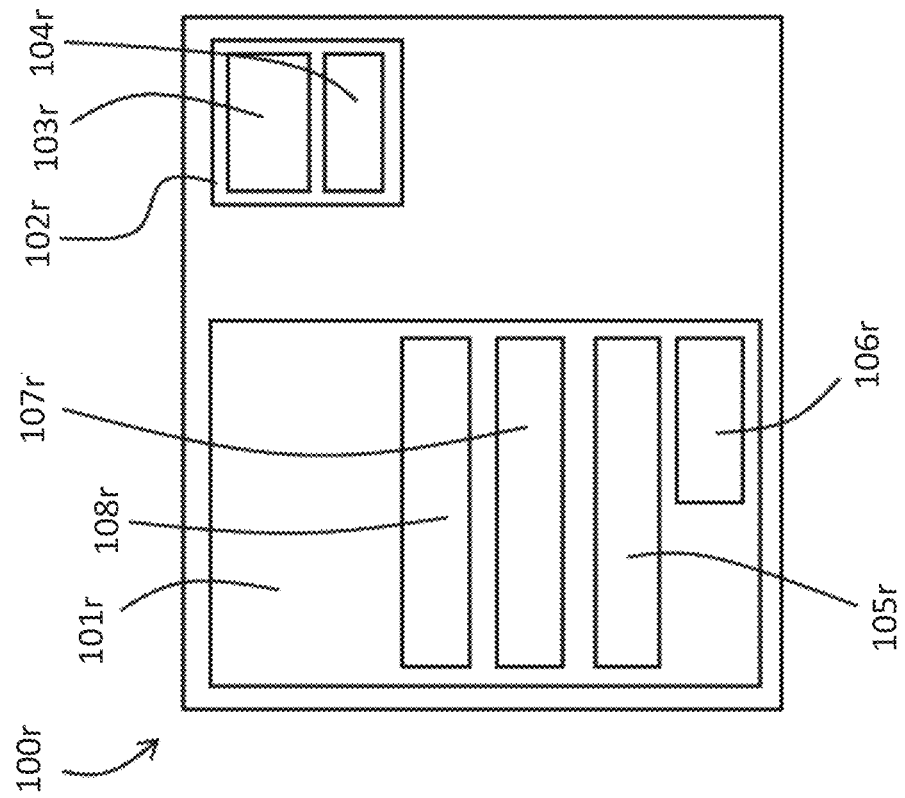

FIG. 55A is a schematic of a smoking substitute system of the sixteenth mode.

FIG. 55B is a schematic of a variation of the smoking substitute system of FIG. 55A.

FIG. 56A is a front view of a first embodiment of the sixteenth mode of a smoking substitute system with the consumable engaged with the device.

FIG. 56B is a front view of the first embodiment of the sixteenth mode of the smoking substitute system with the consumable disengaged from the device.

Figure 56C:
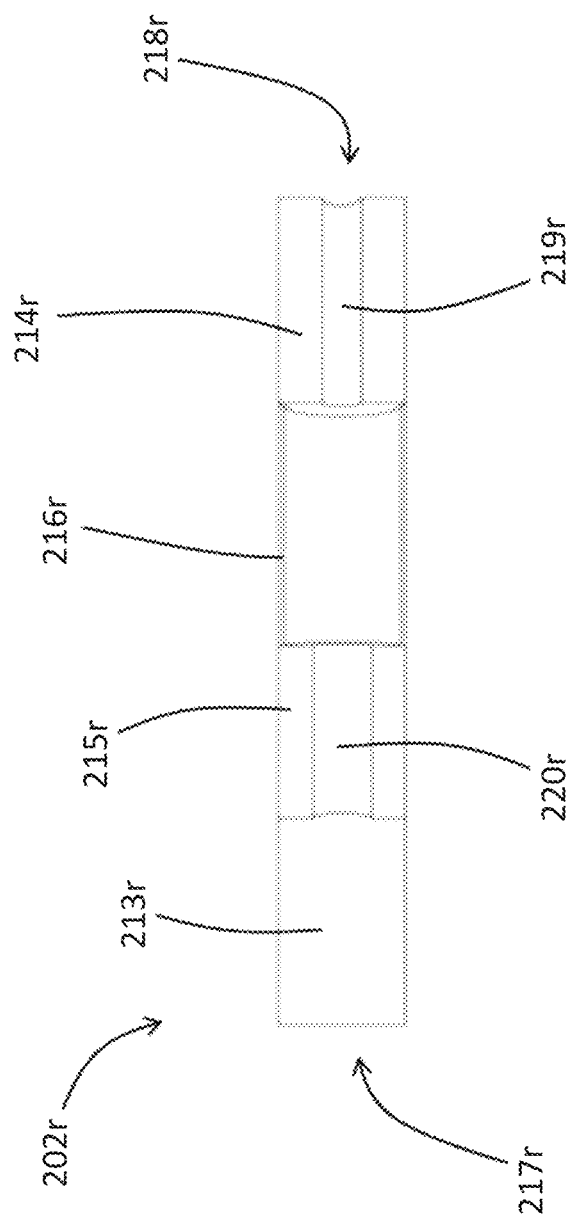

FIG. 56C is a section view of the consumable of the first embodiment of the sixteenth mode of the smoking substitute system.

Figures 56D, 56E:
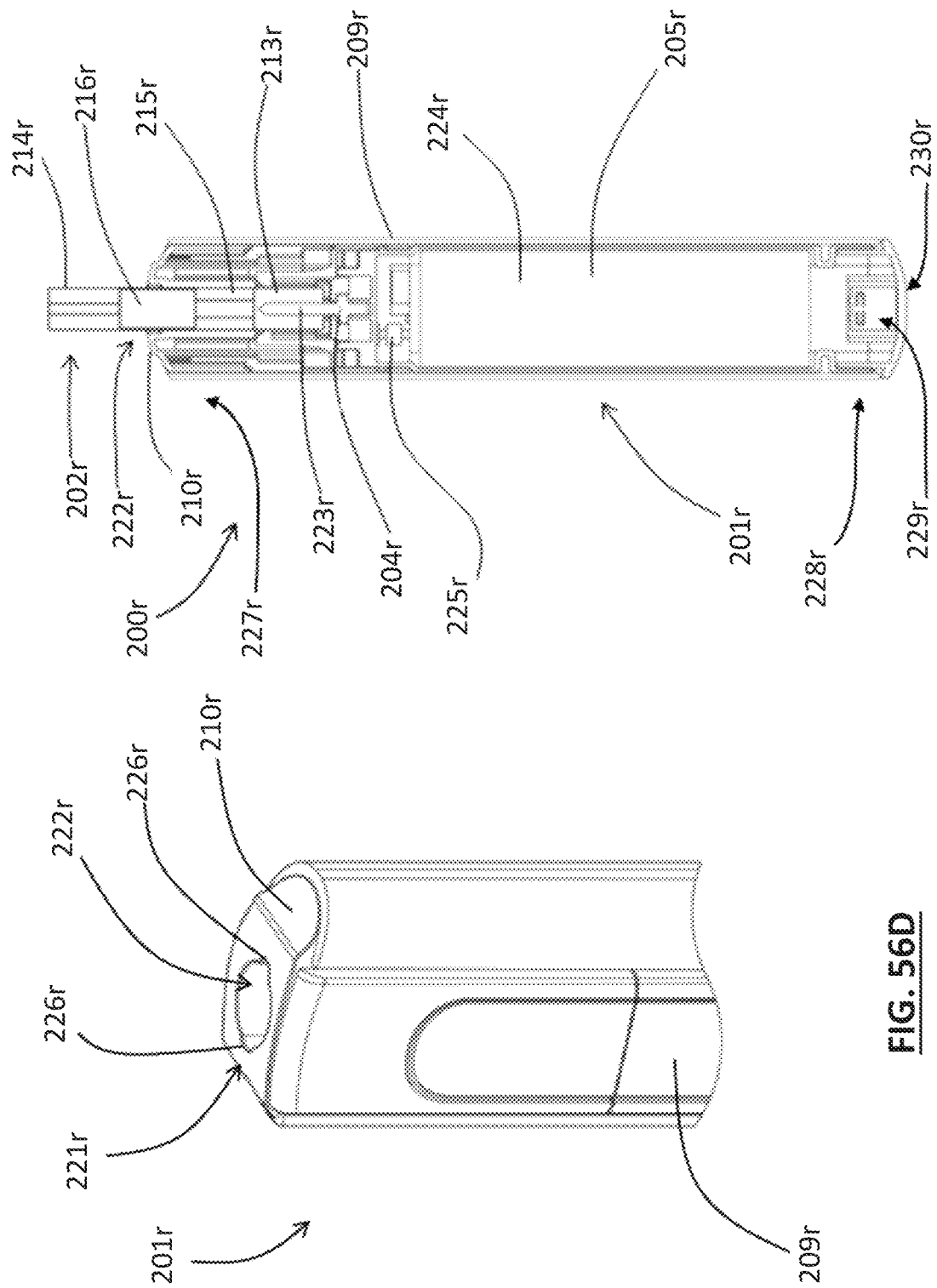

FIG. 56D is a detailed view of an end of the device of the first embodiment of the sixteenth mode of the smoking substitute system.

FIG. 56E is a section view of the first embodiment of the sixteenth mode of the substitute smoking system.

FIGS. 56F-56H illustrate a schematic front view, perspective view and a section view of a first embodiment of the sixteenth mode of a closure of the smoking substitute system when in the first position.

FIGS. 56I-56K illustrate a schematic front view, perspective view and a section view of a first embodiment of the sixteenth mode of a closure of the smoking substitute system when in the second position.

FIG. 57A to 57E illustrate schematic perspective views of an embodiment of the sixteenth mode of the substitute smoking system comprising a closure.

Figure 58B:
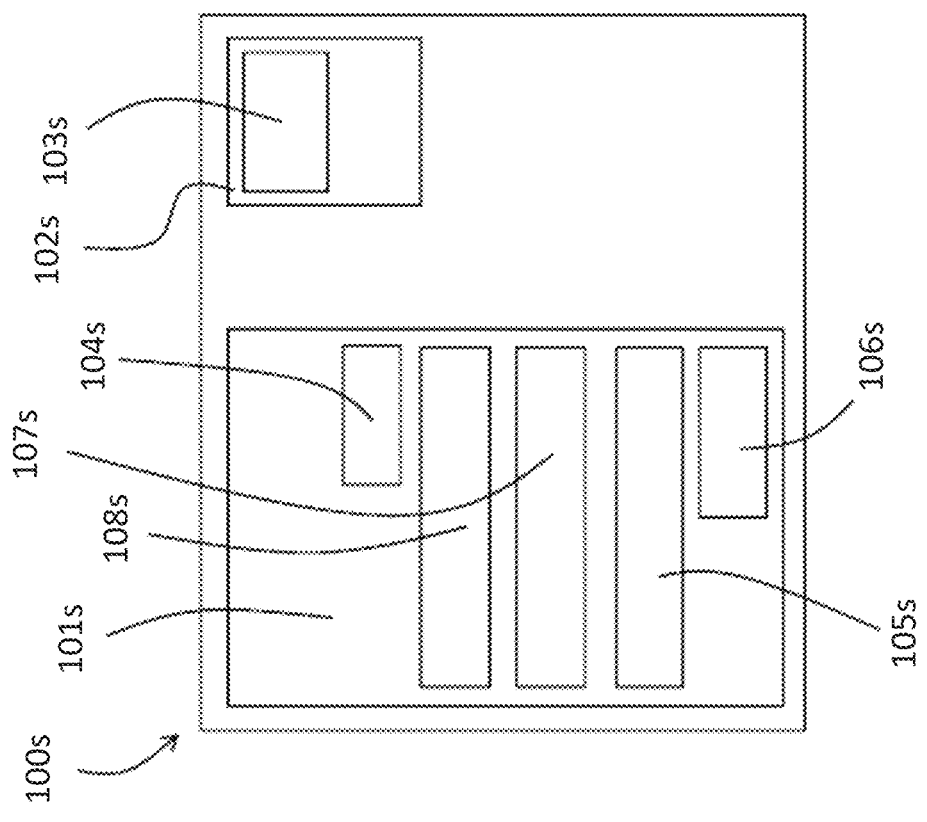
Figure 58A:
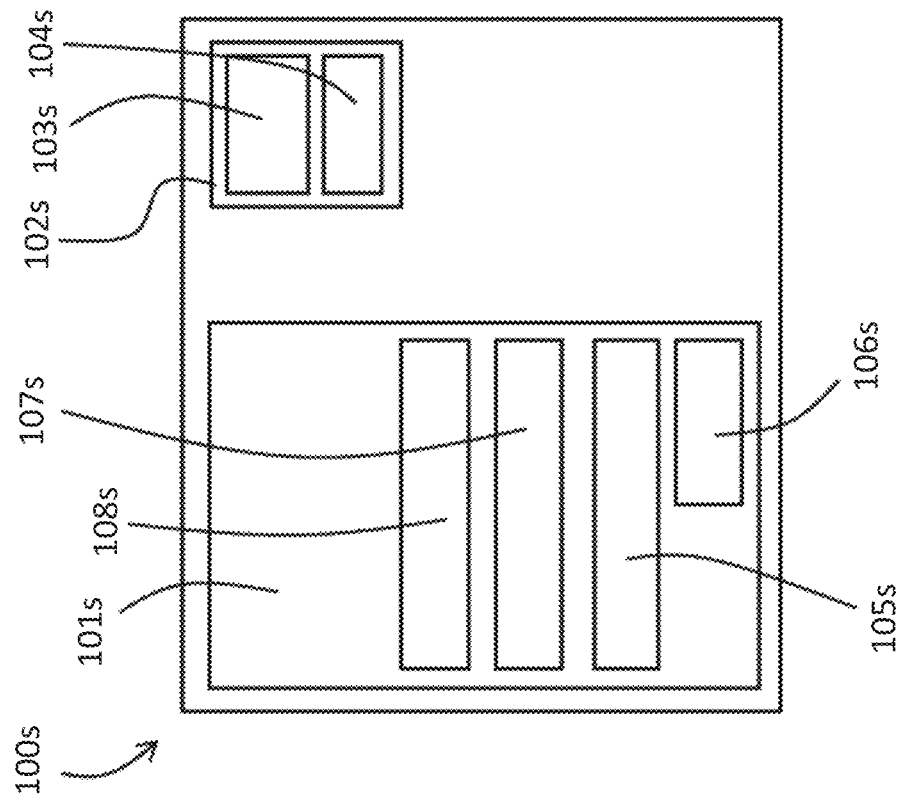

FIG. 58A is a schematic of a smoking substitute system of the seventeenth mode.

FIG. 58B is a schematic of a variation of the smoking substitute system of FIG. 58A.

FIG. 59A is a front view of a first embodiment of the seventeenth mode of a smoking substitute system with the consumable engaged with the device.

FIG. 59B is a front view of the first embodiment of the seventeenth mode of the smoking substitute device.

Figure 59C:
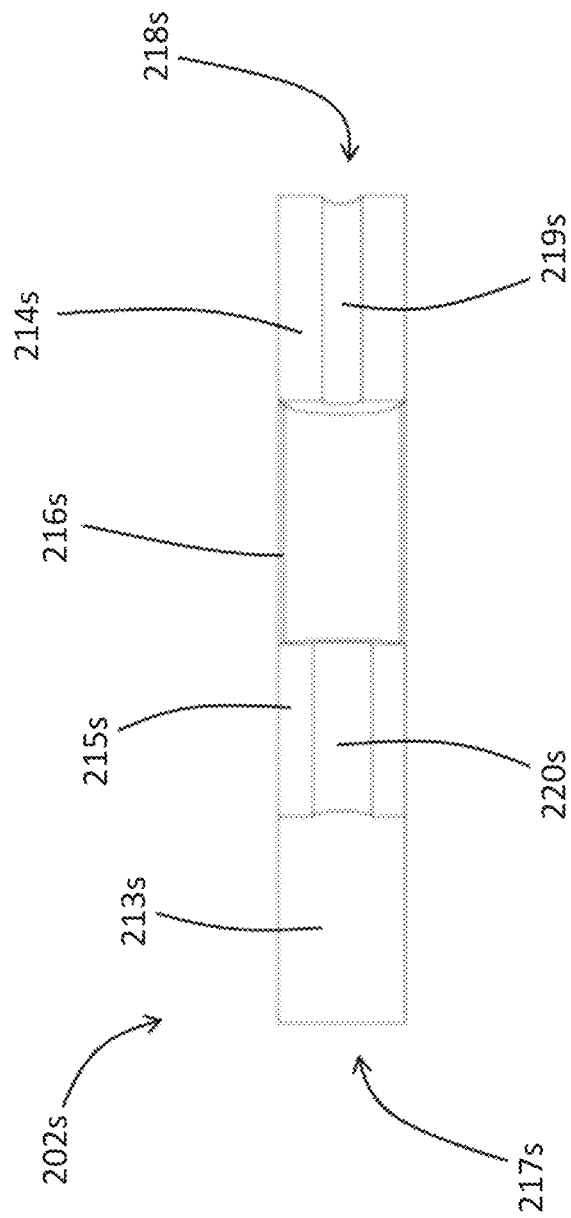

FIG. 59C is a section view of the consumable of the first embodiment of the seventeenth mode of the smoking substitute system.

FIG. 59D is a detailed view of the first end of the smoking substitute device of the seventeenth mode.

FIG. 59E is a sectional view of the second embodiment of the seventeenth mode of the smoking substitute system.

Figure 60:
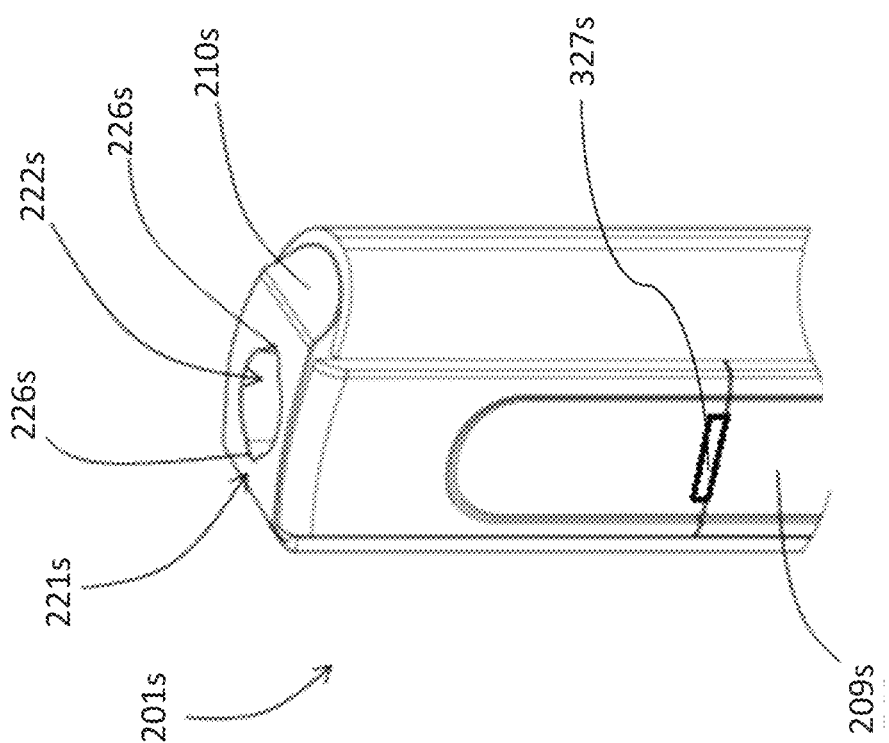

FIG. 60 is detailed view of a first end of a third embodiment of the seventeenth mode of the smoking substitute device.

Figure 61:
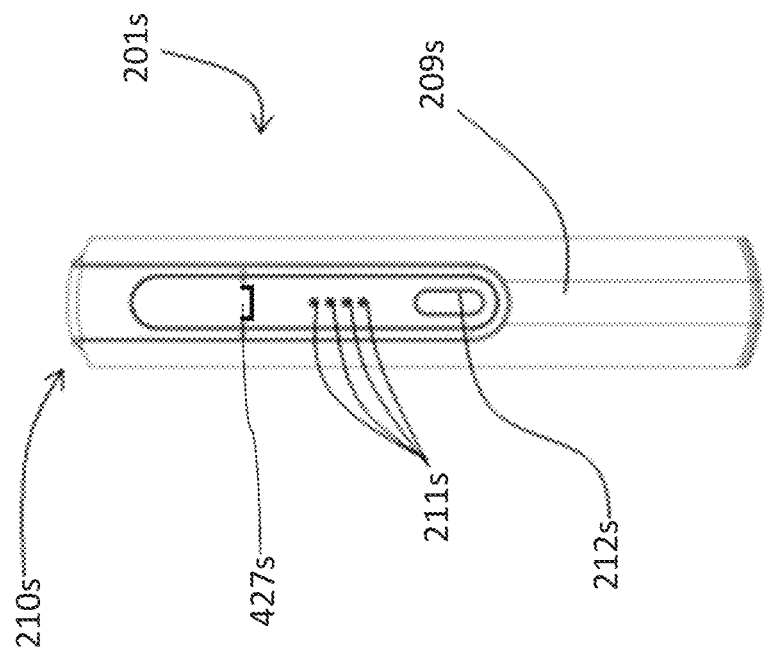

FIG. 61 is a front view of the fourth embodiment of the seventeenth mode of the smoking substitute device.

FIG. 62A is a schematic of a smoking substitute system of the eighteenth mode.

FIG. 62B is a schematic of a variation of the smoking substitute system of FIG. 62A.

FIG. 63A is a front view of a first embodiment of the eighteenth mode of a smoking substitute system with the consumable engaged with the device.

FIG. 63B is a front view of the first embodiment of the eighteenth mode of the smoking substitute system with the consumable disengaged from the device.

Figure 63C:
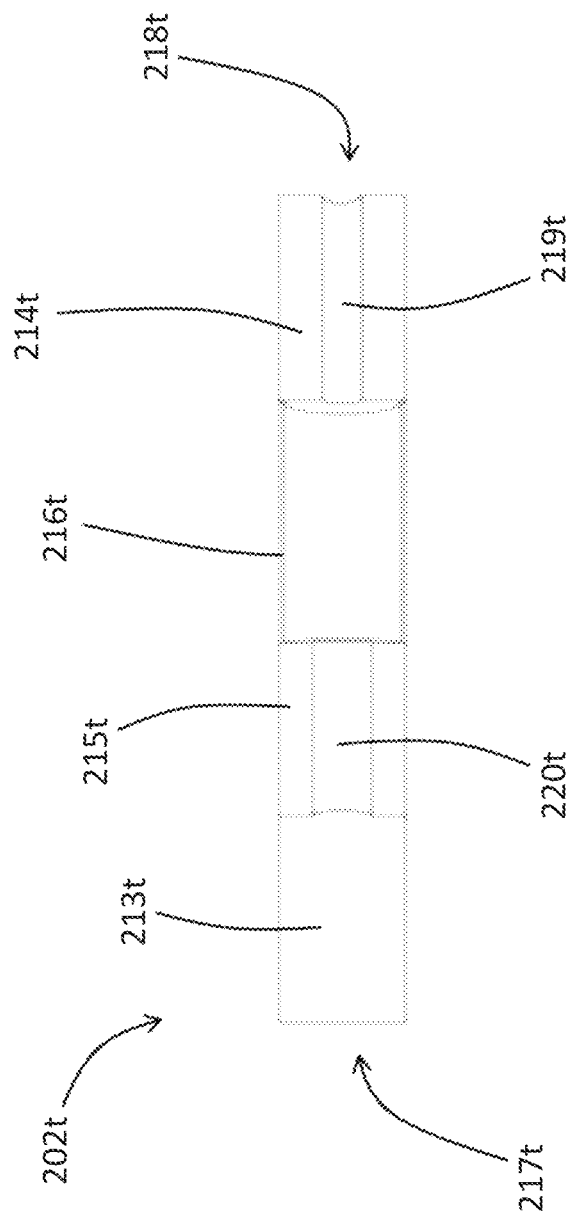

FIG. 63C is a section view of the consumable of the first embodiment of the eighteenth mode of the smoking substitute system.

FIG. 63D is a detailed view of an end of the device of the first embodiment of the eighteenth mode of the smoking substitute system.

FIG. 63E is a section view of the first embodiment of the eighteenth mode of the smoking substitute system.

Figure 63F:
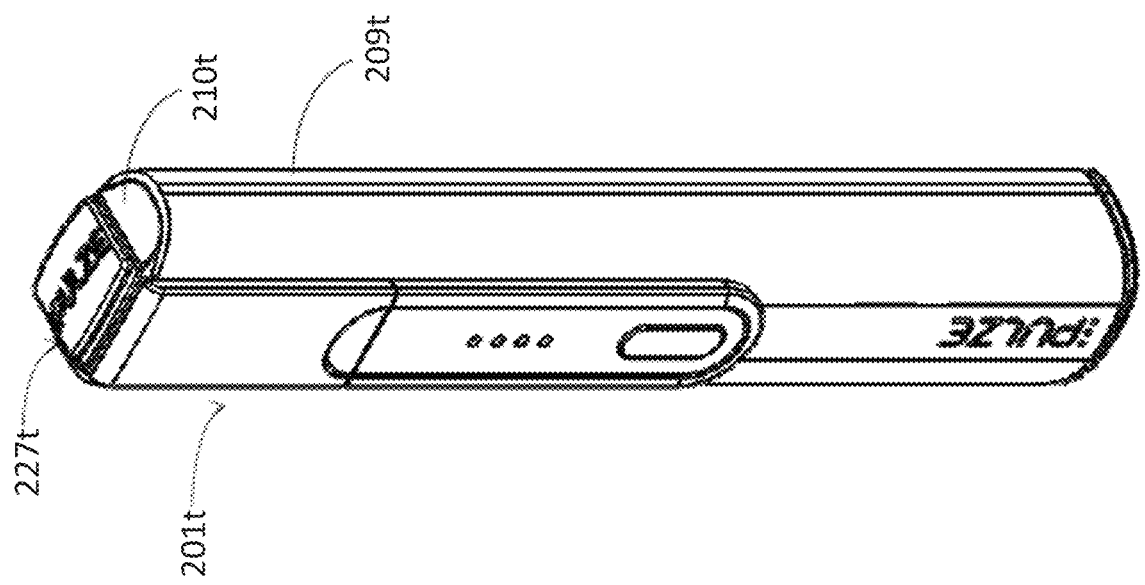

FIG. 63F is a perspective view of an HNB device of the eighteenth mode with a stopper engaged within a cavity of the HNB device.

Figure 64:
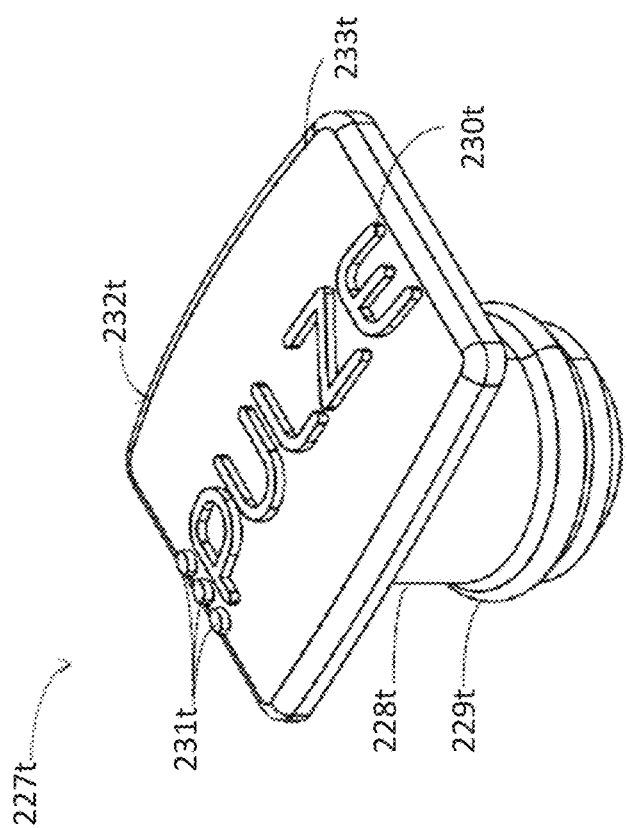

FIG. 64 is a perspective view of the stopper of FIG. 63F.

Figure 65:
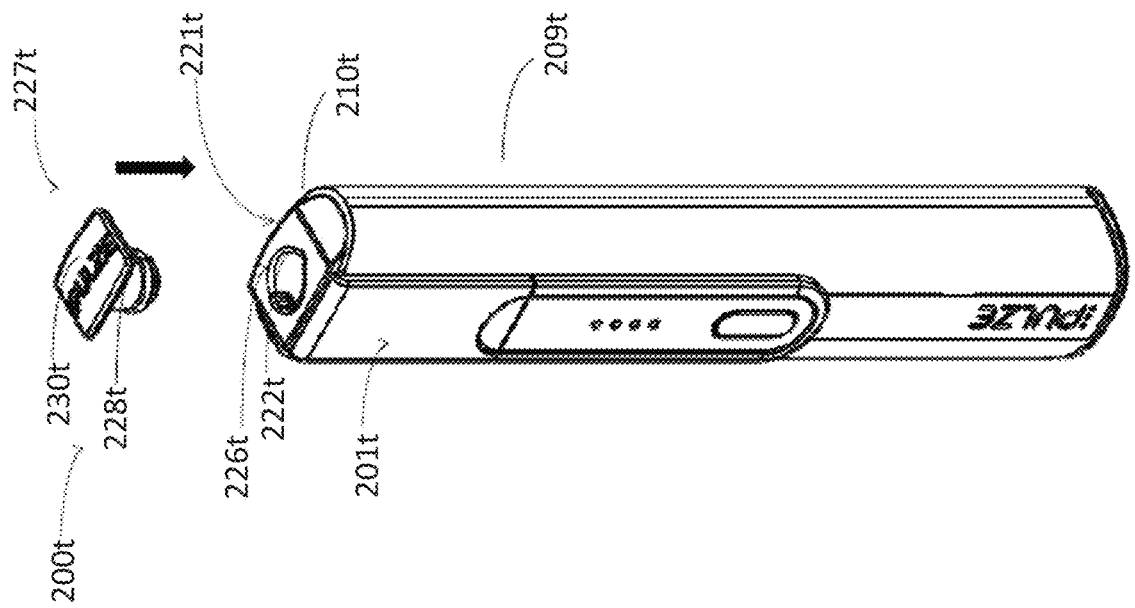

FIG. 65 is a perspective view of the HNB device of the eighteenth mode with the stopper disengaged from the cavity of the HNB device.

Figure 66A:
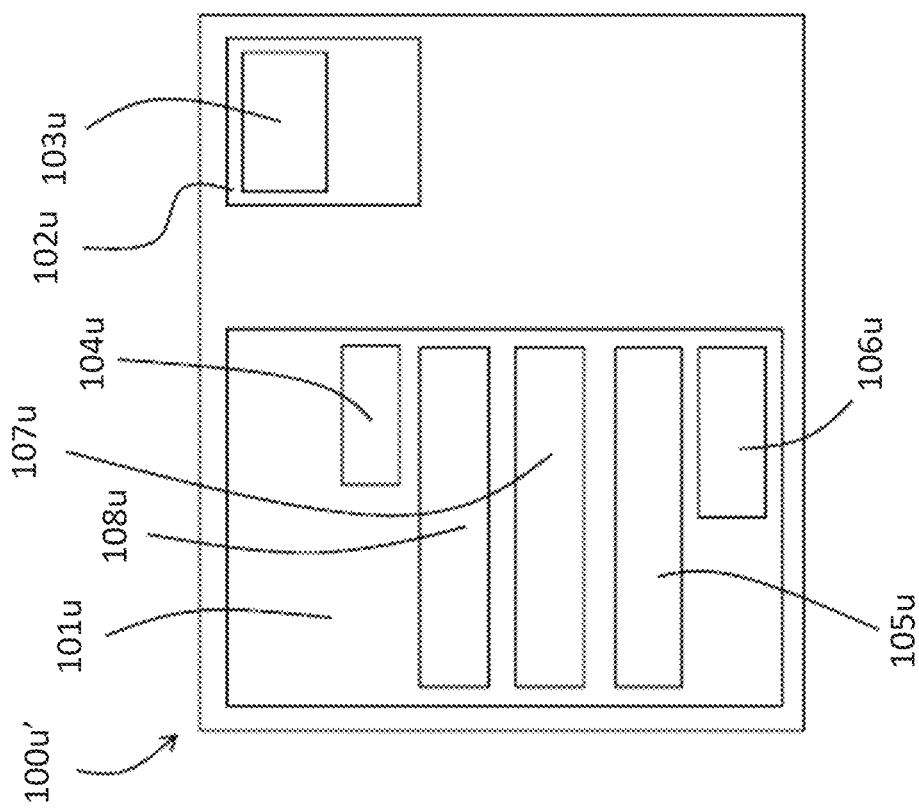

FIG. 66A is a schematic of a smoking substitute system of the nineteenth mode.

Figure 66B:
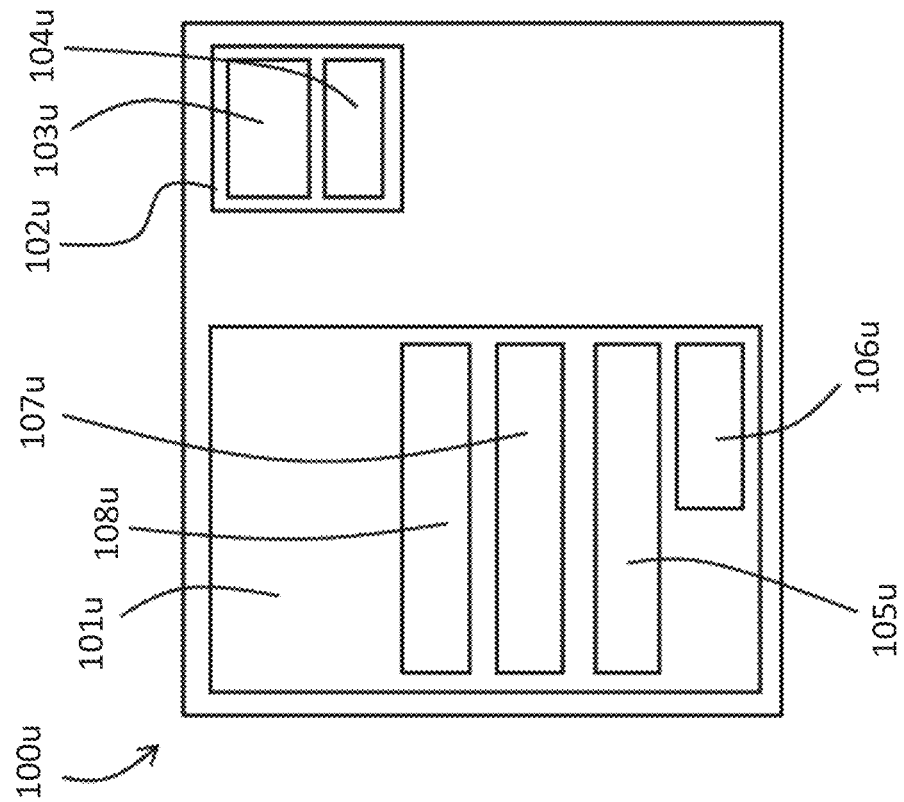

FIG. 66B is a schematic of a variation of the smoking substitute system of FIG. 66A.

Figure 67A:
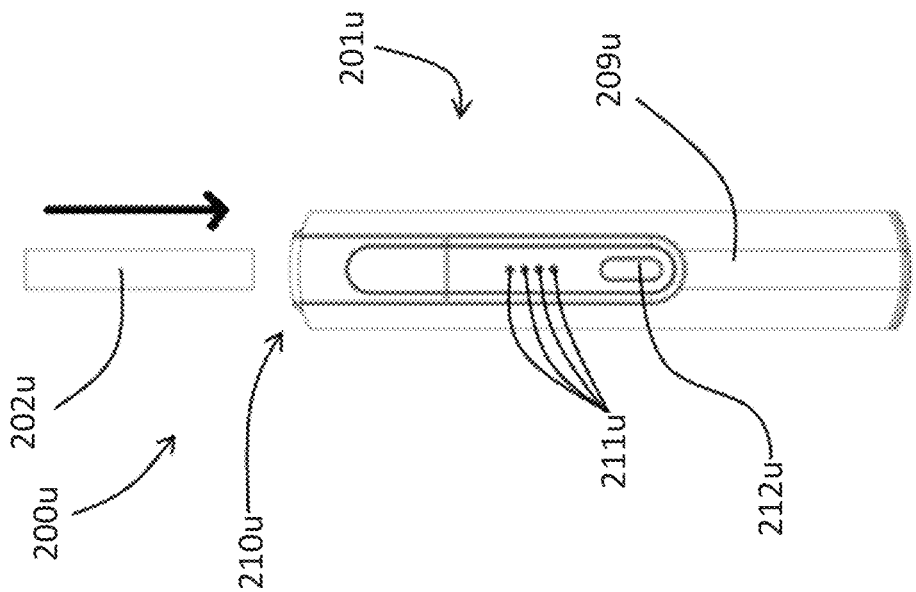

FIG. 67A is a front view of a first embodiment of the nineteenth mode of a smoking substitute system with the consumable engaged with the device.

Figure 67B:
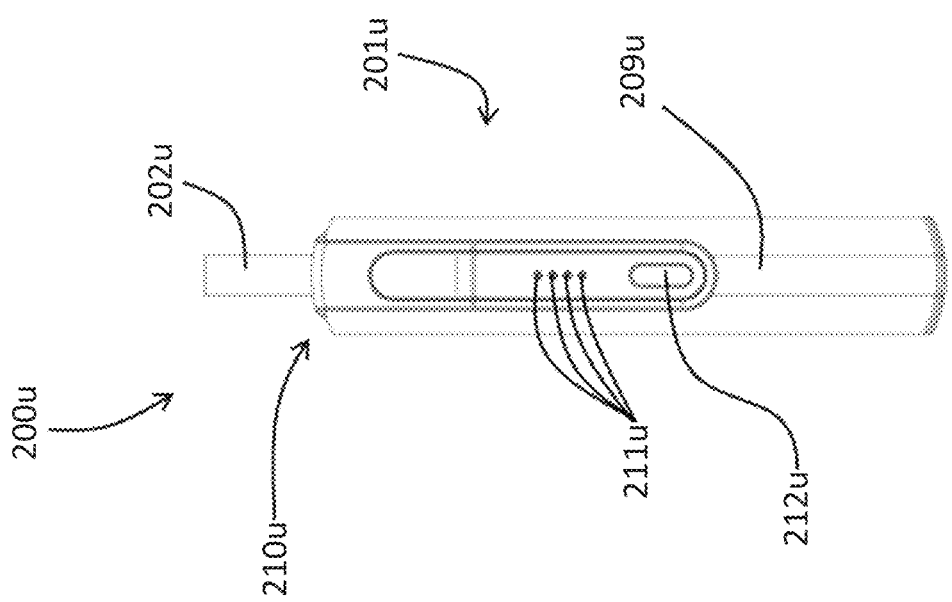

FIG. 67B is a front view of the first embodiment of the nineteenth mode of the smoking substitute system with the consumable disengaged from the device.

Figure 67C:
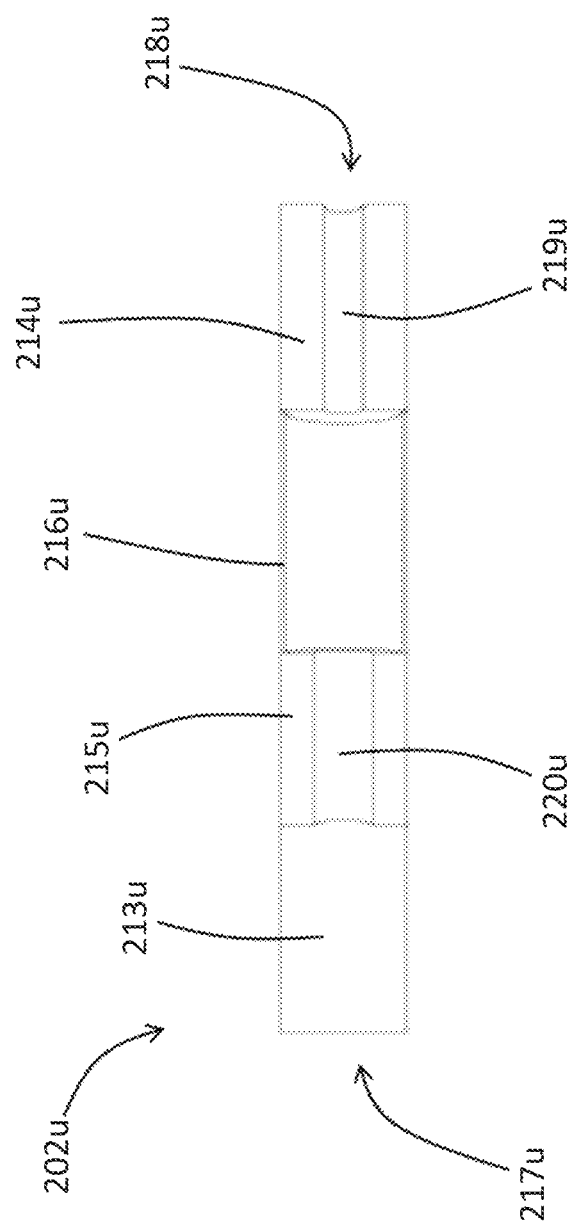

FIG. 67C is a section view of the consumable of the first embodiment of the nineteenth mode of the smoking substitute system.

Figure 67E:
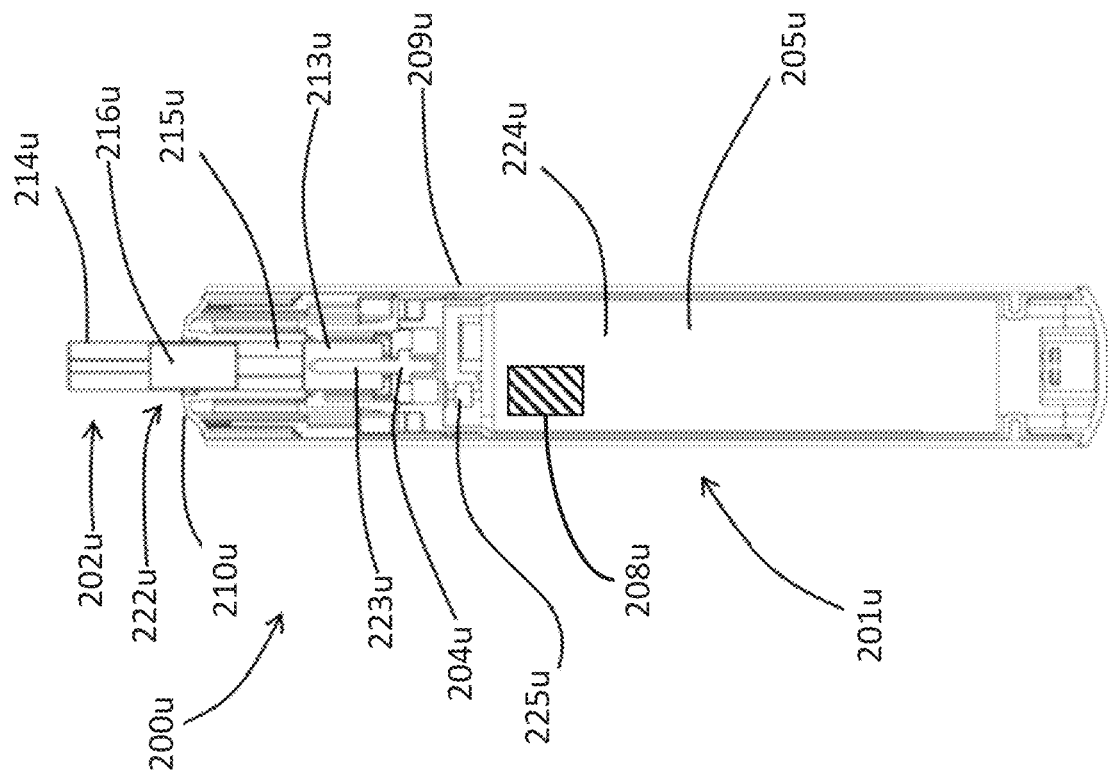
Figure 67D:
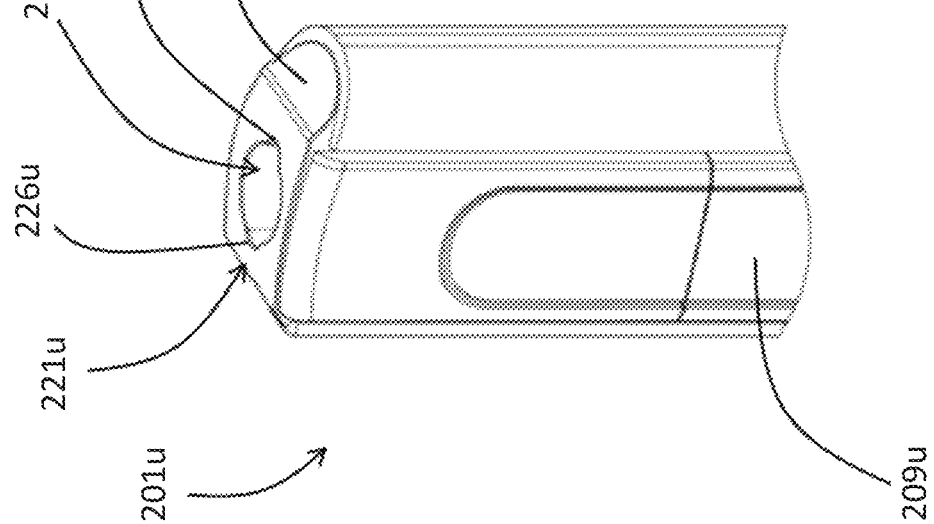

FIG. 67D is a detailed view of an end of the device of the first embodiment of the nineteenth mode of the smoking substitute system.

FIG. 67E is a section view of the first embodiment of the nineteenth mode of the substitute smoking system.

Figure 67F:
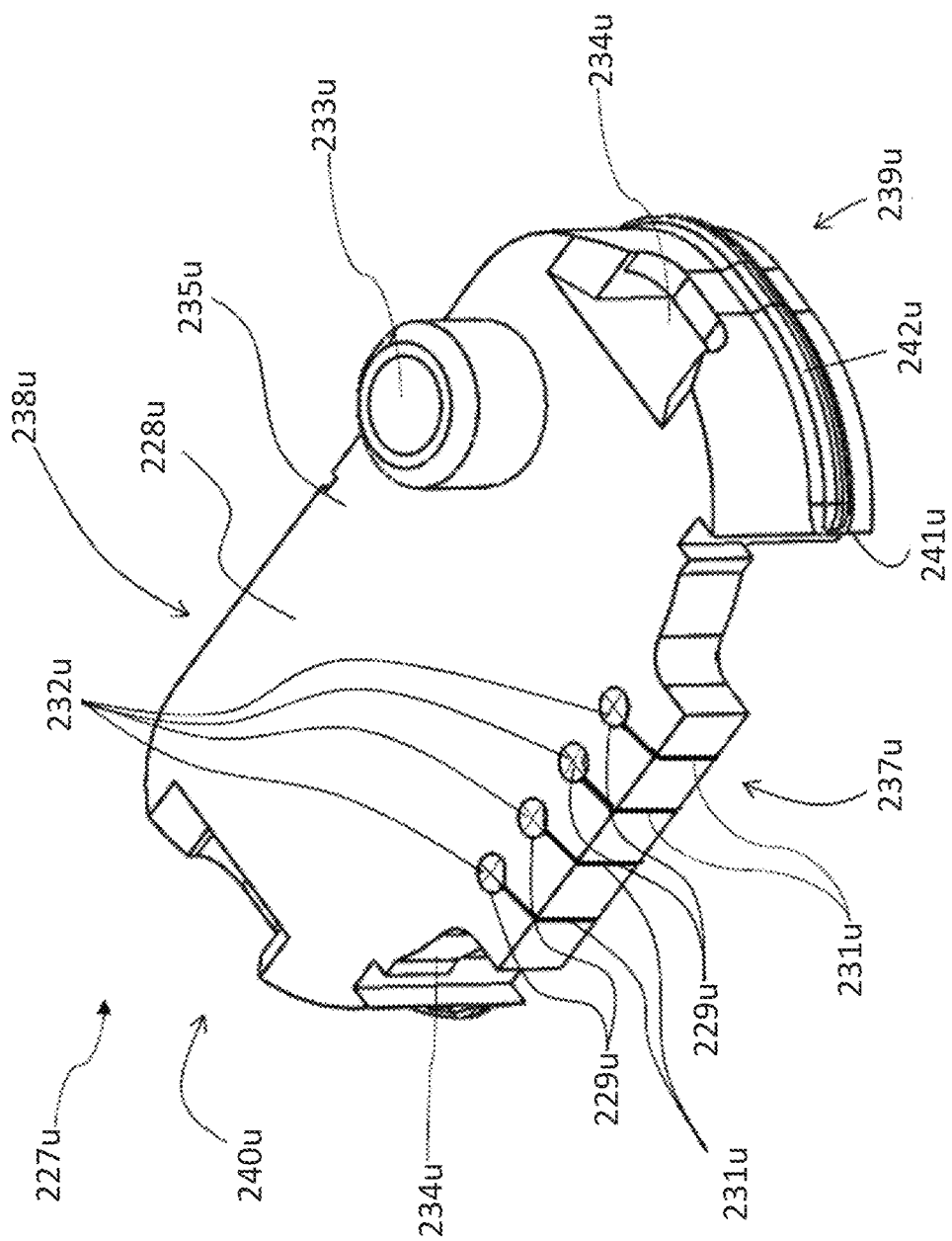

FIG. 67F is a perspective view of a wire harness member of the first embodiment of the nineteenth mode.

Figure 67G:
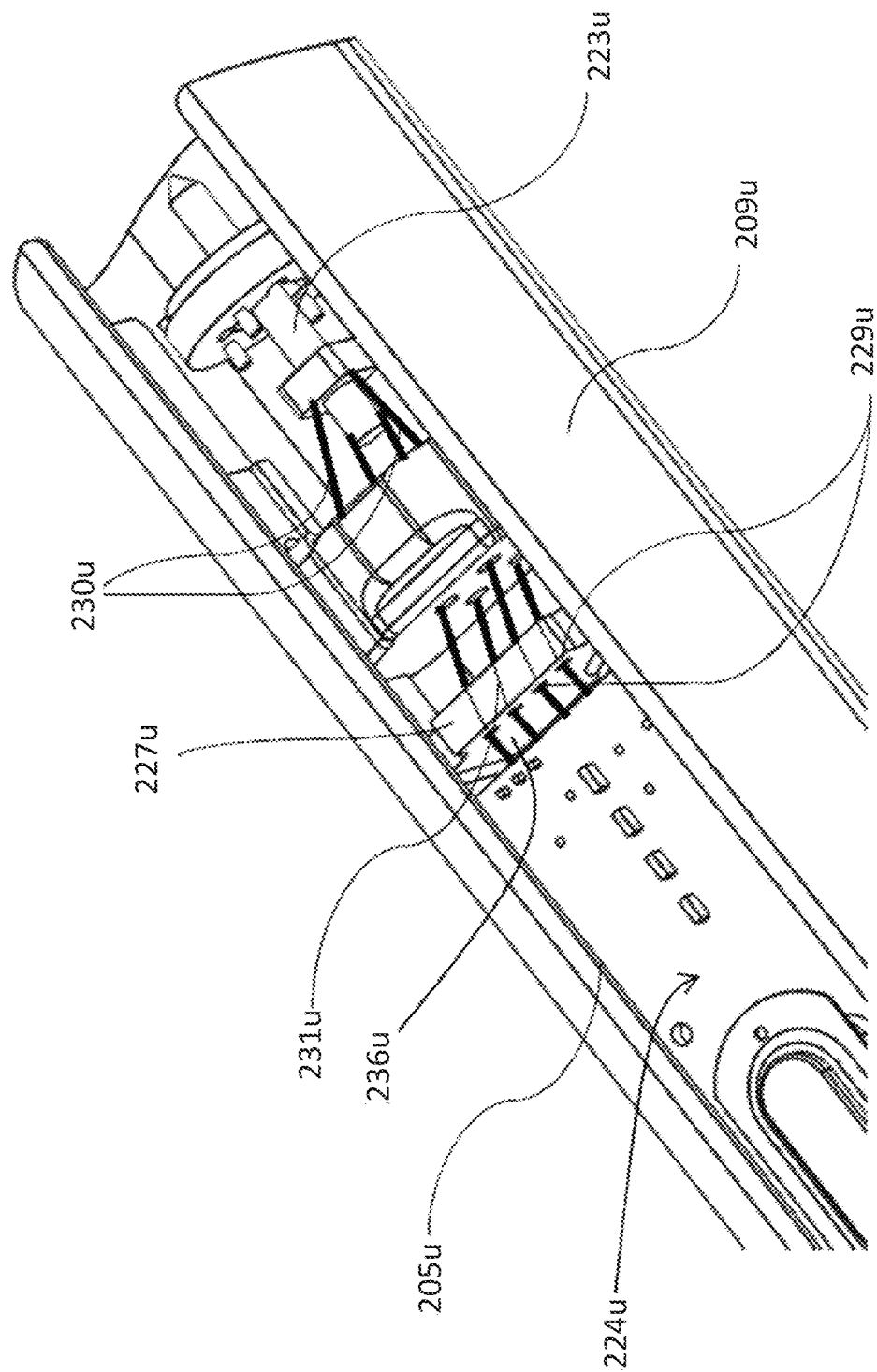

FIG. 67G is partial sectional view of an end of a device forming part of the system of the first embodiment of the nineteenth mode.

Figure 67H:
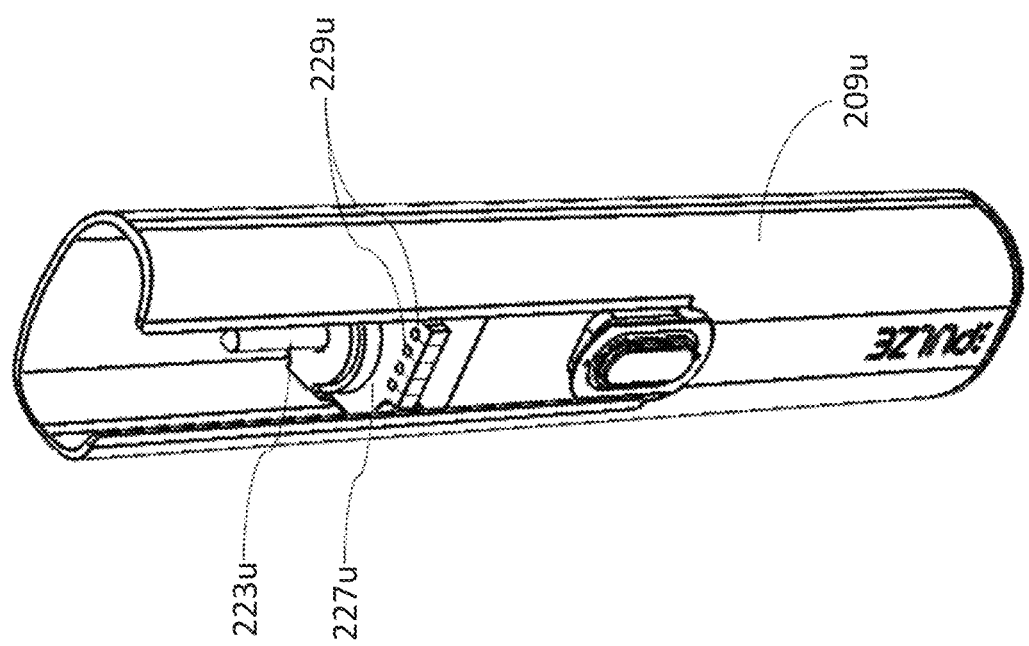

FIG. 67H is a perspective view of the device of the first embodiment of the nineteenth mode.

Figure 68B:
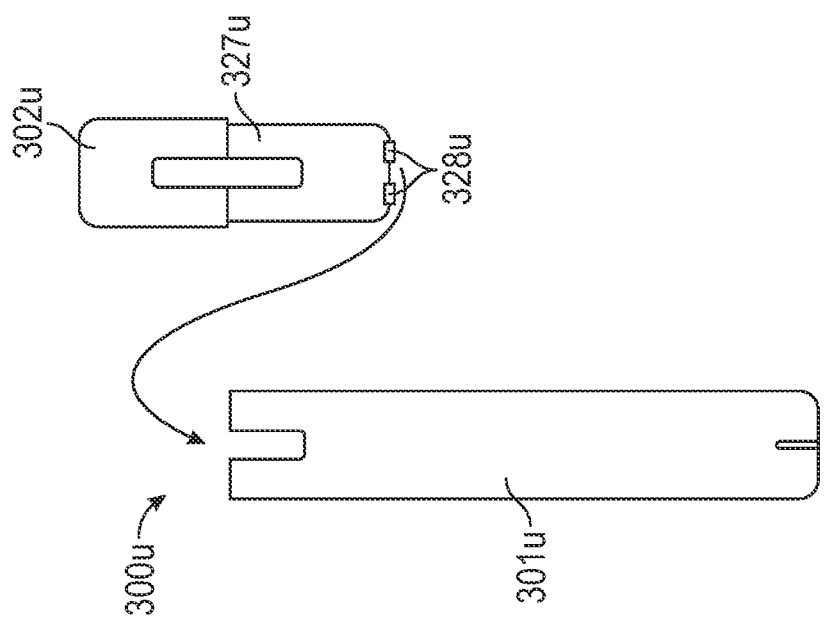
Figure 68A:
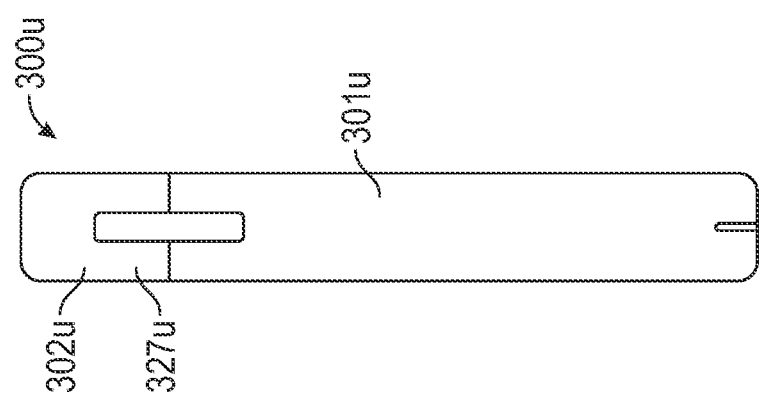

FIG. 68A is a front view of a second embodiment of the nineteenth mode of a smoking substitute system with the consumable engaged with the device.

FIG. 68B is a front view of the second embodiment of the nineteenth mode of the smoking substitute system with the consumable disengaged from the device.

Figure 69:
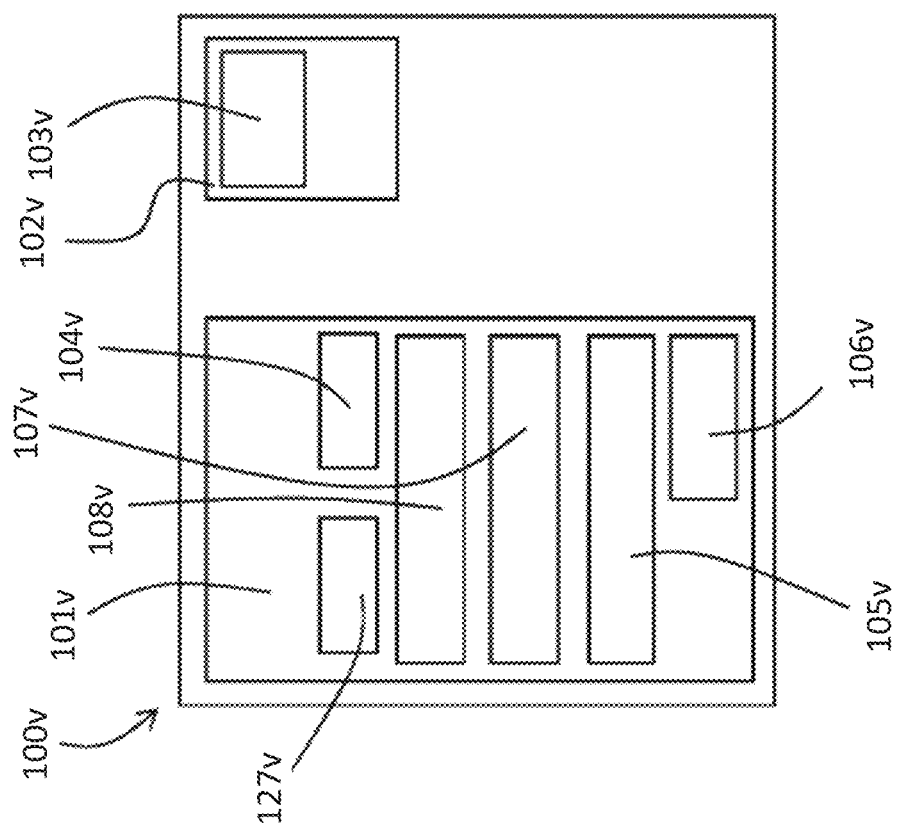

FIG. 69 is a schematic of a smoking substitute system of the twentieth mode.

FIG. 70A is a front view of a first embodiment of the twentieth mode of a smoking substitute system with the consumable engaged with the device.

FIG. 70B is a front view of the first embodiment of the twentieth mode of the smoking substitute system with the consumable disengaged from the device.

Figure 70C:
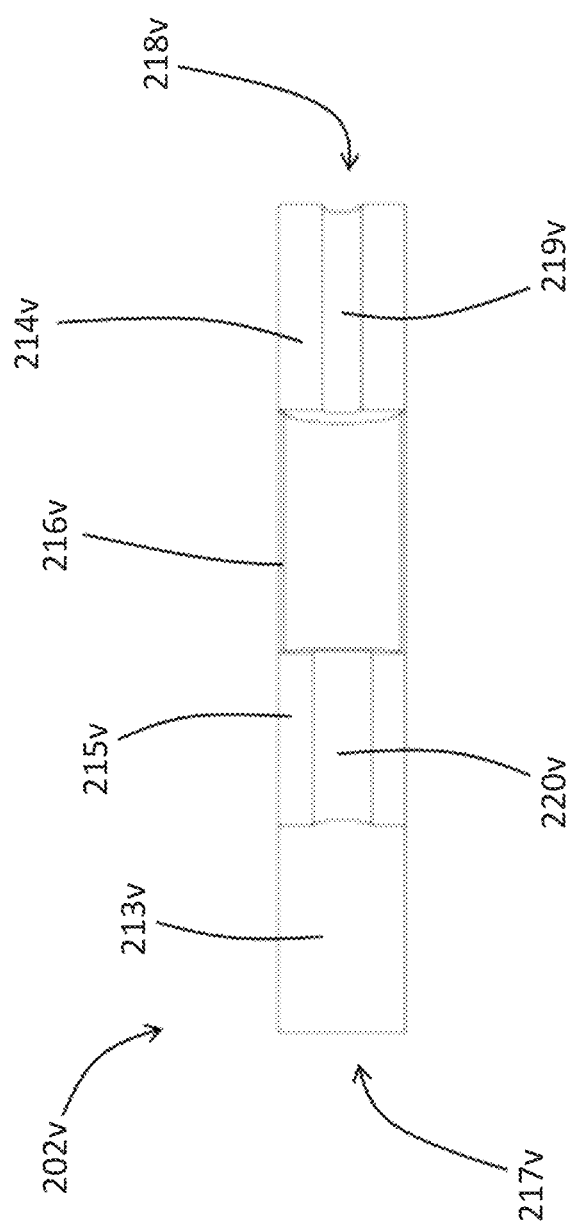

FIG. 70C is a section view of the consumable of the first embodiment of the twentieth mode of the smoking substitute system.

FIG. 70D is a detailed view of an end of the device of the first embodiment of the twentieth mode of the smoking substitute system.

FIG. 70E is a section view of the first embodiment of the twentieth mode of the substitute smoking system.

Figure 70G:
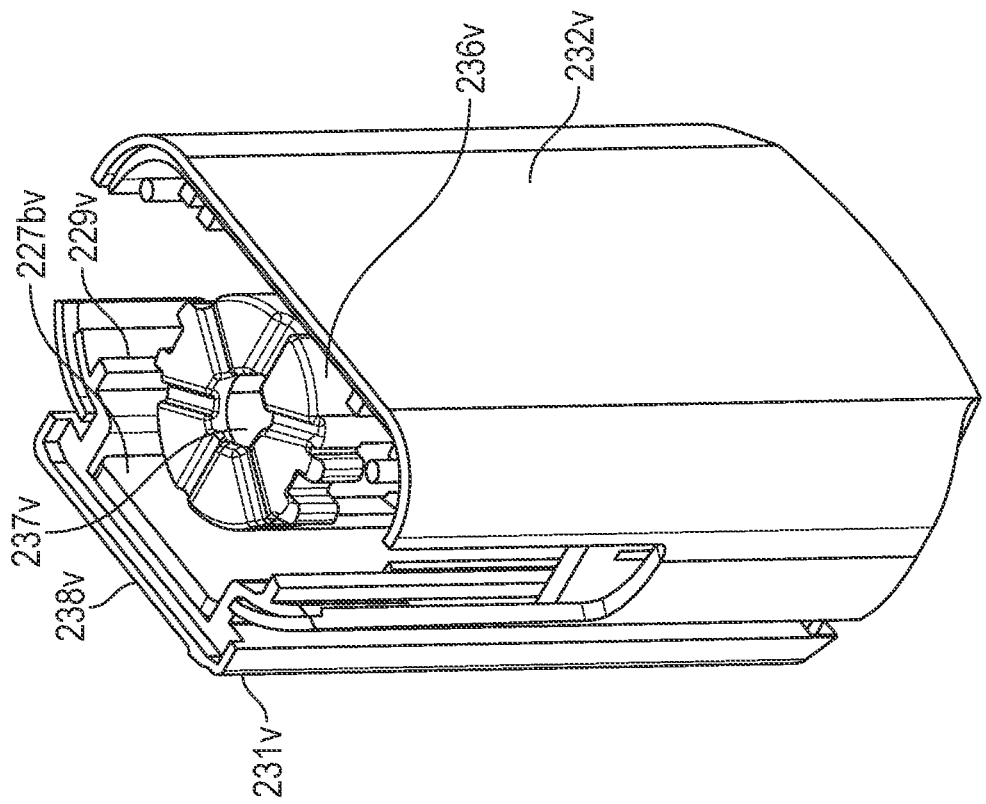
Figure 70F:
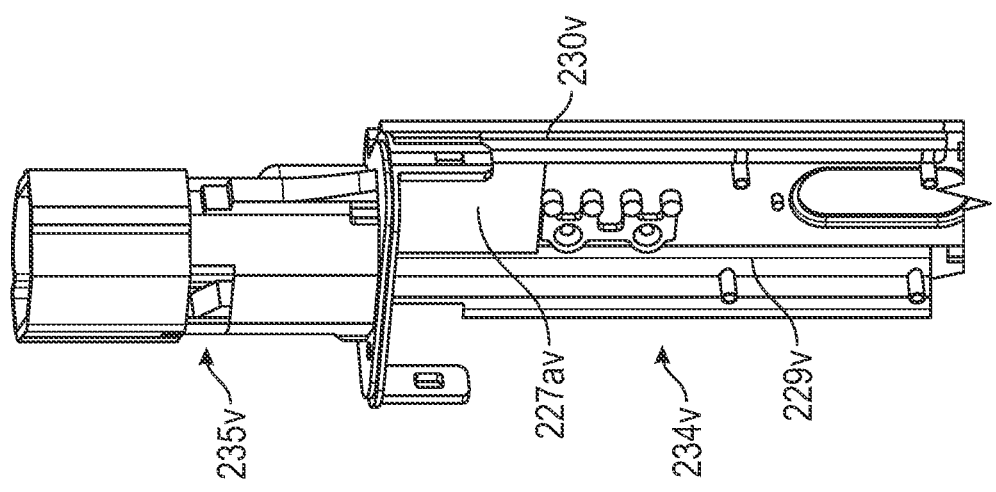

FIG. 70F is a back perspective view of a portion of the body of the housing of the first embodiment of the twentieth mode.

FIG. 70G is a bottom perspective view of a cap of the first embodiment of the twentieth mode.

FIG. 71 is a schematic of a smoking substitute system of the twenty-first mode.

FIG. 72A is a front view of a first embodiment of the twenty-first mode of a smoking substitute system with the consumable engaged with the device.

FIG. 72B is a front view of the first embodiment of the twenty-first mode of the smoking substitute system with the consumable disengaged from the device.

Figure 72C:
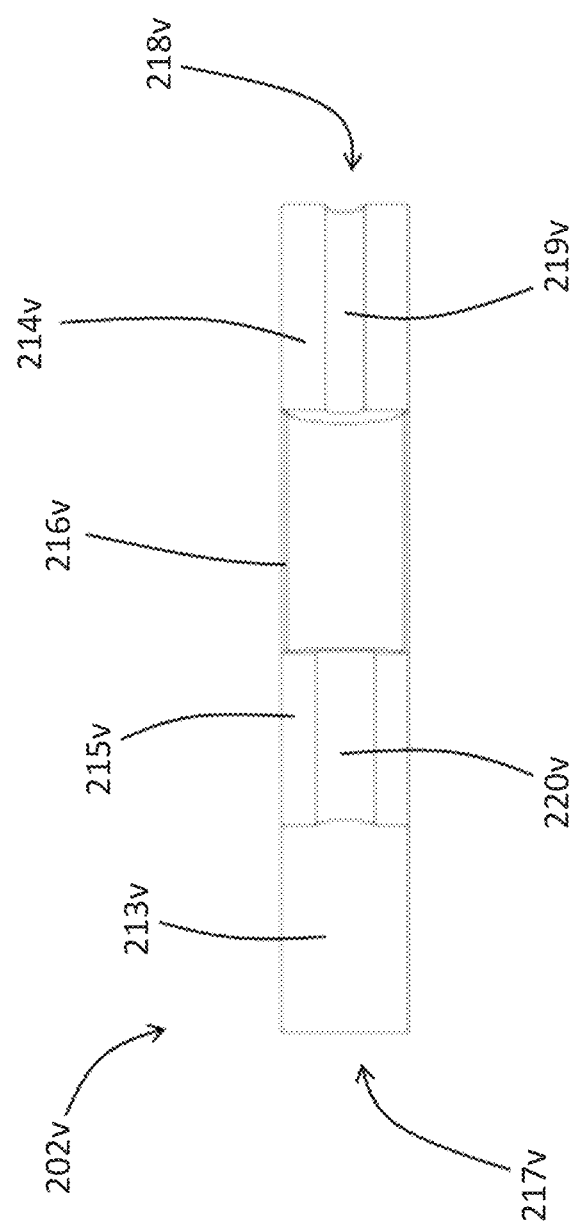

FIG. 72C is a section view of the consumable of the first embodiment of the twenty-first mode of the smoking substitute system.

Figure 72E:
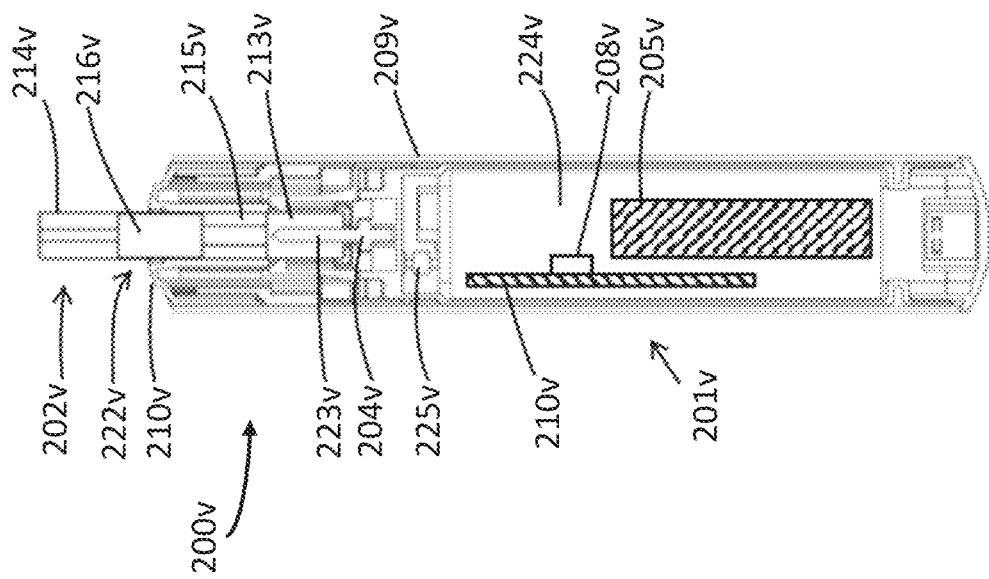
Figure 72D:
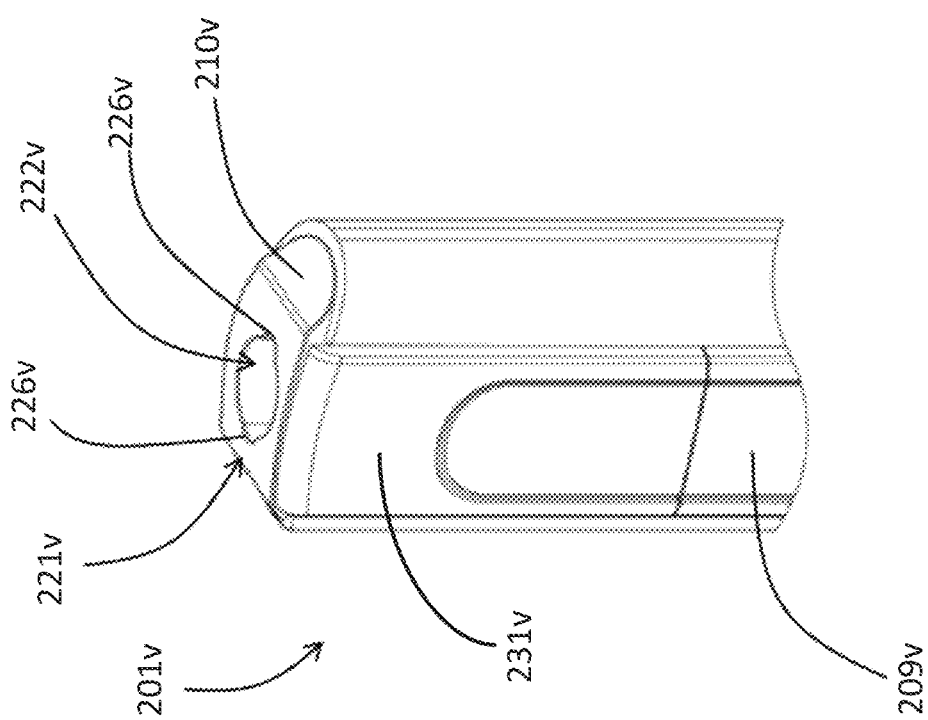

FIG. 72D is a detailed view of an end of the device of the first embodiment of the twenty-first mode of the smoking substitute system.

FIG. 72E is a section view of the first embodiment of the twenty-first mode of the substitute smoking system.

Figure 73A:
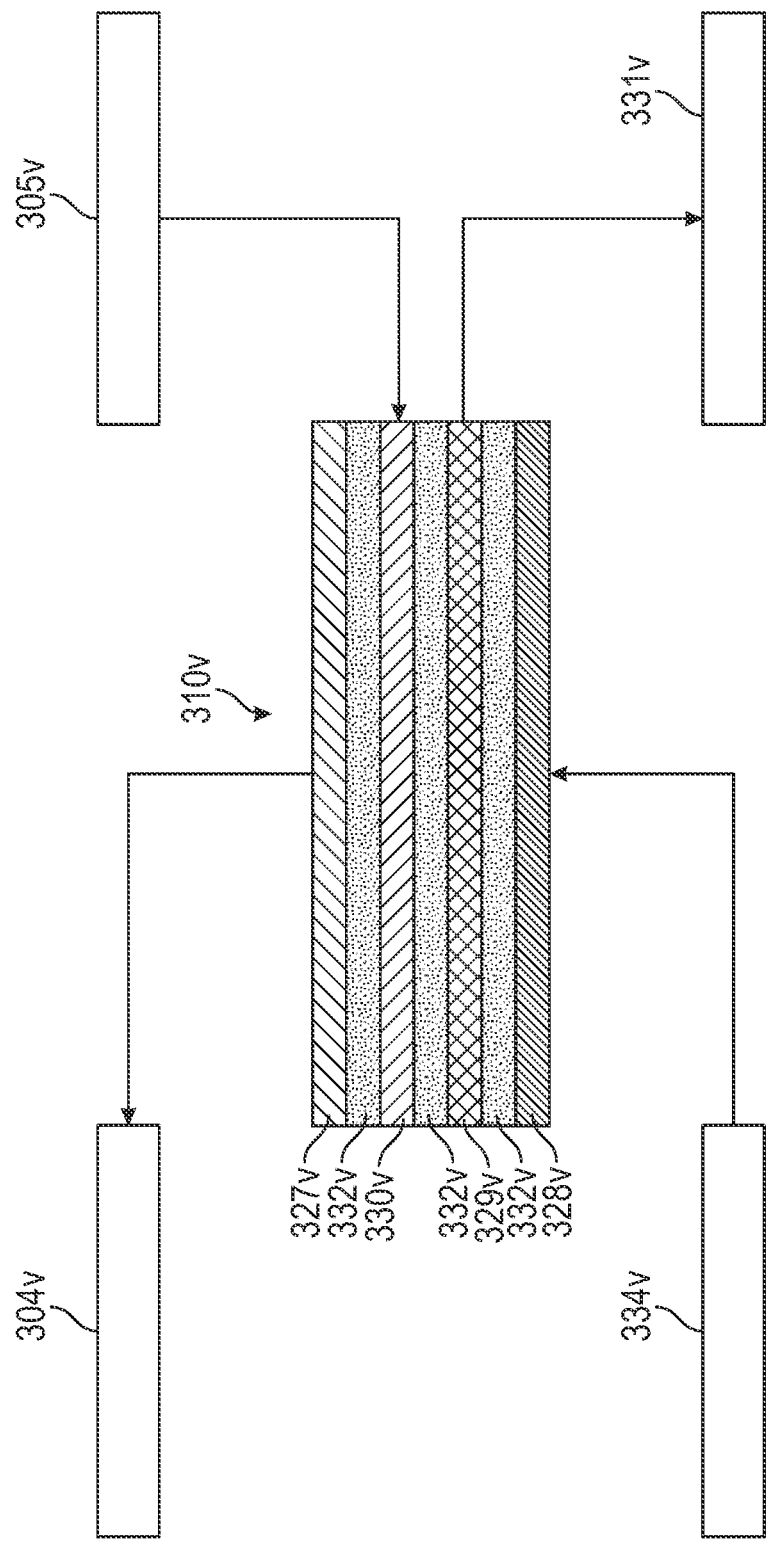

FIG. 73A is a schematic of a smoking substitute device according to a second embodiment of the twenty-first mode of the present disclosure.

Figure 73B:
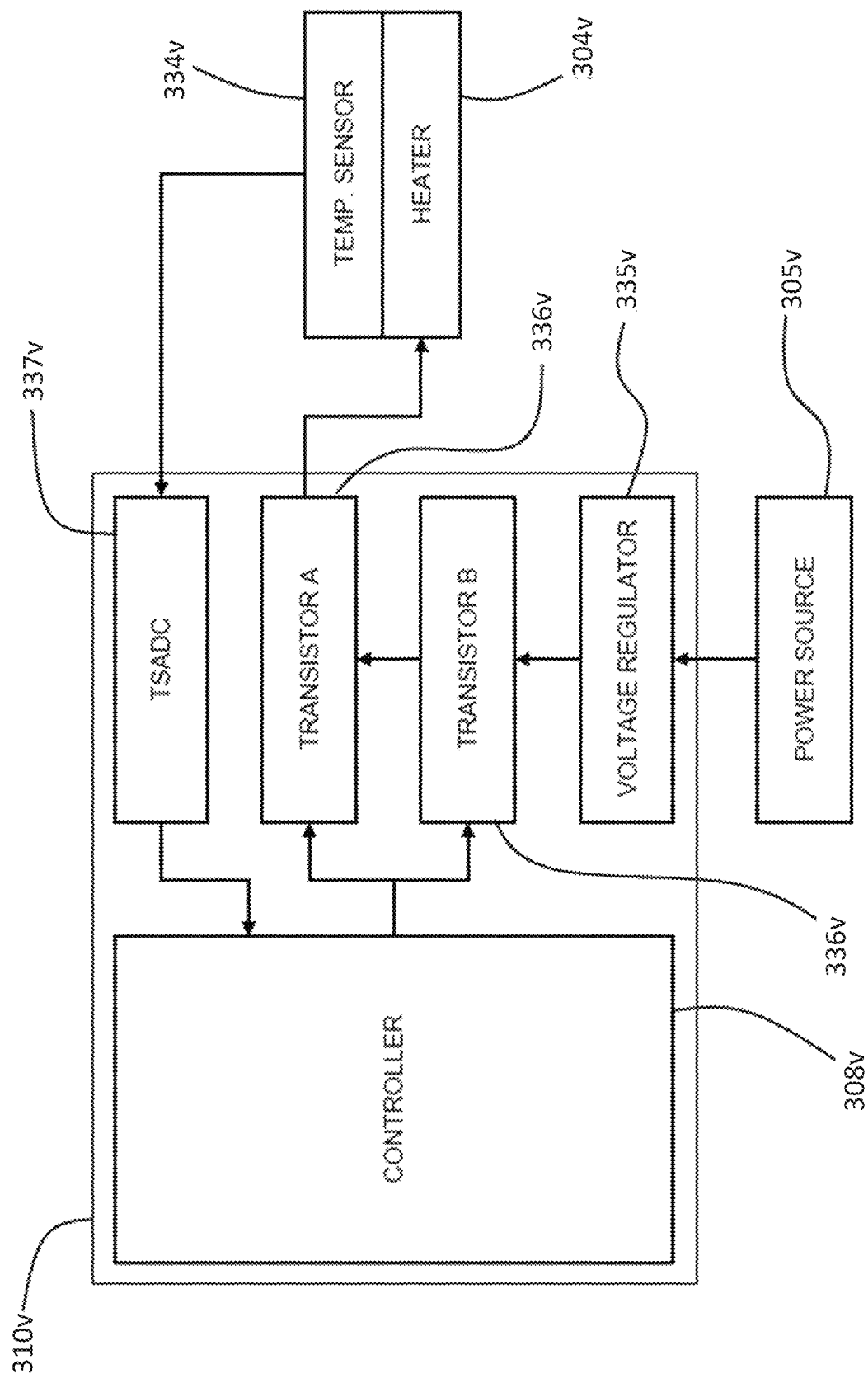

FIG. 73B is a schematic of a PCB of the second embodiment of the twenty-first mode.

Figure 73C:
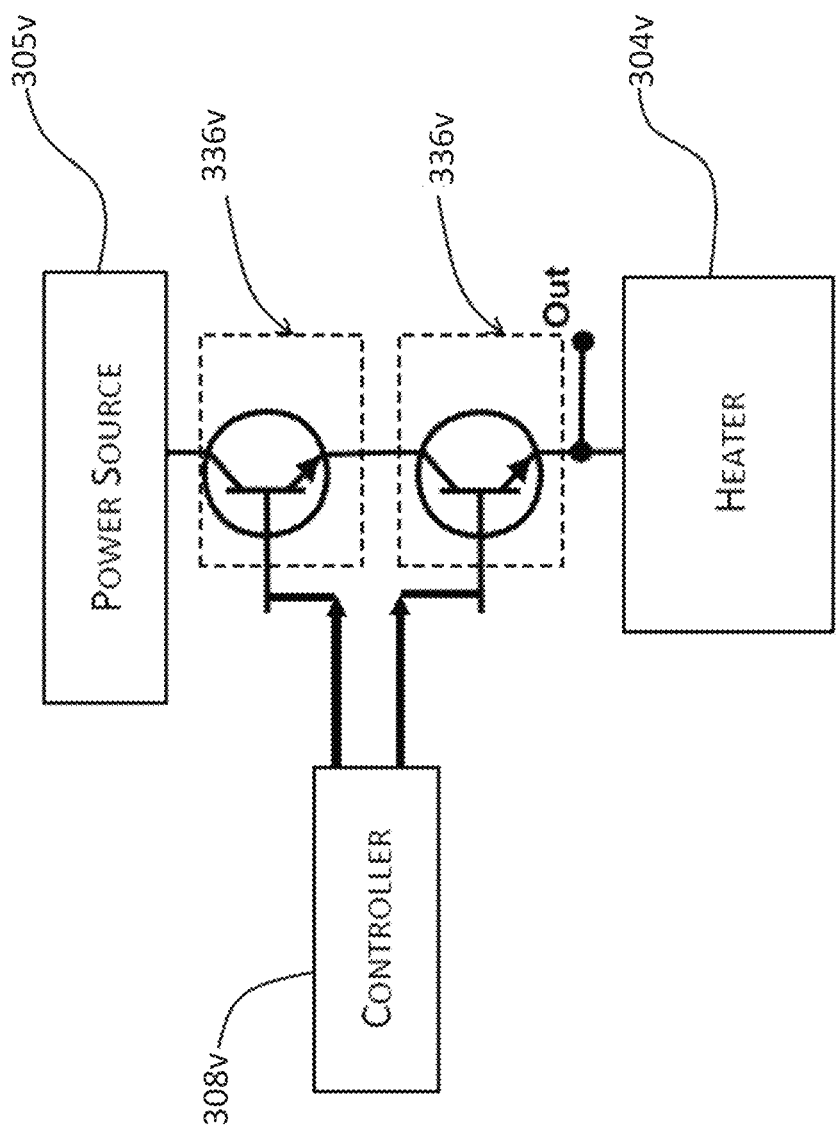

FIG. 73C is an exemplary circuit diagram of a transistor arrangement of the second embodiment of the twenty-first mode.

DETAILED DESCRIPTION OF THE FIGURES

First Mode: A Smoking Substitute Kit which Provides a Secondary Safety Feature

Aspects and embodiments of the first mode of the present disclosure will now be discussed with reference to the accompanying figures. Further aspects and embodiments of the first mode will be apparent to those skilled in the art. All documents mentioned in this text are incorporated herein by reference.

Figure 1B:
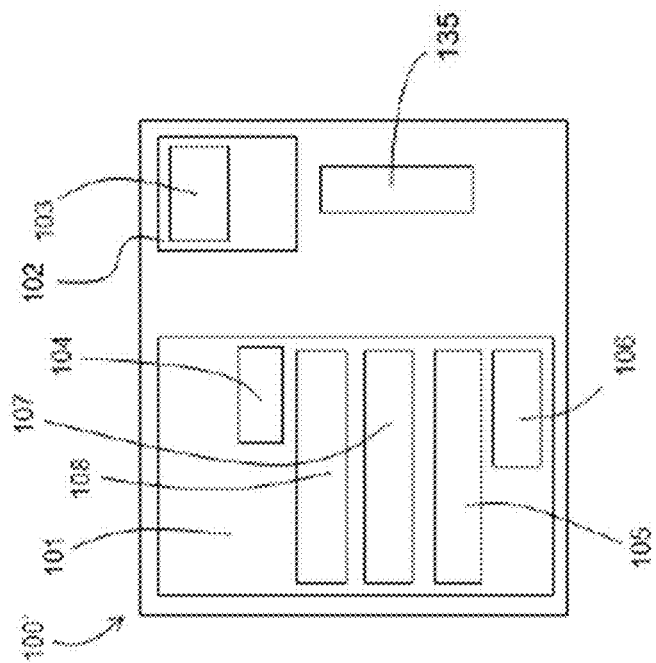
FIG. 1B is a schematic of a variation of the smoking substitute system of FIG. 1A.
Figure 1A:
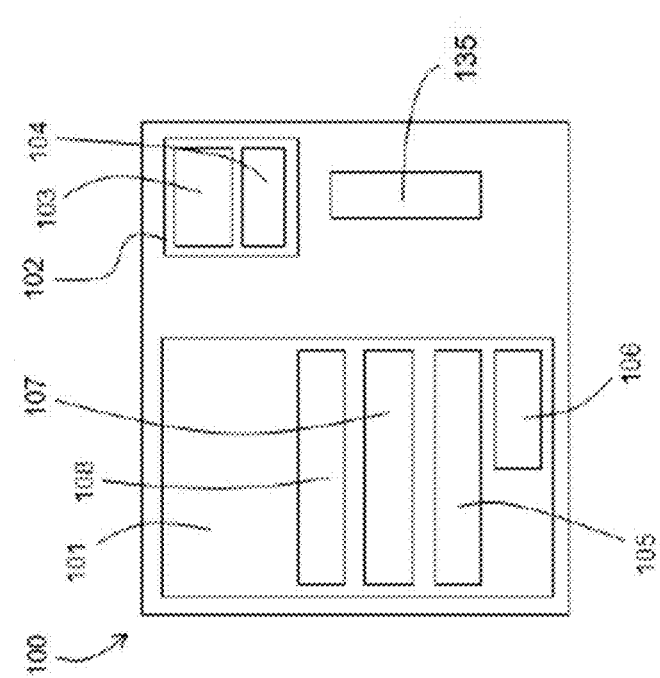
FIG. 1A is a schematic of a smoking substitute system of the first mode.

FIG. 1A is a schematic providing a general overview of a smoking substitute system 100. The system 100 includes a substitute smoking device 101 and an aerosol-forming article in the form of a consumable 102, which comprises an aerosol former 103. The system is configured to vaporize the aerosol former by heating the aerosol former 103 (so as to form a vapor/aerosol for inhalation by a user). The system 100 also includes a tool 135, configured to disengage one or more components of the device 101 from one or more other components of the device 101, and optionally also for performing a cleaning operation of the device 101.

In the illustrated system, the heater 104 forms part of the consumable 102 and is configured to heat the aerosol former 103. In this variation, the heater 104 is electrically connectable to the power source 105, for example, when the consumable 102 is engaged with the device 101. Heat from the heater 104 vaporizes the aerosol former 103 to produce a vapor. The vapor subsequently condenses to form an aerosol, which is ultimately inhaled by the user.

The system 100 further comprises a power source 105 that forms part of the device 101. In other embodiments the power source 105 may be external to (but connectable to) the device 101. The power source 105 is electrically connectable to the heater 104 such that it is able to supply power to the heater 104 (i.e., for the purpose of heating the aerosol former 103). Thus, control of the electrical connection of the power source 105 to the heater 104 provides control of the state of the heater 104. The power source 105 may be a power store, for example a battery or rechargeable battery (e.g., a lithium-ion battery).

The system 100 further comprises an I/O module comprising a connector 106 (e.g., in the form of a USB port, Micro USB port, USB-C port, etc.). The connector 106 is configured for connection to an external source of electrical power, e.g., a mains electrical supply outlet. The connector 106 may be used in substitution for the power source 105. That is the connector 106 may be electrically connectable to the heater 104 so as to supply electricity to the heater 104. In such embodiments, the device may not include a power source, and the power source of the system may instead comprise the connector 106 and an external source of electrical power (to which the connector 106 provides electrical connection).

In some embodiments, the connector 106 may be used to charge and recharge the power source 105 where the power source 105 includes a rechargeable battery.

The system 100 also comprises a user interface (UI) 107. Although not shown, the UI 107 may include input means to receive commands from a user. The input means of the UI 107 allows the user to control at least one aspect of the operation of the system 100. The input means may, for example, be in the form of a button, touchscreen, switch, microphone, etc.

The UI 107 also comprises output means to convey information to the user. The output means may, for example, comprise lights (e.g., LEDs), a display screen, speaker, vibration generator, etc.

The system 100 further comprises a controller 108 that is configured to control at least one function of the device 101. In the illustrated embodiment, the controller 108 is a component of the device 101, but in other embodiments may be separate from (but connectable to) the device 101. The controller 108 is configured to control the operation of the heater 104 and, for example, may be configured to control the voltage applied from the power source 105 to the heater 104. The controller 108 may be configured to toggle the supply of power to the heater 104 between an on state, in which the full output voltage of the power source 105 is applied to the heater 104, and an off state, in which the no voltage is applied to the heater 104.

Although not shown, the system 100 may also comprise a voltage regulator to regulate the output voltage from the power source 105 to form a regulated voltage. The regulated voltage may then be applied to the heater 104.

In addition to being connected to the heater 104, the controller 108 is operatively connected to the UI 107. Thus, the controller 108 may receive an input signal from the input means of the UI 107. Similarly, the controller 108 may transmit output signals to the UI 107. In response, the output means of the UI 107 may convey information, based on the output signals, to a user. The controller also comprises a memory 109, which is a non-volatile memory. The memory 109 includes instructions, which, when implemented, cause the controller to perform certain tasks or steps of a method.

FIG. 1B is a schematic showing a variation of the system 100 of FIG. 1A. In the system 100' of FIG. 1B, the heater 104 forms part of the device 101, rather than the consumable 102. In this variation, the heater 104 is electrically connected to the power source 105.

FIG. 2A and FIG. 2B illustrate a heated-tobacco (HT) smoking substitute system 200. The system 200 is an example of the systems 100, 100' described in relation to FIG. 1A or FIG. 1B. System 200 includes an HT device 201 and an HT consumable 202. The description of FIG. 1A and FIG. 1B above is applicable to the system 200 of FIG. 2A and FIG. 2B, and will thus not be repeated.

The device 201, the consumable 202 and the tool 235 are configured such that the consumable 202 and the tool (as shown in FIG. 5A) may be selectively engaged with the device 201. FIG. 2A shows the device 201 and the consumable 202 in an engaged state, whilst FIG. 2B shows the device 201 and the consumable 202 in a disengaged state.

The device 201 comprises a body 209 and cap 210. In use the cap 210 is engaged at an end of the body 209. Although not apparent from the figures, the cap 210 is moveable relative to the body 209. In particular, the cap 210 is slidable and can slide along a longitudinal axis of the body 209.

As shown in FIG. 7E, the body 209 defines a transverse cavity 227 extending orthogonal to the longitudinal axis of the body 209. The transverse cavity 227 opens through and extends from a first side wall of the body 209 towards and surrounding at least a portion of the heating element. The transverse cavity 227 is located on the body 209 such that at least a base 228 of the heating element is juxtaposed with the transverse cavity 227. The transverse cavity 227 extends from a first side wall of the body 209 to and through a second side wall opposite to the first side wall of the body 209. That is, the transverse cavity 227 forms a through hole extending through the body 209.

The device 201 comprises an output means (forming part of the UI of the device 201) in the form of a plurality of light-emitting diodes (LEDs) 211 arranged linearly along the longitudinal axis of the device 201 and on an outer surface of the body 209 of the device 201. A button 212 is also arranged on an outer surface of the body 209 of the device 201 and is axially spaced (i.e., along the longitudinal axis) from the plurality of LEDs 211.

Figure 2C:
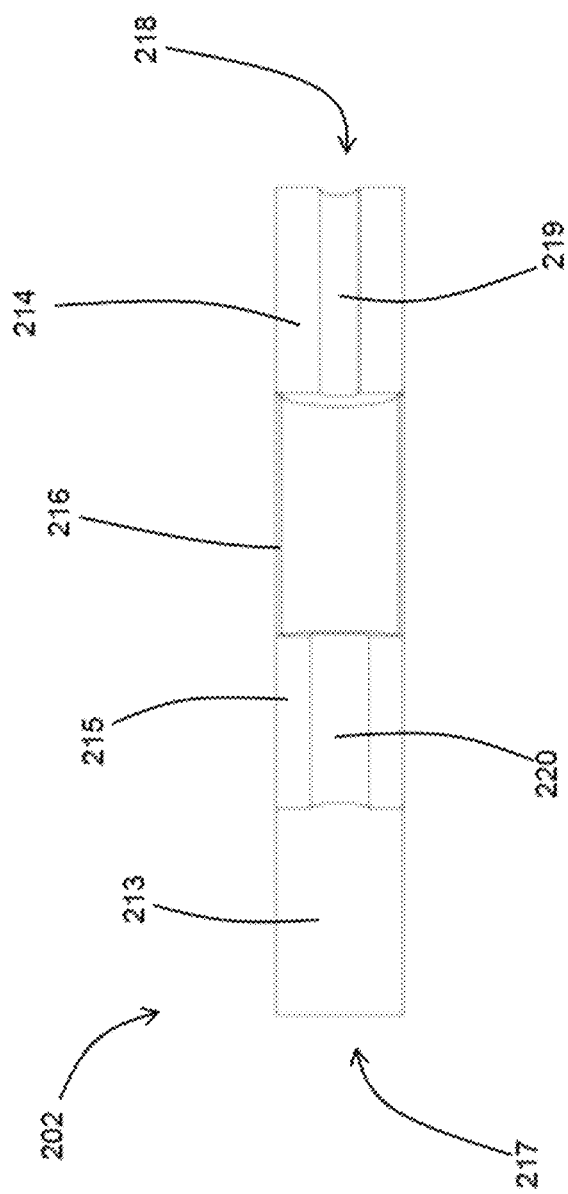
FIG. 2C is a section view of the embodiment of the consumable of the first embodiment of the first mode of the smoking substitute system.

FIG. 2C shows a detailed section view of the consumable of 202 of the system 200. The consumable 202 generally resembles a cigarette. In that respect, the consumable 202 has a generally cylindrical form with a diameter of 7 mm and an axial length of 70 mm. The consumable 202 comprises an aerosol forming substrate 213, a terminal filter element 215, an upstream filter element 215 and a spacer element 216. In other embodiments, the consumable may further comprise a cooling element. A cooling element may exchange heat with vapor that is formed by the aerosol-forming substrate 213 in order to cool the vapor so as to facilitate condensation of the vapor.

The aerosol-forming substrate 213 is substantially cylindrical and is located at an upstream end 217 of the consumable 202, and comprises the aerosol former of the system 200. In that respect, the aerosol forming substrate 213 is configured to be heated by the device 201 to release a vapor. The released vapor is subsequently entrained in an airflow flowing through the aerosol-forming substrate 213. The airflow is produced by the action of the user drawing on a downstream 218 (i.e., terminal or mouth end) of the consumable 202.

In the present embodiment, the aerosol forming substrate 213 comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213 may comprise a gathered sheet of homogenized (e.g., paper/slurry recon) tobacco or gathered shreds/strips formed from such a sheet.

In order to generate an aerosol, the aerosol forming substrate 213 comprises at least one volatile compound that is intended to be vaporized/aerosolized and that may provide the user with a recreational and/or medicinal effect when inhaled. The aerosol-forming substrate 213 may further comprise one or more additives. For example, such additives may be in the form of humectants (e.g., propylene glycol and/or vegetable glycerin), flavorants, fillers, aqueous/non-aqueous solvents and/or binders.

The terminal filter element 214 is also substantially cylindrical, and is located downstream of the aerosol forming substrate 213 at the downstream end 218 of the consumable 202. The terminal filter element 214 is in the form of a hollow bore filter element having a bore 219 (e.g., for airflow) formed therethrough. The diameter of the bore 219 is 2 mm. The terminal filter element 214 is formed of a porous (e.g., monoacetate) filter material. As set forth above, the downstream end 218 of the consumable 202 (i.e., where the terminal filter 214 is located) forms a mouthpiece portion of the consumable 202 upon which the user draws. Airflow is drawn from the upstream end 217, thorough the components of the consumable 202, and out of the downstream end 218. The airflow is driven by the user drawing on the downstream end 218 (i.e., the mouthpiece portion) of the consumable 202.

The upstream filter element 215 is located axially adjacent to the aerosol-forming substrate 213, between the aerosol-forming substrate 213 and the terminal filter element 214. Like the terminal filter 214, the upstream filter element 215 is in the form of a hollow bore filter element, such that it has a bore 220 extending axially therethrough. In this way, the upstream filter 215 may act as an airflow restrictor. The upstream filter element 215 is formed of a porous (e.g., monoacetate) filter material. The bore 220 of the upstream filter element 214 has a larger diameter (3 mm) than the terminal filter element 214.

The spacer 216 is in the form of a cardboard tube, which defines a cavity or chamber between the upstream filter element 215 and the terminal filter element 214. The spacer 216 acts to allow both cooling and mixing of the vapor/aerosol from the aerosol-forming substrate 213. The spacer has an external diameter of 7 mm and an axial length of 14 mm.

Although not apparent from the figure, the aerosol-forming substrate 213, upstream filter 215 and spacer 216 are circumscribed by a paper wrapping layer. The terminal filter 214 is circumscribed by a tipping layer that also circumscribes a portion of the paper wrapping layer (so as to connect the terminal filter 214 to the remaining components of the consumable 202). The upstream filter 215 and terminal filter 214 are circumscribed by further wrapping layers in the form of plug wraps.

Figure 2E:
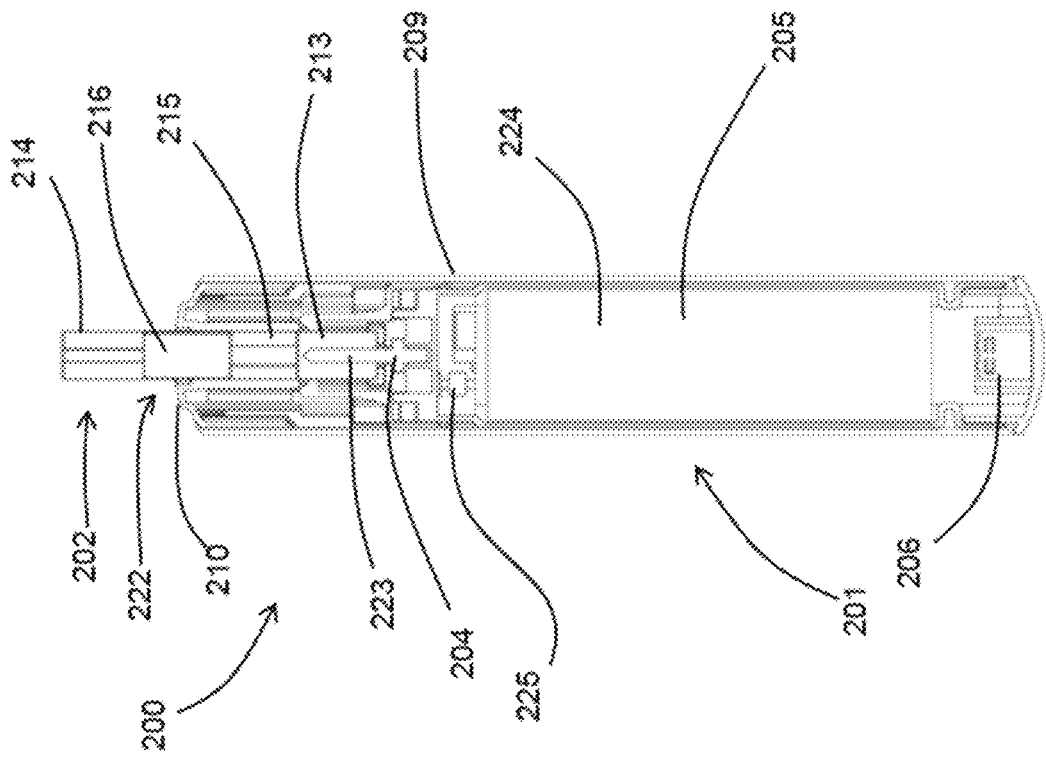
FIG. 2E is a section view of the embodiment of the first mode of the substitute smoking system.
Figure 2D:
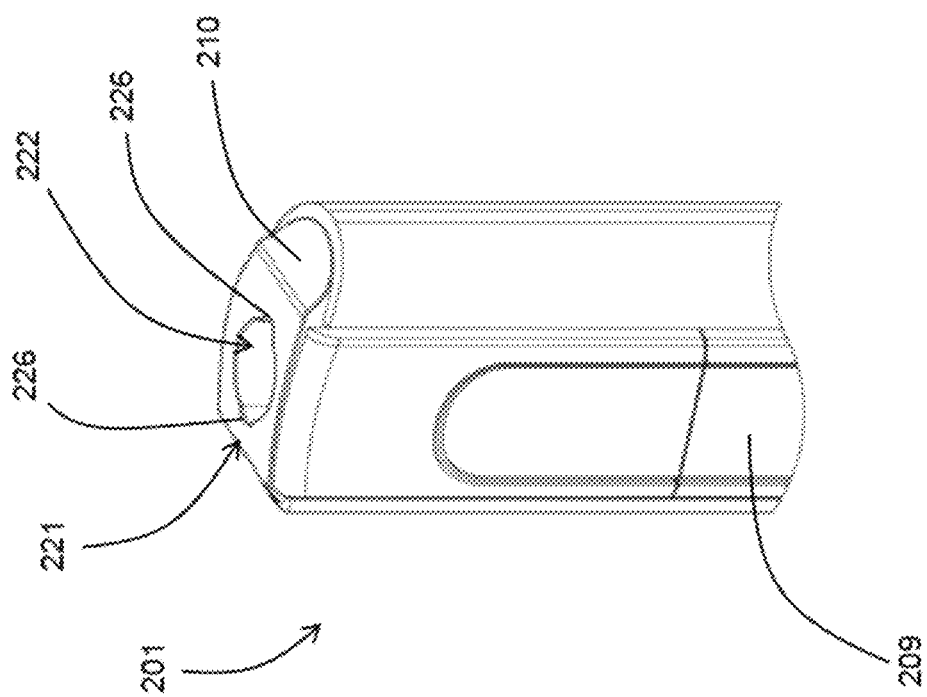
FIG. 2D is a detailed view of an end of the device of the embodiment of the first mode of the smoking substitute system.

Returning now to the device 201, FIG. 2D illustrates a detailed view of the end of the device 201 that is configured to engage with the consumable 202. The cap 210 of the device 201 includes an opening 221 to an internal cavity 222 (more apparent from FIG. 2D) defined by the cap 210. The opening 221 and the cavity 222 are formed so as to receive at least a portion of the consumable 202. During engagement of the consumable 202 with the device 201, a portion of the consumable 202 is received through the opening 221 and into the cavity 222. After engagement (see FIG. 2B), the downstream end 218 of the consumable 202 protrudes from the opening 221 and thus also protrudes from the device 201. The opening 221 includes laterally disposed notches 226. When a consumable 202 is received in the opening 221, these notches 226 remain open and could, for example, be used for retaining a cover in order to cover the end of the device 201.

FIG. 2E shows a cross section through a central longitudinal plane through the device 201. The device 201 is shown with the consumable 202 engaged therewith. Further, as illustrated, at least one locking arm 229 extends from the body 209. The locking arms 229 lock or retain the cap 210 with the body 209. In the embodiment as illustrated, two locking arms 229 are present. In an embodiment, any suitable number of locking arms 229 may be provided. The locking arms 229 extend substantially along the longitudinal axis of the body 209 as shown. The locking arms 229 are provided with a locking protrusion 231 at a distal end, i.e., an end distal from an end of the locking arm 229 that is connected to the body 209. The locking protrusion 231 extends transversely to the longitudinal axis of the body 209. The locking protrusion 231 extends transversely to the longitudinal axis of the corresponding locking arm 229. The locking arms 229 are positioned such that when the cap 210 is mounted on the body 209, the locking arms 229 engage the cap 210 to retain the cap 210 on the body 209.

In the embodiment as shown, the cap 210 may be provided with a slot 232 extending along the longitudinal axis of the body 209 (when the cap 210 is retained on the body 209), and the locking protrusions 231 may be configured or positioned to engage the slot 232. The slot 232 may be elongated such that the cap 210 may be moved or slid relative to the body 209 along the longitudinal axis of the body 209. The locking protrusion 231 may have an abutment surface 233 to engage a peripheral surface 234 of the cap 210 that defines the slot 232. The abutment surface 233 may block movement of the cap 210 in one direction by abutting the peripheral surface 234 to retain or lock the cap 210 with the body 209.

The cap 210 is movable between a first position and a second position. FIG. 2A, FIG. 2B, FIG. 2D and FIG. 4A illustrate the device 200 with the cap 210 in the first position. When the cap 210 is in the first position, the cap 210 conceals the heating element 223, as illustrated. In the first position, the cap 210 may completely cover the transverse cavity 227 to conceal the heating element 223.

FIG. 3 and FIG. 4B illustrate the device 200 with the cap 210 in the second position. When the cap 210 is in the second position, the cap 210 at least partially exposes the heating element 223. In the second position, the cap 210 at least partially uncovers the transverse cavity 227 to partially or completely expose the heating element 223. When the heating element 223 is exposed, the heating element 223 may be examined visually to ascertain if cleaning of the heating element 223 is required. If required, when the cap 210 is in the second position, the heating element 223 may be at least partly cleaned by blowing air through the opening or simply shaking, tilting and or tapping the device gently to dislodge and remove the debris. A cleaning tool may also be pushed into the transverse cavity 227 to clean the heating element 223. In the second position, the abutment surface 233 of the cap 210 may abut the peripheral surface 234 as discussed in the foregoing description.

The device 201 comprises a heater 204 comprising heating element 223. The heater 204 forms part of the body 209 of the device 201 and is rigidly mounted to the body 209. In the illustrated embodiment, the heater 204 is a rod heater with a heating element 223 having a circular transverse profile. In other embodiments the heater may be in the form of a blade heater (e.g., heating element with a rectangular transverse profile) or a tube heater (e.g., heating element with a tubular form).

The heating element 223 of the heater 204 projects from an internal base of the cavity 222 along a longitudinal axis towards the opening 221. As is apparent from the figure, the length (i.e., along the longitudinal axis) of the heating element is less than a depth of the cavity 222. In this way, the heating element 223 does not protrude from or extend beyond the opening 221.

When the consumable 202 is received in the cavity 222 (as is shown in FIG. 2E), the heating element 223 penetrates the aerosol-forming substrate 213 of the consumable 202. In particular, the heating element 223 extends for nearly the entire axial length of the aerosol-forming substrate 213 when inserted therein. Thus, when the heater 204 is activated, heat is transferred radially from an outer circumferential surface the heating element 223 to the aerosol-forming substrate 213.

The smoking substitute system of the present disclosure may further include a removal key (also referred to herein as a tool) 235 for separation of the cap 210 from the body 209. The removal key or tool 235 may be configured to displace the locking arms 229 to enable separation of the cap 210 from the body 209. FIG. 5A, FIG. 5B, and FIG. 5C illustrate a tool 235 in accordance with an embodiment. The tool 235 may comprise a cap removal portion 235a and a cleaning tool portion 235b. The cap removal tool portion 235a has at least one unlocking arm 230. In the embodiment as illustrated, two unlocking arms 230 are provided. The number of unlocking arms 230 may be provided as required and may correspond to the number of locking arms 229. In an embodiment, the number of unlocking arms 230 may correspond to the number of locking arms 229. The unlocking arms 230 are adapted to engage the locking arms 229 to displace the locking arms 229 for separating the cap 210 from the body 209. Each unlocking arm 230 may be provided with an unlocking projection 236. The unlocking projection 236 may extend in a direction transverse to the longitudinal axis of the unlocking arm 230. The unlocking projections 236 are adapted to engage the locking protrusions 231 to displace the locking protrusions 231 for releasing the cap 210 from the body 209.

The removal key 235 may include a central rod 237 extending from a connector 246. A collar 238 may be positioned concentrically on the central rod 237. The collar 238 may be placed movably on the rod such that the collar 238 moves relative to the central rod 237 along a longitudinal axis of the central rod 237. The connector 246 and the collar 238 form the main body of the tool. That is, as illustrated in FIG. 5B and FIG. 5C, the cleaning portion 241 and central rod 237 extend from either side of the connector 246, whilst the collar 238 is configured to engage with the cover 242, via the central rod. As shown in FIG. 5C, when a cover is engaged with the collar 238, it covers the cap removal portion and collar 238 abuts the connector 246, e.g., together the collar 238 and the connector 246 form the main body of the tool.

Figure 6B:
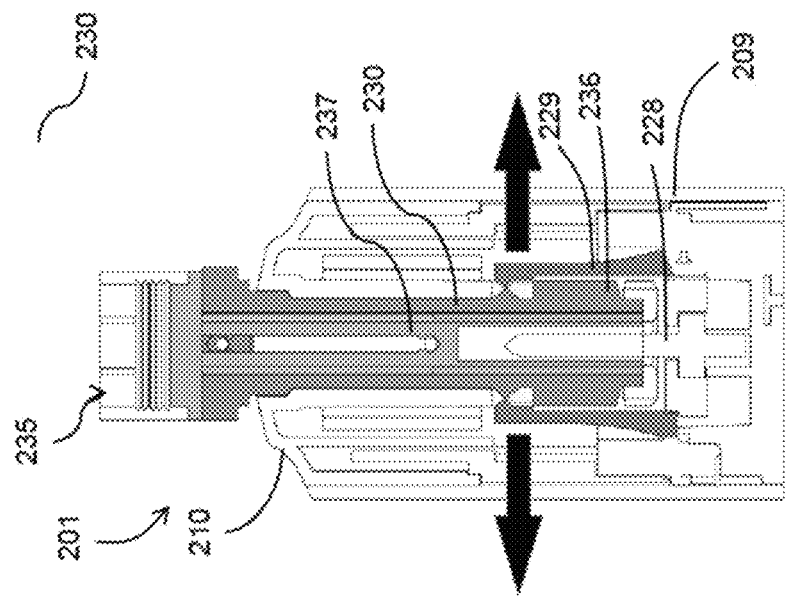
FIG. 6B illustrates a section view showing the removal key inserted in the cavity in unlocking position.
Figure 6A:
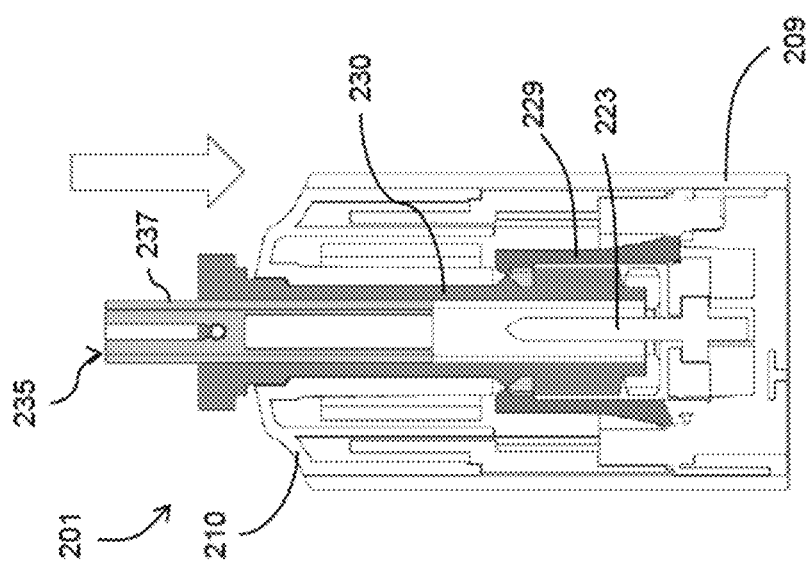
FIG. 6A illustrates a section view showing the removal key inserted in the cavity in insertion position.

The unlocking arms 230 may extend from the collar 238 along the longitudinal axis of the central rod 237. The collar 238 may be movable on the central rod 237 between an insertion portion and an unlocking position. In the insertion position, the central rod 237 may be kept away from the unlocking protrusions 236 and the unlocking arms 230 may flex radially inwards relative to the longitudinal axis of the central rod 237. In FIG. 58 and FIG. 6A, the collar 238 is shown in the insertion position. In the unlocking position, the central rod 237 moves in juxtaposition with the unlocking protrusions 236 to prevent flexing of the unlocking arms 230 in a direction radially inwards relative to the longitudinal axis of the central rod 237. FIG. 6B illustrates the collar 238 in the unlocking position. Suitable provision may be provided on the collar 238 and the rod to enable and/or guide movement of the collar 238 between the insertion position and the unlocking position. The collar 238 may be biased to move towards the insertion position using any suitable means such as a coil spring. The central rod 237 acts a separator of the unlocking arms 230. In some embodiments, the separator includes a heater cavity for receiving the heater 223 of the device 201 when the removal key 235 is engaged with the cavity 222.

The removal key or tool 235 may be configured for insertion into the cavity 222 as shown through FIGS. 7A-7E. The unlocking protrusions 236 are configured such that when the unlocking arms 230 are inserted into the cavity 222, the unlocking arm 230 displaces the locking arms 229 to release engagement of the locking arms 229 from the slots 232, and in particular to displace the locking protrusions 231 from the slots 232. In the embodiment as illustrated, the unlocking protrusions 236 are configured such that when inserted into the cavity 222, the unlocking protrusions 236 enter the slots 232 defined in the cap 210 to displace the locking protrusions 231, in order to dislodge and release the cap 210 from engagement with the body 209. The unlocking protrusions 236 may have dimensions that interfere with the width of the cavity 222. Thus, in order to allow insertion of the unlocking arms 230 in the cavity 222, in the insertion position, the central rod 237 is away from the distal ends of the unlocking arms 230 to allow the distal ends of the unlocking arms 230 to flex radially inwards to enable insertion of the unlocking arms 230 with the unlocking protrusions 236 into the cavity 222. The flexing may be achieved when the unlocking protrusions 236 abut and slide against an inner surface 239 of cap 210 defining the internal cavity 222. The unlocking protrusions 236, as shown in the embodiment illustrated, may be provided with tapered surfaces 240 to guide the flexing movement of the unlocking arms 230 in and out from the cavity 222 and the slots 232. FIG. 7A shows the removal key 235 being inserted in the cavity 222 with the collar 238 in the insertion position.

In the initial stage, the removal key 235 may be pushed towards the body 209 (as indicated by directional arrow in FIG. 6A) to insert the unlocking arms 230 into the cavity 222 until the collar 238 abuts the opening of the cavity 222 as shown in FIG. 6A and FIG. 7B. At this stage, as shown in FIG. 6A, the unlocking arms 230 enter the slots 232 defined in the cap 210. At this stage, the unlocking protrusions 236 may not completely displace the locking protrusions 231 as required for separation of the cap 210. Further, the central rod 237 may be pushed into the cavity 222 to move the collar 238 (relative to the central rod 237) to the unlocking position as shown in FIG. 6C. On pushing the central rod 237, the unlocking protrusion 236 may be pushed radially outward to enter the slots 232 properly and occupy the slot 232 as shown in FIG. 6B, to displace and move the locking protrusions 231 radially outward (shown by the arrows) to remove them from the slots 232. After this, the cap 210 along with removal key 235 may be pulled away from the body 209 to separate the cap 210 from the body 209 as shown in FIG. 7D. FIG. 7E illustrates cap 210 completely separated from the body 209.

The removal key or tool 235 may have a cleaning tool portion 235b as an additional feature for cleaning the heating element 223. The cleaning tool portion may have cleaning means in form of a brush or cleaning bristles 241 as shown in FIG. 5C. The cleaning bristles 241 may extend from the central rod 237 in a direction opposite to the direction of extension of the unlocking arms 230, as shown in FIG. 5C. The cleaning bristles 241 may be rubbed on the outer surface of the heating element 223 to clean or scrape off any debris or residuals from the heating element 223.

The removal key or tool 235 may include a first cover 242 to cover the cap removal portion 235a and thus also the unlocking arms 230 when not in use. Further, a second cover 243 may be provided to cover the cleaning tool portion 235b and thus also the cleaning bristles 241 when not in use. The covers 242, 243 may be designed such that the tool 235 may visually resemble a consumable for the smoking substitute system. Suitable provisions may be provided to retain the cover on the removal key or tool 235. The tool 235 is generally elongate and may have a generally circular transverse cross-sectional shape.

Figure 8B:
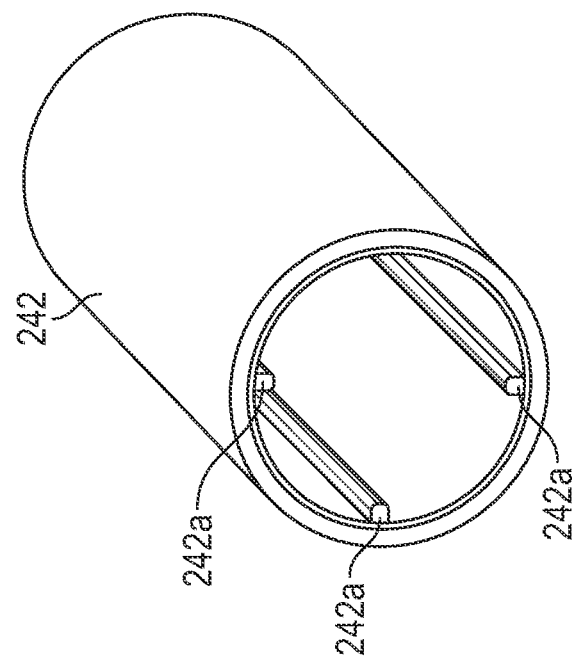
FIG. 8B illustrates perspective view of the cover shown in FIG. 8A.
Figure 8A:
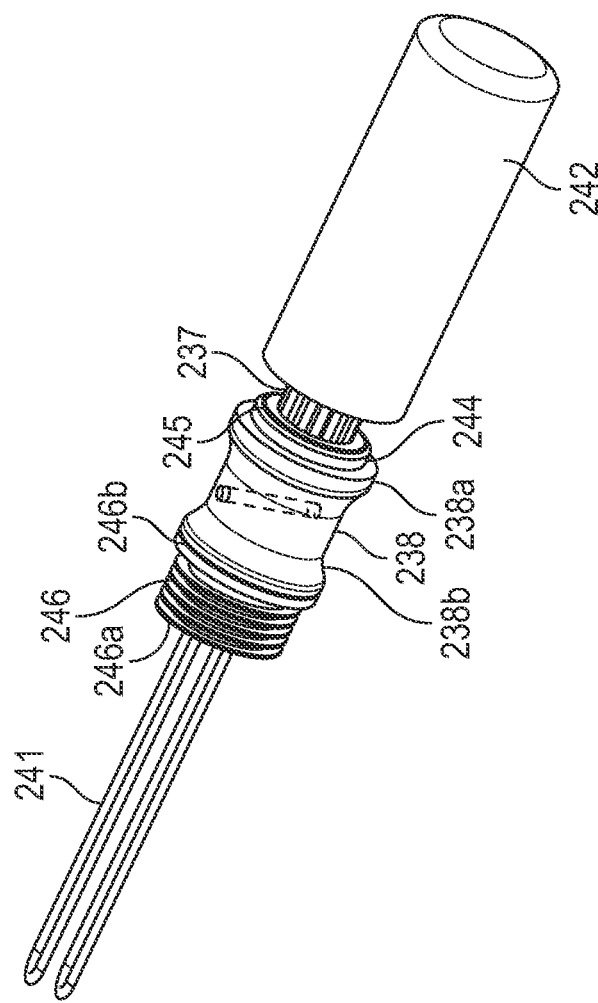
FIG. 8A illustrates a perspective view of an embodiment of the first mode of a tool with the cover partially covering the tool.

As shown in FIG. 8A, the tool 235 comprises two separable parts between which relative rotation should be prevented. The two separable parts may be the first cover 242 and the collar 238 of the main body. In an embodiment of the present disclosure the two separable parts have co-operating interacting features that, when engaged with one another, prevent relative rotation of the two parts. Further, the cooperating features may include a notch, depression or groove 245 formed on a flange portion 244 on the collar 238 and a protrusion 242a formed at an opening of a cavity of the cover 242. Alternatively, the flange portion 244 of the collar 238 may have a protrusion and the opening of the cavity of the cover 242 may include a notch, depression or groove. The notch 245 and the protrusion 242a interact to prevent the relative rotation. As shown, there is more than one notch-protrusion pairs provided between the collar 238 and the cover 242.

As shown in FIG. 8B, the first cover 242 has one or more protrusions 242a around its periphery. The protrusion 242a may be an elongated surface or channel extending parallel to the longitudinal axis of the central rod 237. The protrusion 242a extends longitudinally from the peripheral surface towards the other end (i.e., away from the peripheral surface). Further, as shown in FIG. 8A, the collar 238 comprises a front end 238a and a rear end 238b. The front end 238a is connected with a flange portion 244. The flange portion 244 has a circular cross section or but it may have a rectangular cross section or any other geometrical shape in other embodiments. The flange 244 comprises one or more notches 245 around its periphery which correspond with the protrusion 242a of the cover. The size of the notch 245 corresponds to the width of the protrusion 242a so that the protrusion 242a is secured in the depression 245 when the cover 242 is engaged with the collar 238 of the main body. The depression 245 and protrusion 242a may fit together through push or bump fit.

The bump fit or push fit may have a non-circular profile such as oval or hexagonal or trapezoidal or any other non-circular profile to prevent rotation between the cover 242 and collar 238. The flange 244 may also have a central hole over which the collar 238 moves along the longitudinal direction over the central rod 237 parallel to the longitudinal axis of the central rod 237. The collar 238 along with the flange 244 is positioned coaxially with the central rod 237 in such a manner that the collar 238 travels longitudinally along the axis of the central rod 237.

As shown in FIG. 8A, the cleaning tool portion comprises a connector 246 and the elongated member or brush 241. The connector 246 has a first end 246a and a second end 246b. The rear end 238b of the collar 238 abuts or touches with the first end 246a of a connector 244 and the brush 241 is extended from the second end 246b of the connector 246. In an embodiment of the present disclosure, threads are formed in between the first end 246a of the connector 246 the second end 246b of the connector. The second cover 243 has threads on its periphery and henceforth the second cover 243 is screw threaded with the threads of the connector 244 and thus and covers the cleaning tool portion. In an embodiment of the present disclosure, the brush 241 is formed by a pair of elongated members with circular ends at the tip thereby connecting the members. The elongated bars enable the cleaning of the heater surface and removes all the debris and other foreign particles.

As noted above, the removal key or tool 235 has a collar 238. The collar is placed in between the cap removal portion 235a and the cleaning tool portion 235b. The collar 238 may include the visual indicator for alignment (for example, a dot or marking on the collar). As illustrated in FIG. 5D and FIG. 5E which illustrate an alternative configuration of the tool 235, the collar 238 may have two ends, i.e., a first end 238a and a second end 238b. At the first position i.e., the position at which the tool 235 is not in use (as shown in FIG. 5D), the first end 238a of the collar touches the cover 243 of the cleaning tool portion and the second end 238b of the collar abuts with the cover 242 of the cap removal tool portion 235a.

The length of the collar 238 is defined as the measurement of the ends which is measured orthogonally to a longitudinal axis of a central rod 237. In an embodiment of the present disclosure, the collar has a length of at least 3 mm. In an alternate embodiment of the present disclosure the collar has a length more than 5 mm and more preferably more than 10 mm. The width of the collar is defined as the measurement of the ends which is measured parallelly to the longitudinal axis of the central rod 237. The collar may also have a periphery 238c which connects the first end and of the collar with the second end of the collar having a concave or a convex shape. The concave shape is the shape where the width of the collar 238 is wider than the width of the cleaning portion 235b, or the cover 243 of the cleaning portion. The concave shape is also the shape where the width of the collar 238 is wider than width of the cap removal portion 235b, or the cover 242 of the cap removal portion. The convex is the shape where the width of the collar 238 is narrower than the width of the cleaning portion, or the cover of the cleaning portion. The convex shape is also the shape where the width of the collar is narrower than the cap removal portion, or the cover of the cap removal portion. The concave or convex shape of the periphery 238c allows the user to sufficiently grip the tool when pulling both parts of the tool apart such that the tool can transform into its second position. At the second position, the cover of the cap removal tool is removed, and the collar moves longitudinally away from the cleaning tool portion. The longitudinal movement of the collar relative to the cap removal end of the tool activates the cap removal mechanism.

The cap removal end of the tool may be the end of the cleaning tool portion. The collar may form a handle portion of the tool 235.

The device 201 further comprises an electronics cavity 224. A power source, in the form of a rechargeable battery 205 (a lithium-ion battery), is located in electronics cavity 224.

The device 201 includes a connector (i.e., forming part of an IO module of the device 201) in the form of a USB port 206. The connector may alternatively be, for example, a micro-USB port or a USB-C port for examples. The USB port 206 may be used to recharge the rechargeable battery 205.

The device 201 includes a controller (not shown) located in the electronics cavity 224. The controller comprises a microcontroller mounted on a printed circuit board (PCB). The USB port 206 is also connected to the controller 208 (i.e., connected to the PCB and microcontroller).

The controller 208 is configured to control at least one function of the device 201. For example, the controller 208 is configured to control the operation of the heater 204. Such control of the operation of the heater 204 may be accomplished by the controller toggling the electrical connection of the rechargeable battery 205 to the heater 204. For example, the controller 208 is configured to control the heater 204 in response to a user depressing the button 212. Depressing the button 212 may cause the controller to allow a voltage (from the rechargeable battery 205) to be applied to the heater 204 (so as to cause the heating element 223 to be heated).

The controller is also configured to control the LEDs 211 in response to (e.g., a detected) a condition of the device 201 or the consumable 202. For example, the controller may control the LEDs to indicate whether the device 201 is in an on state or an off state (e.g., one or more of the LEDs may be illuminated by the controller when the device is in an on state).

The device 201 comprises a further input means (i.e., in addition to the button 212) in the form of a puff sensor 225. The puff sensor 225 is configured to detect a user drawing (i.e., inhaling) at the downstream end 218 of the consumable 202. The puff sensor 225 may, for example, be in the form of a pressure sensor, flowmeter or a microphone. The puff sensor 225 is operatively connected to the controller 208 in the electronics cavity 224, such that a signal from the puff sensor 225, indicative of a puff state (i.e., drawing or not drawing), forms an input to the controller 208 (and can thus be responded to by the controller 208).

Further aspects of the present disclosure will now be described with reference to FIG. 9 to FIG. 14.

Figure 9B:
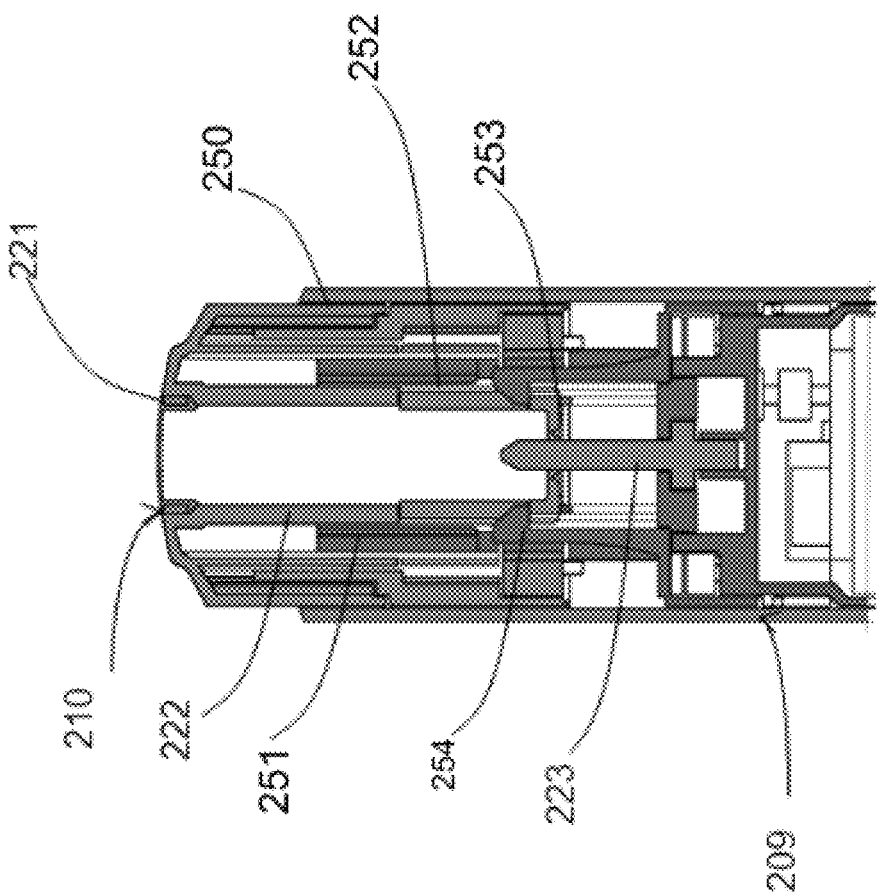
FIG. 9B is a sectional view of the cap and a portion of the main body of the device of FIG. 9A with the cap in a partially disengaged position.
Figure 9A:
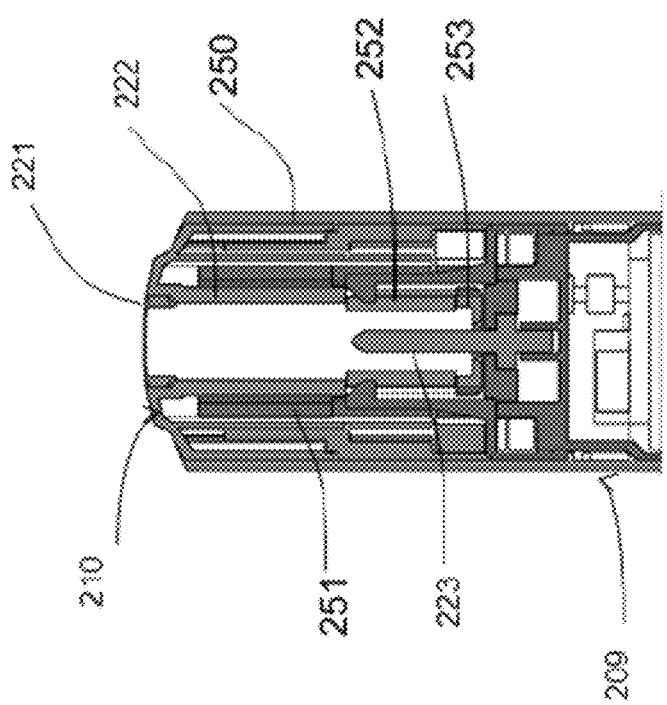
FIG. 9A is a sectional view of the cap and a portion of the main body of the device, of an embodiment of the first mode of the smoking substitute system.

FIG. 9A and FIG. 9B correspond generally to FIG. 4A and FIG. 4B and show cross sections through a central longitudinal plane of the device 201, without having the consumable 202 engaged with the cap 210. Further, FIG. 9A shows that the cap 210 is engaged to the body 209, while FIG. 9B shows that the cap 210 is partially disengaged (e.g., can be slidable along a longitudinal axis of the cap 210, but can still be engaged with the body 209, and shifted) from the body 209.

The body 209 of the device 201 includes a plurality of guideways. A plurality of first guideways 250 can be defined on an inner circumference of the body 209, at the body 209 and the cap 210 interface.

The plurality of first guideways 250 are configured to receive the cap 210 and allow downward movement of the cap 210, so as to accommodate the cap 210 or a portion of the cap 210 in the body 209. Further, a plurality of second guideways 251 are also defined in the body 209, about the heater 204. The plurality of second guideways 251 are configured to receive the cap 210 such that the cavity defined by the cap 210 is circumscribed by the plurality of second guideways 229, during engagement of the cap 210 with the body 209. The cavity 222 of the cap 210 can be configured to traverse on the plurality of second guideways 251 to circumscribe the heating element 223 of the heater 204, upon engagement of the cap 210 with the body 209.

In the illustrated embodiment, the cavity 222 or a portion of the cavity 222 may be defined with a through opening or slit 252 (e.g., a portion of wall defining the cavity 222 is provided with a through opening). The slit 252 in the cavity 222 may be configured to circumscribe or partially circumscribe the heating element 223, upon engagement of the cap 210 with the body. The cavity 222 may further include the rigid base region 253, defined downstream of the slit 230. The rigid base region 253 may be configured to seat around a portion of the heating element 223, which is extending from the body of the device 201.

The body further comprises at least one flexure bearing 254, each of which may take the form of a moveable or flexible hinge. In an illustrative embodiment, the at least one flexure bearing 254 of the device 201 comprises two moveable hinges in the form of living hinges (as e.g., two living hinges facing each other are shown in FIG. 9A and FIG. 9B). The at least one flexure bearing 254 may be located proximal to the heating element 223, and can be defined downstream of the plurality of second guideways 251 defined in the body. The at least one flexure bearing 254 may be configured to extend along the length of the heating element 223. The at least one flexure bearing 254 may be adapted to engage with an external surface of the cavity 222, when the cap 210 may be received by the body 209.

As apparent from FIG. 9A, each of the at least one flexure bearing 254 (i.e., moveable hinge) is fixedly connected to the body 209 of the device 201, and includes a locking element or hook 255 at a distal end. The hook 255 may extend laterally from the end of each of the at least one flexure bearing 254, and may be defined in a wedge shape. The hook 255 of the at least one flexure bearing 254 is configured to ride along the cavity 222 of the cap 210 (that is, on the walls defining the cavity 222 of the cap 210), until the hook 255 is adapted to engage with the slit 252 defined on the at least one side of the cavity 222 of the cap 210. Portion of the cavity 222 defining the slit 252 may be adapted to accommodate (or receive) the hook 255 of the at least one flexure bearing 254, upon engagement of the cap and the body. The hook 255 of the at least one flexure bearing 254 is adapted to be displaceable (that is, e.g., an inward and outward movement with regard to e.g., the heater element 223) in the slit 252 of the cavity 222, with respect to the heating element 223 of the heater 204. In this way, the consumable 202 when inserted into the cavity 222 of the cap 210 may be held in engagement with the heater element 223. The locking elements may in particularly not protrude into the cavity, so to not provide any obstacle for a consumable.

During lifting of the cap 210 (e.g., upward movement of the cap 210 or pull force applied on the cap 210 along a longitudinal axis of the device 201) for disengaging the cap 210 from the body 209, the hook 255 of the at least one flexure bearing 254 is configured to restrain disengagement (i.e., stopping further movement of the cap in a longitudinal direction) of the cap 210, as apparent from FIG. 9B. The hook 255 of the at least one flexure bearing 254 is configured to engage with the rigid base region 253 of the cavity 222 defined in the cap 210. Thus, the cap 210 may be partially disengaged (that is, the cap can still be engaged with the body, but shifted or lifted) from the body 209, in response to operation of the at least one flexure bearing 254 in the body, during lifting of the cap 210. That is, the cap 210 may be allowed to be lifted to a height (e.g., distance along longitudinal axis of the device 201) defined by the length of the at least one flexure bearing 254 and position of the hook 255 on the at least one flexure bearing 254 in the body 209. However, the cap 210 is restrained from completely disengaging (e.g., being removed or dislodged) from the body 209 of the device 201. The height and thickness of the rigid base region 253 may be considered as a restricting factor for disengagement of the cap 210 and the body 209. In respect to this, a portion of the heating element 223 or the heater 204 may be exposed, upon lifting (or shifting) the cap 210 with respect to the body. In order for complete access (e.g., exposure) to the heater or the heating element 223 in the device 201, there may be a requirement of disengagement of the cap 210 completely from the body 209.

Figure 10B:
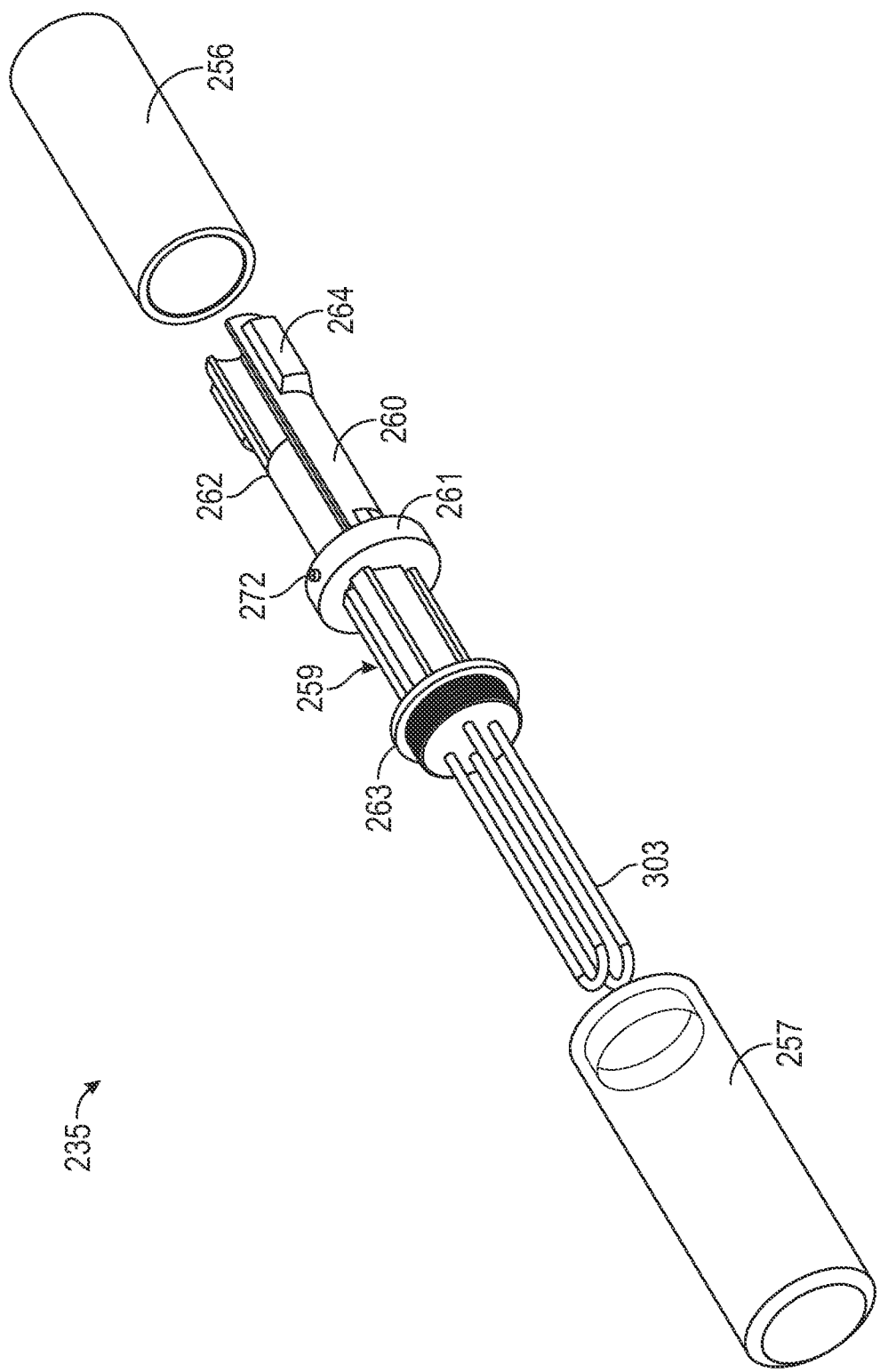
FIG. 10B is an exploded view of the tool of the smoking substitute system of the first mode.

The tool 235 is illustrated in FIG. 10A, and is configured for disengaging the cap 210 and the body of the device 201. The tool 235 is an example of the tool 135 defined in the first embodiment of the system 100, as illustrated in FIG. 1A or the removal key described hereinbefore. The tool 235 comprises cap removal portion 301 and a cleaning portion 302, for disengaging the cap 210 and the body 209 of the device 201 and for cleaning the device 201 (i.e., the heating element 223). The cap removal portion 301 and the cleaning portion 302 may be separated by a base element 263. The cap removal portion 301 and the cleaning portion 302 may be configured to extend on either side of the base element 263. Further, the cap removal portion 301 and the cleaning portion 302 may extend in a substantially opposite direction to each other. The cap removal portion 301 may be enclosed by a first enclosure 256 and the cleaning portion 302 may be enclosed by a second enclosure 257 respectively. The first enclosure 256 and the second enclosure 257 may be engaged with the tool 235 by at least one of threaded connection, snap fitted connection and an interference fit connection. As apparent from FIG. 10B, the first enclosure 256 is operated (i.e., removed) to access the cap removal portion 301 of the tool 235 for disengaging the cap 210 and the body of the device 201, while the second enclosure 257 enclosing the cleaning portion 302 is held as a grip portion (e.g., for gripping with fingers of the user) for the user to grip and operate the tool 235. That is, the first enclosure 256, may be adapted as gripping unit, while operating the cleaning portion 302 and the second enclosure 257 may be adapted as gripping unit, while operating the cap removal portion 301. In alternative arrangements, the second enclosure 257 can instead be configured to be accessible for encompassing components for functions such as a storage compartment, a spray unit (e.g., dispensing mouth refresher) and the like.

The tool 235, at the first enclosure 256, is configured to encompass a rigid member 258 (also referred to herein as a static member) and a movable member 259. Each of the rigid member 258 and the movable member 259 are configured to extend in a direction opposite to the second enclosure 257 (e.g., along the longitudinal axis of the tool 235 and in a direction to be accommodated within the first enclosure 256).

As apparent in FIG. 10D, the first enclosure 256 may be engaged with the collar portion 261 of the rigid member 258, by snap fit connection, to enclose the cap removal portion 301. The second enclosure 257, may engaged to the base element 263 by a threaded connection, to enclose the cleaning portion 302 of the tool 235.

The rigid member 258 includes a plurality of flexible engaging arms 260. In an illustrative embodiment, the rigid member 255 is defined with a collar 261, where the plurality of flexible engaging arms 260 is adapted to extend from the collar 261. The movable member 259 and the rigid member 258 are co-axial such that, the movable member 259 or a portion of the movable member 259 is radially housed (e.g., about the perimeter) by the collar 261. The collar 261 may be configured to separate the first enclosure 256 from the second enclosure 257. On the other hand, the movable member 259 is fixed (e.g., fastened, adhesive bonded, snap fitted, and the like) to the second enclosure 257. The collar 261 and the movable member 259 can be relatively moved with respect to each other (e.g., the movable member 259 can move with respect to position of the collar 261, or vice versa).

In the illustrated embodiment, the movable member 259 includes a plunger 262 (e.g., acting as a body segment having a profile such as, but not limited to, cylindrical, cuboidal, rod-like, etc.), where a portion of the plunger 262 is fixed to the base element 263 of the second enclosure 257 and is configured to extend from the base element 257. The movable member 259 is co-axially slidable within the collar 261 of the rigid member 258, between a first position (e.g., the collar 261 being distal from the second enclosure 257) and a second position (e.g., the collar 261 being proximal to the second enclosure 257), through displacement of the second enclosure 257 about the collar 261. That is, the movable member 259 may be linearly retracted to the first position and slid forward to the second position relative to position of the collar 261 by selective operation of the second enclosure 257.

As apparent in FIG. 10C, the plunger 262 of the movable member 259 is configured with a sliding path 270 (e.g., a groove inscribed on an outer circumference of the plunger 262). The sliding path 270 may be defined with one or more slots 271 (as seen in FIG. 11), preferably at distal ends of the sliding path 270.

The rigid member 258 is configured to accommodate an element 272 (e.g., the element may be a pin having a profile such as cylindrical, rod like, etc.). The element 272 may extend from the collar 261 of the rigid member 258 into a sliding path 270 coaxially defined on the plunger 262 of the movable member 259 along the longitudinal axis. The element 272 may facilitate in visually indicating an orientation of the tool 235, relative to the device 201. This visual indication, may facilitate in precise positioning/engaging of the tool 235 with the device 201. The element 272 may be guided within the sliding path 270 and may be configured to occupy the one or more slots 271 in the sliding path 270, to lock the movable member 259 selectively in the first position and the second position. The element 272 may be optionally provided with a resilient member (not shown), to enable the element 272 to effectively occupy the one or more slots 271 defined in the sliding path 270.

As also apparent in FIG. 10C, the plunger 262 of the movable member 259 may be configured with a smooth outer surface, which may facilitate easy sliding of the plunger 262 within the collar 261 of the rigid member 258. The plunger 262 may be defined with a recess 269, which may extend from an end of the plunger 262 (i.e., the recess 269 extends within an inner solid structure of the plunger 262). As an example, the recess 269 may have a profile such as cylindrical, cuboidal and the like. However, the profile may be configured to, preferably, match with the profile of the heating element of the heater. The plunger 262 and the recess 269 defined within the plunger 262 may be configured to remove, e.g., scrape off, debris in the device 201, simultaneously while facilitating disengaging the cap 210 and the body 209 of the device 201.

The plurality of flexible engaging arms 260 may be configured to relatively extend with respect to an axial axis of the collar 261, and in-turn to that of the tool 235. The plurality of flexible engaging arms 260 can extend either substantially straight (that is, parallelly or axially extended) from the collar 261, or can be angularly extended with respect to the axial axis of the collar 261. As apparent from FIG. 10C, each of the plurality of flexible engaging arms 260 are angularly extended with respect to the axial axis of the tool 235 and are configured to incline towards the axial axis of the tool 235 (e.g., bend inwards or towards center). The plurality of flexible engaging arms 260 is operable from a first condition (e.g., at angularly inclined towards the axial axis of the tool 235) to a second condition (e.g., at axially extended to be parallel to the axial axis of the tool 235).

As apparent in FIG. 10D, the cleaning portion 302 of the tool comprises one or more cleaning elements 303, which extend from an end of the base element 263. The one or more cleaning elements 303 may be joined to the base element 263 (e.g., by adhesives for plastic or fiber cleaning elements and by welding or brazing for metal cleaning elements). The one or more cleaning elements 303 may be at least one of brushes or bristles. The one or more cleaning elements 303, may facilitate in cleaning the heating element 223 of the heater 204 (i.e., the cleaning elements 303 may facilitate in cleaning the aerosol forming article substrate and other debris adhering to the heating element 223). Cleaning of the heating element 223 facilitates in effective heat dissipation by the heating element 223 and, thus improving efficiency of the device 201.

The tool 235 is insertable into the cap 210 of the device 201, as apparent from FIG. 11. The insertion of the tool 235 can be performed through the opening 221 defined in the cap 210. The tool 235 may be insertable into the cap 210 upon removal (e.g., dislodging, ejecting, disposing and the like) of the consumable or a portion of the consumable that may be residing in the cavity 222. In the illustration of FIG. 11, the tool 235 is positioned such that, the plurality of flexible engaging arms 260 are configured to engage with the opening 221 in the cap 210 (e.g., in a position where the second enclosure 257 of the tool 235 is gripped by the user and coaxially positioned with the opening 221 defined in the cap 210). The plurality of flexible engaging arms 260 may slide into the cavity 222 through the opening 221 in the cap 210. At this instance, the movable member 259 is drawn to the first position (that is, away from the cap 210) so that, the plurality of flexible engaging arms 260 are introduced into the cavity in the first condition.

During engagement of the tool 235 with the device 201, the element 272 disposed in the rigid member 258, facilitates the user to visualize the orientation of the tool 235 relative to the device 201. The position of the element 272 in the tool 235, determines the orientation of the tool 235 for precisely securing the flexible arms 260 of the tool 235 within the cavity 222 of the cap 210, to disengage the cap 210 and the body 209. For the instance, the position of the element 272 aligning with a front face or a back face of the device 201, corresponds to correct orientation of the tool 235 relative to the device 201, which may facilitate in precisely securing the flexible engaging arms 260 (thus, the tool 235) with the cavity 222 of the cap 210. At this instance, the movable member 259 is drawn to the first position from the second position (i.e., if the movable member 259 is at the second position). During displacement of the movable member 259 to the first position (that is, away from the cap 210), the element 272 disengages from the slot 271 corresponding to the second position, and traverses within the slidable path 270 of the movable member 259. Then, the element 272 may engage with the slot 271 corresponding to the first position and hence, locks the movable member 259 in the first position, so that, the plurality of flexible engaging arms 260 are introduced into the cavity 222 in the first condition.

Figure 12B:
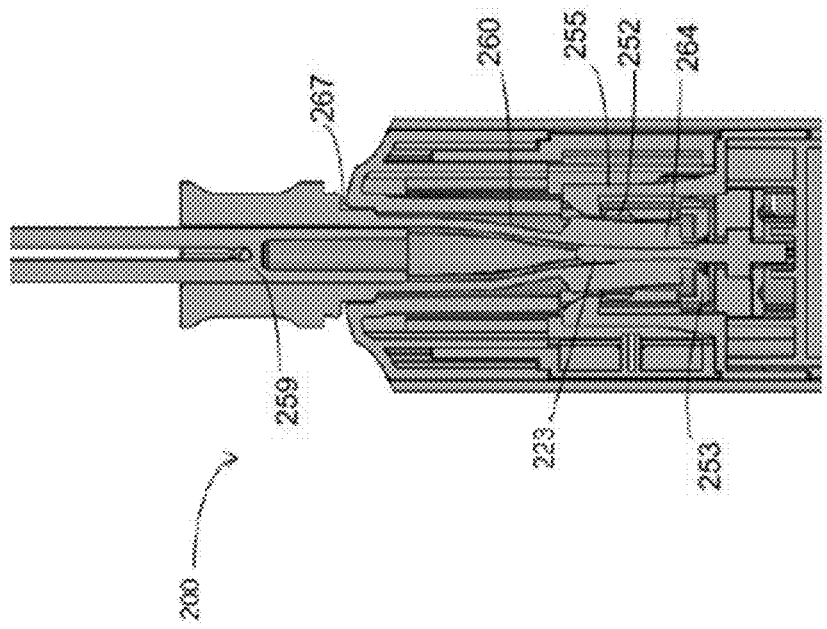
FIG. 12B is a sectional view of portion of FIG. 12A.
Figure 12A:
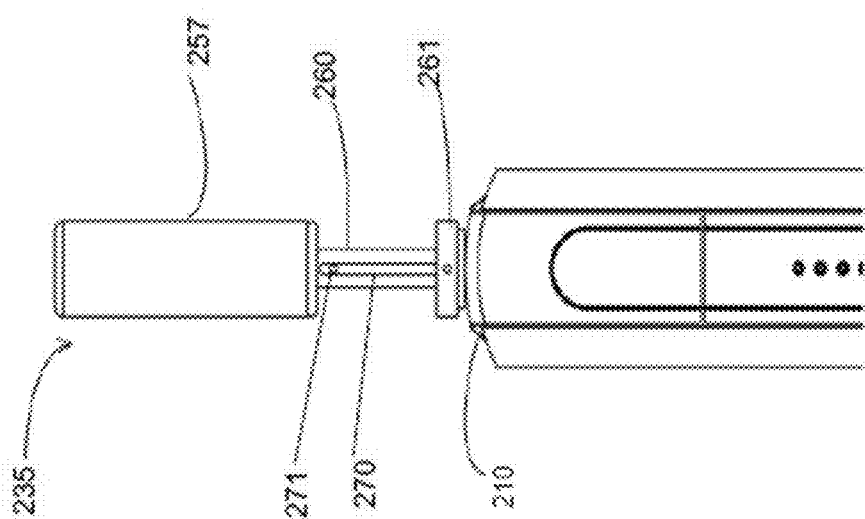
FIG. 12A is a front view of the cap and the main body of the device of the first mode, with the tool inserted into the cap.

The plurality of flexible engaging arms 260 are configured to slide inside the cavity 222, through the opening 221 in the cap 210, until the collar 261 abuts a top surface of the cap 210, as apparent from FIG. 12A. The collar 261 can be defined to exceed an outer diameter of the opening 221 of the cap 210, whereby the collar 261 is configured to restrict further movement of the tool 235 into the cap 210. Moreover, the plurality of flexible engaging arms 260 are configured such that, upon abutment of the collar 261 with the top surface of the cap 210, each of the plurality of engaging arms 260 is configured to engage with the rigid base region 253 of the cavity 222.

In some arrangements it is proposed that an end of the at least one flexible engaging arm of the plurality of flexible engaging arms 260 is configured to engage at least a portion of circumference of the cavity 222. During engagement with the cavity 222, the end of the at least one flexible engaging arm of the plurality of flexible engaging arms 260 may be configured to scrape debris deposited in the cavity 222 (e.g., a portion of an inner wall or walls of the cavity 222). Moreover, the plurality of flexible engaging arms 260 may be configured such that, upon abutment of the collar 261 with the top surface of the cap 210, the end of each of the plurality of engaging arms 260 defines a clearance with the rigid base region 253 of the cavity 222. The clearance between the end of each of the plurality of flexible engaging arms 260 and the rigid base region 253 of the cavity may assist in accommodating debris, scraped from the cavity 222. This clearance between each of the plurality of flexible engaging arms 260 and the rigid base region 253 may avoid impaction of the debris into other components of the cap and the device 201. The clearance between each of the plurality of flexible engaging arms 260 and the rigid base region 253 may be about 0.5 mm to about 1.5 mm. Preferably, the clearance may be 1 mm. However, the clearance may be varied based on requirement of degree of contact between the plurality of flexible engaging arms 260 and the cavity 222. In some embodiments, the clearance may be varied in accordance with the profile of each of the plurality of flexible engaging arms 260.

Each of the plurality of flexible engaging arms 260 may include a protruding tab 264, where the protruding tab 264 is configured to extend outwardly from an external surface of a respective flexible engaging arm of the plurality of flexible engaging arms 260. The protruding tab 264 is positioned away from the collar 261 in each of the plurality of flexible engaging arms 260. That is, the protruding tab 264 of each of the plurality of flexible engaging arms 260 is configured to be inserted into the cavity 222 before the collar 261 is abutted to the top surface of the cap 210. The plurality of flexible engaging arms 260 is configured to extend in the first condition, while the movable member 259 is operated to the first position, as can be seen in FIG. 12B.

In the present embodiment, at least one flexible engaging arm of the plurality of flexible engaging arms 260 is provided with a locating tab 267. The locating tab 267 may extend laterally (i.e., in a direction perpendicular to the longitudinal axis of the tool 235) from an external surface of at least one flexible engaging arm of the plurality of flexible engaging arms 260. The locating tab 267 may longitudinally extend (e.g., in the direction of longitudinal axis of the tool 235) from the collar 261 along at least one flexible engaging arm of the plurality of flexible engaging arms 260, till a defined length. The defined length of the locating tab 267 may be equal to depth of the notches 226, which are laterally disposed on the opening 221 (e.g., on a portion of circumference of the opening 221) in the cap 210. In an embodiment, the locating tab 267 may extend from the collar 261 or a narrow gap may be defined between the collar 261 and the locating tab 267. The locating tab 267 may be receivable by at least one notch of the notches 226 in the cap 210, in at least one defined orientation. The at least one defined orientation may define alignment of the tool 235 with respect to the device 201, for insertion of the tool 235 into the cap 210, to disengage the cap 210 and the body 209 of the device 201.

The tool 235 may be oriented to align the locating tab 267 with at least one notch of the notches 226 in the cap 210. The locating tab 267 may also be profiled to match with profile of at least one notch of the notches 226, for the tool 235 to be insertable into in the opening 221 of the cap 210. Further, the locating tab 267 may be configured to restrict abutment of the collar 261 with the top surface of the cap 210 if there is any deviation in orientation of the locating tab 267 with at least one corresponding notch of the notches 226 in the cap 210.

Upon orientation of the tool 235 and alignment of the locating tab 267 with the at least one notch of the notches 226 in the cap 210, a portion of the tool 235 may be inserted into the cavity 222 and may be allowed for disengagement of the cap 210 and the body 209. On complete alignment of the locating tab 267 with the at least one notch of the notches 226 in the cap 210, the at least one notch of the notches 226 may define a dead stop (e.g., restrained from further longitudinal and lateral movement), as seen in FIG. 12B. Also, the locating tab 267 may facilitate in engaging the protruding tab 264 with the at least one flexure bearing 254 of the body 209, on complete alignment with the at least one notch of the notches 226 in the cap 210. In the present embodiment, the cap 210 may be defined with two notches 226 at side face (i.e., lateral side) of the cap 210, and in-turn the device 201. The locating tabs 267 on the at least one flexible engaging arm of the plurality of flexible engaging arms 260 are configured such that, when the locating tab 267 meets at least one notch of the notches 226, the tool 235 is considered to be aligned completely with the device 201 to disengage the cap 210 and the body 209.

In some embodiments, the locating tab 267 may also be accompanied by a visual marker 272, for visual indication of orientation of the tool 235 with respect to the device 201 (as apparent in FIG. 11 and FIG. 12A). The visual marker 272 may be disposed in the collar 261 and may correspond to a visible end of the element 272 described above. Alternatively, the visual marker can simply be a mark provided on the collar, in the event that the element 272 is not provided. The visual marker facilitates visual indication of orientation of the tool 235 relative to the device 201. The position of the visual marker 272 in the tool 235 determines the orientation of the tool 235 for precisely securing the plurality of flexible arms 260 within the cavity 222 of the cap 210, to disengage the cap 210 and the body 209. For the instance, position of the visual marker 272 aligned with a front face or a rear face of the device 201 may correspond to correct orientation of the tool 235 relative to the device 201. This may facilitate the tool 235 in precisely securing the plurality of flexible engaging arms 260 with the cavity 222 of the cap 210, and the collar 261 may be abutted with the top surface of the cap 210.

Upon insertion of the tool having the plurality of flexible engaging arms 260 into the cap 210, the hook 255 of the at least one flexure bearing 254 is configured to engage the protruding tabs 264 of the plurality of flexible engaging arms 260, through the slit 252 of the cavity 222. By inserting the tool, the plurality of flexible engaging arms 260 are deformed, e.g., bent inwardly, to be positioned adjacent to the at least one flexure bearing 254. The hook 255 of the at least one flexure bearing 254 is received by the slit 252 in the cavity 222, in a locked condition, where the hook 255 is configured to restrain disengagement of the cap 210. As the protruding tab 264 is configured to engage with the hook 255 of the at least one flexure bearing 254, the protruding tab 264 and in-turn the plurality of flexible engaging arms is configured to be deformed (that is, translated) to the first condition. At this condition, the cap 210 may not be disengaged (that is, dislodged or removed) from the body, in response to insertion of the tool 235 into the cavity 222 (that is, the rigid base region 253 of the cavity 222 is restrained by the hook 255 of the at least one flexure bearing 254).

The tool 235 may be operated by operating the movable member 259 from the first position to the second position (that is, towards the cap 210), through selective displacement of the second enclosure 257, as apparent from FIG. 12A and FIG. 12B. During movement of the movable member 259 from the first position, at least a portion of the plunger 262 is configured to contact and trace the inner wall of the cavity 222 (e.g., along the inner wall, in similar sense to the end of at least one flexible engaging arm of the plurality of flexible engaging arms 260). The plunger 262 or at least a portion of the plunger 262 may be configured to scrape debris deposited on at least of circumferential portion of the cavity (e.g., inner wall). The scraped debris may be traversed along with the plunger 262, during movement of the movable member towards the second position, towards the rigid base region 253 of the cavity 222. On further displacement of the plunger 262 of the movable member 259, the recess 269 defined in the plunger 262, may be configured to enclose the heating element 223, (e.g., the recess 269 of the plunger 257 may contact the heating element 223, or a small clearance may be maintained between the recess 269 and outer surface of the heating element, during enclosing of the heating element). Preferably, a small clearance may be provided between the recess 269 and the heating element 223, to avoid any damage to the heating element 223. From the instance, since the recess 269 begins to enclose the heating element 223, at least a portion of the recess 269 (i.e., an end face of the recess), facilitates in removing (i.e., scraping) the debris deposited on the outer surface of the heating element 223, and thus cleaning the device 201.

Figure 13B:
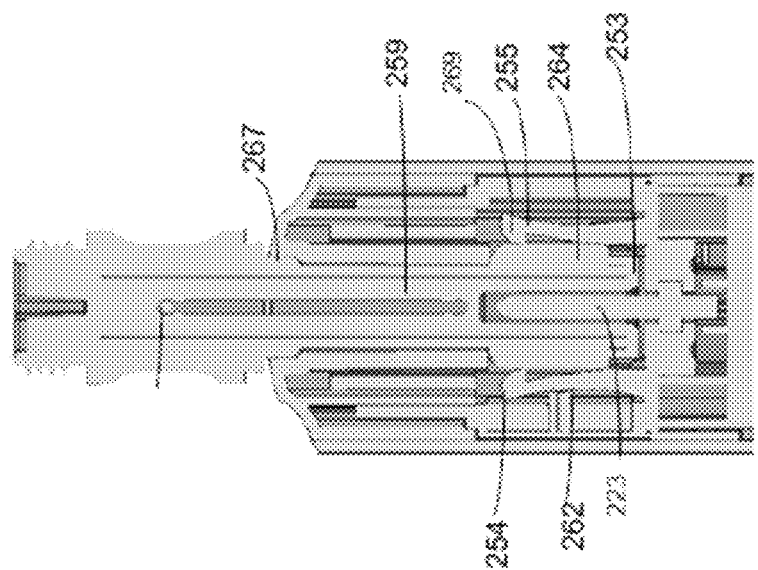
FIG. 13B is a sectional view of a portion of FIG. 12A.
Figure 13A:
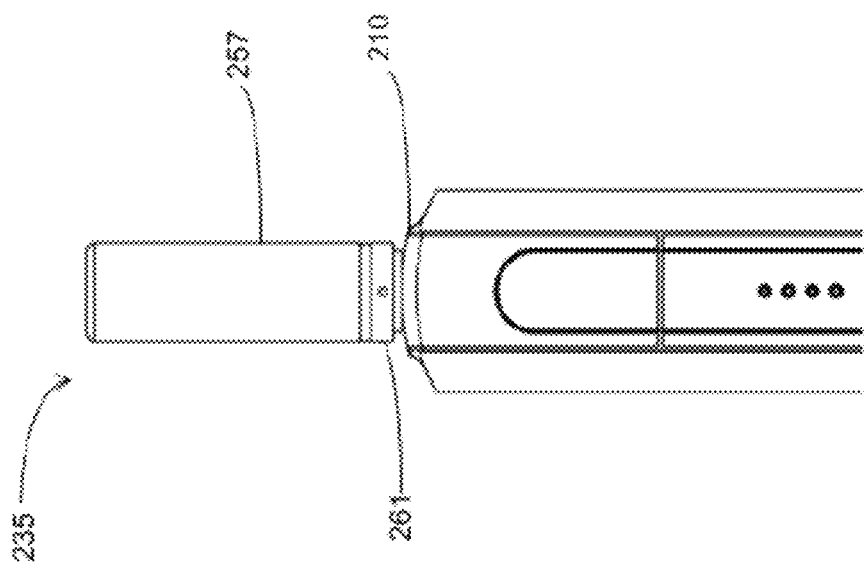
FIG. 13A is a front view of the cap with tool of the first mode in operating condition to disengage the cap and the body of the device.

The operation of the movable member 259 to the second position is also configured to operate or translate (e.g., deform or displace) at least one flexible engaging arm of the plurality of flexible engaging arms 260 to the second condition from the first condition. In this respect, the protruding tab 254 of at least one flexible engaging arm of the plurality of flexible engaging arms 260 is configured to displace (e.g., deform outwardly or move about a width of the device 201) the hook 255 of the at least one flexure bearing 254 to an un-locked position. At this position, the hook 255 of the at least one flexure bearing 254 is displaced outwardly away from the slit 252 of the cavity 222 and the heating element 223 of the device 201, as illustrated in FIG. 13B).

The hook 255 of the at least one flexure bearing 254, upon displacement to the un-locked position, by the protruding tab 264, is configured to disengage (or move away) from the rigid base portion of the cavity 222, for lifting of the cap 210. In other words, hook 255 of the at least one flexure bearing 254 may be moved outwardly and thus are not situated in the slit 252 anymore, so that the locking of the least one flexure bearing 254 is released and the cap 210 is removable. As a result of this, the cap 210 may be disengaged ((that is, dislodged or removed) from the body by pulling force (e.g., upward force applied on the cap 210 and the tool 235, or downward force applied on the body), as apparent from FIG. 14A.

Figure 14B:
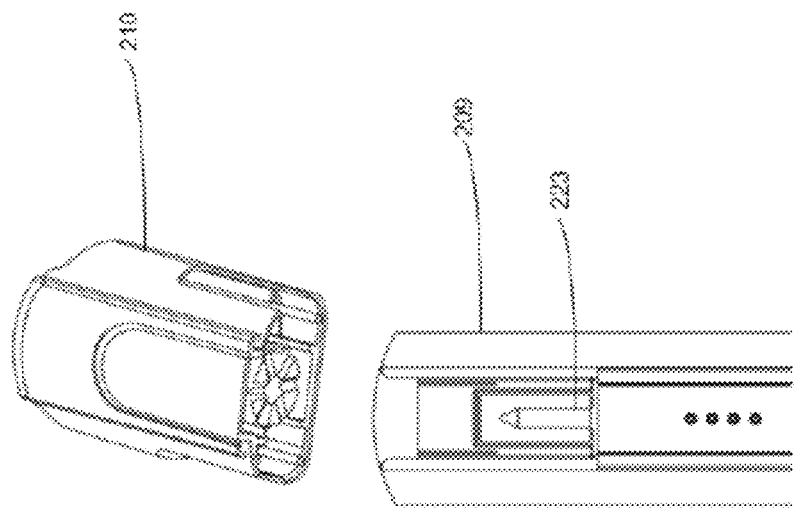
FIG. 14B is an exploded perspective view of the device and the cap of the first mode.
Figure 14A:
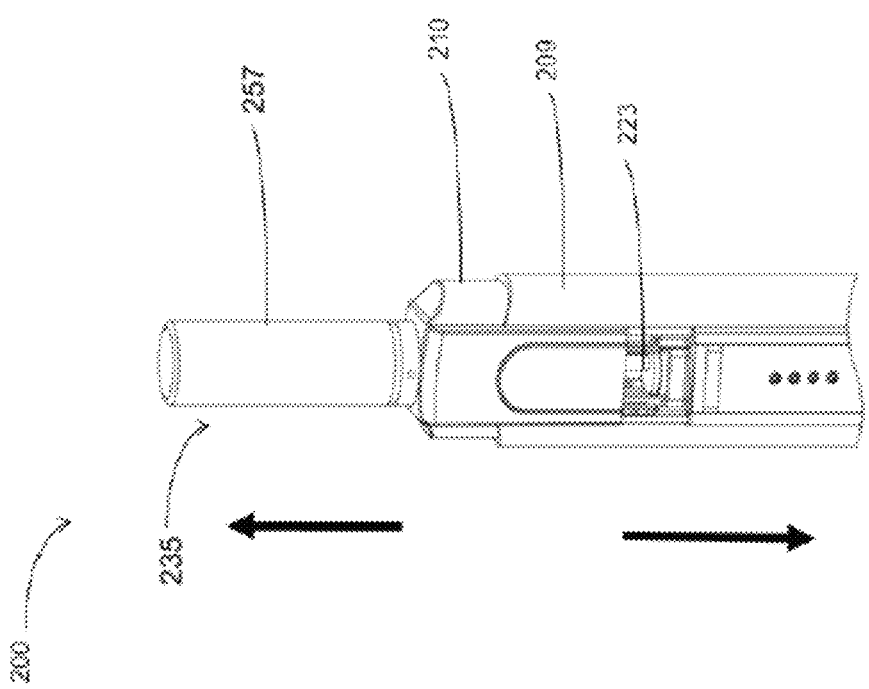
FIG. 14A is a perspective view of the cap of the first mode being disengaged from the main body of the device, along with the tool.

FIG. 14B illustrates disengagement of the cap 210 and the body, for exposure of a portion of the heating element 223 or the heater 204.

The disengagement of the cap 210 and the body of the device 201 and cleaning of the device 201 may be performed by the tool 235, and a method for such disengagement and cleaning is performed and initiated by inserting the tool 235 into the cap 210. The tool 235 through the plurality of flexible engaging arms 260 of the rigid member 258 is inserted into the cap 210, at the opening 221 defined in the top surface of the cap 210. The movable member 259 of the tool 235 is operated to the first position (that is, away from the cap 210) before the plurality of flexible engaging arms 260 can be inserted into the cap 210. The plurality of flexible engaging arms 260 of the rigid member 258 are configured to be insertable into the cap 210 in the first condition, to engage the slit 252 defined in the cavity 222 of the cap 210. While, inserting the flexible engaging arms 260 into the cavity 222 of the device 201, the visual indication marker or element 272 provided in the rigid member 259 provides an indication corresponding to orientation of the tool 201 relative to the device 201, such that the tool 235 can be inserted in a defined orientation. The plurality of flexible engaging arms 260, in the cavity 222 of the cap 210, are held in the first condition by the at least one flexure bearing 254 defined in the body of the device 201. At this point, the cap 210 may be partially disengaged, as the cap 210 may be retrained by the at least one flexure bearing 254, restraining the rigid base region 253 of the cap 210.

The movable member 259 of the tool 235 is then operated (e.g., moved or displaced) from the first position to the second position (that is, into the cavity 222 defined by the cap 210) such that, the plunger 262 of the movable member 259 contacts and traces the cavity 222 of the device 201 (e.g., the inner wall of cavity of the cap), during displacement of the movable member 259 from the first position. This tracing of the plunger 262 along the inner wall of the cavity 222, may facilitate in scraping the debris deposited on the inner wall of the cavity 222. Upon further displacement from the first position, the plunger 262 may contact the flexible engaging arms 260 and thus facilitates in operating the flexible engaging arms 260 to second condition from first condition, which facilitates in disengaging the cap 210 and the body 209.

Operation of the movable member 259 from the first position to the second position also causes the plurality of flexible engaging arms 256 to be translated (e.g., deformed) to the second condition from the first condition. While the plunger 262 contacts with the flexible engaging arms 260, the recess 269 of the plunger 262 receives the heating element 223 (e.g., encloses the heating element). As the heating element 223 is enclosed, the recess 269 may contact the heating element 223 and thus may scrape off debris deposited on the heating element 223. The plunger 262 of the movable member 259 is configured to operate the plurality of flexible engaging arms 260 such that, the protruding tabs 264 of the plurality of flexible engaging arms 260 is configured to assist the slit 252 of the cavity 222 defined by the cap 210 to retain (e.g., regain) its original profile (that is, as though no external forces are acted upon). The retaining of the profile by the slit of the cavity 222 may performed by displacement of the hook 255 on the at least one flexure bearing 254 of the body 209. The plunger 262 of the movable member 259 is configured to operate the plurality of flexible engaging arms 260 such that, the protruding tabs 264 of the plurality of flexible engaging arms 260 is configured to displace the hook 255 of the at least one flexure bearing 254 from the slit 252. This operates the hook 255 of the at least one flexure bearing 254 from the locked position in the slit 252 to the un-locked position. This way, the slit 252 is unobstructed (that is, free to be displaced or moved or lifted) by the hook 255 of the at least one flexure bearing 254. At this point, the rigid base region 253 of the cavity 222 is disengaged by the at least one flexure bearing 254, thereby allowing disengagement of the cap 210 and the body.

In some embodiments, upon disengaging of the cap 210 and the body 209 from the device 201, optionally the second enclosure 257 may be operated (i.e., disengaged or removed to expose the cleaning portion 302). Once, the second enclosure 257 is disengaged, the first enclosure 256 may be engaged, in order to enclose the cap removal portion 301 of the tool, such that the first enclosure 256 may be adapted as a gripping unit to operate the cleaning portion 302, by the user. The cleaning elements 303 of the cleaning portion 302 may be bought in contact with the heating element 223 (i.e., exposed as a result of disengaging the cap 210 and the body 209 of the device 201), and thus facilitating in cleaning the heating element 223 of the heater 204 (thus the device 201).

Second Mode: A Heated Tobacco Device Comprising a Mechanism for Easy Removal of a Consumable from the Device Aspects and embodiments of the second mode of the present disclosure will now be discussed with reference to the accompanying figures. Further aspects and embodiments of the second mode will be apparent to those skilled in the art. All documents mentioned in this text are incorporated herein by reference.

Figure 15:
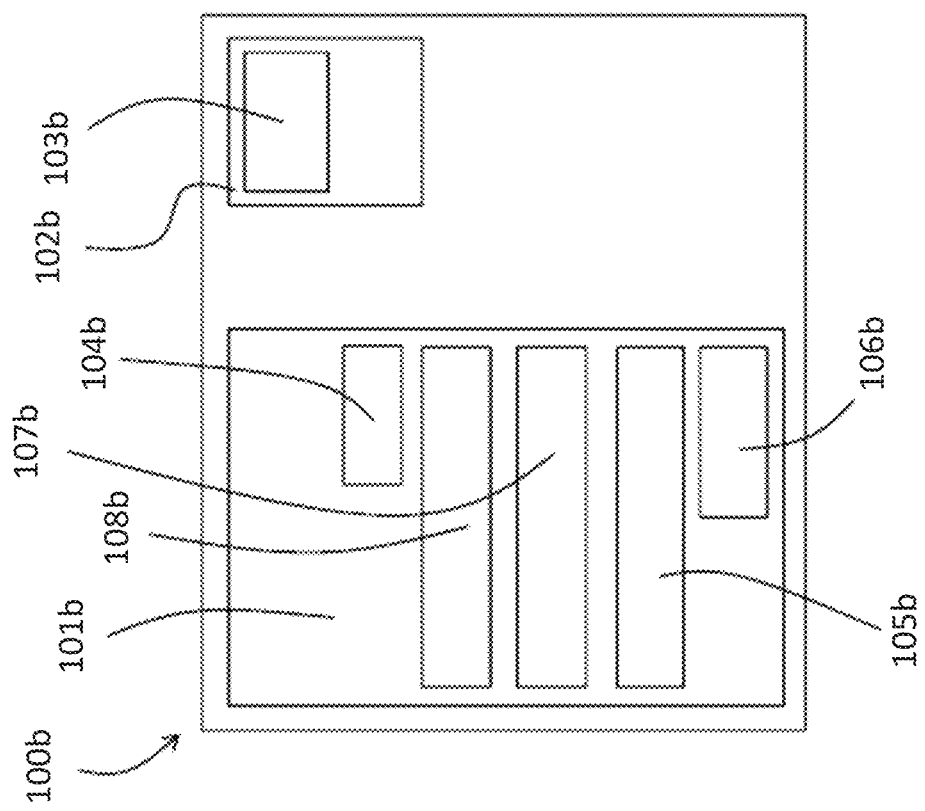
FIG. 15 is a schematic of a smoking substitute system of the second mode.

FIG. 15 is a schematic providing a general overview of a smoking substitute system 100b. The system 100b includes a substitute smoking device 101b and an aerosol-forming article in the form of a consumable 102b, which comprises an aerosol former 103b. The system is configured to vaporize the aerosol former by heating the aerosol former 103b (so as to form a vapor/aerosol for inhalation by a user).

The heater 104b forms part of the device 101b and is configured to heat the aerosol former 103b. The heater 104b is electrically connected to a power source 105b. Heat from the heater 104b vaporizes the aerosol former 103b to produce a vapor. The vapor subsequently condenses to form an aerosol, which is ultimately inhaled by the user.

As above, the system 100b further comprises a power source 105b that forms part of the device 101b. In other embodiments the power source 105b may be external to (but connectable to) the device 101b. The power source 105b is electrically connected to the heater 104b such that it is able to supply power to the heater 104b (i.e., for the purpose of heating the aerosol former 103b). Thus, control of the electrical connection of the power source 105b to the heater 104b provides control of the state of the heater 104b. The power source 105b may be a power store, for example a battery or rechargeable battery (e.g., a lithium-ion battery).

The system 100b further comprises an I/O module comprising a connector 106b (e.g., in the form of a USB port, Micro USB port, USB-C port, etc.). The connector 106b is configured for connection to an external source of electrical power, e.g., a mains electrical supply outlet. The connector 106b may be used in substitution for the power source 105b. That is the connector 106b may be electrically connectable to the heater 104b so as to supply electricity to the heater 104b. In such embodiments, the device may not include a power source, and the power source of the system may instead comprise the connector 106b and an external source of electrical power (to which the connector 106b provides electrical connection).

In some embodiments, the connector 106b may be used to charge and recharge the power source 105b where the power source 105b includes a rechargeable battery.

The system 100b also comprises a user interface (UI) 107b. Although not shown, the UI 107b may include input means to receive commands from a user. The input means of the UI 107b allows the user to control at least one aspect of the operation of the system 100b. The input means may, for example, be in the form of a button, touchscreen, switch, microphone, etc.

The UI 107*b* also comprises output means to convey information to the user. The output means may, for example, comprise lights (e.g., LEDs), a display screen, speaker, vibration generator, etc.

The system 100*b* further comprises a controller 108*b* that is configured to control at least one function of the device 101*b*. In the illustrated embodiment, the controller 108*b* is a component of the device 101*b*, but in other embodiments may be separate from (but connectable to) the device 101*b*. The controller 108*b* is configured to control the operation of the heater 104*b* and, for example, may be configured to control the voltage applied from the power source 105*b* to the heater 104*b*. The controller 108*b* may be configured to toggle the supply of power to the heater 104*b* between an on state, in which the full output voltage of the power source 105*b* is applied to the heater 104*b*, and an off state, in which the no voltage is applied to the heater 104*b*.

Although not shown, the system 100*b* may also comprise a voltage regulator to regulate the output voltage from the power source 105*b* to form a regulated voltage. The regulated voltage may then be applied to the heater 104*b*.

In addition to being connected to the heater 104*b*, the controller 108*b* is operatively connected to the UI 107*b*. Thus, the controller 108*b* may receive an input signal from the input means of the UI 107*b*. Similarly, the controller 108*b* may transmit output signals to the UI 107*b*. In response, the output means of the UI 107*b* may convey information, based on the output signals, to a user. The controller also comprises a memory 109*b*, which is a non-volatile memory. The memory 109*b* includes instructions, which, when implemented, cause the controller to perform certain tasks or steps of a method.

FIG. 16A and FIG. 16B illustrate a heated-tobacco (HT) smoking substitute system 200*b*. The system 200*b* is an example of the system 100*b* described in relation to FIG. 15. System 200*b* includes an HT device 201*b* and an HT consumable 202*b*. The description of FIG. 15 above is applicable to the system 200*b* of FIG. 16A and FIG. 16B, and will thus not be repeated.

The device 201*b* and the consumable 202*b* are configured such that the consumable 202*b* can be engaged with the device 201*b*. FIG. 16A shows the device 201*b* and the consumable 202*b* in an engaged state, whilst FIG. 16B shows the device 201*b* and the consumable 202*b* in a disengaged state.

The device 201*b* comprises a body 209*b* comprising a housing and an article interaction component, in the form of a cap 210*b*. In use the cap 210*b* is engaged at an end of the body 209*b*. Although not apparent from the figures, the cap 210*b* is moveable relative to the body 209*b*. In particular, the cap 210*b* is rotatable with respect to the body 209*b* and is additionally movable longitudinally away from the body. Whilst not shown, this movement may be accommodated by mounting the cap 210*b* to the body 209*b* via a helical track or threaded connection.

The device 201*b* comprises an output means (forming part of the UI of the device 201*b*) in the form of a plurality of light-emitting diodes (LEDs) 211*b* arranged linearly along the longitudinal axis of the device 201*b* and on an outer surface of the body 209*b* of the device 201*b*. A button 212*b* is also arranged on an outer surface of the body 209*b* of the device 201*b* and is axially spaced (i.e., along the longitudinal axis) from the plurality of LEDs 211*b*.

Figure 16C:
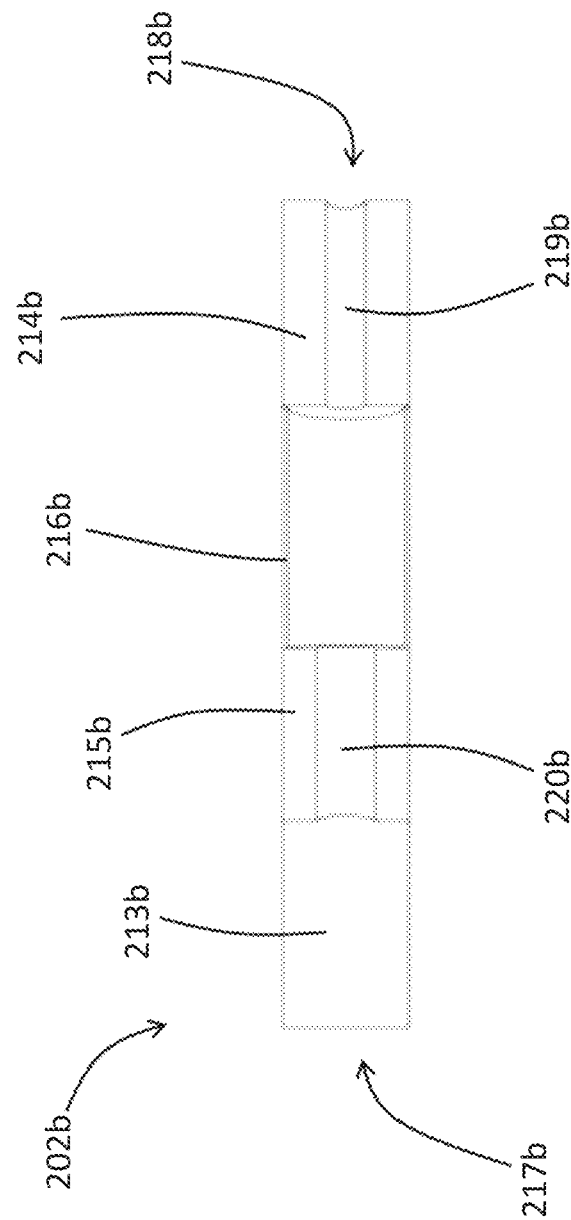
FIG. 16C is a section view of the consumable of the first embodiment of the second mode of the smoking substitute system.

FIG. 16C show a detailed section view of the consumable 202*b* of the system 200*b*. The consumable 202*b* generally resembles a cigarette. In that respect, the consumable 202*b* has a generally cylindrical form with a diameter of 7 mm and an axial length of 70 mm. The consumable 202*b* comprises an aerosol forming substrate 213*b*, a terminal filter element 214*b*, an upstream filter element 215*b* and a spacer element 216*b*. In other embodiments, the consumable may further comprise a cooling element. A cooling element may exchange heat with vapor that is formed by the aerosol-forming substrate 213*b* in order to cool the vapor so as to facilitate condensation of the vapor.

The aerosol-forming substrate 213*b* is substantially cylindrical and is located at an upstream end 217*b* of the consumable 202*b*, and comprises the aerosol former of the system 200*b*. In that respect, the aerosol forming substrate 213*b* is configured to be heated by the device 201*b* to release a vapor. The released vapor is subsequently entrained in an airflow flowing through the aerosol-forming substrate 213*b*. The airflow is produced by the action of the user drawing on a downstream 218*b* (i.e., terminal or mouth) end of the consumable 202*b*.

In the present embodiment, the aerosol forming substrate 213*b* comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213*b* may comprise a gathered sheet of homogenized (e.g., paper/slurry recon) tobacco or gathered shreds/strips formed from such a sheet.

In order to generate an aerosol, the aerosol forming substrate 213*b* comprises at least one volatile compound that is intended to be vaporized/aerosolized and that may provide the user with a recreational and/or medicinal effect when inhaled. The aerosol-forming substrate 213*b* may further comprise one or more additives. For example, such additives may be in the form of humectants (e.g., propylene glycol and/or vegetable glycerin), flavorants, fillers, aqueous/non-aqueous solvents and/or binders.

The terminal filter element 214*b* is also substantially cylindrical and is located downstream of the aerosol forming substrate 213*b* at the downstream end 218*b* of the consumable 202*b*. The terminal filter element 214*b* is in the form of a hollow bore filter element having a bore 219*b* (e.g., for airflow) formed therethrough. The diameter of the bore 219*b* is 2 mm. The terminal filter element 214*b* is formed of a porous (e.g., monoacetate) filter material. As set forth above, the downstream end 218*b* of the consumable 202*b* (i.e., where the terminal filter 214*b* is located) forms a mouthpiece portion of the consumable 202*b* upon which the user draws. Airflow is drawn from the upstream end 217*b*, thorough the components of the consumable 202*b*, and out of the downstream end 218*b*. The airflow is driven by the user drawing on the downstream end 218*b* (i.e., the mouthpiece portion) of the consumable 202*b*.

The upstream filter element 215*b* is located axially adjacent to the aerosol-forming substrate 213*b*, between the aerosol-forming substrate 213*b* and the terminal filter element 214*b*. Like the terminal filter 214*b*, the upstream filter element 215*b* is in the form of a hollow bore filter element, such that it has a bore 220*b* extending axially therethrough. In this way, the upstream filter 215*b* may act as an airflow restrictor. The upstream filter element 215*b* is formed of a porous (e.g., monoacetate) filter material. The bore 220*b* of the upstream filter element 215*b* has a larger diameter (3 mm) than the terminal filter element 214*b*.

The spacer 216b is in the form of a cardboard tube, which defines a cavity or chamber between the upstream filter element 215b and the terminal filter element 214b. The spacer 216b acts to allow both cooling and mixing of the vapor/aerosol from the aerosol-forming substrate 213b. The spacer has an external diameter of 7 mm and an axial length of 14 mm.

Although not apparent from the figure, the aerosol-forming substrate 213b, upstream filter 215b and spacer 216b are circumscribed by a paper wrapping layer. The terminal filter 214b is circumscribed by a tipping layer that also circumscribes a portion of the paper wrapping layer (so as to connect the terminal filter 214b to the remaining components of the consumable 202b). The upstream filter 215b and terminal filter 214b are circumscribed by further wrapping layers in the form of plug wraps.

Figure 16E:
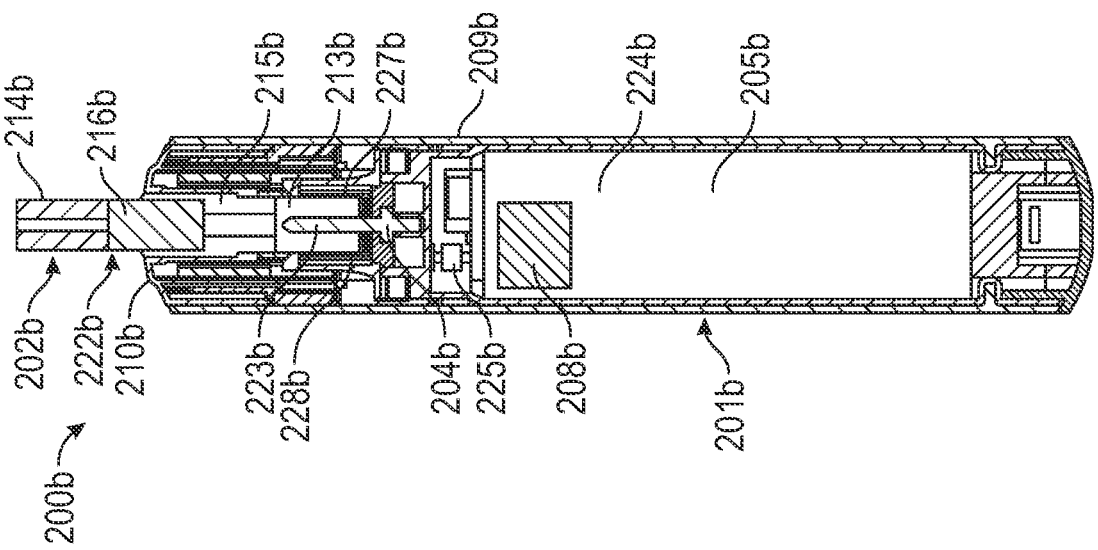
FIG. 16E is a section view of the first embodiment of the second mode of the substitute smoking system.
Figure 16D:
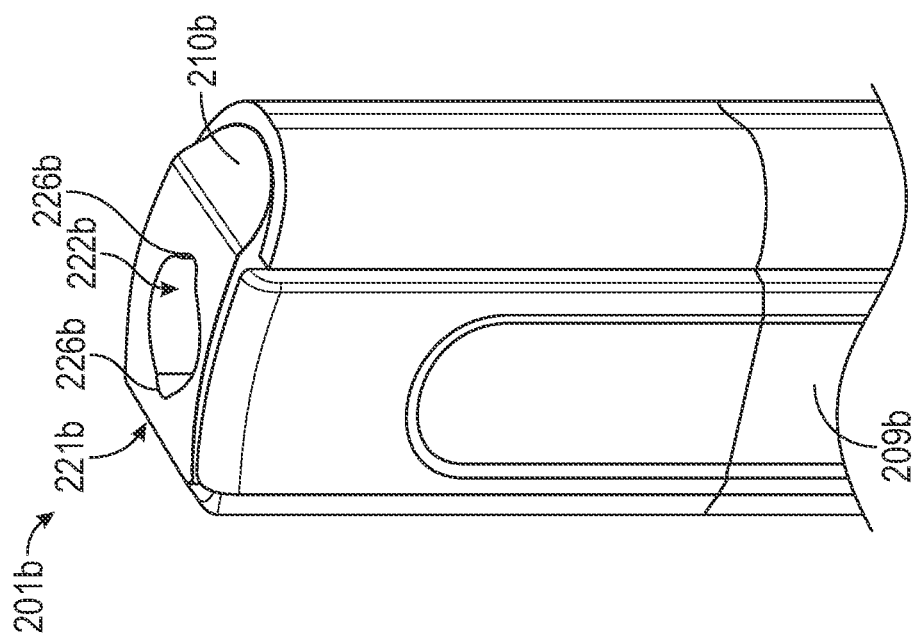
FIG. 16D is a detailed view of an end of the device of the first embodiment of the second mode of the smoking substitute system.

Returning now to the device 201b, FIG. 16D illustrates a detailed view of the end of the device 201b that is configured to engage with the consumable 202b. The cap 210b of the device 201b includes an opening 221b to an internal cavity 222b (more apparent from FIG. 16D) defined by the cap 210b. The opening 221b and the cavity 222b are formed so as to receive at least a portion of the consumable 202b.

FIG. 16E shows a cross section through a central longitudinal plane through the device 201b. The device 201b is shown with the consumable 202b engaged therewith. As is apparent from this figure, the cap 210b comprises a generally circumferential sidewall 227b and a base portion 228b that define the cavity 222b. The sidewall 227b is oriented on an incline to a longitudinal axis of the device 201b such that the cavity 222b is narrower at the base portion 228b than the opening 221b. In this respect, the cavity 222b has a generally frustoconical shape.

During engagement of the consumable 202b with the device 201b, a portion of the consumable 202b is received through the opening 221b and into the cavity 222b. After engagement (see FIG. 16B), the downstream end 218b of the consumable 202b protrudes from the opening 221b and thus also protrudes from the device 201b. The opening 221b includes laterally disposed notches 226b. When a consumable 202b is received in the opening 221b, these notches 226b remain open and could, for example, be used for retaining a cover in order to cover the end of the device 201b.

Due to the frustoconical shape of the cavity 222b (and the tapered nature of the sidewall 227b), when the consumable 202b is received in the cavity 222b, the consumable 202b forms a friction fit with a lower end of the sidewall 227b (proximate the base portion 228b). This allows the cap 210b to grip the consumable 202b. Thus, when the cap 210b is rotated relative to the body 209b (as is discussed above), the consumable 202b is also caused to rotate (i.e., via the frictional grip between the sidewall 227b and the consumable 202b). This can provide easier and cleaner removal of the consumable 202b from the heater 223b after the consumable 202b has been consumed. Although not shown, the sidewall 227b may comprise e.g., longitudinal ribs (or another gripping feature) for facilitating grip of the consumable 202b.

The device 201b comprises a heater 204b comprising heating element 223b. The heater 204b forms part of the body 209b of the device 201b and is rigidly mounted to the body 209b. In the illustrated embodiment, the heater 204b is a rod heater having a generally cylindrical configuration. The heater 204b comprises a heating element 223b having a circular transverse profile. In other embodiments the heater may be in the form of a tube heater (e.g., heating element with a tubular form).

The heating element 223b of the heater 204b projects from an internal base of the cavity 222b along a longitudinal axis towards the opening 221b. The heater 204b is configured to protrude into the cap 210b through an aperture formed in the base portion 228b of the cavity 222b. As is apparent from the figure, the length (i.e., along the longitudinal axis) of the heating element is less than a depth of the cavity 222b. In this way, the heating element 223b does not protrude from or extend beyond the opening 221b.

When the consumable 202b is received in the cavity 222b (as is shown in FIG. 16E), the heating element 223b penetrates the aerosol-forming substrate 213b of the consumable 202b. In particular, the heating element 223b extends for nearly the entire axial length of the aerosol-forming substrate 213b when inserted therein. Thus, when the heater 204b is activated, heat is transferred radially from an outer circumferential surface the heating element 223b to the aerosol-forming substrate 213b.

When the cap 210b is rotated about a longitudinal axis of the heater 204b and moved in a direction away from the body 209b, the consumable 202b which is gripped by the cap 210b also moves away. Thereby the consumable 202b is at least partially withdrawn from the heater 204b causing the consumable 202b to disengage with the heater 204b.

The device 201b further comprises an electronics cavity 224b. A power source, in the form of a rechargeable battery 205b (a lithium-ion battery), is located in electronics cavity 224b.

The device 201b includes a connector (i.e., forming part of an IO module of the device 201b) in the form of a USB port 206b. The connector may alternatively be, for example, a micro-USB port or a USB-C port for examples. The USB port 206b may be used to recharge the rechargeable battery 205b.

The device 201b includes a controller 208b located in the electronics cavity 224b. The controller comprises a microcontroller mounted on a printed circuit board (PCB). The USB port 206b is also connected to the controller 208b (i.e., connected to the PCB and microcontroller).

The controller 208b is configured to control at least one function of the device 202b. For example, the controller 208b is configured to control the operation of the heater 204b. Such control of the operation of the heater 204b may be accomplished by the controller 208b toggling the electrical connection of the rechargeable battery 205b to the heater 204b. For example, the controller 208b is configured to control the heater 204b in response to a user depressing the button 212b. Depressing the button 212b may cause the controller to allow a voltage (from the rechargeable battery 205b) to be applied to the heater 204b (so as to cause the heating element 223b to be heated).

The controller is also configured to control the LEDs 211b in response to (e.g., a detected) a condition of the device 201b or the consumable 202b. For example, the controller may control the LEDs to indicate whether the device 201b is in an on state or an off state (e.g., one or more of the LEDs may be illuminated by the controller when the device is in an on state).

The device 201b comprises a further input means (i.e., in addition to the button 212b) in the form of a puff sensor 225b. The puff sensor 225b is configured to detect a user drawing (i.e., inhaling) at the downstream end 218b of the consumable 202b. The puff sensor 225b may, for example, be in the form of a pressure sensor, flowmeter or a microphone. The puff sensor 225b is operatively connected to the controller 208b in the electronics cavity 224b, such that a signal from the puff sensor 225b, indicative of a puff state (i.e., drawing or not drawing), forms an input to the controller 208b (and can thus be responded to by the controller 208b).

Figure 16G:
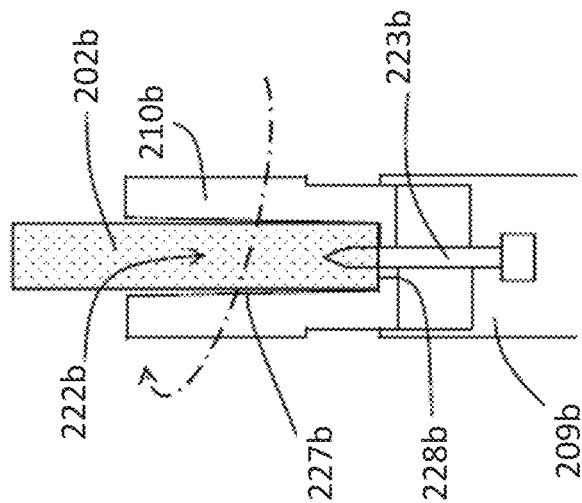
FIG. 16F and FIG. 16G are schematic views illustrating the operation of a cap of the first embodiment of the second mode of the substitute smoking system.
Figure 16F:
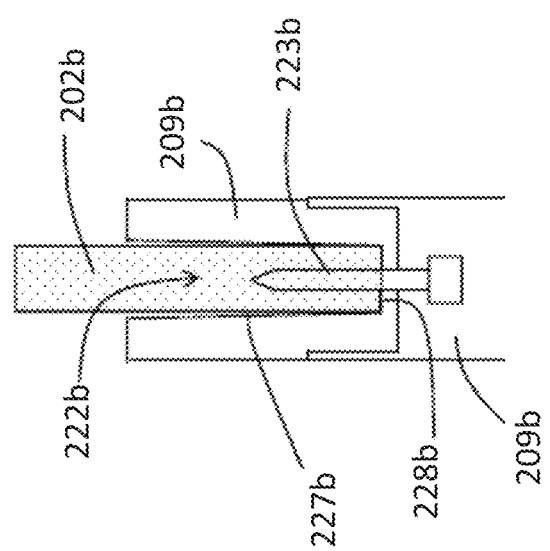

FIG. 16F and FIG. 16G schematically illustrate the interaction of the cap 210b and the body 209b. As described above, the cap 210b is both rotatable relative to the body 209b and movable along a longitudinal axis away from the body 209b. In FIG. 16F, a consumable 202b is received in the cavity 222b of the cap 210b so as to be penetrated by the heating element 223b. This is the position of the cap 210b during operation of the device 201b (i.e., during heating of the consumable 202b by the heating element 223b).

In FIG. 16G the consumable is partly removed from the heating element 223b. In this figure, the cap 210b has been moved longitudinally whilst also being rotated by a user (as is depicted by the arrow). Because there is a friction fit between the consumable 202b and the frustoconical sidewall 227b of the cavity 222b, when the cap 210b is moved in this way, the consumable 202b is rotated. Similarly, as the cap 210b moves longitudinally, the base portion 228b of the cavity 228b contacts the consumable 202b and lifts it or moves it along the heating element 223b. The rotation of the consumable 202b may facilitate clean removal of the consumable 202b from the heating element 223b.

Figure 17B:
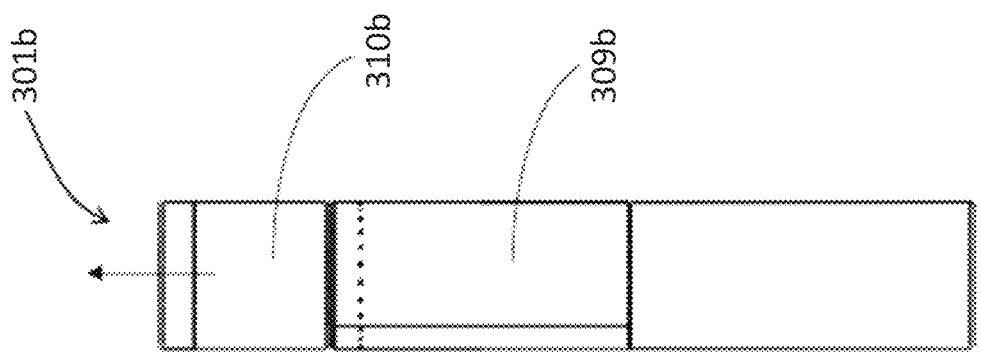
FIG. 17A and FIG. 17B are front views of a second embodiment of the second mode of a substitute smoking system.
Figure 17A:
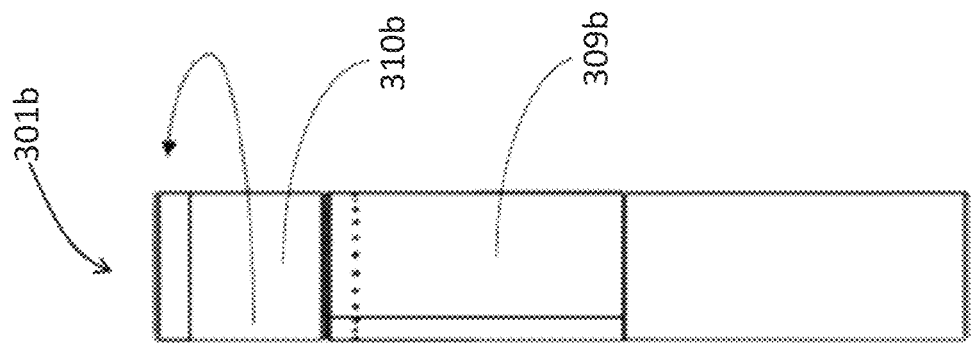

FIG. 17A and FIG. 17B depict a further embodiment of the device 301b. This device 301b is generally the same as that described above, but is cylindrical in shape. In FIG. 17A, the cap 310b engaged with the body 309b. In this position a user may rotate the cap 310b, which in turn rotates a consumable (not shown) engaged with the device 301b. This may be performed by a user to disengage or dislodge the consumable from a heating element of the device 301b. Unlike the previously described embodiment, the cap 310b does not move longitudinally as it is rotated. Rather, and as shown in FIG. 17B, the cap 310b may be moved in a longitudinal direction, separate to any rotation, away from the body 309b by a user. This may move the consumable (again, not shown) along a heating element of the device so as to at least partially remove the consumable from the heating element.

Third Mode: An Aerosol-Forming Delivery System Such as an HNB System

Figure 18:
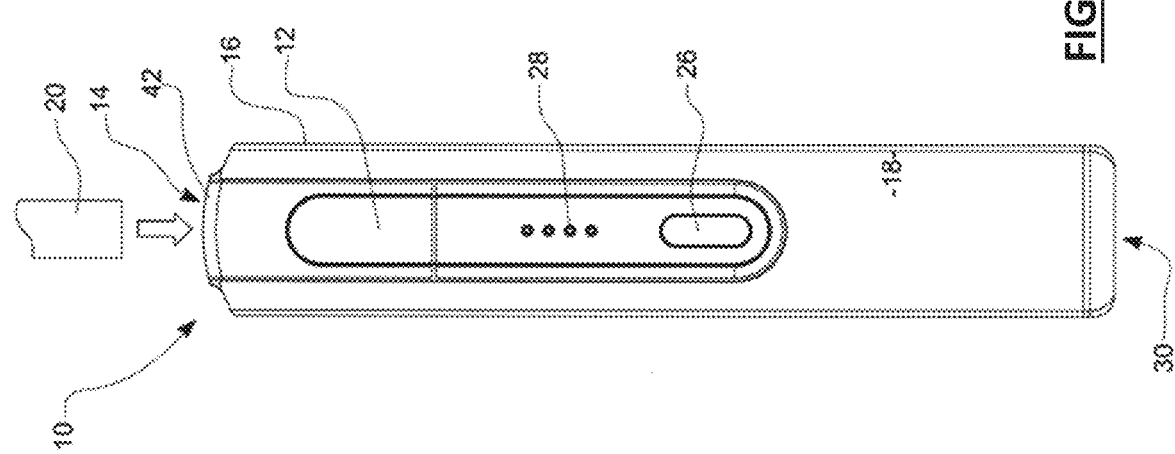
FIG. 18 shows a view of an exemplary embodiment of the third mode of a smoking substitute device in accordance with the present disclosure.

FIG. 18 shows a view of an exemplary embodiment of the third mode of a smoking substitute device 10, here exemplarily an HNB device 10.

The HNB device 10 comprises a rod-shaped heating element 12, which projects into a cavity 14 within the main body 16 of the device 10. A smoking substitute consumable 20 may be inserted into the cavity 14 of the main body 12 of the device 10 such that the heating rod 12 penetrates an aerosol-forming substrate, e.g., tobacco material in one outer part, e.g., the lower part of the smoking substitute consumable 20, distal from an outward facing opening 42 of cavity 14. Heating of e.g., reconstituted tobacco in the aerosol-forming substrate is affected by powering the heating element 12, with a power source 18, e.g., a rechargeable battery 18 incorporated in the smoking substitute device 10. As the tobacco is heated, moisture and volatile compounds (e.g., nicotine) within the tobacco and possibly a humectant are released as a vapor and entrained within an airflow generated by inhalation by the user.

Heating of the tobacco by the heating element 12 may be activated by the user pressing an actuator 26, here exemplarily activation switch 26, on a side surface of the main body 16 of the smoking substitute device 10. Display element 28, here exemplarily a number of LEDs, is arranged in the vicinity of the activation switch 26 on the side surface of main body 16.

At the bottom of smoking substitute device 10, a charging connector 30 is depicted. The charging connector 30 may be embodied as a standard USB connector, e.g., mini-USB or micro-USC. Preferably, the charging connector 30 is embedded as a symmetrical connector, like a USB-C connector. Alternatively, the charging connector 30 may be embodied as a lightning connector. The charging connector 30 may provide a connection for either energy or data or both.

Figure 19:
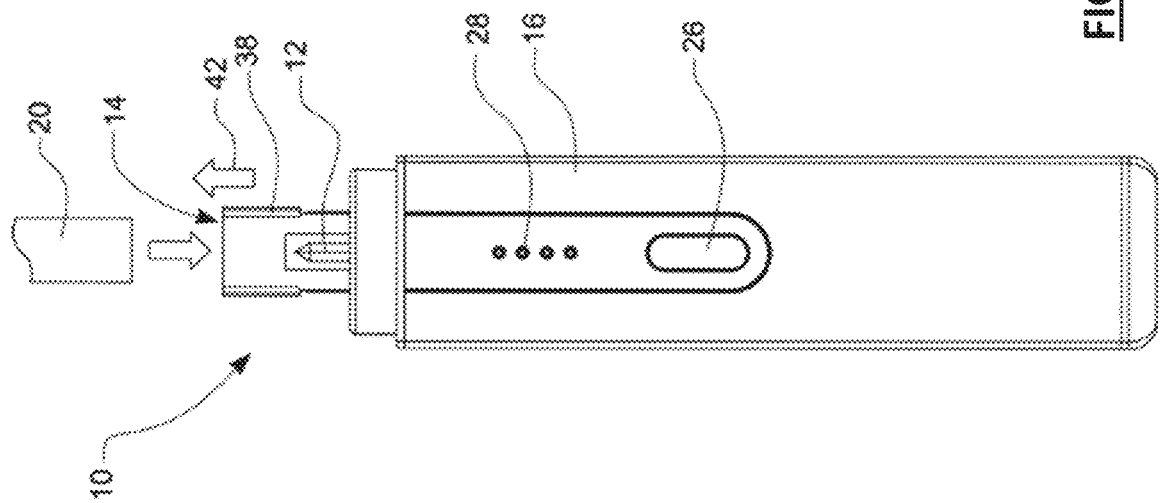
FIG. 19 shows exemplary embodiment of the third mode of a smoking substitute device in accordance with the present disclosure.

Now referring to FIG. 19, an exemplary embodiment of the third mode of a smoking substitute device in accordance with the present disclosure is depicted.

Smoking substitute device 10, embodied as a heat-not-burn smoking substitute device, comprises main body 16 with a protruding heating element 12. Part of the main body 16 extends in the area of the heating element 12 thereby forming the cavity 14 for receiving a smoking substitute consumable 20. Smoking substitute consumable 20 is only indicated and about to be inserted into the cavity 14, indicated by the downward arrow in FIG. 19. Surrounding the cavity 14 is a shroud 38 substantially surrounding the cavity 14.

When the smoking substitute consumable 20 is inserted into the cavity 14, the shroud 38 covers an outer circumferential area of the smoking substitute consumable 20 thereby separating or isolating the outside of the shroud 38 from heat generated within the shroud 38 and in particular within the cavity 14 by heating element 12 for heating of aerosol releasing material within the smoking substitute consumable 20. In other words, the isolative shroud is providing a heat barrier between a heated smoking substitute consumable 20 and the outside of the smoking substitute device 10 such that a user of the smoking substitute device 10 may not come in contact with the heated smoking substitute consumable 20 or in case the area of the isolative shroud is indeed touched by the user, receives only a moderate heat not resulting in injury.

Shroud 38 comprises aperture 40 which is arranged distal from the outward facing opening 42 of cavity 14 and is thus arranged in the vicinity of heating element 12. The aperture may be used for cleaning heating element 12 e.g., by insertion of a suitable cleaning element into aperture 40 to scrub off excess tobacco material or residue tobacco material from heating element 12. At the same time, aperture 40 is small enough and distant enough from heating element 12 so that a user may not reach or come in contact with heating element 12 through aperture 40.

For operating the smoking substitute device 10, a control element 26, e.g., a button or activation switch, is provided which can further comprise a display element 28 for display of operation or other information to a user of the smoking substitute device 10.

Figure 20:
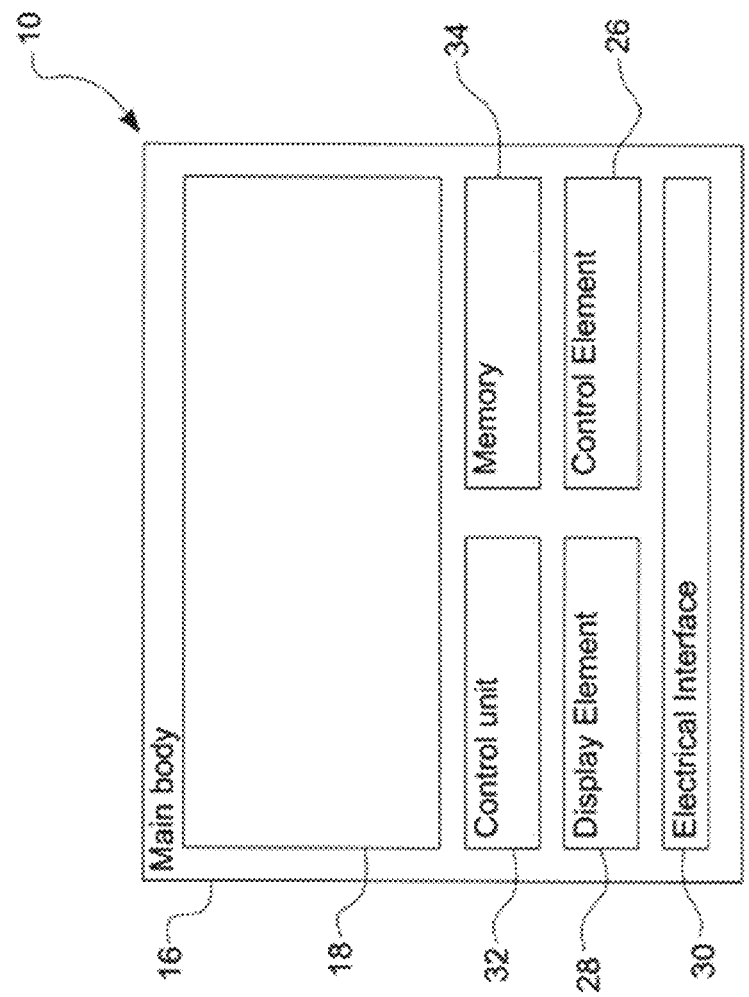
FIG. 20 shows a schematic of an exemplary embodiment of the third mode of a smoking substitute device in accordance with the present disclosure.

Now referring to FIG. 20, which shows a schematic of an exemplary embodiment of the third mode of a smoking substitute device in accordance with the present disclosure.

Smoking substitute device 10 comprises a main body 16 or housing and a power source 18, e.g., a rechargeable battery. Further provided is a control unit 32, which may include a microprocessor. Memory 34 is provided for storing e.g., control instructions for control unit 32 or the microprocessor. Memory 34 is preferably provided as non-volatile memory. Smoking substitute device 10 may further comprise a display element 28, which may be embodied as a single or a plurality of LEDs or organic LEDs. The LEDs are possibly adapted for displaying different colors in accordance with instructions from the control unit 32 and memory 34, depicting different modes of operation with different colors of smoking substitute device 10 or generally different information directed to the user operating the smoking substitute device 10. A control element 26 is provided, e.g., an actuator or activation switch, with which the smoking substitute device may be switched on and off, an operation may be initiated and/or a mode of operation may be set.

Further, an electrical interface 30 or charging connector 30 is provided, which may be incorporated in the main body 16 and which may include one or more electrical contacts. The electrical interface 30 may be located in, and preferably at the bottom of, an aperture in an end section of the main body 16. Electrical interface 30 may be adapted to be coupled with an external charging station to receive power for charging the power source 18. Alternatively, electrical interface 30 may be embodied as a charging connector 30, which may be a USB or lightning connection. Preferably, the charging connector 30 is embodied as a USB-C connector, which is an example of a symmetrical connector.

Fourth Mode: A Smoking Substitute System with a Smoking Substitute Device Having a Cap Movable Between Two Positions Aspects and embodiments of the fourth mode of the present disclosure will now be discussed with reference to the accompanying figures. Further aspects and embodiments will be apparent to those skilled in the art. All documents mentioned in this text are incorporated herein by reference.

Figure 21:
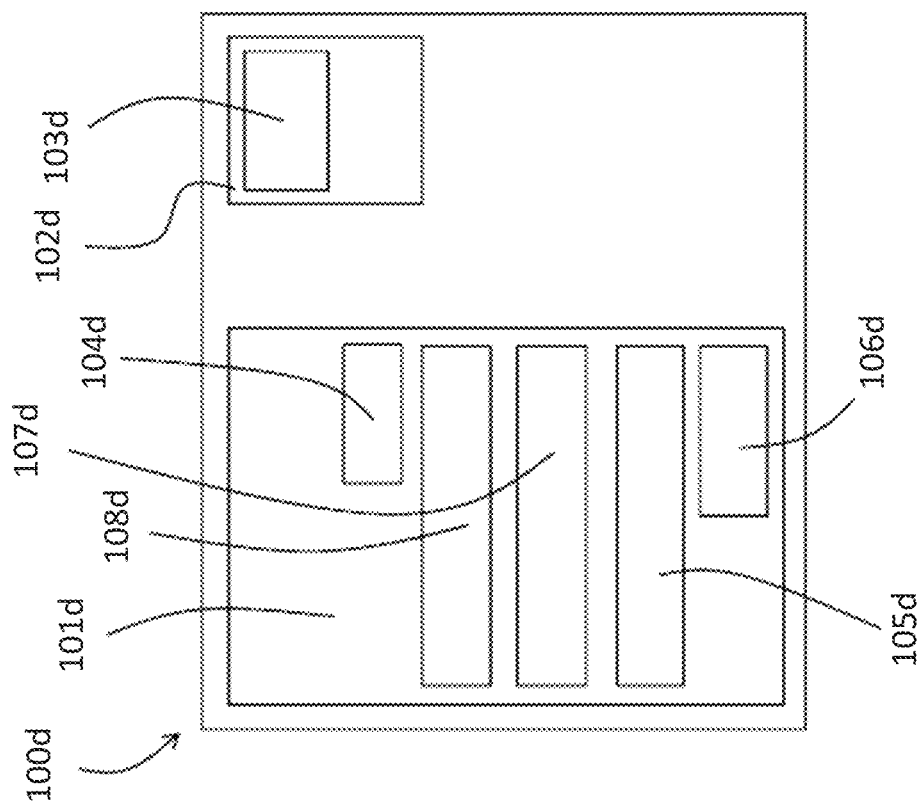
FIG. 21 is a schematic of a smoking substitute system of the fourth mode.

FIG. 21 is a schematic providing a general overview of a smoking substitute system 100d. The system 100d includes a substitute smoking device 101d and an aerosol-forming article in the form of a consumable 102d, which comprises an aerosol former 103d. The system is configured to vaporize the aerosol former by heating the aerosol former 103d (so as to form a vapor/aerosol for inhalation by a user).

In the illustrated system, the heater 104d forms part of the device 101d and is configured to heat the aerosol former 103d. Heat from the heater 104d vaporizes the aerosol former 103d to produce a vapor. The vapor subsequently condenses to form an aerosol, which is ultimately inhaled by the user.

The system 100d further comprises a power source 105d that forms part of the device 101d. In other embodiments the power source 105d may be external to (but connectable to) the device 101d. The power source 105d is electrically connectable to the heater 104d such that it is able to supply power to the heater 104d (i.e., for the purpose of heating the aerosol former 103d). Thus, control of the electrical connection of the power source 105d to the heater 104d provides control of the state of the heater 104d. The power source 105d may be a power store, for example a battery or rechargeable battery (e.g., a lithium-ion battery).

The system 100d further comprises an I/O module comprising a connector 106d (e.g., in the form of a USB port, Micro USB port, USB-C port, etc.). The connector 106d is configured for connection to an external source of electrical power, e.g., a mains electrical supply outlet. The connector 106d may be used in substitution for the power source 105d. That is the connector 106d may be electrically connectable to the heater 104d so as to supply electricity to the heater 104d. In such embodiments, the device may not include a power source, and the power source of the system may instead comprise the connector 106d and an external source of electrical power (to which the connector 106d provides electrical connection).

In some embodiments, the connector 106d may be used to charge and recharge the power source 105d where the power source 104d includes a rechargeable battery.

The system 100d also comprises a user interface (UI) 107d. Although not shown, the UI 107d may include input means to receive commands from a user. The input means of the UI 107d allows the user to control at least one aspect of the operation of the system 100d. The input means may, for example, be in the form of a button, touchscreen, switch, microphone, etc.

The UI 107d also comprises output means to convey information to the user. The output means may, for example, comprise lights (e.g., LEDs), a display screen, speaker, vibration generator, etc.

The system 100d further comprises a controller 108d that is configured to control at least one function of the device 101d. In the illustrated embodiment, the controller 108d is a component of the device 101d, but in other embodiments may be separate from (but connectable to) the device 101d. The controller 108d is configured to control the operation of the heater 104d and, for example, may be configured to control the voltage applied from the power source 105d to the heater 104d. The controller 108d may be configured to toggle the supply of power to the heater 105d between an on state, in which the full output voltage of the power source 105d is applied to the heater 104d, and an off state, in which the no voltage is applied to the heater 104d.

Although not shown, the system 100d may also comprise a voltage regulator to regulate the output voltage from the power source 105d to form a regulated voltage. The regulated voltage may then be applied to the heater 104d.

In addition to being connected to the heater 104d, the controller 108d is operatively connected to the UI 107d. Thus, the controller 108d may receive an input signal from the input means of the UI 107d. Similarly, the controller 108d may transmit output signals to the UI 107d. In response, the output means of the UI 107d may convey information, based on the output signals, to a user.

FIG. 22A and FIG. 22B illustrate a heated-tobacco (HT) smoking substitute system 200d. The system 200d is an example of the systems 100d, described in relation to FIG. 21. System 200d includes an HT device 201d and an HT consumable 202d. The description of FIG. 21 above is applicable to the system 200d of FIG. 22A and FIG. 22B, and will thus not be repeated.

The device 201d and the consumable 202d are configured such that the consumable 202d can be engaged with the device 201d. FIG. 22A shows the device 201d and the consumable 202d in an engaged state, whilst FIG. 22B shows the device 201d and the consumable 202d in a disengaged state.

The device 201d comprises a body 209d and cap 210d. In use the cap 209d is engaged at an end of the body 209d. Although not apparent from the figures, the cap 210d is moveable relative to the body 209d. In particular, the cap 210d is sliceable and can slide along a longitudinal axis of the body 209d.

As shown in FIG. 27e, the body 209d defines a transverse cavity 227d extending orthogonal to the longitudinal axis of the body 209d. The transverse cavity 227d opens through and extends from a first side wall of the body 209d towards and surrounding at least a portion of the heating element. The transverse cavity 227d is located on the body 209d such that at least a base 228d of the heating element is juxtaposed with the transverse cavity 227d. The transverse cavity 227d extends from a first side wall of the body 209d to and through a second side wall opposite to the first side wall of the body 209d. That is, the transverse cavity 227d forms a through hole extending through the body 209d.

The device 201d comprises an output means (forming part of the UI of the device 201d) in the form of a plurality of light-emitting diodes (LEDs) 211d arranged linearly along the longitudinal axis of the device 201d and on an outer surface of the body 209d of the device 201d. A button 212d is also arranged on an outer surface of the body 209d of the device 201d and is axially spaced (i.e., along the longitudinal axis) from the plurality of LEDs 211d.

Figure 22C:
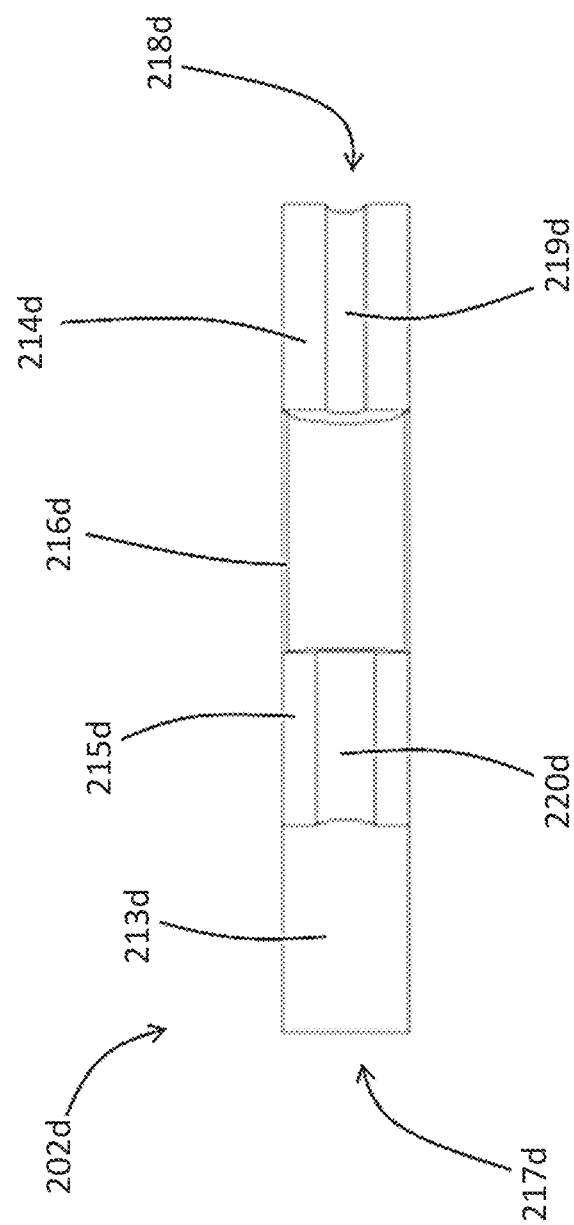
FIG. 22C is a section view of the consumable of the first embodiment of the fourth mode of the smoking substitute system.

FIG. 22C show a detailed section view of the consumable 202d of the system 200d. The consumable 202d generally resembles a cigarette. In that respect, the consumable 202d has a generally cylindrical form with a diameter of 7 mm and an axial length of 70 mm. The consumable 202d comprises an aerosol forming substrate 213d, a terminal filter element 214d, an upstream filter element 215d and a spacer element 216d. In other embodiments, the consumable may further comprise a cooling element. A cooling element may exchange heat with vapor that is formed by the aerosol-forming substrate 213d in order to cool the vapor so as to facilitate condensation of the vapor.

The aerosol-forming substrate 213d is substantially cylindrical and is located at an upstream end 217d of the consumable 202d, and comprises the aerosol former of the system 200d. In that respect, the aerosol forming substrate 213d is configured to be heated by the device 201d to release a vapor. The released vapor is subsequently entrained in an airflow flowing through the aerosol-forming substrate 213d. The airflow is produced by the action of the user drawing on a downstream 218d (i.e., terminal or mouth end) of the consumable 202d.

In the present embodiment, the aerosol forming substrate 213d comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213d may comprise a gathered sheet of homogenized (e.g., paper/slurry recon) tobacco or gathered shreds/strips formed from such a sheet.

In order to generate an aerosol, the aerosol forming substrate 213d comprises at least one volatile compound that is intended to be vaporized/aerosolized and that may provide the user with a recreational and/or medicinal effect when inhaled. The aerosol-forming substrate 213d may further comprise one or more additives. For example, such additives may be in the form of humectants (e.g., propylene glycol and/or vegetable glycerin), flavorants, fillers, aqueous/non-aqueous solvents and/or binders.

The terminal filter element 214d is also substantially cylindrical, and is located downstream of the aerosol forming substrate 213d at the downstream end 218d of the consumable 202d. The terminal filter element 214d is in the form of a hollow bore filter element having a bore 219d (e.g., for airflow) formed therethrough. The diameter of the bore 219d is 2 mm. The terminal filter element 214d is formed of a porous (e.g., monoacetate) filter material. As set forth above, the downstream end 218d of the consumable 202d (i.e., where the terminal filter 214d is located) forms a mouthpiece portion of the consumable 202d upon which the user draws. Airflow is drawn from the upstream end 217d, thorough the components of the consumable 202d, and out of the downstream end 218d. The airflow is driven by the user drawing on the downstream end 218d (i.e., the mouthpiece portion) of the consumable 202d.

The upstream filter element 215d is located axially adjacent to the aerosol-forming substrate 213d, between the aerosol-forming substrate 213d and the terminal filter element 214d. Like the terminal filter 214d, the upstream filter element 215d is in the form of a hollow bore filter element, such that it has a bore 220d extending axially therethrough. In this way, the upstream filter 215d may act as an airflow restrictor. The upstream filter element 215d is formed of a porous (e.g., monoacetate) filter material. The bore 220d of the upstream filter element 214d has a larger diameter (3 mm) than the terminal filter element 214d.

The spacer 216d is in the form of a cardboard tube, which defines a cavity or chamber between the upstream filter element 215d and the terminal filter element 214d. The spacer 216d acts to allow both cooling and mixing of the vapor/aerosol from the aerosol-forming substrate 213d. The spacer has an external diameter of 7 mm and an axial length of 14 mm.

Although not apparent from the figure, the aerosol-forming substrate 213d, upstream filter 215d and spacer 216d are circumscribed by a paper wrapping layer. The terminal filter 214d is circumscribed by a tipping layer that also circumscribes a portion of the paper wrapping layer (so as to connect the terminal filter 214d to the remaining components of the consumable 202d). The upstream filter 215d and terminal filter 214d are circumscribed by further wrapping layers in the form of plug wraps.

Returning now to the device 201d, FIG. 22D illustrates a detailed view of the end of the device 201d that is configured to engage with the consumable 202d. The cap 210d of the device 201d includes an opening 221d to an internal cavity 222d (more apparent from FIG. 22D) defined by the cap 210d. The opening 221d and the cavity 222d are formed so as to receive at least a portion of the consumable 202d. During engagement of the consumable 202d with the device 201d, a portion of the consumable 202d is received through the opening 221d and into the cavity 222d. After engagement (see FIG. 22B), the downstream end 218d of the consumable 202d protrudes from the opening 221d and thus also protrudes from the device 201d. The opening 221d includes laterally disposed notches 226d. When a consumable 202d is received in the opening 221d, these notches 226d remain open and could, for example, be used for retaining a cover in order to cover the end of the device 201d.

FIG. 22E shows a cross section through a central longitudinal plane through the device 201d. The device 201d is shown with the consumable 202d engaged therewith. Further, as illustrated, at least one locking arm 229d extends from the body 209d. The locking arms 229d lock or retain the cap 210d with the body 209d. In the embodiment as illustrated, two locking arms 229d are present. In an embodiment, any suitable number of locking arms 229d may be provided. The locking arms 229d extend substantially along the longitudinal axis of the body 209d as shown. The locking arms 229d are provided with a locking protrusion 231d at a distal end, i.e., an end distal from an end of the locking arm 229d that is connected to the body 209d. The locking protrusion 231d extend transversely to the longitudinal axis of the body 209d. The locking arms 229d are positioned such that when the cap 210d is mounted on the body 209d, the locking arms 229d engage the cap 210d to retain the cap 210d on the body 209d.

In the embodiment as shown, the cap 210d may be provided with a slot 232d extending along the longitudinal axis of the body 209d (when the cap 210d is retained on the body 209d), and the locking protrusions 231d may be configured or positioned to engage the slot 232d. The slot 232d may be elongated such that the cap 210d may be moved or slid relative to the body 209d along the longitudinal axis of the body 209d. The locking protrusion 231d may have an abutment surface 233d to engage a peripheral surface 234d of the cap 210d that defines the slot 232d. The abutment surface 233d may block movement of the cap 210d in one direction by abutting the peripheral surface 234d to retain or lock the cap 210d with the body 209d.

The cap 210d is movable between a first position and a second position. FIG. 2A, FIG. 2B, FIG. 2D, and FIG. 4A illustrate the device 200d with the cap 210d in the first position. When the cap 210d is in the first position, the cap 210d conceals the heating element 223d, as illustrated. In the first position, the cap 210d completely covers the transverse cavity 227d to conceal the heating element 223d.

FIG. 23 and FIG. 24B illustrate the device 200d with the cap 210d in the second position. When the cap 210d is in the second position, the cap 210d at least partially exposes the heating element 223d. In the second position, the cap 210d does not cover the transverse cavity 227d to partially expose the heating element 223d. When the heating element 223d is partially exposed, the heating element 223d may be examined visually to ascertain if cleaning of the heating element 223d is required. If required, when the cap 210d is in the second position, the heating element 223d may be cleaned by blowing air through the opening or simply shaking, tilting and or tapping the device gently to dislodge and remove loose debris. In the second position, the abutment surface 233d of the cap 210d may abut the peripheral surface 234d as discussed in the foregoing description.

The device 201d comprises a heater 204d comprising heating element 223d. The heater 204d forms part of the body 209d of the device 201d and is rigidly mounted to the body 209d. In the illustrated embodiment, the heater 204d is a rod heater with a heating element 223d having a circular transverse profile. In other embodiments the heater may be in the form of a blade heater (e.g., heating element with a rectangular transverse profile) or a tube heater (e.g., heating element with a tubular form).

The heating element 223d of the heater 204d projects from an internal base of the cavity 222d along a longitudinal axis towards the opening 221d. As is apparent from the figure, the length (i.e., along the longitudinal axis) of the heating element is less than a depth of the cavity 222d. In this way, the heating element 223d does not protrude from or extend beyond the opening 221d.

When the consumable 202d is received in the cavity 222d (as is shown in FIG. 22E), the heating element 223d penetrates the aerosol-forming substrate 213d of the consumable 202d. In particular, the heating element 223d extends for nearly the entire axial length of the aerosol-forming substrate 213d when inserted therein. Thus, when the heater 204d is activated, heat is transferred radially from an outer circumferential surface of the heating element 223d to the aerosol-forming substrate 213d.

The smoking substitute system of the present disclosure may further include a tool 235d for separation of the cap 210d from the body 209d. The tool 235d may be configured to displace the locking arms 229d to enable separation of the cap 210d from the body 209d. FIG. 5A, FIG. 5B, and FIG. 5C illustrate a tool 235d in accordance with an embodiment. The tool 235d has at least one unlocking arm 230d. In the embodiment as illustrated, two unlocking arms 230d are provided. The number of unlocking arms 230d may be provided as required. In an embodiment, the number of unlocking arms 230d may correspond to the number of locking arms 229d. The unlocking arms 230d are adapted to engage the locking arms 229d to displace the locking arms 229d for separating the cap 210d from the body 209d. Each unlocking arm 230d may be provided with an unlocking protrusion 236d. The unlocking protrusion 236d may extend in a direction orthogonal to the longitudinal axis of the unlocking arm 230d. The unlocking protrusions 236d are adapted to engage the locking protrusions 231d to displace the locking protrusions 231d for releasing the cap 210d from the body 209d.

Figure 26A:
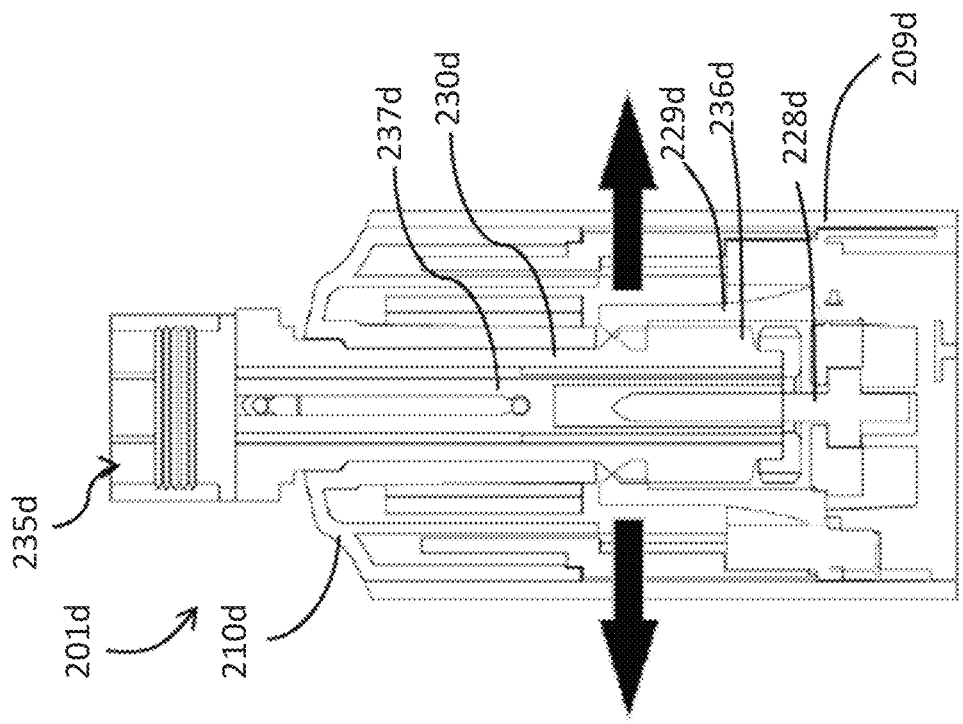
FIG. 26A is a section view of the first embodiment of the fourth mode with the tool inserted in the cavity in insertion position.
Figure 26B:
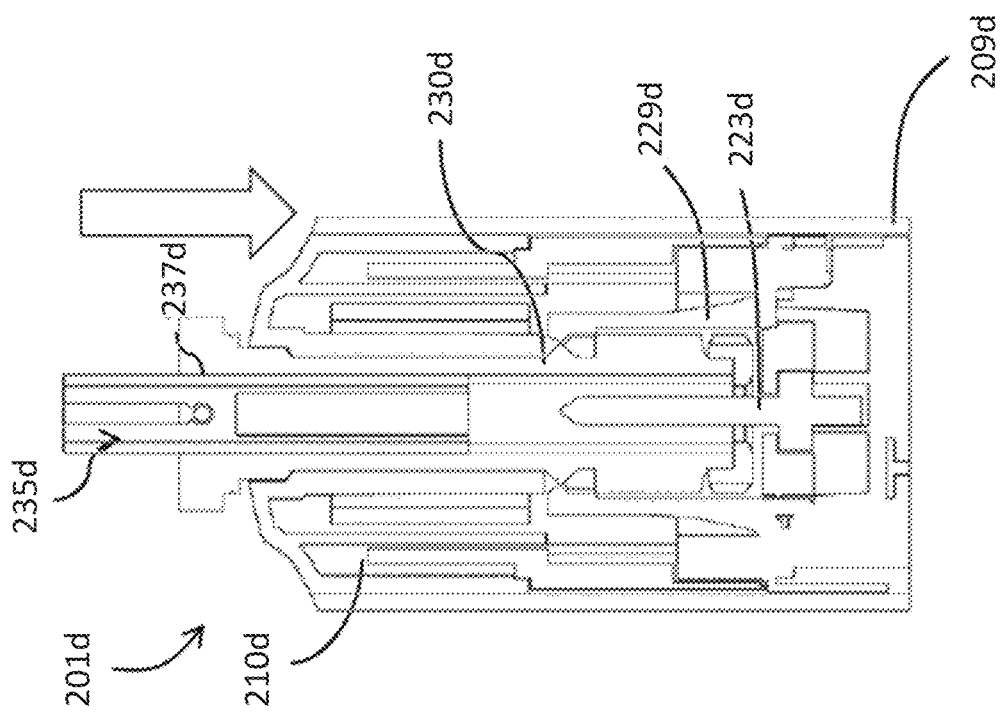
FIG. 26B is a section view of the first embodiment of the fourth mode with the tool inserted in the cavity in unlocking position.

The tool 235d may include a central rod 237d. A collar 238d may be positioned concentrically around the central rod 237d. The collar 238d may be placed movably on the rod such that the collar 238d moves relative to the central rod 237d along a longitudinal axis of the central rod 237d. The unlocking arms 230d may extend from the collar 238d along the longitudinal axis of the central rod 237d. The collar 238d may be movable on the central rod 237d between an insertion position and an unlocking position. In the insertion position, the central rod 237d may be kept away from the unlocking protrusions 236d and the unlocking arms 230d may flex radially inwards relative to the longitudinal axis of the central rod 237d. In FIG. 25B and FIG. 26A, the collar 238d is shown in the insertion position. In the unlocking position, the central rod 237d moves in juxtaposition with the unlocking protrusions 236d to prevent flexing of the unlocking arms 230d in a direction radially inwards relative to the longitudinal axis of the central rod 237d. FIG. 26B illustrates the collar 238d in the unlocking position. Suitable provision may be provided on the collar 238d and the rod to enable and/or guide movement of the collar 238d between the insertion position and the unlocking position. The collar 238d may be biased to move towards the insertion position using any suitable means such as a coil spring.

The tool 235d may be configured for insertion into the cavity 222d as shown through FIGS. 7A-E. The unlocking protrusions 236d are configured such that when the unlocking arms 230d are inserted into the cavity 222d, the unlocking arm 230d displaces the locking arms 229d to release engagement of the locking arms 229d from the slots 232d. In the embodiment as illustrated, the unlocking protrusions 236d are configured such that when inserted into the cavity 222d, the unlocking protrusions 236d enter the slots 232d defined in the cap 210d to displace the locking protrusions 231d, in order to dislodge the cap 210d from the body 209d. The unlocking protrusions 236d may have dimensions that interfere with the width of the cavity 222d. Thus, in order to allow insertion of the unlocking arms 230d in the cavity 222d, in the insertion position, the central rod 237d is away from the distal ends of the unlocking arms 230d to allow the distal ends of the unlocking arms 230d to flex radially inwards to enable insertion of the unlocking arms 230d with the unlocking protrusions 236d into the cavity 222d. The flexing may be achieved when the unlocking protrusions 236d abut and slide against an inner surface 239d of cap 210d defining the internal cavity 222d. The unlocking protrusions 236d, as shown in the embodiment illustrated, may be provided with tapered surfaces 240d to guide the flexing movement of the unlocking arms 230d in and out from the cavity 222d and the slots 232d. FIG. 27a shows the tool 235d being inserted in the cavity 222d with the collar 238d in the insertion position.

In the initial stage, the tool 235d may be pushed towards the body 209d (as indicated by directional arrow in FIG. 26A) to insert the unlocking arms 230d into the cavity 222d until the collar 238*d* abuts the opening of the cavity 222*d* as shown in FIG. 26A and FIG. 27*b*. At this stage, as shown in FIG. 26A, the unlocking arms 230*d* enter the slots 232*d* defined in the cap 210*d*. At this stage, the unlocking protrusions 236*d* may not completely displace the locking protrusions 231*d* as required for separation of the cap 210*d*. Further, the central rod 237*d* may be pushed into the cavity 222*d* to move the collar 238*d* (relative to the central rod 237*d*) to the unlocking position as shown in FIG. 26*c*. On pushing the central rod 237*d*, the unlocking protrusion 236*d* may be pushed radially outward to enter the slots 232*d* properly and occupy the slot 232*d* as shown in FIG. 26B, to displace and move the locking protrusions 231*d* radially outward (shown by the arrows) to remove them from the slots 232*d*. After this, the cap 210*d* along with tool 235*d* may be pulled away from the body 209*d* to separate the cap 210*d* from the body 209*d* as shown in FIG. 27*d*. FIG. 27*e* illustrates cap 210*d* completely separated from the body 209*d*.

The tool 235*d* may further have a cleaning means for cleaning the heating element 223*d*. The cleaning means may be in form of cleaning bristles 241*d* as shown in FIG. 25C. The cleaning bristles 241*d* may extend from the central rod 237*d* in a direction opposite to the direction of extension of the unlocking arms 230*d*, as shown in FIG. 25C. The cleaning bristles 241*d* may be rubbed on the outer surface of the heating element 223*d* to clean or scrap off any debris or residuals from the heating element 223*d*.

The tool 235*d* may include a first cover 242*d* to cover the unlocking arms 230*d* when not in use.

Further, a second cover 243*d* may be provided to cover the cleaning bristles 241*d* when not in use. The covers 242*d*, 243*d* may be designed such that the tool 235*d* may visually resemble a consumable for the smoking substitute system. Suitable provisions may be provided to retain the cover on the tool 235*d*.

The device 202*d* further comprises an electronics cavity 224*d*. A power source, in the form of a rechargeable battery 205*d* (a lithium-ion battery), is located in electronics cavity 224*d*.

The device 202*d* includes a connector (i.e., forming part of an IO module of the device 201*d*) in the form of a USB port 206*d*. The connector may alternatively be, for example, a micro-USB port or a USB-C port for examples. The USB port 206*d* may be used to recharge the rechargeable battery 205*d*.

The device 202*d* includes a controller (not shown) located in the electronics cavity 224*d*. The controller comprises a microcontroller mounted on a printed circuit board (PCB). The USB port 206*d* is also connected to the controller 208*d* (i.e., connected to the PCB and microcontroller).

The controller 208*d* is configured to control at least one function of the device 202*d*. For example, the controller 208*d* is configured to control the operation of the heater 204*d*. Such control of the operation of the heater 204*d* may be accomplished by the controller toggling the electrical connection of the rechargeable battery 205*d* to the heater 204*d*. For example, the controller 208*d* is configured to control the heater 204*d* in response to a user depressing the button 212*d*. Depressing the button 212*d* may cause the controller to allow a voltage (from the rechargeable battery 205*d*) to be applied to the heater 204*d* (so as to cause the heating element 223*d* to be heated).

The controller is also configured to control the LEDs 211*d* in response to (e.g., a detected) a condition of the device 201*d* or the consumable 202*d*. For example, the controller may control the LEDs to indicate whether the device 201*d* is in an on state or an off state (e.g., one or more of the LEDs may be illuminated by the controller when the device is in an on state).

The device 202*d* comprises a further input means (i.e., in addition to the button 212*d*) in the form of a puff sensor 225*d*. The puff sensor 225*d* is configured to detect a user drawing (i.e., inhaling) at the downstream end 218*d* of the consumable 202*d*. The puff sensor 225*d* may, for example, be in the form of a pressure sensor, flowmeter or a microphone. The puff sensor 225*d* is operatively connected to the controller 208*d* in the electronics cavity 224*d*, such that a signal from the puff sensor 225*d*, indicative of a puff state (i.e., drawing or not drawing), forms an input to the controller 208*d* (and can thus be responded to by the controller 208*d*).

Fifth Mode: A Smoking Substitute Device Provided with Increased Stability of the Consumable During Removal Aspects and embodiments of the fifth mode of the present disclosure will now be discussed with reference to the accompanying figures. Further aspects and embodiments of the fifth mode will be apparent to those skilled in the art. All documents mentioned in this text are incorporated herein by reference.

Figure 28:
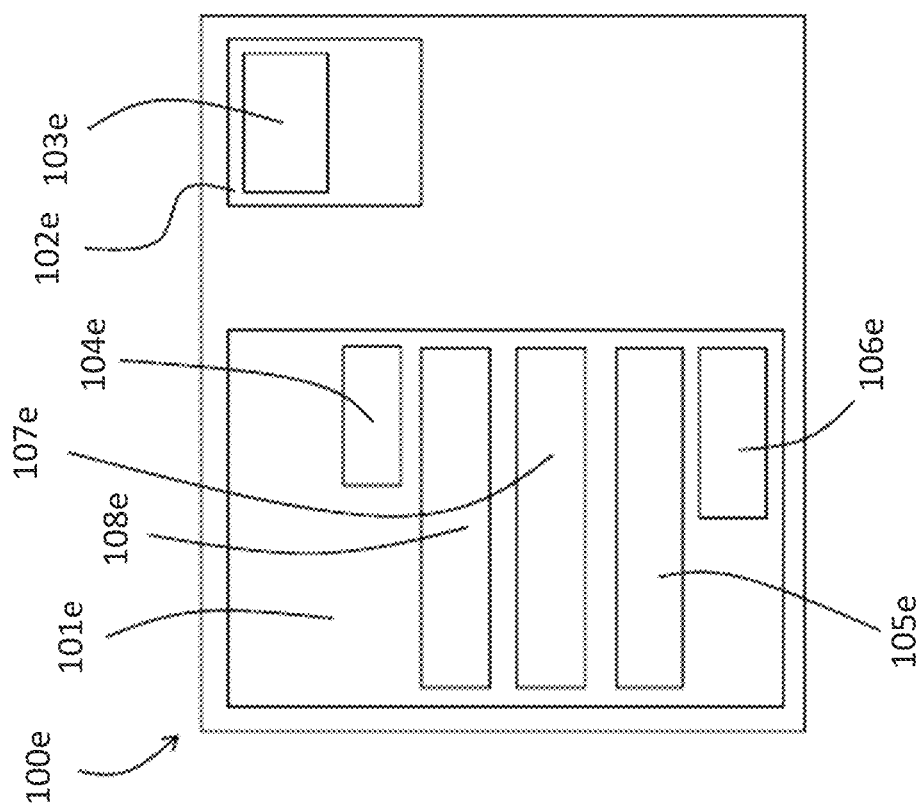
FIG. 28 is a schematic of a smoking substitute system of the fifth mode.

FIG. 28 is a schematic providing a general overview of a smoking substitute system 100*e*. The system 100*e* includes a substitute smoking device 101*e* and an aerosol-forming article in the form of a consumable 102*e*, which comprises an aerosol former 103*e*. The system is configured to vaporize the aerosol former by heating the aerosol former 103*e* (so as to form a vapor/aerosol for inhalation by a user).

The heater 104*e* forms part of the device 101*e* and is configured to heat the aerosol former 103*e*. The heater 104*e* is electrically connected to a power source 105*e*. Heat from the heater 104*e* vaporizes the aerosol former 103*e* to produce a vapor. The vapor subsequently condenses to form an aerosol, which is ultimately inhaled by the user.

As above, the system 100*e* comprises a power source 105*e* that forms part of the device 101*e*. In other embodiments the power source 105*e* may be external to (but connectable to) the device 101*e*. The power source 105*e* is electrically connected to the heater 104*e* such that it is able to supply power to the heater 104*e* (i.e., for the purpose of heating the aerosol former 103*e*). Thus, control of the electrical connection of the power source 105*e* to the heater 104*e* provides control of the state of the heater 104*e*. The power source 105*e* may be a power store, for example a battery or rechargeable battery (e.g., a lithium-ion battery).

The system 100*e* further comprises an I/O module comprising a connector 106*e* (e.g., in the form of a USB port, Micro USB port, USB-C port, etc.). The connector 106*e* is configured for connection to an external source of electrical power, e.g., a mains electrical supply outlet. The connector 106*e* may be used in substitution for the power source 105*e*. That is, the connector 106*e* may be electrically connectable to the heater 104*e* so as to supply electricity to the heater 104*e*. In such embodiments, the device may not include a power source, and the power source of the system may instead comprise the connector 106*e* and an external source of electrical power (to which the connector 106*e* provides electrical connection).

In some embodiments, the connector 106*e* may be used to charge and recharge the power source 105*e* where the power source 105*e* includes a rechargeable battery.

The system 100*e* also comprises a user interface (UI) 107*e*. Although not shown, the UI 107*e* may include input means to receive commands from a user. The input means of the UI 107*e* allows the user to control at least one aspect of the operation of the system 100e. The input means may, for example, be in the form of a button, touchscreen, switch, microphone, etc.

The UI 107e also comprises output means to convey information to the user. The output means may, for example, comprise lights (e.g., LEDs), a display screen, speaker, vibration generator, etc.

The system 100e further comprises a controller 108e that is configured to control at least one function of the device 101e. In the illustrated embodiment, the controller 108e is a component of the device 101e, but in other embodiments may be separate from (but connectable to) the device 101e. The controller 108e is configured to control the operation of the heater 104e and, for example, may be configured to control the voltage applied from the power source 105e to the heater 104e. The controller 108e may be configured to toggle the supply of power to the heater 104e between an on state, in which the full output voltage of the power source 105e is applied to the heater 104e, and an off state, in which the no voltage is applied to the heater 104e.

Although not shown, the system 100e may also comprise a voltage regulator to regulate the output voltage from the power source 105e to form a regulated voltage. The regulated voltage may then be applied to the heater 104e.

In addition to being connected to the heater 104e, the controller 108e is operatively connected to the UI 107e. Thus, the controller 108e may receive an input signal from the input means of the UI 107e. Similarly, the controller 108e may transmit output signals to the UI 107e. In response, the output means of the UI 107e may convey information, based on the output signals, to a user. The controller also comprises a memory 109e, which is a non-volatile memory. The memory 109e includes instructions, which, when implemented, cause the controller to perform certain tasks or steps of a method.

FIG. 29A and FIG. 29B illustrate a heated-tobacco (HT) smoking substitute system 200e. The system 200e is an example of the system 100e described in relation to FIG. 28. System 200e includes an HT device 201e and an HT consumable 202e. The description of FIG. 28 above is applicable to the system 200e of FIG. 29A and FIG. 29B, and will thus not be repeated.

The device 201e and the consumable 202e are configured such that the consumable 202e can be engaged with the device 201e. FIG. 29A shows the device 201e and the consumable 202e in an engaged state, whilst FIG. 29B shows the device 201e and the consumable 202e in a disengaged state.

The device 201e comprises a body 209e and cap 210e. In use the cap 210e is engaged at an end of the body 209e. Although not apparent from the figures, the cap 210e is moveable relative to the body 209e. In particular, the cap 210e is slidable and can slide along a longitudinal axis of the body 209e between first and second positions by a sliding mechanism.

The device 201e comprises an output means (forming part of the UI of the device 201e) in the form of a plurality of light-emitting diodes (LEDs) 211e arranged linearly along the longitudinal axis of the device 201e and on an outer surface of the body 209e of the device 201e. A button 212e is also arranged on an outer surface of the body 209e of the device 201e and is axially spaced (i.e., along the longitudinal axis) from the plurality of LEDs 211e.

Figure 29C:
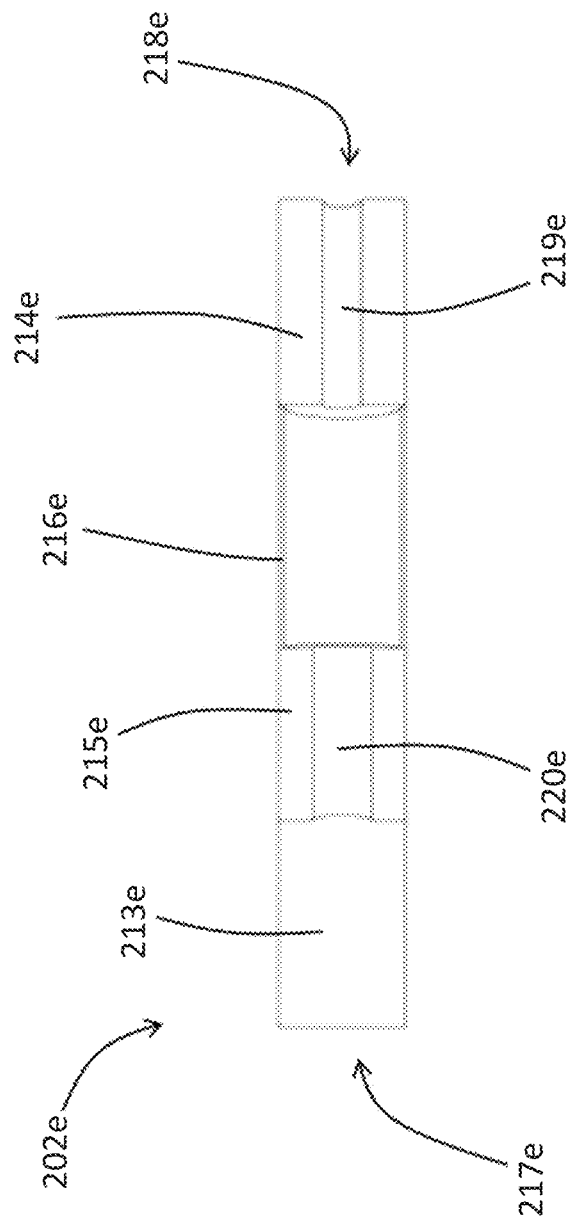
FIG. 29C is a section view of the consumable of the first embodiment of the fifth mode of the smoking substitute system.

FIG. 29C show a detailed section view of the consumable 202e of the system 200e. The consumable 202e generally resembles a cigarette. In that respect, the consumable 202e has a generally cylindrical form with a diameter of 7 mm and an axial length of 70 mm. The consumable 202e comprises an aerosol forming substrate 213e, a terminal filter element 214e, an upstream filter element 215e and a spacer element 216e. In other embodiments, the consumable may further comprise a cooling element. A cooling element may exchange heat with vapor that is formed by the aerosol-forming substrate 213e in order to cool the vapor so as to facilitate condensation of the vapor.

The aerosol-forming substrate 213e is substantially cylindrical and is located at an upstream end 217e of the consumable 202e, and comprises the aerosol former of the system 200e. In that respect, the aerosol forming substrate 213e is configured to be heated by the device 201e to release a vapor. The released vapor is subsequently entrained in an airflow flowing through the aerosol-forming substrate 213e. The airflow is produced by the action of the user drawing on a downstream 218e (i.e., terminal or mouth) end of the consumable 202e.

In the present embodiment, the aerosol forming substrate 213e comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213e may comprise a gathered sheet of homogenized (e.g., paper/slurry recon) tobacco or gathered shreds/strips formed from such a sheet.

In order to generate an aerosol, the aerosol forming substrate 213e comprises at least one volatile compound that is intended to be vaporized/aerosolized and that may provide the user with a recreational and/or medicinal effect when inhaled. The aerosol-forming substrate 213e may further comprise one or more additives. For example, such additives may be in the form of humectants (e.g., propylene glycol and/or vegetable glycerin), flavorants, fillers, aqueous/non-aqueous solvents and/or binders.

The terminal filter element 214e is also substantially cylindrical, and is located downstream of the aerosol forming substrate 213e at the downstream end 218e of the consumable 202e. The terminal filter element 214e is in the form of a hollow bore filter element having a bore 219e (e.g., for airflow) formed therethrough. The diameter of the bore 219e is 2 mm. The terminal filter element 214e is formed of a porous (e.g., monoacetate) filter material. As set forth above, the downstream end 218e of the consumable 202e (i.e., where the terminal filter 214e is located) forms a mouthpiece portion of the consumable 202e upon which the user draws. Airflow is drawn from the upstream end 217e, thorough the components of the consumable 202e, and out of the downstream end 218e. The airflow is driven by the user drawing on the downstream end 218e (i.e., the mouthpiece portion) of the consumable 202e.

The upstream filter element 215e is located axially adjacent to the aerosol-forming substrate 213e, between the aerosol-forming substrate 213e and the terminal filter element 214e. Like the terminal filter 214e, the upstream filter element 215e is in the form of a hollow bore filter element, such that it has a bore 220e extending axially therethrough. In this way, the upstream filter 215e may act as an airflow restrictor. The upstream filter element 215e is formed of a porous (e.g., monoacetate) filter material. The bore 220e of the upstream filter element 215e has a larger diameter (3 mm) than the terminal filter element 214e.

The spacer 216e is in the form of a cardboard tube, which defines a cavity or chamber between the upstream filter element 215e and the terminal filter element 214e. The spacer 216e acts to allow both cooling and mixing of the vapor/aerosol from the aerosol-forming substrate 213e. The spacer has an external diameter of 7 mm and an axial length of 14 mm.

Although not apparent from the figure, the aerosol-forming substrate 213e, upstream filter 215e and spacer 216e are circumscribed by a paper wrapping layer. The terminal filter 214e is circumscribed by a tipping layer that also circumscribes a portion of the paper wrapping layer (so as to connect the terminal filter 214e to the remaining components of the consumable 202e). The upstream filter 215e and terminal filter 214e are circumscribed by further wrapping layers in the form of plug wraps.

Figures 29D, 29E:
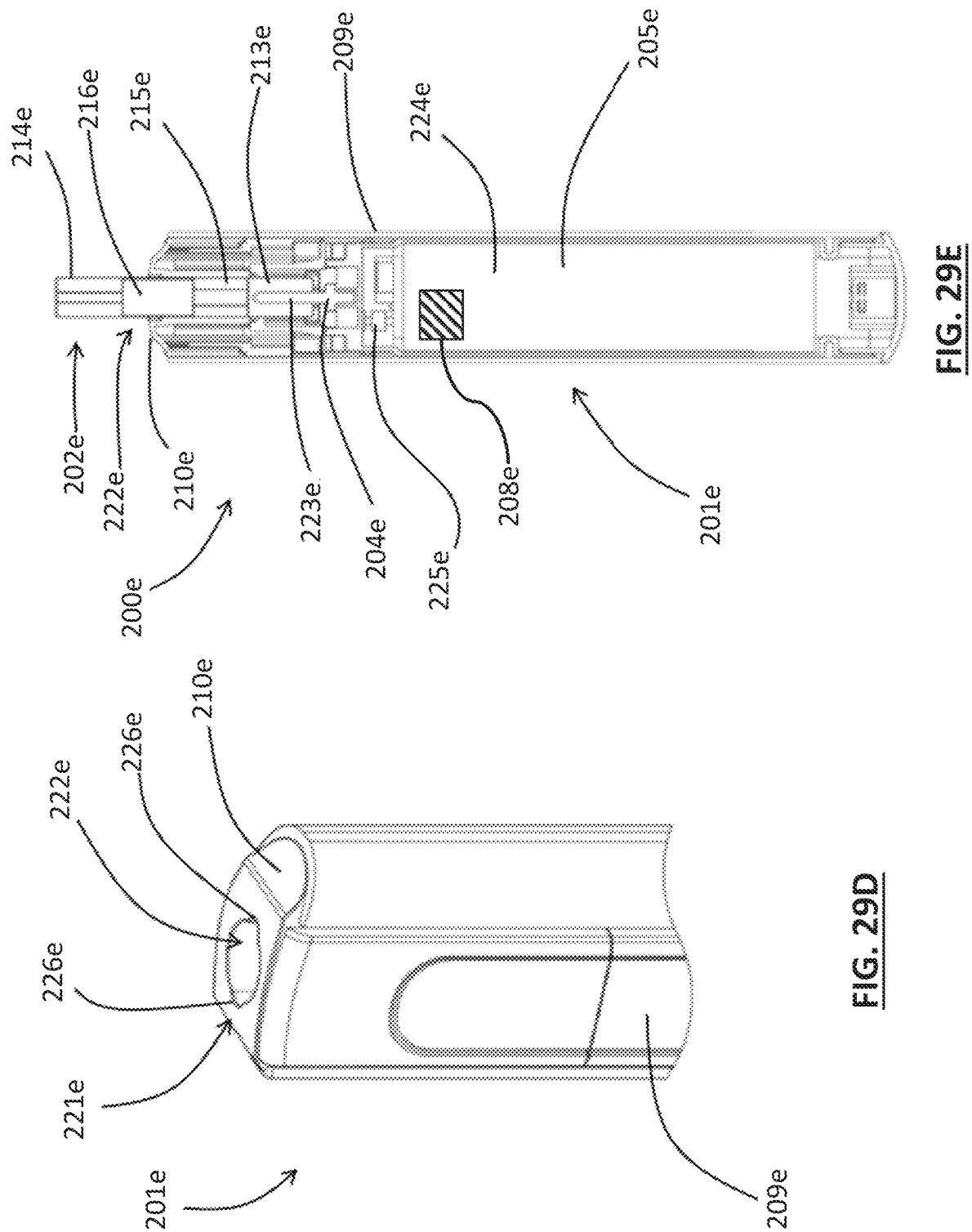
FIG. 29D is a detailed view of an end of the device of the first embodiment of the fifth mode of the smoking substitute system.
FIG. 29E is a section view of the first embodiment of the fifth mode of the substitute smoking system.

Returning now to the device 201e, FIG. 29D illustrates a detailed view of the end of the device 201e that is configured to engage with the consumable 202e. The cap 210e of the device 201e includes an opening 221e to an internal cavity 222e (more apparent from FIG. 29D) defined by the cap 210e. The opening 221e and the cavity 222e are formed so as to receive at least a portion of the consumable 202e. During engagement of the consumable 202e with the device 201e, a portion of the consumable 202e is received through the opening 221e and into the cavity 222e. After engagement (see FIG. 29B), the downstream end 218e of the consumable 202e protrudes from the opening 221e and thus also protrudes from the device 201e. The opening 221e includes laterally disposed notches 226e. When a consumable 202e is received in the opening 221e, these notches 226e remain open and could, for example, be used for retaining a cover in order to cover the end of the device 201e.

FIG. 29E shows a cross section through a central longitudinal plane through the device 201e. The device 201e is shown with the consumable 202e engaged therewith.

The device 201e comprises a heater 204e comprising heating element 223e. The heater 204e forms part of the body 209e of the device 201e and is rigidly mounted to the body 209e. In the illustrated embodiment, the heater 204e is a rod heater with a heating element 223e having a circular transverse profile. In other embodiments the heater may be in the form of a blade heater (e.g., heating element with a rectangular transverse profile) or a tube heater (e.g., heating element with a tubular form).

The heating element 223e of the heater 204e projects from an internal base of the cavity 222e along a longitudinal axis towards the opening 221e. As is apparent from the figure, the length (i.e., along the longitudinal axis) of the heating element is less than a depth of the cavity 222e. In this way, the heating element 223e does not protrude from or extend beyond the opening 221e.

When the consumable 202e is received in the cavity 222e (as is shown in FIG. 29E), the heating element 223e penetrates the aerosol-forming substrate 213e of the consumable 202e. In particular, the heating element 223e extends for nearly the entire axial length of the aerosol-forming substrate 213e when inserted therein. Thus, when the heater 204e is activated, heat is transferred radially from an outer circumferential surface the heating element 223e to the aerosol-forming substrate 213e.

The device 201e further comprises an electronics cavity 224e. A power source, in the form of a rechargeable battery 205e (a lithium-ion battery), is located in electronics cavity 224e.

The device 201e includes a connector (i.e., forming part of an IO module of the device 201e) in the form of a USB port 206e. The connector may alternatively be, for example, a micro-USB port or a USB-C port for examples. The USB port 206e may be used to recharge the rechargeable battery 205e.

The device 201e includes a controller 208e located in the electronics cavity 224e. The controller comprises a microcontroller mounted on a printed circuit board (PCB). The USB port 206e is also connected to the controller 208e (i.e., connected to the PCB and microcontroller).

The controller 208e is configured to control at least one function of the device 202e. For example, the controller 208e is configured to control the operation of the heater 204e. Such control of the operation of the heater 204e may be accomplished by the controller toggling the electrical connection of the rechargeable battery 205e to the heater 204e. For example, the controller 208e is configured to control the heater 204e in response to a user depressing the button 212e. Depressing the button 212e may cause the controller to allow a voltage (from the rechargeable battery 205e) to be applied to the heater 204e (so as to cause the heating element 223e to be heated).

The controller is also configured to control the LEDs 211e in response to (e.g., a detected) a condition of the device 201e or the consumable 202e. For example, the controller may control the LEDs to indicate whether the device 201e is in an on state or an off state (e.g., one or more of the LEDs may be illuminated by the controller when the device is in an on state).

The device 201e comprises a further input means (i.e., in addition to the button 212e) in the form of a puff sensor 225e. The puff sensor 225e is configured to detect a user drawing (i.e., inhaling) at the downstream end 218e of the consumable 202e. The puff sensor 225e may, for example, be in the form of a pressure sensor, flowmeter or a microphone. The puff sensor 225e is operatively connected to the controller 208e in the electronics cavity 224e, such that a signal from the puff sensor 225e, indicative of a puff state (i.e., drawing or not drawing), forms an input to the controller 208e (and can thus be responded to by the controller 208e).

Figure 29F:
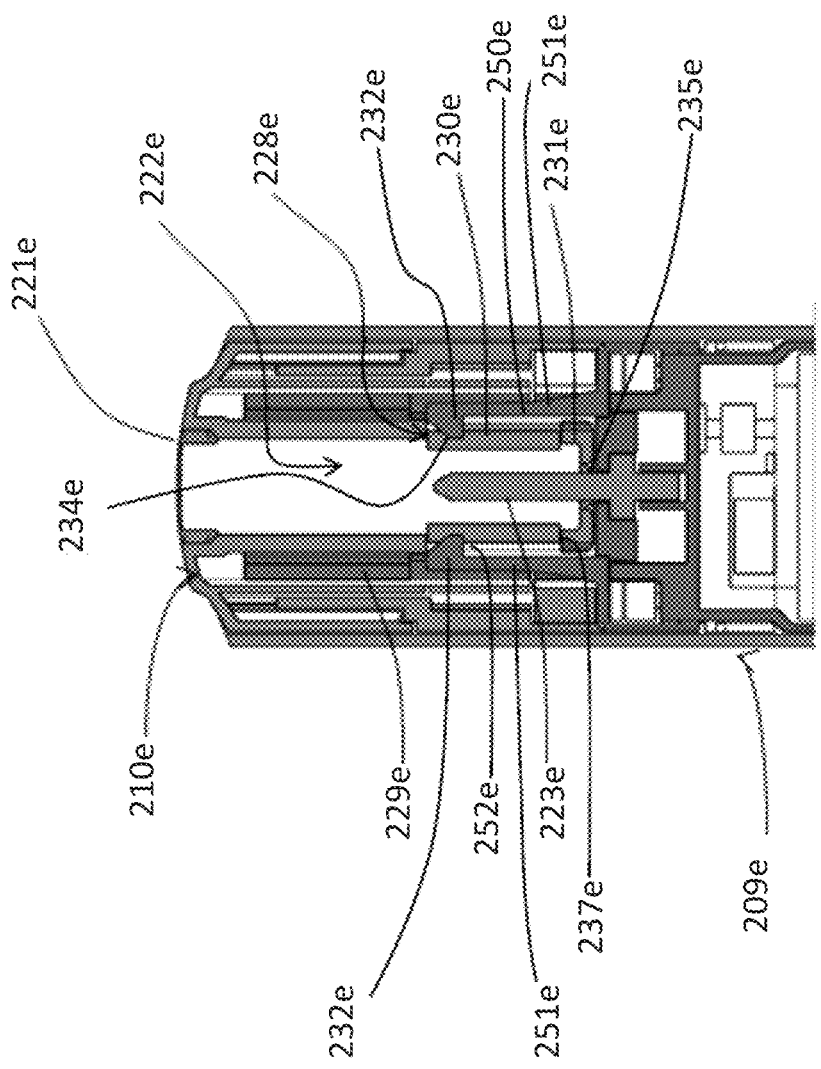
FIG. 29F is a detail section view of a portion of the first embodiment of the fifth mode, showing a cap of the device in the first position.
Figure 29G:
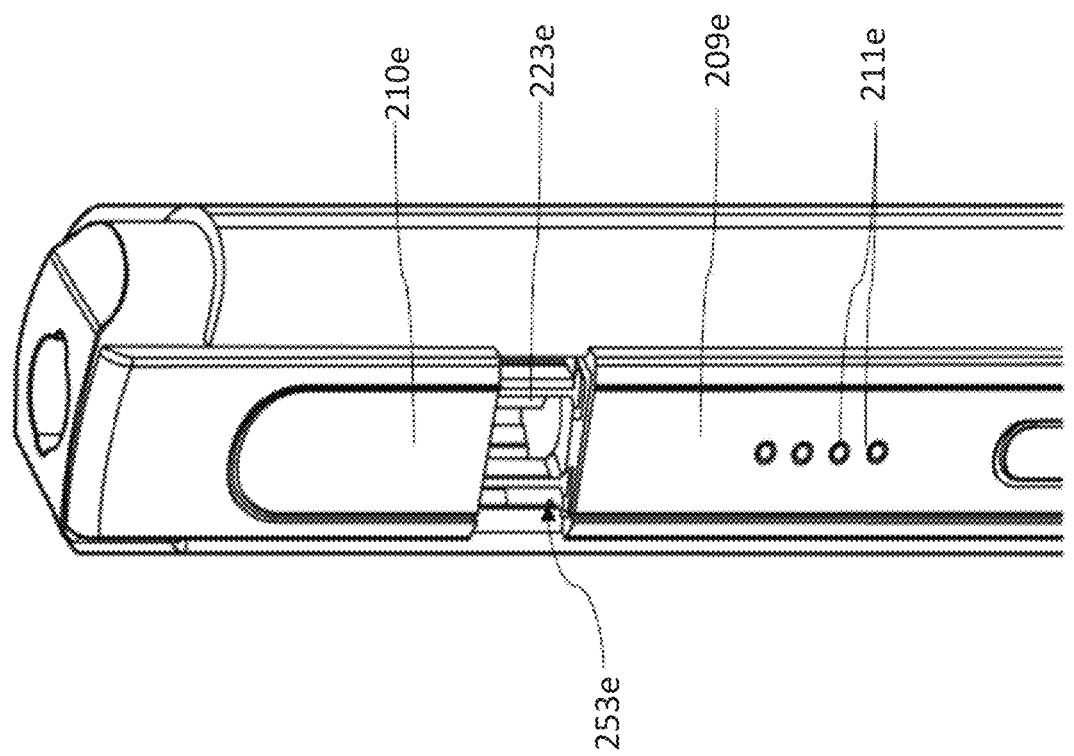
FIG. 29G is a perspective view of the first embodiment of the fifth mode showing the cap in the second position.
Figure 29H:
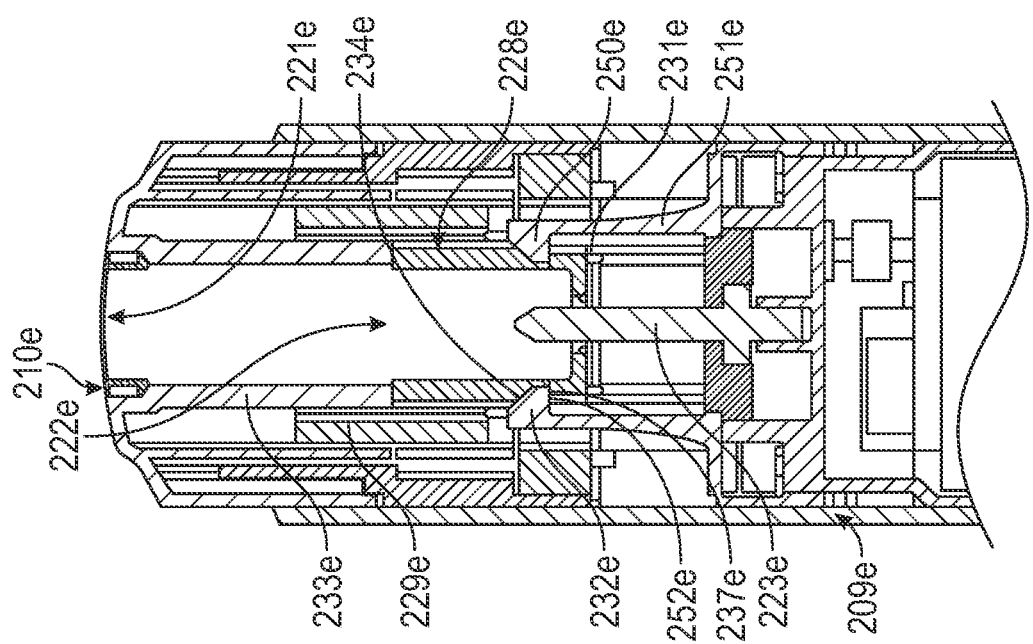
FIG. 29H is a detail section view of the first embodiment of the fifth mode, showing the cap in the second position.

As is set forth above, the cap 210e is slidable between first and second positions. This is best illustrated by FIG. 29F, FIG. 29G, FIG. 29H. and FIG. 29F shows the cap 210e in the first position. In this position, a central portion 233e of the cap 210e is received in a cavity defined by a tubular portion 229e of the device body 209e. A base portion 231e of the cap 210e abuts a base of the cavity (of the body 209e) and the heating element 223e projects longitudinally through an aperture 235e formed in the base portion 231e.

The body 209e comprises two stop features in the form of spaced opposing elongate engagement members 250e that extend longitudinally. The engagement members 250e each comprise a flexible arm 251e and an inwardly protruding hook portion 232e disposed at a distal end of the flexible arm 251e. Each hook portion 232e comprises an engagement surface 252e (defining an underside of the hook portion 232e) and an opposing ramp surface 234e (which defines a distal leading surface of the hook portion 232e). The elongate engagement members 250e are configured to flex such that their respective hook portions 232e move laterally (with respect to the longitudinal axis) between an engaged position and a disengaged position. In this respect, the hook portions 232e each define a free end of their respective engagement member 250e.

When the cap 210e is received in the tubular portion 229e of the body 209e, the hook portions 232e are moved outwards by contact of a leading edge of the cap 210e with the ramp surfaces 234e, and then subsequently snap into longitudinally extending apertures 228e formed in the cap 210e. The elongate nature of these apertures 228e allows the cap 210e to move longitudinally with respect to the body 209e (whilst engaged) between the first and second positions. In this respect, the apertures 228e into which the hook portions 232e act as guides that guide the cap 210e along a longitudinal axis.

As discussed above, in FIG. 29F the cap 210e is shown in the first position. Conversely, in FIG. 29G and FIG. 29H, the cap 210e is shown in the second position in which the cap 210e has been slid in a longitudinal direction away from the body 209e. When in this second position, a gap 253e is formed between the cap 210e and the body 209e for accessing the heating element 223e (See FIG. 29G).

In the second position, the engagement surfaces 252e of the hook portions 232e abut (i.e., so as to engage with) respective lower edges 237e of the apertures 228e formed in cap 210e. This interaction between the lower edges 237e and the engagement surfaces 252e prevents further longitudinal movement of the cap 210e away from the body 209e. The cap 210e may be partially retained in the first and second positions by detents such as bump features (e.g., protrusions interacting with the hook portions 232e) or an arrangement of magnets.

The cap 210e can only be fully disengaged (or released) from the body 209e by moving the hook portions 232e outwardly. This may be performed through the use of a tool (not shown) inserted into the cavity 222e of the cap 210e so as to force the hook portions 232e outwards.

For clarity, the consumable 202e is not shown in FIG. 29F, FIG. 29G, and FIG. 29H. However, it should be appreciated that when a consumable 202e is engaged with the device 201e, it substantially fills the cavity 222e (as shown in FIG. 29E). Thus, in the first position, substantially the entire length of the heating element 223e is received in the consumable 202e. When the cap 210e is moved longitudinally towards the second position, the base portion 231e of the cap 210e engages an upstream end of the consumable 202e and moves the consumable 202e longitudinally along the heating element 223e (to the second position). At this point, the engagement of the hook portions 232e with the edges 237e of the apertures 228e prevents further longitudinal movement of the cap 210e. In the second position, a distal end of the heating element 223e projects into the cavity 222e, such that when a consumable is received in the cavity 222e, that portion of the heating element 223e projects into the consumable 202e. Thus, a portion at the distal end of the heating element 223e is received in the consumable 202e in both of the first and second positions, and during movement between the first and second positions. This is at least partly a result of the longitudinal length of the heating element 223e being larger than the distance the cap 210e moves between the first and second positions.

Whilst not shown, a portion (e.g., outer surface) of the cap 210e may comprise a gripping region (e.g., a tactile finish), to facilitate gripping of the cap 210e by a user during movement of the cap 210e between the first position and the second position. Further, the device 201e may be configured to prevent the use of heater when the cap 210e is in second position by means of a sensor which can detect position of the cap 210e. The sensor may form part of the body 209e of the device 201e to detect the position of the cap 210e.

Sixth Mode: A HNB Device Having Air Inlets for Facilitating Airflow to Enter the Housing of the HNB Device Adjacent to an End of Aerosol-Forming Article Aspects and embodiments of the sixth mode of the present disclosure will now be discussed with reference to the accompanying figures. Further aspects and embodiments of the sixth mode will be apparent to those skilled in the art. All documents mentioned in this text are incorporated herein by reference.

Figure 30B:
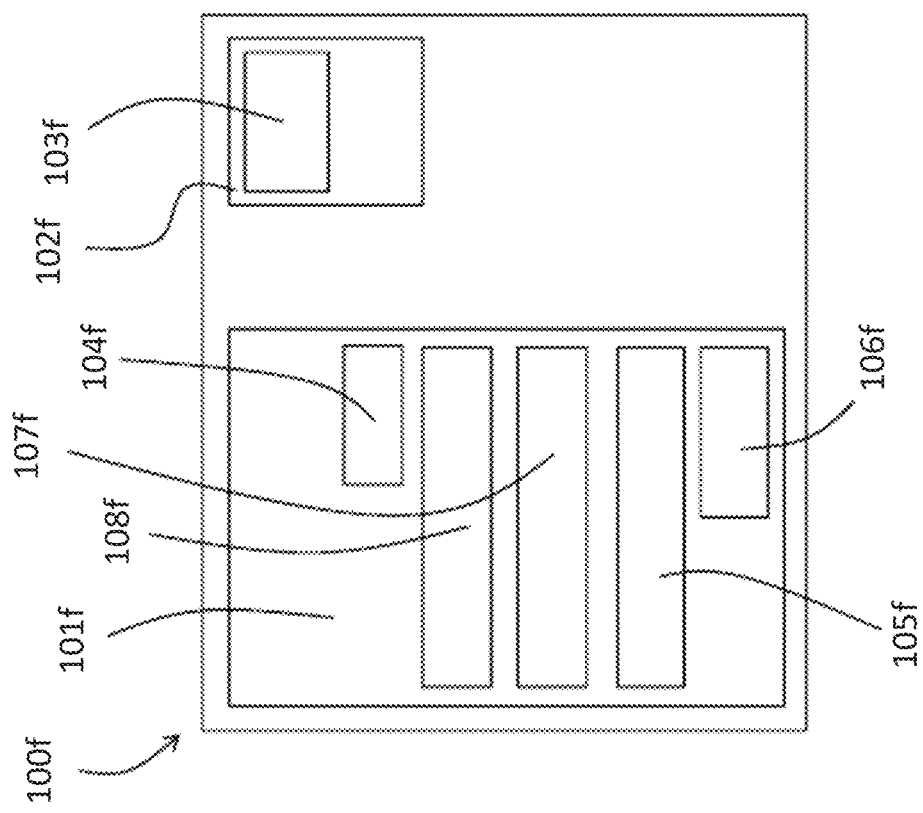
FIG. 30B is a schematic of a variation of the smoking substitute system of FIG. 30A.
Figure 30A:
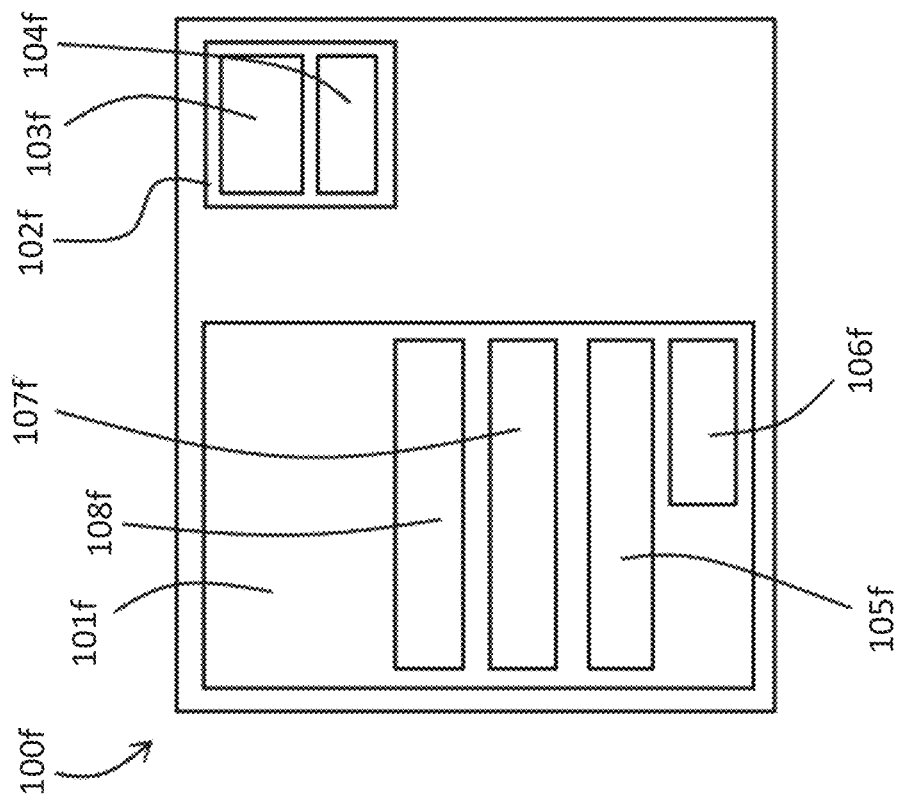
FIG. 30A is a schematic of a smoking substitute system of the sixth mode.

FIG. 30A is a schematic providing a general overview of a smoking substitute system 100f. The system 100f includes a substitute smoking device 101f and an aerosol-forming article in the form of a consumable 102f, which comprises an aerosol former 103f. The system is configured to vaporize the aerosol former by heating the aerosol former 103f (so as to form a vapor/aerosol for inhalation by a user).

In the illustrated system, the heater 104f forms part of the consumable 102f and is configured to heat the aerosol former 103f. In this variation, the heater 104f is electrically connectable to the power source 105f, for example, when the consumable 102f is engaged with the device 101f. Heat from the heater 104f vaporizes the aerosol former 103f to produce a vapor. The vapor subsequently condenses to form an aerosol, which is ultimately inhaled by the user.

The system 100f further comprises a power source 105f that forms part of the device 101f. In other embodiments the power source 105f may be external to (but connectable to) the device 101f. The power source 105f is electrically connectable to the heater 104f such that it is able to supply power to the heater 104f (i.e., for the purpose of heating the aerosol former 103f). Thus, control of the electrical connection of the power source 105f to the heater 104f provides control of the state of the heater 104f. The power source 105f may be a power store, for example a battery or rechargeable battery (e.g., a lithium-ion battery).

The system 100f further comprises an I/O module comprising a connector 106f (e.g., in the form of a USB port, Micro USB port, USB-C port, etc.). The connector 106f is configured for connection to an external source of electrical power, e.g., a mains electrical supply outlet. The connector 106f may be used in substitution for the power source 105f. That is the connector 106f may be electrically connectable to the heater 104f so as to supply electricity to the heater 104f. In such embodiments, the device may not include a power source, and the power source of the system may instead comprise the connector 106f and an external source of electrical power (to which the connector 106f provides electrical connection).

In some embodiments, the connector 106f may be used to charge and recharge the power source 105f where the power source 105f includes a rechargeable battery.

The system 100f also comprises a user interface (UI) 107f. Although not shown, the UI 107f may include input means to receive commands from a user. The input means of the UI 107f allows the user to control at least one aspect of the operation of the system 100f. The input means may, for example, be in the form of a button, touchscreen, switch, microphone, etc.

The UI 107f also comprises output means to convey information to the user. The output means may, for example, comprise lights (e.g., LEDs), a display screen, speaker, vibration generator, etc.

The system 100f further comprises a controller 108f that is configured to control at least one function of the device 101f. In the illustrated embodiment, the controller 108f is a component of the device 101f, but in other embodiments may be separate from (but connectable to) the device 101f.

The controller 108f is configured to control the operation of the heater 104f and, for example, may be configured to control the voltage applied from the power source 105f to the heater 104f. The controller 108f may be configured to toggle the supply of power to the heater 104f between an on state, in which the full output voltage of the power source 105f is applied to the heater 104f, and an off state, in which the no voltage is applied to the heater 104f.

Although not shown, the system 100f may also comprise a voltage regulator to regulate the output voltage from the power source 105f to form a regulated voltage. The regulated voltage may then be applied to the heater 104f.

In addition to being connected to the heater 104f, the controller 108f is operatively connected to the UI 107f. Thus, the controller 108f may receive an input signal from the input means of the UI 107f. Similarly, the controller 108f may transmit output signals to the UI 107f. In response, the output means of the UI 107f may convey information, based on the output signals, to a user. The controller also comprises a memory 109f, which is a non-volatile memory. The memory 109f includes instructions, which, when implemented, cause the controller to perform certain tasks or steps of a method.

FIG. 30B is a schematic showing a variation of the system 100f of FIG. 30A. In the system 100r of FIG. 30B, the heater 104f forms part of the device 101f, rather than the consumable 102f. In this variation, the heater 104f is electrically connected to the power source 105f.

FIG. 31A illustrates a heated-tobacco (HT) smoking substitute system 200f. The system 200f is an example of the systems 100f, 100r described in relation to FIG. 30A or FIG. 30B. System 200f includes an HT device 201f and an HT consumable 202f. The description of FIG. 30A and FIG. 30B above is applicable to the system 200f of FIG. 31A and FIG. 31B, and will thus not be repeated.

The device 201f and the consumable 202f are configured such that the consumable 202f can be engaged with the device 201f. FIG. 31A shows the smoking substitute system 200f comprising a heat not burn device 201f (hereinafter referred as heat not burn device) and the consumable 202f, engaged with the heat not burn device 201f.

Referring to FIG. 2B, the device 201f comprises a housing 209f and a cap 210f. In use the cap 210f is engaged at an end of the housing 209f. Although not apparent from the figures, the cap 210f is moveable relative to the housing 209f. In particular, the cap 210f is slideable and can slide along a longitudinal axis of the housing 209f.

In an embodiment, and referring to FIG. 31B, the housing 209f of the device 201f, may be an elongated member, with a length of the housing 209f greater than thickness of the housing 209f. Thus, the major surface of the housing 209f may be at least one of a front face and a rear face of the housing 209f, which possess surface area greater than that of the side surfaces. The first major surface may be a front face of the housing 209f.

The device 201f comprises an output means (forming part of the UI of the device 201f) in the form of a plurality of light-emitting diodes (LEDs) 211f arranged linearly along the longitudinal axis of the device 201f and on an outer surface of the housing 209f of the device 201f. A button 212f is also arranged on an outer surface of the housing 209f of the device 201f and is axially spaced (i.e., along the longitudinal axis) from the plurality of LEDs 211f.

Figure 31C:
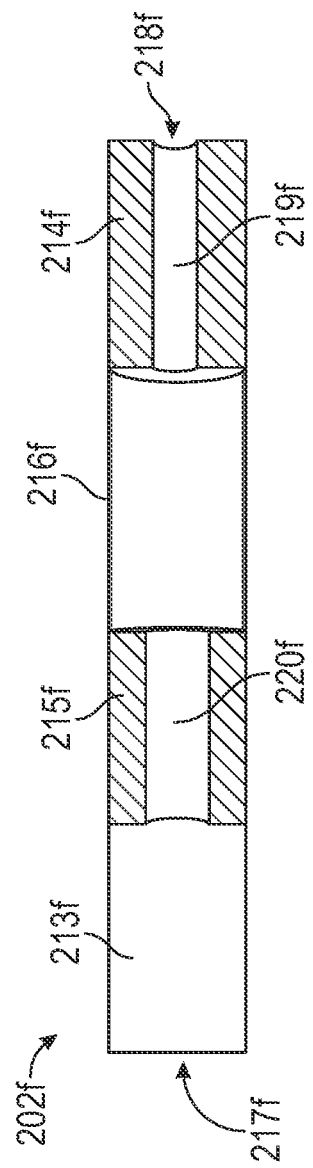
FIG. 31C is a section view of the consumable of the first embodiment of the sixth mode of the smoking substitute system.
Figure 31F:
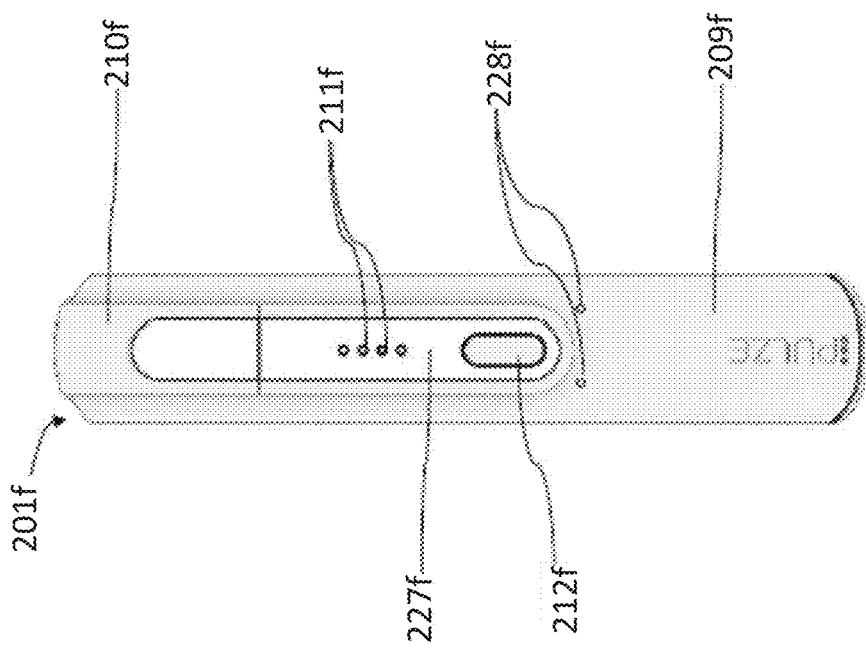
FIG. 31F is a front view of the first embodiment of the sixth mode of the heat not burn device, showing a plurality of air inlets defined at the housing.

FIG. 31C show a detailed section view of the consumable 202f of the system 200f. The consumable 202f generally resembles a cigarette. In that respect, the consumable 202f has a generally cylindrical form with a diameter of 7 mm and an axial length of 70 mm. The consumable 202f comprises an aerosol forming substrate 213f, a terminal filter element 214f, an upstream filter element 215f and a spacer element 216f. In other embodiments, the consumable may further comprise a cooling element. A cooling element may exchange heat with vapor that is formed by the aerosol-forming substrate 213f in order to cool the vapor so as to facilitate condensation of the vapor.

The aerosol-forming substrate 213f is substantially cylindrical and is located at an upstream end 217f of the consumable 202f, and comprises the aerosol former of the system 200f. In that respect, the aerosol forming substrate 213f is configured to be heated by the device 201f to release a vapor. The released vapor is subsequently entrained in an airflow flowing through the aerosol-forming substrate 213f. The airflow is produced by the action of the user drawing on a downstream 218f (i.e., terminal or mouth) end of the consumable 202f.

In the present embodiment, the aerosol forming substrate 213f comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213f may comprise a gathered sheet of homogenized (e.g., paper/slurry recon) tobacco or gathered shreds/strips formed from such a sheet.

In order to generate an aerosol, the aerosol forming substrate 213f comprises at least one volatile compound that is intended to be vaporized/aerosolized and that may provide the user with a recreational and/or medicinal effect when inhaled. The aerosol-forming substrate 213f may further comprise one or more additives. For example, such additives may be in the form of humectants (e.g., propylene glycol and/or vegetable glycerin), flavorants, fillers, aqueous/non-aqueous solvents and/or binders.

The terminal filter element 214f is also substantially cylindrical, and is located downstream of the aerosol forming substrate 213f at the downstream end 218f of the consumable 202f. The terminal filter element 214f is in the form of a hollow bore filter element having a bore 219f (e.g., for airflow) formed therethrough. The diameter of the bore 219f is 2 mm. The terminal filter element 214f is formed of a porous (e.g., monoacetate) filter material. As set forth above, the downstream end 218f of the consumable 202f (i.e., where the terminal filter 214f is located) forms a mouthpiece portion of the consumable 202f upon which the user draws. Airflow is drawn from the upstream end 217f, thorough the components of the consumable 202f, and out of the downstream end 218f. The airflow is driven by the user drawing on the downstream end 218f (i.e., the mouthpiece portion) of the consumable 202f.

The upstream filter element 215f is located axially adjacent to the aerosol-forming substrate 213f, between the aerosol-forming substrate 213f and the terminal filter element 214f. Like the terminal filter 214f, the upstream filter element 215f is in the form of a hollow bore filter element, such that it has a bore 220f extending axially therethrough. In this way, the upstream filter 215f may act as an airflow restrictor. The upstream filter element 215f is formed of a porous (e.g., monoacetate) filter material. The bore 220f of the upstream filter element 215f has a larger diameter (3 mm) than the terminal filter element 214f.

The spacer 216f is in the form of a cardboard tube, which defines a cavity or chamber between the upstream filter element 215f and the terminal filter element 214f. The spacer 216f acts to allow both cooling and mixing of the vapor/aerosol from the aerosol-forming substrate 213f. The spacer has an external diameter of 7 mm and an axial length of 14 mm.

Although not apparent from the figure, the aerosol-forming substrate 213f, upstream filter 215f and spacer 216f are circumscribed by a paper wrapping layer. The terminal filter 214f is circumscribed by a tipping layer that also circumscribes a portion of the paper wrapping layer (so as to connect the terminal filter 214f to the remaining components of the consumable 202f). The upstream filter 215f and terminal filter 214f are circumscribed by further wrapping layers in the form of plug wraps.

Returning now to the device 201f, FIG. 31D illustrates a detailed view of the end of the device 201f that is configured to engage with the consumable 202f. The cap 210f of the device 201f includes an opening 221f to an internal cavity 222f (more apparent from FIG. 31D) defined by the cap 210f. The opening 221f and the cavity 222f are formed so as to receive at least a portion of the consumable 202f. During engagement of the consumable 202f with the device 201f, a portion of the consumable 202f is received through the opening 221f and into the cavity 222f. After engagement (see FIG. 31B), the downstream end 218f of the consumable 202f protrudes from the opening 221f and thus also protrudes from the device 201f. The opening 221f includes laterally disposed notches 226f. When a consumable 202f is received in the opening 221f, these notches 226f remain open and could, for example, be used for retaining a cover in order to cover the end of the device 201f.

FIG. 31E shows a cross section through a central longitudinal plane through the device 201f. The device 201f is shown with the consumable 202f engaged therewith.

The device 201f comprises a heater 204f comprising heating element 223f. The heater 204f forms part of the housing 209f of the device 201f and is rigidly mounted to the housing 209f. In the illustrated embodiment, the heater 204f is a rod heater with a heating element 223f having a circular transverse profile. In other embodiments the heater may be in the form of a blade heater (e.g., heating element with a rectangular transverse profile) or a tube heater (e.g., heating element with a tubular form).

The heating element 223f of the heater 204f projects from an internal base of the cavity 222f along a longitudinal axis towards the opening 221f. As is apparent from the figure, the length (i.e., along the longitudinal axis) of the heating element is less than a depth of the cavity 222f. In this way, the heating element 223f does not protrude from or extend beyond the opening 221f.

When the consumable 202f is received in the cavity 222f (as is shown in FIG. 31E), the heating element 223f penetrates the aerosol-forming substrate 213f of the consumable 202f. In particular, the heating element 223f extends for nearly the entire axial length of the aerosol-forming substrate 213f when inserted therein. Thus, when the heater 204f is activated, heat is transferred radially from an outer circumferential surface the heating element 223f to the aerosol-forming substrate 213f.

The device 201f further comprises an electronics cavity 224f. A power source, in the form of a rechargeable battery 205f (a lithium-ion battery), is located in electronics cavity 224f.

The device 201f includes a connector (i.e., forming part of an IO module of the device 201f) in the form of a USB port 206f. The connector may alternatively be, for example, a micro-USB port or a USB-C port for examples. The USB port 206f may be used to recharge the rechargeable battery 205f.

The device 201f includes a controller (not shown) located in the electronics cavity 224f. The controller comprises a microcontroller mounted on a printed circuit board (PCB). The USB port 206f is also connected to the controller 208f (i.e., connected to the PCB and microcontroller).

The controller 208f is configured to control at least one function of the device 201f. For example, the controller 208f is configured to control the operation of the heater 204f. Such control of the operation of the heater 204f may be accomplished by the controller toggling the electrical connection of the rechargeable battery 205f to the heater 204f. For example, the controller 208f is configured to control the heater 204f in response to a user depressing the button 212f. Depressing the button 212f may cause the controller to allow a voltage (from the rechargeable battery 205f) to be applied to the heater 204f (so as to cause the heating element 223f to be heated).

The controller is also configured to control the LEDs 211f in response to (e.g., a detected) a condition of the device 201f or the consumable 202f. For example, the controller may control the LEDs to indicate whether the device 201f is in an on state or an off state (e.g., one or more of the LEDs may be illuminated by the controller when the device is in an on state).

The device 201f comprises a further input means (i.e., in addition to the button 212f) in the form of a puff sensor 225f. The puff sensor 225f is configured to detect a user drawing (i.e., inhaling) at the downstream end 218f of the consumable 202f. The puff sensor 225f may, for example, be in the form of a pressure sensor, flowmeter or a microphone. The puff sensor 225f is operatively connected to the controller 208f in the electronics cavity 224f, such that a signal from the puff sensor 225f, indicative of a puff state (i.e., drawing or not drawing), forms an input to the controller 208f (and can thus be responded to by the controller 208f).

Referring to FIG. 2F, the housing 209f of the device 201f, is defined with a raised surface 227f. The raised surface 227f extends along a longitudinal axis of the housing 209f, and extends through a substantial length of the housing 209f. Further, the raised surface 227f is configured to accommodate a power button 212f, which is adapted to switch ON/OFF the device 201f, and a plurality of LEDs 211f, which is adapted to indicate operating conditions of the device 201f. The raised surface 227f is adapted to allow the user to hold the device 201f during usage of the device 201f. Further, the raised surface 227f is provided with a tactile finish, which facilitates in gripping the device 201f, by the user.

Further referring to FIG. 2F, the housing 209f of the device 201f is defined with two air inlets 228f, to allow air flow into the housing 209f. The air inlets 228f are defined as a through hole or an apertures. In an embodiment, the plurality of air inlets 228f are defined adjacent to the raised surface 227f on the first major surface of the housing 209f. As an example, the major surface is a front face of the housing 209f. Further, the plurality of air inlets 228f are configured to allow airflow adjacent to the end of the aerosol-forming article or consumable 202f and through the consumable 202f (as seen in FIG. 31E).

In an illustrated embodiment, the plurality of air inlets 228f are defined at the sides of an end of the raised surface 227f on the first major surface of the housing 209f. This location of the plurality of air inlets 228f at the sides of the end of the raised surface 227f, allows air flow to enter into the housing 209f adjacent to the consumable 202f. Further, the plurality of air inlets 228f allow flow of air through the consumable 202f. In some embodiments, the plurality of air inlets 228f, are defined at both sides of the raised surface 227f, at any location along the substantial length of the raised surface 227f.

In some embodiments, as the plurality of air inlets 228f are configured in vicinity of the gripping region (thus, the raised surface 227f), the plurality of air inlets 228f are susceptible to be blocked, during use, by the user. The plurality of air inlets 228f as defined in the housing 209f, may be configured such that, upon blocking of the one or more air inlets of the plurality of air inlets 228f, the other air inlets of the plurality of air inlets 228f, may allow air flow into the housing 209f, adjacent to the consumable 202f.

In some embodiments, the plurality of air inlets 228f are configured to regulate the air flow into the housing 209f, by blocking one or more of the plurality of air inlets 228f, by the user's finger, during usage of the device 201f.

In some embodiments, upon drawing of the aerosol from the device 201f, the pressure inside the device may decrease and, thus the air from the surroundings may enter into the housing 209f through the plurality of air inlets 228f. The air entering the housing 209f adjacent to directly flow toward an end of the consumable 202f before flowing therethrough. The air flowing through the consumable 202f may mix with the aerosol and heat generated by the heating element 223f (as seen in FIG. 31E). This mixing of the air with the aerosol and the heat generated may facilitate in increasing aerosol formation and total particulate matter (TPM) output of the aerosol.

Seventh Mode: A Heat not Burn (HNB) Device Having Air Inlets for Facilitating Airflow to Enter the Housing of the HNB Device Adjacent to a Base of Heating Element Aspects and embodiments of the seventh mode of the present disclosure will now be discussed with reference to the accompanying figures. Further aspects and embodiments of the seventh mode will be apparent to those skilled in the art. All documents mentioned in this text are incorporated herein by reference.

Figure 32B:
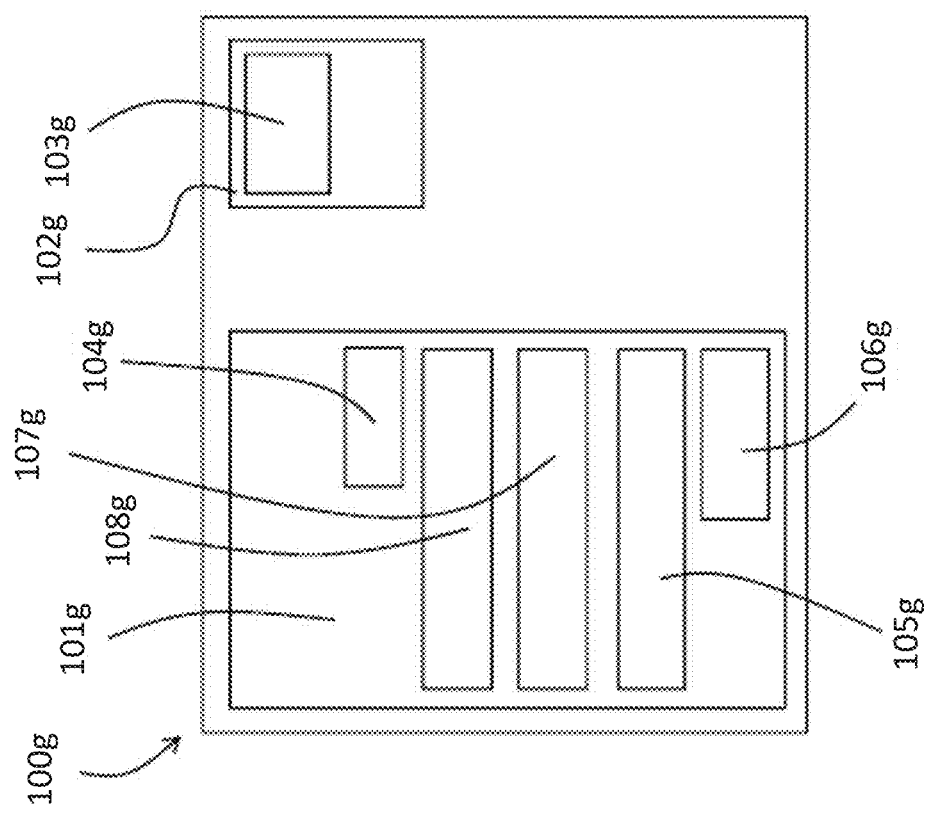
FIG. 32B is a schematic of a variation of the smoking substitute system of FIG. 32A.
Figure 32A:
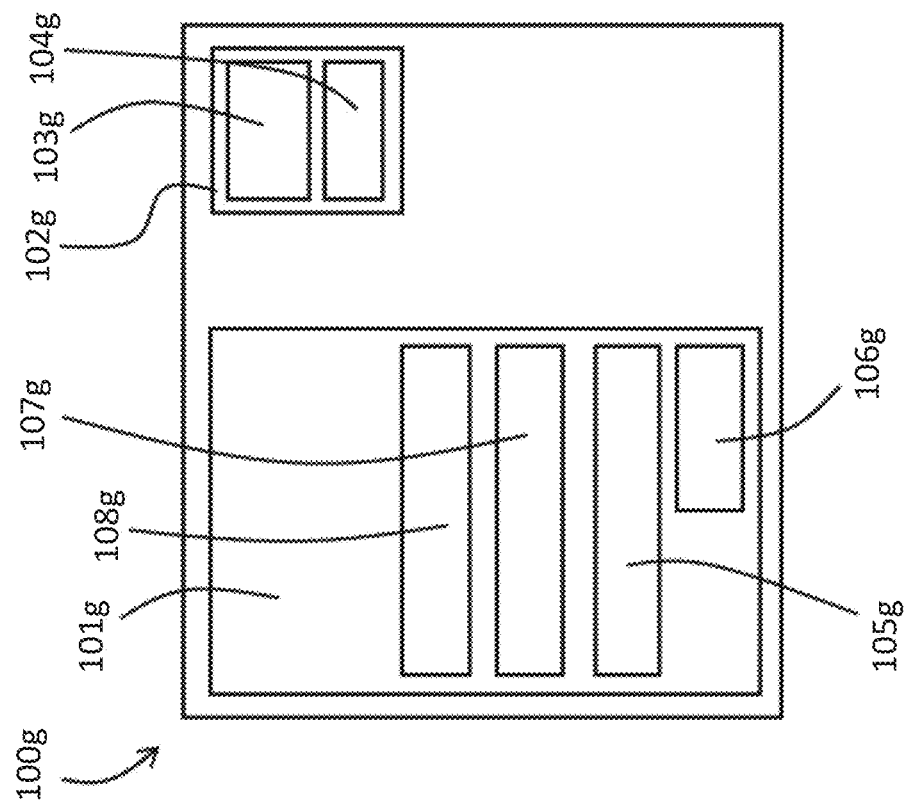
FIG. 32A is a schematic of a smoking substitute system of the seventh mode.

FIG. 32A is a schematic providing a general overview of a smoking substitute system 100g. The system 100g includes a heat not burn device 101g and an aerosol-forming article in the form of a consumable 102g, which comprises an aerosol former 103g. The system is configured to vaporize the aerosol former by heating the aerosol former 103g (so as to form a vapor/aerosol for inhalation by a user).

In the illustrated system, the heater 104g forms part of the consumable 102g and is configured to heat the aerosol former 103g. In this variation, the heater 104g is electrically connectable to the power source 105g, for example, when the consumable 102g is engaged with the device 101g. Heat from the heater 104g vaporizes the aerosol former 103g to produce a vapor. The vapor subsequently condenses to form an aerosol, which is ultimately inhaled by the user.

The system 100g further comprises a power source 105g that forms part of the device 101g. In other embodiments the power source 105g may be external to (but connectable to) the device 101g. The power source 105g is electrically connectable to the heater 104g such that it is able to supply power to the heater 104g (i.e., for the purpose of heating the aerosol former 103g). Thus, control of the electrical connection of the power source 105g to the heater 104g provides control of the state of the heater 104g. The power source 105g may be a power store, for example a battery or rechargeable battery (e.g., a lithium-ion battery).

The system 100g further comprises an I/O module comprising a connector 106g (e.g., in the form of a USB port, Micro USB port, USB-C port, etc.). The connector 106g is configured for connection to an external source of electrical power, e.g., a mains electrical supply outlet. The connector 106g may be used in substitution for the power source 105g. That is the connector 106g may be electrically connectable to the heater 104g so as to supply electricity to the heater 104g. In such embodiments, the device may not include a power source, and the power source of the system may instead comprise the connector 106g and an external source of electrical power (to which the connector 106g provides electrical connection).

In some embodiments, the connector 106g may be used to charge and recharge the power source 105g where the power source 105g includes a rechargeable battery.

The system 100g also comprises a user interface (UI) 107g. Although not shown, the UI 107g may include input means to receive commands from a user. The input means of the UI 107g allows the user to control at least one aspect of the operation of the system 100g. The input means may, for example, be in the form of a button, touchscreen, switch, microphone, etc.

The UI 107g also comprises output means to convey information to the user. The output means may, for example, comprise lights (e.g., LEDs), a display screen, speaker, vibration generator, etc.

The system 100g further comprises a controller 108g that is configured to control at least one function of the device 101g. In the illustrated embodiment, the controller 108g is a component of the device 101g, but in other embodiments may be separate from (but connectable to) the device 101g. The controller 108g is configured to control the operation of the heater 104g and, for example, may be configured to control the voltage applied from the power source 105g to the heater 104g. The controller 108g may be configured to toggle the supply of power to the heater 104g between an on state, in which the full output voltage of the power source 105g is applied to the heater 104g, and an off state, in which the no voltage is applied to the heater 104g.

Although not shown, the system 100g may also comprise a voltage regulator to regulate the output voltage from the power source 105g to form a regulated voltage. The regulated voltage may then be applied to the heater 104g.

In addition to being connected to the heater 104g, the controller 108g is operatively connected to the UI 107g. Thus, the controller 108g may receive an input signal from the input means of the UI 107g. Similarly, the controller 108g may transmit output signals to the UI 107g. In response, the output means of the UI 107g may convey information, based on the output signals, to a user. The controller also comprises a memory 109g, which is a non-volatile memory. The memory 109g includes instructions, which, when implemented, cause the controller to perform certain tasks or steps of a method.

FIG. 32B is a schematic showing a variation of the system 100g of FIG. 32A. In the system 100g' of FIG. 32B, the heater 104g forms part of the device 101g, rather than the consumable 102g. In this variation, the heater 104g is electrically connected to the power source 105g.

FIG. 33A illustrates a heated-tobacco (HT) smoking substitute system 200g. The system 200g is an example of the systems 100g, 100g' described in relation to FIG. 32A or FIG. 32B. System 200g includes a heat not burn device 201g and an HT consumable 202g. The description of FIG. 32A and FIG. 32B above is applicable to the system 200g of FIG. 33A and FIG. 33B, and will thus not be repeated.

FIG. 33B illustrates the device 201g and the consumable 202g are configured such that the consumable 202g can be engaged with the device 201g.

The device 201g comprises a housing 209g and a cap 210g. In use, the cap 210g is engaged at an end of the housing 209g. As apparent from the FIG. 33D, the cap 210g is moveable relative to the housing 209g. In particular, the cap 210g is slidable and can slide along a longitudinal axis of the housing 209g.

The device 201g comprises an output means (forming part of the UI of the device 201g) in the form of a plurality of light-emitting diodes (LEDs) 211g arranged linearly along the longitudinal axis of the device 201g and on an outer surface of the housing 209g of the device 201g. A button 212g is also arranged on an outer surface of the housing 209g of the device 201g and is axially spaced (i.e., along the longitudinal axis) from the plurality of LEDs 211g.

Figure 33C:
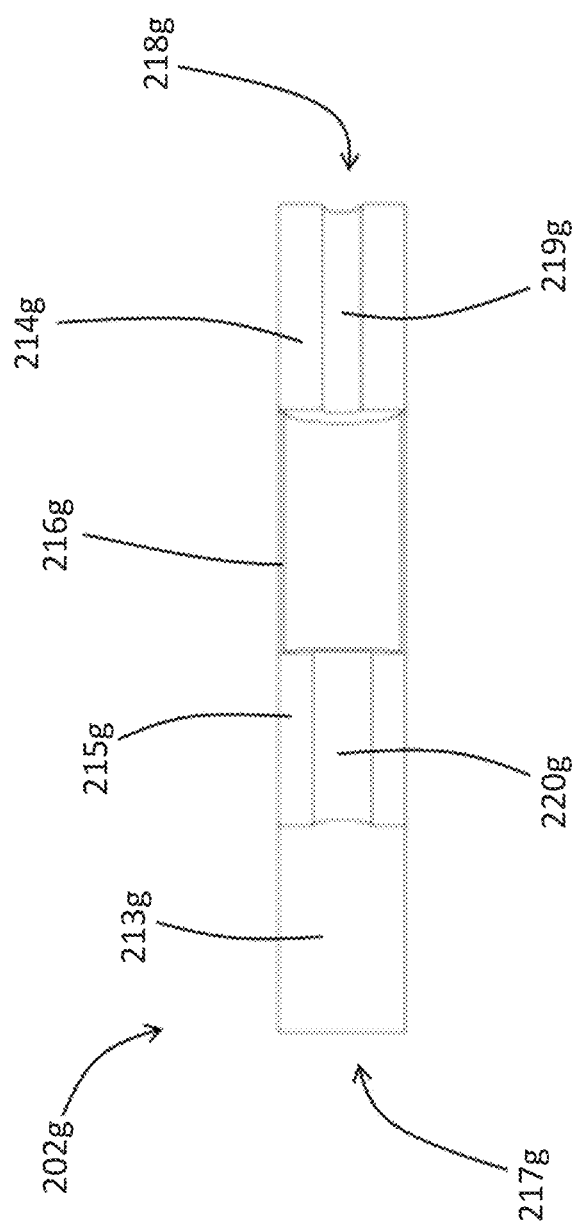
FIG. 33C is a section view of the consumable of the first embodiment of the seventh mode of the smoking substitute system.

FIG. 33C show a detailed section view of the consumable 202g of the system 200g. The consumable 202g generally resembles a cigarette. In that respect, the consumable 202g has a generally cylindrical form with a diameter of 7 mm and an axial length of 70 mm. The consumable 202g comprises an aerosol forming substrate 213g, a terminal filter element 214g, an upstream filter element 215g and a spacer element 216g. In other embodiments, the consumable may further comprise a cooling element. A cooling element may exchange heat with vapor that is formed by the aerosol-forming substrate 213g in order to cool the vapor so as to facilitate condensation of the vapor.

The aerosol-forming substrate 213g is substantially cylindrical and is located at an upstream end 217g of the consumable 202g, and comprises the aerosol former of the system 200g. In that respect, the aerosol forming substrate 213g is configured to be heated by the device 201g to release a vapor. The released vapor is subsequently entrained in an airflow flowing through the aerosol-forming substrate 213g. The airflow is produced by the action of the user drawing on a downstream 218g (i.e., terminal or mouth) end of the consumable 202g.

In the present embodiment, the aerosol forming substrate 213g comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213g may comprise a gathered sheet of homogenized (e.g., paper/slurry recon) tobacco or gathered shreds/strips formed from such a sheet.

In order to generate an aerosol, the aerosol forming substrate 213g comprises at least one volatile compound that is intended to be vaporized/aerosolized and that may provide the user with a recreational and/or medicinal effect when inhaled. The aerosol-forming substrate 213g may further comprise one or more additives. For example, such additives may be in the form of humectants (e.g., propylene glycol and/or vegetable glycerin), flavorants, fillers, aqueous/non-aqueous solvents and/or binders.

The terminal filter element 214g is also substantially cylindrical, and is located downstream of the aerosol forming substrate 213g at the downstream end 218g of the consumable 202g. The terminal filter element 214g is in the form of a hollow bore filter element having a bore 219g (e.g., for airflow) formed therethrough. The diameter of the bore 219g is 2 mm. The terminal filter element 214g is formed of a porous (e.g., monoacetate) filter material. As set forth above, the downstream end 218g of the consumable 202g (i.e., where the terminal filter 214g is located) forms a mouthpiece portion of the consumable 202g upon which the user draws. Airflow is drawn from the upstream end 217g, thorough the components of the consumable 202g, and out of the downstream end 218g. The airflow is driven by the user drawing on the downstream end 218g (i.e., the mouthpiece portion) of the consumable 202g.

The upstream filter element 215g is located axially adjacent to the aerosol-forming substrate 213g, between the aerosol-forming substrate 213g and the terminal filter element 214g. Like the terminal filter 214g, the upstream filter element 215g is in the form of a hollow bore filter element, such that it has a bore 220g extending axially therethrough. In this way, the upstream filter 215g may act as an airflow restrictor. The upstream filter element 215g is formed of a porous (e.g., monoacetate) filter material. The bore 220g of the upstream filter element 215g has a larger diameter (3 mm) than the terminal filter element 214g.

The spacer 216g is in the form of a cardboard tube, which defines a cavity or chamber between the upstream filter element 215g and the terminal filter element 214g. The spacer 216g acts to allow both cooling and mixing of the vapor/aerosol from the aerosol-forming substrate 213g. The spacer has an external diameter of 7 mm and an axial length of 14 mm.

Although not apparent from the figure, the aerosol-forming substrate 213g, upstream filter 215g and spacer 216g are circumscribed by a paper wrapping layer. The terminal filter 214g is circumscribed by a tipping layer that also circumscribes a portion of the paper wrapping layer (so as to connect the terminal filter 214g to the remaining components of the consumable 202g). The upstream filter 215g and terminal filter 214g are circumscribed by further wrapping layers in the form of plug wraps.

Figures 33D, 33E:
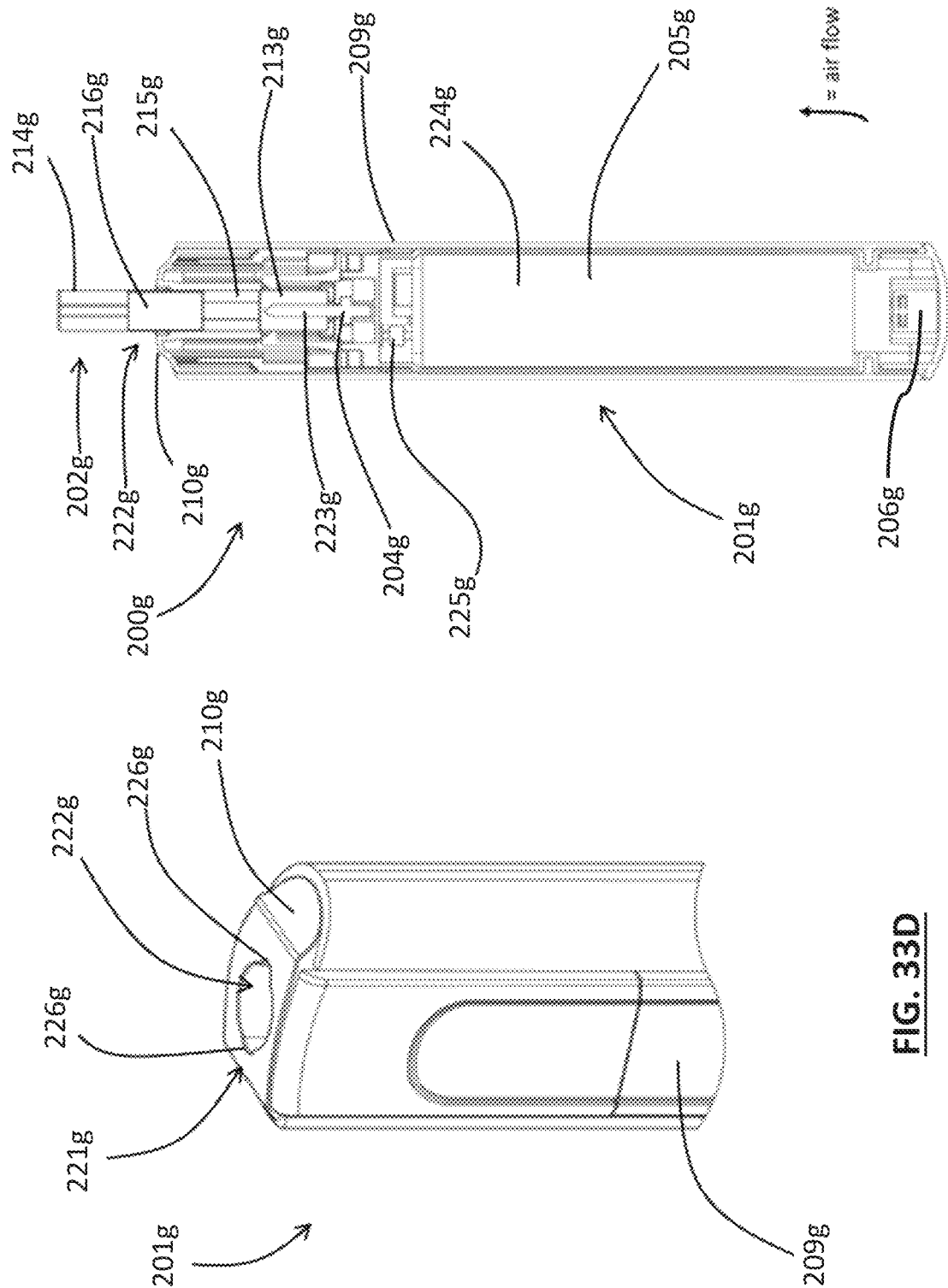
FIG. 33D is a detailed prospective view of a first end of the device of the first embodiment of the seventh mode of the smoking substitute system.
FIG. 33E is a section view of the first embodiment of the seventh mode of the smoking substitute system.

Returning now to the device 201g, FIG. 33D illustrates a detailed view of the end of the device 201g that is configured to engage with the consumable 202g. The cap 210g of the device 201g includes an opening 221g to an internal cavity 222g (more apparent from FIG. 33C) defined by the cap 210g. The opening 221g and the cavity 222g are formed so as to receive at least a portion of the consumable 202g. During engagement of the consumable 202g with the device 201g, a portion of the consumable 202g is received through the opening 221g and into the cavity 222g. After engagement (see FIG. 33B), the downstream end 218g of the consumable 202g protrudes from the opening 221g and thus also protrudes from the device 201g. The opening 221g includes laterally disposed notches 226g. When a consumable 202g is received in the opening 221g, these notches 226g remain open and could, for example, be used for retaining a cover in order to cover the end of the device 201g.

FIG. 33E shows a cross section through a central longitudinal plane through the device 201g. The device 201g is shown with the consumable 202g engaged therewith.

The device 201g comprises a heater 204g comprising heating element 223g. The heating element 223g of the heater 204g is accommodated in the housing 209g, such that the base of the heater element 223g is in connection with the housing 209g, and thus forms part of the housing 209g of the device 201g and is rigidly mounted to the housing 209g. In the illustrated embodiment, the heater 204g is a rod heater with a heating element 223g having a circular transverse profile. In other embodiments the heater may be in the form of a blade heater (e.g., heating element with a rectangular transverse profile) or a tube heater (e.g., heating element with a tubular form).

The heating element 223g of the heater 204g projects from an internal base of the cavity 222g along a longitudinal axis towards the opening 221g. As is apparent from the figure, the length (i.e., along the longitudinal axis) of the heating element is less than a depth of the cavity 222g. In this way, the heating element 223g does not protrude from or extend beyond the opening 221g.

When the consumable 202g is received in the cavity 222g (as is shown in FIG. 33A), the heating element 223g penetrates the aerosol-forming substrate 213g of the consumable 202g. In particular, the heating element 223g extends for nearly the entire axial length of the aerosol-forming substrate 213g when inserted therein. Thus, when the heater 204g is activated, heat is transferred radially from an outer circumferential surface the heating element 223g to the aerosol-forming substrate 213g.

Returning now to the device 201g, FIG. 33D illustrates a detailed view of the end of the device 201g that is configured to engage with the consumable 202g. The cap 210g of the device 201g includes an opening 221g to an internal cavity 222g (more apparent from FIG. 33D) defined by the cap 210g. The opening 221g and the cavity 222g are formed so as to receive at least a portion of the consumable 202g. During engagement of the consumable 202g with the device 201g, a portion of the consumable 202g is received through the opening 221g and into the cavity 222g. After engagement (see FIG. 33B), the downstream end 218g of the consumable 202g protrudes from the opening 221g and thus also protrudes from the device 201g. The opening 221g includes laterally disposed notches 226g. When a consumable 202g is received in the opening 221g, these notches 226g remain open and could, for example, be used for retaining a cover in order to cover the end of the device 201g.

The device 201g further comprises an electronics cavity 224g. A power source, in the form of a rechargeable battery 205g (a lithium-ion battery), is located in electronics cavity 224g.

The device 201g includes a connector (i.e., forming part of an IO module of the device 201g) in the form of a USB port 206g. The connector may alternatively be, for example, a micro-USB port or a USB-C port for examples. The USB port 206g may be used to recharge the rechargeable battery 205g.

The device 201g includes a controller (not shown) located in the electronics cavity 224g. The controller comprises a microcontroller mounted on a printed circuit board (PCB). The USB port 206g is also connected to the controller 208g (i.e., connected to the PCB and microcontroller).

The controller 208g is configured to control at least one function of the device 201g. For example, the controller 208g is configured to control the operation of the heater 204g. Such control of the operation of the heater 204g may be accomplished by the controller toggling the electrical connection of the rechargeable battery 205g to the heater 204g. For example, the controller 208g is configured to control the heater 204g in response to a user depressing the button 212g. Depressing the button 212g may cause the controller to allow a voltage (from the rechargeable battery 205g) to be applied to the heater 204g (so as to cause the heating element 223g to be heated).

The controller is also configured to control the LEDs 211g in response to (e.g., a detected) a condition of the device 201g or the consumable 202g. For example, the controller may control the LEDs to indicate whether the device 201g is in an on state or an off state (e.g., one or more of the LEDs may be illuminated by the controller when the device is in an on state).

The device 201g comprises a further input means (i.e., in addition to the button 212g) in the form of a puff sensor 225g. The puff sensor 225g is configured to detect a user drawing (i.e., inhaling) at the downstream end 218g of the consumable 202g. The puff sensor 225g may, for example, be in the form of a pressure sensor, flowmeter or a microphone. The puff sensor 225g is operatively connected to the controller 208g in the electronics cavity 224g, such that a signal from the puff sensor 225g, indicative of a puff state (i.e., drawing or not drawing), forms an input to the controller 208g (and can thus be responded to by the controller 208g).

In an embodiment, and referring to FIG. 33B, the housing 209g of the device 201g, is an elongated member, with a length of the housing 209g greater than thickness of the housing 209g. Thus, the major surface of the housing 209g is at least one of a front face and a rear face of the housing 209g, which possess surface area greater than that of the side surfaces. The first major surface may be a front face of the housing 209g.

Figure 33G:
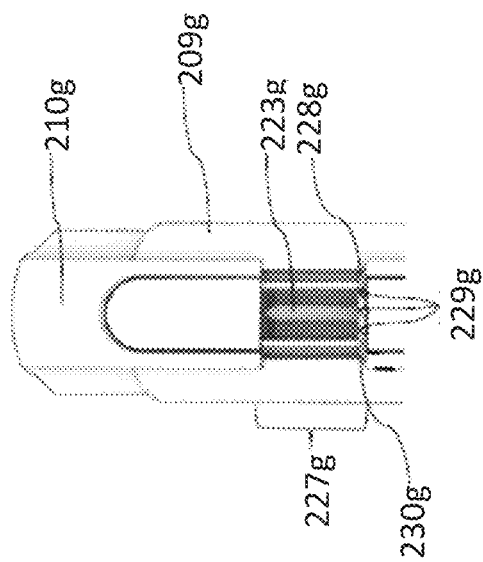
FIG. 33G, illustrates detailed front view of portion A of FIG. 33F.
Figure 33F:
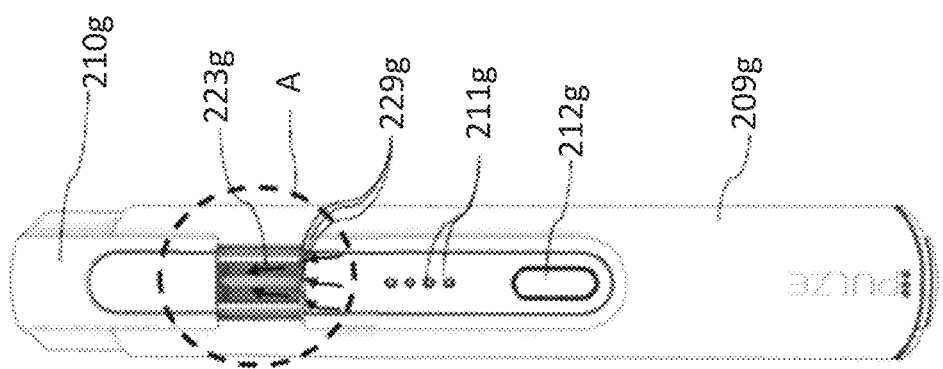
FIG. 33F illustrates front view of the device of the first embodiment of the seventh mode.

Referring to FIG. 33F and FIG. 33G, the housing 209g comprises a cap engaging portion 228g, which may be configured at a first end 227g of the housing 209g. The cap engaging portion 228g, is adapted to receive at least a portion of the cap 210g, thereby to facilitate engagement of the cap 210g and the housing 209g. Further, the cap engaging portion 228g adjoins or extends from a portion of the housing 209g through a step portion 230g, such that the cross-section of the cap engaging portion 228g is less than the cross-section of the housing 209g. The cap engaging portion 228g is configured to surround at least a portion of the heating element 223g.

In the illustrated embodiment, the cap engaging portion 228g is defined with three air inlets 229g. In the illustrated embodiment, the plurality of air inlets 229g are configured on a major surface of the cap engaging portion 228g and each of the plurality of air inlets 229g is configured as through holes to allow air flow into the housing 209g. In other embodiments, the air inlet 229g may be configured as a slit. The plurality of air inlets 229g, may be configured adjacent to each other in a linear series extending transverse to the longitudinal axis of the housing 209g (i.e., the plurality of air inlets extends horizontally). That is, the plurality of air inlets 229g are arranged circumferentially at the same position along the longitudinal axis of the housing 209g. In another embodiment, the plurality of air inlets 229g may be arranged at different location along the longitudinal axis of the housing 209g. The plurality of air inlets 229g may be configured to allow air flow to enter the housing 209g adjacent to the base of the heating element 223g. Further, the plurality of air inlets 229g may be configured to allow air flow onto bottom portion or base of the heating element 223g (as seen in FIG. 33F).

Turning back to FIG. 33E, during operation of the device 201g, the user may puff on the mouthpiece 214g to draw the aerosol generated in the device 201g. During the puff, pressure inside the device 201g drops (i.e., a negative pressure may be created). As shown in FIG. 2F, due to said pressure drop, air from the surroundings enters into the housing 209g, through the plurality of air inlets 229g defined at the cap engaging portion 228g. Further, the air may enter into the housing 209g transverse to the longitudinal axis of the housing 209g. The air entered into the housing 209g, flows adjacent to the base of the heating element 223g, which may mix up with the heat generated by the heating element 223g. Therefor such arrangement may facilitate in improving aerosol generation and total particulate matter (TPM) output of the aerosol and thus, improving efficiency of the device 201g.

Eighth Mode: A Configuration of Selectively Blocking One or More of the Plurality of Openings of an Air Inlet in a Smoking Substitute Device Aspects and embodiments of the eighth mode of the present disclosure will now be discussed with reference to the accompanying figures. Further aspects and embodiments of the eighth mode will be apparent to those skilled in the art. All documents mentioned in this text are incorporated herein by reference.

FIG. 34A is a schematic providing a general overview of a smoking substitute system 100h. The system 100h includes a substitute smoking device 101h and an aerosol-forming article in the form of a consumable 102h, which comprises an aerosol former 103h. The system is configured to vaporize the aerosol former by heating the aerosol former 103h (so as to form a vapor/aerosol for inhalation by a user).

In the illustrated system, the heater 104h forms part of the consumable 102h and is configured to heat the aerosol former 103h. In this variation, the heater 104h is electrically connectable to the power source 105h, for example, when the consumable 102h is engaged with the device 101h. Heat from the heater 104h vaporizes the aerosol former 103h to produce a vapor. The vapor subsequently condenses to form an aerosol, which is ultimately inhaled by the user.

The system 100h further comprises a power source 105h that forms part of the device 101h. In other embodiments the power source 105h may be external to (but connectable to) the device 101h. The power source 105h is electrically connectable to the heater 104h such that it is able to supply power to the heater 104h (i.e., for the purpose of heating the aerosol former 103h). Thus, control of the electrical connection of the power source 105h to the heater 104h provides control of the state of the heater 104h. The power source 105h may be a power store, for example a battery or rechargeable battery (e.g., a lithium-ion battery).

The system 100h further comprises an I/O module comprising a connector 106h (e.g., in the form of a USB port, Micro USB port, USB-C port, etc.). The connector 106h is configured for connection to an external source of electrical power, e.g., a mains electrical supply outlet. The connector 106h may be used in substitution for the power source 105h. That is the connector 106h may be electrically connectable to the heater 104h so as to supply electricity to the heater 104h. In such embodiments, the device may not include a power source, and the power source of the system may instead comprise the connector 106h and an external source of electrical power (to which the connector 106h provides electrical connection).

In some embodiments, the connector 106h may be used to charge and recharge the power source 105h where the power source 105h includes a rechargeable battery.

The system 100h also comprises a user interface (UI) 107h. Although not shown, the UI 107h may include input means to receive commands from a user. The input means of the UI 107h allows the user to control at least one aspect of the operation of the system 100h. The input means may, for example, be in the form of a button, touchscreen, switch, microphone, etc.

The UI 107h also comprises output means to convey information to the user. The output means may, for example, comprise lights (e.g., LEDs), a display screen, speaker, vibration generator, etc.

The system 100h further comprises a controller 108h that is configured to control at least one function of the device 101h. In the illustrated embodiment, the controller 108h is a component of the device 101h, but in other embodiments may be separate from (but connectable to) the device 101h. The controller 108h is configured to control the operation of the heater 104h and, for example, may be configured to control the voltage applied from the power source 105h to the heater 104h. The controller 108h may be configured to toggle the supply of power to the heater 104h between an on state, in which the full output voltage of the power source 105h is applied to the heater 104h, and an off state, in which the no voltage is applied to the heater 104h.

Although not shown, the system 100h may also comprise a voltage regulator to regulate the output voltage from the power source 105h to form a regulated voltage. The regulated voltage may then be applied to the heater 104h.

In addition to being connected to the heater 104h, the controller 108h is operatively connected to the UI 107h. Thus, the controller 108h may receive an input signal from the input means of the UI 107h. Similarly, the controller 108h may transmit output signals to the UI 107h. In response, the output means of the UI 107h may convey information, based on the output signals, to a user. The controller also comprises a memory 109h, which is a non-volatile memory. The memory 109h includes instructions, which, when implemented, cause the controller to perform certain tasks or steps of a method.

FIG. 34B is a schematic showing a variation of the system 100h of FIG. 34A. In the system 100h' of FIG. 34B, the heater 104h forms part of the device 101h, rather than the consumable 102h. In this variation, the heater 104h is electrically connected to the power source 105h.

FIG. 35A and FIG. 35B illustrate a heated-tobacco (HT) smoking substitute system 200h. The system 200h is an example of the systems 100h, 100h' described in relation to FIG. 34A or FIG. 34B. System 200h includes an HT device 201h and an HT consumable 202h. The description of FIG. 34A and FIG. 34B above is applicable to the system 200h of FIG. 35A and FIG. 35B, and will thus not be repeated.

The device 201h and the consumable 202h are configured such that the consumable 202h can be engaged with the device 201h. FIG. 35A shows the device 201h and the consumable 202h in an engaged state, whilst FIG. 35B shows the device 201h and the consumable 202h in a disengaged state.

The device 201h comprises a housing 209h and cap 210h. In use the cap 210h is engaged at an end of the housing 209h. Although not apparent from the figures, the cap 210h is moveable relative to the housing 209h. In particular, the cap 210h is slidable and can slide along a longitudinal axis of the housing 209h.

The device 201h comprises an output means (forming part of the UI of the device 201h) in the form of a plurality of light-emitting diodes (LEDs) 211h arranged linearly along the longitudinal axis of the device 201h and on an outer surface of the housing 209h of the device 201h. A button 212h is also arranged on an outer surface of the housing 209h of the device 201h and is axially spaced (i.e., along the longitudinal axis) from the plurality of LEDs 211h.

Figure 35C:
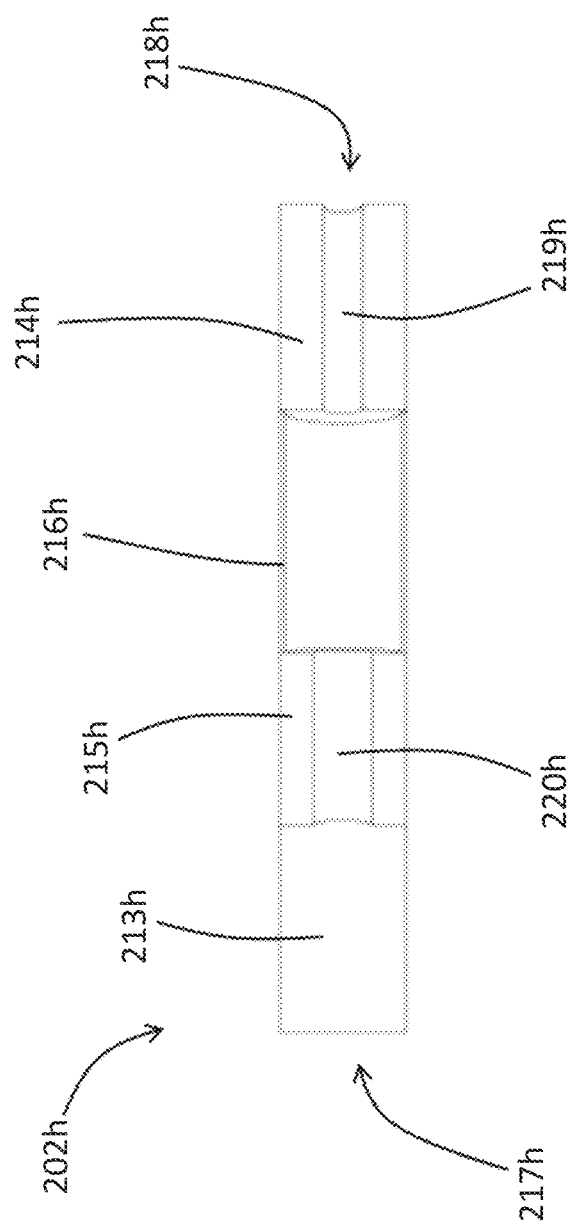
FIG. 35C is a section view of the consumable of the first embodiment of the eighth mode of the smoking substitute system.

FIG. 35C show a detailed section view of the consumable 202h of the system 200h. The consumable 202h generally resembles a cigarette. In that respect, the consumable 202h has a generally cylindrical form with a diameter of 7 mm and an axial length of 70 mm. The consumable 202h comprises an aerosol forming substrate 213h, a terminal filter element 214h, an upstream filter element 215h and a spacer element 216h. In other embodiments, the consumable may further comprise a cooling element. A cooling element may exchange heat with vapor that is formed by the aerosol-forming substrate 213h in order to cool the vapor so as to facilitate condensation of the vapor.

The aerosol-forming substrate 213h is substantially cylindrical and is located at an upstream end 217h of the consumable 202h, and comprises the aerosol former of the system 200h. In that respect, the aerosol forming substrate 213h is configured to be heated by the device 201h to release a vapor. The released vapor is subsequently entrained in an airflow flowing through the aerosol-forming substrate 213h. The airflow is produced by the action of the user drawing on a downstream 218h (i.e., terminal or mouth) end of the consumable 202h.

In the present embodiment, the aerosol forming substrate 213h comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213h may comprise a gathered sheet of homogenized (e.g., paper/slurry recon) tobacco or gathered shreds/strips formed from such a sheet.

In order to generate an aerosol, the aerosol forming substrate 213h comprises at least one volatile compound that is intended to be vaporized/aerosolized and that may provide the user with a recreational and/or medicinal effect when inhaled. The aerosol-forming substrate 213h may further comprise one or more additives. For example, such additives may be in the form of humectants (e.g., propylene glycol and/or vegetable glycerin), flavorants, fillers, aqueous/non-aqueous solvents and/or binders.

The terminal filter element 214h is also substantially cylindrical, and is located downstream of the aerosol forming substrate 213h at the downstream end 218h of the consumable 202h. The terminal filter element 214h is in the form of a hollow bore filter element having a bore 219h (e.g., for airflow) formed therethrough. The diameter of the bore 219h is 2 mm. The terminal filter element 214h is formed of a porous (e.g., monoacetate) filter material. As set forth above, the downstream end 218h of the consumable 202h (i.e., where the terminal filter 214h is located) forms a mouthpiece portion of the consumable 202h upon which the user draws. Airflow is drawn from the upstream end 217h, thorough the components of the consumable 202h, and out of the downstream end 218h. The airflow is driven by the user drawing on the downstream end 218h (i.e., the mouthpiece portion) of the consumable 202h.

The upstream filter element 215h is located axially adjacent to the aerosol-forming substrate 213h, between the aerosol-forming substrate 213h and the terminal filter element 214h. Like the terminal filter 214h, the upstream filter element 215h is in the form of a hollow bore filter element, such that it has a bore 220h extending axially therethrough. In this way, the upstream filter 215h may act as an airflow restrictor. The upstream filter element 215h is formed of a porous (e.g., monoacetate) filter material. The bore 220h of the upstream filter element 215h has a larger diameter (3 mm) than the terminal filter element 214h.

The spacer 216h is in the form of a cardboard tube, which defines a cavity or chamber between the upstream filter element 215h and the terminal filter element 214h. The spacer 216h acts to allow both cooling and mixing of the vapor/aerosol from the aerosol-forming substrate 213h. The spacer has an external diameter of 7 mm and an axial length of 14 mm.

Although not apparent from the figure, the aerosol-forming substrate 213h, upstream filter 215h and spacer 216h are circumscribed by a paper wrapping layer. The terminal filter 214h is circumscribed by a tipping layer that also circumscribes a portion of the paper wrapping layer (so as to connect the terminal filter 214h to the remaining components of the consumable 202h). The upstream filter 215h and terminal filter 214h are circumscribed by further wrapping layers in the form of plug wraps.

Figures 35D, 35E:
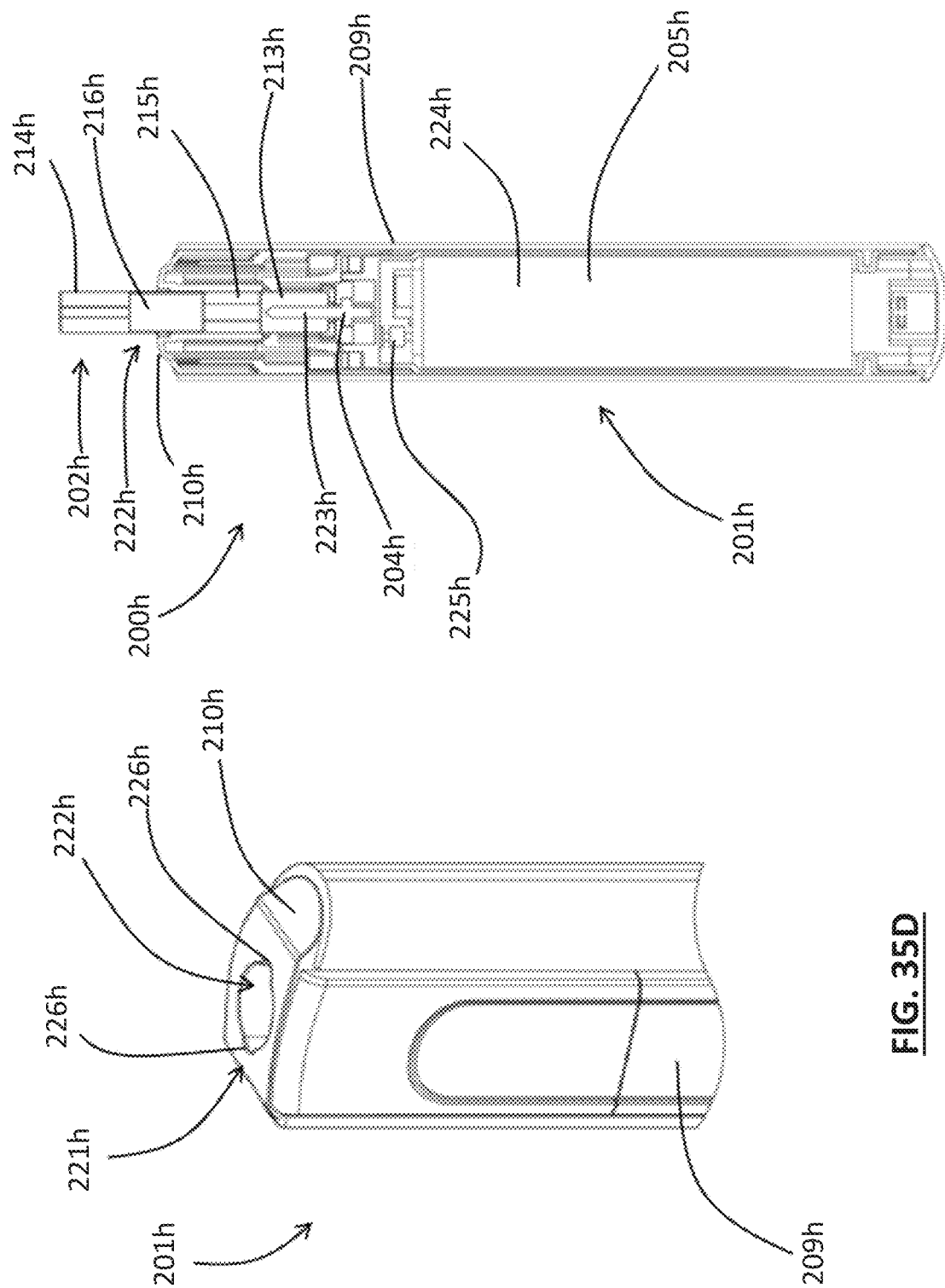
FIG. 35D is a detailed view of an end of the device of the first embodiment of the eighth mode of the smoking substitute system.
FIG. 35E is a section view of the first embodiment of the eighth mode of the smoking substitute system.

Returning now to the device 201h, FIG. 35D illustrates a detailed view of the end of the device 201h that is configured to engage with the consumable 202h. The cap 210h of the device 201h includes an opening 221h to an internal cavity 222h (more apparent from FIG. 35D) defined by the cap 210h. The opening 221h and the cavity 222h are formed so as to receive at least a portion of the consumable 202h. During engagement of the consumable 202h with the device 201h, a portion of the consumable 202h is received through the opening 221h and into the cavity 222h. After engagement (see FIG. 35B), the downstream end 218h of the consumable 202h protrudes from the opening 221h and thus also protrudes from the device 201h. The opening 221h includes laterally disposed notches 226h. When a consumable 202h is received in the opening 221h, these notches 226h remain open and could, for example, be used for retaining a cover in order to cover the end of the device 201h.

FIG. 35E shows a cross section through a central longitudinal plane through the device 201h. The device 201h is shown with the consumable 202h engaged therewith.

The device 201h comprises a heater 204h comprising heating element 223h. The heater 204h forms part of the housing 209h of the device 201h and is rigidly mounted to the housing 209h. In the illustrated embodiment, the heater 204h is a rod heater with a heating element 223h having a circular transverse profile. In other embodiments the heater may be in the form of a blade heater (e.g., heating element with a rectangular transverse profile) or a tube heater (e.g., heating element with a tubular form).

The heating element 223h of the heater 204h projects from an internal base of the cavity 222h along a longitudinal axis towards the opening 221h. As is apparent from the figure, the length (i.e., along the longitudinal axis) of the heating element is less than a depth of the cavity 222h. In this way, the heating element 223h does not protrude from or extend beyond the opening 221h.

When the consumable 202h is received in the cavity 222h (as is shown in FIG. 35E), the heating element 223h penetrates the aerosol-forming substrate 213h of the consumable 202h. In particular, the heating element 223h extends for nearly the entire axial length of the aerosol-forming substrate 213h when inserted therein. Thus, when the heater 204h is activated, heat is transferred radially from an outer circumferential surface the heating element 223h to the aerosol-forming substrate 213h.

The device 201h further comprises an electronics cavity 224h. A power source, in the form of a rechargeable battery 205h (a lithium-ion battery), is located in electronics cavity 224h.

The device 201*h* includes a connector (i.e., forming part of an IO module of the device 201*h*) in the form of a USB port 206*h*. The connector may alternatively be, for example, a micro-USB port or a USB-C port for examples. The USB port 206*h* may be used to recharge the rechargeable battery 205*h*.

The device 201*h* includes a controller (not shown) located in the electronics cavity 224*h*. The controller comprises a microcontroller mounted on a printed circuit board (PCB). The USB port 206*h* is also connected to the controller 208*h* (i.e., connected to the PCB and microcontroller).

The controller 208*h* is configured to control at least one function of the device 201*h*. For example, the controller 208*h* is configured to control the operation of the heater 204*h*. Such control of the operation of the heater 204*h* may be accomplished by the controller toggling the electrical connection of the rechargeable battery 205*h* to the heater 204*h*. For example, the controller 208*h* is configured to control the heater 204*h* in response to a user depressing the button 212*h*. Depressing the button 212*h* may cause the controller to allow a voltage (from the rechargeable battery 205*h*) to be applied to the heater 204*h* (so as to cause the heating element 223*h* to be heated).

The controller is also configured to control the LEDs 211*h* in response to (e.g., a detected) a condition of the device 201*h* or the consumable 202*h*. For example, the controller may control the LEDs to indicate whether the device 201*h* is in an on state or an off state (e.g., one or more of the LEDs may be illuminated by the controller when the device is in an on state).

The device 201*h* comprises a further input means (i.e., in addition to the button 212*h*) in the form of a puff sensor 225*h*. The puff sensor 225*h* is configured to detect a user drawing (i.e., inhaling) at the downstream end 218*h* of the consumable 202*h*. The puff sensor 225*h* may, for example, be in the form of a pressure sensor, flowmeter or a microphone. The puff sensor 225*h* is operatively connected to the controller 208*h* in the electronics cavity 224*h*, such that a signal from the puff sensor 225*h*, indicative of a puff state (i.e., drawing or not drawing), forms an input to the controller 208*h* (and can thus be responded to by the controller 208*h*).

Figure 36B:
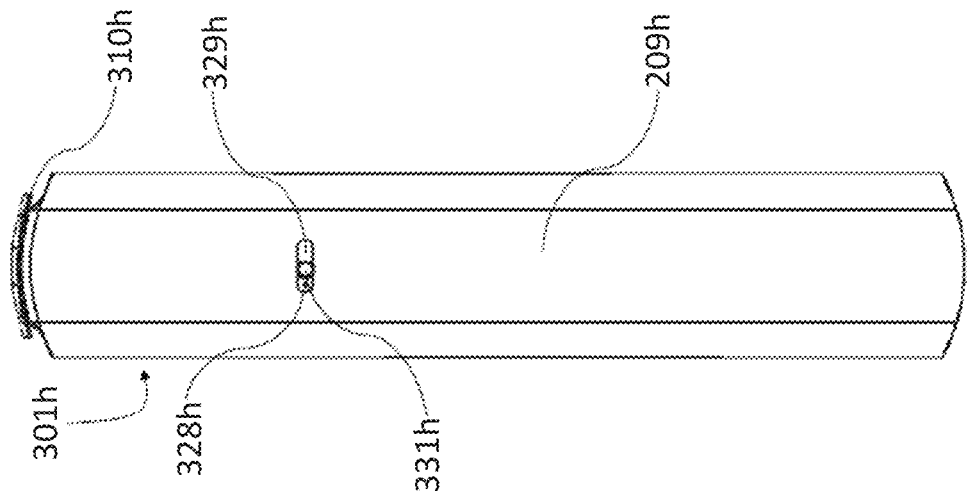
FIG. 36B is a front view of the first embodiment of the eighth mode of the device, with the slidable door blocking one of the plurality of openings of the air inlet.
Figure 36A:
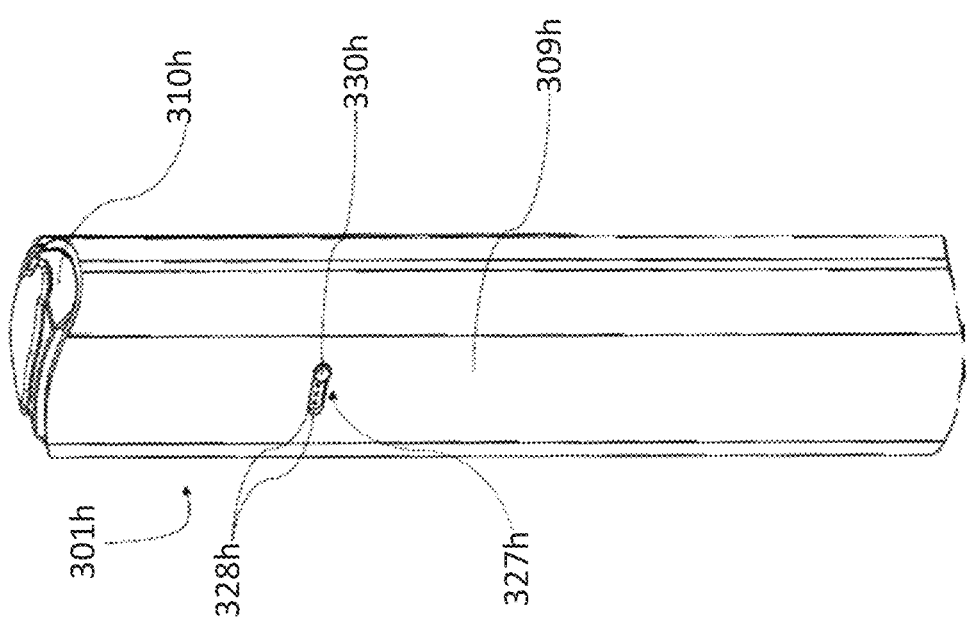
FIG. 36A is a perspective view of the first embodiment of the eighth mode of the device, comprising an air inlet and a slidable door.

Referring to FIG. 33A, the housing 309*h* of the device 301*h* is defined with the air inlet 327*h*. The air inlet 327*h* comprises a plurality of openings 328*h* to facilitate an airflow to enter into the housing 309*h*. Flow of air into the housing 309*h*, may aid improving aerosol formation in the device 301*h*. The plurality of openings 328*h* of the air inlet 327*h*, are configured to be blocked or closed so as to vary the quantity of airflow entering into the housing 309*h*. The one or more of the plurality of openings 328*h* of the air inlet 327*h*, may be selectively blocked by a closure member disposed at the housing 309*h*. In the illustrated embodiment, the closure member disposed in the housing 309*h* is a door 329*h* (as shown in FIG. 36B). The door 309*h* is slidably disposed in the housing 309*h*, parallel to the plurality of openings 328*h* of the air inlet 327*h* (i.e., in front of the plurality of openings). As apparent in FIG. 36A, the door 329*h* is displaceable (i.e., slidable) within a slot or a groove defined in the housing 309*h*. As an example, the door 329*h* may comprise rails (not shown in figures), to facilitate sliding movement of the door 329*h*.

In the illustrated embodiment, the door 329*h* is configured with a knob 330*h*, which may assist in sliding the door 329*h*, to block the one or more of the plurality of openings 328*h*. The door 329*h* is arranged to slide or toggle between an open position (as apparent in FIG. 36A) and a partially closed position (i.e., the door blocking the one or more of the plurality of openings 328*h*, (as apparent in FIG. 36B). Upon sliding of the door 329*h* from the open position, the door 329*h* blocks and thus closes the one or more of the plurality of openings 328*h* of the air inlet 327*h*. Such blocking of the one or more of the plurality of openings 328*h* assists in varying or controlling the quantity of airflow entering into the housing 309*h* of the device 301*h*, which may facilitate in regulating the operational parameters of the device 301*h*.

Referring to FIG. 37A, which illustrates a device 401*h* according to a second embodiment, where the closure which blocks the one or more of the plurality of openings 428*h* of the air inlet 427*h* is a ring 431*h*. The ring 431*h* is disposed in the housing 409*h*, and configured to be operated transverse to a longitudinal axis of the housing 409*h*, to block the one or more of the plurality of openings 428*h* of the air inlet 427*h* (as apparent in FIG. 4A). The ring 431*h* is threadedly engaged to the housing 409*h*, such that the ring 431*h* can be operated by turning the ring in a clockwise or an anti-clock wise direction. Operating (thus turning) of the ring 431*h* blocks or unblocks the one or more plurality of openings 428*h* of the air inlet 427*h* to vary the quantity of airflow entering into the housing 409*h* of the device 401*h*.

In another embodiment, the user operating the device 201*h* may use fingers to block the one or more of the plurality of openings 228*h* of the air inlet 227*h*, to vary the quantity of air flow into the housing 209*h* of the device 201*h*.

In another embodiment, the cap 210*h* (as apparent from FIG. 35A), is configured with the slidable movement between the open position and the closed position along the longitudinal axis of the housing 209*h*. The slidable movement is adapted to block the one or more of the plurality of openings 228*h* of the air inlet 227*h*. As an example, the cap 210*h* is configured such that the extent to which the cap 210*h* is moved or displaced towards the closed position (i.e., the cap engaged with the housing), facilitates in blocking the one or more of the plurality of openings 228*h* of the air inlet 227*h*.

In some embodiments, blocking the one or more of the plurality of openings 228*h* of the air inlet 227*h*, may facilitate in varying the quantity of airflow entering into the housing 209*h*, which facilitates in regulating operational parameters such as aerosol drawing resistance, aerosol temperature and aerosol generation of the consumable 202*h*.

Ninth Mode: A Heated Tobacco Device Comprising a Provision for Activating a Crush Ball Aspects and embodiments of the ninth mode of the present disclosure will now be discussed with reference to the accompanying figures. Further aspects and embodiments of the ninth mode will be apparent to those skilled in the art. All documents mentioned in this text are incorporated herein by reference.

Figure 38B:
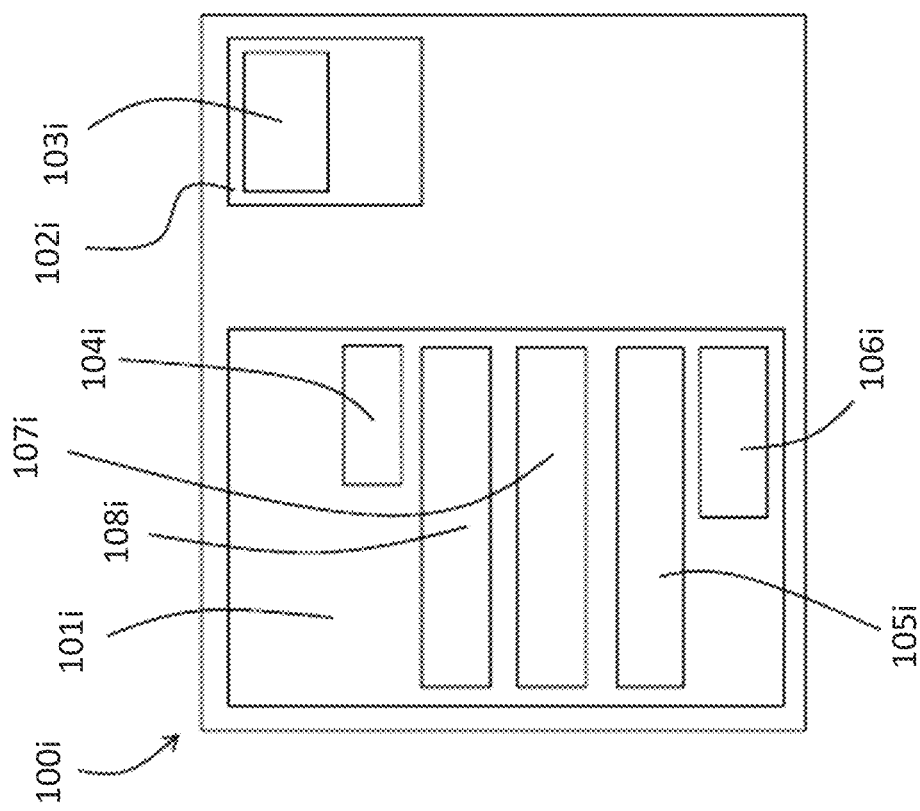
FIG. 38B is a schematic of a variation of the smoking substitute system of FIG. 38A.
Figure 38A:
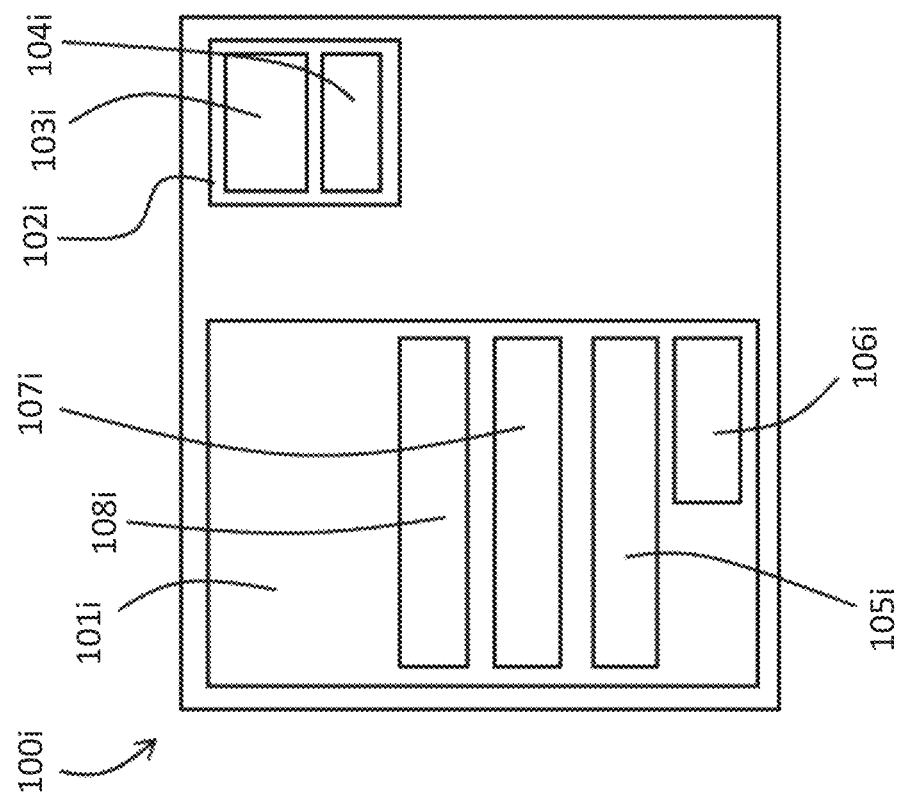
FIG. 38A is a schematic of a smoking substitute system of the ninth mode.

FIG. 38A is a schematic providing a general overview of a smoking substitute system 100*i*. The system 100*i* includes a substitute smoking device 101*i* and an aerosol-forming article in the form of a consumable 102*i*, which comprises an aerosol former 103*i*. The system is configured to vaporize the aerosol former by heating the aerosol former 103*i* (so as to form a vapor/aerosol for inhalation by a user).

In the illustrated system, the heater 104*i* forms part of the consumable 102*i* and is configured to heat the aerosol former 103*i*. In this variation, the heater 104*i* is electrically connectable to the power source 105*i*, for example, when the consumable 102*i* is engaged with the device 101*i*. Heat from the heater 104*i* vaporizes the aerosol former 103*i* to produce a vapor. The vapor subsequently condenses to form an aerosol, which is ultimately inhaled by the user.

The system 100*i* further comprises a power source 105*i* that forms part of the device 101*i*. In other embodiments the power source 105*i* may be external to (but connectable to) the device 101*i*. The power source 105*i* is electrically connectable to the heater 104*i* such that it is able to supply power to the heater 104*i* (i.e., for the purpose of heating the aerosol former 103*i*). Thus, control of the electrical connection of the power source 105*i* to the heater 104*i* provides control of the state of the heater 104*i*. The power source 105*i* may be a power store, for example a battery or rechargeable battery (e.g., a lithium-ion battery).

The system 100*i* further comprises an I/O module comprising a connector 106*i* (e.g., in the form of a USB port, Micro USB port, USB-C port, etc.). The connector 106*i* is configured for connection to an external source of electrical power, e.g., a mains electrical supply outlet. The connector 106*i* may be used in substitution for the power source 105*i*. That is the connector 106*i* may be electrically connectable to the heater 104*i* so as to supply electricity to the heater 104*i*. In such embodiments, the device may not include a power source, and the power source of the system may instead comprise the connector 106*i* and an external source of electrical power (to which the connector 106*i* provides electrical connection).

In some embodiments, the connector 106*i* may be used to charge and recharge the power source 105*i* where the power source 105*i* includes a rechargeable battery.

The system 100*i* also comprises a user interface (UI) 107*i*. Although not shown, the UI 107*i* may include input means to receive commands from a user. The input means of the UI 107*i* allows the user to control at least one aspect of the operation of the system 100*i*. The input means may, for example, be in the form of a button, touchscreen, switch, microphone, etc.

The UI 107*i* also comprises output means to convey information to the user. The output means may, for example, comprise lights (e.g., LEDs), a display screen, speaker, vibration generator, etc.

The system 100*i* further comprises a controller 108*i* that is configured to control at least one function of the device 101*i*. In the illustrated embodiment, the controller 108*i* is a component of the device 101*i*, but in other embodiments may be separate from (but connectable to) the device 101*i*. The controller 108*i* is configured to control the operation of the heater 104*i* and, for example, may be configured to control the voltage applied from the power source 105*i* to the heater 104*i*. The controller 108*i* may be configured to toggle the supply of power to the heater 104*i* between an on state, in which the full output voltage of the power source 105*i* is applied to the heater 104*i*, and an off state, in which the no voltage is applied to the heater 104*i*.

Although not shown, the system 100*i* may also comprise a voltage regulator to regulate the output voltage from the power source 105*i* to form a regulated voltage. The regulated voltage may then be applied to the heater 104*i*.

In addition to being connected to the heater 104*i*, the controller 108*i* is operatively connected to the UI 107*i*. Thus, the controller 108*i* may receive an input signal from the input means of the UI 107*i*. Similarly, the controller 108*i* may transmit output signals to the UI 107*i*. In response, the output means of the UI 107*i* may convey information, based on the output signals, to a user. The controller also comprises a memory 109*i*, which is a non-volatile memory. The memory 109*i* includes instructions, which, when implemented, cause the controller to perform certain tasks or steps of a method.

FIG. 38B is a schematic showing a variation of the system 100*i* of FIG. 38A. In the system 100*i'* of FIG. 38B, the heater 104*i* forms part of the device 101*i*, rather than the consumable 102*i*. In this variation, the heater 104*i* is electrically connected to the power source 105*i*.

FIG. 39A and FIG. 39B illustrate a heated-tobacco (HT) smoking substitute system 200*i*. The system 200*i* is an example of the systems 100*i*, 100*i'* described in relation to FIG. 38A or FIG. 38B. System 200*i* includes an HT device 201*i* and an HT consumable 202*i*. The description of FIG. 38A and FIG. 38B above is applicable to the system 200*i* of FIG. 39A and FIG. 39B, and will thus not be repeated.

The device 201*i* and the consumable 202*i* are configured such that the consumable 202*i* can be engaged with the device 201*i*. FIG. 39A shows the device 201*i* and the consumable 202*i* in an engaged state, whilst FIG. 39B shows the device 201*i* and the consumable 202*i* in a disengaged state.

The device 201*i* comprises a body 209*i* and cap 210*i*. In use the cap 210*i* is engaged at an end of the body 209*i*. Although not apparent from the figures, the cap 210*i* is moveable relative to the body 209*i*. In particular, the cap 210*i* is slidable and can slide along a longitudinal axis of the body 209*i*.

The device 201*i* comprises an output means (forming part of the UI of the device 201*i*) in the form of a plurality of light-emitting diodes (LEDs) 211*i* arranged linearly along the longitudinal axis of the device 201*i* and on an outer surface of the body 209*i* of the device 201*i*. A button 212*i* is also arranged on an outer surface of the body 209*i* of the device 201*i* and is axially spaced (i.e., along the longitudinal axis) from the plurality of LEDs 211*i*.

FIG. 39C show a detailed section view of the consumable 202*i* of the system 200*i*. The consumable 202*i* generally resembles a cigarette. In that respect, the consumable 202*i* has a generally cylindrical form with a diameter of 7 mm and an axial length of 70 mm. The consumable 202*i* comprises an aerosol forming substrate 213*i*, a terminal filter element 214*i*, an upstream filter element 215*i* and a spacer element 216*i*. In other embodiments, the consumable may further comprise a cooling element. A cooling element may exchange heat with vapor that is formed by the aerosol-forming substrate 213*i* in order to cool the vapor so as to facilitate condensation of the vapor.

The aerosol-forming substrate 213*i* is substantially cylindrical and is located at an upstream end 217*i* of the consumable 202*i*, and comprises the aerosol former of the system 200*i*. In that respect, the aerosol forming substrate 213*i* is configured to be heated by the device 201*i* to release a vapor. The released vapor is subsequently entrained in an airflow flowing through the aerosol-forming substrate 213*i*. The airflow is produced by the action of the user drawing on a downstream 218*i* (i.e., terminal or mouth) end of the consumable 202*i*.

In the present embodiment, the aerosol forming substrate 213*i* comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213*i* may comprise a gathered sheet of homogenized (e.g., paper/slurry recon) tobacco or gathered shreds/strips formed from such a sheet.

In an aspect, the consumable is heat-not-burn type. The consumable may comprise a crush ball having a flavorant and/or another aerosol forming substance. The crush ball comprises an external shell that is susceptible to being pierced, broken, fractured, ruptured etc. to release its contents. The crush ball is configured to release the flavorant and/or aerosol forming substance into an aerosol vapor from the heated tobacco upon being crushed/activated.

In order to generate the aerosol, the aerosol forming substrate 213i comprises at least one volatile compound that is intended to be vaporized/aerosolized and that may provide the user with a recreational and/or medicinal effect when inhaled. The aerosol-forming substrate 213i may further comprise one or more additives. For example, such additives may be in the form of humectants (e.g., propylene glycol and/or vegetable glycerin), flavorants, fillers, aqueous/non-aqueous solvents and/or binders.

The terminal filter element 214i is also substantially cylindrical and is located downstream of the aerosol forming substrate 213i at the downstream end 218i of the consumable 202i. The terminal filter element 214i is in the form of a hollow bore filter element having a bore 219i (e.g., for airflow) formed therethrough. The diameter of the bore 219i is 2 mm. The terminal filter element 214i is formed of a porous (e.g., monoacetate) filter material. As set forth above, the downstream end 218i of the consumable 202i (i.e., where the terminal filter 214i is located) forms a mouthpiece portion of the consumable 202i upon which the user draws. Airflow is drawn from the upstream end 217i, thorough the components of the consumable 202i, and out of the downstream end 218i. The airflow is driven by the user drawing on the downstream end 218i (i.e., the mouthpiece portion) of the consumable 202i.

The upstream filter element 215i is located axially adjacent to the aerosol-forming substrate 213i, between the aerosol-forming substrate 213i and the terminal filter element 214i. Like the terminal filter 214i, the upstream filter element 215i is in the form of a hollow bore filter element, such that it has a bore 220i extending axially therethrough. In this way, the upstream filter 215i may act as an airflow restrictor. The upstream filter element 215i is formed of a porous (e.g., monoacetate) filter material. The bore 220i of the upstream filter element 215i has a larger diameter (3 mm) than the terminal filter element 214i.

The spacer 216i is in the form of a cardboard tube, which defines a cavity or chamber between the upstream filter element 215i and the terminal filter element 214i. The spacer 216i acts to allow both cooling and mixing of the vapor/aerosol from the aerosol-forming substrate 213i. The spacer has an external diameter of 7 mm and an axial length of 14 mm.

Although not apparent from the figure, the aerosol-forming substrate 213i, upstream filter 215i and spacer 216i are circumscribed by a paper wrapping layer. The terminal filter 214i is circumscribed by a tipping layer that also circumscribes a portion of the paper wrapping layer (so as to connect the terminal filter 214i to the remaining components of the consumable 202i). The upstream filter 215i and terminal filter 214i are circumscribed by further wrapping layers in the form of plug wraps.

Figures 39D, 39E:
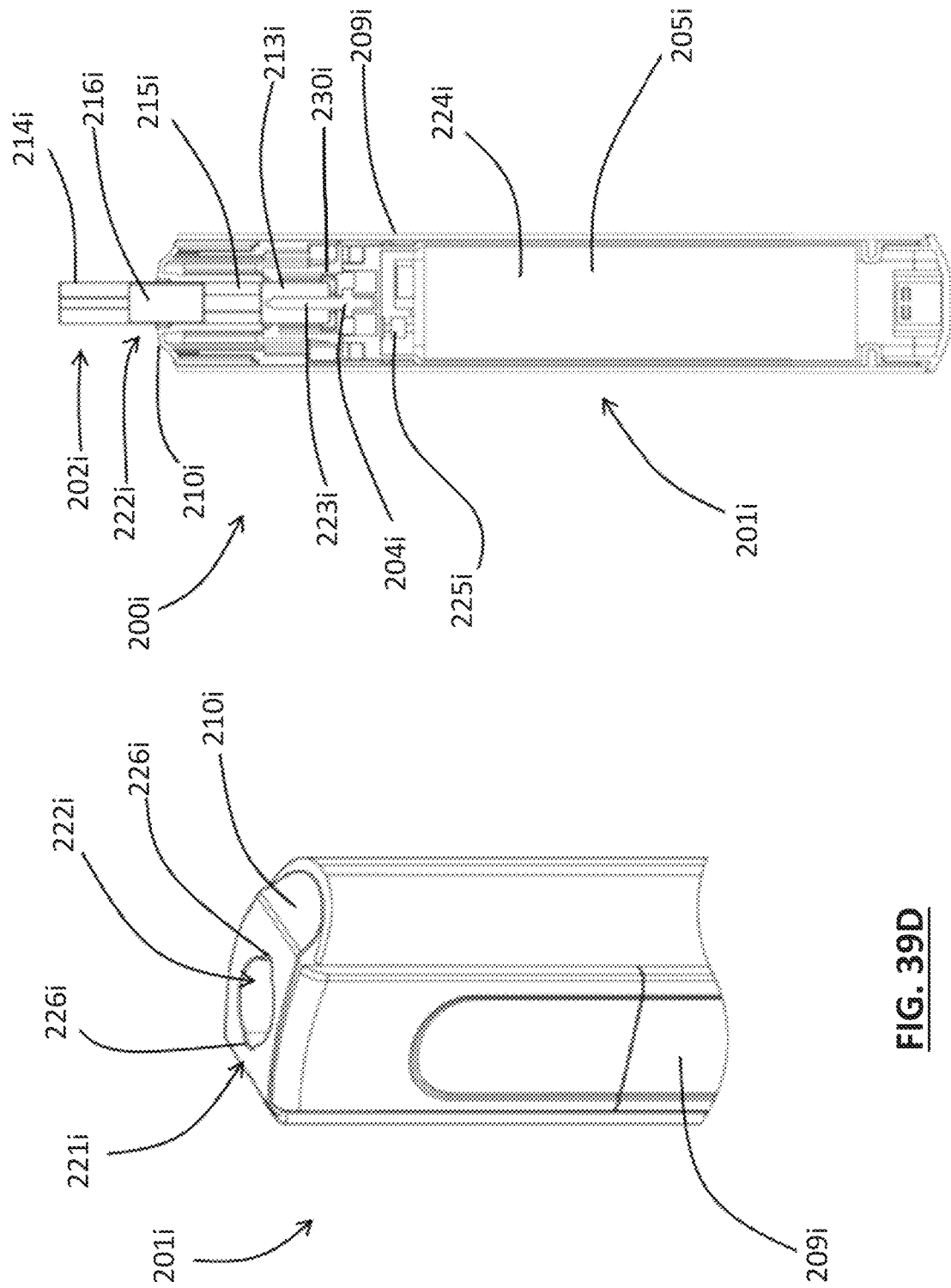
FIG. 39D is a detailed view of an end of the device of the first embodiment of the ninth mode of the smoking substitute system.
FIG. 39E is a section view of the first embodiment of the ninth mode of the substitute smoking system.

Returning now to the device 201i, FIG. 39D illustrates a detailed view of the end of the device 201i that is configured to engage with the consumable 202i. The cap 210i of the device 201i includes an opening 221i to an internal cavity 222i (more apparent from FIG. 39D) defined by the cap 210i. The opening 221i and the cavity 222i are formed so as to receive at least a portion of the consumable 202i.

During engagement of the consumable 202i with the device 201i, a portion of the consumable 202i is received through the opening 221i and into the cavity 222i. After engagement (see FIG. 39B), the downstream end 218i of the consumable 202i protrudes from the opening 221i and thus also protrudes from the device 201i. The opening 221i includes laterally disposed notches 226i. When a consumable 202i is received in the opening 221i, these notches 226i remain open and could, for example, be used for retaining a cover in order to cover the end of the device 201i.

In one aspect, the activator may be operationally configured with the cap 210i of the device. During usage, a rotational motion of the cap 210i in a pre-defined manner causes the activator to activate the crush ball within the consumable.

FIG. 39E shows a cross section through a central longitudinal plane through the device 201i. The device 201i is shown with the consumable 202i engaged therewith.

The device 201i comprises a heater 204i comprising heating element 223i. The heater 204i forms part of the body 209i of the device 201i and is rigidly mounted to the body 209i. In the illustrated embodiment, the heater 204i is a rod heater with a heating element 223i having a circular transverse profile. In other embodiments the heater may be in the form of a blade heater (e.g., heating element with a rectangular transverse profile) or a tube heater (e.g., heating element with a tubular form).

The heating element 223i of the heater 204i projects from an internal base of the cavity 222i along a longitudinal axis towards the opening 221i. As is apparent from the figure, the length (i.e., along the longitudinal axis) of the heating element is less than a depth of the cavity 222i. In this way, the heating element 223i does not protrude from or extend beyond the opening 221i.

When the consumable 202i is received in the cavity 222i (as is shown in FIG. 39E), the heating element 223i penetrates the aerosol-forming substrate 213i of the consumable 202i. In particular, the heating element 223i extends for nearly the entire axial length of the aerosol-forming substrate 213i when inserted therein. Thus, when the heater 204i is activated, heat is transferred radially from an outer circumferential surface the heating element 223i to the aerosol-forming substrate 213i.

An activator (not shown) is provided within the wall of the cavity 222i. The activator comprises a portion of the cavity wall which is configured to elastically deform upon application of an external force and intrude into the cavity to transmit the force to the contents therein. The portion of the wall is flexible to permit inward deformation of the activator and restriction of the cavity cross-section at that point. The activator is capable of undergoing elastic deformation when the external force is applied. The external force is applied by the user pressing/squeezing a region on the outer wall of the device which is operably connected to the elastic wall of the cavity. The elastic properties cause the activator to regain its original shape upon removal of the external force. In a non-limiting aspect, the activator may be configured with a resilient means.

In another embodiment of the activator (not shown), two prongs are provided on opposite sides of the inner walls of the cavity 222i. The two prongs protrude inwardly towards a specific region of the cavity and are actuable by a user. When the user actuates the two prongs, they move inwards applying force to the crush ball within the consumable to rupture the crush ball. Alternatively, the prongs may pierce the consumable and the outer shell of the crush ball to release its contents. The prongs are movable by the user pressing a button on the external wall of the device which is operably connected with the prongs, thereby causing them to move inwards and activate the crush ball when the button is pressed.

In another embodiment (not shown), the activator is a piercing member such as, but not limited to, a pin. The pin is configured to penetrate inwards into the specific region of the cavity upon application of an external force by the user. The pin may have a generally cylindrical configuration with a conical tip extending towards the crush ball. The conical tip, upon activation of the activator, pierces the crush ball within the consumable engaged with the device.

In another embodiment (not shown), the inner wall of the cavity $222i$ includes a movable iris-like aperture located at a position corresponding to the position of a crush ball within a consumable engaged with the device. When actuated by the user by triggering a movable actuator on the outside of the device, the aperture restricts, applying a squeezing force to the consumable and breaking the crush ball within the consumable. The actuator is spring-loaded such that the aperture returns to its original open configuration.

The device $201i$ further comprises an electronics cavity $224i$. A power source, in the form of a rechargeable battery $205i$ (a lithium-ion battery), is located in electronics cavity $224i$.

The device $201i$ includes a connector (i.e., forming part of an IO module of the device $201i$) in the form of a USB port $206i$. The connector may alternatively be, for example, a micro-USB port or a USB-C port for examples. The USB port $206i$ may be used to recharge the rechargeable battery $205i$.

The device $201i$ includes a controller (not shown) located in the electronics cavity $224i$. The controller comprises a microcontroller mounted on a printed circuit board (PCB). The USB port $206i$ is also connected to the controller $208i$ (i.e., connected to the PCB and microcontroller).

The controller $208i$ is configured to control at least one function of the device $201i$. For example, the controller $208i$ is configured to control the operation of the heater $204i$. Such control of the operation of the heater $204i$ may be accomplished by the controller toggling the electrical connection of the rechargeable battery $205i$ to the heater $204i$. For example, the controller $208i$ is configured to control the heater $204i$ in response to a user depressing the button $212i$. Depressing the button $212i$ may cause the controller to allow a voltage (from the rechargeable battery $205i$) to be applied to the heater $204i$ (so as to cause the heating element $223i$ to be heated).

In an embodiment, the controller $208i$ is configured to control the heater $204i$ based on the activation of the activator. During use of the HNB device if the activator is activated to crush open the crush ball, the heater $204i$ may be controlled to operate at a different power than it otherwise would. In one aspect, the controller $208i$ is configured to reduce the power supplied to the heater $204i$ upon activation of the crush ball. For this purpose, one or more sensing means of the HNB device may be configured to provide an input signal to the controller $208i$. Optionally, the controller $208i$ may be configured to change the duration for which heat is supplied to the consumable $202i$ based on the activation of the activator. In the ongoing example, the controller $208i$ extends the time duration of heat supply to the consumable $202i$ by the heater $204i$. Thereby, the aerosol vapor may be regulated for enhanced user experience.

The controller is also configured to control the LEDs $211i$ in response to (e.g., a detected) a condition of the device $201i$ or the consumable $202i$. For example, the controller may control the LEDs to indicate whether the device $201i$ is in an on state or an off state (e.g., one or more of the LEDs may be illuminated by the controller when the device is in an on state).

The device $201i$ comprises a further input means (i.e., in addition to the button $212i$) in the form of a puff sensor $225i$. The puff sensor $225i$ is configured to detect a user drawing (i.e., inhaling) at the downstream end $218i$ of the consumable $202i$. The puff sensor $225i$ may, for example, be in the form of a pressure sensor, flowmeter or a microphone. The puff sensor $225i$ is operatively connected to the controller $208i$ in the electronics cavity $224i$, such that a signal from the puff sensor $225i$, indicative of a puff state (i.e., drawing or not drawing), forms an input to the controller $208i$ (and can thus be responded to by the controller $208i$).

Tenth Mode: A Heat not Burn (HNB) Device Having a Thermally Conductive Shroud Thermally Connected to a Heating Element for Heating a HNB Consumable Aspects and embodiments of the tenth mode of the present disclosure will now be discussed with reference to the accompanying figures. Further aspects and embodiments will be apparent to those skilled in the art. All documents mentioned in this text are incorporated herein by reference.

Figure 40:
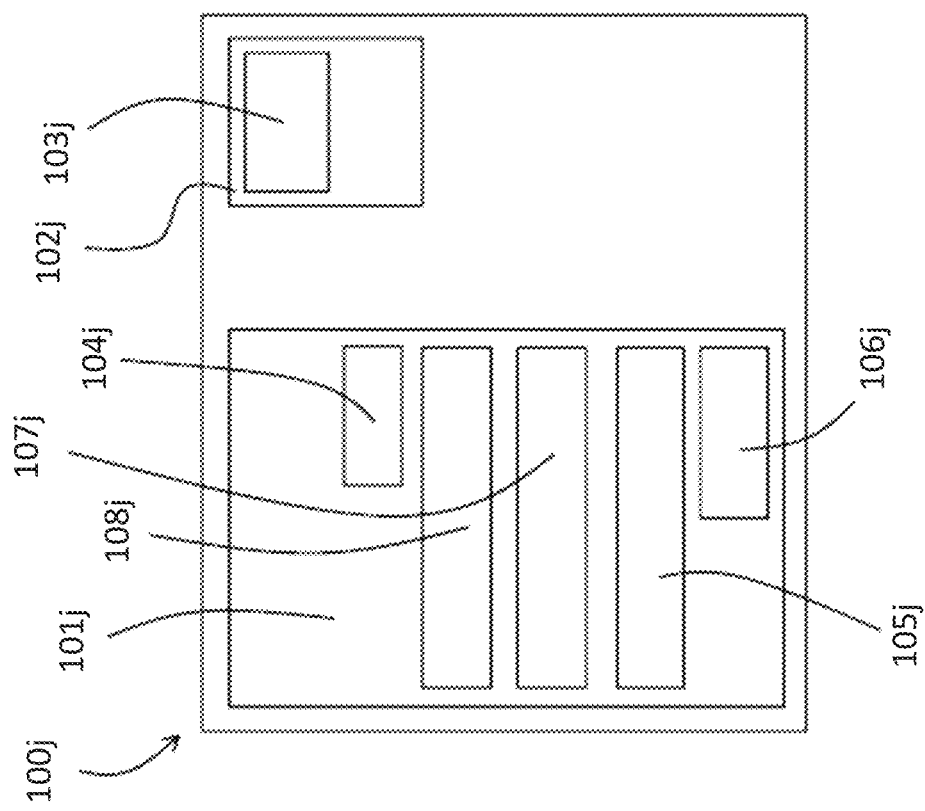
FIG. 40 is a schematic of a smoking substitute system of the tenth mode.

FIG. 40 is a schematic providing a general overview of a smoking substitute system $100j$. The system $100j$ includes a substitute smoking device $101j$ and an aerosol-forming article in the form of a consumable $102j$, which comprises an aerosol former $103j$. The system is configured to vaporize the aerosol former by heating the aerosol former $103j$ (so as to form a vapor/aerosol for inhalation by a user).

The heater $104j$ forms part of the device $101j$ and is configured to heat the aerosol former $103j$. The heater $104j$ is electrically connected to a power source $105j$, for example, when the consumable $102j$ is engaged with the device $101j$. Heat from the heater $104j$ vaporizes the aerosol former $103j$ to produce a vapor. The vapor subsequently condenses to form an aerosol, which is ultimately inhaled by the user.

The system $100j$ further comprises a power source $105j$ that forms part of the device $101j$. In other embodiments the power source $105j$ may be external to (but connectable to) the device $101j$. The power source $105j$ is electrically connected to the heater $104j$ such that it is able to supply power to the heater $104j$ (i.e., for the purpose of heating the aerosol former $103j$). Thus, control of the electrical connection of the power source $105j$ to the heater $104j$ provides control of the state of the heater $104j$. The power source $105j$ may be a power store, for example a battery or rechargeable battery (e.g., a lithium-ion battery).

The system $100j$ further comprises an I/O module comprising a connector $106j$ (e.g., in the form of a USB port, Micro USB port, USB-C port, etc.). The connector $106j$ is configured for connection to an external source of electrical power, e.g., a mains electrical supply outlet. The connector $106j$ may be used in substitution for the power source $105j$. That is the connector $106j$ may be electrically connectable to the heater $104j$ so as to supply electricity to the heater $104j$. In such embodiments, the device may not include a power source, and the power source of the system may instead comprise the connector $106j$ and an external source of electrical power (to which the connector $106j$ provides electrical connection).

In some embodiments, the connector $106j$ may be used to charge and recharge the power source $105j$ where the power source $105j$ includes a rechargeable battery.

The system 100j also comprises a user interface (UI) 107j. Although not shown, the UI 107j may include input means to receive commands from a user. The input means of the UI 107j allows the user to control at least one aspect of the operation of the system 100j. The input means may, for example, be in the form of a button, touchscreen, switch, microphone, etc.

The UI 107j also comprises output means to convey information to the user. The output means may, for example, comprise lights (e.g., LEDs), a display screen, speaker, vibration generator, etc.

The system 100j further comprises a controller 108j that is configured to control at least one function of the device 101j. In the illustrated embodiment, the controller 108j is a component of the device 101j, but in other embodiments may be separate from (but connectable to) the device 101j. The controller 108j is configured to control the operation of the heater 104j and, for example, may be configured to control the voltage applied from the power source 105j to the heater 104j. The controller 108j may be configured to toggle the supply of power to the heater 104j between an on state, in which the full output voltage of the power source 105j is applied to the heater 104j, and an off state, in which the no voltage is applied to the heater 104j.

Although not shown, the system 100j may also comprise a voltage regulator to regulate the output voltage from the power source 105j to form a regulated voltage. The regulated voltage may then be applied to the heater 104j.

In addition to being connected to the heater 104j, the controller 108j is operatively connected to the UI 107j. Thus, the controller 108j may receive an input signal from the input means of the UI 107j.

Similarly, the controller 108j may transmit output signals to the UI 107j. In response, the output means of the UI 107j may convey information, based on the output signals, to a user. The controller also comprises a memory 109j, which is a non-volatile memory. The memory 109j includes instructions, which when implemented, cause the controller to perform certain tasks or steps of a method.

FIG. 41A and FIG. 41B illustrate a heated-tobacco (HT) smoking substitute system 200j. The system 200j is an example of the system 100j described in relation to FIG. 40. System 200j includes an HT device 201j and an HT consumable 202j. The description of FIG. 40 above is applicable to the system 200j of FIG. 41A and FIG. 41B, and will thus not be repeated.

The device 201j and the consumable 202j are configured such that the consumable 202j can be engaged with the device 201j. FIG. 41A shows the device 201j and the consumable 202j in an engaged state, whilst FIG. 41B shows the device 201j and the consumable 202j in a disengaged state.

The device 201j comprises a body 209j and cap 210j. In use the cap 210j is engaged at an end of the body 209j. Although not apparent from the figures, the cap 210j is moveable relative to the body 209j. In particular, the cap 210j is slidable and can slide along a longitudinal axis of the body 209j.

The device 201j comprises an output means (forming part of the UI of the device 201j) in the form of a plurality of light-emitting diodes (LEDs) 211j arranged linearly along the longitudinal axis of the device 201j and on an outer surface of the body 209j of the device 201j. A button 212j is also arranged on an outer surface of the body 209j of the device 201j and is axially spaced (i.e., along the longitudinal axis) from the plurality of LEDs 211j.

Figure 41C:
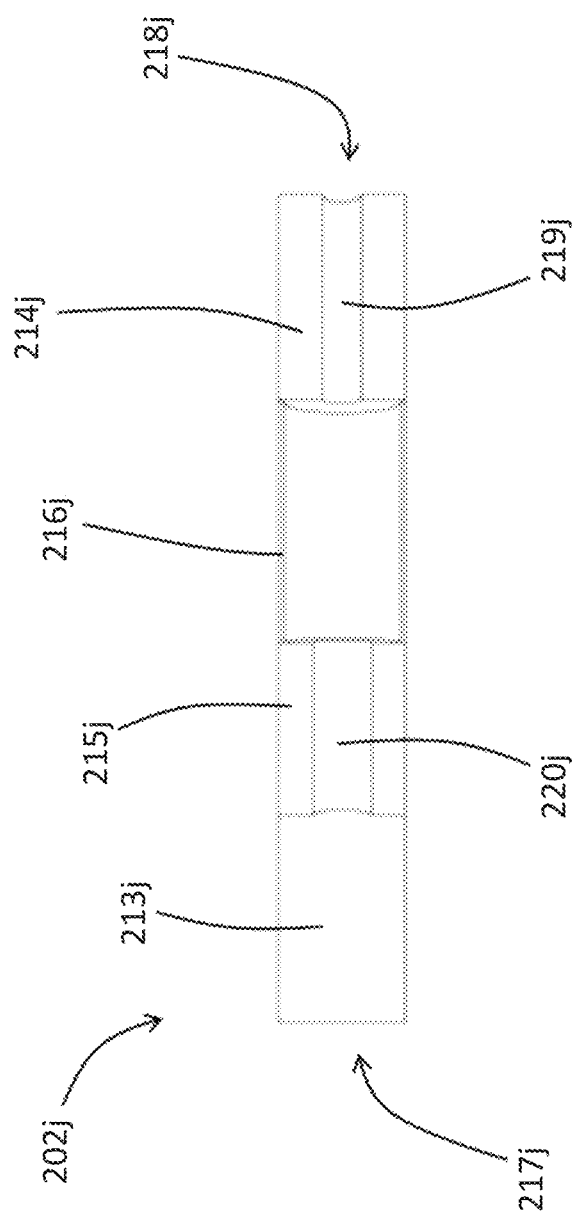
FIG. 41C is a section view of the consumable of the first embodiment of the tenth mode of the smoking substitute system.

FIG. 41C show a detailed section view of the consumable 202j of the system 200j. The consumable 202j generally resembles a cigarette. In that respect, the consumable 202j has a generally cylindrical form with a diameter of 7 mm and an axial length of 70 mm. The consumable 202j comprises an aerosol forming substrate 213j, a terminal filter element 214j, an upstream filter element 215j and a spacer element 216j. In other embodiments, the consumable may further comprise a cooling element. A cooling element may exchange heat with vapor that is formed by the aerosol-forming substrate 213j in order to cool the vapor so as to facilitate condensation of the vapor.

The aerosol-forming substrate 213j is substantially cylindrical and is located at an upstream end 217j of the consumable 202j, and comprises the aerosol former of the system 200j. In that respect, the aerosol forming substrate 213j is configured to be heated by the device 201j to release a vapor. The released vapor is subsequently entrained in an airflow flowing through the aerosol-forming substrate 213j. The airflow is produced by the action of the user drawing on a downstream 218j (i.e., terminal or mouth end) of the consumable 202j.

In the present embodiment, the aerosol forming substrate 213j comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213j may comprise a gathered sheet of homogenized (e.g., paper/slurry recon) tobacco or gathered shreds/strips formed from such a sheet.

In order to generate an aerosol, the aerosol forming substrate 213j comprises at least one volatile compound that is intended to be vaporized/aerosolized and that may provide the user with a recreational and/or medicinal effect when inhaled. The aerosol-forming substrate 213j may further comprise one or more additives. For example, such additives may be in the form of humectants (e.g., propylene glycol and/or vegetable glycerin), flavorants, fillers, aqueous/non-aqueous solvents and/or binders.

The terminal filter element 214j is also substantially cylindrical, and is located downstream of the aerosol forming substrate 213j at the downstream end 218j of the consumable 202j. The terminal filter element 214j is in the form of a hollow bore filter element having a bore 219j (e.g., for airflow) formed therethrough. The diameter of the bore 219j is 2 mm. The terminal filter element 214j is formed of a porous (e.g., monoacetate) filter material. As set forth above, the downstream end 218j of the consumable 202j (i.e., where the terminal filter 214j is located) forms a mouthpiece portion of the consumable 202j upon which the user draws. Airflow is drawn from the upstream end 217j, thorough the components of the consumable 202j, and out of the downstream end 218j. The airflow is driven by the user drawing on the downstream end 218j (i.e., the mouthpiece portion) of the consumable 202j.

The upstream filter element 214j is located axially adjacent to the aerosol-forming substrate 213j, between the aerosol-forming substrate 213j and the terminal filter element 214j. Like the terminal filter 214j, the upstream filter element 215j is in the form of a hollow bore filter element, such that it has a bore 220j extending axially therethrough. In this way, the upstream filter 215j may act as an airflow restrictor. The upstream filter element 215j is formed of a porous (e.g., monoacetate) filter material. The bore 220j of the upstream filter element 214j has a larger diameter (3 mm) than the terminal filter element 214j.

The spacer 216j is in the form of a cardboard tube, which defines a cavity or chamber between the upstream filter element 215j and the terminal filter element 214j. The spacer 216j acts to allow both cooling and mixing of the vapor/aerosol from the aerosol-forming substrate 213j. The spacer has an external diameter of 7 mm and an axial length of 14 mm.

Although not apparent from the figure, the aerosol-forming substrate 213j, upstream filter 215j and spacer 216j are circumscribed by a paper wrapping layer. The terminal filter 214j is circumscribed by a tipping layer that also circumscribes a portion of the paper wrapping layer (so as to connect the terminal filter 214j to the remaining components of the consumable 202j). The upstream filter 215j and terminal filter 214j are circumscribed by further wrapping layers in the form of plug wraps.

Returning now to the device 201j, FIG. 41D illustrates a detailed view of the end of the device 201j that is configured to engage with the consumable 202j. The cap 210j of the device 201j includes an opening 221j to an internal cavity 222j (more apparent from FIG. 41D) defined by the cap 210j. The opening 221j and the cavity 222j are formed so as to receive at least a portion of the consumable 202j.

During engagement of the consumable 202j with the device 201j, a portion of the consumable 202j is received through the opening 221j and into the cavity 222j. After engagement (see FIG. 41B), the downstream end 218j of the consumable 202j protrudes from the opening 221j and thus protrudes also from the device 201j. The opening 221j includes laterally disposed notches 226j. When a consumable 202j is received in the opening 221j, these notches 226j remain open and could, for example, be used for retaining a cover to cover the end of the device 201j.

FIG. 41E shows a cross section through a central longitudinal plane through the device 201j. The device 201j is shown with the consumable 202j engaged therewith.

The device 201j comprises a heater 204j comprising heating element 223j. The heater 204j forms part of the body 209j of the device 201j and is rigidly mounted to the body 209j and projects into a cavity 251j defined by a shroud 250j (which will be discussed in more detail below). In the illustrated embodiment, the heater 204j is a rod heater with a heating element 223j having a circular transverse profile. In other embodiments the heater may be in the form of a blade heater (e.g., heating element with a rectangular transverse profile) or a tube heater (e.g., heating element with a tubular form that is inserted into the substrate of the consumable 202j).

The heating element 223j of the heater 204j projects from an internal base of the cavity 222j along a longitudinal axis towards the opening 221j. As is apparent from the figure, the length (i.e., along the longitudinal axis) of the heating element is less than a depth of the cavity 222j. In this way, the heating element 223j does not protrude from or extend beyond the opening 221j.

When the consumable 202j is received in the cavity 222j (as is shown in FIG. 41E), the heating element 223j penetrates the aerosol-forming substrate 213j of the consumable 202j. In particular, the heating element 223j extends for nearly the entire axial length of the aerosol-forming substrate 213j when inserted therein. Thus, when the heater 204j is activated, heat is transferred radially from an outer circumferential surface the heating element 223j to the aerosol-forming substrate 213j.

As mentioned above, the device 201j further includes a thermally conductive shroud 250j. This shroud 250j and the heater 204j are shown in more detail in FIG. 41F and FIG. 41G. The shroud 250j defines a cavity 251j for receipt of the HNB consumable 202j and, as is set forth above, the heater 204j projects into the cavity 251j of the shroud 250j such that when a consumable 202j is received in the cavity 251j defined by the shroud, the heater 204j penetrates the aerosol-forming substrate 213j of the consumable 202j.

The thermally conductive shroud 250j is tubular and, like the heater 204j, extends along the longitudinal axis. The heater 204j extends along a central axis of the shroud 250j, such that the heater 204j and shroud 250j are generally concentrically arranged. In particular, the heater 204j and shroud 250j extend longitudinally (within the cavity 222j of the device 201j) to approximately the same extent. That is, the length (i.e., in the longitudinal direction) of the heater 204j is approximately the same as the length of the shroud 250j. Thus, the shroud 250j extends along an external portion of the consumable 202j that is adjacent to the aerosol-forming substrate 213j of the consumable 202j.

As may be appreciated from FIG. 41E, the shroud 250j is configured so as to enclose a portion of the HNB consumable 202j such that an inner surface 253j of the shroud 250j surrounds and faces an outer wrapping layer of the consumable 202j when received in the cavity 251j. An opposing outer 254j circumferential surface of the shroud 250j faces away from the HNB consumable 202j when received in the cavity 251j. Although not apparent from the figures, the inner surface 253j comprises a coating that provides it with a higher thermal emissivity than the outer surface 254j. Thus, in operation, more heat is radiated from the inner surface 253j (towards the consumable 202j) than the outer surface 254j (away from the consumable 202j).

The shroud 250j has a substantially circular cross-section and thus the cavity 251j defined by the shroud 250j also has a circular cross-section such that it is particularly suitable for receipt of a consumable 202j having circular cross-section. It should be appreciated that in other embodiments the shroud 250j may have a rectangular, triangular, polygonal or other suitable cross section to surround or enclose a HNB consumable having an alternative shape.

Figure 41G:
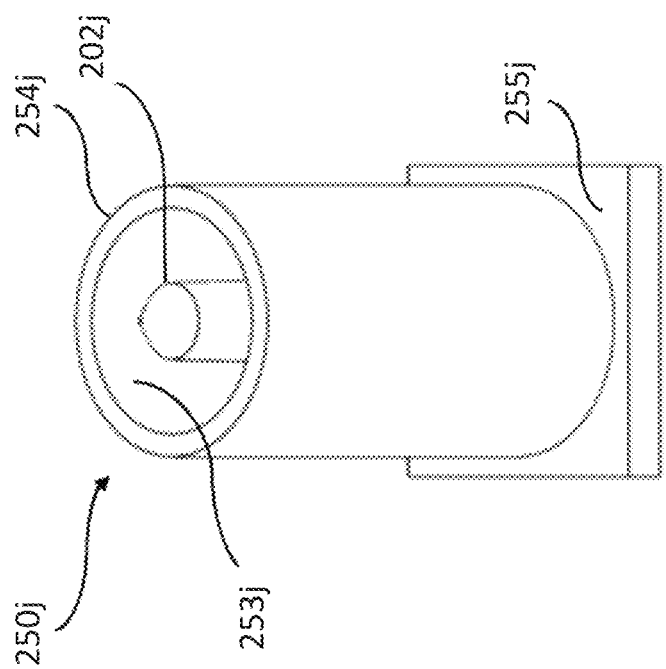
FIG. 41G is perspective view of the first embodiment of the tenth mode of the thermally conductive shroud of a smoking substitute system.
Figure 41F:
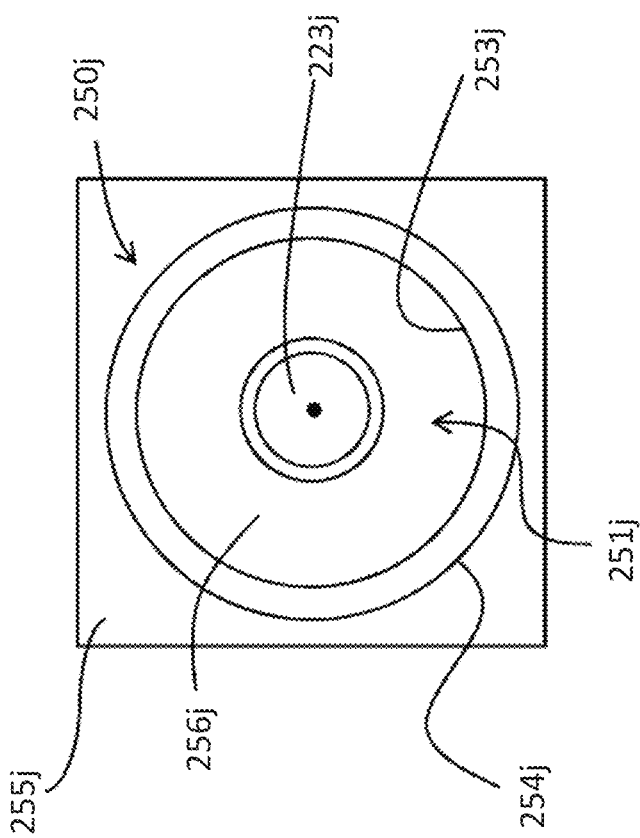
FIG. 41F is a top view of a first embodiment of the tenth mode of a thermally conductive shroud of a smoking substitute system.

As is apparent from FIG. 41F and FIG. 41G, a mount 255j is provided for mounting the heater 204j to the device 201j. The mount 255j has a generally cuboid shape and comprises a central aperture through which the heater 204j projects. In the illustrated embodiment, the mount 255j defines a thermally conductive path 256j that extends from the heater 202j to the shroud 250j. Thus, when the heater 204j is active, heat is transferred from the heater 204j, along the thermally conductive path 256j (in this case being a portion of the mount 255j) to the shroud 250j so as to heat the shroud 250j. In this way, the shroud 250j may supply heat to the consumable 202j through an outer wrapping layer of the consumable 202j. As may be apparent, this can lead to more even heating of the consumable 202j, which can be achieved without the provision of multiple heaters.

The shroud may be formed of one or more of a ceramic material, aluminum and stainless steel, or any other suitable material (e.g., being thermally conductive). The mount 255j may comprise a thermally insulative material (such as zirconia) for restricting heat transfer between the heater 204j and the housing of the device 201j. However, the portion of the mount 255j that defines the thermally conductive path 256j (i.e., the upper surface between the heater 204j and the shroud 250j) comprises a thermally conductive material, such as a thermally conductive plastic, ceramic or metal.

This portion of the mount may be substantially surrounded by the thermally insulative portion of the mount so as to prevent heat transfer between the thermally conductive path 256*j* and the rest of the device 201*j*.

Although not immediately apparent from the figures, the shroud 250*j* forms part of the cap 210*j* of the device 201*j*. In this respect, the shroud 250*j* is movable (with the cap 210*j*) with respect to heater 204*j* and the mount 255*j*. Thus, when the cap 210*j* is disengaged from the body 209*j*, or is slid away from the heater 204*j* (along the longitudinal axis), the shroud 250*j* is not in contact with the mount 255*j*. The shroud 250*j* can then be brought into contact with the mount 255*j* by sliding the cap 210*j* along the longitudinal axis towards the mount 255*j* so as to be engaged with the body 209*j*. In particular, this brings a base (or bottom end) of the mount 255*j* into contact with an upper surface of the mount 255*j* defining the thermally conductive path 256*j*.

Whilst not shown, the device 201*j* or the cap 210*j* may further comprise an insulative housing that at least partially surrounds the shroud 250*j* in order to restrict heat transfer from the shroud to the body 209*j* of the device 201*j*. At least a portion of the insulative housing may define an outer surface of the body 209*j* of the device 201*j*.

Returning to FIG. 41E, the device 201*j* further comprises an electronics cavity 224*j*. A power source, in the form of a rechargeable battery 205*j* (a lithium-ion battery), is located in electronics cavity 224*j*.

The device 201*j* includes a connector (i.e., forming part of an IO module of the device 201*j*) in the form of a USB port 206*j*. The connector may alternatively be, for example, a micro-USB port or a USB-C port for examples. The USB port 206*j* may be used to recharge the rechargeable battery 205*j*.

The device 201*j* includes a controller (not shown) located in the electronics cavity 224*j*. The controller comprises a microcontroller mounted on a printed circuit board (PCB). The USB port 206*j* is also connected to the controller (i.e., connected to the PCB and microcontroller).

The controller is configured to control at least one function of the device 201*j*. For example, the controller is configured to control the operation of the heater 204*j*. Such control of the operation of the heater 204*j* may be accomplished by the controller toggling the electrical connection of the rechargeable battery 205*j* to the heater 204*j*. For example, the controller is configured to control the heater 204*j* in response to the user depressing the button 212*j*. Depressing the button 212*j* may cause the controller to allow a voltage (from the rechargeable battery 205*j*) to be applied to the heater 204*j* (so as to cause the heating element 223*j* to be heated).

The controller is also configured to control the LEDs 211*j* in response to (e.g., a detected) a condition of the device 201*j* or the consumable 202*j*. For example, the controller may control the LEDs to indicate whether the device 201*j* is in an on state or an off state (e.g., one or more of the LEDs may be illuminated by the controller when the device is in an on state).

The device 202*j* comprises a further input means (i.e., in addition to the button 212*j*) in the form of a puff sensor 225*j*. The puff sensor 225*j* is configured to detect a user drawing (i.e., inhaling) at the downstream end 218*j* of the consumable 202*j*. The puff sensor 225*j* may, for example, be in the form of a pressure sensor, flowmeter or a microphone. The puff sensor 225*j* is operatively connected to the controller in the electronics cavity 224*j*, such that a signal from the puff sensor 225*j*, indicative of a puff state (i.e., drawing or not drawing), forms an input to the controller (and can thus be responded to by the controller).

Eleventh Mode: A Smoking Substitute Device Having a Cap Configured to be in Physical Contact with the Heating Element Aspects and embodiments of the eleventh mode of the present disclosure will now be discussed with reference to the accompanying figures. Further aspects and embodiments will be apparent to those skilled in the art. All documents mentioned in this text are incorporated herein by reference.

Figure 42A:
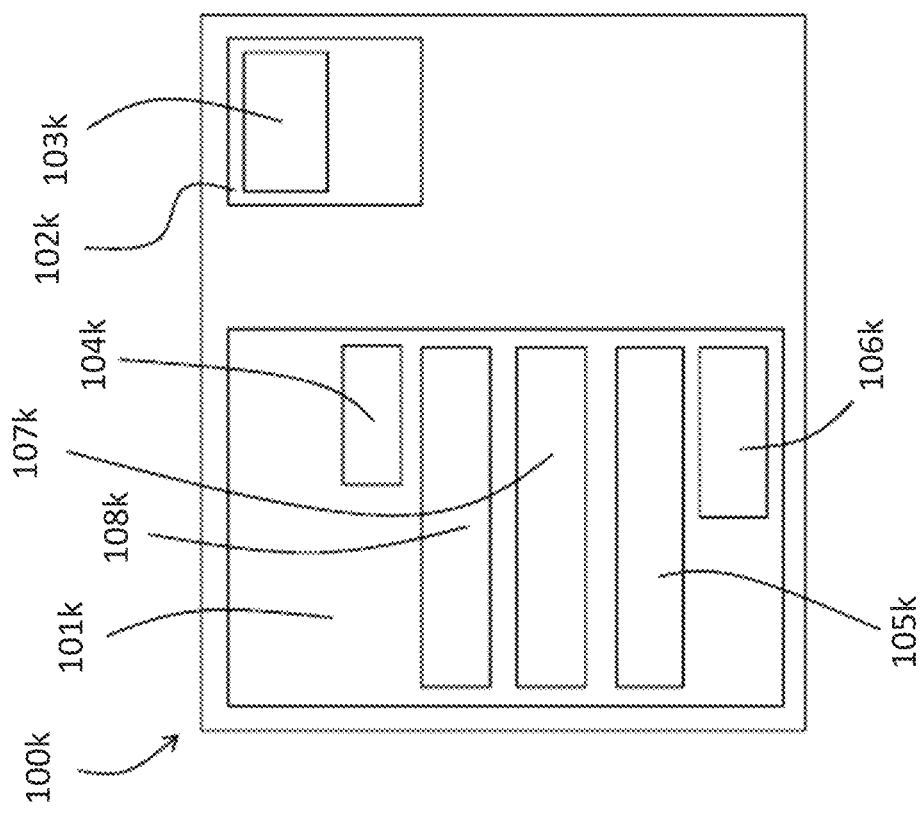
FIG. 42A is a schematic of a smoking substitute system of the eleventh mode.

FIG. 42A is a schematic providing a general overview of a smoking substitute system 100*k*. The system 100*k* includes a substitute smoking device 101*k* and an aerosol-forming article in the form of a consumable 102*k*, which comprises an aerosol former 103*k*. The system is configured to vaporize the aerosol former by heating the aerosol former 103*k* (so as to form a vapor/aerosol for inhalation by a user).

In the illustrated system, the heater 104*k* forms part of the consumable 102*k* and is configured to heat the aerosol former 103*k*. In this variation, the heater 104*k* is electrically connectable to the power source 105*k*, for example, when the consumable 102*k* is engaged with the device 101*k*. Heat from the heater 104*k* vaporizes the aerosol former 103*k* to produce a vapor. The vapor subsequently condenses to form an aerosol, which is ultimately inhaled by the user.

The system 100*k* further comprises a power source 105*k* that forms part of the device 101*k*. In other embodiments the power source 105*k* may be external to (but connectable to) the device 101*k*. The power source 105*k* is electrically connectable to the heater 104*k* such that it is able to supply power to the heater 104*k* (i.e., for the purpose of heating the aerosol former 103*k*). Thus, control of the electrical connection of the power source 105*k* to the heater 104*k* provides control of the state of the heater 104*k*. The power source 105*k* may be a power store, for example a battery or rechargeable battery (e.g., a lithium-ion battery).

The system 100*k* further comprises an I/O module comprising a connector 106*k* (e.g., in the form of a USB port, Micro USB port, USB-C port, etc.). The connector 106*k* is configured for connection to an external source of electrical power, e.g., a mains electrical supply outlet. The connector 106*k* may be used in substitution for the power source 105*k*. That is the connector 106*k* may be electrically connectable to the heater 104*k* so as to supply electricity to the heater 104*k*. In such embodiments, the device may not include a power source, and the power source of the system may instead comprise the connector 106*k* and an external source of electrical power (to which the connector 106*k* provides electrical connection).

In some embodiments, the connector 106*k* may be used to charge and recharge the power source 105*k* where the power source 105*k* includes a rechargeable battery.

The system 100*k* also comprises a user interface (UI) 107*k*. Although not shown, the UI 107*k* may include input means to receive commands from a user. The input means of the UI 107*k* allows the user to control at least one aspect of the operation of the system 100*k*. The input means may, for example, be in the form of a button, touchscreen, switch, microphone, etc.

The UI 107*k* also comprises output means to convey information to the user. The output means may, for example, comprise lights (e.g., LEDs), a display screen, speaker, vibration generator, etc.

The system 100*k* further comprises a controller 108*k* that is configured to control at least one function of the device 101*k*. In the illustrated embodiment, the controller 108*k* is a component of the device 101*k*, but in other embodiments may be separate from (but connectable to) the device 101*k*. The controller 108*k* is configured to control the operation of the heater 104*k* and, for example, may be configured to control the voltage applied from the power source 105*k* to the heater 104*k*. The controller 108*k* may be configured to toggle the supply of power to the heater 104*k* between an on state, in which the full output voltage of the power source 105*k* is applied to the heater 104*k*, and an off state, in which the no voltage is applied to the heater 104*k*.

Although not shown, the system 100*k* may also comprise a voltage regulator to regulate the output voltage from the power source 105*k* to form a regulated voltage. The regulated voltage may then be applied to the heater 104*k*.

In addition to being connected to the heater 104*k*, the controller 108*k* is operatively connected to the UI 107*k*. Thus, the controller 108*k* may receive an input signal from the input means of the UI 107*k*. Similarly, the controller 108*k* may transmit output signals to the UI 107*k*. In response, the output means of the UI 107*k* may convey information, based on the output signals, to a user. The controller also comprises a memory 109*k*, which is a non-volatile memory. The memory 109*k* includes instructions, which, when implemented, cause the controller to perform certain tasks or steps of a method.

Figure 42B:
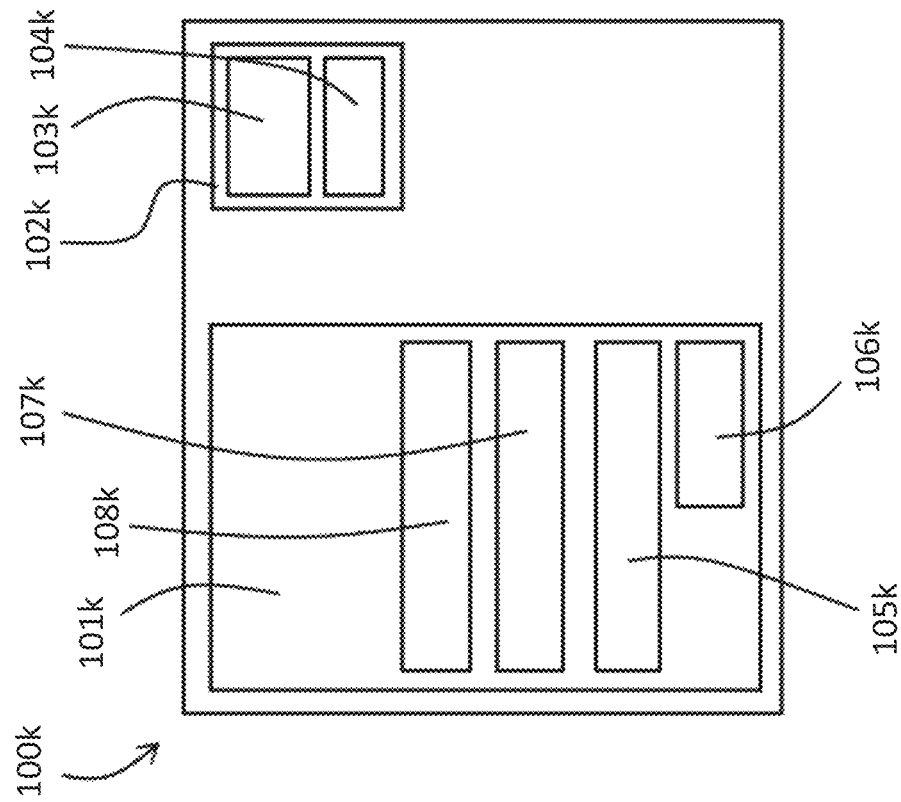
FIG. 42B is a schematic of a variation of the smoking substitute system of FIG. 42A.

FIG. 42B is a schematic showing a variation of the system 100*k* of FIG. 42A. In the system 100*k'* of FIG. 42B, the heater 104*k* forms part of the device 101*k*, rather than the consumable 102*k*. In this variation, the heater 104*k* is electrically connected to the power source 105*k*. In the illustrated embodiment, the heater 104*k* forms part of the device 101*k*.

FIG. 43A and FIG. 43B illustrate a heated-tobacco (HT) smoking substitute system 200*k*. The system 200*k* is an example of the systems 100*k*, 100*k'* described in relation to FIG. 42A or FIG. 42B. System 200*k* includes an HT device 201*k* and an HT consumable 202*k*. The description of FIG. 42A and FIG. 42B above is applicable to the system 200*k* of FIG. 43A and FIG. 43B, and will thus not be repeated.

The device 201*k* and the consumable 202*k* are configured such that the consumable 202*k* can be engaged with the device 201*k*. FIG. 43A shows the device 201*k* and the consumable 202*k* in an engaged state, whilst FIG. 43B shows the device 201*k* and the consumable 202*k* in a disengaged state.

The device 201*k* comprises a body 209*k* and cap 210*k*. In use the cap 210*k* is engaged at an end of the body 209*k*. Although not apparent from the figures, the cap 210*k* is moveable relative to the body 209*k*. In particular, the cap 210*k* is slidable and can slide along a longitudinal axis of the body 209*k*. In other embodiments, the cap may be, or may additionally be, rotatable around the longitudinal axis of the body 209*k*.

The device 201*k* comprises an output means (forming part of the UI of the device 201*k*) in the form of a plurality of light-emitting diodes (LEDs) 211*k* arranged linearly along the longitudinal axis of the device 201*k* and on an outer surface of the body 209*k* of the device 201*k*. A button 212*k* is also arranged on an outer surface of the body 209*k* of the device 201*k* and is axially spaced (i.e., along the longitudinal axis) from the plurality of LEDs 211*k*.

Figure 43C:
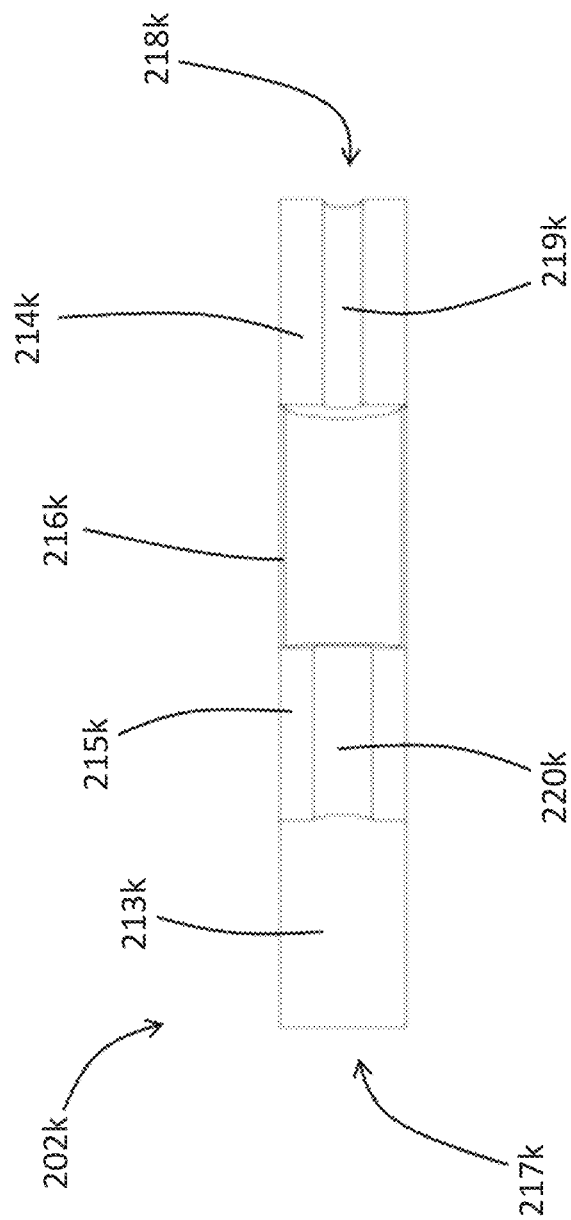
FIG. 43C is a section view of the consumable of the first embodiment of the eleventh mode of the smoking substitute system.

FIG. 43C show a detailed section view of the consumable 202*k* of the system 200*k*. The consumable 202*k* generally resembles a cigarette. In that respect, the consumable 202*k* has a generally cylindrical form with a diameter of 7 mm and an axial length of 70 mm. The consumable 202*k* comprises an aerosol forming substrate 213*k*, a terminal filter element 214*k*, an upstream filter element 215*k* and a spacer element 216*k*. In other embodiments, the consumable may further comprise a cooling element. A cooling element may exchange heat with vapor that is formed by the aerosol-forming substrate 213*k* in order to cool the vapor so as to facilitate condensation of the vapor.

The aerosol-forming substrate 213*k* is substantially cylindrical and is located at an upstream end 217*k* of the consumable 202*k*, and comprises the aerosol former of the system 200*k*. In that respect, the aerosol forming substrate 213*k* is configured to be heated by the device 201*k* to release a vapor. The released vapor is subsequently entrained in an airflow flowing through the aerosol-forming substrate 213*k*. The airflow is produced by the action of the user drawing on a downstream 218*k* (i.e., terminal or mouth end) of the consumable 202*k*.

In the present embodiment, the aerosol forming substrate 213*k* comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213*k* may comprise a gathered sheet of homogenized (e.g., paper/slurry recon) tobacco or gathered shreds/strips formed from such a sheet.

In order to generate an aerosol, the aerosol forming substrate 213*k* comprises at least one volatile compound that is intended to be vaporized/aerosolized and that may provide the user with a recreational and/or medicinal effect when inhaled. The aerosol-forming substrate 213*k* may further comprise one or more additives. For example, such additives may be in the form of humectants (e.g., propylene glycol and/or vegetable glycerin), flavorants, fillers, aqueous/non-aqueous solvents and/or binders.

The terminal filter element 214*k* is also substantially cylindrical, and is located downstream of the aerosol forming substrate 213*k* at the downstream end 218*k* of the consumable 202*k*. The terminal filter element 214*k* is in the form of a hollow bore filter element having a bore 219*k* (e.g., for airflow) formed therethrough. The diameter of the bore 219*k* is 2 mm. The terminal filter element 214*k* is formed of a porous (e.g., monoacetate) filter material. As set forth above, the downstream end 218*k* of the consumable 202*k* (i.e., where the terminal filter 214*k* is located) forms a mouthpiece portion of the consumable 202*k* upon which the user draws. Airflow is drawn from the upstream end 217*k*, thorough the components of the consumable 202*k*, and out of the downstream end 218*k*. The airflow is driven by the user drawing on the downstream end 218*k* (i.e., the mouthpiece portion) of the consumable 202*k*.

The upstream filter element 215*k* is located axially adjacent to the aerosol-forming substrate 213*k*, between the aerosol-forming substrate 213*k* and the terminal filter element 214*k*. Like the terminal filter 214*k*, the upstream filter element 215*k* is in the form of a hollow bore filter element, such that it has a bore 220*k* extending axially therethrough. In this way, the upstream filter 215*k* may act as an airflow restrictor. The upstream filter element 215*k* is formed of a porous (e.g., monoacetate) filter material. The bore 220*k* of the upstream filter element 215*k* has a larger diameter (3 mm) than the terminal filter element 214*k*.

The spacer 216*k* is in the form of a cardboard tube, which defines a cavity or chamber between the upstream filter element 215*k* and the terminal filter element 214*k*. The spacer 216*k* acts to allow both cooling and mixing of the vapor/aerosol from the aerosol-forming substrate 213k. The spacer has an external diameter of 7 mm and an axial length of 14 mm.

Although not apparent from the figure, the aerosol-forming substrate 213k, upstream filter 215k and spacer 216k are circumscribed by a paper wrapping layer. The terminal filter 214k is circumscribed by a tipping layer that also circumscribes a portion of the paper wrapping layer (so as to connect the terminal filter 214k to the remaining components of the consumable 202k). The upstream filter 215k and terminal filter 214k are circumscribed by further wrapping layers in the form of plug wraps.

Figures 43D, 43E:
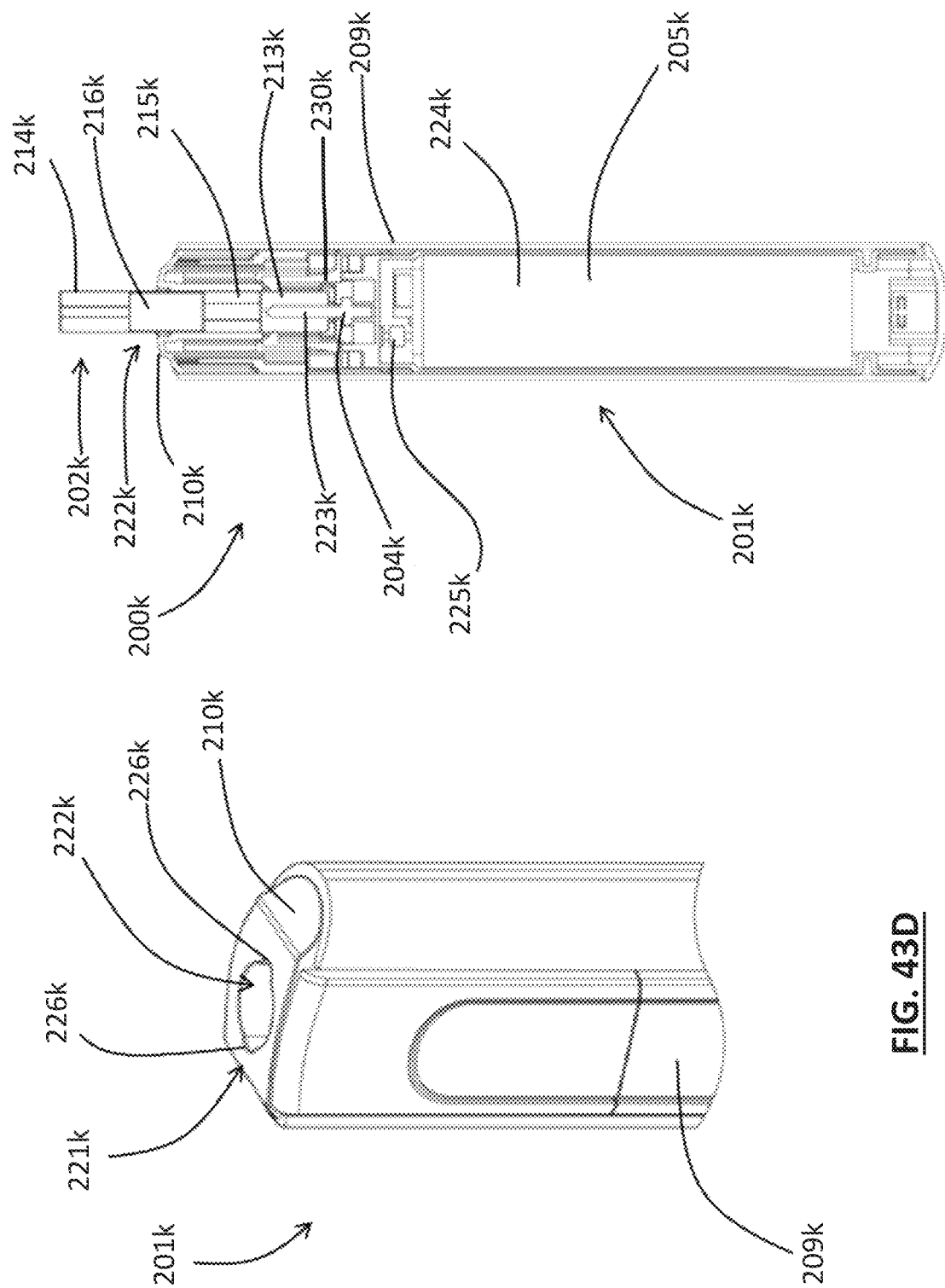
FIG. 43D is a detailed view of an end of the device of the first embodiment of the eleventh mode of the smoking substitute system.
FIG. 43E is a section view of the first embodiment of the eleventh mode of the smoking substitute system.

Returning now to the device 201k, FIG. 43D illustrates a detailed view of the end of the device 201k that is configured to engage with the consumable 202k. The cap 210k of the device 201k includes an opening 221k to a cavity or an internal cavity 222k (more apparent from FIG. 43D) defined by the cap 210k.

The opening 221k and the cavity 222k are formed so as to receive at least a portion of the consumable 202k. During engagement of the consumable 202k with the device 201k, a portion of the consumable 202k is received through the opening 221k and into the cavity 222k. After engagement (see FIG. 43B), the downstream end 218k of the consumable 202k protrudes from the opening 221k and thus protrudes also from the device 201k. The opening 221k includes laterally disposed notches 226k. When a consumable 202k is received in the opening 221k, these notches 226k remain open and could, for example, be used for retaining a cover to cover the end of the device 201k.

As shown in FIG. 43E, the cap 210k of the device 201k comprises an aperture 230k configured to allow the heating element to extend therethrough into the cavity 222k. When mounted, the aperture 230k is abut and in physical contact with a surface of the heating element 223k. In this example, the aperture 230k surrounds and is in physical contract with the periphery of the heating element 223k. The cap 210k is movable with respect to the heating element 223k. In a non-limiting manner, the movement of the cap 210k may either be slidable along a longitudinal axis of the heating element 223k or rotatable about the longitudinal axis of the heating element 223k. In the illustrated embodiment, the heating element 223k resembles or in the shape of a cylindrical rod. Accordingly, the cap 210k is slidable with respect to the said heating element 223k. During movement of the cap 210k with respect to the heating element 223k, e.g., when removing an exhausted aerosol forming substrate, the physical contact between the aperture 230k and the heating element 223k results in the removal of residue formed on the heating element 223k by a scraping action.

In some other embodiments, the aperture 230k comprises bristles (not shown) that abuts the heating element. That is said bristles form between the aperture 230k and the heating element. The bristles are flexible and configured to bias against the surface of the heating element. Therefore, as the cap is moved along the longitudinal direction of the heating element, the bristles scrub the surface of the heating element. Such arrangement reduces wear on the heating element, as well as allowing the surface of the heating element to be cleaned in a more efficient manner.

FIG. 43E shows a cross section through a central longitudinal plane through the device 201k. The device 201k is shown with the consumable 202k engaged therewith.

The device 201k comprises a heater 204k comprising heating element 223k. The heater 204k forms part of the body 209k of the device 201k and is rigidly mounted to the body 209k. In the illustrated embodiment, the heater 204k is a rod heater with a heating element 223k having a circular transverse profile. In other embodiments the heater may be in the form of a blade heater (e.g., heating element with a rectangular transverse profile) or a tube heater (e.g., heating element with a tubular form).

The heating element 223k of the heater 204k projects from an internal base of the cavity 222k along a longitudinal axis towards the opening 221k. As is apparent from the figure, the length (i.e., along the longitudinal axis) of the heating element is less than a depth of the cavity 222k. In this way, the heating element 223k does not protrude from or extend beyond the opening 221k.

When the consumable 202k is received in the cavity 222k (as is shown in FIG. 43E), the heating element 223k penetrates the aerosol-forming substrate 213k of the consumable 202k. In particular, the heating element 223k extends for nearly the entire axial length of the aerosol-forming substrate 213k when inserted therein. Thus, when the heater 204k is activated, heat is transferred radially from an outer circumferential surface the heating element 223k to the aerosol-forming substrate 213k.

The device 201k further comprises an electronics cavity 224k. A power source, in the form of a rechargeable battery 205k (a lithium-ion battery), is located in electronics cavity 224k.

The device 201k includes a connector (i.e., forming part of an IO module of the device 201k) in the form of a USB port 206k. The connector may alternatively be, for example, a micro-USB port or a USB-C port for examples. The USB port 206k may be used to recharge the rechargeable battery 205k.

The device 201k includes a controller (not shown) located in the electronics cavity 224k. The controller comprises a microcontroller mounted on a printed circuit board (PCB). The USB port 206k is also connected to the controller 208k (i.e., connected to the PCB and microcontroller).

The controller 208k is configured to control at least one function of the device 201k. For example, the controller 208k is configured to control the operation of the heater 204k. Such control of the operation of the heater 204k may be accomplished by the controller toggling the electrical connection of the rechargeable battery 205k to the heater 204k. For example, the controller 208k is configured to control the heater 204k in response to a user depressing the button 212k. Depressing the button 212k may cause the controller to allow a voltage (from the rechargeable battery 205k) to be applied to the heater 204k (so as to cause the heating element 223k to be heated).

The controller is also configured to control the LEDs 211k in response to (e.g., a detected) a condition of the device 201k or the consumable 202k. For example, the controller may control the LEDs to indicate whether the device 201k is in an on state or an off state (e.g., one or more of the LEDs may be illuminated by the controller when the device is in an on state).

The device 202k comprises a further input means (i.e., in addition to the button 212k) in the form of a puff sensor 225k. The puff sensor 225k is configured to detect a user drawing (i.e., inhaling) at the downstream end 218k of the consumable 202k. The puff sensor 225k may, for example, be in the form of a pressure sensor, flowmeter or a microphone. The puff sensor 225k is operatively connected to the controller 208k in the electronics cavity 224k, such that a signal from the puff sensor 225k, indicative of a puff state (i.e., drawing or not drawing), forms an input to the controller 208k (and can thus be responded to by the controller 208k).

Twelfth Mode: A HNB Device Comprising a Housing and a Cartridge Receivable by the Housing, Such that the Housing Substantially Encloses the Cartridge Aspects and embodiments of the twelfth mode of the present disclosure will now be discussed with reference to the accompanying figures. Further aspects and embodiments will be apparent to those skilled in the art. All documents mentioned in this text are incorporated herein by reference.

Figure 44B:
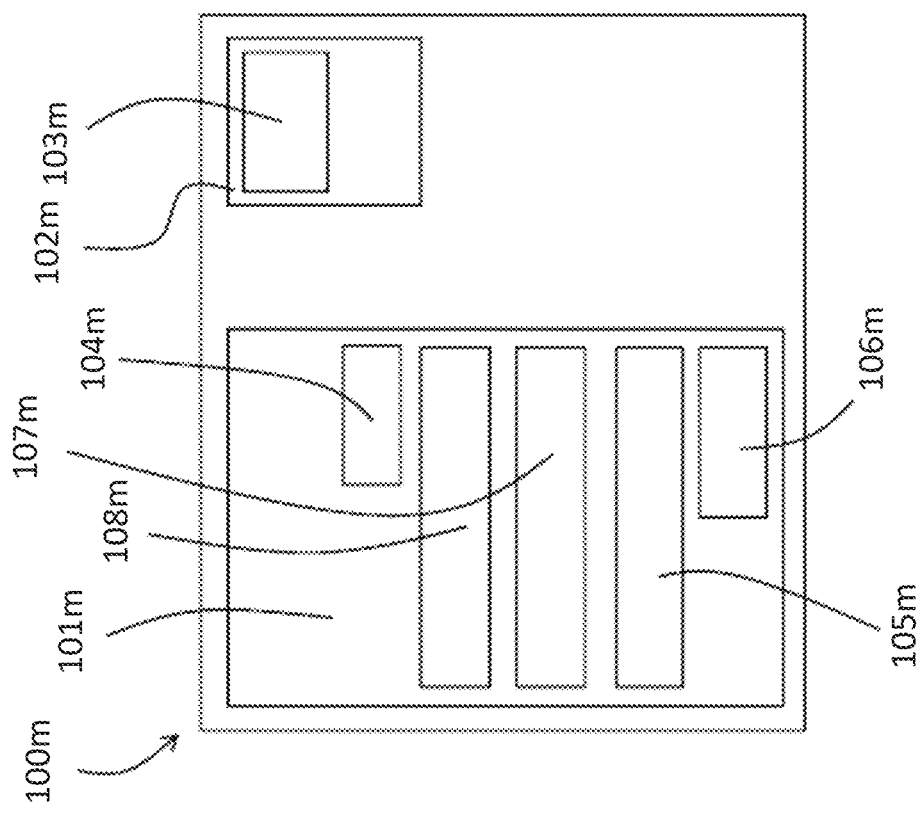
Figure 44A:
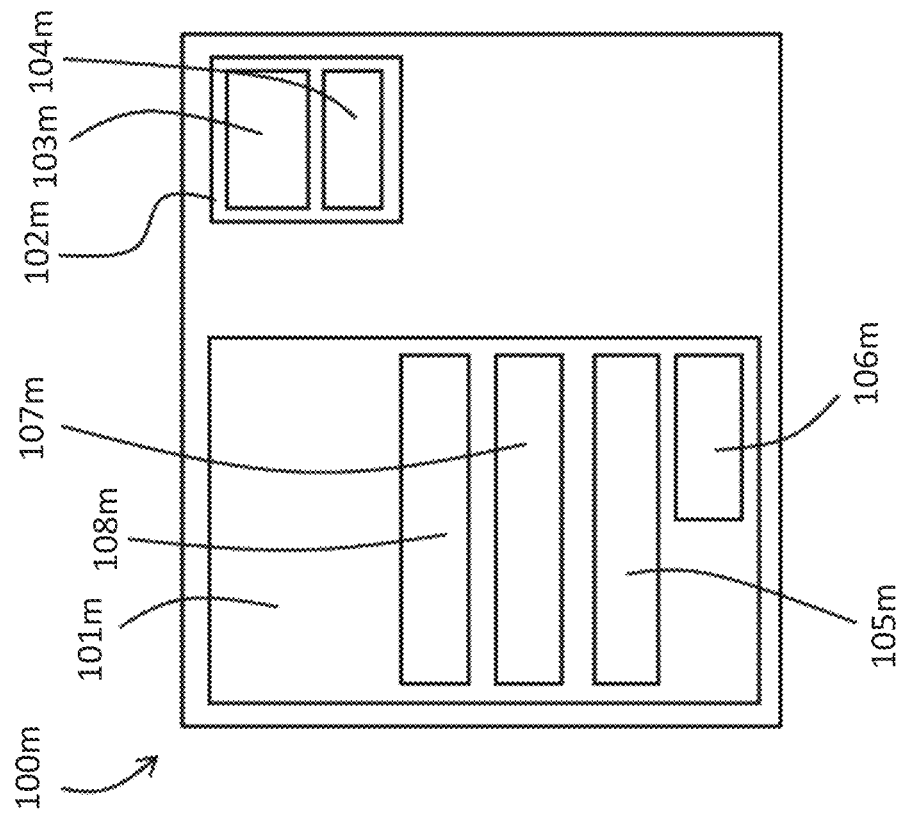

FIG. 44A is a schematic providing a general overview of a smoking substitute system 100m. The system 100m includes a HNB device (hereinafter also referred as device) 101m and an aerosol-forming article in the form of a consumable 102m, which comprises an aerosol former 103m. The system is configured to vaporize the aerosol former by heating the aerosol former 103m (so as to form a vapor/aerosol for inhalation by a user).

In the illustrated system, the heater 104m forms part of the consumable 102m and is configured to heat the aerosol former 103m. In this variation, the heater 104m is electrically connectable to the power source 105m, for example, when the consumable 102m is engaged with the device 101m. Heat from the heater 104m vaporizes the aerosol former 103m to produce a vapor. The vapor subsequently condenses to form an aerosol, which is ultimately inhaled by the user.

The system 100m further comprises a power source 105m that forms part of the device 101m. In other embodiments the power source 105m may be external to (but connectable to) the device 101m. The power source 105m is electrically connectable to the heater 104m such that it is able to supply power to the heater 104m (i.e., for the purpose of heating the aerosol former 103m). Thus, control of the electrical connection of the power source 105m to the heater 104m provides control of the state of the heater 104m. The power source 105m may be a power store, for example a battery or rechargeable battery (e.g., a lithium-ion battery).

The system 100m further comprises an I/O module comprising a connector 106m (e.g., in the form of a USB port, Micro USB port, USB-C port, etc.). The connector 106m is configured for connection to an external source of electrical power, e.g., a mains electrical supply outlet. The connector 106m may be used in substitution for the power source 105m. That is the connector 106m may be electrically connectable to the heater 104m so as to supply electricity to the heater 104m. In such embodiments, the device may not include a power source, and the power source of the system may instead comprise the connector 106m and an external source of electrical power (to which the connector 106m provides electrical connection).

In some embodiments, the connector 106m may be used to charge and recharge the power source 105m where the power source 105m includes a rechargeable battery.

The system 100m also comprises a user interface (UI) 107m. Although not shown, the UI 107m may include input means to receive commands from a user. The input means of the UI 107m allows the user to control at least one aspect of the operation of the system 100m. The input means may, for example, be in the form of a button, touchscreen, switch, microphone, etc.

The UI 107m also comprises output means to convey information to the user. The output means may, for example, comprise lights (e.g., LEDs), a display screen, speaker, vibration generator, etc.

The system 100m further comprises a controller 108m that is configured to control at least one function of the device 101m. In the illustrated embodiment, the controller 108m is a component of the device 101m, but in other embodiments may be separate from (but connectable to) the device 101m. The controller 108m is configured to control the operation of the heater 104m and, for example, may be configured to control the voltage applied from the power source 105m to the heater 104m. The controller 108m may be configured to toggle the supply of power to the heater 104m between an on state, in which the full output voltage of the power source 105m is applied to the heater 104m, and an off state, in which the no voltage is applied to the heater 104m.

Although not shown, the system 100m may also comprise a voltage regulator to regulate the output voltage from the power source 105m to form a regulated voltage. The regulated voltage may then be applied to the heater 104m.

In addition to being connected to the heater 104m, the controller 108m is operatively connected to the UI 107m. Thus, the controller 108m may receive an input signal from the input means of the UI 107m. Similarly, the controller 108m may transmit output signals to the UI 107m. In response, the output means of the UI 107m may convey information, based on the output signals, to a user. The controller also comprises a memory 109m, which is a non-volatile memory. The memory 109m includes instructions, which, when implemented, cause the controller to perform certain tasks or steps of a method.

FIG. 44B is a schematic showing a variation of the system 100m of FIG. 44A. In the system 100m' of FIG. 44B, the heater 104m forms part of the device 101m, rather than the consumable 102m. In this variation, the heater 104m is electrically connected to the power source 105m.

FIG. 45A and FIG. 45B illustrate a heated-tobacco (HT) smoking substitute system 200m. The system 200m is an example of the systems 100m, 100m' described in relation to FIG. 44A or FIG. 44B. System 200m includes an HT device 201m and an HT consumable 202m. The description of FIG. 44A and FIG. 44B above is applicable to the system 200m of FIG. 45A and FIG. 45B, and will thus not be repeated.

The device 201m and the consumable 202m are configured such that the consumable 202m can be engaged with the device 201m. FIG. 45A shows the device 201m and the consumable 202m in an engaged state, whilst FIG. 45B shows the device 201m and the consumable 202m in a disengaged state.

Figure 46A:
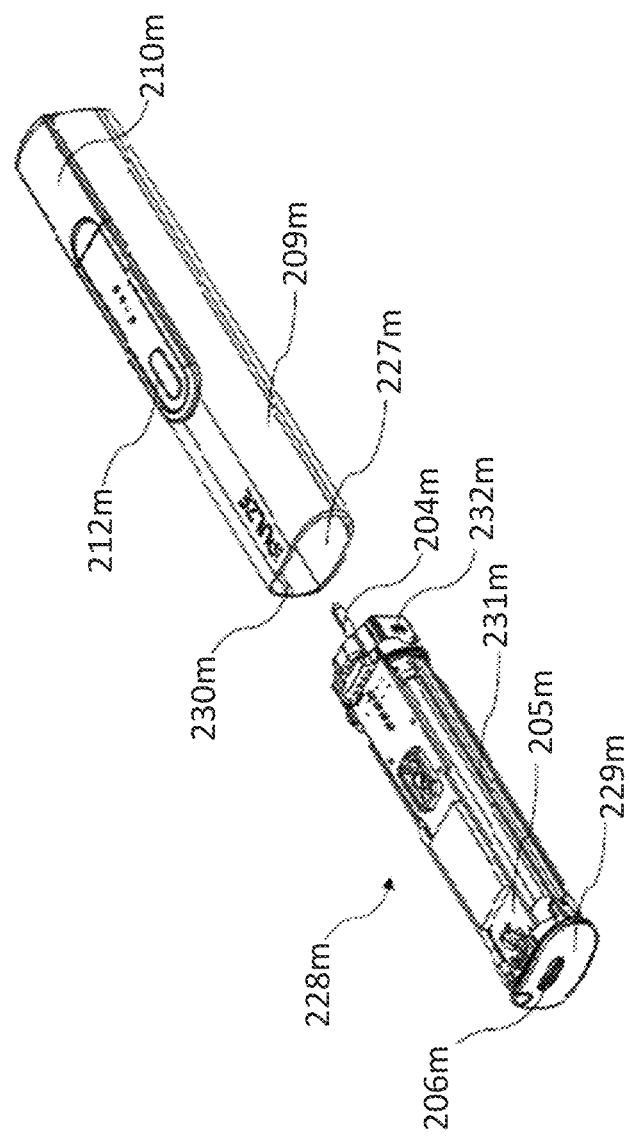

The device 201m comprises a body and cap 210m. The body comprises a hollow elongate housing 209m which contains a cartridge. In use the cap 210m is engaged at an end of the body. Although not apparent from the figures, the cap 210m is moveable relative to the body. In particular, the cap 210m is slidable and can slide along a longitudinal axis of the body. The housing 209m comprises an opening 227m (as seen in FIG. 46A) at one end i.e., the end opposite the cap 210m, configured to receive and accommodate the cartridge 228m within the housing 209m.

The device 201m comprises an output means (forming part of the UI of the device 201m) in the form of a plurality of light-emitting diodes (LEDs) 211m arranged linearly along the longitudinal axis of the device 201m and on an outer surface of the housing 209m of the device 201m. A button 212m is also arranged on an outer surface of the housing 209m of the device 201m and is axially spaced (i.e., along the longitudinal axis) from the plurality of LEDs 211m.

Figure 45C:
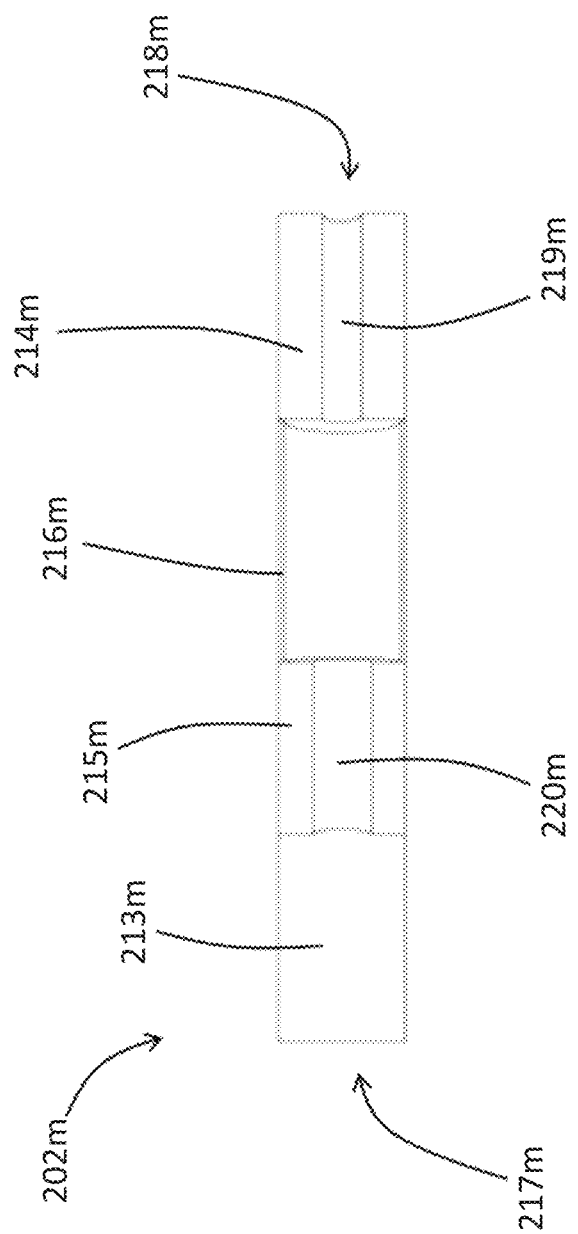

FIG. 45C show a detailed section view of the consumable 202m of the system 200m. The consumable 202m generally resembles a cigarette. In that respect, the consumable 202m has a generally cylindrical form with a diameter of 7 mm and an axial length of 70 mm. The consumable 202m comprises an aerosol forming substrate 213m, a terminal filter element 214m, an upstream filter element 215m and a spacer element 216m. In other embodiments, the consumable may further comprise a cooling element. A cooling element may exchange heat with vapor that is formed by the aerosol-forming substrate 213m in order to cool the vapor so as to facilitate condensation of the vapor.

The aerosol-forming substrate 213m is substantially cylindrical and is located at an upstream end 217m of the consumable 202m, and comprises the aerosol former of the system 200m. In that respect, the aerosol forming substrate 213m is configured to be heated by the device 201m to release a vapor. The released vapor is subsequently entrained in an airflow flowing through the aerosol-forming substrate 213m. The airflow is produced by the action of the user drawing on a downstream 218m (i.e., terminal or mouth) end of the consumable 202m.

In the present embodiment, the aerosol forming substrate 213m comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213m may comprise a gathered sheet of homogenized (e.g., paper/slurry recon) tobacco or gathered shreds/strips formed from such a sheet.

In order to generate an aerosol, the aerosol forming substrate 213m comprises at least one volatile compound that is intended to be vaporized/aerosolized and that may provide the user with a recreational and/or medicinal effect when inhaled. The aerosol-forming substrate 213m may further comprise one or more additives. For example, such additives may be in the form of humectants (e.g., propylene glycol and/or vegetable glycerin), flavorants, fillers, aqueous/non-aqueous solvents and/or binders.

The terminal filter element 214m is also substantially cylindrical, and is located downstream of the aerosol forming substrate 213m at the downstream end 218m of the consumable 202m. The terminal filter element 214m is in the form of a hollow bore filter element having a bore 219m (e.g., for airflow) formed therethrough. The diameter of the bore 219m is 2 mm. The terminal filter element 214m is formed of a porous (e.g., monoacetate) filter material. As set forth above, the downstream end 218m of the consumable 202m (i.e., where the terminal filter 214m is located) forms a mouthpiece portion of the consumable 202m upon which the user draws. Airflow is drawn from the upstream end 217m, thorough the components of the consumable 202m, and out of the downstream end 218m. The airflow is driven by the user drawing on the downstream end 218m (i.e., the mouthpiece portion) of the consumable 202m.

The upstream filter element 215m is located axially adjacent to the aerosol-forming substrate 213m, between the aerosol-forming substrate 213m and the terminal filter element 214m. Like the terminal filter 214m, the upstream filter element 215m is in the form of a hollow bore filter element, such that it has a bore 220m extending axially therethrough. In this way, the upstream filter 215m may act as an airflow restrictor. The upstream filter element 215m is formed of a porous (e.g., monoacetate) filter material. The bore 220m of the upstream filter element 215m has a larger diameter (3 mm) than the terminal filter element 214m.

The spacer 216m is in the form of a cardboard tube, which defines a cavity or chamber between the upstream filter element 215m and the terminal filter element 214m. The spacer 216m acts to allow both cooling and mixing of the vapor/aerosol from the aerosol-forming substrate 213m. The spacer has an external diameter of 7 mm and an axial length of 14 mm.

Although not apparent from the figure, the aerosol-forming substrate 213m, upstream filter 215m and spacer 216m are circumscribed by a paper wrapping layer. The terminal filter 214m is circumscribed by a tipping layer that also circumscribes a portion of the paper wrapping layer (so as to connect the terminal filter 214m to the remaining components of the consumable 202m). The upstream filter 215m and terminal filter 214m are circumscribed by further wrapping layers in the form of plug wraps.

Returning now to the device 201m, FIG. 45D illustrates a detailed view of the end of the device 201m that is configured to engage with the consumable 202m. The cap 210m of the device 201m includes an opening 221m to an internal cavity 222m (more apparent from FIG. 45D) defined by the cap 210m. The opening 221m and the cavity 222m are formed so as to receive at least a portion of the consumable 202m. During engagement of the consumable 202m with the device 201m, a portion of the consumable 202m is received through the opening 221m and into the cavity 222m. After engagement (see FIG. 45B), the downstream end 218m of the consumable 202m protrudes from the opening 221m and thus also protrudes from the device 201m. The opening 221m includes laterally disposed notches 226m. When a consumable 202m is received in the opening 221m, these notches 226m remain open and could, for example, be used for retaining a cover in order to cover the end of the device 201m.

FIG. 45E shows a cross section through a central longitudinal plane through the device 201m. The device 201m is shown with the consumable 202m engaged therewith.

The device 201m comprises a heater 204m comprising heating element 223m, which may be accommodated within the cartridge 228m [shown in FIG. 46A]. The heater 204m forms part of the cartridge 228m of the device 201m and is rigidly supported in the housing 209m when the cartridge is engaged with the housing. In the illustrated embodiment, the heater 204m is a rod heater with a heating element 223m having a circular transverse profile. In other embodiments the heater may be in the form of a blade heater (e.g., heating element with a rectangular transverse profile) or a tube heater (e.g., heating element with a tubular form).

The heating element 223m of the heater 204m projects from an internal base of the cavity 222m along a longitudinal axis towards the opening 221m. As is apparent from the figure, the length (i.e., along the longitudinal axis) of the heating element is less than a depth of the cavity 222m. In this way, the heating element 223m does not protrude from or extend beyond the opening 221m.

When the consumable 202m is received in the cavity 222m (as is shown in FIG. 45E), the heating element 223m penetrates the aerosol-forming substrate 213m of the consumable 202m. In particular, the heating element 223m extends for nearly the entire axial length of the aerosol-forming substrate 213m when inserted therein. Thus, when the heater 204m is activated, heat is transferred radially from an outer circumferential surface the heating element 223m to the aerosol-forming substrate 213m.

The device 201m further comprises an electronics cavity 224m, contained in the cartridge 228m [shown in FIG. 46A]. A power source, in the form of a rechargeable battery 205m (a lithium-ion battery), is located in electronics cavity 224m.

The device 201m includes a connector (i.e., forming part of an IO module of the device 201m) in the form of a USB port 206m. The connector may alternatively be, for example, a micro-USB port or a USB-C port for examples. The USB port 206m may be used to recharge the rechargeable battery 205m. The connector 206m may be included at one end of the cartridge 228m.

The device 201m includes a controller (not shown) located in the electronics cavity 224m. The controller comprises a microcontroller mounted on a printed circuit board (PCB). The USB port 206m is also connected to the controller 208m (i.e., connected to the PCB and microcontroller).

The controller 208m is configured to control at least one function of the device 201m. For example, the controller 208m is configured to control the operation of the heater 204m. Such control of the operation of the heater 204m may be accomplished by the controller toggling the electrical connection of the rechargeable battery 205m to the heater 204m. For example, the controller 208m is configured to control the heater 204m in response to a user depressing the button 212m. Depressing the button 212m may cause the controller to allow a voltage (from the rechargeable battery 205m) to be applied to the heater 204m (so as to cause the heating element 223m to be heated).

The controller is also configured to control the LEDs 211m in response to (e.g., a detected) a condition of the device 201m or the consumable 202m. For example, the controller may control the LEDs to indicate whether the device 201m is in an on state or an off state (e.g., one or more of the LEDs may be illuminated by the controller when the device is in an on state).

The device 201m comprises a further input means (i.e., in addition to the button 212m) in the form of a puff sensor 225m. The puff sensor 225m is configured to detect a user drawing (i.e., inhaling) at the downstream end 218m of the consumable 202m. The puff sensor 225m may, for example, be in the form of a pressure sensor, flowmeter or a microphone. The puff sensor 225m is operatively connected to the controller 208m in the electronics cavity 224m, such that a signal from the puff sensor 225m, indicative of a puff state (i.e., drawing or not drawing), forms an input to the controller 208m (and can thus be responded to by the controller 208m).

FIG. 46A, illustrates the device 201m, disassembled into a cartridge 228m and a hollow elongate housing 209m. The housing 209m, includes an opening 227m at one end (i.e., the opening 227m is at an end opposite to the end configured to receive the cap 210m and the aerosol forming article 202m). The opening 227m is configured to receive the cartridge 228m. In the embodiment shown, the housing 209m has a substantially circular cross-section (in this case, a superellipse). In some embodiments, the housing 209m may be configured with a rectangular or a square cross-section. Further, the housing 209m has a continuous internal profile i.e., uniform internal cross-section throughout the length of the housing 209m. This facilitates receiving the cartridge 228m through the length of the housing 209m. The inner surface of the housing 209m is also configured with a plurality of guideways 230m. The guideways 230m facilitate the sliding of the cartridge 228m within the housing 209m and ensure that the cartridge remains in the correct position within the housing. The cartridge 228m includes a plurality of rails 231m, which correspond in geometry with the guideways 230m, such that the rails 231m ride along the guideways 230m during insertion of the cartridge 228m.

The housing 209m and cartridge 228m are configured with a retaining mechanism, which facilitates retaining the cartridge 228m within the housing 209m, upon insertion of the cartridge 228m into the housing 209m. The retaining mechanism comprises protrusion 232m (and a corresponding protrusion on the opposite side of the cartridge, not shown) and complementary recesses (not show) on the inner surface of the housing. The recesses are located such that when the cartridge is fully inserted into the housing, the protrusions 232m snap into the recesses to hold the cartridge in place. The protrusions 232m have a triangular cross section which tapers in the direction of insertion, allowing for easy insertion and secure retention of the cartridge. The user may remove the cartridge by prising the cartridge away from the housing the break the snap fit between the protrusions 232m and the recesses, The housing 209m is made of a metallic material. This protects the components housed within the cartridge 228m. The housing 209m has a unitary structure, i.e., is formed from a single piece of material.

In other embodiments, the retainer mechanism comprises a magnetic mechanism including at least one magnet disposed at a side of the housing 209m. The magnets help secure the cartridge 228m within the housing 209m. In some embodiments, the magnets may be positioned in both the housing 209m and the cartridge 228m, such that the magnets attract each other, to secure the cartridge 228m within the housing 209m.

The outer surface of the housing 209m has a smooth surface finish. This improves aesthetic appearance and feel of the housing 209m (thus, the device 201m). As an example, the smooth surface of the outer surface of the housing 209m may be obtained by a manufacturing process including a polishing process.

Further referring to FIG. 46A, the cartridge 228m is broadly configured to accommodate the heater 204m and the power source 205m. Further, the cartridge 228m is also configured to accommodate the components of the device 201m such as puff sensor 225m, electrical circuits, input means etc. In some embodiments, the cartridge 228m may be defined with a plurality of compartments (not shown), such that each of the plurality of compartments may be configured to accommodate at least one component such as power source 205m, heater 204m etc. of the device 201m. In some embodiments, the cartridge 228m may comprise a casing (not shown), which may be configured to enclose at least a portion of the components disposed in the cartridge 228m. This may facilitate in rigidly securing the components accommodated within the cartridge 228m.

The cartridge 228m is configured with a stopping feature 229m, which limits the extent of insertion of the cartridge 228m into the housing 209m. The stopping feature 229m is a lip at one end of the cartridge 228m which extends outwardly further than the internal diameter of the housing 209m. In this way, the stopping feature 229m abuts the rim of the opening 227m of the housing 209m, preventing further insertion into the housing 209m.

Figure 46B:
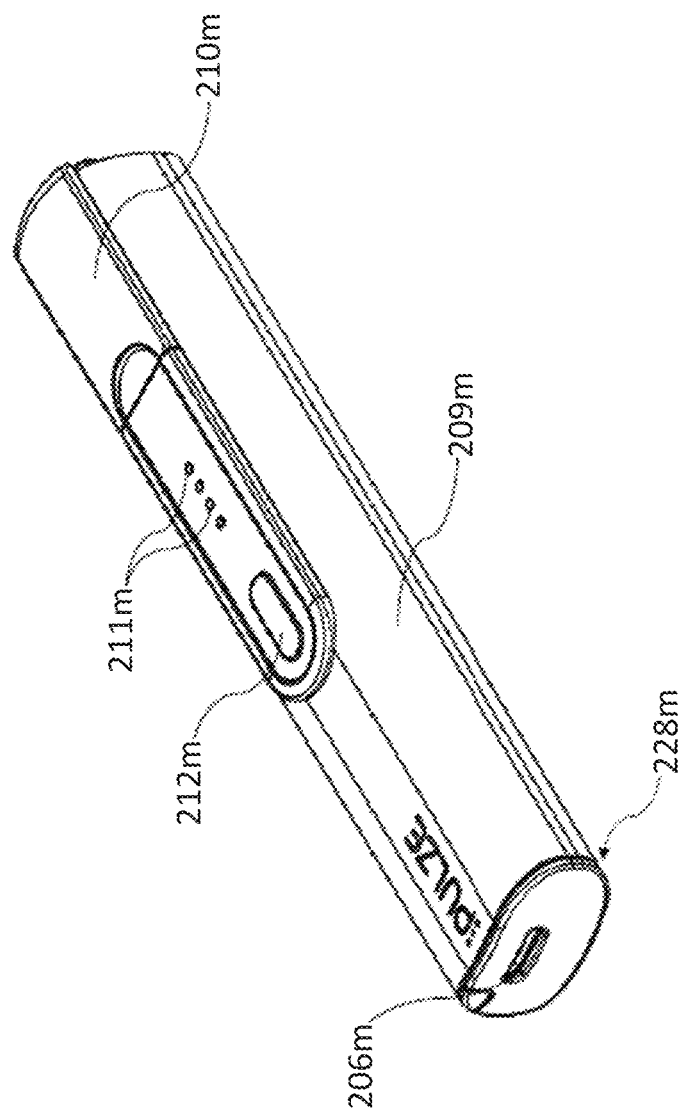

FIG. 46B illustrates the cartridge 228m accommodated within the housing 209m (and therefore only the end of the cartridge is visible). During insertion of the cartridge 228m into the housing 209m, the rails 231m [shown in FIG. 46A] defined in the cartridge 228m engage with the corresponding guideways 230m [shown in FIG. 46A] configured in the housing 209m. This allows the cartridge 228m to slide within the housing 209m. The cartridge 228m extends substantially along the length of the housing 209m. When fully inserted, abutment of the stopping feature 229m prevents further insertion of the cartridge 228m into the housing 209m.

Upon, insertion of the cartridge 228m into the housing 209m, the cartridge 228m is retained within the housing 209m by the retainer mechanism.

Providing the device 201m having a housing 209m and removable cartridge 228m makes it easier to manufacture/assemble the device and also makes it easy for the user to access the internal components for inspection, maintenance or repair/replacement. It also provides a means to replace the external housing 209m should it become damaged or should the user decide to modify the appearance of the device by using a housing of different external geometry/color, etc.

Thirteenth Mode: The Configuration of a Cap of a Smoking Substitute Device

Aspects and embodiments of the thirteenth mode of the present disclosure will now be discussed with reference to the accompanying figures. Further aspects and embodiments will be apparent to those skilled in the art. All documents mentioned in this text are incorporated herein by reference.

Figure 47B:
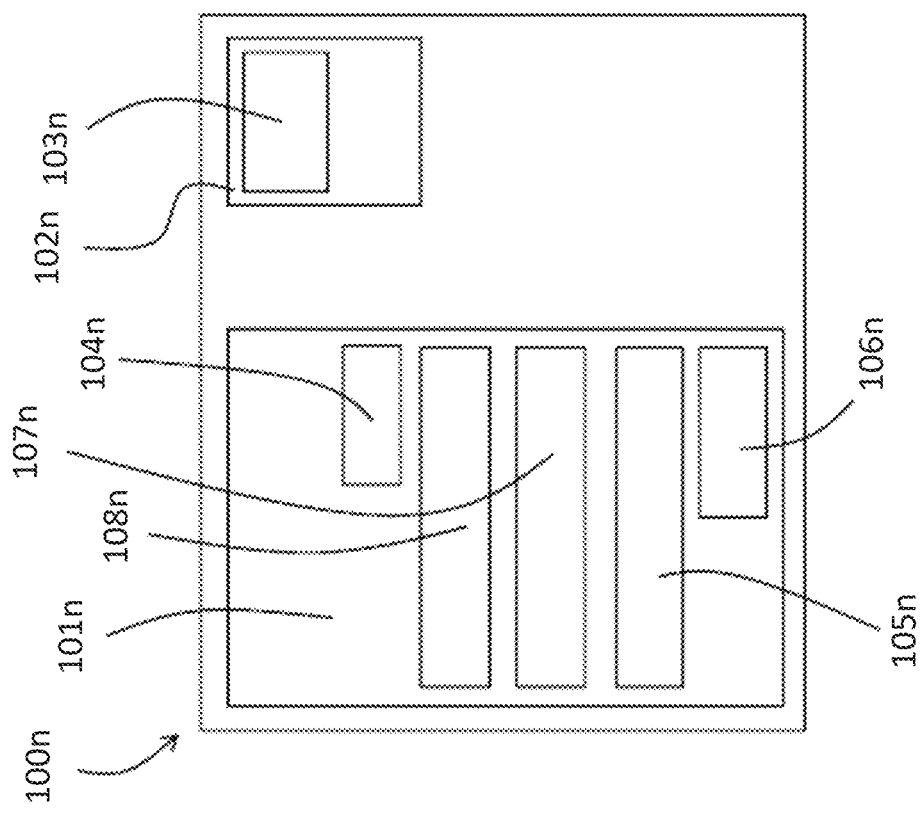
Figure 47A:
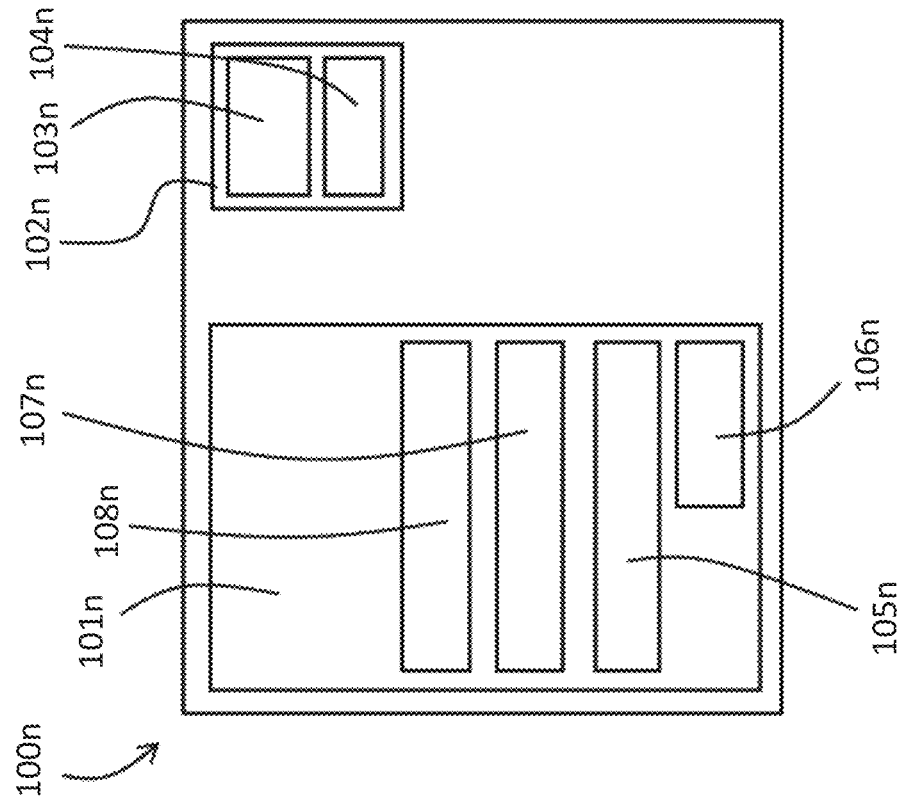

FIG. 47A is a schematic providing a general overview of a smoking substitute system 100n. The system 100n includes a substitute smoking device 101n and an aerosol-forming article in the form of a consumable 102n, which comprises an aerosol former 103n. The system is configured to vaporize the aerosol former by heating the aerosol former 103n (so as to form a vapor/aerosol for inhalation by a user).

In the illustrated system, the heater 104n forms part of the consumable 102n and is configured to heat the aerosol former 103n. Heat from the heater 104n vaporizes the aerosol former 103n to produce a vapor. The vapor subsequently condenses to form an aerosol, which is ultimately inhaled by the user.

The system 100n further comprises a power source 105n that forms part of the device 101n. In other embodiments the power source 105n may be external to (but connectable to) the device 101n. The power source 105n is electrically connectable to the heater 104n such that it is able to supply power to the heater 104n (i.e., for the purpose of heating the aerosol former 103n). Thus, control of the electrical connection of the power source 105n to the heater 104n provides control of the state of the heater 104n. The power source 105n may be a power store, for example a battery or rechargeable battery (e.g., a lithium-ion battery).

The system 100n further comprises an I/O module comprising a connector 106n (e.g., in the form of a USB port, Micro USB port, USB-C port, etc.). The connector 106n is configured for connection to an external source of electrical power, e.g., a mains electrical supply outlet. The connector 106n may be used in substitution for the power source 105n. That is the connector 106n may be electrically connectable to the heater 104n so as to supply electricity to the heater 104n. In such embodiments, the device may not include a power source, and the power source of the system may instead comprise the connector 106n and an external source of electrical power (to which the connector 106n provides electrical connection).

In some embodiments, the connector 106n may be used to charge and recharge the power source 105n where the power source 104n includes a rechargeable battery.

The system 100n also comprises a user interface (UI) 107n. Although not shown, the UI 107n may include input means to receive commands from a user. The input means of the UI 107n allows the user to control at least one aspect of the operation of the system 100n. The input means may, for example, be in the form of a button, touchscreen, switch, microphone, etc.

The UI 107n also comprises output means to convey information to the user. The output means may, for example, comprise lights (e.g., LEDs), a display screen, speaker, vibration generator, etc.

The system 100n further comprises a controller 108n that is configured to control at least one function of the device 101n. In the illustrated embodiment, the controller 108n is a component of the device 101n, but in other embodiments may be separate from (but connectable to) the device 101n. The controller 108n is configured to control the operation of the heater 104n and, for example, may be configured to control the voltage applied from the power source 105n to the heater 104n. The controller 108n may be configured to toggle the supply of power to the heater 105n between an on state, in which the full output voltage of the power source 105n is applied to the heater 104n, and an off state, in which the no voltage is applied to the heater 104n.

Although not shown, the system 100n may also comprise a voltage regulator to regulate the output voltage from the power source 105n to form a regulated voltage. The regulated voltage may then be applied to the heater 104n.

In addition to being connected to the heater 104n, the controller 108n is operatively connected to the UI 107n. Thus, the controller 108n may receive an input signal from the input means of the UI 107n. Similarly, the controller 108n may transmit output signals to the UI 107n. In response, the output means of the UI 107n may convey information, based on the output signals, to a user.

FIG. 47B is a schematic showing a variation of the system 100n of FIG. 47A. In the system 100n' of FIG. 47B, the heater 104n forms part of the consumable 102n, rather than the device 101n. In this variation, the heater 104n is electrically connectable to the power source 105n, for example, when the consumable 102n is engaged with the device 101n.

The systems 100n, 100n' of FIG. 47A and FIG. 47B may be implemented as one of two broad categories of system, each in accordance with the present disclosure: a heated tobacco (HT) system or an e-cigarette system. A description of each category of system follows.

FIG. 48A and FIG. 48B illustrate a heated-tobacco (HT) smoking substitute system 200n. The system 200n is an example of the systems 100n, 100n' described in relation to FIG. 47A or FIG. 47B. System 200n includes an HT device 201n and an HT consumable 202n. The description of FIG. 47A and FIG. 47B above is applicable to the system 200n of FIG. 48A and FIG. 48B, and will thus not be repeated.

The device 201n and the consumable 202n are configured such that the consumable 202n can be engaged with the device 201n. FIG. 48A shows the device 201n and the consumable 202n in an engaged state, whilst FIG. 48B shows the device 201n and the consumable 202n in a disengaged state.

The device 201n comprises a body 209n and cap 210n. In use the cap 210n is engaged at an end of the body 209n. Although not apparent from the figures, the cap 210n is moveable relative to the body 209n. In particular, the cap 210n is slidable and can slide along a longitudinal axis of the body 209n.

The device 201n comprises an output means (forming part of the UI of the device 201n) in the form of a plurality of light-emitting diodes (LEDs) 211n arranged linearly along the longitudinal axis of the device 201n and on an outer surface of the body 209n of the device 201n. A button 212n is also arranged on an outer surface of the body 209n of the device 201n and is axially spaced (i.e., along the longitudinal axis) from the plurality of LEDs 211n.

FIG. 48C show a detailed section view of the consumable 202n of the system 200n. The consumable 202n generally resembles a cigarette. In that respect, the consumable 202n has a generally cylindrical form with a diameter of 7 mm and an axial length of 70 mm. The consumable 202n comprises an aerosol forming substrate 213n, a terminal filter element 214n, an upstream filter element 215n and a spacer element 216n. In other embodiments, the consumable may further comprise a cooling element. A cooling element may exchange heat with vapor that is formed by the aerosol-forming substrate 213n in order to cool the vapor so as to facilitate condensation of the vapor.

The aerosol-forming substrate 213n is substantially cylindrical and is located at an upstream end 217n of the consumable 202n, and comprises the aerosol former of the system 200n. In that respect, the aerosol forming substrate 213n is configured to be heated by the device 201n to release a vapor. The released vapor is subsequently entrained in an airflow flowing through the aerosol-forming substrate 213n. The airflow is produced by the action of the user drawing on a downstream 218n (i.e., terminal or mouth end) of the consumable 202n.

In the present embodiment, the aerosol forming substrate 213n comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213n may comprise a gathered sheet of homogenized (e.g., paper/slurry recon) tobacco or gathered shreds/strips formed from such a sheet.

In order to generate an aerosol, the aerosol forming substrate 213n comprises at least one volatile compound that is intended to be vaporized/aerosolized and that may provide the user with a recreational and/or medicinal effect when inhaled. The aerosol-forming substrate 213n may further comprise one or more additives. For example, such additives may be in the form of humectants (e.g., propylene glycol and/or vegetable glycerin), flavorants, fillers, aqueous/non-aqueous solvents and/or binders.

The terminal filter element 214n is also substantially cylindrical, and is located downstream of the aerosol forming substrate 213n at the downstream end 218n of the consumable 202n. The terminal filter element 214n is in the form of a hollow bore filter element having a bore 219n (e.g., for airflow) formed therethrough. The diameter of the bore 219n is 2 mm. The terminal filter element 214n is formed of a porous (e.g., monoacetate) filter material. As set forth above, the downstream end 218n of the consumable 202n (i.e., where the terminal filter 214n is located) forms a mouthpiece portion of the consumable 202n upon which the user draws. Airflow is drawn from the upstream end 217n, thorough the components of the consumable 202n, and out of the downstream end 218n. The airflow is driven by the user drawing on the downstream end 218n (i.e., the mouthpiece portion) of the consumable 202n.

The upstream filter element 215n is located axially adjacent to the aerosol-forming substrate 213n, between the aerosol-forming substrate 213n and the terminal filter element 214n. Like the terminal filter 214n, the upstream filter element 215n is in the form of a hollow bore filter element, such that it has a bore 220n extending axially therethrough. In this way, the upstream filter 215n may act as an airflow restrictor. The upstream filter element 215n is formed of a porous (e.g., monoacetate) filter material. The bore 220n of the upstream filter element 214n has a larger diameter (3 mm) than the terminal filter element 214n.

The spacer 216n is in the form of a cardboard tube, which defines a cavity or chamber between the upstream filter element 215n and the terminal filter element 214n. The spacer 216n acts to allow both cooling and mixing of the vapor/aerosol from the aerosol-forming substrate 213n. The spacer has an external diameter of 7 mm and an axial length of 14 mm.

Although not apparent from the figure, the aerosol-forming substrate 213n, upstream filter 215n and spacer 216n are circumscribed by a paper wrapping layer. The terminal filter 214n is circumscribed by a tipping layer that also circumscribes a portion of the paper wrapping layer (so as to connect the terminal filter 214n to the remaining components of the consumable 202n). The upstream filter 215n and terminal filter 214n are circumscribed by further wrapping layers in the form of plug wraps.

Returning now to the device 201n, FIG. 48D illustrates a detailed view of the end of the device 201n that is configured to engage with the consumable 202n. The cap 210n of the device 201n includes an opening 221n to an internal cavity 222n (more apparent from FIG. 48D) defined by the cap 210n. The opening 221n and the cavity 222n are formed so as to receive at least a portion of the consumable 202n. During engagement of the consumable 202n with the device 201n, a portion of the consumable 202n is received through the opening 221n and into the cavity 222n. After engagement (see FIG. 48B), the downstream end 218n of the consumable 202n protrudes from the opening 221n and thus also protrudes from the device 201n. The opening 221n includes laterally disposed notches 226n. When a consumable 202n is received in the opening 221n, these notches 226n remain open and could, for example, be used for retaining a cover in order to cover the end of the device 201n.

FIG. 48E shows a cross section through a central longitudinal plane through the device 201n. The device 201n is shown with the consumable 202n engaged therewith.

The device 201n comprises a heater 204n comprising heating element 223n. The heater 204n forms part of the body 209n of the device 201n and is rigidly mounted to the body 209n. In the illustrated embodiment, the heater 204n is a rod heater with a heating element 223n having a circular transverse profile. In other embodiments the heater may be in the form of a blade heater (e.g., heating element with a rectangular transverse profile) or a tube heater (e.g., heating element with a tubular form).

The heating element 223n of the heater 204n projects from an internal base of the cavity 222n along a longitudinal axis towards the opening 221n. As is apparent from the figure, the length (i.e., along the longitudinal axis) of the heating element is less than a depth of the cavity 222n. In this way, the heating element 223n does not protrude from or extend beyond the opening 221n.

When the consumable 202n is received in the cavity 222n (as is shown in FIG. 48E), the heating element 223n penetrates the aerosol-forming substrate 213n of the consumable 202n. In particular, the heating element 223n extends for nearly the entire axial length of the aerosol-forming substrate 213n when inserted therein. Thus, when the heater 204n is activated, heat is transferred radially from an outer circumferential surface the heating element 223n to the aerosol-forming substrate 213n.

The device 202n further comprises an electronics cavity 224n. A power source, in the form of a rechargeable battery 205n (a lithium-ion battery), is located in electronics cavity 224n.

The device 202n includes a connector (i.e., forming part of an IO module of the device 201n) in the form of a USB port 206n. The connector may alternatively be, for example, a micro-USB port or a USB-C port for examples. The USB port 206n may be used to recharge the rechargeable battery 205n.

The device 202n includes a controller (not shown) located in the electronics cavity 224n. The controller comprises a microcontroller mounted on a printed circuit board (PCB). The USB port 206n is also connected to the controller 208n (i.e., connected to the PCB and microcontroller).

The controller 208n is configured to control at least one function of the device 202n. For example, the controller 208n is configured to control the operation of the heater 204n. Such control of the operation of the heater 204n may be accomplished by the controller toggling the electrical connection of the rechargeable battery 205n to the heater 204n. For example, the controller 208n is configured to control the heater 204n in response to a user depressing the button 212n. Depressing the button 212n may cause the controller to allow a voltage (from the rechargeable battery 205n) to be applied to the heater 204n (so as to cause the heating element 223n to be heated).

The controller is also configured to control the LEDs 211n in response to (e.g., a detected) a condition of the device 201n or the consumable 202n. For example, the controller may control the LEDs to indicate whether the device 201n is in an on state or an off state (e.g., one or more of the LEDs may be illuminated by the controller when the device is in an on state).

The device 202n comprises a further input means (i.e., in addition to the button 212n) in the form of a puff sensor 225n. The puff sensor 225n is configured to detect a user drawing (i.e., inhaling) at the downstream end 218n of the consumable 202n. The puff sensor 225n may, for example, be in the form of a pressure sensor, flowmeter or a microphone. The puff sensor 225n is operatively connected to the controller 208n in the electronics cavity 224n, such that a signal from the puff sensor 225n, indicative of a puff state (i.e., drawing or not drawing), forms an input to the controller 208n (and can thus be responded to by the controller 208n).

According to an aspect of the present disclosure, the cap 210n is slidably engaged with a housing (a body 209n) of the smoking substitute device to move in a longitudinal direction of the device. A portion of the cap 210n is received in an end cavity of the body 209n. The cap 210n is configured to slide between seated or engaged position and a raised position. When the in the raised position, the cap may be lifted from the seated position by between 0.3 and 3 cm. When the cap is in the raised position it may remain engaged with the device and not completely removed. In some embodiments, the user may be substantially stopped from disengaging the cap 210n from the device 201n by moving the cap 210n in the manner described. The cap 210n may be stopped at the raised position.

Returning to FIG. 48D, the body 209n includes an opening on a first traverse side 241n through which a portion of the cap 210n is exposed for a user interaction. Opposing the opening 240n a grip surface is provided on the body 209n. The cap 210n movement from the engaged position to the raised position is relative to the grip surface. When the user holds the device 201n, a finger or thumb can be used to push the cap 210n to the raised position while a second finger is around the opposing side of the device resting against the grip surface. The user may therefore be able to easily use a one-handed movement to push the cap 210n in the raised position by moving the finger on the side of the opening 240n, relative to the finger on the opposite side 242n against the grip surface. In some embodiments, when the cap 210n is in a raised position, a portion of the heater of the device may be exposed for user access. This may permit cleaning of the portion of the heater of the device.

In some embodiments, the grip surface may have a non-slip finish. For example, a matt, tactile, rough or textured finish. Substantially the whole housing may have such a finish, or the particular grip portion may have such a finish. The non-slip finish may further improve the ease with which the user can move the cap 210n.

In some embodiments, the cap 210n includes a grip portion 243n to facilitate the movement of the cap 210n between the engaged position and the raised position. In an embodiment, the grip portion 243n may be defined in the face of the cap 210n that is collocated with the opening 240n when the cap 210n is seated. The grip portion 243n may be non-slip. For example, the grip portion 243n may have a matt, tactile, rough or textured finish for ease of sliding the cap 210n from the engaged position to the raised position by a user.

In some embodiments, the grip portion 243n is delineated from the rest of the cap surface by a lip 244n. The lip 244n may have a complementary shape to the tip of a typical of user's finger/thumb, thereby allowing the user to slide/move the cap 210n from the engaged position to the raised position. For example, the lip 244n may be a concave lip.

The provision of the grip portion 243n may facilitate single handed operation of the device and to the slide the cap 210n. The grip portion may have a shape and size to accommodate the user's finger/thumb for moving the cap 210n. Conveniently, the grip portion 243n is provided towards an end of the cap 210n distal from an opening 222n provided on the cap 210n. The opening 222n provided on the cap is configured to receive the consumable 202n. Optionally, the grip portion 243n may be configured to cover at least 50% of a total length of the cap. Also, the point of interaction of the user with the grip portion may be 10%-50% of the length of the cap 210n. Further, this achieves an easy cap 210n movement as the user force is applied in the longitudinal direction of the device. Further, a user output means (e.g., a light) is provided on the housing at a predetermined distance from the grip portion. The predetermined distance is at least 2 centimeters from the grip portion. This may prevent the user's finger, when in place for moving the cap, from obscuring the user output means from view.

Fourteenth Mode: A Smoking Substitute Device Provided with a Cap Displacement Feature Aspects and embodiments of the fourteenth mode of the present disclosure will now be discussed with reference to the accompanying figures. Further aspects and embodiments will be apparent to those skilled in the art. All documents mentioned in this text are incorporated herein by reference.

FIG. 49A is a schematic providing a general overview of a smoking substitute system 100p. The system 100p includes a substitute smoking device 101p and an aerosol-forming article in the form of a consumable 102p, which comprises an aerosol former 103p. The system is configured to vaporize the aerosol former by heating the aerosol former 103p (so as to form a vapor/aerosol for inhalation by a user).

In the illustrated system, the heater 104p forms part of the consumable 102p and is configured to heat the aerosol former 103$p$. In this variation, the heater 104$p$ is electrically connectable to the power source 105$p$, for example, when the consumable 102$p$ is engaged with the device 101$p$. Heat from the heater 104$p$ vaporizes the aerosol former 103$p$ to produce a vapor. The vapor subsequently condenses to form an aerosol, which is ultimately inhaled by the user.

The system 100$p$ further comprises a power source 105$p$ that forms part of the device 101$p$. In other embodiments the power source 105$p$ may be external to (but connectable to) the device 101$p$. The power source 105$p$ is electrically connectable to the heater 104$p$ such that it is able to supply power to the heater 104$p$ (i.e., for the purpose of heating the aerosol former 103$p$). Thus, control of the electrical connection of the power source 105$p$ to the heater 104$p$ provides control of the state of the heater 104$p$. The power source 105$p$ may be a power store, for example a battery or rechargeable battery (e.g., a lithium-ion battery).

The system 100$p$ further comprises an I/O module comprising a connector 106$p$ (e.g., in the form of a USB port, Micro USB port, USB-C port, etc.). The connector 106$p$ is configured for connection to an external source of electrical power, e.g., a mains electrical supply outlet. The connector 106$p$ may be used in substitution for the power source 105$p$. That is the connector 106$p$ may be electrically connectable to the heater 104$p$ so as to supply electricity to the heater 104$p$. In such embodiments, the device may not include a power source, and the power source of the system may instead comprise the connector 106$p$ and an external source of electrical power (to which the connector 106$p$ provides electrical connection).

In some embodiments, the connector 106$p$ may be used to charge and recharge the power source 105$p$ where the power source 105$p$ includes a rechargeable battery.

The system 100$p$ also comprises a user interface (UI) 107$p$. Although not shown, the UI 107$p$ may include input means to receive commands from a user. The input means of the UI 107$p$ allows the user to control at least one aspect of the operation of the system 100$p$. The input means may, for example, be in the form of a button, touchscreen, switch, microphone, etc.

The UI 107$p$ also comprises output means to convey information to the user. The output means may, for example, comprise lights (e.g., LEDs), a display screen, speaker, vibration generator, etc.

The system 100$p$ further comprises a controller 108$p$ that is configured to control at least one function of the device 101$p$. In the illustrated embodiment, the controller 108$p$ is a component of the device 101$p$, but in other embodiments may be separate from (but connectable to) the device 101$p$. The controller 108$p$ is configured to control the operation of the heater 104$p$ and, for example, may be configured to control the voltage applied from the power source 105$p$ to the heater 104$p$. The controller 108$p$ may be configured to toggle the supply of power to the heater 104$p$ between an on state, in which the full output voltage of the power source 105$p$ is applied to the heater 104$p$, and an off state, in which the no voltage is applied to the heater 104$p$.

Although not shown, the system 100$p$ may also comprise a voltage regulator to regulate the output voltage from the power source 105$p$ to form a regulated voltage. The regulated voltage may then be applied to the heater 104$p$.

In addition to being connected to the heater 104$p$, the controller 108$p$ is operatively connected to the UI 107$p$. Thus, the controller 108$p$ may receive an input signal from the input means of the UI 107$p$. Similarly, the controller 108$p$ may transmit output signals to the UI 107$p$. In response, the output means of the UI 107$p$ may convey information, based on the output signals, to a user. The controller also comprises a memory 109$p$, which is a non-volatile memory. The memory 109$p$ includes instructions, which, when implemented, cause the controller to perform certain tasks or steps of a method.

FIG. 49B is a schematic showing a variation of the system 100$p$ of FIG. 49A. In the system 100$p'$ of FIG. 49B, the heater 104$p$ forms part of the device 101$p$, rather than the consumable 102$p$. In this variation, the heater 104$p$ is electrically connected to the power source 105$p$.

FIG. 50A and FIG. 50B illustrate a heated-tobacco (HT) smoking substitute system 200$p$. The system 200$p$ is an example of the systems 100$p$, 100$p'$ described in relation to FIG. 49A or FIG. 49B. System 200$p$ includes an HT device 201$p$ and an HT consumable 202$p$. The description of FIG. 49A and FIG. 49B above is applicable to the system 200$p$ of FIG. 50A and FIG. 50B, and will thus not be repeated.

The device 201$p$ and the consumable 202$p$ are configured such that the consumable 202$p$ can be engaged with the device 201$p$. FIG. 50A shows the device 201$p$ and the consumable 202$p$ in an engaged state, whilst FIG. 50B shows the device 201$p$ and the consumable 202$p$ in a disengaged state.

The device 201$p$ comprises a body 209$p$ and cap 210$p$. In use the cap 210$p$ is engaged at an end of the body 209$p$. Although not apparent from the figures, the cap 210$p$ is moveable relative to the body 209$p$. In particular, the cap 210$p$ is slidable and can slide along a longitudinal axis of the body 209$p$, by a sliding mechanism.

The device 201$p$ comprises an output means (forming part of the UI of the device 201$p$) in the form of a plurality of light-emitting diodes (LEDs) 211$p$ arranged linearly along the longitudinal axis of the device 201$p$ and on an outer surface of the body 209$p$ of the device 201$p$. A button 212$p$ is also arranged on an outer surface of the body 209$p$ of the device 201$p$ and is axially spaced (i.e., along the longitudinal axis) from the plurality of LEDs 211$p$.

FIG. 50C show a detailed section view of the consumable 202$p$ of the system 200$p$. The consumable 202$p$ generally resembles a cigarette. In that respect, the consumable 202$p$ has a generally cylindrical form with a diameter of 7 mm and an axial length of 70 mm. The consumable 202$p$ comprises an aerosol forming substrate 213$p$, a terminal filter element 214$p$, an upstream filter element 215$p$ and a spacer element 216$p$. In other embodiments, the consumable may further comprise a cooling element. A cooling element may exchange heat with vapor that is formed by the aerosol-forming substrate 213$p$ in order to cool the vapor so as to facilitate condensation of the vapor.

The aerosol-forming substrate 213$p$ is substantially cylindrical and is located at an upstream end 217$p$ of the consumable 202$p$, and comprises the aerosol former of the system 200$p$. In that respect, the aerosol forming substrate 213$p$ is configured to be heated by the device 201$p$ to release a vapor. The released vapor is subsequently entrained in an airflow flowing through the aerosol-forming substrate 213$p$. The airflow is produced by the action of the user drawing on a downstream 218$p$ (i.e., terminal or mouth) end of the consumable 202$p$.

In the present embodiment, the aerosol forming substrate 213$p$ comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213p may comprise a gathered sheet of homogenized (e.g., paper/slurry recon) tobacco or gathered shreds/strips formed from such a sheet.

In order to generate an aerosol, the aerosol forming substrate 213p comprises at least one volatile compound that is intended to be vaporized/aerosolized and that may provide the user with a recreational and/or medicinal effect when inhaled. The aerosol-forming substrate 213p may further comprise one or more additives. For example, such additives may be in the form of humectants (e.g., propylene glycol and/or vegetable glycerin), flavorants, fillers, aqueous/non-aqueous solvents and/or binders.

The terminal filter element 214p is also substantially cylindrical, and is located downstream of the aerosol forming substrate 213p at the downstream end 218p of the consumable 202p. The terminal filter element 214p is in the form of a hollow bore filter element having a bore 219p (e.g., for airflow) formed therethrough. The diameter of the bore 219p is 2 mm. The terminal filter element 214p is formed of a porous (e.g., monoacetate) filter material. As set forth above, the downstream end 218p of the consumable 202p (i.e., where the terminal filter 214p is located) forms a mouthpiece portion of the consumable 202p upon which the user draws. Airflow is drawn from the upstream end 217p, thorough the components of the consumable 202p, and out of the downstream end 218p. The airflow is driven by the user drawing on the downstream end 218p (i.e., the mouthpiece portion) of the consumable 202p.

The upstream filter element 215p is located axially adjacent to the aerosol-forming substrate 213p, between the aerosol-forming substrate 213p and the terminal filter element 214p. Like the terminal filter 214p, the upstream filter element 215p is in the form of a hollow bore filter element, such that it has a bore 220p extending axially therethrough. In this way, the upstream filter 215p may act as an airflow restrictor. The upstream filter element 215p is formed of a porous (e.g., monoacetate) filter material. The bore 220p of the upstream filter element 215p has a larger diameter (3 mm) than the terminal filter element 214p.

The spacer 216p is in the form of a cardboard tube, which defines a cavity or chamber between the upstream filter element 215p and the terminal filter element 214p. The spacer 216p acts to allow both cooling and mixing of the vapor/aerosol from the aerosol-forming substrate 213p. The spacer has an external diameter of 7 mm and an axial length of 14 mm.

Although not apparent from the figure, the aerosol-forming substrate 213p, upstream filter 215p and spacer 216p are circumscribed by a paper wrapping layer. The terminal filter 214p is circumscribed by a tipping layer that also circumscribes a portion of the paper wrapping layer (so as to connect the terminal filter 214p to the remaining components of the consumable 202p). The upstream filter 215p and terminal filter 214p are circumscribed by further wrapping layers in the form of plug wraps.

Returning now to the device 201p, FIG. 50D illustrates a detailed view of the end of the device 201p that is configured to engage with the consumable 202p. The cap 210p of the device 201p includes an opening 221p to an internal cavity 222p (more apparent from FIG. 50D) defined by the cap 210p. The opening 221p and the cavity 222p are formed so as to receive at least a portion of the consumable 202p. During engagement of the consumable 202p with the device 201p, a portion of the consumable 202p is received through the opening 221p and into the cavity 222p. After engagement (see FIG. 50B), the downstream end 218p of the consumable 202p protrudes from the opening 221p and thus also protrudes from the device 201p. The opening 221p includes laterally disposed notches 226p. When a consumable 202p is received in the opening 221p, these notches 226p remain open and could, for example, be used for retaining a cover in order to cover the end of the device 201p.

FIG. 50E shows a cross section through a central longitudinal plane through the device 201p. The device 201p is shown with the consumable 202p engaged therewith.

The device 201p comprises a heater 204p comprising heating element 223p. The heater 204p forms part of the body 209p of the device 201p and is rigidly mounted to the body 209p. In the illustrated embodiment, the heater 204p is a rod heater with a heating element 223p having a circular transverse profile. In other embodiments the heater may be in the form of a blade heater (e.g., heating element with a rectangular transverse profile) or a tube heater (e.g., heating element with a tubular form).

The heating element 223p of the heater 204p projects from an internal base of the cavity 222p along a longitudinal axis towards the opening 221p. As is apparent from the figure, the length (i.e., along the longitudinal axis) of the heating element is less than a depth of the cavity 222p. In this way, the heating element 223p does not protrude from or extend beyond the opening 221p.

When the consumable 202p is received in the cavity 222p (as is shown in FIG. 50E), the heating element 223p penetrates the aerosol-forming substrate 213p of the consumable 202p. In particular, the heating element 223p extends for nearly the entire axial length of the aerosol-forming substrate 213p when inserted therein. Thus, when the heater 204p is activated, heat is transferred radially from an outer circumferential surface the heating element 223p to the aerosol-forming substrate 213p.

The device 201p further comprises an electronics cavity 224p. A power source, in the form of a rechargeable battery 205p (a lithium-ion battery), is located in electronics cavity 224p.

The device 201p includes a connector (i.e., forming part of an IO module of the device 201p) in the form of a USB port 206p. The connector may alternatively be, for example, a micro-USB port or a USB-C port for examples. The USB port 206p may be used to recharge the rechargeable battery 205p.

The device 201p includes a controller (not shown) located in the electronics cavity 224p. The controller comprises a microcontroller mounted on a printed circuit board (PCB). The USB port 206p is also connected to the controller 208p (i.e., connected to the PCB and microcontroller).

The controller 208p is configured to control at least one function of the device 201p. For example, the controller 208p is configured to control the operation of the heater 204p. Such control of the operation of the heater 204p may be accomplished by the controller toggling the electrical connection of the rechargeable battery 205p to the heater 204p. For example, the controller 208p is configured to control the heater 204p in response to a user depressing the button 212p. Depressing the button 212p may cause the controller to allow a voltage (from the rechargeable battery 205p) to be applied to the heater 204p (so as to cause the heating element 223p to be heated).

The controller is also configured to control the LEDs 211p in response to (e.g., a detected) a condition of the device 201p or the consumable 202p. For example, the controller may control the LEDs to indicate whether the device 201p is in an on state or an off state (e.g., one or more of the LEDs may be illuminated by the controller when the device is in an on state).

The device 201p comprises a further input means (i.e., in addition to the button 212p) in the form of a puff sensor 225p. The puff sensor 225p is configured to detect a user drawing (i.e., inhaling) at the downstream end 218p of the consumable 202p. The puff sensor 225p may, for example, be in the form of a pressure sensor, flowmeter or a microphone. The puff sensor 225p is operatively connected to the controller 208p in the electronics cavity 224p, such that a signal from the puff sensor 225p, indicative of a puff state (i.e., drawing or not drawing), forms an input to the controller 208p (and can thus be responded to by the controller 208p).

FIG. 50F illustrates a cross-section through a central longitudinal plane of the device 201p, with the cap 210p engaged with the body 209p. In the illustrated embodiment, the body 209p of the device 201p (seen in FIG. 50B), includes first and second guideways 228p, 229p, which facilitate movement or displacement of the cap 210p between a first position in which the cap is fully engaged with the body (as seen in FIG. 50F) and a second position in which the cap is longitudinally displaced from the body. A plurality of first guideways 228p may be defined on an inner circumference of the body 209p, at the interface of the body 209p and the cap 210p. The plurality of first guideways 228p are configured to receive the cap 201p and allow movement of the cap 210p relative to the body 209p, so as to accommodate the cap 210p or a portion of the cap 210p in the body 209p. Further, a plurality of second guideways 229p are also defined in the body 209p, about the heating element 223p. The plurality of second guideways 229p are configured to receive the cap 210p such that the cavity 222p defined by the cap 210p is circumscribed by the plurality of second guideways 229p, during engagement of the cap 210p with the body 209p. The cavity 222p of the cap 210p is configured to traverse on the plurality of second guideways 229p to circumscribe the heating element 223p, upon engagement of the cap 210p with the body 209p.

In some embodiments, the cap 210p may be displaced relative to the body 209p, by a threaded mechanism.

In some embodiments, the cap 210p and the body 209p are engaged together (i.e., in a close fit) by at least one connecting mechanism, for example a snap fit connection, a magnetic connection and the like, which facilitate in retaining the cap 210p in the first position.

The body 209p further comprises a retainer mechanism (e.g., a detent mechanism), for retaining the cap 210p in the second position relative to the body 209p. The retainer mechanism includes two flexure bearings 232p facing each other. The two flexure bearings 232p are located proximal to the heating element 223p. The two flexure bearings 232p are adapted to engage with an external surface of a walls of the cavity 222p, when the cap 210p is received by the body 209p.

As apparent from the FIG. 50F, when the cap 210p is in the first position (i.e., when the cap 210p is in engagement with the body 209p), the flexure bearings 232p are configured to abut the deformable region 230p of the cavity 222p. The deformable region 230p, deforms due to the force applied by the flexure bearing 232p. The flexure bearing 232p is adapted to deform the deformable region 230p of the cavity 222p towards the heating element 223p of the heater 204p. The deformable region 230p is configured to selectively deform in response to movement of the cap 210p about the flexure bearing 232p.

In an illustrative embodiment as seen in FIG. 50G and FIG. 50H, movement or displacement of the cap 210p from the first position to the second position (e.g., upward movement of the cap 210p as seen in the Figures) is carried out by applying a pull force or an upward force on the cap 210p along a longitudinal axis of the device 201p. During movement of the cap 210p from the first position, the flexure bearings 232p are configured to restrain movement of the cap 210p from the body 209p, as apparent from FIG. 50G beyond the second position (i.e., the lifted condition of the cap 210p from the body 209p). The flexure bearings 232p are configured to engage with the rigid base region 231p of the cavity 222p defined in the cap 210p. Thus, movement of the cap 210p beyond the second position is restricted. That is, the cap 210p is allowed to be lifted to a height (e.g., distance along longitudinal axis of the device 201p) defined between the first position and the second position. As an example, the displacement of the cap between the first position and the second position may range from about 2 mm to about 15 mm, and preferably may be about 5 mm to 8 mm. In a preferred embodiment, the displacement of the cap between the first position and the second position may be about 7 mm. This movement of the cap 210p from the first position to the second position facilitates lifting the consumable 202p away from the heating element along a longitudinal axis. This movement of the cap 210p from the first position to the second position provides an aperture 251p through which the heating element may be inspected/cleaned. Further, the cap 210p is retained in the second position by at least one of the detent mechanism and the magnetic mechanism, which facilitates in maintaining the aperture 251p, to access the heating element 223p.

A portion (e.g., outer surface) of the cap 210p is configured with a tactile (high friction) finish, to facilitate gripping during movement or displacement of the cap 210p between the first position and the second position.

The movement of the cap 210p between the first position and the second position eliminates the need to completely disengage the cap 210p from the body 209p, to access the heating element 223p, which may require periodic cleaning for removing debris accumulated on the heating element 223p, for effective dissipation of heat for generating aerosol.

FIG. 51 illustrates a tool 250p inserted into the cap 210p for removing the cap 210p from the body of the device. The tool 250p is configured to interact with the retainer mechanism (i.e., the flexure bearing 232p). The flexure bearings 232p are deformed to move outwardly away from the deformable region 230p and the heating element 223p of the device when the tool is engaged. This outward movement of the flexure bearing 232p facilitates the movement of the cap 210p beyond the second position and its disengagement from the body 209p (as seen in FIG. 52).

Fifteenth Mode: A Smoking Substitute Device Having a Heating Element that is Deactivated when a Cap of the Device is Moved to Expose the Heater Aspects and embodiments of the fifteenth mode of the present disclosure will now be discussed with reference to the accompanying figures. Further aspects and embodiments will be apparent to those skilled in the art. All documents mentioned in this text are incorporated herein by reference.

FIG. 53A is a schematic providing a general overview of a smoking substitute system 100q. The system 100q includes a substitute smoking device 101q and an aerosol-forming article in the form of a consumable 102q, which comprises an aerosol former 103q. The system is configured to vaporize the aerosol former by heating the aerosol former 103q (so as to form a vapor/aerosol for inhalation by a user).

In the illustrated system, the heater $104q$ forms part of the consumable $102q$ and is configured to heat the aerosol former $103q$. In this variation, the heater $104q$ is electrically connectable to the power source $105q$, for example, when the consumable $102q$ is engaged with the device $101q$. Heat from the heater $104q$ vaporizes the aerosol former $103q$ to produce a vapor. The vapor subsequently condenses to form an aerosol, which is ultimately inhaled by the user.

The system $100q$ further comprises a power source $105q$ that forms part of the device $101q$. In other embodiments the power source $105q$ may be external to (but connectable to) the device $101q$. The power source $105q$ is electrically connectable to the heater $104q$ such that it is able to supply power to the heater $104q$ (i.e., for the purpose of heating the aerosol former $103q$). Thus, control of the electrical connection of the power source $105q$ to the heater $104q$ provides control of the state of the heater $104q$. The power source $105q$ may be a power store, for example a battery or rechargeable battery (e.g., a lithium-ion battery).

The system $100q$ further comprises an I/O module comprising a connector $106q$ (e.g., in the form of a USB port, Micro USB port, USB-C port, etc.). The connector $106q$ is configured for connection to an external source of electrical power, e.g., a mains electrical supply outlet. The connector $106q$ may be used in substitution for the power source $105q$. That is the connector $106q$ may be electrically connectable to the heater $104q$ so as to supply electricity to the heater $104q$. In such embodiments, the device may not include a power source, and the power source of the system may instead comprise the connector $106q$ and an external source of electrical power (to which the connector $106q$ provides electrical connection).

In some embodiments, the connector $106q$ may be used to charge and recharge the power source $105q$ where the power source $105q$ includes a rechargeable battery.

The system $100q$ also comprises a user interface (UI) $107q$. Although not shown, the UI $107q$ may include input means to receive commands from a user. The input means of the UI $107q$ allows the user to control at least one aspect of the operation of the system $100q$. The input means may, for example, be in the form of a button, touchscreen, switch, microphone, etc.

The UI $107q$ also comprises output means to convey information to the user. The output means may, for example, comprise lights (e.g., LEDs), a display screen, speaker, vibration generator, etc.

The system $100q$ further comprises a controller $108q$ that is configured to control at least one function of the device $101q$. In the illustrated embodiment, the controller $108q$ is a component of the device $101q$, but in other embodiments may be separate from (but connectable to) the device $101q$. The controller $108q$ is configured to control the operation of the heater $104q$ and, for example, may be configured to control the voltage applied from the power source $105q$ to the heater $104q$. The controller $108q$ may be configured to toggle the supply of power to the heater $104q$ between an on state, in which the full output voltage of the power source $105q$ is applied to the heater $104q$, and an off state, in which the no voltage is applied to the heater $104q$.

Although not shown, the system $100q$ may also comprise a voltage regulator to regulate the output voltage from the power source $105q$ to form a regulated voltage. The regulated voltage may then be applied to the heater $104q$.

In addition to being connected to the heater $104q$, the controller $108q$ is operatively connected to the UI $107q$. Thus, the controller $108q$ may receive an input signal from the input means of the UI $107q$.

Similarly, the controller $108q$ may transmit output signals to the UI $107q$. In response, the output means of the UI $107q$ may convey information, based on the output signals, to a user. The controller also comprises a memory $109q$, which is a non-volatile memory. The memory $109q$ includes instructions, which, when implemented, cause the controller to perform certain tasks or steps of a method.

FIG. 53B is a schematic showing a variation of the system $100q$ of FIG. 53A. In the system $100q'$ of FIG. 53B, the heater $104q$ forms part of the device $101q$, rather than the consumable $102q$. In this variation, the heater $104q$ is electrically connected to the power source $105q$.

FIG. 54A and FIG. 54B illustrate a heated-tobacco (HT) smoking substitute system $200q$. The system $200q$ is an example of the systems $100q$, $100q'$ described in relation to FIG. 53A or FIG. 53B. System $200q$ includes an HT device $201q$ and an HT consumable $202q$. The description of FIG. 53A and FIG. 53B above is applicable to the system $200q$ of FIG. 54A and FIG. 54B, and will thus not be repeated.

The device $201q$ and the consumable $202q$ are configured such that the consumable $202q$ can be engaged with the device $201q$. FIG. 54A shows the device $201q$ and the consumable $202q$ in an engaged state, whilst FIG. 54B shows the device $201q$ and the consumable $202q$ in a disengaged state.

The device $201q$ comprises a main body $209q$ and cap $210q$. In use the cap $210q$ is engaged at an end of the main body $209q$. Although not apparent from the figures, the cap $210q$ is moveable relative to the main body $209q$. In particular, the cap $210q$ is slidable and can slide along a longitudinal axis of the main body $209q$.

The device $201q$ comprises an output means (forming part of the UI of the device $201q$) in the form of a plurality of light-emitting diodes (LEDs) $211q$ arranged linearly along the longitudinal axis of the device $201q$ and on an outer surface of the main body $209q$ of the device $201q$. A button $212q$ is also arranged on an outer surface of the main body $209q$ of the device $201q$ and is axially spaced (i.e., along the longitudinal axis) from the plurality of LEDs $211q$.

FIG. 54C show a detailed section view of the consumable $202q$ of the system $200q$. The consumable $202q$ generally resembles a cigarette. In that respect, the consumable $202q$ has a generally cylindrical form with a diameter of 7 mm and an axial length of 70 mm. The consumable $202q$ comprises an aerosol forming substrate $213q$, a terminal filter element $214q$, an upstream filter element $215q$ and a spacer element $216q$. In other embodiments, the consumable may further comprise a cooling element. A cooling element may exchange heat with vapor that is formed by the aerosol-forming substrate $213q$ in order to cool the vapor so as to facilitate condensation of the vapor.

The aerosol-forming substrate $213q$ is substantially cylindrical and is located at an upstream end $217q$ of the consumable $202q$, and comprises the aerosol former of the system $200q$. In that respect, the aerosol forming substrate $213q$ is configured to be heated by the device $201q$ to release a vapor. The released vapor is subsequently entrained in an airflow flowing through the aerosol-forming substrate $213q$. The airflow is produced by the action of the user drawing on a downstream $218q$ (i.e., terminal or mouth) end of the consumable $202q$.

In the present embodiment, the aerosol forming substrate $213q$ comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213q may comprise a gathered sheet of homogenized (e.g., paper/slurry recon) tobacco or gathered shreds/strips formed from such a sheet.

In order to generate an aerosol, the aerosol forming substrate 213q comprises at least one volatile compound that is intended to be vaporized/aerosolized and that may provide the user with a recreational and/or medicinal effect when inhaled. The aerosol-forming substrate 213q may further comprise one or more additives. For example, such additives may be in the form of humectants (e.g., propylene glycol and/or vegetable glycerin), flavorants, fillers, aqueous/non-aqueous solvents and/or binders.

The terminal filter element 214q is also substantially cylindrical, and is located downstream of the aerosol forming substrate 213q at the downstream end 218q of the consumable 202q. The terminal filter element 214q is in the form of a hollow bore filter element having a bore 219q (e.g., for airflow) formed therethrough. The diameter of the bore 219q is 2 mm. The terminal filter element 214q is formed of a porous (e.g., monoacetate) filter material. As set forth above, the downstream end 218q of the consumable 202q (i.e., where the terminal filter 214q is located) forms a mouthpiece portion of the consumable 202q upon which the user draws. Airflow is drawn from the upstream end 217q, thorough the components of the consumable 202q, and out of the downstream end 218q. The airflow is driven by the user drawing on the downstream end 218q (i.e., the mouthpiece portion) of the consumable 202q.

The upstream filter element 215q is located axially adjacent to the aerosol-forming substrate 213q, between the aerosol-forming substrate 213q and the terminal filter element 214q. Like the terminal filter 214q, the upstream filter element 215q is in the form of a hollow bore filter element, such that it has a bore 220q extending axially therethrough. In this way, the upstream filter 215q may act as an airflow restrictor. The upstream filter element 215q is formed of a porous (e.g., monoacetate) filter material. The bore 220q of the upstream filter element 215q has a larger diameter (3 mm) than the terminal filter element 214q.

The spacer 216q is in the form of a cardboard tube, which defines a cavity or chamber between the upstream filter element 215q and the terminal filter element 214q. The spacer 216q acts to allow both cooling and mixing of the vapor/aerosol from the aerosol-forming substrate 213q. The spacer has an external diameter of 7 mm and an axial length of 14 mm.

Although not apparent from the figure, the aerosol-forming substrate 213q, upstream filter 215q and spacer 216q are circumscribed by a paper wrapping layer. The terminal filter 214q is circumscribed by a tipping layer that also circumscribes a portion of the paper wrapping layer (so as to connect the terminal filter 214q to the remaining components of the consumable 202q). The upstream filter 215q and terminal filter 214q are circumscribed by further wrapping layers in the form of plug wraps.

Returning now to the device 201q, FIG. 54D illustrates a detailed view of the end of the device 201q that is configured to engage with the consumable 202q. The cap 210q of the device 201q includes an opening 221q to an internal cavity 222q (more apparent from FIG. 54D) defined by the cap 210q. The opening 221q and the cavity 222q are formed so as to receive at least a portion of the consumable 202q. During engagement of the consumable 202q with the device 201q, a portion of the consumable 202q is received through the opening 221q and into the cavity 222q. After engagement (see FIG. 54B), the downstream end 218q of the consumable 202q protrudes from the opening 221q and thus also protrudes from the device 201q. The opening 221q includes laterally disposed notches 226q. When a consumable 202q is received in the opening 221q, these notches 226q remain open and could, for example, be used for retaining a cover in order to cover the end of the device 201q.

FIG. 54E shows a cross section through a central longitudinal plane through the device 201q. The device 201q is shown with the consumable 202q engaged therewith.

The device 201q comprises a heater 204q comprising heating element 223q. The heater 204q forms part of the main body 209q of the device 201q and is rigidly mounted to the main body 209q. In the illustrated embodiment, the heater 204q is a rod heater with a heating element 223q having a circular transverse profile. In other embodiments the heater may be in the form of a blade heater (e.g., heating element with a rectangular transverse profile) or a tube heater (e.g., heating element with a tubular form).

The heating element 223q of the heater 204q projects from an internal base of the cavity 222q along a longitudinal axis towards the opening 221q. As is apparent from the figure, the length (i.e., along the longitudinal axis) of the heating element is less than a depth of the cavity 222q. In this way, the heating element 223q does not protrude from or extend beyond the opening 221q.

When the consumable 202q is received in the cavity 222q (as is shown in FIG. 54E), the heating element 223q penetrates the aerosol-forming substrate 213q of the consumable 202q. In particular, the heating element 223q extends for nearly the entire axial length of the aerosol-forming substrate 213q when inserted therein. Thus, when the heater 204q is activated, heat is transferred radially from an outer circumferential surface the heating element 223q to the aerosol-forming substrate 213q.

The device 201q further comprises an electronics cavity 224q. A power source, in the form of a rechargeable battery 205q (a lithium-ion battery), is located in electronics cavity 224q.

The device 201q includes a connector (i.e., forming part of an IO module of the device 201q) in the form of a USB port. The connector may alternatively be, for example, a micro-USB port or a USB-C port for examples. The USB port may be used to recharge the rechargeable battery 205q.

The device 201q includes a controller (not shown) located in the electronics cavity 224q. The controller comprises a microcontroller mounted on a printed circuit board (PCB). The USB port is also connected to the controller (i.e., connected to the PCB and microcontroller).

The controller (not shown) is configured to control at least one function of the device 201q. For example, the controller is configured to control the operation of the heater 204q. Such control of the operation of the heater 204q may be accomplished by the controller toggling the electrical connection of the rechargeable battery 205q to the heater 204q. For example, the controller is configured to control the heater 204q in response to a user depressing the button 212q. Depressing the button 212q may cause the controller to allow a voltage (from the rechargeable battery 205q) to be applied to the heater 204q (so as to cause the heating element 223q to be heated).

The controller is also configured to control the LEDs 211q in response to (e.g., a detected) a condition of the device 201q or the consumable 202q. For example, the controller may control the LEDs to indicate whether the device 201q is in an on state or an off state (e.g., one or more of the LEDs may be illuminated by the controller when the device is in an on state).

The device 201q comprises a further input means (i.e., in addition to the button 212q) in the form of a puff sensor 225q. The puff sensor 225q is configured to detect a user drawing (i.e., inhaling) at the downstream end 218q of the consumable 202q. The puff sensor 225q may, for example, be in the form of a pressure sensor, flowmeter or a microphone. The puff sensor 225q is operatively connected to the controller in the electronics cavity 224q, such that a signal from the puff sensor 225q, indicative of a puff state (i.e., drawing or not drawing), forms an input to the controller (and can thus be responded to by the controller).

The device 201q further comprises means to help retain the cap 210q on the main body 209q of the device 201q when engaged therewith. This is illustrated in FIG. 54F and FIG. 54G, which respectively show the cap 210q in an open position (removed from the main body 209q) and a closed position (engaged with the main body 209q). As is shown in these figures, the main body 209q comprises magnets 227q mounted in a wall of the main body 209q that defines the cavity 222q. In particular, the magnets 227q are mounted such that they each define a portion of the wall of the cavity 222q and so as to oppose each other either side of the heating element 223q. As is apparent in particular from FIG. 54G, the cap 210q also comprises two corresponding magnets 228q. These magnets 228q are mounted to a portion of the cap 210q that is received in the cavity 222q when the cap 210q is engaged with the main body 209q. When the cap 210q is in the closed position, the magnets 228q of the cap 210q align with the magnets 227q of the main body 209q so as to magnetically interact. In this way, the cap 210q is at least partly retained on the main body 209q by the magnets 227q, 228q. The magnets 227q, 228q also assist a user in engaging the cap 210q with the main body 209q (i.e., by magnetic attraction). The magnets 227q, 228q may thus provide a form of feedback to the user (i.e., such that a user knows when the cap 210q is correctly engaged). Further, the magnets 227q, 228q ensure the cap 210q is aligned on the main body 209q. This may, for example, ensure that the cap 210q takes the same position on the main body 209q each time it is engaged with the main body 209q. This may help to ensure, for example, that air passages between the cap 210q and the main body 209q are consistent.

The device 201q further comprises a Hall effect sensor 229q. As will be described further below, the Hall effect sensor 229q allows the device 201q to detect whether the cap 210q is an open or closed position. In the present case, in the open position, the cap 210q is fully disengaged with the main body 209q of the device 210q.

The Hall effect sensor 229q is disposed on the main body 209q at a wall defining the cavity 222q. As is apparent from FIG. 54G, when the cap 210q is in the closed position (received in the cavity 222q) the Hall effect sensor 229q aligns with a magnet 228q of the cap 210q. When the cap 210q is in this position, the Hall effect sensor 229q detects the presence of the magnet 228q and transmits a signal (in the form of a voltage) to the controller of the device 201q (e.g., by wired connection with the controller). When the cap 210q is in the open position, the Hall effect sensor 229q does not detect the presence of the magnet 228q and no signal is transmitted to the controller. Thus, a lack of signal (or voltage) is indicative of the cap 210q being in the open position. In response to a lack of signal from the Hall effect sensor 229q, the controller may operate as described above. That is, the controller may prevent activation of the heater 204q. For example, the controller may not cause activation of the heater 204q even when signaled to do so by a user input. The prevention of activation of the heater 204q may be performed by a restriction or prevention of power supply from the source 205q to the heater 204q.

Sixteenth Mode: A Heat-not-Burn Device Having a Closure for Covering an Opening of a Cavity Configured for Receipt of at Least a Portion of a Consumable Aspects and embodiments of the sixteenth mode of the present disclosure will now be discussed with reference to the accompanying figures. Further aspects and embodiments will be apparent to those skilled in the art. All documents mentioned in this text are incorporated herein by reference.

FIG. 55A is a schematic providing a general overview of a smoking substitute system 100r. The system 100r includes a substitute smoking device 101r and an aerosol-forming article in the form of a consumable 102r, which comprises an aerosol former 103r. The system is configured to vaporize the aerosol former by heating the aerosol former 103r (so as to form a vapor/aerosol for inhalation by a user).

In the illustrated system, the heater 104r forms part of the consumable 102r and is configured to heat the aerosol former 103r. Heat from the heater 104r vaporizes the aerosol former 103r to produce a vapor. The vapor subsequently condenses to form an aerosol, which is ultimately inhaled by the user.

The system 100r further comprises a power source 105r that forms part of the device 101r. In other embodiments the power source 105r may be external to (but connectable to) the device 101r. The power source 105r is electrically connectable to the heater 104r such that it is able to supply power to the heater 104r (i.e., for the purpose of heating the aerosol former 103r). Thus, control of the electrical connection of the power source 105r to the heater 104r provides control of the state of the heater 104r. The power source 105r may be a power store, for example a battery or rechargeable battery (e.g., a lithium-ion battery).

The system 100r further comprises an I/O module comprising a connector 106r (e.g., in the form of a USB port, Micro USB port, USB-C port, etc.). The connector 106r is configured for connection to an external source of electrical power, e.g., a mains electrical supply outlet. The connector 106r may be used in substitution for the power source 105r. That is the connector 106r may be electrically connectable to the heater 104r so as to supply electricity to the heater 104r. In such embodiments, the device may not include a power source, and the power source of the system may instead comprise the connector 106r and an external source of electrical power (to which the connector 106r provides electrical connection).

In some embodiments, the connector 106r may be used to charge and recharge the power source 105r where the power source 105r includes a rechargeable battery.

The system 100r also comprises a user interface (UI) 107r. Although not shown, the UI 107r may include input means to receive commands from a user. The input means of the UI 107r allows the user to control at least one aspect of the operation of the system 100r. The input means may, for example, be in the form of a button, touchscreen, switch, microphone, etc.

The UI 107r also comprises output means to convey information to the user. The output means may, for example, comprise lights (e.g., LEDs), a display screen, speaker, vibration generator, etc.

The system 100r further comprises a controller 108r that is configured to control at least one function of the device 101r. In the illustrated embodiment, the controller 108r is a component of the device 101r, but in other embodiments may be separate from (but connectable to) the device 101r. The controller 108r is configured to control the operation of the heater 104r and, for example, may be configured to control the voltage applied from the power source 105r to the heater 104r. The controller 108r may be configured to toggle the supply of power to the heater 104r between an on state, in which the full output voltage of the power source 105r is applied to the heater 104r, and an off state, in which the no voltage is applied to the heater 104r.

Although not shown, the system 100r may also comprise a voltage regulator to regulate the output voltage from the power source 105r to form a regulated voltage. The regulated voltage may then be applied to the heater 104r.

In addition to being connected to the heater 104r, the controller 108r is operatively connected to the UI 107r. Thus, the controller 108r may receive an input signal from the input means of the UI 107r. Similarly, the controller 108r may transmit output signals to the UI 107r. In response, the output means of the UI 107r may convey information, based on the output signals, to a user.

FIG. 55B is a schematic showing a variation of the system 100r of FIG. 55A. In the system 100r' of FIG. 55B, the heater 104r forms part of the consumable 102r, rather than the device 101r. In this variation, the heater 104r is electrically connectable to the power source 105r, for example, when the consumable 102r is engaged with the device 101r.

The systems 100r, 100r' of FIG. 55A and FIG. 55B may be implemented as one of two broad categories of system, each in accordance with the present disclosure: a heated tobacco (HT) system or an e-cigarette system. A description of each category of system follows.

FIG. 56A and FIG. 56B illustrate a heated-tobacco (HT) smoking substitute system 200r. The system 200r is an example of the systems 100r, 100r' described in relation to FIG. 56A and FIG. 56B. System 200r includes a heat-not burn (HNB) device 201r and an HT consumable 202r. The description of FIG. 56A and FIG. 56B above is applicable to the system 200r of FIG. 57A and FIG. 57B, and will thus not be repeated.

The device 201r and the consumable 202r are configured such that the consumable 202r can be engaged with the device 201r. FIG. 56A shows the device 201r and the consumable 202r in an engaged state, whilst FIG. 56B shows the device 201r and the consumable 202r in a disengaged state.

The device 201r comprises a body 209r and cap 210r. In use the cap 210r is engaged at an end of the body 209r. Although not apparent from the figures, the cap 210r is moveable relative to the body 209r. In particular, the cap 210r is slidable and can slide along a longitudinal axis of the body 209r.

The device 201r comprises an output means (forming part of the UI of the device 201r) in the form of a plurality of light-emitting diodes (LEDs) 211r arranged linearly along the longitudinal axis of the device 201r and on an outer surface of the body 209r of the device 201r. A button 212r is also arranged on an outer surface of the body 209r of the device 201r and is axially spaced (i.e., along the longitudinal axis) from the plurality of LEDs 211r.

FIG. 56C show a detailed section view of the consumable 202r of the system 200r. The consumable 202r generally resembles a cigarette. In that respect, the consumable 202r has a generally cylindrical form with a diameter of 7 mm and an axial length of 70 mm. The consumable 202r comprises an aerosol forming substrate 213r, a terminal filter element 214r, an upstream filter element 215r and a spacer element 216r. In other embodiments, the consumable may further comprise a cooling element. A cooling element may exchange heat with vapor that is formed by the aerosol-forming substrate 213r in order to cool the vapor so as to facilitate condensation of the vapor.

The aerosol-forming substrate 213r is substantially cylindrical and is located at an upstream end 217r of the consumable 202r, and comprises the aerosol former of the system 200r. In that respect, the aerosol forming substrate 213r is configured to be heated by the device 201r to release a vapor. The released vapor is subsequently entrained in an airflow flowing through the aerosol-forming substrate 213r. The airflow is produced by the action of the user drawing on a downstream 218r (i.e., terminal or mouth end) of the consumable 202r.

In the present embodiment, the aerosol forming substrate 213r comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213r may comprise a gathered sheet of homogenized (e.g., paper/slurry recon) tobacco or gathered shreds/strips formed from such a sheet.

In order to generate an aerosol, the aerosol forming substrate 213r comprises at least one volatile compound that is intended to be vaporized/aerosolized and that may provide the user with a recreational and/or medicinal effect when inhaled. The aerosol-forming substrate 213r may further comprise one or more additives. For example, such additives may be in the form of humectants (e.g., propylene glycol and/or vegetable glycerin), flavorants, fillers, aqueous/non-aqueous solvents and/or binders.

The terminal filter element 214r is also substantially cylindrical, and is located downstream of the aerosol forming substrate 213r at the downstream end 218r of the consumable 202r. The terminal filter element 214r is in the form of a hollow bore filter element having a bore 219r (e.g., for airflow) formed therethrough. The diameter of the bore 219r is 2 mm. The terminal filter element 214r is formed of a porous (e.g., monoacetate) filter material. As set forth above, the downstream end 218r of the consumable 202r (i.e., where the terminal filter 214r is located) forms a mouthpiece portion of the consumable 202r upon which the user draws. Airflow is drawn from the upstream end 217r, thorough the components of the consumable 202r, and out of the downstream end 218r. The airflow is driven by the user drawing on the downstream end 218r (i.e., the mouthpiece portion) of the consumable 202r.

The upstream filter element 215r is located axially adjacent to the aerosol-forming substrate 213r, between the aerosol-forming substrate 213r and the terminal filter element 214r. Like the terminal filter 214r, the upstream filter element 215r is in the form of a hollow bore filter element, such that it has a bore 220r extending axially therethrough. In this way, the upstream filter 215r may act as an airflow restrictor. The upstream filter element 215r is formed of a porous (e.g., monoacetate) filter material. The bore 220r of the upstream filter element 215r has a larger diameter (3 mm) than the terminal filter element 214r.

The spacer 216r is in the form of a cardboard tube, which defines a cavity or chamber between the upstream filter element 215r and the terminal filter element 214r. The spacer 216r acts to allow both cooling and mixing of the vapor/aerosol from the aerosol-forming substrate 213r. The spacer has an external diameter of 7 mm and an axial length of 14 mm.

Although not apparent from the figure, the aerosol-forming substrate 213r, upstream filter 215r and spacer 216r are circumscribed by a paper wrapping layer. The terminal filter 214r is circumscribed by a tipping layer that also circumscribes a portion of the paper wrapping layer (so as to connect the terminal filter 214r to the remaining components of the consumable 202r). The upstream filter 215r and terminal filter 214r are circumscribed by further wrapping layers in the form of plug wraps.

Returning now to the device 201r, FIG. 56D illustrates a detailed view of the end of the device 201r that is configured to engage with the consumable 202r. The cap 210r of the device 201r includes an opening 221r to an internal cavity 222r (more apparent from FIG. 56D) defined by the cap 210r. The opening 221r and the cavity 222r are formed so as to receive at least a portion of the consumable 202r. During engagement of the consumable 202r with the device 201r, a portion of the consumable 202r is received through the opening 221r and into the cavity 222r. After engagement (see FIG. 56B), the downstream end 218r of the consumable 202r protrudes from the opening 221r and thus also protrudes from the device 201r. The opening 221r includes laterally disposed notches 226r. When a consumable 202r is received in the opening 221r, these notches 226r remain open and could, for example, be used for retaining a cover in order to cover the end of the device 201r.

FIG. 56E shows a cross section through a central longitudinal plane through the device 201r. The device 201r is shown with the consumable 202r engaged therewith.

The device 201r comprises a heater 204r comprising heating element 223r. The heater 204r forms part of the body 209r of the device 201r and is rigidly mounted to the body 209r. In the illustrated embodiment, the heater 204r is a rod heater with a heating element 223r having a circular transverse profile. In other embodiments the heater may be in the form of a blade heater (e.g., heating element with a rectangular transverse profile) or a tube heater (e.g., heating element with a tubular form).

The heating element 223r of the heater 204r projects from an internal base of the cavity 222r along a longitudinal axis towards the opening 221r. As is apparent from the figure, the length (i.e., along the longitudinal axis) of the heating element is less than a depth of the cavity 222r. In this way, the heating element 223r does not protrude from or extend beyond the opening 221r.

When the consumable 202r is received in the cavity 222r (as is shown in FIG. 56E), the heating element 223r penetrates the aerosol-forming substrate 213r of the consumable 202r. In particular, the heating element 223r extends for nearly the entire axial length of the aerosol-forming substrate 213r when inserted therein. Thus, when the heater 204r is activated, heat is transferred radially from an outer circumferential surface the heating element 223r to the aerosol-forming substrate 213r.

The device 201r further comprises an electronics cavity 224r. A power source, in the form of a rechargeable battery 205r (a lithium-ion battery), is located in electronics cavity 224r.

The device 201r includes a connector (i.e., forming part of an IO module of the device 201r) in the form of a USB port 206r. The connector may alternatively be, for example, a micro-USB port or a USB-C port for examples. The USB port 206r may be used to recharge the rechargeable battery 205r.

The device 201r includes a controller (not shown) located in the electronics cavity 224r. The controller comprises a microcontroller mounted on a printed circuit board (PCB). The USB port 206r is also connected to the controller 208r (i.e., connected to the PCB and microcontroller).

The controller 208r is configured to control at least one function of the device 201r. For example, the controller 208r is configured to control the operation of the heater 204r. Such control of the operation of the heater 204r may be accomplished by the controller toggling the electrical connection of the rechargeable battery 205r to the heater 204r. For example, the controller 208r is configured to control the heater 204r in response to a user depressing the button 212r. Depressing the button 212r may cause the controller to allow a voltage (from the rechargeable battery 205r) to be applied to the heater 204r (so as to cause the heating element 223r to be heated).

The controller is also configured to control the LEDs 211r in response to (e.g., a detected) a condition of the device 201r or the consumable 202r. For example, the controller may control the LEDs to indicate whether the device 201r is in an on state or an off state (e.g., one or more of the LEDs may be illuminated by the controller when the device is in an on state).

The device 201r comprises a further input means (i.e., in addition to the button 212r) in the form of a puff sensor 225r. The puff sensor 225r is configured to detect a user drawing (i.e., inhaling) at the downstream end 218r of the consumable 202r. The puff sensor 225r may, for example, be in the form of a pressure sensor, flowmeter or a microphone. The puff sensor 225r is operatively connected to the controller 208r in the electronics cavity 224r, such that a signal from the puff sensor 225r, indicative of a puff state (i.e., drawing or not drawing), forms an input to the controller 208r (and can thus be responded to by the controller 208r).

Referring to FIGS. 56F-56K and FIG. 56E, which illustrate a portion of body 209r defining the cavity 222r (i.e., internal cavity), the cavity 222r includes an opening 221r for receipt of the heat-not-burn consumable 202r therein (best shown in FIG. 56E). Further, the body 209r comprises a closure 250r which is configured to selectively cover the opening 221r of the cavity 222r. The closure 250r is moveable between a first position and a second position such that in the first position the closure 250r covers the opening 221r and in the second position the closure 250r is retracted away from the opening 250r. In the second position, the closure 250r is also configured to be substantially concealed within the body 209r.

The closure 250r is a sliding closure comprising a planar flexible sheet of plastics material. In this way, when the sheet is retracted into the second position it may bend or flex to conform to the internal structure of the body of the device to be more easily accommodated.

Further, the closure 250r is interposed between the opening 221r to the cavity 222r and the heater 204r. The closure 250r is located between the opening 221r to the cavity 222r and the maximum extent of the rod heater 204r (not shown). The provision of the closure 250r prevents dirt/dust getting into the cavity 222r, thereby preventing damage to the heater 204r enclosed within the body 209r. Further, the provision of closure 250r may prevent any material present within the aerosol forming article such as tobacco falling out of the device during transit.

According to an aspect, the closure may be a sliding closure as shown in FIGS. 56F-56K. Referring to FIGS. 56F-56K, the closure is a planar sheet of plastics material, disposed within the body 209r of the HNB device 201r or a cap 210r. The body 209r or the cap 210r of the HNB device 201r includes a guideway 253r around the opening 221r through which the planar sheet passes. The body includes a slot 251r in the outer wall of the device. The slot 251r accommodates a knob 252r which is connected to the planar sheet of the closure via a connector which passes through the slot 251r. The slot 251r is defined longitudinally along longitudinal axis of the body 209r, such that the slot 251r may slidably receive the connector. The closure 250r slidably moves between a first position in which the closure 250r covers the opening 221r (seen in FIG. 56F, FIG. 56G, and FIG. 56H) and a second position in which the closure 250r is retracted and concealed within the body (with the opening 221r and cavity 222r left open), as shown in FIG. 56I, FIG. 56J, and FIG. 56K. The user can move the closure 250r between the first position and the second position by sliding the knob 252r along the slot 251r.

When the knob 252r is at one terminal position in the slot 251r (the "top" of the slot 251r as seen in FIGS. 56F-56K) the closure is in the first position and the opening is covered. When the knob 252r is at the other terminal position in the slot 251r (the "bottom" of the slot 251r as seen in FIGS. 56F-56K) the closure is in the second position. As shown in FIGS. 56F-56K when the closure 250r is in first position, an upper portion of the closure 250r covers the opening 221r to the cavity 222r, and when the closure 250r is moved from the first position to the second position, the upper portion of the closure slides to open the opening 221r to the cavity 222r. In the second position, the closure 250r is configured to be substantially concealed within the body 209r.

In some embodiments, the first position is a terminal position along the path of travel of the closure, and the second position is a terminal position along the path of travel of the closure. Thus, the closure may move along a path of travel which terminates at each end in the first and second positions respectively.

By "substantially concealed within the body", it is meant that a substantial part of the closure lies within the body of the device such that it does not protrude beyond the outer wall of the body of the device, although at least part of the closure may still be visible when looking into the cavity of the device. In some embodiments, "substantially concealed within the body" means that the portion of the closure which, when in the first position, covers the opening, does not protrude beyond the outer wall of the body of the device when in the second position. In some embodiments, "substantially concealed within the body" also means that the closure in not visible, or not substantially visible, when looking into the cavity, for example some or all of the closure may be concealed behind the wall of the device so is not visible.

Referring to FIG. 57A to FIG. 57E, which illustrate a smoking substitute device having a closure that may be a swiveling closure such as a ball valve (as shown in FIG. 57A to FIG. 57E), wherein the closure 250r may be a cylindrical shaped member having a bore 254r therethrough. The closure 250r is mounted concealed within the body 209r such that the closure 250r rotates between a first position and a second position, as illustrated in FIGS. 57A/C and FIGS. 57B/D. The bore is a through-hole perpendicular to an axis of rotation of the closure 250r. When the closure 250r is in the second position, the bore is aligned along with longitudinal axis of the body 209r such that the bore 254r and cavity 222r provide a passage for the insertion of a consumable 202r through the opening 221r. When the closure 250r in first position the bore 254r is aligned in a direction which is not parallel with the cavity 222r, thereby closing the opening 221r of the cavity 222r.

Further, the closure 250r or ball valve may include a handle 260r, shown in FIG. 57E, allowing the user to move the closure 250r between the first position and the second position. E.g., the user may hold the smoking substitute device 201r and operate the handle with one's thumb, thereby providing a one hand operation. The position may trigger a switching on/off of the smoking substitute device and/or the operation of the device, to allow a pure one hand operation. In an embodiment, a portion of the ball valve may be exposed to an outer surface of the body 250r to facilitate the user to rotate the ball valve manually between the first position and the second position. Furthermore, the closure 250r may be biased into one or more of the first and second positions.

In some embodiments, the closure comprises a swinging closure, such as a concealed trap door within the device body. For example, the closure may comprise a hinged sheet of material which is biased into the first position (closed) in which the sheet covers the opening, wherein when force is applied to the sheet in a direction into the device to overcome the bias, the sheet swings via the hinge into the second position (open), allowing insertion of a consumable into the cavity. In this way, the user is able to open the closure simply by pressing the end of a consumable against the sheet, into the device, which pushes the closure away from the opening to allow the consumable to pass into the device. In some embodiments, the trap door is biased into the first position (closed). For example, the trap door may be spring-loaded.

In some embodiments, the device comprises means to hold the closure in one or more of the first position and the second position. In some embodiments, the means to hold the closure comprises an interaction between the closure and a part of the body of the device which occurs at or close to the first and/or second position. In some embodiments, the means to hold the closure comprises a detent comprising a raised feature on a surface of the device body and/or the closure. In some embodiments, the means to hold the closure comprises an interference fit provided between the closure and the body of the device when in the first and/or second positions, wherein the interference fit is removed as the closure moves away from the first and/or second position to facilitate movement between the positions.

The heat-not-burn device 201r also comprises a sensor (not shown in figures) for detecting a position of the closure 250r. The sensor is communicatively coupled with the controller 208r to receive a signal from the sensor.

Further, the controller 208r is configured to receive the signal from the sensor, indicative of a position of the closure 250r. Based on the position of the closure 250r, the controller 208r controls activation and deactivation of heater 204r in response to the received signal. The sensor may detect the first position and the second position of the closure 250r. The sensor may generate a signal based on the determination of position of the closure 250r in the first position. Further, upon receiving the signal from the sensor, the controller 208r may deactivate the power supply to the device 201r, thereby preventing activation of the heater 204r. Similarly, the sensor is configured to generate another signal, based on the determination of the position of the closure 250r in the second position. Consequently, the controller 208r may activate the heater 204r for heating the consumable 202r received within the cavity 222r. In this way, the heater cannot be activated when the closure 250r is "closed". This provides a safer and more efficient device since accidental activation of the heater 204r e.g., in a pocket or bag is prevented, which saves battery life and is safer. When the user opens the closure 250r, the controller 208r then permits the activation of the heater 204r (e.g., by an appropriate input on a user interface).

In another aspect the present disclosure discloses a method of operating a heat not burn device 201r, the method comprises steps of determining a position of a closure 250r for covering an opening 221r of the device 201r into which a heat-not-burn consumable 202r is received in use. Secondly, a heater 204r of the device 201r is controlled based on the determined position of the closure 250r. The position of the closure 250r is determined by at least one sensor (not shown in figures) disposed in the device 201r.

Further, the method of operating the heat not burn 201r may comprise disabling activation of the heater 204r. The activation and disabling activation of the heater 204r may be controlled by a controller 208r, based on the position of the closure 250r. The position of the closure 250r may be detected by a sensor configured within the device 201r and communicatively coupled with the controller 208r.

In another aspect, the power supply (i.e., power source) of the device may be disabled by the controller 208r when the closure 205r is in the first position. The disabling activation of the device 201r based on the position of the closure 250r may facilitate optimum working of the device 201r.

Seventeenth Mode: A Smoking Substitute Device with an Improved Air Inlet

Aspects and embodiments of the seventeenth mode of the present disclosure will now be discussed with reference to the accompanying figures. Further aspects and embodiments will be apparent to those skilled in the art. All documents mentioned in this text are incorporated herein by reference.

FIG. 58A is a schematic providing a general overview of a smoking substitute system 100s. The system 100s includes a substitute smoking device 101s and an aerosol-forming article in the form of a consumable 102s, which comprises an aerosol former 103s. The system is configured to vaporize the aerosol former by heating the aerosol former 103s (so as to form a vapor/aerosol for inhalation by a user).

In the illustrated system, the heater 104s forms part of the consumable 102s and is configured to heat the aerosol former 103s. In this variation, the heater 104s is electrically connectable to the power source 105s, for example, when the consumable 102s is engaged with the device 101s. Heat from the heater 104s vaporizes the aerosol former 103s to produce a vapor. The vapor subsequently condenses to form an aerosol, which is ultimately inhaled by the user.

The system 100s further comprises a power source 105s that forms part of the device 101s. In other embodiments the power source 105s may be external to (but connectable to) the device 101s. The power source 105s is electrically connectable to the heater 104s such that it is able to supply power to the heater 104s (i.e., for the purpose of heating the aerosol former 103s). Thus, control of the electrical connection of the power source 105s to the heater 104s provides control of the state of the heater 104s. The power source 105s may be a power store, for example a battery or rechargeable battery (e.g., a lithium-ion battery).

The system 100s further comprises an I/O module comprising an electrical connection 106s (e.g., in the form of a USB port, Micro USB port, USB-C port, etc.). The electrical connection 106 is configured for connection to an external source of electrical power, e.g., a mains electrical supply outlet. The electrical connection 106s may be used in substitution for the power source 105s. That is the electrical connection 106s may be electrically connectable to the heater 104s so as to supply electricity to the heater 104s. In such embodiments, the device may not include a power source, and the power source of the system may instead comprise the electrical connection 106s and an external source of electrical power.

In some embodiments, the electrical connection 106s may be used to charge and recharge the power source 105s where the power source 105s includes a rechargeable battery.

In some embodiments, the electrical connection 106s, may be configured to provide an air inlet, to facilitate flow of air into the housing i.e., underneath the heater 104s (thus the heating element).

The system 100s also comprises a user interface (UI) 107s. Although not shown, the UI 107s may include input means to receive commands from a user. The input means of the UI 107s allows the user to control at least one aspect of the operation of the system 100s. The input means may, for example, be in the form of a button, touchscreen, switch, microphone, etc.

The UI 107s also comprises output means to convey information to the user. The output means may, for example, comprise lights (e.g., LEDs), a display screen, speaker, vibration generator, etc.

The system 100s further comprises a controller 108s that is configured to control at least one function of the device 101s. In the illustrated embodiment, the controller 108s is a component of the device 101s, but in other embodiments may be separate from (but connectable to) the device 101s. The controller 108s is configured to control the operation of the heater 104s and, for example, may be configured to control the voltage applied from the power source 105s to the heater 104s. The controller 108s may be configured to toggle the supply of power to the heater 104s between an on state, in which the full output voltage of the power source 105s is applied to the heater 104s, and an off state, in which the no voltage is applied to the heater 104s.

Although not shown, the system 100s may also comprise a voltage regulator to regulate the output voltage from the power source 105s to form a regulated voltage. The regulated voltage may then be applied to the heater 104s.

In addition to being connected to the heater 104s, the controller 108s is operatively connected to the UI 107s. Thus, the controller 108s may receive an input signal from the input means of the UI 107s. Similarly, the controller 108s may transmit output signals to the UI 107s. In response, the output means of the UI 107s may convey information, based on the output signals, to a user. The controller also comprises a memory 109s, which is a non-volatile memory. The memory 109s includes instructions, which, when implemented, cause the controller to perform certain tasks or steps of a method.

FIG. 58B is a schematic showing a variation of the system 100s of FIG. 58A. In the system 100s' of FIG. 58B, the heater 104s forms part of the device 101s, rather than the consumable 102s. In this variation, the heater 104s is electrically connected to the power source 105s.

FIG. 59A illustrates a heated-tobacco (HT) smoking substitute system 200s. The system 200s is an example of the systems 100s, 100s' described in relation to FIG. 58A or FIG. 58B. System 200s includes a smoking substitute device 201s and an HT consumable 202s. The description of FIG. 58A and FIG. 58B above is applicable to the system 200s of FIG. 59A and FIG. 59B, and will thus not be repeated.

FIG. 59B illustrates the device 201s of the smoking substitute system 200s. The device 201s is configured to receive a consumable 202s (as seen in FIG. 59A), which may facilitate in generating aerosol under operating conditions of the device 201s.

The device 201s comprises a housing 209s and cap 210s. In use, the cap 210s is engageable at a first end of the housing 209s. Although not apparent from the figures, the cap 210s is moveable relative to the housing 209s. In particular, the cap 210s is slidable and can slide along a longitudinal axis of the housing 209s.

In some embodiments, the cap 210s is movable along a longitudinal axis of the housing 209s.

The device 201s comprises an output means (forming part of the UI of the device 201s) in the form of a plurality of light-emitting diodes (LEDs) 211s arranged linearly along the longitudinal axis of the device 201s and on an outer surface of the housing 209s of the device 201s. A button 212s is also arranged on an outer surface of the housing 209s of the device 201s and is axially spaced (i.e., along the longitudinal axis) from the plurality of LEDs 211s.

FIG. 59C show a detailed section view of the consumable 202s of the system 200s. The consumable 202s generally resembles a cigarette. In that respect, the consumable 202s has a generally cylindrical form with a diameter of 7 mm and an axial length of 70 mm. The consumable 202s comprises an aerosol forming substrate 213s, a terminal filter element 214s, an upstream filter element 215s and a spacer element 216s. In other embodiments, the consumable may further comprise a cooling element. A cooling element may exchange heat with vapor that is formed by the aerosol-forming substrate 213s in order to cool the vapor so as to facilitate condensation of the vapor.

The aerosol-forming substrate 213s is substantially cylindrical and is located at an upstream end 217s of the consumable 202s, and comprises the aerosol former of the system 200s. In that respect, the aerosol forming substrate 213s is configured to be heated by the device 201s to release a vapor. The released vapor is subsequently entrained in an airflow flowing through the aerosol-forming substrate 213s. The airflow is produced by the action of the user drawing on a downstream 218s (i.e., terminal or mouth) end of the consumable 202s.

In the present embodiment, the aerosol forming substrate 213s comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213s may comprise a gathered sheet of homogenized (e.g., paper/slurry recon) tobacco or gathered shreds/strips formed from such a sheet.

In order to generate an aerosol, the aerosol forming substrate 213s comprises at least one volatile compound that is intended to be vaporized/aerosolized and that may provide the user with a recreational and/or medicinal effect when inhaled. The aerosol-forming substrate 213s may further comprise one or more additives. For example, such additives may be in the form of humectants (e.g., propylene glycol and/or vegetable glycerin), flavorants, fillers, aqueous/non-aqueous solvents and/or binders.

The terminal filter element 214s is also substantially cylindrical, and is located downstream of the aerosol forming substrate 213s at the downstream end 218s of the consumable 202s. The terminal filter element 214s is in the form of a hollow bore filter element having a bore 219s (e.g., for airflow) formed therethrough. The diameter of the bore 219s is 2 mm. The terminal filter element 214s is formed of a porous (e.g., monoacetate) filter material. As set forth above, the downstream end 218s of the consumable 202s (i.e., where the terminal filter 214s is located) forms a mouthpiece portion of the consumable 202s upon which the user draws. Airflow is drawn from the upstream end 217s, thorough the components of the consumable 202s, and out of the downstream end 218s. The airflow is driven by the user drawing on the downstream end 218s (i.e., the mouthpiece portion) of the consumable 202s.

The upstream filter element 215s is located axially adjacent to the aerosol-forming substrate 213s, between the aerosol-forming substrate 213s and the terminal filter element 214s. Like the terminal filter 214s, the upstream filter element 215s is in the form of a hollow bore filter element, such that it has a bore 220s extending axially therethrough. In this way, the upstream filter 215s may act as an airflow restrictor. The upstream filter element 215s is formed of a porous (e.g., monoacetate) filter material. The bore 220s of the upstream filter element 215s has a larger diameter (3 mm) than the terminal filter element 214s.

The spacer 216s is in the form of a cardboard tube, which defines a cavity or chamber between the upstream filter element 215s and the terminal filter element 214s. The spacer 216s acts to allow both cooling and mixing of the vapor/aerosol from the aerosol-forming substrate 213s. The spacer has an external diameter of 7 mm and an axial length of 14 mm.

Although not apparent from the figure, the aerosol-forming substrate 213s, upstream filter 215s and spacer 216s are circumscribed by a paper wrapping layer. The terminal filter 214s is circumscribed by a tipping layer that also circumscribes a portion of the paper wrapping layer (so as to connect the terminal filter 214s to the remaining components of the consumable 202s). The upstream filter 215s and terminal filter 214s are circumscribed by further wrapping layers in the form of plug wraps.

Returning now to the device 201s, FIG. 59D illustrates a detailed view of the first end of the device 201s that is configured to engage with the cap 210s. The cap 210s and the housing 209s are engaged by the mechanism, wherein the mechanism is at least one of a snap fit mechanism, a magnetic lock mechanism or any other mechanism that serves the purpose engaging the cap 210s with the housing 209s. The cap 210s of the device 201s includes an opening 221s to an internal cavity 222s (more apparent from FIG. 59D) defined by the cap 210s. The opening 221s and the cavity 222s are formed so as to receive at least a portion of the consumable 202s. During engagement of the consumable 202s with the device 201s, a portion of the consumable 202s is received through the opening 221s and into the cavity 222s. After engagement (see FIG. 59B), the downstream end 218s of the consumable 202s protrudes from the opening 221s and thus also protrudes from the device 201s. The opening 221s includes laterally disposed notches 226s. When a consumable 202s is received in the opening 221s, these notches 226s remain open and could, for example, be used for retaining a cover in order to cover the end of the device 201s.

FIG. 59E shows a cross section through a central longitudinal plane through the device 201s. The device 201s is shown with the consumable 202s engaged therewith.

The device 201s comprises a heater 204s comprising heating element 223s. The heater 204s forms part of the housing 209s of the device 201s and is rigidly mounted to the housing 209s. In the illustrated embodiment, the heater 204s is a rod heater with a heating element 223s having a circular transverse profile. In other embodiments the heater may be in the form of a blade heater (e.g., heating element with a rectangular transverse profile) or a tube heater (e.g., heating element with a tubular form).

In an embodiment, the heating element 223s of the heater 204s may be configured to penetrate through at least a portion of the consumable 202s, so as the transfer heat to the consumable 202s to generate aerosol.

The heating element 223s of the heater 204s projects from an internal base of the cavity 222s along a longitudinal axis towards the opening 221s. As is apparent from the figure, the length (i.e., along the longitudinal axis) of the heating element is less than a depth of the cavity 222s. In this way, the heating element 223s does not protrude from or extend beyond the opening 221s.

When the consumable 202s is received in the cavity 222s (as is shown in FIG. 59E), the heating element 223s penetrates the aerosol-forming substrate 213s of the consumable 202s. In particular, the heating element 223s extends for nearly the entire axial length of the aerosol-forming substrate 213s when inserted therein. Thus, when the heater 204s is activated, heat is transferred radially from an outer circumferential surface the heating element 223s to the aerosol-forming substrate 213s.

Returning back to FIG. 59B and FIG. 59D which illustrates the device 201s, with the cap 210s and the housing 209s engaged with one another, in order to enclose at least a portion of the heating element 223s of the heater 204s (seen in FIG. 59D). The cap 210s and the housing 209s may be configured to define a gap 227s between the cap 210s and the housing 209s, upon engagement of the cap 210s and the housing 209s. The cap 210s and the housing 209s may be engaged with an interference fit, so as to form the gap 227s between the cap 210s and the housing 209s.

In the illustrated embodiment of FIG. 59D, the gap 227s defined between the cap 210s and the housing 209s upon engagement, may be configured as an air inlet, to facilitate flow of air into the housing 209s. Due to such an engagement of the cap 210s and the housing 209s, the air inlet 227s (thus the gap), may be configured to extend in a direction transverse to longitudinal axis of the housing 209s, e.g., extend linearly and transversely in a major surface of the housing 209s, with respect to longitudinal axis of the housing 209s. Further, the air inlet 227s may be configured to facilitate flow of air adjacent to the heating element 223s. Furthermore, the air inlet 227s may configured to facilitate flow of air towards a base of the heating element, e.g., underneath the heating element 223s of the heater 204s residing within the housing 209s.

In an embodiment, and referring to FIG. 59B, the housing 209s of the device 201s, may be an elongated member, with a length of the housing 201s greater than thickness of the housing 209s. Thus, the major surface of the housing 209s may be at least one of a front face and a rear face of the housing 209s, which possess surface area greater than that of the side surfaces. Now, referring back to FIG. 59E, the device 201s comprises an electronics cavity 224s. A power source, in the form of a rechargeable battery 205s (a lithium-ion battery), is located in electronics cavity 224s.

The device 201s includes an electrical connection 206s (i.e., forming part of an IO module of the device 201s) in the form of a Universal Serial Bus port (USB port), disposed at a second end of the housing 209s. In an embodiment, the second end may be a bottom end. The connector may alternatively be, for example, a micro-USB port or a USB-C port for examples. The electrical connection 206s may be used to recharge the rechargeable battery 205s. In the illustrated embodiment as shown in FIG. 59E, the electrical connection 206s may be configured to provide with an air inlet 228s, to facilitate flow of air into the housing 209s. The air inlet 228s provided in the electrical connection 206s, may be an aperture or a slit configured at an end wall (not shown) of the electrical connection 206s. The air may enter through the air inlet 228s provided in the electrical connection 206s and may flow through a substantial length of the housing 209s. Also, the air entering the housing 209s, flows towards the base of the heating element 223s, e.g., underneath the heating element 223s of the heater 204s (indicated with arrows). Thus, the air inlet in the electrical connection 206s may facilitate in flow of air underneath the heating element 223s, to improve aerosol formation.

Referring to FIG. 60, illustrates a detailed view of a third embodiment of the first end of the housing 209s. As shown in FIG. 60, the cap 210s of the device 201s is provided with a notch 327s, e.g., configured with a slit or a provision, which is configured to act as an air inlet. The notch 327s is formed on an edge of the cap 210s. The notch 327s is configured to facilitate flow of air underneath the heating element 223s of the heater 204s, accommodated in the housing 209s.

In some embodiments, the cap 210s may be configured with through holes or apertures on one of the major surface, to facilitate flow of air into the housing 209s and underneath the heating element 223s.

Referring to FIG. 61 illustrates a front view of the device 201s. In this embodiment, the housing 209s of the device is defined with a notch 427s. The notch 427s is defined at an interface of the cap 210s and the housing 209s. The notch 427s is formed on an edge of the housing 209s, and act as the air inlet. The notch 427s is configured to facilitate flow of air underneath the heating element 223s accommodated in the housing 209s.

In an embodiment, the air from the surroundings may be drawn through either of the gap 227s defined between the cap 210s and the housing 209s, and the air inlet 228s provided in the USB port 206s, into the housing 209s as the user draws aerosol through the consumable 202s. The aerosol may be formed due to interaction of the consumable 202s with the heat generated by the heating element 223s. Upon drawing the aerosol, pressure developed inside the housing 209s of the device 201s decreases due to which, the air from the surroundings may enters into the housing 209s (i.e., underneath the heating element 223s), through the air inlets 227s, 228s configured in the device 201s. The flow of air into the housing 209s (i.e., underneath the heating element 223s), mixes with the heat generated from the heating element 223s, which facilitates in improving aerosol generation and total particulate matter (TPM) output of the aerosol.

In some embodiments, the air inlets configured in the device 201s, account to minimum form factor changes and do not interfere with the design of the device 201s. Since, the air inlets are defined within or between essential components (e.g., the cap 210s, the housing 209s, the electrical connection 206s) of the device 201s, this feature may facilitate in defining the air inlets, without affecting or altering the profile of the device 201s.

The device 201s includes a controller (not shown) located in the electronics cavity 224s. The controller comprises a microcontroller mounted on a printed circuit board (PCB). The USB port 206s is also connected to the controller 208s (i.e., connected to the PCB and microcontroller).

The controller 208s is configured to control at least one function of the device 202s. For example, the controller 208s is configured to control the operation of the heater 204s. Such control of the operation of the heater 204s may be accomplished by the controller toggling the electrical connection of the rechargeable battery 205s to the heater 204s. For example, the controller 208s is configured to control the heater 204s in response to a user depressing the button 212s. Depressing the button 212s may cause the controller to allow a voltage (from the rechargeable battery 205s) to be applied to the heater 204s (so as to cause the heating element 223s to be heated).

The controller is also configured to control the LEDs 211s in response to (e.g., a detected) a condition of the device 201s or the consumable 202s. For example, the controller may control the LEDs to indicate whether the device 201s is in an on state or an off state (e.g., one or more of the LEDs may be illuminated by the controller when the device is in an on state).

The device 201s comprises a further input means (i.e., in addition to the button 212s) in the form of a puff sensor 225s. The puff sensor 225s is configured to detect a user drawing (i.e., inhaling) at the downstream end 218s of the consumable 202s. The puff sensor 225s may, for example, be in the form of a pressure sensor, flowmeter or a microphone. The puff sensor 225s is operatively connected to the controller 208s in the electronics cavity 224s, such that a signal from the puff sensor 225s, indicative of a puff state (i.e., drawing or not drawing), forms an input to the controller 208s (and can thus be responded to by the controller 208s).

Eighteenth Mode: A Stopper for a Smoking Substitute Device

Aspects and embodiments of the eighteenth mode of the present disclosure will now be discussed with reference to the accompanying figures. Further aspects and embodiments will be apparent to those skilled in the art. All documents mentioned in this text are incorporated herein by reference.

FIG. 62A is a schematic providing a general overview of a smoking substitute system 100t. The system 100t includes a substitute smoking device 101t and an aerosol-forming article in the form of a consumable 102t, which comprises an aerosol former 103t. The system is configured to vaporize the aerosol former by heating the aerosol former 103t (so as to form a vapor/aerosol for inhalation by a user). The system 100t also includes a stopper 127t that may be configured to close at least one portion of the device 100t. For example, the stopper 127t may be configured to close an opening adapted to receive the aerosol-forming article in the device 101t. The provision of the stopper 127t may prevent entry of foreign objects into the HNB device 101t, and also residual odor of the aerosol-forming article may be concealed in the device 101t, when the device 101t is not in use.

In the illustrated system, the heater 104t forms part of the consumable 102t and is configured to heat the aerosol former 103t. In this variation, the heater 104t is electrically connectable to the power source 105t, for example, when the consumable 102t is engaged with the device 101t. Heat from the heater 104t vaporizes the aerosol former 103t to produce a vapor. The vapor subsequently condenses to form an aerosol, which is ultimately inhaled by the user.

The system 100t further comprises a power source 105t that forms part of the device 101t. In other embodiments the power source 105t may be external to (but connectable to) the device 101t. The power source 105t is electrically connectable to the heater 104t such that it is able to supply power to the heater 104t (i.e., for the purpose of heating the aerosol former 103t). Thus, control of the electrical connection of the power source 105t to the heater 104t provides control of the state of the heater 104t. The power source 105t may be a power store, for example a battery or rechargeable battery (e.g., a lithium-ion battery).

The system 100t further comprises an I/O module comprising a connector 106t (e.g., in the form of a USB port, Micro USB port, USB-C port, etc.). The connector 106t is configured for connection to an external source of electrical power, e.g., a mains electrical supply outlet. The connector 106t may be used in substitution for the power source 105t. That is the connector 106t may be electrically connectable to the heater 104t so as to supply electricity to the heater 104t. In such embodiments, the device may not include a power source, and the power source of the system may instead comprise the connector 106t and an external source of electrical power (to which the connector 106t provides electrical connection).

In some embodiments, the connector 106t may be used to charge and recharge the power source 105t where the power source 105t includes a rechargeable battery.

The system 100t also comprises a user interface (UI) 107t. Although not shown, the UI 107t may include input means to receive commands from a user. The input means of the UI 107t allows the user to control at least one aspect of the operation of the system 100t. The input means may, for example, be in the form of a button, touchscreen, switch, microphone, etc.

The UI 107t also comprises output means to convey information to the user. The output means may, for example, comprise lights (e.g., LEDs), a display screen, speaker, vibration generator, etc.

The system 100t further comprises a controller 108t that is configured to control at least one function of the device 101t. In the illustrated embodiment, the controller 108t is a component of the device 101t, but in other embodiments may be separate from (but connectable to) the device 101t. The controller 108t is configured to control the operation of the heater 104t and, for example, may be configured to control the voltage applied from the power source 105t to the heater 104t. The controller 108t may be configured to toggle the supply of power to the heater 104t between an on state, in which the full output voltage of the power source 105t is applied to the heater 104t, and an off state, in which the no voltage is applied to the heater 104t.

Although not shown, the system 100t may also comprise a voltage regulator to regulate the output voltage from the power source 105t to form a regulated voltage. The regulated voltage may then be applied to the heater 104t.

In addition to being connected to the heater 104t, the controller 108t is operatively connected to the UI 107t. Thus, the controller 108t may receive an input signal from the input means of the UI 107t. Similarly, the controller 108t may transmit output signals to the UI 107t. In response, the output means of the UI 107t may convey information, based on the output signals, to a user. The controller also comprises a memory 109t, which is a non-volatile memory. The memory 109t includes instructions, which, when implemented, cause the controller to perform certain tasks or steps of a method.

FIG. 62B is a schematic showing a variation of the system 100t of FIG. 62A. In the system 100t' of FIG. 62B, the heater 104t forms part of the device 101t, rather than the consumable 102t. In this variation, the heater 104t is electrically connected to the power source 105t.

FIG. 63A and FIG. 63B illustrate a heated-tobacco (HT) smoking substitute system 200t. The system 200t is an example of the systems 100t, 100t' described in relation to FIG. 62A or FIG. 62B. System 200t includes an HT device 201t and an HT consumable 202t. The description of FIG. 62A and FIG. 62B above is applicable to the system 200t of FIG. 63A and FIG. 63B, and will thus not be repeated.

The device 201t and the consumable 202t are configured such that the consumable 202t can be engaged with the device 201t. FIG. 63A shows the device 201t and the consumable 202t in an engaged state, whilst FIG. 63B shows the device 201t and the consumable 202t in a disengaged state.

The device 201t comprises a body 209t and cap 210t. In use the cap 210t is engaged at an end of the body 209t. Although not apparent from the figures, the cap 210t is moveable relative to the body 209t. In particular, the cap 210t is slidable and can slide along a longitudinal axis of the body 209t.

The device 201t comprises an output means (forming part of the UI of the device 201t) in the form of a plurality of light-emitting diodes (LEDs) 211t arranged linearly along the longitudinal axis of the device 201t and on an outer surface of the body 209t of the device 201t. A button 212t is also arranged on an outer surface of the body 209t of the device 201t and is axially spaced (i.e., along the longitudinal axis) from the plurality of LEDs 211t.

FIG. 63C show a detailed section view of the consumable 202t of the system 200t. The consumable 202t generally resembles a cigarette. In that respect, the consumable 202t has a generally cylindrical form with a diameter of 7 mm and an axial length of 70 mm. The consumable 202t comprises an aerosol forming substrate 213t, a terminal filter element 214t, an upstream filter element 215t and a spacer element 216t. In other embodiments, the consumable may further comprise a cooling element. A cooling element may exchange heat with vapor that is formed by the aerosol-forming substrate 213t in order to cool the vapor so as to facilitate condensation of the vapor.

The aerosol-forming substrate 213t is substantially cylindrical and is located at an upstream end 217t of the consumable 202t, and comprises the aerosol former of the system 200t. In that respect, the aerosol forming substrate 213t is configured to be heated by the device 201t to release a vapor. The released vapor is subsequently entrained in an airflow flowing through the aerosol-forming substrate 213t. The airflow is produced by the action of the user drawing on a downstream 218t (i.e., terminal or mouth) end of the consumable 202t.

In the present embodiment, the aerosol forming substrate 213t comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213t may comprise a gathered sheet of homogenized (e.g., paper/slurry recon) tobacco or gathered shreds/strips formed from such a sheet.

In order to generate an aerosol, the aerosol forming substrate 213t comprises at least one volatile compound that is intended to be vaporized/aerosolized and that may provide the user with a recreational and/or medicinal effect when inhaled. The aerosol-forming substrate 213t may further comprise one or more additives. For example, such additives may be in the form of humectants (e.g., propylene glycol and/or vegetable glycerin), flavorants, fillers, aqueous/non-aqueous solvents and/or binders.

The terminal filter element 214t is also substantially cylindrical, and is located downstream of the aerosol forming substrate 213t at the downstream end 218t of the consumable 202t. The terminal filter element 214t is in the form of a hollow bore filter element having a bore 219t (e.g., for airflow) formed therethrough. The diameter of the bore 219t is 2 mm. The terminal filter element 214t is formed of a porous (e.g., monoacetate) filter material. As set forth above, the downstream end 218t of the consumable 202t (i.e., where the terminal filter 214t is located) forms a mouthpiece portion of the consumable 202t upon which the user draws. Airflow is drawn from the upstream end 217t, thorough the components of the consumable 202t, and out of the downstream end 218t. The airflow is driven by the user drawing on the downstream end 218t (i.e., the mouthpiece portion) of the consumable 202t.

The upstream filter element 215t is located axially adjacent to the aerosol-forming substrate 213t, between the aerosol-forming substrate 213t and the terminal filter element 214t. Like the terminal filter 214t, the upstream filter element 215t is in the form of a hollow bore filter element, such that it has a bore 220t extending axially therethrough. In this way, the upstream filter 215t may act as an airflow restrictor. The upstream filter element 215t is formed of a porous (e.g., monoacetate) filter material. The bore 220t of the upstream filter element 215t has a larger diameter (3 mm) than the terminal filter element 214t.

The spacer 216t is in the form of a cardboard tube, which defines a cavity or chamber between the upstream filter element 215t and the terminal filter element 214t. The spacer 216t acts to allow both cooling and mixing of the vapor/aerosol from the aerosol-forming substrate 213t. The spacer has an external diameter of 7 mm and an axial length of 14 mm.

Although not apparent from the figure, the aerosol-forming substrate 213t, upstream filter 215t and spacer 216t are circumscribed by a paper wrapping layer. The terminal filter 214t is circumscribed by a tipping layer that also circumscribes a portion of the paper wrapping layer (so as to connect the terminal filter 214t to the remaining components of the consumable 202t). The upstream filter 215t and terminal filter 214t are circumscribed by further wrapping layers in the form of plug wraps.

Returning now to the device 201t, FIG. 63D illustrates a detailed view of the end of the device 201t that is configured to engage with the consumable 202t. The cap 210t of the device 201t includes an opening 221t to an internal cavity 222t (more apparent from FIG. 63D) defined by the cap 210t. The opening 221t and the cavity 222t are formed so as to receive at least a portion of the consumable 202t. During engagement of the consumable 202t with the device 201t, a portion of the consumable 202t is received through the opening 221t and into the cavity 222t. After engagement (see FIG. 63B), the downstream end 218t of the consumable 202t protrudes from the opening 221t and thus also protrudes from the device 201t. The opening 221t includes laterally disposed notches 226t. When a consumable 202t is received in the opening 221t, these notches 226t remain open and could, for example, be used for retaining a cover in order to cover the end of the device 201t.

FIG. 63E shows a cross section through a central longitudinal plane through the device 201t. The device 201t is shown with the consumable 202t engaged therewith.

The device 201t comprises a heater 204t comprising heating element 223t. The heater 204t forms part of the body 209t of the device 201t and is rigidly mounted to the body 209t. In the illustrated embodiment, the heater 204t is a rod heater with a heating element 223t having a circular transverse profile. In other embodiments the heater may be in the form of a blade heater (e.g., heating element with a rectangular transverse profile) or a tube heater (e.g., heating element with a tubular form).

The heating element 223t of the heater 204t projects from an internal base of the cavity 222t along a longitudinal axis towards the opening 221t. As is apparent from the figure, the length (i.e., along the longitudinal axis) of the heating element is less than a depth of the cavity 222t. In this way, the heating element 223t does not protrude from or extend beyond the opening 221t.

When the consumable 202t is received in the cavity 222t (as is shown in FIG. 63E), the heating element 223t penetrates the aerosol-forming substrate 213t of the consumable 202t. In particular, the heating element 223t extends for nearly the entire axial length of the aerosol-forming substrate 213t when inserted therein. Thus, when the heater 204t is activated, heat is transferred radially from an outer circumferential surface the heating element 223t to the aerosol-forming substrate 213t.

The device 201t further comprises an electronics cavity 224t. A power source, in the form of a rechargeable battery 205t (a lithium-ion battery), is located in electronics cavity 224t.

The device 201t includes a connector (i.e., forming part of an IO module of the device 201t) in the form of a USB port 206t. The connector may alternatively be, for example, a micro-USB port or a USB-C port for examples. The USB port 206t may be used to recharge the rechargeable battery 205t.

The device 201t includes a controller (not shown) located in the electronics cavity 224t. The controller comprises a microcontroller mounted on a printed circuit board (PCB). The USB port 206t is also connected to the controller 208t (i.e., connected to the PCB and microcontroller).

The controller 208t is configured to control at least one function of the device 202t. For example, the controller 208t is configured to control the operation of the heater 204t. Such control of the operation of the heater 204t may be accomplished by the controller toggling the electrical connection of the rechargeable battery 205t to the heater 204t. For example, the controller 208t is configured to control the heater 204t in response to a user depressing the button 212t. Depressing the button 212t may cause the controller to allow a voltage (from the rechargeable battery 205t) to be applied to the heater 204t (so as to cause the heating element 223t to be heated).

The controller is also configured to control the LEDs 211t in response to (e.g., a detected) a condition of the device 201t or the consumable 202t. For example, the controller may control the LEDs to indicate whether the device 201t is in an on state or an off state (e.g., one or more of the LEDs may be illuminated by the controller when the device is in an on state).

The device 201t comprises a further input means (i.e., in addition to the button 212t) in the form of a puff sensor 225t. The puff sensor 225t is configured to detect a user drawing (i.e., inhaling) at the downstream end 218t of the consumable 202t. The puff sensor 225t may, for example, be in the form of a pressure sensor, flowmeter or a microphone. The puff sensor 225t is operatively connected to the controller 208t in the electronics cavity 224t, such that a signal from the puff sensor 225t, indicative of a puff state (i.e., drawing or not drawing), forms an input to the controller 208t (and can thus be responded to by the controller 208t).

Turning now to FIG. 63F, which is a perspective view of the system 200t with the stopper 227t engaged with the device 201t. Further, the stopper 227t is configured to close the cavity 222t defined in the cap 210t. In particular, the stopper 227t is configured to close opening 221t of the cap 210t when the consumable 202t is removed (e.g., disengaged or dislodged from the device 201t). Upon removal of the consumable 202t from the device 201t, the cavity 222t defined in the cap 210t may be vulnerable to entry of foreign objects. The stopper 227t is configured to close (e.g., cover) the opening 221t of the cavity 222t to prevent entry of the foreign objects by engaging with the cap 210t, and in-turn the device 201t. The stopper 227t is configured to provide ingress protection to components (e.g., heating element 223t) of the device 201t that may be accessible through the opening 221t of the cap 210t. Additionally, the stopper 227t is configured to conceal odor of generated due to burning of the consumable 222t, when the device 201t is not in use.

The stopper 227t may be defined with a projection 228t, as detailed in FIG. 64. The projection 228t may be extended along the longitudinal axis of the stopper 227t, to co-operate with the opening 221t defined in the cap 210t, as shown in FIG. 65. The projection 228t is engageable with the opening 221t, about which the cavity 222t in the cap 210t is defined. The opening 221t defined in the cap 210t is configured to receive at least one of the consumable 202t and the stopper 227t, in accordance with requirement of the user.

As shown in FIG. 64, the stopper 227t includes a head portion 232t having a lateral surface 233t. A portion of the lateral surface 233t of the head portion 232t is configured as a visual indication portion 230t to indicate at least one of a brand, a category, a flavor, a numeral, a symbol, and the like corresponding to the HNB device 201t. In the illustrative embodiment, the visual indication portion 230t is a name of the product, which may be embossed on the lateral surface 233t of the stopper 227t. Also, the indication on the visual indication portion 231t may be formed by means such as, but not limited to, engraving, painting, stickering, and the like. Further, a tactile surface 231t is defined about (e.g., on at least one side) in at least a portion of the stopper 227t. The tactile surface 231t may assist in gripping the stopper 227t during operation (that is, to partially and/or completely remove the stopper 227t from the cap 210t). The tactile surface 231t may be at least one of a protrusion, a groove, a protuberance, and the like, which may be defined on the surface of the stopper 227t, to aid the user in gripping of the stopper 227t. The at least one visual indication 230t and the tactile surface 231t provides a tactile sense (that is, sense of touch and feel) to the user of the device 201t.

Referring now to FIG. 65, the stopper 227t is configured to engage with the opening 221t of the cap 210t to form an air-tight seal or hermetic seal. In the illustrated embodiment, an end of the projection 228t is defined with a threaded portion 229t, as seen in FIG. 64, which operably engages with the opening 221t defined in the cap 210t. Referring back to FIG. 64, the projection 228t may be extended from the head portion 232t in the form of shank (e.g., a cylindrical or conical extension). An end of the projection 228t may be defined with the threaded portion 229t. The threaded portion 229t of the projection 228t may restrain movement of the stopper 227t in at least one of a lateral direction and a longitudinal direction, thereby preventing inadvertent removal (that is, disengagement or dislodging) of the stopper 227t from the cap 210t. The projection 228t may alternatively be provisioned with at least one ridge, which may be defined on an outer periphery of the projection 228t. The at least one ridge (not visible in Figures) may be configured to engage with at least one notch of the notches 226t laterally disposed about the cavity 222t of the cap 210t. In this way, the projection 228t, and in-turn the stopper 227t, may be received by the opening 221t of the cavity 222t in at least one defined orientation. Also, this defined orientation of the stopper 227*t* may assist the user in insertion of the consumable 202*t* into the device 201*t*. Additionally, the stopper 227*t* may be removed from the device 201*t* by either torquing in a defined direction or by application of normal force along longitudinal direction of the device 201*t*, to expose the cavity 222*t* defined in the cap 210*t*.

In an illustrative embodiment, upon removal of the stopper 227*t* from the device 201*t*, the stopper is configured to engage with at least one of an airflow inlet [not shown in Figures] and a power input port [not shown in Figures] of the device 201*t*. In this way, the stopper 227*t* may be prevented from being inadvertently misplaced. Further, the stopper 227*t* may be configured to change airflow configuration into and/or through the device, when engaged with the airflow inlet of the device 201*t*. Additionally, the stopper 227*t* may be engaged with the power input port of the device 201*t*, to restrict concurrent operation of the heating element of the device 201*t* and the external power source. The restriction of concurrent operation of the heating element of the device 201*t* and the external power source may avoid malfunctioning of the device 201*t*.

In an exemplary embodiment, the stopper 227*t* may be formed from a deformable material, which may be selected from at least one of rubber, silicone, leather and deformable polymer. Meanwhile, the stopper 227*t* may also be made of hard and rugged materials so as to be retrofittable with the device 201*t*, based on requirement of the user.

Nineteenth Mode: A Smoking Substitute System Comprising a Wire Harness Member

Aspects and embodiments of the nineteenth mode of the present disclosure will now be discussed with reference to the accompanying figures. Further aspects and embodiments will be apparent to those skilled in the art. All documents mentioned in this text are incorporated herein by reference.

FIG. 66A is a schematic providing a general overview of a smoking substitute system 100*u*. The system 100*u* includes a substitute smoking device 101*u* and an aerosol-forming article in the form of a consumable 102*u*, which comprises an aerosol former 103*u*. The system is configured to vaporize the aerosol former by heating the aerosol former 103*u* (so as to form a vapor/aerosol for inhalation by a user).

In the illustrated system, the heater 104*u* forms part of the consumable 102*u* and is configured to heat the aerosol former 103*u*. In this variation, the heater 104*u* is electrically connectable to the power source 105*u*, for example, when the consumable 102*u* is engaged with the device 101*u*. Heat from the heater 104*u* vaporizes the aerosol former 103*u* to produce a vapor. The vapor subsequently condenses to form an aerosol, which is ultimately inhaled by the user.

The system 100*u* further comprises a power source 105*u* that forms part of the device 101*u*. In other embodiments the power source 105*u* may be external to (but connectable to) the device 101*u*. The power source 105*u* is electrically connectable to the heater 104*u* such that it is able to supply power to the heater 104*u* (i.e., for the purpose of heating the aerosol former 103*u*). Thus, control of the electrical connection of the power source 105*u* to the heater 104*u* provides control of the state of the heater 104*u*. The power source 105*u* may be a power store, for example a battery or rechargeable battery (e.g., a lithium-ion battery).

The system 100*u* further comprises an I/O module comprising a connector 106*u* (e.g., in the form of a USB port, Micro USB port, USB-C port, etc.). The connector 106*u* is configured for connection to an external source of electrical power, e.g., a mains electrical supply outlet. The connector 106*u* may be used in substitution for the power source 105*u*.

That is the connector 106*u* may be electrically connectable to the heater 104*u* so as to supply electricity to the heater 104*u*. In such embodiments, the device may not include a power source, and the power source of the system may instead comprise the connector 106*u* and an external source of electrical power (to which the connector 106*u* provides electrical connection).

In some embodiments, the connector 106*u* may be used to charge and recharge the power source 105*u* where the power source 105*u* includes a rechargeable battery.

The system 100*u* also comprises a user interface (UI) 107*u*. Although not shown, the UI 107*u* may include input means to receive commands from a user. The input means of the UI 107*u* allows the user to control at least one aspect of the operation of the system 100*u*. The input means may, for example, be in the form of a button, touchscreen, switch, microphone, etc.

The UI 107*u* also comprises output means to convey information to the user. The output means may, for example, comprise lights (e.g., LEDs), a display screen, speaker, vibration generator, etc.

The system 100*u* further comprises a controller 108*u* that is configured to control at least one function of the device 101*u*. In the illustrated embodiment, the controller 108*u* is a component of the device 101*u*, but in other embodiments may be separate from (but connectable to) the device 101*u*. The controller 108*u* is configured to control the operation of the heater 104*u* and, for example, may be configured to control the voltage applied from the power source 105*u* to the heater 104*u*. The controller 108*u* may be configured to toggle the supply of power to the heater 104*u* between an on state, in which the full output voltage of the power source 105*u* is applied to the heater 104*u*, and an off state, in which the no voltage is applied to the heater 104*u*.

Although not shown, the system 100*u* may also comprise a voltage regulator to regulate the output voltage from the power source 105*u* to form a regulated voltage. The regulated voltage may then be applied to the heater 104*u*.

In addition to being connected to the heater 104*u*, the controller 108*u* is operatively connected to the UI 107*u*. Thus, the controller 108*u* may receive an input signal from the input means of the UI 107*u*.

Similarly, the controller 108*u* may transmit output signals to the UI 107*u*. In response, the output means of the UI 107*u* may convey information, based on the output signals, to a user. The controller also comprises a memory 109*u*, which is a non-volatile memory. The memory 109*u* includes instructions, which, when implemented, cause the controller to perform certain tasks or steps of a method.

FIG. 66B is a schematic showing a variation of the system 100*u* of FIG. 66A. In the system 100*u*' of FIG. 66B, the heater 104*u* forms part of the device 101*u*, rather than the consumable 102*u*. In this variation, the heater 104*u* is electrically connected to the power source 105*u*.

The systems 100*u*, 100*u*' of FIG. 66A and FIG. 66B may be implemented as one of two broad categories of system, each in accordance with the present disclosure: a heated tobacco (HT) system or an e-cigarette system. A description of each category of system follows.

FIG. 67A and FIG. 67B illustrate a heated-tobacco (HT) smoking substitute system 200*u*. The system 200*u* is an example of the systems 100*u*, 100*u*' described in relation to FIG. 66A or FIG. 66B. System 200*u* includes an HT device 201*u* and an HT consumable 202*u*. The description of FIG. 66A and FIG. 66B above is applicable to the system 200*u* of FIG. 67A and FIG. 67B, and will thus not be repeated.

The device 201u and the consumable 202u are configured such that the consumable 202u can be engaged with the device 201u. FIG. 67A shows the device 201u and the consumable 202u in an engaged state, whilst FIG. 67B shows the device 201u and the consumable 202u in a disengaged state.

The device 201u comprises a housing 209u (also referred to as body herein) and cap 210u. In use the cap 210u is engaged at an end of the housing 209u. Although not apparent from the figures, the cap 210u is moveable relative to the housing 209u. In particular, the cap 210u is slidable and can slide along a longitudinal axis of the body 209u.

The device 201u comprises an output means (forming part of the UI of the device 201u) in the form of a plurality of light-emitting diodes (LEDs) 211u arranged linearly along the longitudinal axis of the device 201u and on an outer surface of the housing 209u of the device 201u. A button 212u is also arranged on an outer surface of the housing 209u of the device 201u and is axially spaced (i.e., along the longitudinal axis) from the plurality of LEDs 211u.

FIG. 67C shows a detailed section view of the consumable 202u of the system 200u. The consumable 202u generally resembles a cigarette. In that respect, the consumable 202u has a generally cylindrical form with a diameter of 7 mm and an axial length of 70 mm. The consumable 202u comprises an aerosol forming substrate 213u, a terminal filter element 214u, an upstream filter element 215u and a spacer element 216u. In other embodiments, the consumable may further comprise a cooling element. A cooling element may exchange heat with vapor that is formed by the aerosol-forming substrate 213u in order to cool the vapor so as to facilitate condensation of the vapor.

The aerosol-forming substrate 213u is substantially cylindrical and is located at an upstream end 217u of the consumable 202u, and comprises the aerosol former of the system 200u. In that respect, the aerosol forming substrate 213u is configured to be heated by the device 201u to release a vapor. The released vapor is subsequently entrained in an airflow flowing through the aerosol-forming substrate 213u. The airflow is produced by the action of the user drawing on a downstream 218u (i.e., terminal or mouth) end of the consumable 202u.

In the present embodiment, the aerosol forming substrate 213u comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213u may comprise a gathered sheet of homogenized (e.g., paper/slurry recon) tobacco or gathered shreds/strips formed from such a sheet.

In order to generate an aerosol, the aerosol forming substrate 213u comprises at least one volatile compound that is intended to be vaporized/aerosolized and that may provide the user with a recreational and/or medicinal effect when inhaled. The aerosol-forming substrate 213u may further comprise one or more additives. For example, such additives may be in the form of humectants (e.g., propylene glycol and/or vegetable glycerin), flavorants, fillers, aqueous/non-aqueous solvents and/or binders.

The terminal filter element 214u is also substantially cylindrical, and is located downstream of the aerosol forming substrate 213u at the downstream end 218u of the consumable 202u. The terminal filter element 214u is in the form of a hollow bore filter element having a bore 219u (e.g., for airflow) formed therethrough. The diameter of the bore 219u is 2 mm. The terminal filter element 214u is formed of a porous (e.g., monoacetate) filter material. As set forth above, the downstream end 218u of the consumable 202u (i.e., where the terminal filter 214u is located) forms a mouthpiece portion of the consumable 202u upon which the user draws. Airflow is drawn from the upstream end 217u, thorough the components of the consumable 202u, and out of the downstream end 218u. The airflow is driven by the user drawing on the downstream end 218u (i.e., the mouthpiece portion) of the consumable 202u.

The upstream filter element 215u is located axially adjacent to the aerosol-forming substrate 213u, between the aerosol-forming substrate 213u and the terminal filter element 214u. Like the terminal filter 214u, the upstream filter element 215u is in the form of a hollow bore filter element, such that it has a bore 220u extending axially therethrough. In this way, the upstream filter 215u may act as an airflow restrictor. The upstream filter element 215u is formed of a porous (e.g., monoacetate) filter material. The bore 220u of the upstream filter element 215u has a larger diameter (3 mm) than the terminal filter element 214u.

The spacer 216u is in the form of a cardboard tube, which defines a cavity or chamber between the upstream filter element 215u and the terminal filter element 214u. The spacer 216u acts to allow both cooling and mixing of the vapor/aerosol from the aerosol-forming substrate 213u. The spacer has an external diameter of 7 mm and an axial length of 14 mm.

Although not apparent from the figure, the aerosol-forming substrate 213u, upstream filter 215u and spacer 216u are circumscribed by a paper wrapping layer. The terminal filter 214u is circumscribed by a tipping layer that also circumscribes a portion of the paper wrapping layer (so as to connect the terminal filter 214u to the remaining components of the consumable 202u). The upstream filter 215u and terminal filter 214u are circumscribed by further wrapping layers in the form of plug wraps.

Returning now to the device 201u, FIG. 67D illustrates a detailed view of the end of the device 201u that is configured to engage with the consumable 202u. The cap 210u of the device 201u includes an opening 221u to an internal cavity 222u (more apparent from FIG. 67D) defined by the cap 210u. The opening 221u and the cavity 222u are formed so as to receive at least a portion of the consumable 202u. During engagement of the consumable 202u with the device 201u, a portion of the consumable 202u is received through the opening 221u and into the cavity 222u. After engagement (see FIG. 67B), the downstream end 218u of the consumable 202u protrudes from the opening 221u and thus also protrudes from the device 201u. The opening 221u includes laterally disposed notches 226u. When a consumable 202u is received in the opening 221u, these notches 226u remain open and could, for example, be used for retaining a cover in order to cover the end of the device 201u.

FIG. 67E shows a cross section through a central longitudinal plane through the device 201u. The device 201u is shown with the consumable 202u engaged therewith.

The device 201u comprises a heater 204u comprising heating element 223u. The heater 204u forms part of the housing 209u of the device 201u and is rigidly mounted to the housing 209u. In the illustrated embodiment, the heater 204u is a rod heater with a heating element 223u having a circular transverse profile. In other embodiments the heater may be in the form of a blade heater (e.g., heating element with a rectangular transverse profile) or a tube heater (e.g., heating element with a tubular form).

The heating element 223u of the heater 204u projects from an internal base of the cavity 222u along a longitudinal axis towards the opening 221u. As is apparent from the figure, the length (i.e., along the longitudinal axis) of the heating element is less than a depth of the cavity 222u. In this way, the heating element 223u does not protrude from or extend beyond the opening 221u.

When the consumable 202u is received in the cavity 222u (as is shown in FIG. 67E), the heating element 223u penetrates the aerosol-forming substrate 213u of the consumable 202u. In particular, the heating element 223u extends for nearly the entire axial length of the aerosol-forming substrate 213u when inserted therein. Thus, when the heater 204u is activated, heat is transferred radially from an outer circumferential surface the heating element 223u to the aerosol-forming substrate 213u.

The device 201u further comprises an electronics cavity 224u. A power source, in the form of a rechargeable battery 205u (a lithium-ion battery), is located in electronics cavity 224u.

The device 201u includes a connector (i.e., forming part of an IO module of the device 201u) in the form of a USB port 206u. The connector may alternatively be, for example, a micro-USB port or a USB-C port for examples. The USB port 206u may be used to recharge the rechargeable battery 205u.

The device 201u includes a controller 208u located in the electronics cavity 224u. The controller comprises a microcontroller mounted on a printed circuit board (PCB). The USB port 206u is also connected to the controller 208u (i.e., connected to the PCB and microcontroller).

The controller 208u is configured to control at least one function of the device 202u. For example, the controller 208u is configured to control the operation of the heater 204u. Such control of the operation of the heater 204u may be accomplished by the controller toggling the electrical connection of the rechargeable battery 205u to the heater 204u. For example, the controller 208u is configured to control the heater 204u in response to a user depressing the button 212u. Depressing the button 212u may cause the controller to allow a voltage (from the rechargeable battery 205u) to be applied to the heater 204u (so as to cause the heating element 223u to be heated).

The controller is also configured to control the LEDs 211u in response to (e.g., a detected) a condition of the device 201u or the consumable 202u. For example, the controller may control the LEDs to indicate whether the device 201u is in an on state or an off state (e.g., one or more of the LEDs may be illuminated by the controller when the device is in an on state).

The device 201u comprises a further input means (i.e., in addition to the button 212u) in the form of a puff sensor 225u. The puff sensor 225u is configured to detect a user drawing (i.e., inhaling) at the downstream end 218u of the consumable 202u. The puff sensor 225u may, for example, be in the form of a pressure sensor, flowmeter or a microphone. The puff sensor 225u is operatively connected to the controller 208u in the electronics cavity 224u, such that a signal from the puff sensor 225u, indicative of a puff state (i.e., drawing or not drawing), forms an input to the controller 208u (and can thus be responded to by the controller 208u).

Whilst not shown in FIG. 67E, the puff sensor 225u is supported in the device 201u by a wire harness member 227u. This wire harness member 227u is shown in FIG. 67F, which is a perspective view of the wire harness member 227u. The wire harness member 227u is adapted to accommodate one or more wires 230u (see FIG. 67G), extending between the heating element 223u and the power source 205u of the device 201u. The wire harness member 227u comprises a body 228u and four apertures 229u (in the form of holes) extending through the body 228u from an in use upper surface 235u to an opposing in use lower surface 236u of the body 228u. The wire harness member 227u further comprises four corresponding slits 231u. Each slit 231u extends from a corresponding aperture 229u to a first edge 237u of the body 228u (that forms part of the periphery of the body 228u). As will be described further with respect to FIG. 67G, the apertures 229u are configured to receive wires 230u of the device 201u.

In an embodiment, the shape of the body 228u may be configured to correspond to the shape of the inner surface of the housing 209u of the device 201u.

The aperture 229u are spaced from one another and are arranged along a substantially straight line that is parallel to, but spaced from, the first edge 237u. Thus, all of the aperture 229u are spaced from the first edge 237u by the same distance. As a result, the slits 231u are all the same length (i.e., the distance from one end of the slit 231u at the corresponding aperture 229u to the opposing end at the first edge 127u). The spacing of the apertures 229u means that there is a separating wall (i.e., portion of the body 228u) between each of the apertures 229u. This separation of the aperture 229u may facilitate separation of wires received through the apertures 229u (i.e., so as to avoid contact between wires).

Although not immediately apparent from the figure, each aperture 229u and slit 231u corresponding slit 231uu comprises a frangible membrane 232u extending thereacross. This membrane 232u is in the form of a thinner portion of the body 228u that is configured to break (i.e., with minimal resistance) when a wire is inserted into the aperture 229u via the slit 231u corresponding slit 231uu. Thus, because in FIG. 67F no wire has been received in the aperture 229u, the frangible membrane 232u is shown intact. Each membrane 232u is elastic (e.g., formed of and elastic material) such that they each deform and break as a wire is being received into the aperture 229u and then generally return to their (approximate) original shape once the wire is received in the aperture 232u (except, of course, for the break or split). Thus, the membranes 232u are configured so as to surround respective wires once received in their corresponding apertures 229u. This can create a hermetic seal extending across the body 229u.

In addition to the first edge 237u, the body 228u of the wire harness member 228u comprises a second edge 238u spaced from and opposing the first edge 237u. The body 228u also comprises first 239u and second 240u rounded ends that extend between the first 237u and second 238u edges. The first 239u and second 240u ends, and first 237u and second 238u edges define the periphery of the body 228u. A downwardly projecting lip 241u extends along the periphery and, in particular, along the first 239u and second 240u ends, and the second edge 238u (i.e., not along the first edge 237u). This lip 241u defines a thicker portion of the body 228u at the periphery and is thicker than a central portion of the body 228u. The lip 241u comprises an outwardly projecting rib 242u, which extends for the length of the lip 241u (about the periphery of the body 228u). This rib 242u locates in a corresponding groove formed in an internal wall of the housing 209u and helps to form a seal between the wire harness member 228u and the housing 209u.

The body 228u includes two of cut-outs 234u (from an otherwise generally obround shape) formed in the first edge 237u. The cut-outs are spaced either side of the apertures 229u and slots 231u and are formed so as to complement the internal shape of the housing 209u (i.e., to ensure a close fit between the wire harness member 227u and the housing 209u). The body 228u also comprises a recess 233u configured to accommodate (and support) the puff sensor 225u.

FIG. 67G is an exploded view of the device 201u with wire harness member 227u installed therein. The wire harness member 227u is located between the heater 204u and the power source 205u. The body 228u is formed of an elastomeric material, such as a silicone material, and is formed as a unitary structure. When received in the housing 209u, the body 228u is under compression, which helps to form a seal between the housing 209u and the body 228u. Because the body 228u is formed of a thermally insulative material, this seal helps to prevent heat transfer between the heater 204u and the power source 205u (and other sensitive electronics located in the electronics cavity 224u).

As is apparent from FIG. 67G and FIG. 67H, the wire harness member 227u supports wires 230u (in the apertures 229u) extending between the heater 204u and the power source 205u. In particular, the apertures 229u support the wires 230u so as to be spaced from both the housing 209u and each other. This can help to prevent short circuits forming in the device 201u. Such short circuits are further avoided by the fact that the body 228u is formed of an electrically insulative material. Further, spacing the wires 230u from the housing 209u, can help to prevent heat transfer between the housing 209u (which may receive heat from the heater 204u) and the wires 230u. The apertures 229u and slots 231u provide a simple way of assembling the wires 230u in this way.

The heater 204u is positioned above the wire harness member 227u and the power source 205u is positioned below the wire harness member 227u. Further, the wire harness member 227u is positioned such that the first edge 237u is at a front face of the device 201u.

FIG. 68A and FIG. 68B illustrate an e-cigarette smoking substitute system 300u. The system 300u is an example of the systems 100u, 100u' of FIG. 66A and FIG. 66B and comprises an e-cigarette device 301u and an e-cigarette consumable 302u. The description of FIG. 66A and FIG. 66B above is applicable to the system of FIG. 68A and FIG. 68B, and will not be repeated.

The device 301u and the consumable 302u are configured such that the consumable 302u can be engaged with the device 301u. FIG. 68A shows the device 301u and the consumable 302u in an engaged state, whilst FIG. 68B shows the device 301u and the consumable 302u in a disengaged state. During engagement a portion of the consumable 302u is received in a cavity 322u of the device 301u. The consumable 302u is retained in the device 301u via an interference fit (although in other embodiments, the device and consumable could be engaged by screwing one onto (or onto) the other, through a bayonet fitting, or by way of a snap engagement mechanism).

The consumable 302u includes a tank 327u. The tank 327u defines a reservoir for the storage of an aerosol-former, which in this embodiment, is in the form of e-liquid.

In this present embodiment, the consumable 302u is a "single-use" consumable. That is, upon exhausting the e-liquid in the tank 327u, the intention is that the user disposes of the whole consumable 302u. In other embodiments, the e-liquid (i.e., aerosol former) may be the only part of the system that is truly "single-use". In such embodiments, the tank may be refillable with e-liquid or the e-liquid may be stored in a non-consumable component of the system. For example, the e-liquid may be stored in a tank located in the device or stored in another component that is itself not single-use (e.g., a refillable cartomizer).

In the illustrated system 300u, a heater 304u is located in the consumable 302u and is configured to heat and vaporize the e-liquid (stored in the tank 327u). Although not shown, the heater 304u comprises a porous wick and a resistive heating element. The porous wick conveys e-liquid from the tank 327u to the heating element. The heating element is a heating filament that is helically wound around a portion of the porous wick, such that when the heating element is heated (e.g., by the action of electrical current passing through the heating element), heat is transferred from the heating element to the e-liquid conveyed by the wick. This transfer of heat vaporizes the e-liquid and the resultant vapor is entrained in an airflow passing through the consumable 302u (i.e., driven by a user drawing on a downstream end 318u of the consumable 302u). Between the vaporization point at the coil and the downstream end 318u (i.e., the mouth end), the vapor condenses into an aerosol, and is subsequently inhaled by the user.

Like the previously described embodiment, the device 301u comprises a power source in the form of a rechargeable battery (not shown) and a connector in the form of a USB port (not shown). The device 301u further comprises controller (also not shown). The rechargeable battery, connector and controller are similar (and operate in a similar manner) to the corresponding components of the embodiment described above with respect to FIG. 67A to FIG. 67H.

The consumable 302u includes a pair of heater electrical contacts 328u disposed on a device-facing end surface of the consumable 302u. The heater electrical contacts 328u are electrically connected to the heater 304u in the consumable 302u, such that a voltage applied across the heater electrical contacts 328u generally corresponds to a voltage applied across the resistive heating element of the heater 304u.

Whilst the interior of the device 301u is not shown, it should be appreciated that the wire harnessing member as described above could form part of this device 301u. When the consumable 302u is engaged with the device 301u, the heater electrical contacts 328u are brought into electrical contact with corresponding device electrical contacts (not shown) on the device 301u. The device electrical contacts are electrically connected (directly or indirectly) to the rechargeable battery (which may be via wires that pass through a wire harness member (such as that described above). The controller may thus be configured to control the voltage applied across the device electrical contacts from the rechargeable battery. By controlling the voltage applied across the device electrical contacts, the voltage applied to the heater 304u is correspondingly controlled.

The device 301u includes an output means (forming part of the UI of the system 300u) in the form of a single light-emitting diode ("LED") 311. The LED 311u is operatively connected to the controller, such that controller can control the illumination of the LED 311u. The controller is configured to illuminate the LED when then the heater 304u is active.

The device 301u also includes an input means in the form of a puff sensor (not shown). The puff sensor is the same as that described above with respect to the embodiment shown in FIG. 67A to FIG. 67H.

Twentieth Mode: A Smoking Substitute Device Having a Heat Dissipation Element in the Housing Aspects and embodiments of the twentieth mode of the present disclosure will now be discussed with reference to the accompanying figures. Further aspects and embodiments will be apparent to those skilled in the art. All documents mentioned in this text are incorporated herein by reference.

FIG. 69 is a schematic providing a general overview of a smoking substitute system 100v. The system 100v includes a substitute smoking device 101v and an aerosol-forming article in the form of a consumable 102v, which comprises an aerosol former 103v. The system is configured to vaporize the aerosol former by heating the aerosol former 103v (so as to form a vapor/aerosol for inhalation by a user).

In the illustrated system, the heater 104v forms part of the device 101v and is configured to heat the aerosol former 103v. In this variation, the heater 104v is electrically connected to the power source 105v.

Heat from the heater 104v vaporizes the aerosol former 103v to produce a vapor. The vapor subsequently condenses to form an aerosol, which is ultimately inhaled by the user.

The system 100v further comprises a power source 105v that forms part of the device 101v. In other embodiments the power source 105v may be external to (but connectable to) the device 101v. The power source 105v is electrically connected to the heater 104v such that it is able to supply power to the heater 104v (i.e., for the purpose of heating the aerosol former 103v). Thus, control of the electrical connection of the power source 105v to the heater 104v provides control of the state of the heater 104v. The power source 105v may be a power store, for example a battery or rechargeable battery (e.g., a lithium-ion battery).

The system 100v further comprises a heat dissipation element 127v. The heat dissipation element dissipates heat to prevent localized heating.

The system 100v further comprises an I/O module comprising a connector 106v (e.g., in the form of a USB port, Micro USB port, USB-C port, etc.). The connector 106v is configured for connection to an external source of electrical power, e.g., a mains electrical supply outlet. The connector 106v may be used in substitution for the power source 105v. That is the connector 106v may be electrically connectable to the heater 104v so as to supply electricity to the heater 104v. In such embodiments, the device may not include a power source, and the power source of the system may instead comprise the connector 106v and an external source of electrical power (to which the connector 106v provides electrical connection).

In some embodiments, the connector 106v may be used to charge and recharge the power source 105v where the power source 105v includes a rechargeable battery.

The system 100v also comprises a user interface (UI) 107v. Although not shown, the UI 107v may include input means to receive commands from a user. The input means of the UI 107v allows the user to control at least one aspect of the operation of the system 100v. The input means may, for example, be in the form of a button, touchscreen, switch, microphone, etc.

The UI 107v also comprises output means to convey information to the user. The output means may, for example, comprise lights (e.g., LEDs), a display screen, speaker, vibration generator, etc.

The system 100v further comprises a controller 108v that is configured to control at least one function of the device 101v. In the illustrated embodiment, the controller 108v is a component of the device 101v, but in other embodiments may be separate from (but connectable to) the device 101v.

The controller 108v is configured to control the operation of the heater 104v and, for example, may be configured to control the voltage applied from the power source 105v to the heater 104v. The controller 108v may be configured to toggle the supply of power to the heater 104v between an on state, in which the full output voltage of the power source 105v is applied to the heater 104v, and an off state, in which the no voltage is applied to the heater 104v.

Although not shown, the system 100v may also comprise a voltage regulator to regulate the output voltage from the power source 105v to form a regulated voltage. The regulated voltage may then be applied to the heater 104v.

In addition to being connected to the heater 104v, the controller 108v is operatively connected to the UI 107v. Thus, the controller 108v may receive an input signal from the input means of the UI 107v. Similarly, the controller 108v may transmit output signals to the UI 107v. In response, the output means of the UI 107v may convey information, based on the output signals, to a user. The controller also comprises a memory 109v, which is a non-volatile memory. The memory 109v includes instructions, which, when implemented, cause the controller to perform certain tasks or steps of a method.

FIG. 70A and FIG. 70B illustrate a heated-tobacco (HT) smoking substitute system 200v. The system 200v is an example of the system 100v described in relation to FIG. 69. System 200v includes an HT device 201v and an HT consumable 202v. The description of FIG. 69 above is applicable to the system 200v of FIG. 70A and FIG. 70B, and will thus not be repeated.

The device 201v and the consumable 202v are configured such that the consumable 202v can be engaged with the device 201v. FIG. 70A shows the device 201v and the consumable 202v in an engaged state, whilst FIG. 70B shows the device 201v and the consumable 202v in a disengaged state.

The device 201v comprises a housing. The housing defines an outer surface 228v of the device 201v. The housing includes a body 209v and cap 210v. In use the cap 210v is engaged at an end of the body 209v. Although not apparent from the figures, the cap 210v is moveable relative to the body 209v. In particular, the cap 210v is slidable and can slide along a longitudinal axis of the body 209v.

The device 201v comprises an output means (forming part of the UI of the device 201v) in the form of a plurality of light-emitting diodes (LEDs) 211v arranged linearly along the longitudinal axis of the device 201v and on an outer surface of the body 209v of the device 201v. A button 212v is also arranged on an outer surface of the body 209v of the device 201v and is axially spaced (i.e., along the longitudinal axis) from the plurality of LEDs 211v.

FIG. 70C show a detailed section view of the consumable 202v of the system 200v. The consumable 202v generally resembles a cigarette. In that respect, the consumable 202v has a generally cylindrical form with a diameter of 7 mm and an axial length of 70 mm. The consumable 202v comprises an aerosol forming substrate 213v, a terminal filter element 214v, an upstream filter element 215v and a spacer element 216v. In other embodiments, the consumable may further comprise a cooling element. A cooling element may exchange heat with vapor that is formed by the aerosol-forming substrate 213v in order to cool the vapor so as to facilitate condensation of the vapor.

The aerosol-forming substrate 213v is substantially cylindrical and is located at an upstream end 217v of the consumable 202v, and comprises the aerosol former of the system 200v. In that respect, the aerosol forming substrate 213ν is configured to be heated by the device 201ν to release a vapor. The released vapor is subsequently entrained in an airflow flowing through the aerosol-forming substrate 213ν. The airflow is produced by the action of the user drawing on a downstream 218ν (i.e., terminal or mouth) end of the consumable 202ν.

In the present embodiment, the aerosol forming substrate 213ν comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213ν may comprise a gathered sheet of homogenized (e.g., paper/slurry recon) tobacco or gathered shreds/strips formed from such a sheet.

In order to generate an aerosol, the aerosol forming substrate 213ν comprises at least one volatile compound that is intended to be vaporized/aerosolized and that may provide the user with a recreational and/or medicinal effect when inhaled. The aerosol-forming substrate 213ν may further comprise one or more additives. For example, such additives may be in the form of humectants (e.g., propylene glycol and/or vegetable glycerin), flavorants, fillers, aqueous/non-aqueous solvents and/or binders.

The terminal filter element 214ν is also substantially cylindrical, and is located downstream of the aerosol forming substrate 213ν at the downstream end 218ν of the consumable 202ν. The terminal filter element 214ν is in the form of a hollow bore filter element having a bore 219ν (e.g., for airflow) formed therethrough. The diameter of the bore 219ν is 2 mm. The terminal filter element 214ν is formed of a porous (e.g., monoacetate) filter material. As set forth above, the downstream end 218ν of the consumable 202ν (i.e., where the terminal filter 214ν is located) forms a mouthpiece portion of the consumable 202ν upon which the user draws. Airflow is drawn from the upstream end 217ν, thorough the components of the consumable 202ν, and out of the downstream end 218ν. The airflow is driven by the user drawing on the downstream end 218ν (i.e., the mouthpiece portion) of the consumable 202ν.

The upstream filter element 215ν is located axially adjacent to the aerosol-forming substrate 213ν, between the aerosol-forming substrate 213ν and the terminal filter element 214ν. Like the terminal filter 214ν, the upstream filter element 215ν is in the form of a hollow bore filter element, such that it has a bore 220ν extending axially therethrough. In this way, the upstream filter 215ν may act as an airflow restrictor. The upstream filter element 215ν is formed of a porous (e.g., monoacetate) filter material. The bore 220ν of the upstream filter element 215ν has a larger diameter (3 mm) than the terminal filter element 214ν.

The spacer 216ν is in the form of a cardboard tube, which defines a cavity or chamber between the upstream filter element 215ν and the terminal filter element 214ν. The spacer 216ν acts to allow both cooling and mixing of the vapor/aerosol from the aerosol-forming substrate 213ν. The spacer has an external diameter of 7 mm and an axial length of 14 mm.

Although not apparent from the figure, the aerosol-forming substrate 213ν, upstream filter 215ν and spacer 216ν are circumscribed by a paper wrapping layer. The terminal filter 214ν is circumscribed by a tipping layer that also circumscribes a portion of the paper wrapping layer (so as to connect the terminal filter 214ν to the remaining components of the consumable 202ν). The upstream filter 215ν and terminal filter 214ν are circumscribed by further wrapping layers in the form of plug wraps.

Returning now to the device 201ν, FIG. 70D illustrates a detailed view of the end of the device 201ν that is configured to engage with the consumable 202ν. The cap 210ν of the device 201ν includes an opening 221ν to an internal cavity 222ν (more apparent from FIG. 70D) defined by the cap 210ν. The opening 221ν and the cavity 222ν are formed so as to receive at least a portion of the consumable 202ν. During engagement of the consumable 202ν with the device 201ν, a portion of the consumable 202ν is received through the opening 221ν and into the cavity 222ν. After engagement (see FIG. 70B), the downstream end 218ν of the consumable 202ν protrudes from the opening 221ν and thus also protrudes from the device 201ν. The opening 221ν includes laterally disposed notches 226ν. When a consumable 202ν is received in the opening 221ν, these notches 226ν remain open and could, for example, be used for retaining a cover in order to cover the end of the device 201ν.

FIG. 70E shows a cross section through a central longitudinal plane through the device 201ν. The device 201ν is shown with the consumable 202ν engaged therewith.

The device 201ν comprises a heater 204ν comprising heating element 223ν. The heater 204ν forms part of the body 209ν of the device 201ν and is rigidly mounted to the body 209ν. In the illustrated embodiment, the heater 204ν is a rod heater with a heating element 223ν having a circular transverse profile. In other embodiments the heater may be in the form of a blade heater (e.g., heating element with a rectangular transverse profile) or a tube heater (e.g., heating element with a tubular form).

The heating element 223ν of the heater 204ν projects from an internal base of the cavity 222ν along a longitudinal axis towards the opening 221ν. As is apparent from the figure, the length (i.e., along the longitudinal axis) of the heating element is less than a depth of the cavity 222ν. In this way, the heating element 223ν does not protrude from or extend beyond the opening 221ν.

When the consumable 202ν is received in the cavity 222ν (as is shown in FIG. 70E), the heating element 223ν penetrates the aerosol-forming substrate 213ν of the consumable 202ν. In particular, the heating element 223ν extends for nearly the entire axial length of the aerosol-forming substrate 213ν when inserted therein. Thus, when the heater 204ν is activated, heat is transferred radially from an outer circumferential surface the heating element 223ν to the aerosol-forming substrate 213ν.

The device 201ν further comprises an electronics cavity 224ν. A power source, in the form of a rechargeable battery (a lithium-ion battery), is located in electronics cavity 224ν.

The device 201ν includes a connector (i.e., forming part of an IO module of the device 201ν) in the form of a USB port 206ν. The connector may alternatively be, for example, a micro-USB port or a USB-C port for examples. The USB port 206ν may be used to recharge the rechargeable battery 205ν.

The device 201ν includes a controller 208ν located in the electronics cavity 224ν. The controller comprises a microcontroller mounted on a printed circuit board (PCB). The USB port 206ν is also connected to the controller 208ν (i.e., connected to the PCB and microcontroller).

The controller 208ν is configured to control at least one function of the device 201ν. For example, the controller 208ν is configured to control the operation of the heater 204ν. Such control of the operation of the heater 204ν may be accomplished by the controller toggling the electrical connection of the rechargeable battery 205v to the heater 204v. For example, the controller 208v is configured to control the heater 204v in response to a user depressing the button 212v. Depressing the button 212v may cause the controller to allow a voltage (from the rechargeable battery 205v) to be applied to the heater 204v (so as to cause the heating element 223v to be heated).

The controller is also configured to control the LEDs 211v in response to (e.g., a detected) a condition of the device 201v or the consumable 202v. For example, the controller may control the LEDs to indicate whether the device 201v is in an on state or an off state (e.g., one or more of the LEDs may be illuminated by the controller when the device is in an on state).

The device 201v comprises a further input means (i.e., in addition to the button 212v) in the form of a puff sensor 225v. The puff sensor 225v is configured to detect a user drawing (i.e., inhaling) at the downstream end 218v of the consumable 202v. The puff sensor 225v may, for example, be in the form of a pressure sensor, flowmeter or a microphone. The puff sensor 225v is operatively connected to the controller 208v in the electronics cavity 224v, such that a signal from the puff sensor 225v, indicative of a puff state (i.e., drawing or not drawing), forms an input to the controller 208v (and can thus be responded to by the controller 208v).

The device 201v further includes first 227av and second 227bv heat dissipation elements for thermal management of the device 201v. These are shown in FIG. 70F and FIG. 70G. As will be described in more detail below, both of the heat dissipation elements 227v are disposed between the heating element 223v and an outer surface 228v of the body 209v (or housing). In this way, heat from the heating element 223v may absorb heat radiated from the heating element 228v and may distribute that heat over an increased area.

The first heat dissipation element 227av is shown in FIG. 70F. This figure shows a portion of the body 209v of the device 201v. This portion of the body 209v comprises a lower section 234v and an upper section 235v. The upper section 235v supports the heating element 223v and is tubular so as to define a cavity into which the heating element 223v projects. The lower section 234v comprises a panel 230v that (when the body is full assembled) defines part of the electronics cavity 224v of the device 201v. This panel 230v comprises an internal surface 229v, and the first heat dissipation element 227av is mounted to this internal surface 229v. The first heat dissipation element 227av may be attached to the internal surface 229v by an adhesive. Alternatively, the heat dissipation element 227av may be embedded in the housing during manufacturing of the housing and/or may be retained in the housing using a snap lock arrangement.

The first heat dissipation element 227av is in the form of a rectangular plate that is formed of copper. The positioning of the first heat dissipation element 227av, and its shape, mean that heat from the heating element 223v may be distributed across the panel 230v of the body 209v. This helps to avoid localized "hot spots" on the outer surface of the body 209v.

The second heat dissipation element 227bv is shown in FIG. 70G. FIG. 70G is a bottom view of the cap 210v of the device 201v. As is apparent from this view, the cap 210v comprises an internal tubular wall 236v that defines a cavity for receipt of a consumable 202v. The base of the internal wall 236v comprises an opening 237v, through which the heating element 223v projects when the cap 210v is engaged with the body 209v. The cap 210v further comprises two lateral sidewalls 231v, 232v spaced either side of the internal tubular wall 236v (and thus either side of the heating element 223v when the cap 210v is engaged with the body 209v).

The second heat dissipation element 227bv is mounted to an internal surface of one of the lateral sidewalls 231v. In this way, the second heat dissipation element 227bv is spaced from the internal tubular wall 236v by an air gap. When the cap 210v is mounted to the body 209v the second heat dissipation element 227bv is located directly laterally of the heating element 223v. Unlike the first heat dissipation element 227av, the second heat dissipation element 227bv is formed of aluminum. In particular, the aluminum of the second heat dissipation element 227bv is anodized so as have a dark appearance.

The cap 210v further comprises a metallic portion 238v defining part of the outer surface of the lateral sidewall 231v. Whilst not apparent from the figure, this metallic portion is in physical contact with the second heat dissipation element 227bv such that heat can be distributed from the heat dissipation element 227bv to the metallic portion 238v and can then be dissipated to the external environment.

Twenty-First Mode: A Heated Tobacco Device, Including a Multilayer Printed Circuit Board (PCB)

Aspects and embodiments of the twenty-first mode of the present disclosure will now be discussed with reference to the accompanying figures. Further aspects and embodiments will be apparent to those skilled in the art. All documents mentioned in this text are incorporated herein by reference.

FIG. 71 is a schematic providing a general overview of a smoking substitute system 100w. The system 100w includes a substitute smoking device 101w and an aerosol-forming article in the form of a consumable 102w, which comprises an aerosol former 103w.

The system is configured to vaporize the aerosol former by heating the aerosol former 103w (so as to form a vapor/aerosol for inhalation by a user).

In the illustrated system, the heater 104w forms part of the device 101w and is configured to heat the aerosol former 103w. Heat from the heater 104w vaporizes the aerosol former 103w to produce a vapor. The vapor subsequently condenses to form an aerosol, which is ultimately inhaled by the user. In one aspect, the heater 104w comprises a heating track (not shown) and a temperature sensing track (not shown) for measuring the temperature of the heater 104w.

The system 100w further comprises a power source 105w that forms part of the device 101w. In other embodiments the power source 105w may be external to (but connectable to) the device 101w. The power source 105w is electrically connectable to the heater 104w such that the power source 105w is able to supply power to the heater 104w (i.e., for the purpose of heating the aerosol former 103w). Thus, control of the electrical connection of the power source 105w to the heater 104w provides control of the state of the heater 104w. The power source 105w may be a power store, for example a battery or rechargeable battery (e.g., a lithium-ion battery).

The system 100w further comprises an I/O module comprising a connector 106w (e.g., in the form of a USB port, Micro USB port, USB-C port, etc.). The connector 106w is configured for connection to an external source of electrical power, e.g., a mains electrical supply outlet. The connector 106w may be used in substitution for the power source 105w. That is the connector 106w may be electrically connectable to the heater 104w so as to supply electricity to the heater 104w. In such embodiments, the device may not include a power source, and the power source of the system may instead comprise the connector 106w and an external source of electrical power (to which the connector 106w provides electrical connection).

In some embodiments, the connector 106w may be used to charge and recharge the power source 105w where the power source 105w includes a rechargeable battery.

The system 100w also comprises a user interface (UI) 107w. Although not shown, the UI 107w may include input means to receive commands from a user. The input means of the UI 107w allows the user to control at least one aspect of the operation of the system 100w. The input means may, for example, be in the form of a button, touchscreen, switch, microphone, etc.

The UI 107w also comprises output means to convey information to the user. The output means may, for example, comprise lights (e.g., LEDs), a display screen, speaker, vibration generator, etc.

The system 100w further comprises a controller 108w that is configured to control at least one function of the device 101w. In the illustrated embodiment, the controller 108w is a component of the device 101w, but in other embodiments may be separate from (but connectable to) the device 101w. The controller 108w is configured to control the operation of the heater 104w and, for example, may be configured to control the voltage applied from the power source 105w to the heater 104w. The controller 108w may be configured to toggle the supply of power to the heater 105w between an on state, in which the full output voltage of the power source 105w is applied to the heater 104w, and an off state, in which the no voltage is applied to the heater 104w.

The system 100w further comprises a printed circuit board (PCB) 110w with a power layer, a ground layer and top and bottom layers. The power and ground layers are sandwiched between the top and bottom layers.

Although not shown, the system 100w may also comprise a voltage regulator to regulate the output voltage from the power source 105w to form a regulated voltage. The regulated voltage may then be applied to the heater 104w. The power layer of the PCB 110w is connected to the output of the voltage regulator.

In addition to being connected to the heater 104w, the controller 108w is operatively connected to the UI.

Thus, the controller 108w may receive an input signal from the input means of the UI 107w. Similarly, the controller 108w may transmit output signals to the UI 107w. In response, the output means of the UI 107w may convey information, based on the output signals, to a user.

FIG. 72A and FIG. 72B illustrate a heated-tobacco (HT) smoking substitute system 200w. The system 200w is an example of the systems 100w described in relation to FIG. 71. System 200w includes an HT device 201w and an HT consumable 202w. The description of FIG. 71 above is applicable to the system 200w of FIG. 72A and FIG. 72B, and will thus not be repeated.

The device 201w and the consumable 202w are configured such that the consumable 202w can be engaged with the device 201w. FIG. 72A shows the device 201w and the consumable 202w in an engaged state, whilst FIG. 72B shows the device 201w and the consumable 202w in a disengaged state.

The device 201w comprises a body 209w and cap 210w. In use the cap 210w is engaged at an end of the body 209w. Although not apparent from the figures, the cap 210w is moveable relative to the body 209w. In particular, the cap 210w is slidable and can slide along a longitudinal axis of the body 209w. The device 201w comprises an output means (forming part of the UI of the device 201w) in the form of a plurality of light-emitting diodes (LEDs) 211w arranged linearly along the longitudinal axis of the device 201w and on an outer surface of the body 209w of the device 201w. A button 212w is also arranged on an outer surface of the body 209w of the device 201w and is axially spaced (i.e., along the longitudinal axis) from the plurality of LEDs 211w.

FIG. 72C show a detailed section view of the consumable 202w of the system 200w. The consumable 202w generally resembles a cigarette. In that respect, the consumable 202w has a generally cylindrical form with a diameter of 7 mm and an axial length of 70 mm. The consumable 202w comprises an aerosol forming substrate 213w, a terminal filter element 214w, an upstream filter element 215w and a spacer element 216w. In other embodiments, the consumable may further comprise a cooling element. A cooling element may exchange heat with vapor that is formed by the aerosol-forming substrate 213w in order to cool the vapor so as to facilitate condensation of the vapor.

The aerosol-forming substrate 213w is substantially cylindrical and is located at an upstream end 217w of the consumable 202w, and comprises the aerosol former of the system 200w. In that respect, the aerosol forming substrate 213w is configured to be heated by the device 201w to release a vapor. The released vapor is subsequently entrained in an airflow flowing through the aerosol-forming substrate 213w. The airflow is produced by the action of the user drawing on a downstream 218w (i.e., terminal or mouth end) of the consumable 202w.

In the present embodiment, the aerosol forming substrate 213w comprises tobacco material that may, for example, include any suitable parts of the tobacco plant (e.g., leaves, stems, roots, bark, seeds and flowers). The tobacco may comprise one or more of leaf tobacco, stem tobacco, tobacco powder, tobacco dust, tobacco derivatives, expanded tobacco, homogenized tobacco, shredded tobacco, extruded tobacco, cut rag tobacco and/or reconstituted tobacco (e.g., slurry recon or paper recon). For example, the aerosol-forming substrate 213w may comprise a gathered sheet of homogenized (e.g., paper/slurry recon) tobacco or gathered shreds/strips formed from such a sheet.

In order to generate an aerosol, the aerosol forming substrate 213w comprises at least one volatile compound that is intended to be vaporized/aerosolized and that may provide the user with a recreational and/or medicinal effect when inhaled. The aerosol-forming substrate 213w may further comprise one or more additives. For example, such additives may be in the form of humectants (e.g., propylene glycol and/or vegetable glycerin), flavorants, fillers, aqueous/non-aqueous solvents and/or binders.

The terminal filter element 214w is also substantially cylindrical, and is located downstream of the aerosol forming substrate 213w at the downstream end 218w of the consumable 202w. The terminal filter element 214w is in the form of a hollow bore filter element having a bore 219w (e.g., for airflow) formed therethrough. The diameter of the bore 219w is 2 mm. The terminal filter element 214w is formed of a porous (e.g., monoacetate) filter material. As set forth above, the downstream end 218w of the consumable 202w (i.e., where the terminal filter 214w is located) forms a mouthpiece portion of the consumable 202w upon which the user draws. Airflow is drawn from the upstream end 217w, thorough the components of the consumable 202w, and out of the downstream end 218w. The airflow is driven by the user drawing on the downstream end 218w (i.e., the mouthpiece portion) of the consumable 202w.

The upstream filter element 215w is located axially adjacent to the aerosol-forming substrate 213w, between the aerosol-forming substrate 213w and the terminal filter element 214w. Like the terminal filter 214w, the upstream filter element 215w is in the form of a hollow bore filter element, such that it has a bore 220w extending axially therethrough. In this way, the upstream filter 215w may act as an airflow restrictor. The upstream filter element 215w is formed of a porous (e.g., monoacetate) filter material. The bore 220w of the upstream filter element 214w has a larger diameter (3 mm) than the terminal filter element 214w.

The spacer 216w is in the form of a cardboard tube, which defines a cavity or chamber between the upstream filter element 215w and the terminal filter element 214w. The spacer 216w acts to allow both cooling and mixing of the vapor/aerosol from the aerosol-forming substrate 213w. The spacer has an external diameter of 7 mm and an axial length of 14 mm.

Although not apparent from the figure, the aerosol-forming substrate 213w, upstream filter 215w and spacer 216w are circumscribed by a paper wrapping layer. The terminal filter 214w is circumscribed by a tipping layer that also circumscribes a portion of the paper wrapping layer (so as to connect the terminal filter 214w to the remaining components of the consumable 202w). The upstream filter 215w and terminal filter 214w are circumscribed by further wrapping layers in the form of plug wraps.

Returning now to the device 201w, FIG. 72D illustrates a detailed view of the end of the device 201w that is configured to engage with the consumable 202w. The cap 210w of the device 201w includes an opening 221w to an internal cavity 222w (more apparent from FIG. 72D) defined by the cap 210w. The opening 221w and the cavity 222w are formed so as to receive at least a portion of the consumable 202w. During engagement of the consumable 202w with the device 201w, a portion of the consumable 202w is received through the opening 221w and into the cavity 222w. After engagement (see FIG. 72B), the downstream end 218w of the consumable 202w protrudes from the opening 221w and thus protrudes also from the device 201w. The opening 221w includes laterally disposed notches 226w. When a consumable 202w is received in the opening 221w, these notches 226w remain open and could, for example, be used for retaining a cover to cover the end of the device 201w.

FIG. 72E shows a cross section through a central longitudinal plane through the device 201w. The device 201w is shown with the consumable 202w engaged therewith.

The device 201w comprises a heater 204w comprising heating element 223w. The heater 204w forms part of the body 209w of the device 201w and is rigidly mounted to the body 209w. In the illustrated embodiment, the heater 204w is a rod heater with a heating element 223w having a circular transverse profile. In other embodiments the heater may be in the form of a blade heater (e.g., heating element with a rectangular transverse profile) or a tube heater (e.g., heating element with a tubular form).

The heating element 223w of the heater 204w projects from an internal base of the cavity 222w along a longitudinal axis towards the opening 221w. As is apparent from the figure, the length (i.e., along the longitudinal axis) of the heating element is less than a depth of the cavity 222w. In this way, the heating element 223w does not protrude from or extend beyond the opening 221w.

When the consumable 202w is received in the cavity 222w (as is shown in FIG. 72E), the heating element 223w penetrates the aerosol-forming substrate 213w of the consumable 202w. In particular, the heating element 223w extends for nearly the entire axial length of the aerosol-forming substrate 213w when inserted therein. Thus, when the heater 204w is activated, heat is transferred radially from an outer circumferential surface the heating element 223w to the aerosol-forming substrate 213w.

The device 201w further comprises an electronics cavity 224w. A power source, in the form of a rechargeable battery 205w (a lithium-ion battery), is located in electronics cavity 224w.

The device 201w comprises a controller 208w is configured to control at least one function of the device 201w and that is electrically connected to a PCB 210w. The controller is configured to control the operation of the heater 204w, which includes toggling the electrical connection of the rechargeable battery 205w to the heater 204w. As will be described further below this toggling of the electrical connection is done by way of transistors (also electrically connected to the PCB). For example, the controller is configured to control the heater 204w in response to a user depressing the button 212w. Depressing the button 212w may cause the controller to allow a voltage (from the rechargeable battery 205w) to be applied to the heater 204w (so as to cause the heating element 223w to be heated). The controller is also configured to control the LEDs 211w in response to (e.g., a detected) a condition of the device 201w or the consumable 202w. For example, the controller may control the LEDs to indicate whether the device 201w is in an on state or an off state (e.g., one or more of the LEDs may be illuminated by the controller when the device is in an on state).

The device 201w comprises a further input means (i.e., in addition to the button 212w) in the form of a puff sensor 225w. The puff sensor 225w is configured to detect a user drawing (i.e., inhaling) at the downstream end 218w of the consumable 202w. The puff sensor 225w may, for example, be in the form of a pressure sensor, flowmeter or a microphone. The puff sensor 225w is operatively connected to the controller in the electronics cavity 224w, such that a signal from the puff sensor 225w, indicative of a puff state (i.e., drawing or not drawing), forms an input to the controller (and can thus be responded to by the controller).

FIG. 73A is a schematic providing an exemplary PCB 310w connected to a number of components of a device. Such an arrangement may, for example, be used with the device 201w described above. As is apparent from the figure, the PCB 310w is a multilayer PCB and, in particular, includes four layers. The PCB 310w comprises top 327w and bottom 328w layers for electrically connecting and supporting a number of components (e.g., controllers, transistors, etc.). The PCB 310w further comprises a ground layer 329w and a power layer 330w. The power layer 330w is electrically connected to a power source 305w and the ground layer 329w is electrically connected to ground 331w (e.g., such as a ground terminal of the power source 305w).

The layers are separated by insulative layers 332w that may be formed of prepreg. However, although not shown, the top 327w and bottom 328w layers are electrically connected to the ground 329w and power 330w layers by way of e.g., vias (that extend transversely across the PCB 310w). In this way, power from the power source 305w is supplied to components supported by and/or connected to the top 327w and bottom 328w layers of the PCB 310w. As an example, the top layer 327w may be electrically connected to a heater 304w of the device and the bottom layer 328w may be connected to a sensor, such as a temperature sensor 334w.

Traces (i.e., printed circuits) on the PCB 310w allow the heater 304w and sensor 325w to communicate with components (such as a controller) electrically connected to the PCB 310w. FIG. 73B shows how these components may be arranged in more detail. In this figure, a power source 305w, heater 304w and temperature sensor 334w are connected to the PCB 310w. The PCB 310w comprises a voltage regulator 335w, two transistors 336w and a temperature sensor analog-to-digital convertor (TSADC) 337w.

The power source 305w supplies power to the heater 304w, via the voltage regulator 335w and the transistors 336w. The voltage regulator 335w ensures a consistent voltage is applied to the PCB 310w and the transistors 336w provide control of the power supply to the heater 304w.

The controller 308w is connected to both transistors 336w via the same output such that a single signal from the controller 308w controls both transistors 336w (i.e., between on and off conditions) simultaneously. The transistors 336w are arranged in series, such that if one transistor 336w fails, so as to be stuck in an on condition, switching the other transistor 336w to the off condition will prevent supply of power to the heater 304w (see FIG. 73C, which shows this arrangement in more detail).

The arrangement further comprises a temperature sensor 334w, in the form of a temperature sensing track that is mounted to a heating element of the heater 304w so as to be able to measure the temperature of the heater 304w. This temperature sensor 334w is connected to the controller 308w via the TSADC 337w, so as to supply a signal indicative of the temperature of the heater 304w to the controller 308w. In this way, the controller 308w can control the transistors 336w (and thus the heater 304w) in response to this signal. For example, if the sensed temperature exceeds a predetermined desired value, the controller 308w may control the transistors 336w to prevent power supply to the heater 304w. The controller 308w may continue to receive temperature signals and, once the temperature falls below the desired value, the controller 308w may control the transistors 336w to allow power supply to the heater 304w.

Whilst not shown, the controller 308w may also be configured to detect whether there is a short circuit in the heater 304w. This may, for example, be performed by detecting an impedance of the heater 304w. If the impedance falls below a threshold value, the controller 308w may control the transistors 336w to prevent supply of power to the heater 304w.

Conclusion

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilized for realizing the disclosure in diverse forms thereof.

While the disclosure has been described in conjunction with the exemplary embodiments described above, many equivalent modifications and variations will be apparent to those skilled in the art when given this disclosure. Accordingly, the exemplary embodiments of the disclosure set forth above are considered to be illustrative and not limiting. Various changes to the described embodiments may be made without departing from the spirit and scope of the disclosure.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the words "have", "comprise", and "include", and variations such as "having", "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means, for example, +/−10%.

The words "preferred" and "preferably" are used herein refer to embodiments of the disclosure that may provide certain benefits under some circumstances. It is to be appreciated, however, that other embodiments may also be preferred under the same or different circumstances. The recitation of one or more preferred embodiments therefore does not mean or imply that other embodiments are not useful, and is not intended to exclude other embodiments from the scope of the disclosure, or from the scope of the claims.

What is claimed is:

1. A smoking substitute device comprising:
  a heater connected to a main body of the smoking substitute device, the main body including a transverse cavity that opens through a first side wall of the main body and extends transverse to a longitudinal axis of the main body; and
  the smoking substitute device further including a cap covering the transverse cavity and at least a portion of the heater, wherein the cap is releasably engaged with the main body of the smoking substitute device, and wherein the cap is configured to be released from engagement with the main body of the smoking substitute device;
  wherein the cap includes a cavity having an opening for receiving at least a portion of a smoking substitute consumable into the cavity of the cap; and
  wherein, when the cap is engaged with the main body of the smoking substitute device, the heater extends from an internal base of the cavity of the cap towards the opening of the cavity of the cap.

2. The smoking substitute device according to claim 1, wherein the cap is releasably secured to the main body of the smoking substitute device by a retaining means.

3. The smoking substitute device according to claim 2, wherein the retaining means comprises:
  at least one flexible locking arm extending from the main body; and
  a locking protrusion disposed on each of the at least one flexible locking arm, the locking protrusion configured to extend into a corresponding slot located in the cap.

4. The smoking substitute device according to claim 3, wherein each locking protrusion includes a hooked end of a corresponding flexible locking arm.

5. The smoking substitute device according to claim 3, wherein the locking protrusion abuts a first end of the corresponding slot to limit an extent of movement of the cap relative to the main body, and to thereby prevent removal of the cap from the main body.

6. The smoking substitute device according to claim 1, wherein the cavity of the cap is capable of receiving at least a portion of a removal key to release the cap from the main body.

7. The smoking substitute device according to claim 1, wherein a slot is formed through a wall of the cavity of the cap.

8. A smoking substitute kit comprising:
the smoking substitute device according to claim 1; and
a removal key, wherein the cap is configured to be released from engagement with the main body of the smoking substitute device using the removal key.

9. The smoking substitute kit according to claim 8, wherein the cap is releasably secured to the main body of the smoking substitute device by a retaining means, the retaining means comprising: at least one flexible locking arm extending from the main body; and a locking protrusion disposed on each of the at least one flexible locking arm, the locking protrusion configured to extend into a corresponding slot located in the cap, and wherein the removal key includes at least one projection, wherein each of the at least one projection intrudes into the corresponding slot to disengage the locking protrusion from the corresponding slot.

10. The smoking substitute kit according to claim 9, wherein the projection is located on an unlocking arm of the removal key.

11. The smoking substitute kit according to claim 9, wherein the removal key includes two or more locking arms.

12. The smoking substitute kit according to claim 11, wherein the removal key includes a separator to hold the locking arms in a mutually separated position, to thereby disengage each corresponding locking protrusion from the corresponding slot.

13. The smoking substitute kit according to claim 12, wherein the separator is moveable relative to the locking arms.

14. The smoking substitute kit according to claim 8, wherein the removal key comprises:
at least one unlocking arm; and
an unlocking protrusion disposed on the unlocking arm, the unlocking protrusion is configured to displace a corresponding locking protrusion disposed on a locking arm extending from said main body to disengage the locking protrusion from a slot in said cap.

15. The smoking substitute kit of claim 14, wherein the removal key further comprises a cleaning means for cleaning the heater.

16. The smoking substitute kit of claim 15, wherein the cleaning means comprises at least one cleaning bristle.

17. The smoking substitute kit of claim 15, wherein the removal key further comprises a central rod, wherein the at least one unlocking arm extending along a longitudinal axis of the central rod in a first direction and the cleaning means extending in a second direction opposite to the first direction.

18. The smoking substitute kit of claim 17, wherein the removal key further comprises a collar around the central rod having the unlocking arm extended in the first direction, the collar being movable between an insertion position and an unlocking position, wherein in the insertion position the at least one unlocking arm is allowed to flex and in the unlocking position the central rod prevents the flexing of the unlocking arm.

19. The smoking substitute device according to claim 1, wherein the cap includes a rigid base region at a base of the cavity of the cap, the rigid base region being configured to seat around a portion of the heater.

20. The smoking substitute device according to claim 1, wherein the heater comprises a tapered portion to facilitate insertion of the heater into the smoking substitute consumable.

21. A system comprising the smoking substitute device of claim 1 and the smoking substitute consumable.

22. The system of claim 21, wherein the smoking substitute consumable and cavity of the cap are configured such that, when the smoking substitute consumable is received in the cavity of the cap, a downstream end of the smoking substitute consumable protrudes from the opening and from the smoking substitute device.

23. A smoking substitute kit comprising:
a smoking substitute device; and
a removal key;
wherein the smoking substitute device comprises:
a heater connected to a main body of the smoking substitute device; and
a cap covering at least a portion of the heater;
wherein the cap is releasably engageable with a main body of the smoking substitute device; and
wherein the cap is configured to be released from engagement with the main body of the smoking substitute device by engaging the removal key with the cap.

24. The smoking substitute kit of claim 23, wherein the heater comprises a heating element.

25. The smoking substitute kit of claim 24, wherein the heating element comprises a rod that extends from the main body of the device.

26. The smoking substitute kit of claim 23, wherein the removal key is adapted for performing a cleaning operation of the smoking substitute device.

27. The smoking substitute kit of claim 26, wherein the removal key has unlocking means at one end and a cleaning means at another end.

* * * * *

UNITED STATES PATENT AND TRADEMARK OFFICE
CERTIFICATE OF CORRECTION

| | |
|---|---|
| PATENT NO. | : 12,329,201 B2 |
| APPLICATION NO. | : 17/481889 |
| DATED | : June 17, 2025 |
| INVENTOR(S) | : Kate Ferrie et al. |

It is certified that error appears in the above-identified patent and that said Letters Patent is hereby corrected as shown below:

In the Specification

Column 209, Line 50: Delete "58" and replace with -- 5B --

Column 243, Line 25: Delete "100r" and replace with -- 100f' --

Column 243, Line 31: Delete "100r" and replace with -- 100f' --

Signed and Sealed this
Eighteenth Day of November, 2025

John A. Squires
*Director of the United States Patent and Trademark Office*